US006566127B1

(12) United States Patent
Pavco et al.

(10) Patent No.: US 6,566,127 B1
(45) **Date of Patent: *May 20, 2003**

(54) METHOD AND REAGENT FOR THE TREATMENT OF DISEASES OR CONDITIONS RELATED TO LEVELS OF VASCULAR ENDOTHELIAL GROWTH FACTOR RECEPTOR

(75) Inventors: Pamela Pavco, Lafayette, CO (US); James A. McSwiggen, Boulder, CO (US); Dan T. Stinchcomb, Fort Collins, CO (US); Jaime Escobedo, Alamo, CA (US)

(73) Assignees: Ribozyme Pharmaceuticals, Inc., Boulder, CO (US); Chiron Corporation, Emeryville, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/371,772

(22) Filed: Aug. 10, 1999

Related U.S. Application Data

(63) Continuation-in-part of application No. 08/584,040, filed on Jan. 11, 1996, now Pat. No. 6,346,398.
(60) Provisional application No. 60/005,974, filed on Oct. 26, 1995.

(51) Int. Cl.[7] .......... C12N 5/00; C12P 19/34; C07H 21/04
(52) U.S. Cl. .......... 435/325; 435/91.31; 536/24.5
(58) Field of Search .......... 435/91.31, 91.1, 435/325; 536/23.1, 23.2, 24.3, 24.33, 24.31, 24.5

(56) References Cited

U.S. PATENT DOCUMENTS

| | | | | |
|---|---|---|---|---|
| 4,987,071 A | | 1/1991 | Cech et al. | |
| 5,334,711 A | | 8/1994 | Sproat et al. | |
| 5,359,051 A | | 10/1994 | Cook et al. | |
| 5,525,468 A | | 6/1996 | McSwiggen et al. | |
| 5,631,359 A | | 5/1997 | Chowrira et al. | |
| 5,672,695 A | | 9/1997 | Eckstein et al. | |
| 6,346,398 B1 | * | 2/2002 | Pavco et al. | 435/91.31 |

FOREIGN PATENT DOCUMENTS

| | | |
|---|---|---|
| EP | 360257 | 3/1990 |
| WO | WO9103162 | 3/1991 |
| WO | WO9207065 | 9/1991 |
| WO | WO9312569 | 4/1993 |
| WO | WO9315187 | 8/1993 |
| WO | WO9323057 | 11/1993 |
| WO | WO9402595 | 2/1994 |
| WO | WO9411499 | 5/1994 |
| WO | WO9421679 | 9/1994 |
| WO | WO9421791 | 9/1994 |
| WO | WO9511304 | 10/1994 |
| WO | WO9504142 | 2/1995 |
| WO | WO9504818 | 2/1995 |
| WO | WO9513380 | 5/1995 |
| WO | WO9521868 | 8/1995 |
| WO | WO9523225 | 8/1995 |
| WO | WO9610390 | 4/1996 |
| WO | WO9610391 | 4/1996 |
| WO | WO9610392 | 4/1996 |
| WO | WO9622689 | 8/1996 |
| WO | WO9700957 | 1/1997 |
| WO | WO9726270 | 7/1997 |
| WO | WO9813526 | 4/1998 |
| WO | WO9828317 | 7/1998 |
| WO | WO9858058 | 12/1998 |
| WO | WO9916871 | 4/1999 |

OTHER PUBLICATIONS

Usman et al., "Chemical modification of hammerhead ribozymes: activity and nuclease resistance," *Nucleic Acids Syposium Series* 31:163–164 (1994).
International Search Report, PCT/US96/17480.
U.S. patent application Ser. No. 60/005,974, Pavco et al., filed Oct 26, 1995.
U.S. patent application Ser. No. 60/082,404, Thompson et al., filed Apr. 20, 1998.
U.S. patent application Ser. No. 60/101,174, Hartmann et al., filed Sep. 21, 1998.
Aiello, et al., "Vascular Endothelial Growth Factor in Ocular Fluid of Patients with Diabetic Retinopathy and Other Retinal Disorders," 1994 *New Engl. J. Med.* 331, 1480.
Akhtar and Juliano, "Cellular Uptake and Intracellular Fate of AntiSense Oligonucleotides," *Trends Cell Biol.* 2:139–144 (1992).
Bartel and Szostak, "Isolatin of New Ribozymes From a Large Pool of Random Sequences," *Science* 261:1411–1418 (1993).
Beaucage and Iyer, "The Functionalization of Oligonucleotides Via Phosphoramidite Derivatives," *Tetrahedron* 49:1925–1963 (1993).
Beigelman et al., "Chemical Modification of Hammerhead Ribozymes," *J. Biol. Chem.* 270:25702–25708 (1995).
Berkman et al., "Expression of the Vascular Permeability Factor/Vascular Endothelial Growth Factor Gene in Central Nervous System Neoplasms," 1993 *J. Clin. Invest.*91, 153.
Breaker and Joyce, "Inventing and improving ribozyme function: rational design versus iterative selection methods," *TIBTECH* 12:268–275 (1994).
Breaker et al., "A DNA enzyme with $Mg^2$–dependent RNA phosphoesterase activity," *Chemistry & Biology* 2(10):655–660 (1995).
Breaker, "Are engineered proteins getting competition from RNA?" *Current Opinion in Biotechnology* 7:442–448 (1996).

(List continued on next page.)

*Primary Examiner*—Sean McGarry
*Assistant Examiner*—Janet Epps
(74) *Attorney, Agent, or Firm*—McDonnell Boehnen Hulbert & Berghoff

(57) ABSTRACT

The present invention relates to nucleic acid molecules which modulate the synthesis, expression and/or stability of an mRNA encoding one or more receptors of vascular endothelial growth factor.

5 Claims, 35 Drawing Sheets

OTHER PUBLICATIONS

Burger et al., "Experimental Corneal Neovascularization: Biomicroscopic, Angiographic, and Morphologic Correlation," *Cornea* 4:35–41 (1985/1986).
Burgin et al., "Chemically Modified Hammerhead Ribozymes with Improved Catalytic Rates," *Biochemistry* 35:14090–14097 (1996) (volume no mistakenly listed as 6).
Carter, "Adeno–Associated Virus Vectors," *Curr Opi. Biotech.* 3:533–539 (1992).
Caruthers et al., "Chemical Synthesis of Deoxyoligonucleotides and Deoxyoligonucleotide Analogs," *Methods in Enzymology* 211:3–19 (1992).
Cech, "Ribozymes and Their Medical Implications," *JAMA* 260:3030–3034 (1988).
Chartrand et al., "An oligodeoxyribonucleotide that supports catalytic activity in the hammerhead ribozyme domain," *Nucleic Acids Research* 23(20):4092–4096 (1995).
Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20:4581–4589 (1992).
Chowira et al., "In Vitro and in Vivo Comparison of Hammerhead, Hairpin, and Hepatitis Delta Virus Self–Processing Ribozyme Cassettes," *J. Biol. Chem.* 269:25856–25864 (1994).
Christoffersen and Marr, "Riobozymes as Human Therapeutic Agents," *J. Med. Chem.* 38:2023–2037 (1995) (also referred to as Christofferson and Marr).
Collins and Olive, "Reaction Conditions and Kinetics of Self–Cleavage of a Ribozyme Derived From Neurospora VS RNA," *Biochemistry* 32:2795–2799 (1993).
Detmar et al., "Overexpression of Vascular Permeability Factor/Vascular Endothelial Growth Factor and its Receptors in Psoriasisi," *J. Exp. Med.* 180, 1141.
Dreyfus, "Restriction Ribozymes?" *Einstein Quarterly Journal of Biology and Medicine* 6:92–93 (1988).
Dropulic et al., "Functional Characterization of a U5 Ribozyme: Intracellular Suppression of Human Immunodeficiency Virus Type I Expression," *Journal of Virology* 66:1432–1441 (1992).
Duval–Valentin, "Specific inhibition of transcription by triple helix–forming oligonucleotides," *Proc. Nalt. Acad. Sci. USA* 89:504–508 (1992).
Egholm et al., "PNA hybridizes to complementary oligonucleotides obeying the Watson–Crick hydrogen–bonding rules," *Nature* 365:566–568 (1993).
Elkins and Rossi, "Ch. 2—Cellular Delivery of Ribozymes," in *Delivery Strategies for Antisense Oligonucleotide Therapeutics*, edited by Akhtar, CRC Press, pp. 17–220 (1995).
Elroy–Stein and Moss, "Cytoplasmic Expression System Based on Constitutive Synthesis of Bacteriophage T7 RNA Polymerase in Mammalian Cells," *Proc. Natl. Acad. Sci. USA* 87:6743–6747 (1990).
Fava et al., "Vascular Permeability Factor/Endothelial Growth Factor (VPF/VEGF): Accumulation and Expression in Human Synovial Fluids and Rheumatoid Synovial Tissue," 1994 *J. Exp. Med.* 180, 341.
Feldstein et al., "Two sequences participating in the autolytic processing of satellite tobacco ringspot virus complementary RNA," *Gene* 82:53–61 (1989).
Ferrara, "Vascular Endothelial Growth Factor," 1993 *Trends Cardiovas. Med.* 3, 2244.
Folkman and Shing, "Angiogenesis," *J. Biol. Chem.* 267:10931–10934 (1992).
Folkman, "What is the Evidence that Tumors are Angiogenesis Dependent?" *Journal of the National Cancer Institute* 82:4–6 (1990).
Folkman, "Tumor Angiogenesis" 1985 *Adv. Cancer. Res.* 43, 175.
Forster and Altman, "External Guide Sequences for an RNA Enzyme," *Science* 249:783–786 (1990).
Frier et al., 1986, *Proc. Nat. Acad. Sci. USA* 83:9373–9377.
Fong et al., "Role of the Fit–1 Receptor Tyrosine Kinase in Regulating the Assembly of Vascular Endothelium," 1995 *Nature* 376, 66 Corrected from specification.
Gao and Huang, "Cytoplasmic Expression of a Reporter Gene by Co–Delivery of T7 RNA Polymerase and T7 Promoter Sequence with Cationic Liposomes," *Nucleic Acids Research* 21:2867–2872 (1993).
Gitay–Goren et al., "The Binding of Vascular Endothelial Growth Factor to Its Receptos is Dependent on Cell Surface–associated Heparin–like Molecules," 1992 *J. Biol. Chem.* 267, 6093.
Grant et al., "Insulin–like growth factor I acts as an angiogenic agent in rabbit comes and retina: comparative studies with basic fibroblast growth factor," *Diabetologia* 36:282–291 (1993).
Griffin et al., "Group II intron ribozymes that cleave DNA and RNA linkages wit similar efficiency, and lack contacts with substrate 2'–hydroxyl groups," *Chemistry & Biology* 2:761–770 (1995).
Guerrier–Takada et al., "The RNA Moiety of Ribonuclease P Is the Catalytic Subunit of the Enzyme," *Cell* 35:849–857 (1983).
Hampel and Tritz, "RNA Catalytic Properties of the Minimum ( . )s TRSV Sequence," *Biochemistry* 28:4929–4933 (1989).
Hampel et al., "Hairpin' Catalytic RNA Model: Evidence for Helices and Sequence Requirement for Substrate RNA," *Nucleic Acids Research* 18:299–304 (1990).
Haseloff and Gerlach, "Sequences required for self–catalysed cleavage of the satellite RNA of tobacco ringspot virus," *Gene* 82:43–52 (1989).
Haseloff and Gerlach, "Simple RNA Enzymes with New and Highly Specific Endoribonuclease Activities," *Nature* 334:585–591 (1988).
Hertel et al., "Numbering System for the Hammerhead," *Nucleic Acids Research* 20:3252 (1992).
Ishiwata et al., "Physical–Chemistry Characteristics and Biodistribution of Poly(ethylene glycol)–Coated Liposomes Using Poly(oxyethylene) Cholesteryl Ether," *Chem. Pharm. Bull.* 43:1005–1011 (1995) (mistakenly referred to as Ishiwataet).
Ishizaka et al., "Isolation of Active Ribozymes from an RNA Pool of Random Sequences Using an Anchored Substrate RNA," *Biochemical and Biophysical Research Communication* 214(2):403–409 (1995).
Izant and Weintraub, "Constitutive and Conditional Suppression of Exogenous and Endogeneous Genes by Anti–Sense RNA," *Science* 229:345–352 (1985).
Jaeger et al., "Improved Predictions of Secondary Structures for RNA," *Proc. Natl. Acad. Sci. USA* 86:7706–7710 (1989).
Jeffries and Symons, "A Catalytic 13–mer Ribozyme," *Nucleic Acids Research* 17:1371–1377 (1989) (also referred to as Jefferies).

Jellinek et al., "Inhibitions of Receptor Binding by High–Affinity RNA Ligands to Vascular Endothelial Growth Factor," *Biochemistry* 33:10450–10456 (1994).

Joyce et al., "Amplification, mutation and selection of catalytic RNA," *Gene* 82:83–87 (1989).

Joyce, "Directed Molecular Evolution," *Scientific American* 267:90–97 (1992).

Kashani–Sabet et al., "Reversal of the Malignant Phenotype by an Anti–ras Ribozyme," *Antisense Research & Development* 2:3–15 (1992).

Kim and Cech, "Three–dimensional model of the active site of the self–splicing rRNA precursor of Tetrahymena," *Proc. Natl. Acad. Sci. USA* 84:8788–8792 (1987).

Kim et al., "Inhibition of vascular endothelial growth factor–induced angiogenesis suppresses tumour growth in vivo," *Nature* 362:841–844 (1993).

Koch et al., "Vascular Endothelial Growth Factor: A Cytokine Modulating Endothelial Function in Rheumatoid Arthritis," 1994 *J. Immunol.* 152, 4149.

Kore, et al., "Sequence specificity of the hammerhead ribozyme revisistsed; the NIH rule", *Nucleic Acids Research*, 26(18):4116–4120 (1998).

Kumar and Ellington, "Artificial evolution and natural ribozymes," *FASEB J.* 9:1183–1195 (1995).

Lasic and Needham "The 'Stealth' Liposome: A Prototypical Biomaterial," *Chemical Reviews* 95:2601–2627 (1995).

Lepri et al., "Effect of Low Molecular Weight Heparan Sulphate on Angiogenesis in the Rat Cornea after Chemical Cauterization," *Journal of Ocular Pharmacology* 10:273–281 (1994).

L'Hullier et al., "Cytoplasmic Delivery of Ribozymes Leads to Efficient Reduction in α–Lactalbumin mRNA Levels in C1271 Mouse," *EMBO J*, 11:4411–4418 (1992).

Li and Altman, "Cleavage by RNase P of gene N mRNA reduces bacteriophage λ burst size," *Nucleic Acids Research* 24:835–842 (1996).

Lieber et al., "Stable High–Level Gene Expression in Mammalian Cells by T7 Phage RNA Polymerase," *Methods Enzymol.* 217:47–66 (1993).

Limbach et al., "Summary: the modified nucleosides of RNA," *Nucleic Acids Research* 22(12):2183–2196 (1994).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

Liu et al., "Cationic Liposome–mediated intravenous Gene Delivery," *J. Biol. Chem.* 270(42):24864–24870 (1995).

Long and Uhlenbeck, "Kinetic characterization of intramolecular and intermolecular hammerhead RNAs with stem II deletions," *Proc. Natl. Acad. Sci. USA* 91:6977–6981 (1994).

Mathews et al., "A Receptor Tyrosine Kinase cDNA Isolated from a Population of Enriched Primitive Hematopoiectic cells and Exhibiting Close Genetic Linkage to c–kit," 1991, *Proc. Natl. Acad. Sci.*, USA, 88, 9026.

McGarry and Lindquist, "Inhibition of heat shock protein synthesis by heat–inducible antisense RNA," *Proc. Natl. Acad. Sci. USA* 83:399–403 (1986).

Michels and Pyle, "Conversion of a Group II Intron into a New Multiple–Turnover Ribozyme that Selectively Cleaves Oligonucleotides: Elucidation of Reaction Mechanism and Structure/Function Relationships," *Biochemistry* 34:2965–2977 (1995).

Millauer et al., "Glioblastoma Growth Inhibited in vivo by a Dominant–negative Flk–1 Mutant," 1994, *Nature* 367, 576.

Millauer, "High Affinity VEGF Binding and Developmental Expression Suggest Flk–1 as a Major Regulator of Vasculogenesis and Angiogenesis," *Cell* 72:835–846 (1993).

Miller et al., "Vascular Endothelial Growth Factor/Vascular Permeability Factor is Temporally and Spatially Correlated with Ocular Angiogenesis in a Priamate Model," 1994 *Am. J. Pathol.* 145, 574.

Mitra et al., "A mammalian 2–5A system functions as an antiviral pathway in transgenic plants," *Proc. Natl. Acad. Sci. USA* 93:6780–6785 (1996).

Mukhopadhyay et al., "Antisense Regulation of Oncogenes in Human Cancer," *Critical Reviews in Oncogenesis* 7:151–190 (1996).

Nakamaye and Eckstein, "AUA–Cleaving Hammerhead Ribozymes: Attempted Selection for Improved Cleavage," *Biochemistry* 33:1271–1277 (1994.

Nathans and Smith, "Restriction Endonucleases in the Analysis and Restructuring of DNA Molecules," *Ann. Rev. Biochem.* 44:273–293 (1975).

Neufeld et al., "Vascular Endothelial Growth Factor and Its Receptors," *Progress in Growth Factor Research* 5:89–97 (1994).

Norrby, 1997, *APMIS* 105, 417–437.

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Oku et al., "Real–time analysis of liposomal trafficking in tumor–bearing mice by use of positron emission tomography," *Biochimica et Biophysica Acta* 1238:86–90 (1995).

O'Reilly et al., "Angiostatin: A Novel Angiogenesis Inhibitor That Mediates the Suppression of Metastases by a Lewis Lung Carcinoma," *Cell* 79:315–328 (1994).

Orgel, "Selection in vitro," *Proc. R. Soc. London B*, 205:435–442 (1979).

Ormerod et al., "Effects of Altering the Eiconsanoid Precursor Pool on Neovascularization and Inflammation in the Alkali–burned Rabbit Cornea," *American Journal of Pathology* 137:1243–1252 (1990).

Pandey et al., "Role ov B61, the Ligand for the Eck Receptor Tyrosine Kinase, in TNF–α–induced Angiogenesis," *Science* 268:567–569 (1995).

Passaniti et al., "A Simple, Quantitative Method for Assessing Angiogenesis and Antiangiogenic Agents Using Reconstituted Basement Membrane, Heparin, and Fibroblast Growth Factor," *Laboratory Investigation* 67:519–528 (1992).

Perreault et al., "Mixed Deoxyribo–and Ribo–Oligonucleotides with Catalytic Activity," *Nature* 344:565–567 (1990) (often mistakenly listed as Perrault).

Perrotta and Bean, "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Pierce et al., "Vascular endothelial growth factor/vascular permeability factor expression in a mouse model of retinal neovascularization," *Proc. Natl. Acad. Sci. USA* 92:905–909 (1995).

Plouet et al., "Isolation and Characterization of a Newly Identified Endothelial Cell Mitogen Produced by AtT–20 Cells," *EMBO J.* 8, 3801.

Rossi et al., "Ribozymes as Anti–HIV–1 Therapeutic Agents: Principles, Applications, and Problems," *Aids Research and Human Retroviruses* 8:183–189 (1992).

Santoro and Joyce, "A general purpose RNA–cleaving DNA enzyme," *Proc. Natl. Acad. Sci. USA* 94:4262–4266 (1997).

Sarver et al., "Ribozymes as Potential Anti–HIV–1 Therapeutic Agents" *Science* 247:1222–1225 (1990).

Saville and Collins, "A Site–Specific Self–Cleavage Reaction Performed by a Novel RNA In Neurospora Mitochondria," *Cell* 61:685–696 (1990).

Saville and Collins, "RNA–Mediated Ligation of Self–Cleavage Products of a Neurospora Mitochondrial Plasmid Transcript," *Proc. Natl. Acad. Sci. USA* 88:8826–8830 (1991).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Senger et al., "Vascular permeability factor (VPF, VEGF) in tumor biology," *Cancer and Matastasis Reviews* 12:303–324 (1993).

Shalaby et al., "Failure of Blood–island Formation and Vasculogenesis in Flk–1–deficient Mice," 1995 *Nature* 376, 62.

Shweiki et al., "Patterns of Expression of Vascular Endothelial Growth Factor (VEGF) and VEGF Receptors in Mice Suggest a Role in Hormonally Regulated Angiogenesis," 1993 *Clin. Invest.* 91:2235–2243.

Stein and Cheng, "Antisense Oligonucleotides as Therapeutic Agents—Is the Bullet Really Magical?" *Science* 261:1004–1288 (1993).

Szostak, "In Vitro Genes," *TIBS* 17:89–93 (1993).

Taira et al., "Construction of a novel RNA–transcript–trimming plasmid which can be used both in vitro in place of run–off and (G)–free transcriptions and in vivo as multi–sequences transcription vectors," *Nucleic Acids Research* 19:5125–5130 (1991).

Takahashi et al., "Markedly Increased Amounts of Messenger RNAs for Vascular Endothelial Growth Factor Augments Revascularization in a Rabbit Ischemic Hind Limb Model," 1995 *J. Clin. Invest.* 93, 662 Corrected from Specification.

Tang et al., "Examination of the catalytic fitness of the hammerhead ribozyme by in vitor selection," *RNA* 3:914–925 (1997).

Terman et al., "Identification of a New Endothelial Cell Growth Factor Receptor Tyrosine Kinase," 1991 *Oncogene* 6, 1677.

Thompson et al., "Improved accumulation and activity of ribozymes expressed from a tRNA–based RNA polymerase III promoter," *Nucleic Acids Research* 23:2259–2268 (1995).

Torrence et al., "Targeting RNA for degradation with a (2'–5') oligoadenylate–antisense chimera," *Proc. Natl. Acad. Sci. USA* 90:1300–1304 (1993).

Turner et al., "Free Energy Increments for Hydrogen Bonds in Nucleic Acid Base Pairs," *J. Am. Chem. Soc.* 109:3783–3785 (1987).

Turner et al., "Improved Parameters for Prediction of RNA Structure," *Cold Spring Harbor Symposia on Quantitative Biology* vol. LII, pp. 123–133 (1987).

Uhlenbeck, "A Small Catalytic Oligoribonucleotide," *Nature* 328:596–600 (1987).

Usman and Cedergren, "Exploiting the chemical synthesis of RNA," *TIBS* 17:334–339 (1992) (Corrected from Specification).

Usman and McSwiggen, "Ch. 30—Catalytic RNA (Ribozymes) as Drugs," *Annual Reports in Medicinal Chemistry* 30:285–294 (1995).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Usman et al., "Chemical modification of hammerhead ribozymes: activity and nuclease resistance," *Nucleic Acids Syposium Series* 31:163–164 (1994).

Vaish et al., "Isolation of Hammerhead Ribozymes with Altered Core Sequences by in Vitro Selection," *Biochemistry* 36:6495–6501 (1997).

Vaisman et al., "Characterization of the Receptors for Vascular Endothelial Growth," 1990 *J. Biol. Chem.* 265, 19461.

Ventura et al., "Activation of HIV–Specific Ribozyme Activity by Self–Cleavage," *Nucleic Acids Research* 21:3249–3255 (1993).

Weerasinghe et al., "Resistance to Human Immunodeficiency Virus Type 1 (HIV–1) Infection in Human $CD4^+$ Lymphocyte–Derived Cell Lines Conferred by Using Retroviral Vectors Expressing an HIV–1 RNA–Specific Ribozyme," *Journal of Virology* 65:5531–5534 (1994) (Correction from Specification).

Weckbecker et al., 1992, *Angiogenesis: Key principles–Science–Technology–Medicine*, ed. R. Steiner).

Wincott et al., "Synthesis, deprotection, analysis and purification of RNA and ribozymes," *Nucleic Acids Research* 23(14):2677–2684 (1995).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zabner et al., "Adenovirus–Mediated Gene Transfer Transiently Corrects the Chloride Transport Defect in Nasal Epithelia of Patients with Cystic Fibrosis," *Cell* 75:207–216 (1993).

Zaug et al., "The Tetrahymena Ribozyme Acts Like an RNA Restriction Endonuclease," *Nature* 324:429–433 (1986).

Zhou et al., "Synthesis of Functional mRNA in Mammalian Cells by Bacteriophage T3 RNA Polymerase," *Mol. Cell. Biol.* 10:4529–4537 (1990).

Ziche et al., "Angiogenesis Can Be Stimulated or Repressed in vivo by a Change in GM3:GD3 Ganglioside Ratio" *Lab. Invest.* 67:711–715.

* cited by examiner

*Figure 1: Hammerhead Ribozyme*
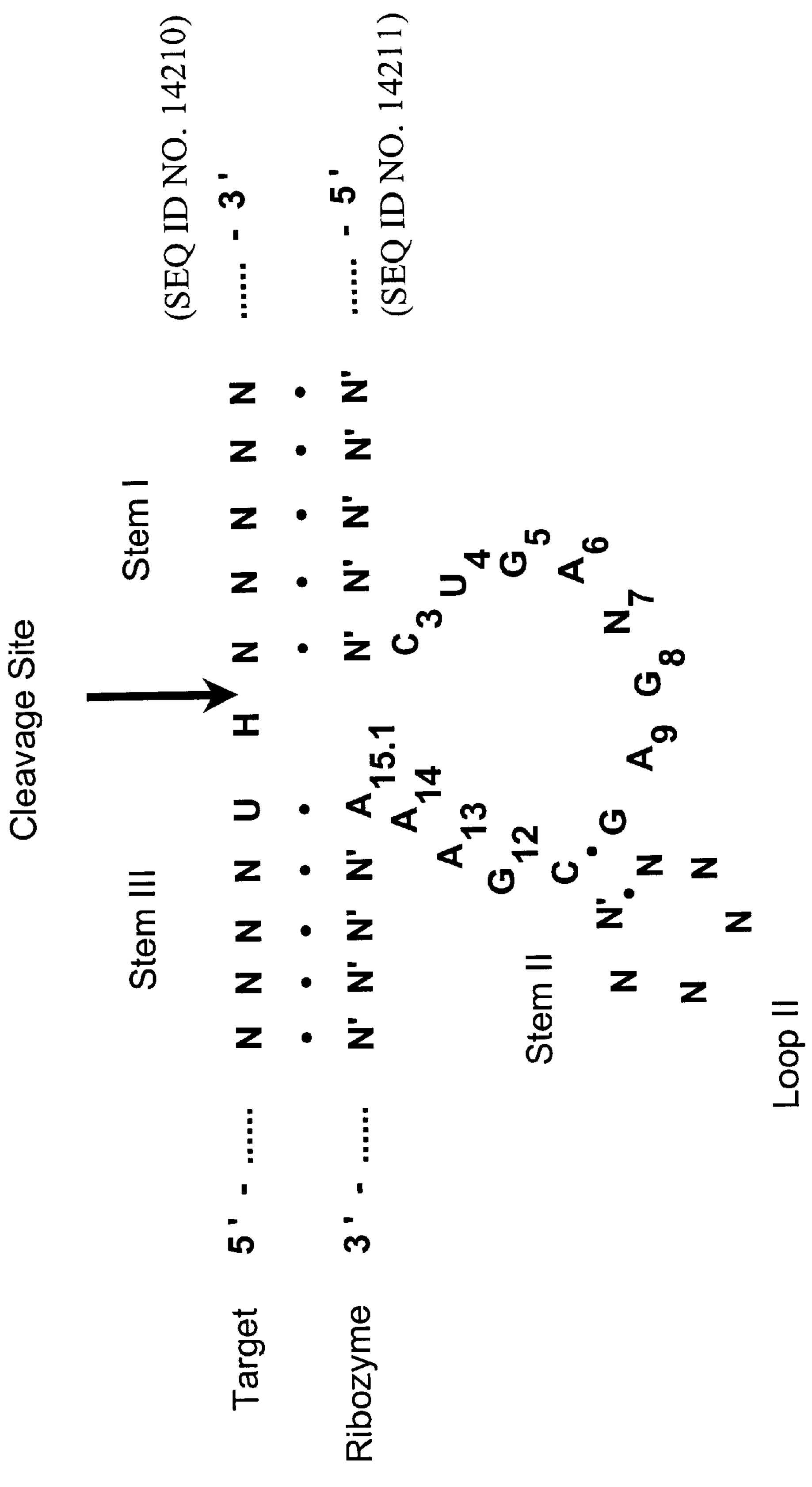

Figure 2. Hammerhead Ribozyme Substrate Motifs
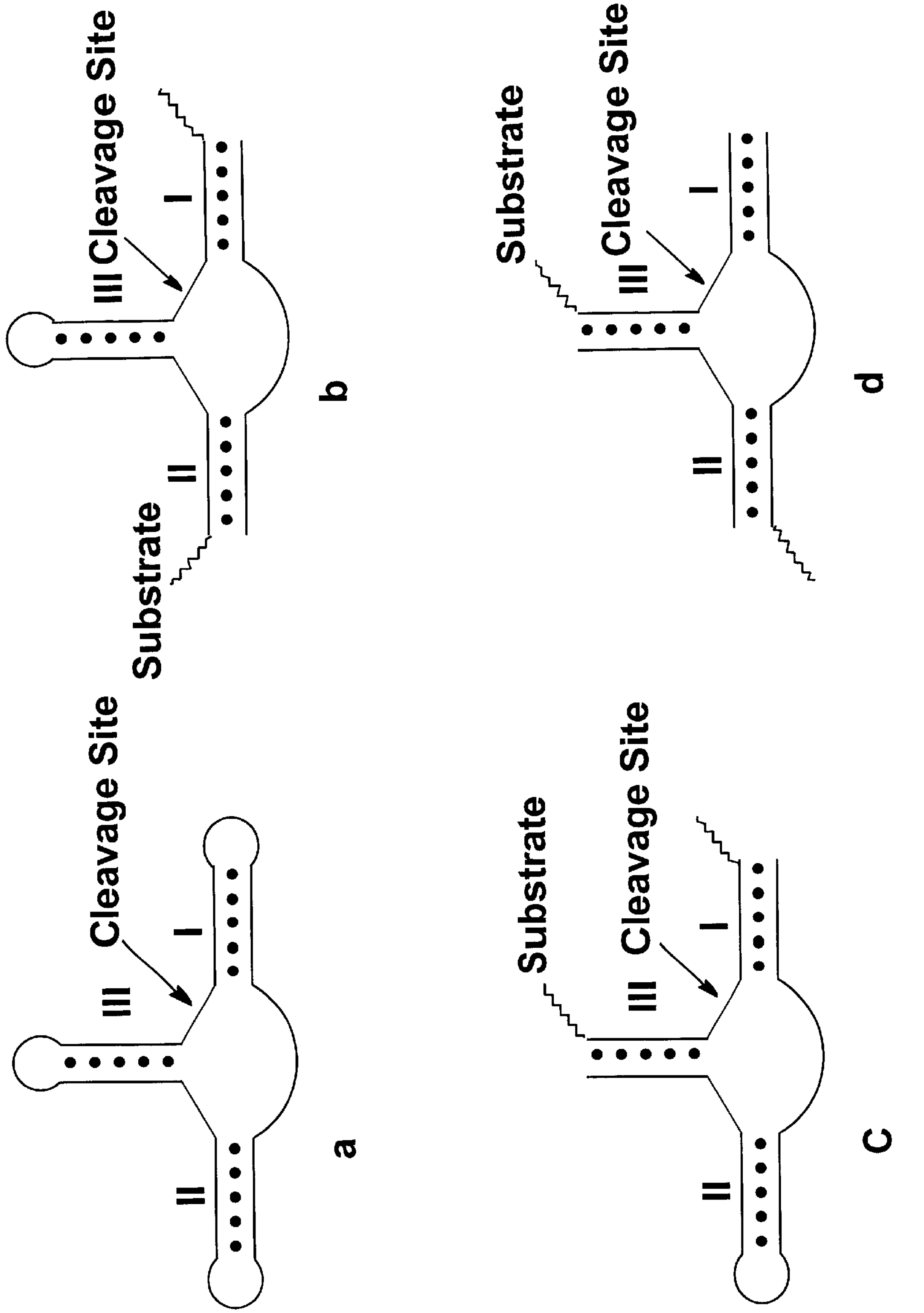

Figure 3: Hairpin Ribozyme
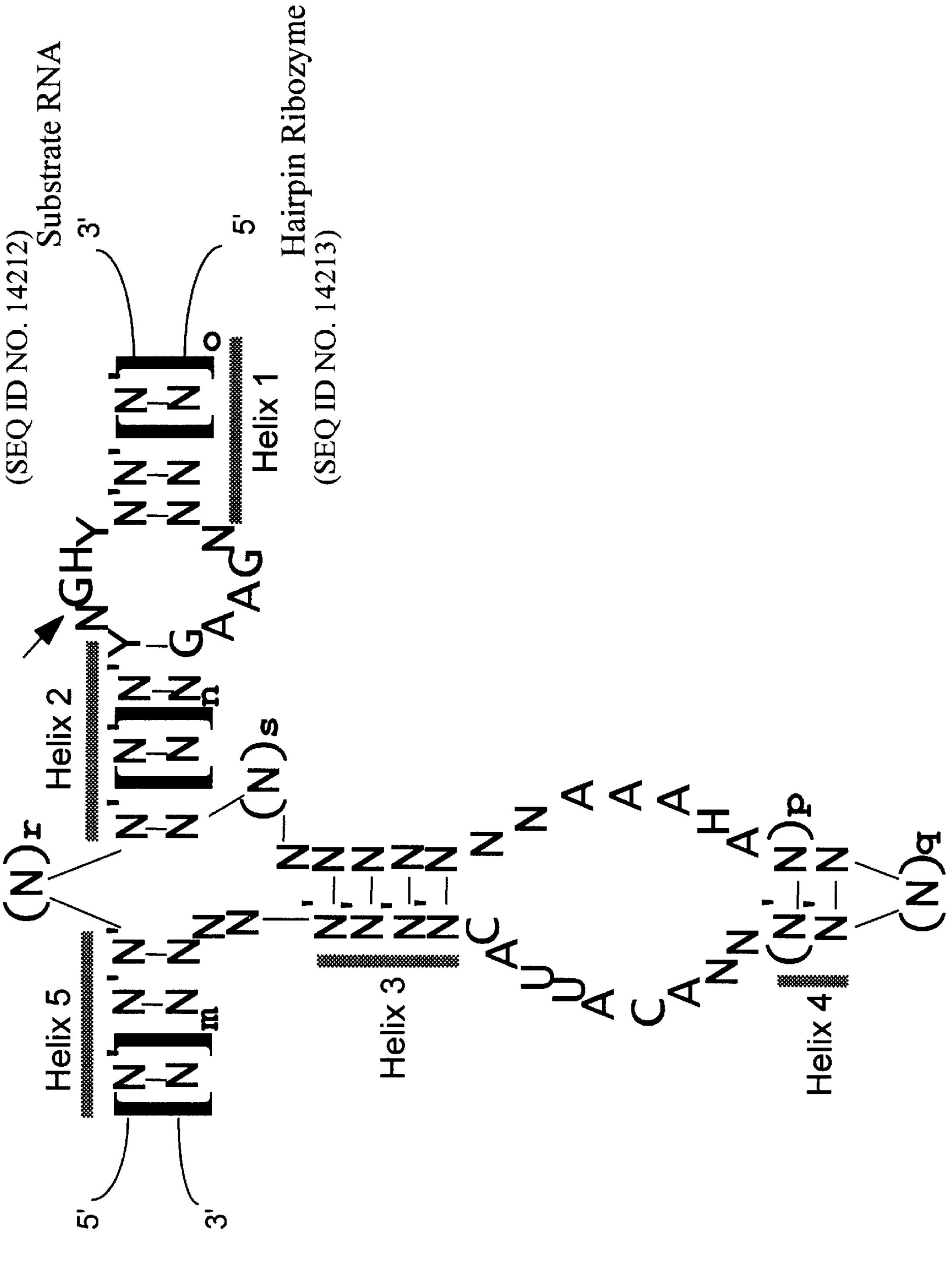

Figure 4: Hepatitis Delta Virus Ribozyme
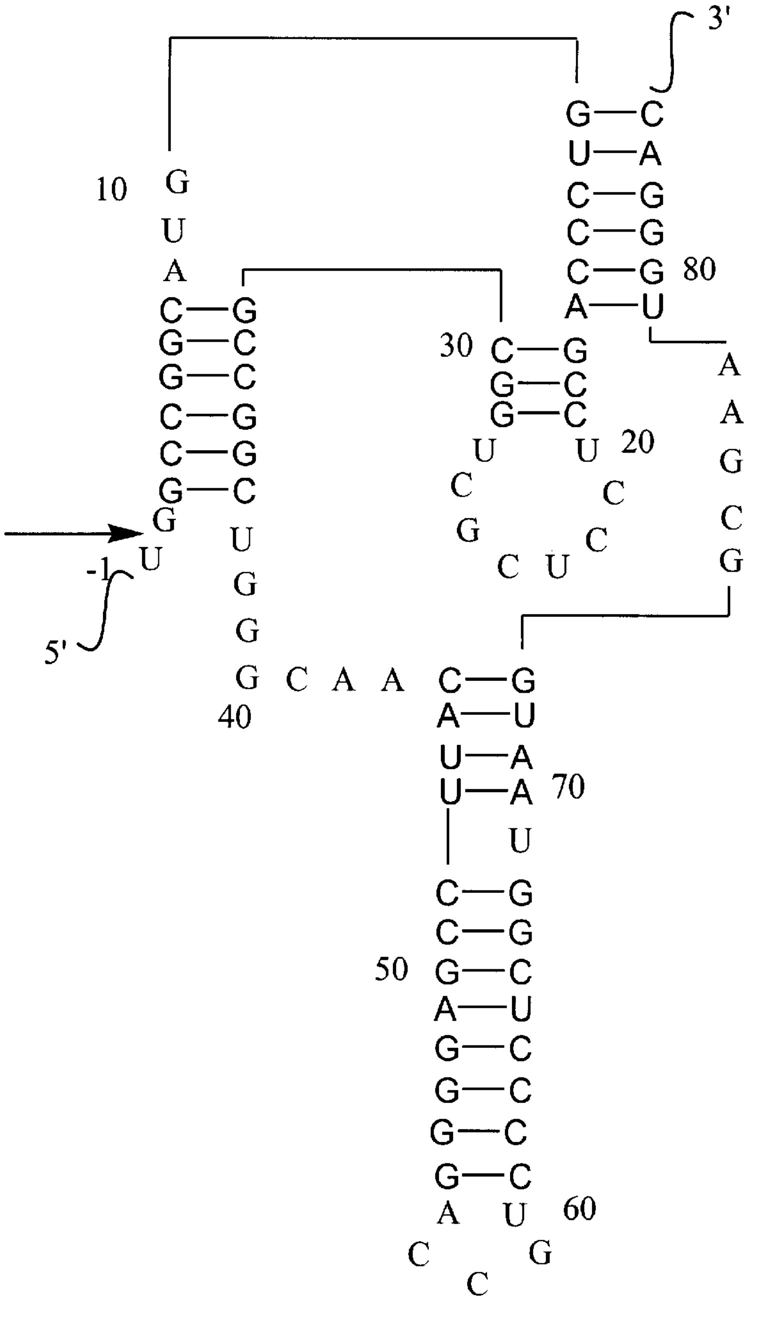
(SEQ ID NO 14214)

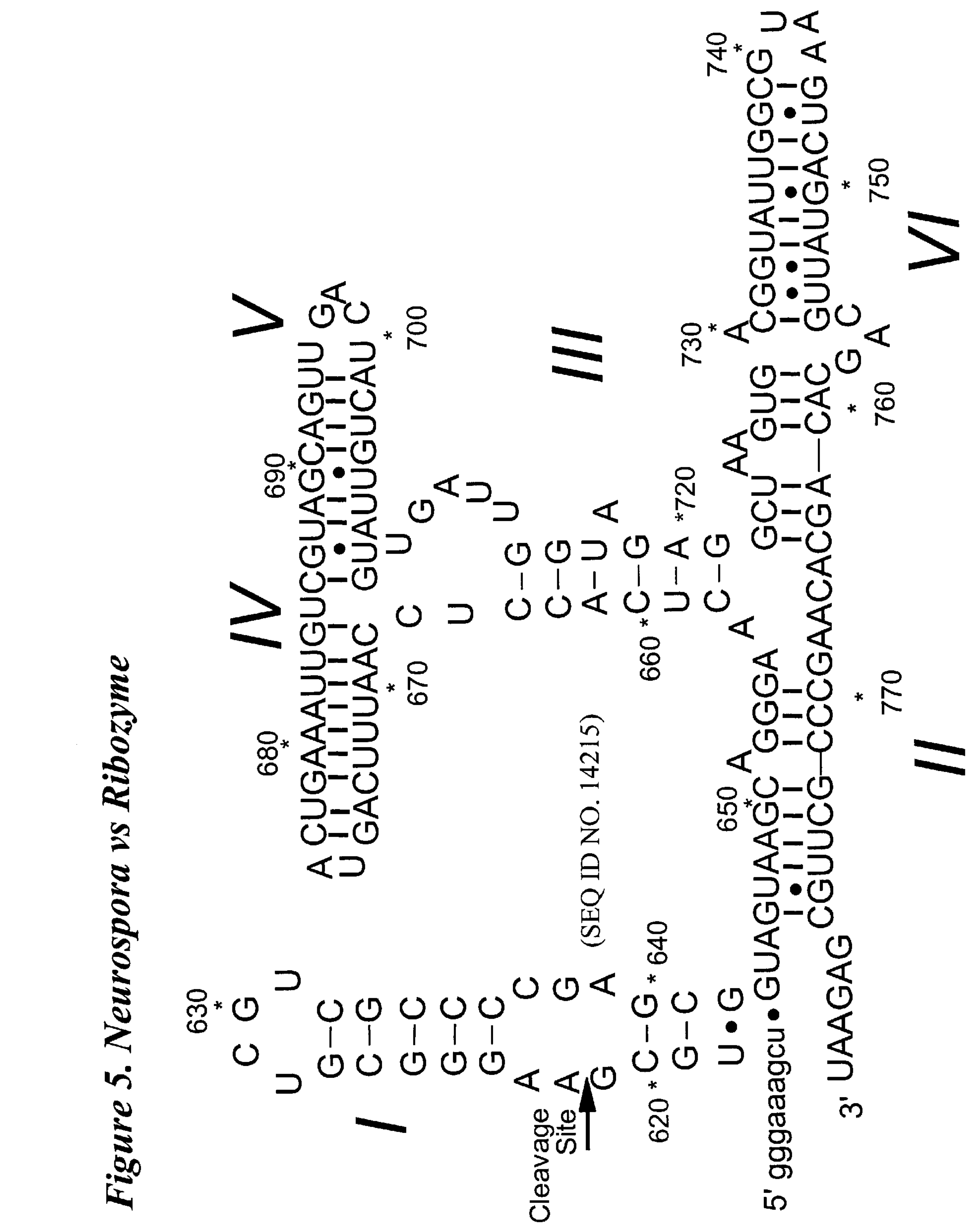
*Figure 5. Neurospora vs Ribozyme*

Figure 6: RNase H Assay
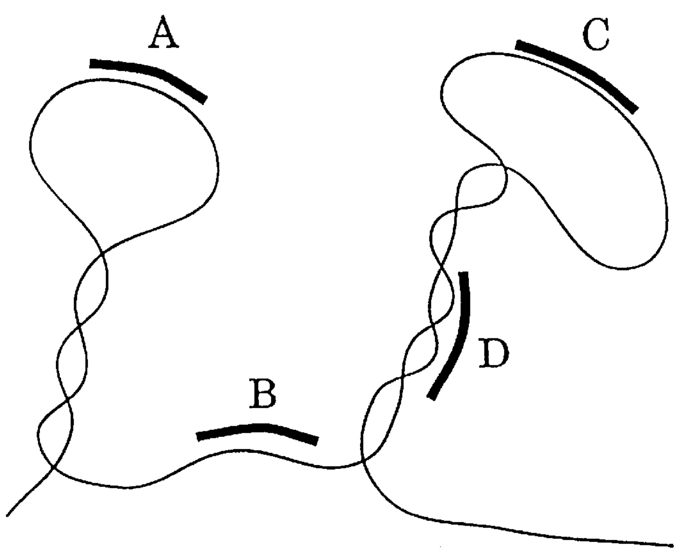
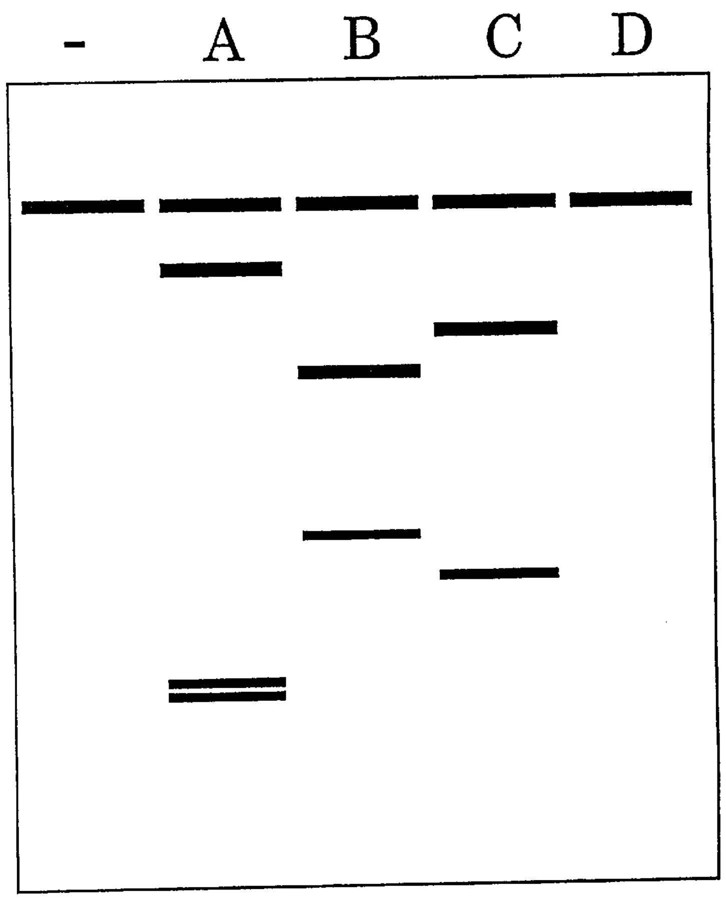
- Body-labeled transcript (not purified)
- DNA oligo (10 nM, 100 nM and 1000 nM)
- RNAse H (0.08 -1.0 u/μl)
- $37^{\circ}C$, 10 min

Figure 9: Specificity of Anti-FLT Ribozyme-Mediated Inhibition of VEGF Binding (Human Microvascular Endothelial Cells)

*Figure 11A1: Hammerhead Ribozymes Targeted Against flt-1 RNA*
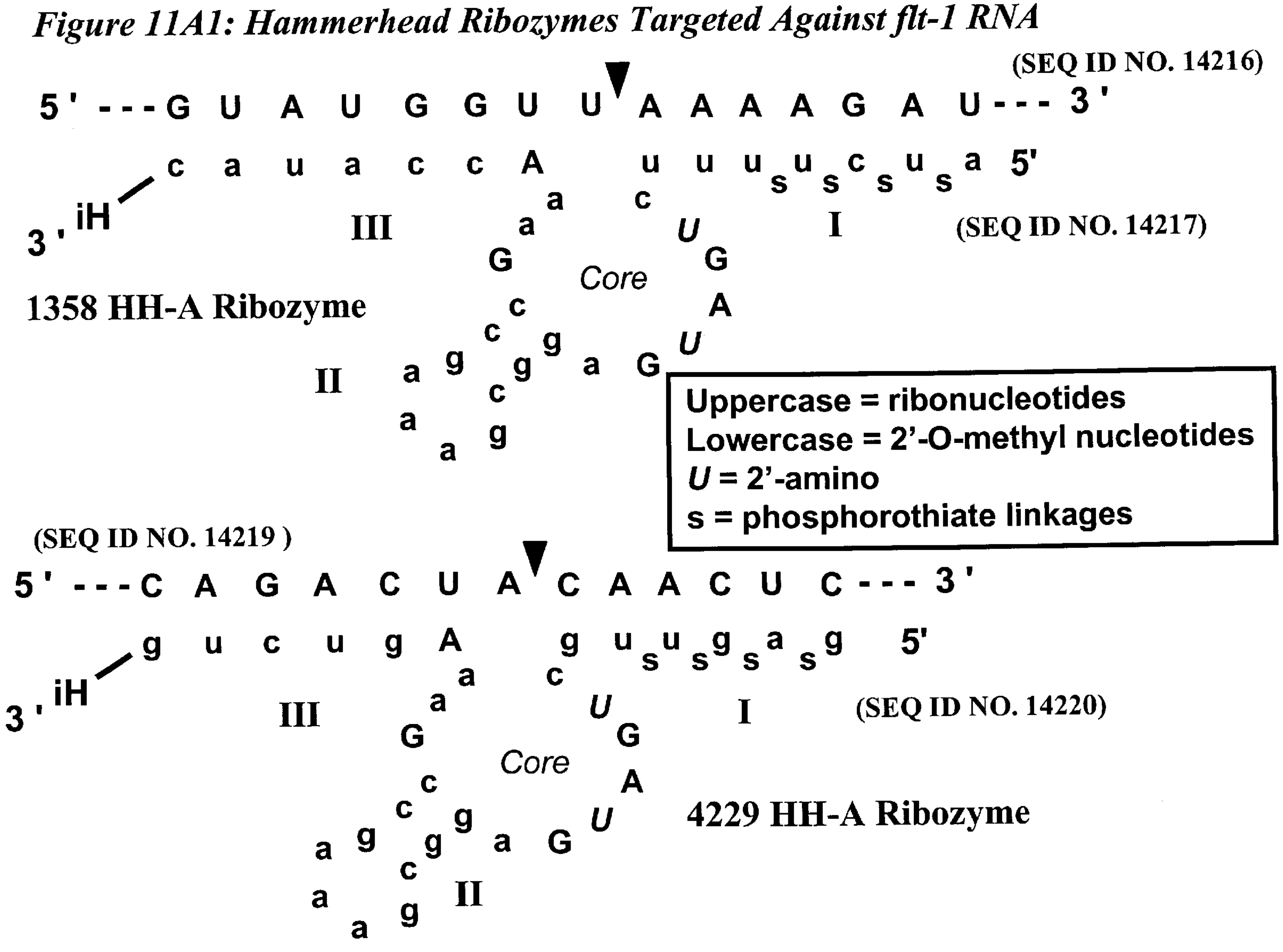

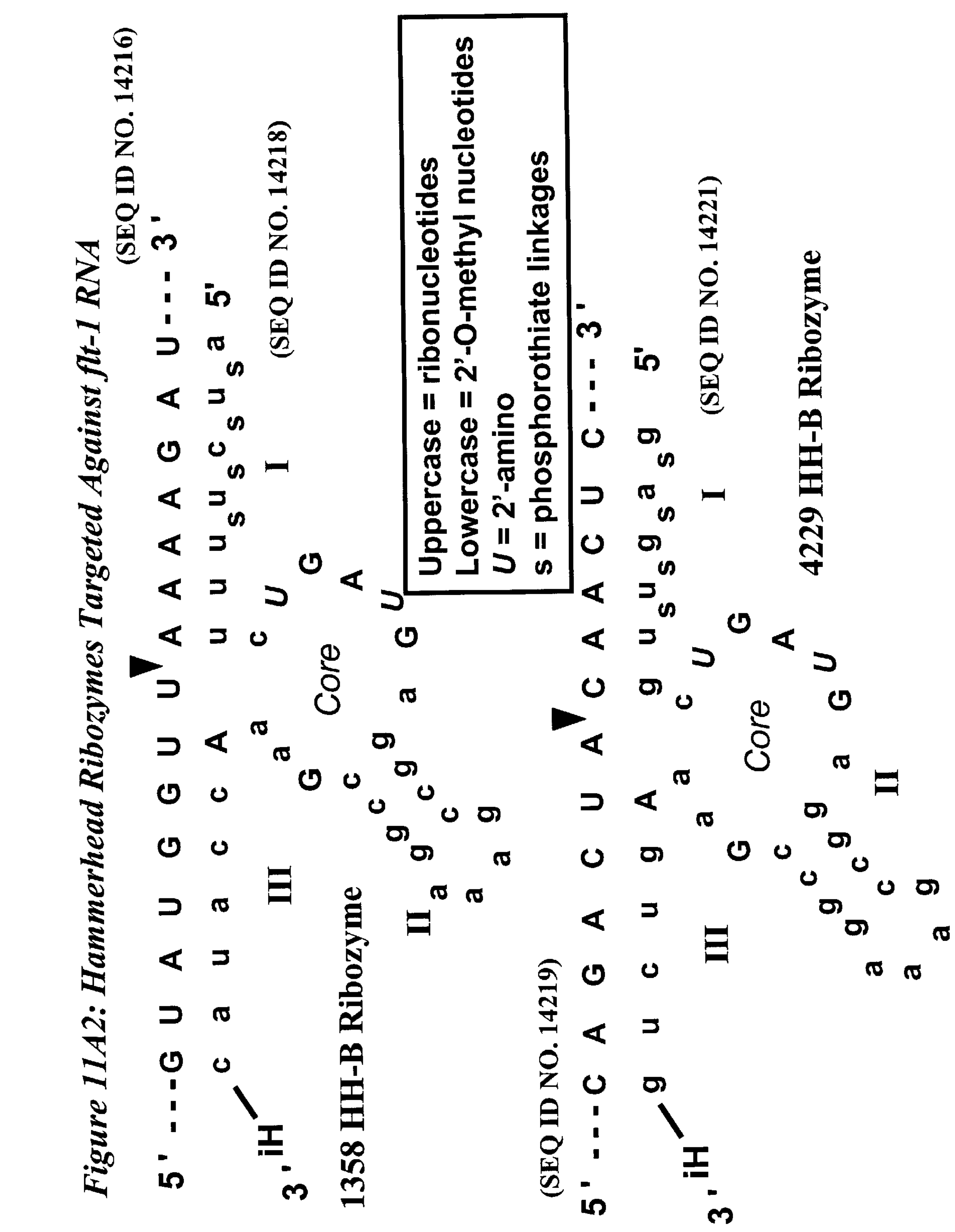

Figure 11A2: Hammerhead Ribozymes Targeted Against flt-1 RNA (SEQ ID NO. 14216)

5'---GUAUGGUU▼AAAAGAU---3'
         c  a u a c c A           u u u$_s$c$_s$u$_s$a 5'    (SEQ ID NO. 14218)
   ³'iH                         a           c   U     I
                          III   G     Core  A
                                 c         G
                             a g g c g a G
                            II   c     c
                                 a   g
                                  a 1358 HH-B Ribozyme Uppercase = ribonucleotides
Lowercase = 2'-O-methyl nucleotides
U = 2'-amino
s = phosphorothioate linkages (SEQ ID NO. 14219)

5'---CAGACUA▼CAACUC---3'
        g u c u g a A            g u$_s$u$_s$g$_s$a$_s$g 5'    (SEQ ID NO. 14221)
   ³'iH                        a          c   U     I
                        III   G     Core  A
                               c         G
                           a g c g a G
                          II   c     c
                               a   g
                                a 4229 HH-B Ribozyme

*Figure 12A1: Hammerhead Ribozymes Targeted Against flt-1 RNA*
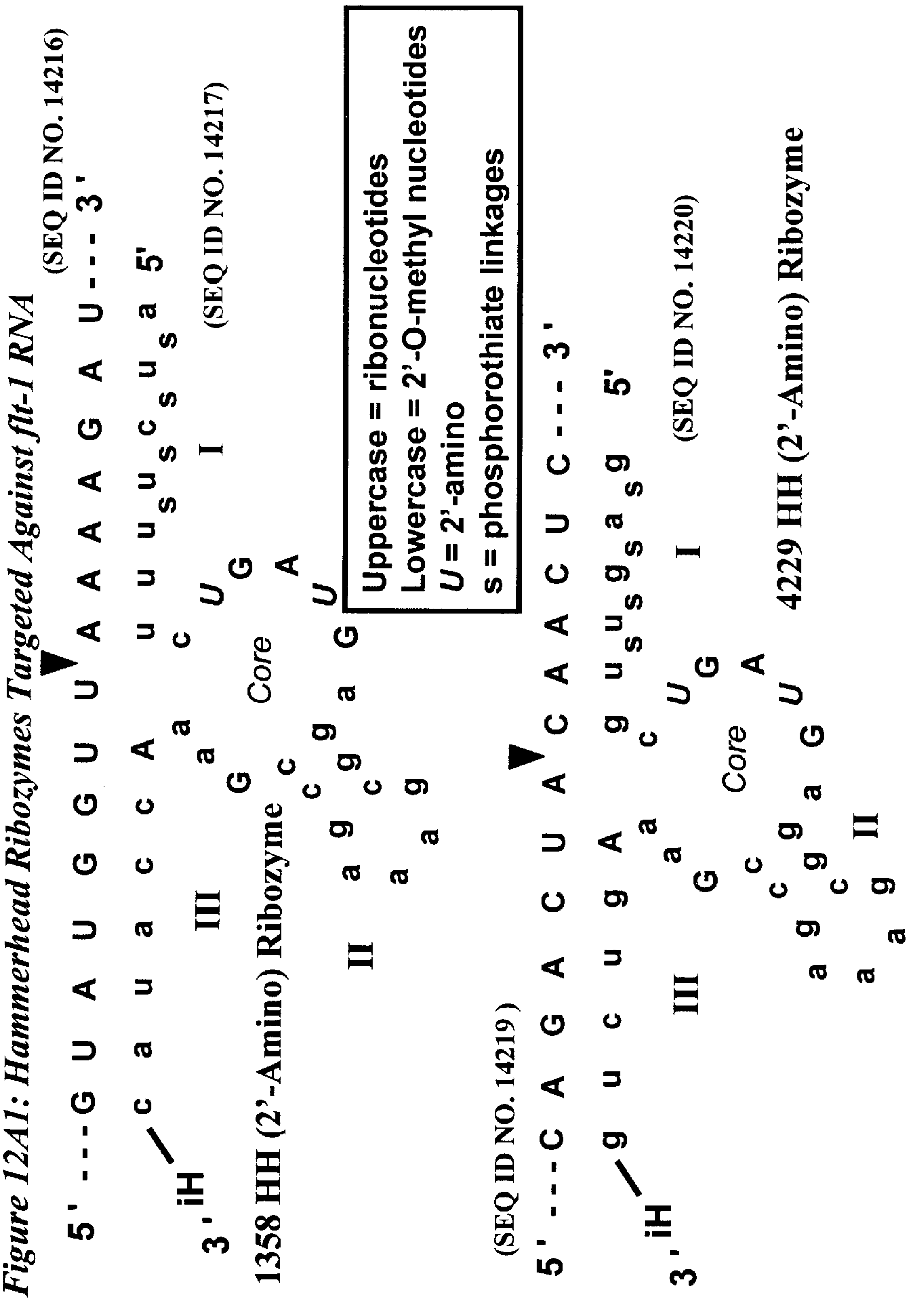

*Figure 12A2: Hammerhead Ribozymes Targeted Against flt-1 RNA*
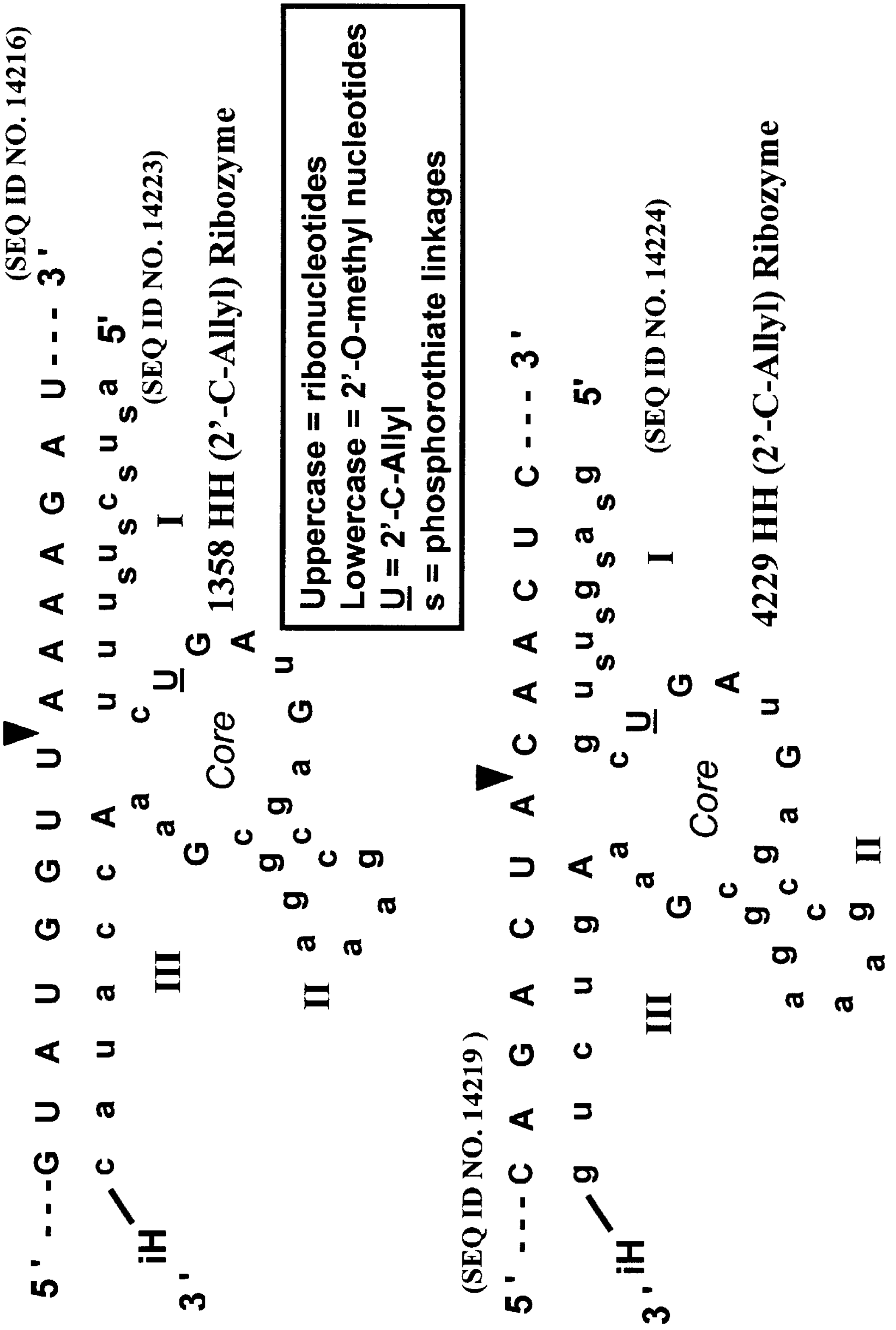

Figure 14: Cleavage of KDR RNA by Hammerhead Ribozymes

Figure 15: Cleavage of KDR RNA by Hammerhead ribozymes

Figure 18: Inhibition of Angiogenesis by Hammerhead Ribozymes *In Vivo*

Figure 19: Ribozyme-mediated inhibition of Cell Proliferation

Figure 20: Target Specificity of Ribozymes

Figure 21: Anti-angiogenic activity of anti-flt ribozyme

Figure 22: Anti-angiogenic activity of anti-kdr ribozyme

Figure 23: Ribozyme-Mediated Inhibition of Tumor Growth

Figure 24: Effect of Ribozyme in Combination with Cytotoxic Agents on Primary Tumor Growth Figure 25: Effect of Ribozyme in Combination with Cytotoxic Agents on Lung Metastases Figure 26 Anti-Flt-1 Ribozyme: ANGIOZYME

METHOD AND REAGENT FOR THE TREATMENT OF DISEASES OR CONDITIONS RELATED TO LEVELS OF VASCULAR ENDOTHELIAL GROWTH FACTOR RECEPTOR

This patent application is a continuation-in-part of Pavco et al., U.S. Ser. No. 08/584,040, filed Jan. 11, 1996, now U.S. Pat. No. 6,346,398 which claims the benefit of Pavco et al., U.S. Ser. No. 60/005,974, filed on Oct. 26, 1995, all of these earlier applications are entitled "Method and Reagent for Treatment of Diseases or Conditions Related To Levels of Vascular Endothelial Growth Factor Receptor". Each of these applications is hereby incorporated by reference herein in it's entirety including the drawings and tables.

The Sequence Listing file named "MBHB00,876-J SequenceListing.txt" (2,998,328 bytes in size) submitted on Compact Disc-Recordable (CD-R) medium ("010813_1449") in compliance with 37 C.F.R. §1.52(e) is incorporated herein by reference.

BACKGROUND OF THE INVENTION

This invention relates to methods and reagents for the treatment of diseases or conditions relating to the levels of expression of vascular endothelial growth factor (VEGF) receptor(s).

The following is a discussion of relevant art, none of which is admitted to be prior art to the present invention.

VEGF, also referred to as vascular permeability factor (VPF) and vasculotropin, is a potent and highly specific mitogen of vascular endothelial cells (for a review see Ferrara, 1993 *Trends Cardiovas. Med.* 3, 244; Neufeld et al., 1994 *Prog. Growth Factor Res.* 5, 89). VEGF induced neovascularization is implicated in various pathological conditions such as tumor angiogenesis, proliferative diabetic retinopathy, hypoxia-induced angiogenesis, rheumatoid arthritis, psoriasis, wound healing and others.

VEGF, an endothelial cell-specific mitogen, is a 34–45 kDa glycoprotein with a wide range of activities that include promotion of angiogenesis, enhancement of vascular-permeability and others. VEGF belongs to the platelet-derived growth factor (PDGF) family of growth factors with approximately 18% homology with the A and B chain of PDGF at the amino acid level. Additionally, VEGF contains the eight conserved cysteine residues common to all growth factors belonging to the PDGF family (Neufeld et al., supra). VEGF protein is believed to exist predominantly as disulfide-linked homodimers; monomers of VEGF have been shown to be inactive (Plouet et al., 1989 *EMBO J.* 8, 3801).

VEGF exerts its influence on vascular endothelial cells by binding to specific high-affinity cell surface receptors. Covalent cross-linking experiments with $^{125}$I-labeled VEGF protein have led to the identification of three high molecular weight complexes of 225, 195 and 175 kDa presumed to be VEGF and VEGF receptor complexes (Vaisman et al., 1990 *J. Biol. Chem.* 265, 19461). Based on these studies VEGF-specific receptors of 180, 150 and 130 kDa molecular mass were predicted. In endothelial cells, receptors of 150 and the 130 kDa have been identified. The VEGF receptors belong to the superfamily of receptor tyrosine kinases (RTKs) characterized by a conserved cytoplasmic catalytic kinase domain and a hydrophylic kinase sequence. The extracellular domains of the VEGF receptors consist of seven immunoglobulin-like domains that are thought to be involved in VEGF binding functions.

The two most abundant and high-affinity receptors of VEGF are flt-1 (fms-like tyrosine kinase) cloned by Shibuya et al., 1990 Oncogene 5, 519 and KDR (kinase-insert-domain-containing receptor) cloned by Terman et al., 1991 Oncogene 6, 1677. The murine homolog of KDR, cloned by Mathews et al., 1991, *Proc. Natl. Acad. Sci., USA*, 88, 9026, shares 85% amino acid homology with KDR and is termed as flk-1 (fetal liver kinase-1). Recently it has been shown that the high-affinity binding of VEGF to its receptors is modulated by cell surface-associated heparin and heparin-like molecules (Gitay-Goren et al., 1992 *J. Biol. Chem.* 267, 6093).

VEGF expression has been associated with several pathological states such as tumor angiogenesis, several forms of blindness, rheumatoid arthritis, psoriasis and others. Following is a brief summary of evidence supporting the involvement of VEGF in various diseases:

1) Tumor angiogenesis: Increased levels of VEGF gene expression have been reported in vascularized and edema-associated brain tumors (Berkman et al., 1993 *J. Clini. Invest.* 91, 153). A more direct demostration of the role of VEGF in tumor angiogenesis was demonstrated by Jim Kim et al., 1993 *Nature* 362,841 wherein, monoclonal antibodies against VEGF were successfully used to inhibit the growth of rhabdomyosarcoma, glioblastoma multiforme cells in nude mice. Similarly, expression of a dominant negative mutated form of the flt-1 VEGF receptor inhibits vascularization induced by human glioblastoma cells in nude mice (Millauer et al., 1994, *Nature* 367, 576).
2) Ocular diseses: Aiello et a/., 1994 *New Engl. J. Med.* 331, 1480, showed that the ocular fluid, of a majority of patients suffering from diabetic retinopathy and other retinal disorders, contains a high concentration of VEGF. Miller et al., 1994 *Am. J. Pathol.* 145, 574, reported elevated levels of VEGF mRNA in patients suffering from retinal ischemia. These observations support a direct role for VEGF in ocular diseases.
3) Psoriasis: Detmar et al. 1994 *J. Exp. Med.* 180, 1141 reported that VEGF and its receptors were over-expressed in psoriatic skin and psoriatic dermal microvessels, suggesting that VEGF plays a significant role in psoriasis.
4) Rheumatoid arthritis: Immunohistochemistry and in situ hybridization studies on tissues from the joints of patients suffering from rheumatoid arthritis show an increased level of VEGF and its receptors (Fava et al., 1994 *J. Exp. Med.* 180, 341). Additionally, Koch et al., 1994 *J. Immunol.* 152, 4149, found that VEGF-specific antibodies were able to significantly reduce the mitogenic activity of synovial tissues from patients suffering from rheumatoid arthritis. These observations support a direct role for VEGF in rheumatoid arthritis.

In addition to the above data on pathological conditions involving excessive angiogenesis, a number of studies have demonstrated that VEGF is both necessary and sufficient for neovascularization. Takashita et al., 1995 *J. Clin. Invest.* 93, 662, demonstrated that a single injection of VEGF augmented collateral vessel development in a rabbit model of ischemia. VEGF also can induce neovascularization when injected into the cornea. Expression of the VEGF gene in CHO cells is sufficient to confer tumorigenic potential to the cells. Kim et al., supra and Millauer et al., supra used monoclonal antibodies against VEGF or a dominant negative form of flk-1 receptor to inhibit tumor-induced neovascularization.

During development, VEGF and its receptors are associated with regions of new vascular growth (Millauer et al., 1993 *Cell* 72, 835; Shalaby et al., 1993 *J. Clin. Invest.* 91, 2235). Furthermore, transgenic mice lacking either of the VEGF receptors are defective in blood vessel formation, in fact these mice do not survive; flk-1 appears to be required for differentiation of endothelial cells, while flt-1 appears to be required at later stages of vessel formation (Shalaby et al., 1995 *Nature* 376, 62; Fung et al., 1995 *Nature* 376, 66). Thus, these receptors must be present to properly signal endothelial cells or their precursors to respond to vascularization-promoting stimuli.

All of the conditions listed above, involve extensive vascularization. This hyper-stimulation of endothelial cells may be alleviated by VEGF antagonists. Thus most of the therapeutic efforts for the above conditions have concentrated on finding inhibitors of the VEGF protein.

Kim et al., 1993 *Nature* 362, 841 have been successful in inhibiting VEGF-induced tumor growth and angiogenesis in nude mice by treating the mice with VEGF-specific monoclonal antibody.

Koch et al., 1994 *J. Immunol.* 152, 4149 showed that the mitogenic activity of microvascular endothelial cells found in rheumatoid arthritis (RA) synovial tissue explants and the chemotactic property of endothelial cells from RA synovial fluid can be neutralized significantly by treatment with VEGF-specific antibodies.

Ullrich et al., International PCT Publication No. WO 94/11499 and Millauer et al., 1994 *Nature* 367, 576 used a soluble form of flk-1 receptor (dominant-negative mutant) to prevent VEGF-mediated tumor angiogenesis in immunodeficient mice.

Kendall and Thomas, International PCT Publication No. WO 94/21679 describe the use of naturally occuring or recombinantly-engineered soluble forms of VEGF receptors to inhibit VEGF activity.

Robinson, International PCT Publication No. WO 95/04142 describes the use of antisense oligonucleotides targeted against VEGF RNA to inhibit VEGF expression. jellinek et al., 1994 *Biochemistry* 33, 10450 describe the use of VEGF-specific high-affinity RNA aptamers to inhibit the binding of VEGF to its receptors.

Rockwell and Goldstein, International PCT Publication No. WO 95/21868, describe the use of anti-VEGF receptor monoclonal antibodies to neutralize the the effect of VEGF on endothelial cells.

SUMMARY OF THE INVENTION

The invention features novel nucleic acid-based techniques [e.g., enzymatic nucleic acid molecules (ribozymes), antisense nucleic acids, 2-5A antisense chimeras, triplex DNA, antisense nucleic acids containing RNA cleaving chemical groups (Cook et al., U.S. Pat. No. 5,359,051)] and methods for their use to down regulate or inhibit the expression of receptors of VEGF (VEGF-R).

In a preferred embodiment, the invention features use of one or more of the nucleic acid-based techniques to inhibit the expression of flt-1 and/or flk-1/KDR receptors.

By "inhibit" it is meant that the activity of VEGF-R or level of mRNAs or equivalent RNAs encoding VEGF-R is reduced below that observed in the absence of the nucleic acid. In one embodiment, inhibition with ribozymes preferably is below that level observed in the presence of an enzymatically inactive or attenuated molecule that is able to bind to the same site on the mRNA, but is unable to cleave that RNA. In another embodiment, inhibition with antisense oligonucleotides is preferably below that level observed in the presence of for example, an oligonucleotide with scrambled sequence or with mismatches. In another embodiment, inhibition of VEGF-R genes with the nucleic acid molecule of the instant invention is greater than in the presence of the nucleic acid molecule than in its absence.

By "enzymatic nucleic acid molecule" it is meant an RNA molecule which has complementarity in a substrate binding region to a specified gene target, and also has an enzymatic activity which is active to specifically cleave target RNA. That is, the enzymatic RNA molecule is able to intermolecularly cleave RNA and thereby inactivate a target RNA molecule. This complementary regions allow sufficient hybridization of the enzymatic RNA molecule to the target RNA and thus permit cleavage. One hundred percent complementarity is preferred, but complementarity as low as 50–75% may also be useful in this invention. The nucleic acids may be modified at the base, sugar, and/or phosphate groups. The term enzymatic nucleic acid is used interchangeably with phrases such as ribozymes, catalytic RNA, enzymatic RNA, catalytic DNA, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The specific enzymatic nucleic acid molecules described in the instant application are not meant to be limiting and those skilled in the art will recognize that all that is important in an enzymatic nucleic acid molecule of this invention is that it have a specific substrate binding site which is complementary to one or more of the target nucleic acid regions, and that it have nucleotide sequences within or surrounding that substrate binding site which impart a nucleic acid cleaving activity to the molecule (Cech et al., U.S. Pat. No. 4,987,071; Cech et al., 1988, JAMA).

By "enzymatic portion" or "catalytic domain" is meant that portion/region of the ribozyme essential for cleavage of a nucleic acid substrate (for example see FIG. 1).

By "substrate binding arm" or "substrate binding domain" is meant that portion/region of a ribozyme which is complementary to (i.e., able to base-pair with) a portion of its substrate. Generally, such complementarity is 100%, but can be less if desired. For example, as few as 10 bases out of 14 may be base-paired. Such arms are shown generally in FIG. 1. That is, these arms contain sequences within a ribozyme which are intended to bring ribozyme and target RNA together through complementary base-pairing interactions. The ribozyme of the invention may have binding arms that are contiguous or non-contiguous and may be of varying lengths. The length of the binding arm(s) are preferably greater than or equal to four nucleotides and of sufficient length to stably interact with the target RNA; specifically 12–100 nucleotides; more specifically 14–24 nucleotides long. If two binding arms are chosen, the design is such that the length of the binding arms are symmetrical (i.e., each of the binding arms is of the same length; e.g., five and five nucleotides, six and six nucleotides or seven and seven nucleotides long) or asymmetrical (i.e., the binding arms are of different length; e.g., six and three nucleotides; three and six nucleotides long; four and five nucleotides long; four and six nucleotides long; four and seven nucleotides long; and the like).

By DNAzyme is meant, an enzymatic nucleic acid molecule lacking a 2'-OH group. In particular embodiments the enzymatic nucleic acid molecule may have an attached linker(s) or other attached or associated groups, moieties, or chains containing one or more nucleotides with 2'-OH groups.

By "sufficient length" is meant an oligonucleotide of greater than or equal to 3 nucleotides.

By "stably interact" is meant, interaction of the oligonucleotides with target nucleic acid (e.g., by forming hydrogen bonds with complementary nucleotides in the target under physiological conditions).

By "equivalent" RNA to VEGF-R is meant to include those naturally occurring RNA molecules having homology (partial or complete) to VEGF-R or encoding for proteins with similar function as VEGF-R in various animals, including human, rodent, primate, rabbit and pig. The equivalent RNA sequence also includes in addition to the coding region, regions such as 5'-untranslated region, 3'-untranslated region, introns, intron-exon junction and the like.

By "homology" is meant the nucleotide sequence of two or more nucleic acid molecules is partially or completely identical.

By "antisense nucleic acid" it is meant a non-enzymatic nucleic acid molecule that binds to target RNA by means of RNA-RNA or RNA-DNA or RNA-PNA (protein nucleic acid; Egholm et al., 1993 *Nature* 365, 566) interactions and alters the activity of the target RNA (for a review see Stein and Cheng, 1993 *Science* 261, 1004). Typically, antisense molecules will be complementary to a target sequence along a single contiguous sequence of the antisense molecule. However, in certain embodiments, an antisense molecule may bind to substrate such that the substrate molecule forms a loop, and/or an antisense molecule may bind such that the antisense molecule forms a loop. Thus, the antisense molecule may be complementary to two (or even more) non-contiguous substrate sequences or two (or even more) non-contiguous sequence portions of an antisense molecule may be complementary to a target sequence or both. 237/198

By "2-5A antisense chimera" it is meant, an antisense oligonucleotide containing a 5' phosphorylated 2'-5'-linked adenylate residues. These chimeras bind to target RNA in a sequence-specific manner and activate a cellular 2-5A-dependent ribonuclease which, in turn, cleaves the target RNA (Torrence et al., 1993 *Proc. Natl. Acad. Sci. USA* 90, 1300).

By "triplex DNA" it is meant an oligonucleotide that can bind to a double-stranded DNA in a sequence-specific manner to form a triple-strand helix. Formation of such triple helix structure has been shown to inhibit transcription of the targeted gene (Duval-Valentin et al., 1992 *Proc. Natl. Acad. Sci. USA* 89, 504).

By "gene" it is meant a nucleic acid that encodes an RNA.

By "complementarity" is meant that a nucleic acid can form hydrogen bond(s) with another RNA sequence by either traditional Watson-Crick or other non-traditional types. In reference to the nucleic molecules of the present invention, the binding free energy for a nucleic acid molecule with its target or complementary sequence is sufficient to allow the relevant function of the nucleic acid to proceed, e.g., ribozyme cleavage, antisense or triple helix inhibition. Determination of binding free energies for nucleic acid molecules is well known in the art (see, e.g., Turner et al., 1987, CSH Symp. Quant. Biol. LII pp.123–133; Frier et al., 1986, Proc. Nat. Acad. Sci. USA 83:9373–9377; Turner et al., 1987, J. Am. Chem. Soc. 109:3783–3785. A percent complementarity indicates the percentage of contiguous residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

Seven basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets. Thus, a single ribozyme molecule is able to cleave many molecules of target RNA. In addition, the ribozyme is a highly specific inhibitor of gene expression, with the specificity of inhibition depending not only on the base-pairing mechanism of binding to the target RNA, but also on the mechanism of target RNA cleavage. Single mismatches, or base-substitutions, near the site of cleavage can completely eliminate catalytic activity of a ribozyme.

Ribozymes that cleave the specified sites in VEGF-R mRNAs represent a novel therapeutic approach to treat tumor angiogenesis, ocular diseases, rhuematoid arthritis, psoriasis and others. Applicant indicates that ribozymes are able to inhibit the activity of VEGF-R (specifically flt-1 and flk-1/KDR) and that the catalytic activity of the ribozymes is required for their inhibitory effect. Those of ordinary skill in the art will find that it is clear from the examples described that other ribozymes that cleave VEGF-R mRNAs may be readily designed and are within the invention.

In one of the preferred embodiments of the inventions described herein, the enzymatic nucleic acid molecule is formed in a hammerhead or hairpin motif, but may also be formed in the motif of a hepatitis delta virus, group I intron, group II intron or RNase P RNA (in association with an RNA guide sequence), Neurospora VS RNA, DNAzymes, NCH cleaving motifs, or G-cleavers. Examples of such hammerhead motifs are described by Dreyfus, supra, Rossi et al., 1992, *AIDS Research and Human Retroviruses* 8, 183; of hairpin motifs by Hampel et al., EP0360257, Hampel and Tritz, 1989 *Biochemistry* 28, 4929, Feldstein et al., 1989, *Gene* 82, 53, Haseloff and Gerlach, 1989, Gene, *82, 43*, and Hampel et al., 1990 *Nucleic Acids Res.* 18, 299; Chowrira & McSwiggen, U.S. Pat. No. 5,631,359; of the hepatitis delta virus motif is described by Perrotta and Been, 1992 *Biochemistry* 31, 16; of the RNase P motif by Guerrier-Takada et al., 1983 *Cell* 35, 849; Forster and Altman, 1990, *Science* 249, 783; Li and Altman, 1996, *Nucleic Acids Res.* 24, 835; Neunospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799; Guo and Collins, 1995, *EMBO. J.* 14, 363); Group II introns are described by Griffin et al., 1995, *Chem. Biol.* 2, 761; Michels and Pyle, 1995, *Biochemistry* 34, 2965; Pyle et al., International PCT Publication No. WO 96/22689; of the Group I intron by Cech et al., U.S. Pat. No. 4,987,071 and of DNAzymes by Usman et al., International PCT Publication No. WO 95/11304; Chartrand et al., 1995, *NAR* 23, 4092; Breaker et al., 1995, Chem. Bio. 2, 655; Santoro et al., 1997, *PNAS* 94, 4262. NCH cleaving motifs are described in Ludwig & Sproat, International PCT Publication No. WO 98/58058; and G-cleavers are described in kore et al., 1998, *Nucleic Acids Research* 26, 4116A4120 and Eckstein et al., International PCT Publication No. WO 99/16871. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule (Cech et al., U.S. Pat. No. 4,987,071).

In preferred embodiments of the present invention, a nucleic acid molecule, e.g., an antisense molecule, a triplex DNA, or a ribozyme, is 13 to 100 nucleotides in length, e.g., in specific embodiments 35, 36, 37, or 38 nucleotides in length (e.g., for particular ribozymes). In particular embodiments, the nucleic acid molecule is 15-100, 17-100, 20-100, 21-100, 23-100, 25-100, 27-100, 30-100, 32-100, 35-100, 40-100, 50-100, 60-100, 70-100, or 80-100 nucleotides in length. Instead of 100 nucleotides being the upper limit on the length ranges specified above, the upper limit of the length range can be, for example, 30, 40, 50, 60, 70, or 80 nucleotides. Thus, for any of the length ranges, the length range for particular embodiments has lower limit as specified, with an upper limit as specified which is greater than the lower limit. For example, in a particular embodiment, the length range can be 35–50 nucleotides in length. All such ranges are expressly included. Also in particular embodiments, a nucleic acid molecule can have a length which is any of the lengths specified above, for example, 21 nucleotides in length.

In a preferred embodiment the invention provides a method for producing a class of enzymatic cleaving agents which exhibit a high degree of specificity for the RNA of a desired target. The enzymatic nucleic acid molecule is preferably targeted to a highly conserved sequence region of target mRNAs encoding VEGF-R proteins (specifically flt-1 and flk-1/KDR) such that specific treatment of a disease or condition can be provided with either one or several enzymatic nucleic acids. Such enzymatic nucleic acid molecules can be delivered exogenously to specific tissue or cellular targets as required. Alternatively, the ribozymes can be expressed from DNA and/or RNA vectors that are delivered to specific cells.

By "highly conserved sequence region" is meant a nucleotide sequence of one or more regions in a nucleic acid molecule does not vary significantly from one generation to the other or from one biological system to the other.

Synthesis of nucleic acids greater than 100 nucleotides in length is difficult using automated methods, and the therapeutic cost of such molecules is prohibitive. In this invention, small nucleic acid motifs (e.g., antisense oligonucleotides, hammerhead or the hairpin ribozymes) are used for exogenous delivery. The simple structure of these molecules increases the ability of the nucleic acid to invade targeted regions of the mRNA structure. However, these nucleic acid molecules can also be expressed within cells from eukaryotic promoters (e.g., Izant and Weintraub, 1985 *Science* 229, 345; McGarry and Lindquist, 1986 *Proc. Natl. Acad. Sci. USA* 83, 399; SullengerScanlon et al, 1991, *Proc. Natl. Acad. Sci. USA*, 88, 10591–5; Kashani-Sabet et al., 1992 *Antisense Res. Dev.*, 2, 3–15; Dropulic et al., 1992 *J. Virol*, 66, 1432–41; Weerasinghe et al., 1991 *J. Virol*, 65, 5531–4; Ojwang et al., 1992 *Proc. Natl. Acad. Sci. USA* 89, 10802–6; Chen et al., 1992 *Nucleic Acids Res*., 20, 4581–9; Sarver et al., 1990 Science 247, 1222–1225; Thompson et al., 1995 *Nucleic Acids Res*. 23, 2259). Those skilled in the art realize that any nucleic acid can be expressed in eukaryotic cells from the appropriate DNA/RNA vector. The activity of such nucleic acids can be augmented by their release from the primary transcript by a ribozyme (Draper et al., PCT WO93/23569, and Sullivan et al., PCT WO94/02595, both hereby incorporated in their totality by reference herein; Ohkawa et al., 1992 *Nucleic Acids Symp. Ser*., 27, 15–6; Taira et al., 1991, *Nucleic Acids Res*., 19, 5125–30; Ventura et al., 1993 *Nucleic Acids Res*., 21, 3249–55; Chowrira et al., 1994 *J. Biol. Chem*. 269, 25856).

Such nucleic acid molecules are useful for the prevention of the diseases and conditions including cancer, diabetic retinopathy, macular degeneration, neovascular glaucoma, myopic degeneration, arthritis, psoriasis, verruca vulgaris, angiofibroma of tuberous sclerosis, pot-wine stains, Sturge Weber syndrome, Kippel-Trenaunay-Weber syndrome, Osler-Weber-Rendu syndrome and any other diseases or conditions that are related to the levels of VEGF-R (specifically flt-1 and flk-1/KDR) in a cell or tissue.

By "related" is meant that the reduction of VEGF-R (specifically flt-1 and flk-1/KDR) RNA levels and thus reduction in the level of the respective protein will relieve, to some extent, the symptoms of the disease or condition.

Ribozymes are added directly, or can be complexed with cationic lipids, packaged within liposomes, or otherwise delivered to target cells or tissues. The nucleic acid or nucleic acid. complexes can be locally administered to relevant tissues ex vivo, or in vivo through injection, infusion pump or stent, with or without their incorporation in biopolymers. In preferred embodiments, the ribozymes have binding arms which are complementary to the sequences in Tables II to IX. Examples of such ribozymes also are shown in Tables II to XVII. Examples of such ribozymes consist essentially of sequences defined in these Tables.

In yet another embodiment, the invention features antisense nucleic acid molecules and 2-5A chimera including sequences complementary to the target sequences shown in tables II to XVII. Such nucleic acid molecules can include sequences as shown for the binding arms of the ribozymes in Tables II to XVII. Similarly, triplex molecules can be provided targeted to the corresponding DNA target regions, and containing the DNA equivalent of a target sequence or a sequence complementary to the specified target (substrate) sequence. Typically, antisense molecules will be complementary to a target sequence along a single contiguous sequence of the antisense molecule. However, in certain embodiments, an antisense molecule may bind to substrate such that the substrate molecule forms a loop, and/or an antisense molecule may bind such that the antisense molecule forms a loop. Thus, the antisense molecule may be complementary to two (or even more) non-contiguous substrate sequences or two (or even more) non-contiguous sequence portions of an antisense molecule may be complementary to a target sequence or both.

By "consists essentially of" is meant that the active ribozyme contains an enzymatic center or core equivalent to those in the examples, and binding arms able to bind mRNA such that cleavage at the target site occurs. Other sequences may be present which do not interfere with such cleavage. Thus, a core region may, for example, include on or more loop or stem-loop structures which do not prevent enzymatic activity. Thus, the underlined regions in the sequences in Tables II, IV, VI, VIII, XIV, and XVI can be such a loop or stem-loop, and can be represented generally as sequence "X". For example, a core sequence can be a conserved sequence, such as 5'-CUGAUGAG-3' and 5'-CGAA-3' connected by "X", where X is 5'-GCCGUUAGGC-3' (SEQ ID NO 14225), or any other Stem II region known in the art.

In another aspect of the invention, ribozymes that cleave target RNA molecules and inhibit VEGF-R (specifically flt-1 and flk-1/KDR) activity are expressed from transcription units inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described above, and persist in target cells. Alternatively, viral vectors may be used that provide for transient expression of ribozymes. Such vectors might be repeatedly administered as necessary. Once expressed, the ribozymes cleave the target mRNA. Delivery of ribozyme expressing vectors could be systemic, such as by intravenous or intramuscular administration, by administration to target cells ex-planted from the patient followed by reintroduction into the patient, or by any other means that would allow for introduction into the desired target cell.

By "vectors" is meant any nucleic acid- and/or viral-based technique used to deliver a desired nucleic acid.

By "patient" is meant an organism which is a donor or recipient of explanted cells or the cells themselves. "Patient" also refers to an organism to which the nucleic acid molecules of the invention can be administered. Preferably, a patient is a mammal or mammalian cells. More preferably, a patient is a human or human cells.

The nucleic acid molecules of the instant invention, individually, or in combination or in conjunction with other drugs, can be used to treat diseases or conditions discussed above. For example, to treat a disease or condition associated with VEGF-R, the patient may be treated, or other appropriate cells may be treated, as is evident to those skilled in the art, individually or in combination with one or more drugs under conditions suitable for the treatment.

In a further embodiment, the described molecules, such as antisene or ribozymes can be used in combination with other known treatments to treat conditions or diseases discussed above. For example, the described molecules could be used in combination with one or more known therapeutic agents to treat cancer.

In another preferred embodiment, the invention features nucleic acid-based techniques (e.g., enzymatic nucleic acid molecules (ribozymes), antisense nucleic acids, 2-5A antisense chimeras, triplex DNA, antisense nucleic acids containing RNA cleaving chemical groups) and methods for their use to down regulate or inhibit the expression of genes (e.g., flt-1 and kdr) capable of inducing angiogenesis.

In another preferred embodiment, the invention features nucleic acid-based techniques (e.g., enzymatic nucleic acid molecules (ribozymes), antisense nucleic acids, 2-5A antisense chimeras, triplex DNA, antisense nucleic acids containing RNA cleaving chemical groups) and methods for their use to down regulate or inhibit the expression of VEGF receptor.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Other features and advantages of the invention will be apparent from the following description of the preferred embodiments thereof, and from the claims.

DESCRIPTION OF THE PREFERRED EMBODIMENTS

First the drawings will be described briefly.

DRAWINGS

FIG. 1 is a diagrammatic representation of the hammerhead ribozyme domain known in the art. Stem II can be ≧2 base-pair long.

FIGS. 2*a*–2*d* is a diagrammatic representation of the hammerhead ribozyme domain known in the art; FIG. 2*b* is a diagrammatic representation of the hammerhead ribozyme as divided by Uhlenbeck (1987, *Nature,* 327, 596–600) into a substrate and enzyme portion; FIG. 2*c* is a similar diagram showing the hammerhead divided by Haseloff and Gerlach (1988, *Nature*, 334, 585–591) into two portions; and FIG. 2*d* is a similar diagram showing the hammerhead divided by Jeffries and Symons (1989, *Nucl. Acids. Res.*, 17, 1371–1371) into two portions.

FIG. 3 is a diagrammatic representation of the general structure of a hairpin ribozyme. Helix 2 (H2) is provided with at least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is ≧1 base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is ≧2 bases. The connecting loop can also be replaced with a non-nucleotide linker molecule. H refers to bases A, U, or C. Y refers to pyrimidine bases. "__" refers to a covalent bond.

FIG. 4 is a representation of the general structure of the hepatitis delta virus ribozyme domain known in the art.

FIG. 5 is a representation of the general structure of the VS RNA ribozyme domain.

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

Figure 7:
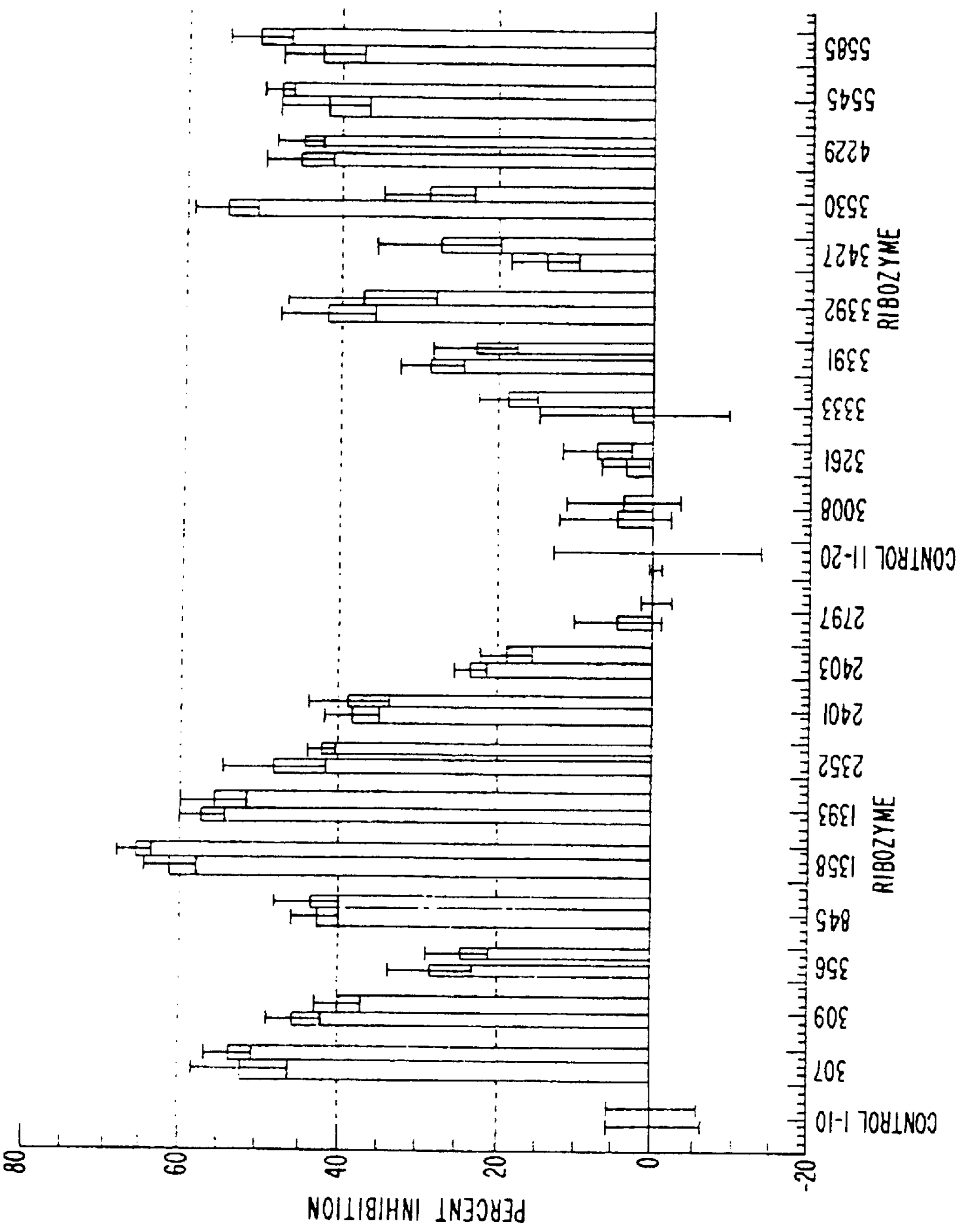

FIG. 7 shows the effect of hammerhead ribozymes targeted against flt-1 receptor on the binding of VEGF to the surface of human microvascular endothelial cells. Sequences of the ribozymes used are shown in Table II; the length of stem 11 region is 3 bp. The hammerhead ribozymes were chemically modified such that the ribozyme consists of ribose residues at five positions (see FIG. 11); U4 and U7 positions contain 2'-NH2 modifications, the remaining nucleotide positions contain 2'-O-methyl substitutions; four nucleotides at the 5' terminus contains phosphorothioate substitutions. Additionally, the 3' end of the ribozyme contains a 3'-3' linked inverted abasic deoxyribose. The results of two separate experiments are shown as separate bars for each set. Each bar represents the average of triplicate samples. The standard deviation is shown with error bars. For the flt-1 data, 500 nM ribozyme (3:1 charge ratio with LipofectAMINE®) was used. Control 1–10 is the control for ribozymes 307–2797, control 11–20 is the control for ribozymes 3008–5585. The Control 1–10 and Control 11–20 represent the treatment of cells with LipofectAMINE® alone without any ribozymes.

Figure 8:
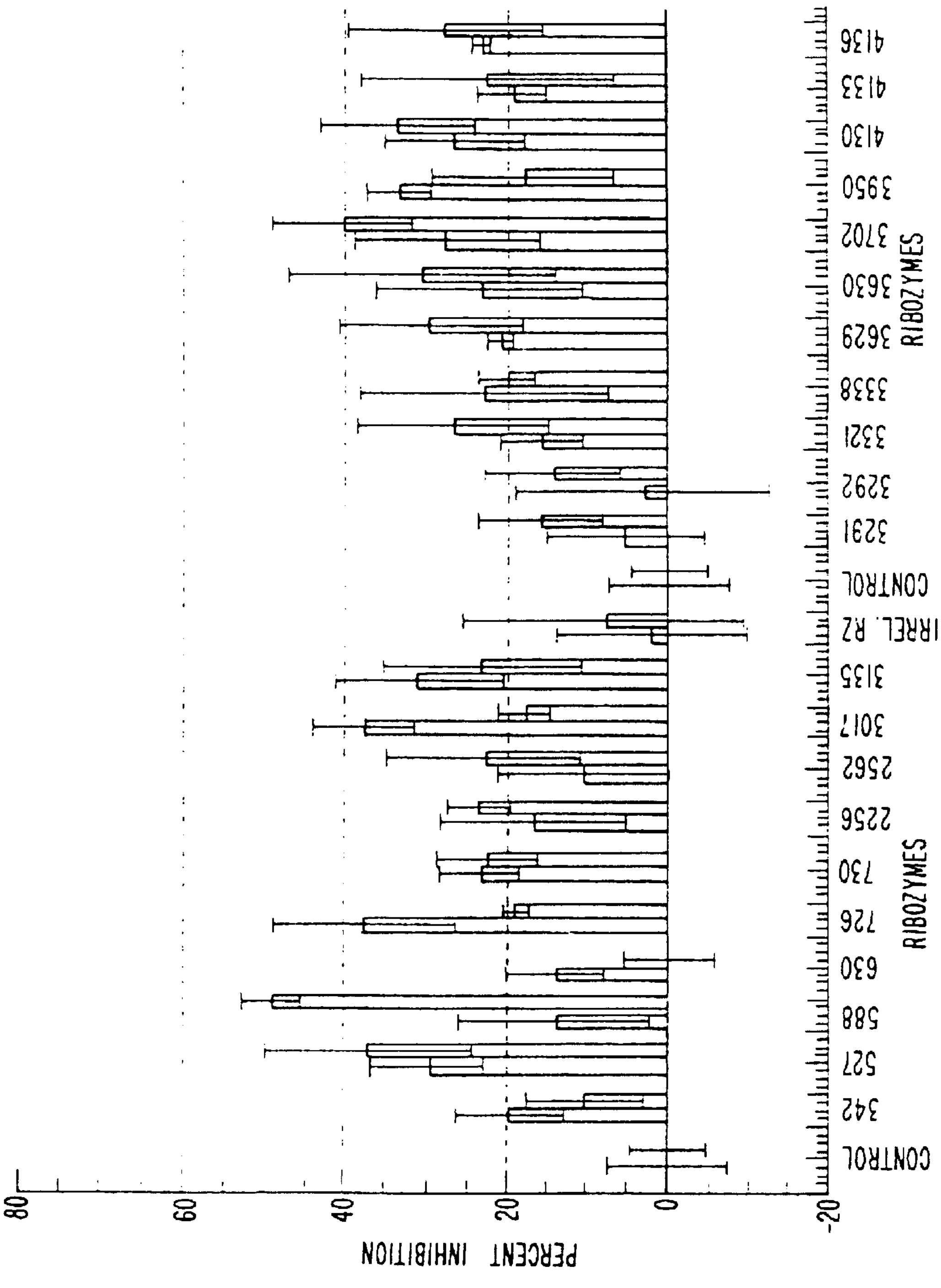

FIG. 8 shows the effect of hammerhead ribozymes targeted against KDR receptor on the binding of VEGF to KDR on the surface of human microvascular endothelial cells. Sequences of the ribozymes used are shown in Table IV; the length of stem II region is 3 bp. The hammerhead ribozymes were chemically modified such that the ribozyme consists of ribose residues at five positions (see FIG. 11); U4 and U7 positions contain 2'-$NH_2$ modifications, the remaining nucleotide positions contain 2'-O-methyl substitutions; four nucleotides at the 5' terminus contains phosphorothioate substitutions. Additionally, the 3' end of the ribozyme contains a 3'-3' linked inverted abasic deoxyribose. The Control 1–10 and Control 11–20 represent the treatment of cells with LipofectAMINE ® alone without any ribozymes. Irrel. RZ, is a control experiment wherein the cells are treated with a non-KDR-targeted ribozyme complexed with Lipofectamine®. 200 nM ribozyme (3:1 charge ratio with LipofectAMINE®) was used. In addition to the KDR-targeted ribozymes, the effect on VEGF binding of a ribozyme targeted to an irrelevant mRNA (irrel. RZ) is also shown. Because the affinity of KDR for VEGF is about 10-fold lower than the affinity of flt-1 for VEGF, a higher concentration of VEGF was used in the binding assay.

Figure 9:
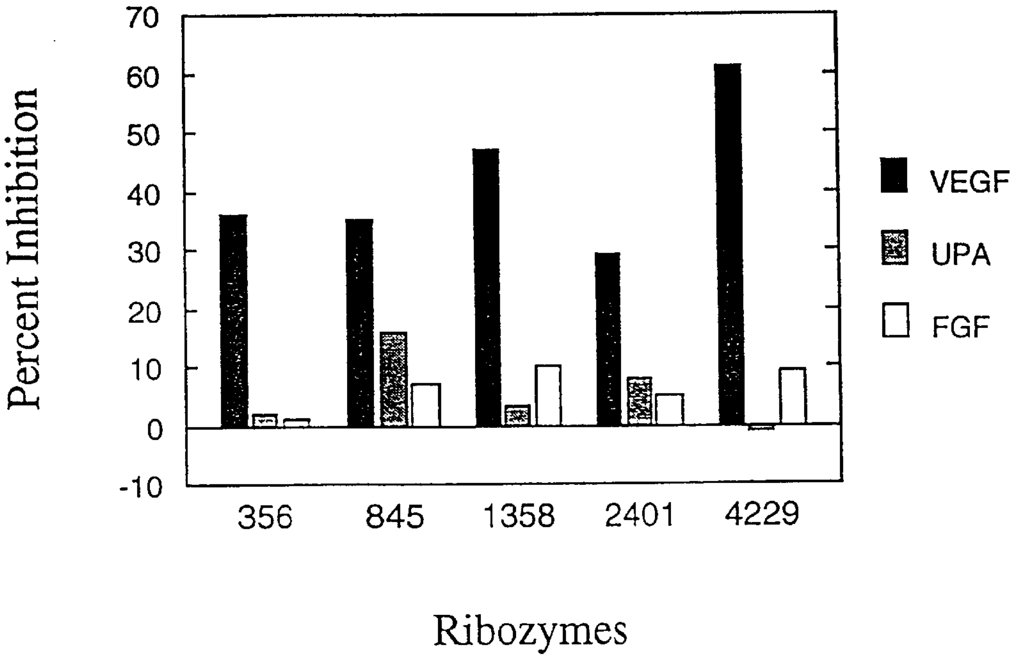

FIG. 9 shows the specificity of hammerhead ribozymes targeted against flt-1 receptor. Inhibition of the binding of VEGF, urokinase plasminogen activator (UPA) and fibroblast growth factor (FGF) to their corresponding receptors as a function of anti-FLT ribozymes is shown. The sequence and description of the ribozymes used are as described under FIG. 7 above. The average of triplicate samples is given; percent inhibition as calculated below.

Figure 10:
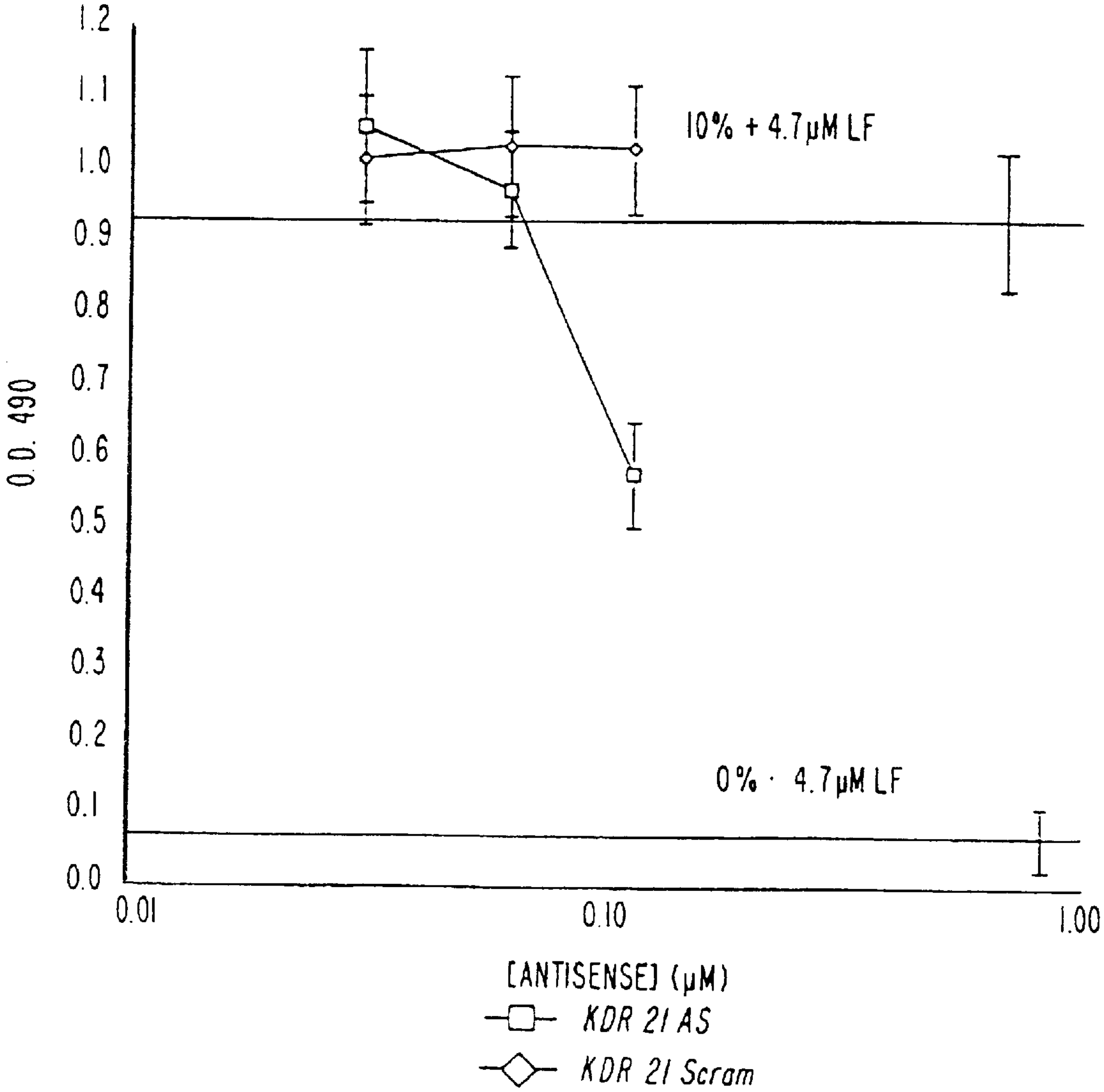

FIG. 10 shows the inhibition of the proliferation of Human aortic endothelial cells (HAEC) mediated by phosphorothioate antisense oligodeoxynucleotides targeted against human KDR receptor RNA. Cell proliferation (O.D. 490) as a function of antisense oligodeoxynucleotide concentration is shown. KDR 21AS represents a 21 nt phosphorothioate antisense oligodeoxynucleotide targeted against KDR RNA. KDR 21 Scram represents a 21 nt phosphorothioate oligodeoxynucleotide having a scrambled sequence. LF represents the lipid carrier Lipofectin.

Figure 11B:
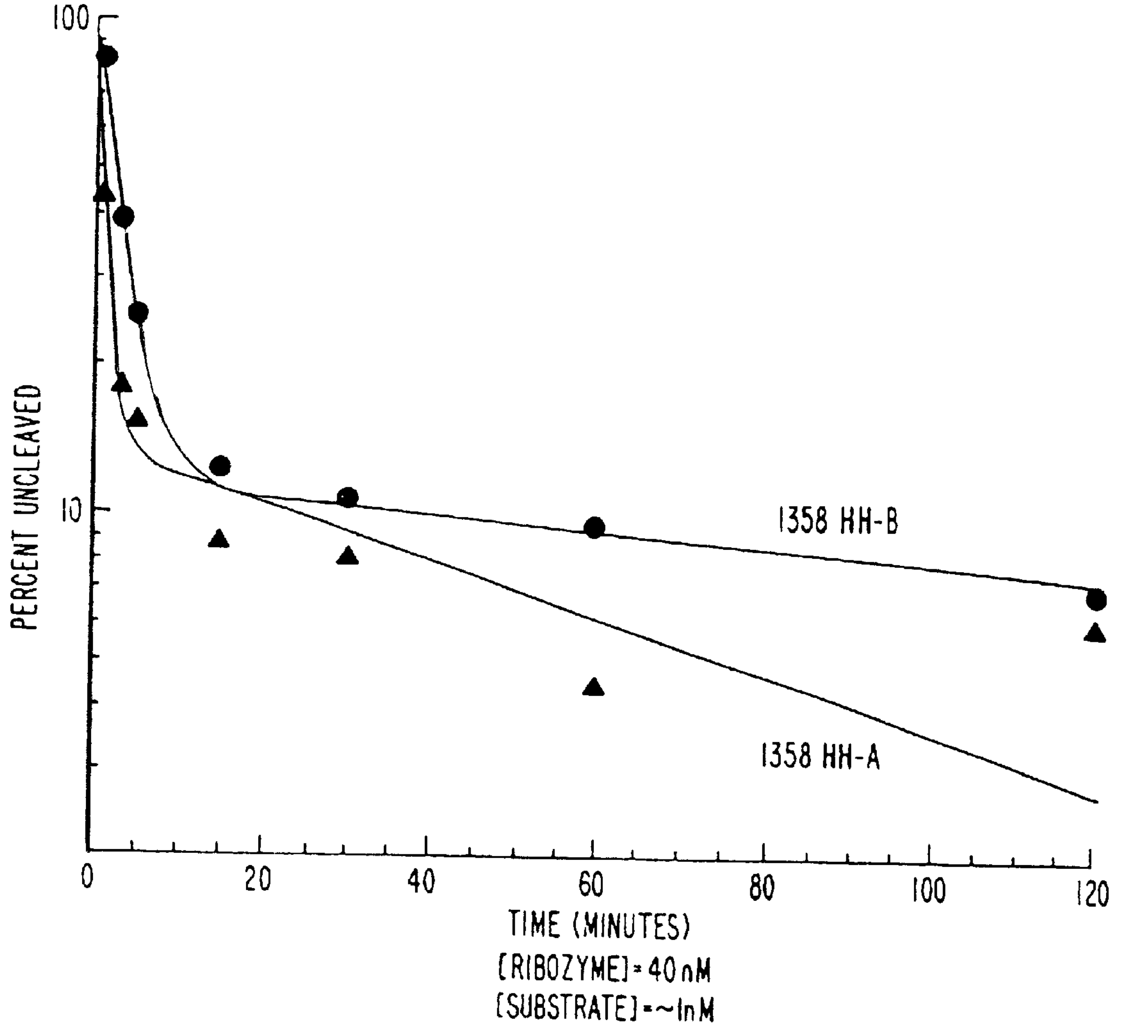
Figure 11C:
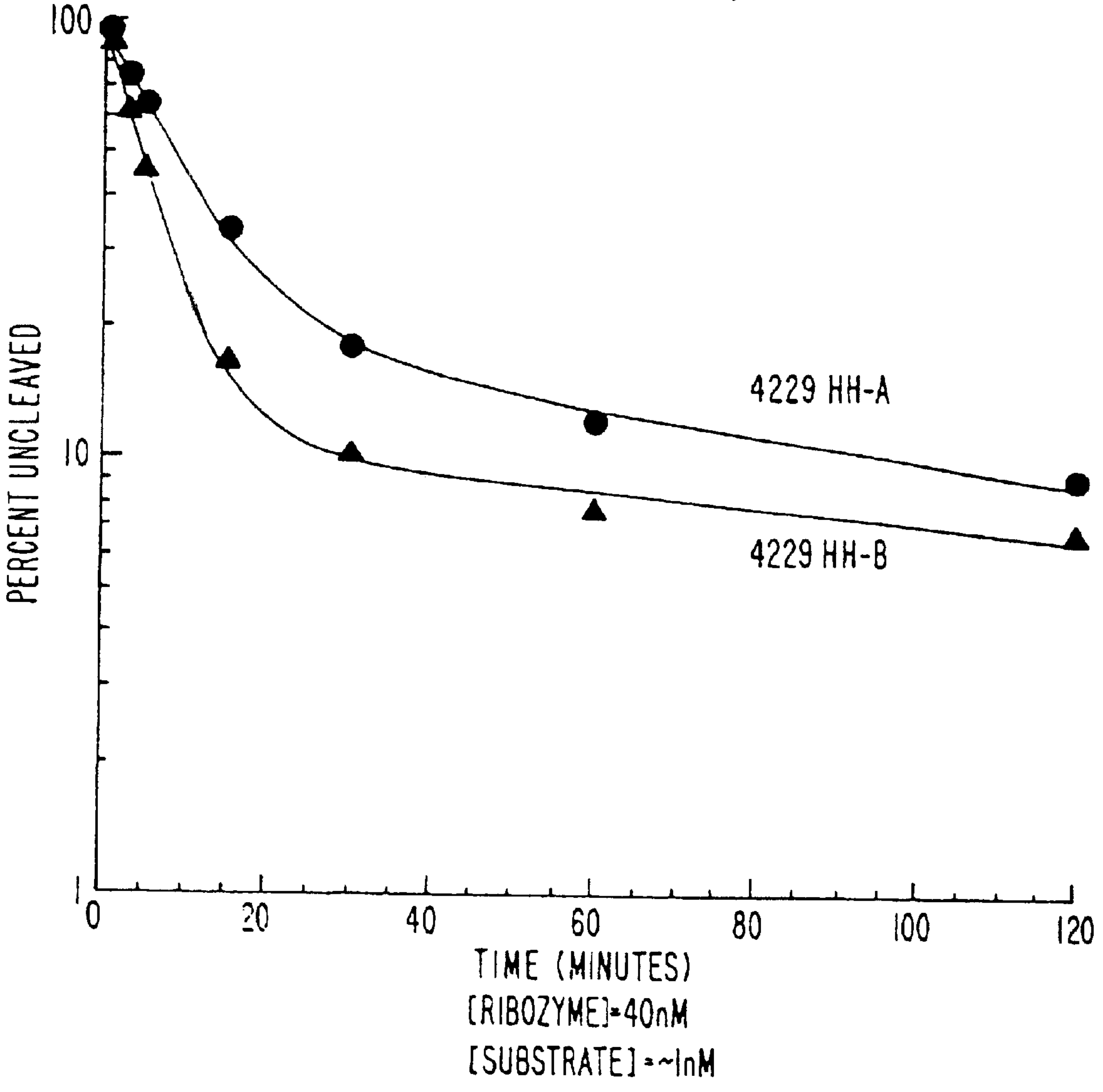

FIGS. 11A–11C show in vitro cleavage of flt-1 RNA by hammerhead ribozymes. 11A1–11A2 diagrammatic representation of hammerhead ribozymes targeted against flt-1 RNA. The hammerhead (HH) ribozymes were chemically modified such that the ribozyme consists of ribose residues at five positions; U4 and U7 positions contain 2'-$NH_2$ modifications, the remaining nucleotide positions contain 2'-O-methyl substitutions; four nucleotides at the 5' terminus contains phosphorothioate substitutions. Additionally, the 3' end of the ribozyme contains a 3'-3' linked inverted abasic deoxyribose (designated as 3'-iH). 1358 HH-A and 4229 HH-A contain 3 base-paired stem 11 region. 1358 HH-B and 4229 HH-B contain 4 base-paired stem 11 region. 11B and 11C, shows in vitro cleavage kinetics of HH ribozymes targeted against sites 1358 and 4229 within the flt-1 RNA.

FIGS. 12A1–12B show inhibition of human microvascular endothelial cell proliferation mediated by anti-flt-1 hammerhead ribozymes. 12A1–12A2 Diagrammatic representation of hammerhead (HH) ribozymes targeted against sites 1358 and 4229 within the flt-1 RNA. 11B Graphical representation of the inhibition of cell proliferation mediated by 1358HH and 4229HH ribozymes.

Figure 13:
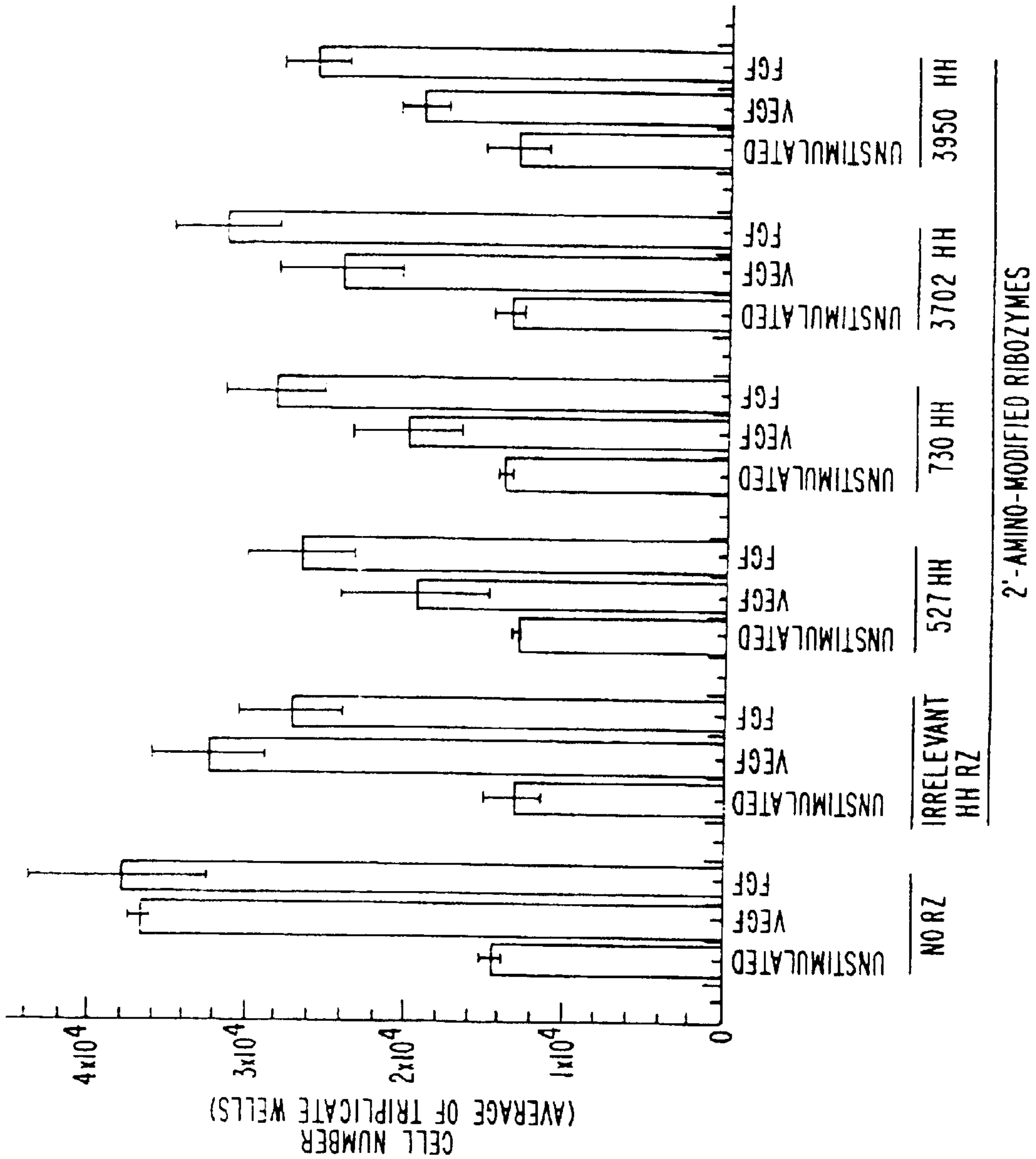

FIG. 13 shows inhibition of human microvascular endothelial cell proliferation mediated by anti-KDR hammerhead ribozymes. The figure is a graphical representation of the inhibition of cell proliferation mediated by hammerhead ribozymes targeted against sites 527, 730, 3702 and 3950 within the KDR RNA. Irrelevant. HH RZ is a hammerhead ribozyme targeted to an irrelevant target. All of these ribozymes, including the Irrelevant HH RZ, were chemically modified such that the ribozyme consists of ribose residues at five positions; U4 and U7 positions contain 2'-$NH_2$ modifications, the remaining nucleotide positions contain 2'-O-methyl substitutions; four nucleotides at the 5' termini contain phosphorothioate substitutions. Additionally, the 3' end of the ribozyme contains a 3'-3' linked inverted abasic deoxyribose (3'-iH).

Figure 14:
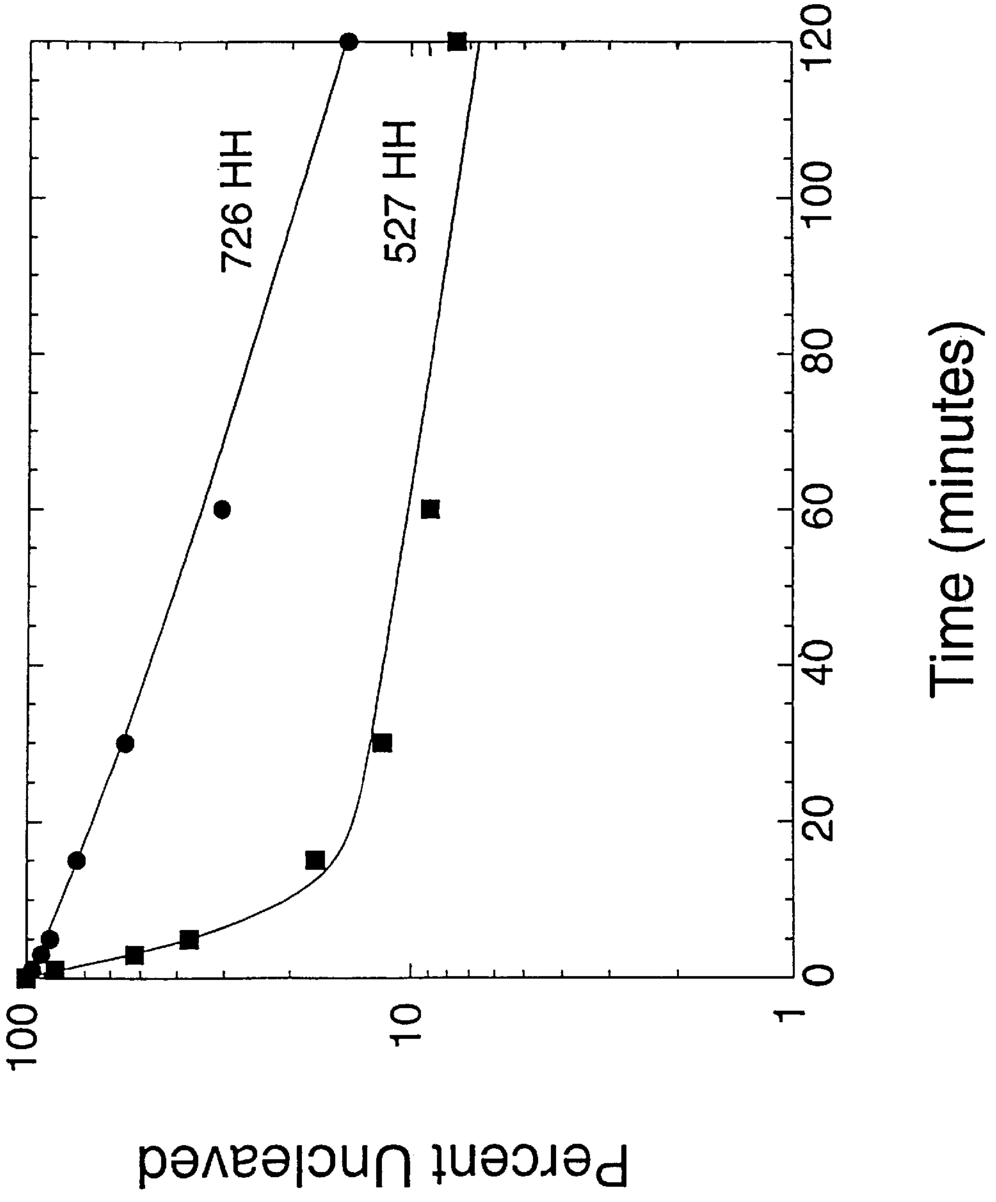

FIG. 14 shows in vitro cleavage of KDR RNA by hammerhead ribozymes. The hammerhead (HH) ribozymes were chemically modified such that the ribozyme consists of ribose residues at five positions; U4 and U7 positions contain 2'-$NH_2$ modifications, the remaining nucleotide positions contain 2'-O-methyl substitutions. Additionally, the 3' end of the ribozyme contains a 3'-3' linked inverted abasic deoxyribose (designated as 3'-iH). 726 HH and 527 HH contain 4 base-paired stem 11 region. Percent in vitro cleavage kinetics as a function of time of HH ribozymes targeted against sites 527 and 726 within the KDR RNA is shown.

Figure 15:
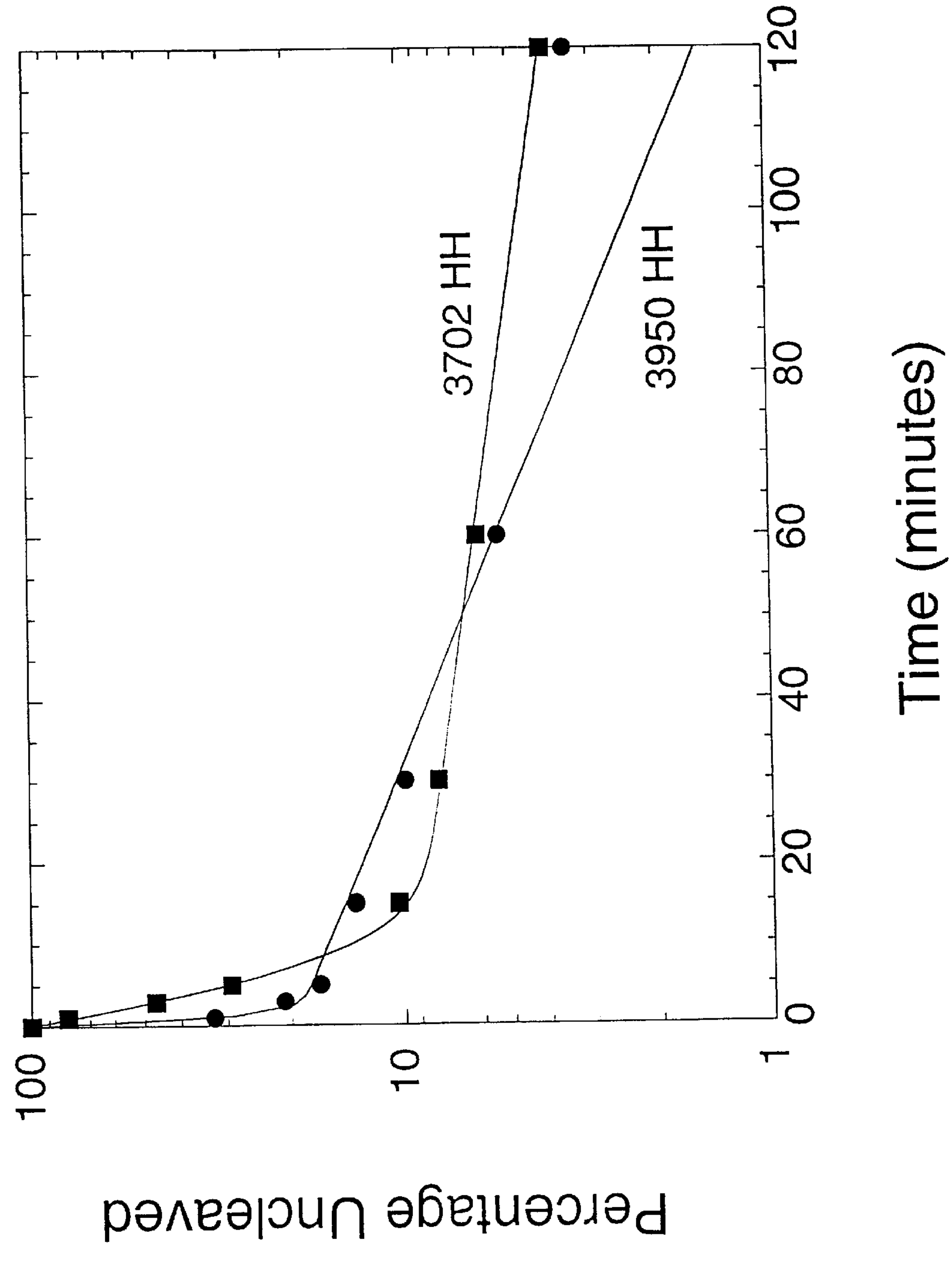

FIG. 15 shows in vitro cleavage of KDR RNA by hammerhead ribozymes. The hammerhead (HH) ribozymes were chemically modified such that the ribozyme consists of ribose residues at five positions; U4 and U7 positions contain 2'-$NH_2$ modifications, the remaining nucleotide positions contain 2'-O-methyl substitutions. Additionally, the 3' end of the ribozyme contains a 3'-3' linked inverted abasic deoxyribose (designated as 3'-iH). 3702 HH and 3950 HH contain 4 base-paired stem 11 region. Percent in vitro cleavage kinetics as a function of time of HH ribozymes targeted against sites 3702 and 3950 within the KDR RNA is shown.

Figure 16:
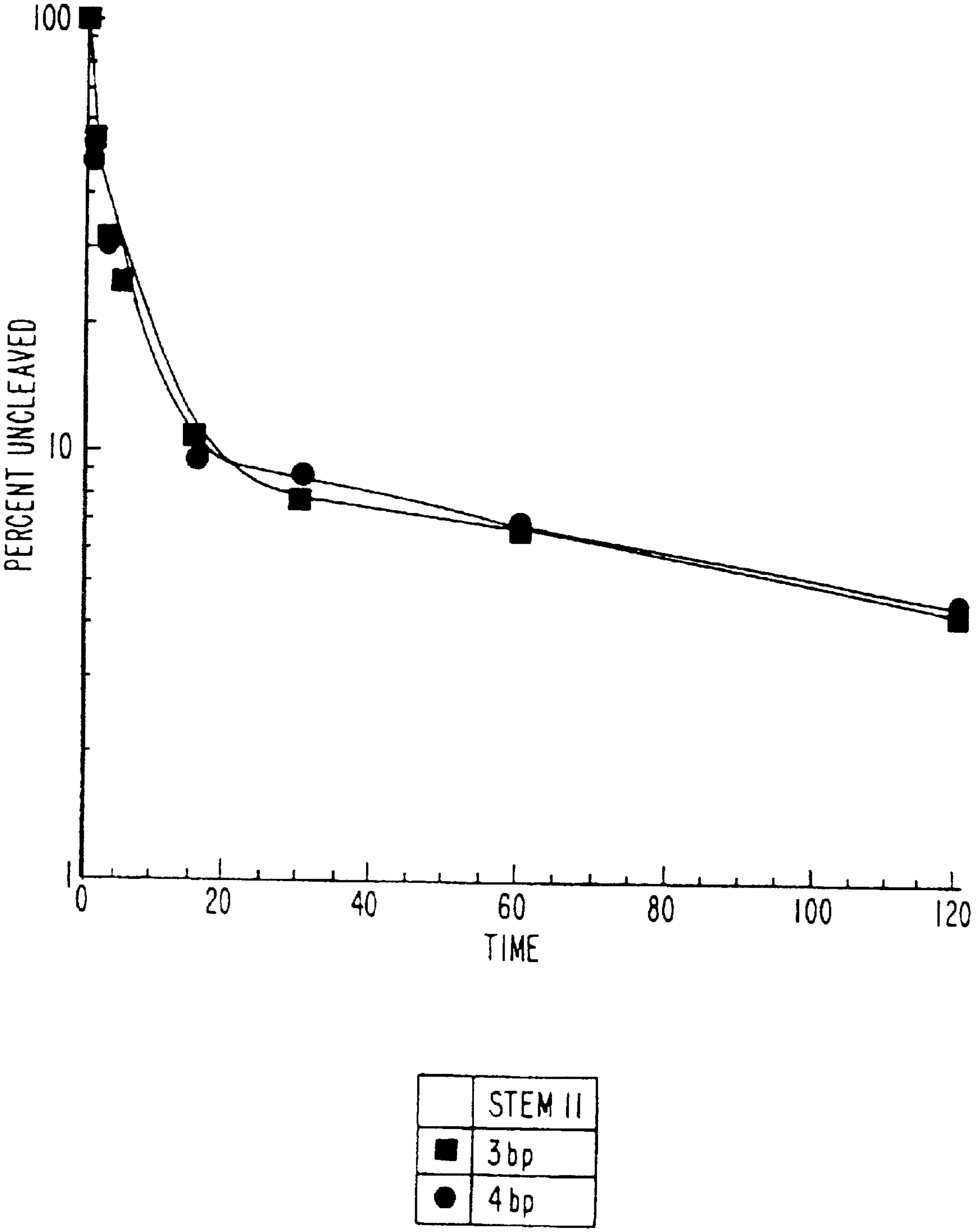

FIG. 16 shows in vitro cleavage of RNA by hammerhead ribozymes that are targeted to sites that are conserved between flt-1 and KDR RNA. The hammerhead (HH) ribozymes were chemically modified such that the ribozyme consists of ribose residues at five positions; U4 and U7 positions contain 2'-$NH_2$ modifications, the remaining nucleotide positions contain 2'-O-methyl substitutions. Additionally, the 3' end of the ribozyme contains a 3'-3' linked inverted abasic deoxyribose (designated as 3'-iH). FLT/KDR-l HH ribozyme was synthesized with either a 4 base-paired or a 3 base-paired stem II region. FLT/KDR-I HH can cleave site 3388 within flt-1 RNA and site 3151 within KDR RNA. Percent in vitro cleavage kinetics as a function of time of HH ribozymes targeted against sites 3702 and 3950 within the KDR RNA is shown.

Figure 17:
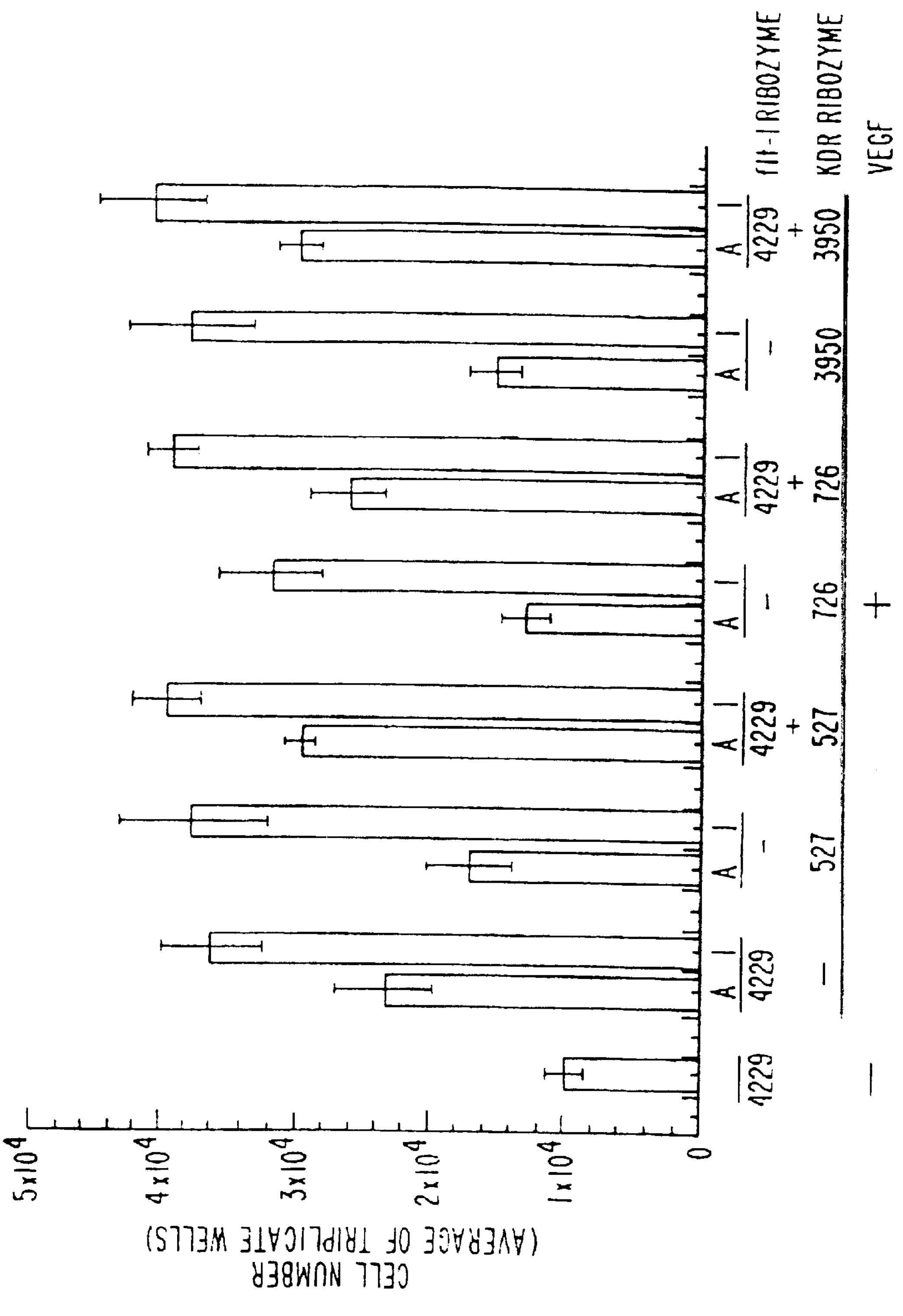

FIG. 17 shows inhibition of human microvascular endothelial cell proliferation mediated by anti-KDR and anti-flt-1 hammerhead ribozymes. The figure is a graphical representation of the inhibition of cell proliferation mediated by hammerhead ribozymes targeted against sites KDR sites—527, 726 or 3950 or flt-1 site 4229. The figure also shows enhanced inhibition of cell proliferation by a combination of flt-1 and KDR hammerhead ribozymes. 4229+527, indicates the treatment of cells with both the fit 4229 and the KDR 527 ribozymes. 4229+726, indicates the treatment of cells with both the fit 4229 and the KDR 726 ribozymes. 4229+3950, indicates the treatment of cells with both the fit 4229 and the KDR 3950 ribozymes. VEGF -, indicates the basal level of cell proliferation in the absence of VEGF. A, indicates catalytically active ribozyme; I, indicates catalytically inactive ribozyme. All of these ribozymes were chemically modified such that the ribozyme consists of ribose residues at five positions; U4 and U7 positions contain 2'-$NH_2$ modifications, the remaining nucleotide positions contain 2'-O-methyl substitutions; four nucleotides at the 5' termini contain phosphorothioate substitutions. Additionally, the 3' end of the ribozyme contains a 3'-3' linked inverted abasic deoxyribose (3'-iH).

Figure 18:
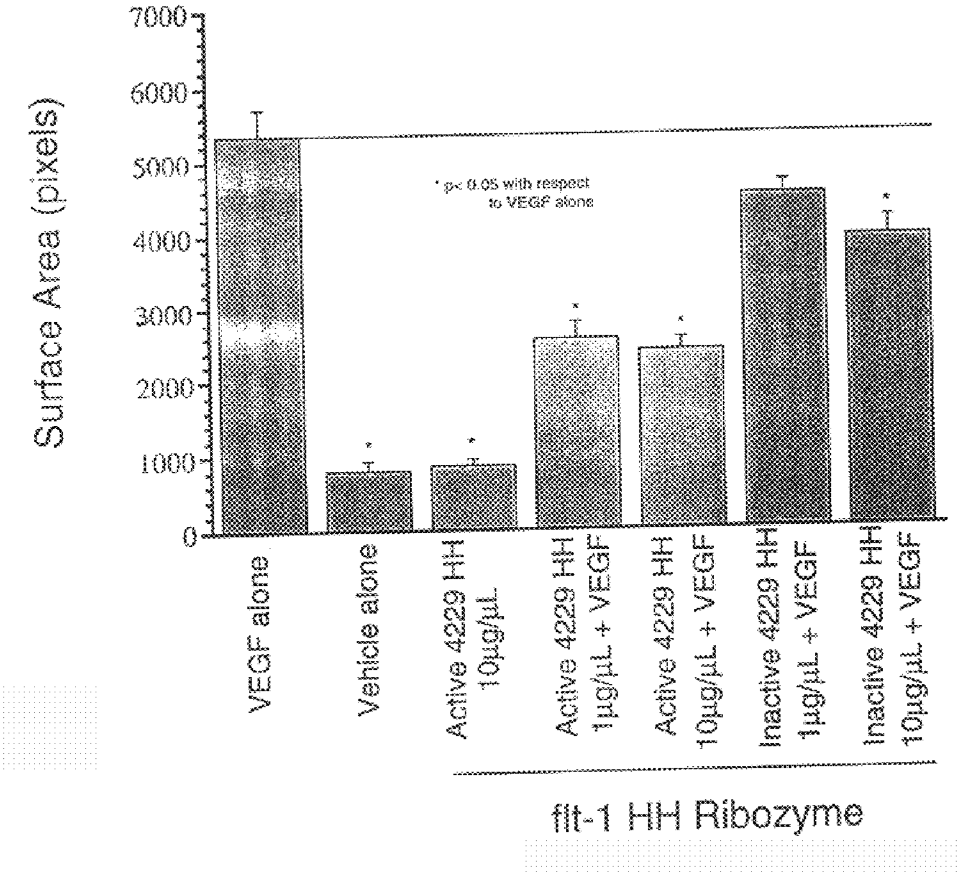

FIG. 18 shows the inhibition of VEGF-induced angiogenesis in rat cornea mediated by anti4it-1 hammerhead ribozyme. All of these ribozymes were chemically modified such that the ribozyme consists of ribose residues at five positions; U4 position contains 2'-C-allyl modifications, the remaining nucleotide positions contain 2'-O-methyl substitutions; four nucleotides at the 5' termini contain phosphorothioate substitutions. Additionally, the 3' end of the ribozyme contains a 3'-3' linked inverted abasic deoxyribose (3'-iH). A decrease in the Surface Area corresponds to a reduction in angiogenesis. VEGF alone, corresponds to treatment of the cornea with VEGF and no ribozymes. Vehicle alone, corresponds to the treatment of the cornea with the carrier alone and no VEGF. This control gives a basal level of Surface Area. Active 4229 HH, corresponds to the treatment of cornea with the flt-1 4229 HH ribozyme in the absence of any VEGF. This control also gives a basal level of Surface Area. Active 4229 HH+VEGF, corresponds to the co-treatment of cornea with the flt-1 4229 HH ribozyme and VEGF. Inactive 4229 HH+VEGF, corresponds to the co-treatment of cornea with a catalytically inactive version of 4229 HH ribozyme and VEGF.

FIGS. 19A–19D show Ribozyme mediated inhibition of cell proliferation. Cultured HMVEC-d were treated with ribozyme or attenuated controls as LIPOFECTAMINE™ complexes. After treatment, cells were stimulated with $VEGF_{165}$ or bFGF and allowed to grow for 48 h prior to determining the cell number. Each ribozyme was tested in triplicate at three concentrations and data are presented as mean cell number per well +SD. The data obtained following ribozyme treatment and VEGF stimulation are presented in panels A & B for anti-Flt-1 ribozymes and panels D & E for anti-KDR ribozymes. Representative data obtained following ribozyme treatment and bFGF stimulation are shown in panel C for one anti-Flt-1 ribozyme and in panel F for one anti-KDR ribozyme. In all panels, active ribozymes are represented with filled symbols;

attenuated controls with open symbols. In addition to the ribozymes and attenuated controls listed in Table XII, a second set having the same sequences but with an additional basepair in the "stem II" region of the ribozyme are also shown for VEGF-induced proliferation studies. These 4 bp stem II ribozymes and attenuated controls have one additional base pair such that the stem II/loop sequence is ggccgaaaggcc (Seq ID No. 14206). Therefore, ribozymes and controls with 3 or 4 basepair stem IIs are denoted with circles and squares, respectively. The data for one irrelevant ribozyme (filled triangle, panel B) are also shown. This irrelevant ribozyme contains an active core sequence but has no binding site in either Flt-1 or KDR mRNA. Its sequence is 5'-$g_sa_sa_sg_s$gaacUGAuGaggccgaaaggccGaaAgauggcT-3' (Seq ID No. 14207) with modifications as in Table XII except that T indicates a 3'-3' inverted deoxythymidine. For reference, the average number of cells in control wells after 48 h in the absence of VEGF or bFGF for each of the panels are as follows: A, B, C, 12477±617; D,E, F, 17182±1053.

Figure 20:
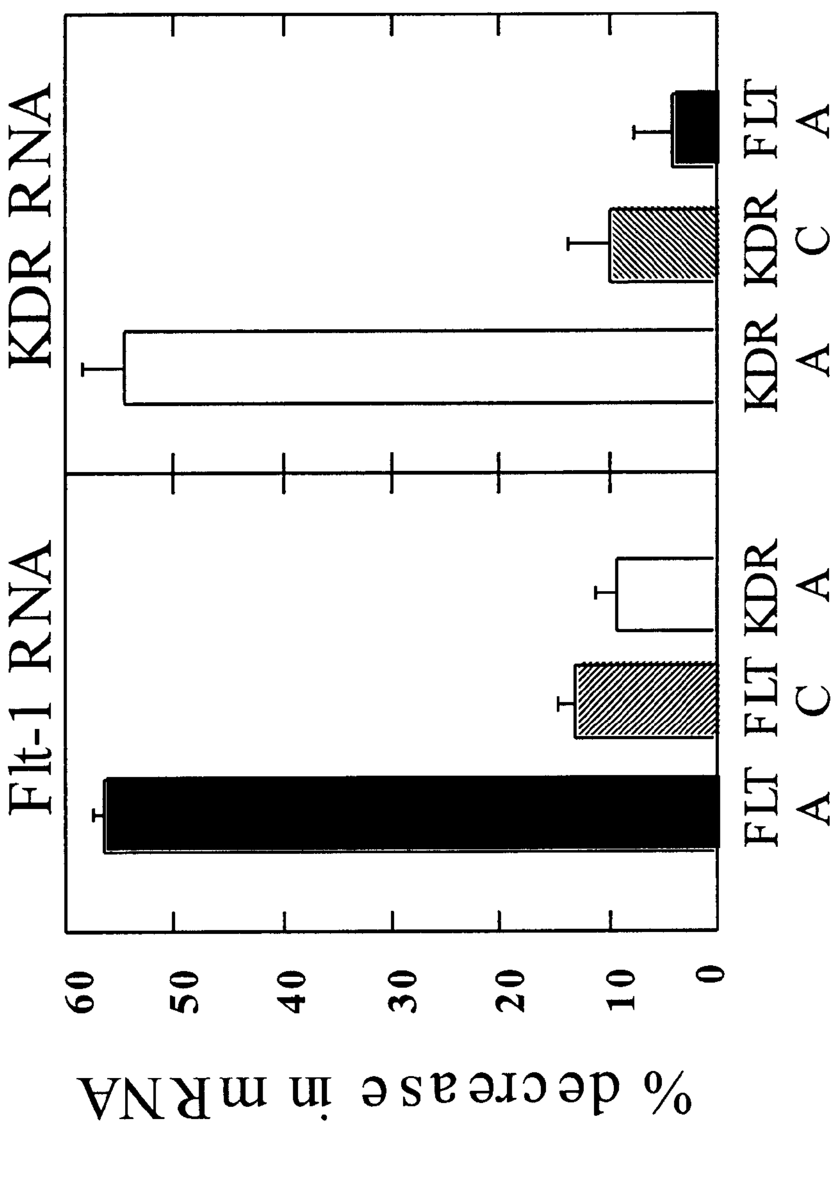

FIG. 20 shows target specificity of anti-Flt-1 and KDR ribozymes. Cultured HMVEC-D were treated with LIPOFECTAMINE™ complexes containing 200 nM active ribozyme (A) or attenuated control (C) and analyzed by RNAse protection following 24 h of VEGF-stimulated growth. Data obtained for ribozymes and attenuated controls that target Flt-1 site 4229 or KDR site 726 are shown. Data were normalized to the level of an internal mRNA control (cyclophilin) and are presented as percent decrease in Flt-1 (left panel) or KDR mRNA (right panel) relative to an untreated control. Error bars indicate the range of duplicate samples.

Figure 21:
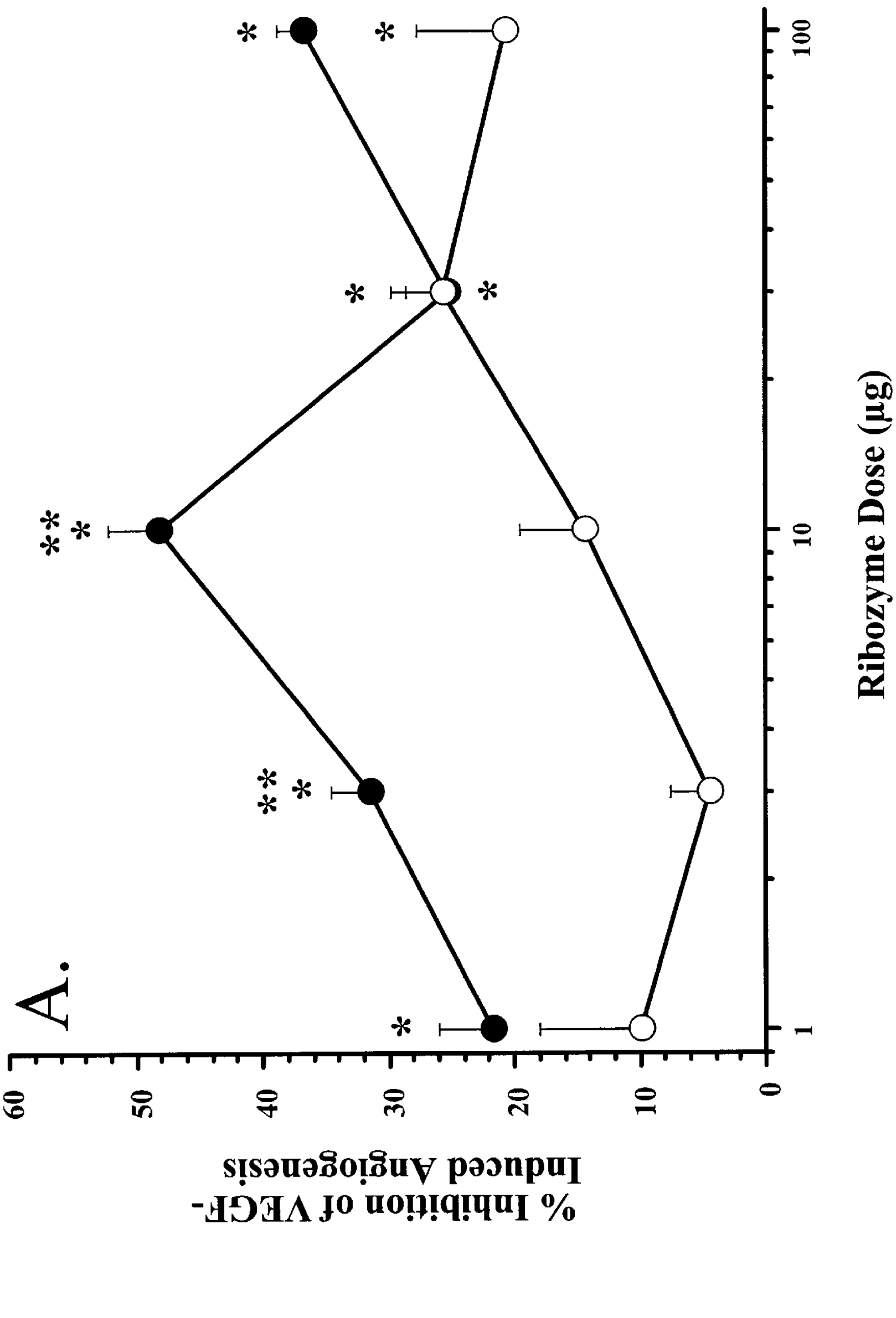
Figure 22:
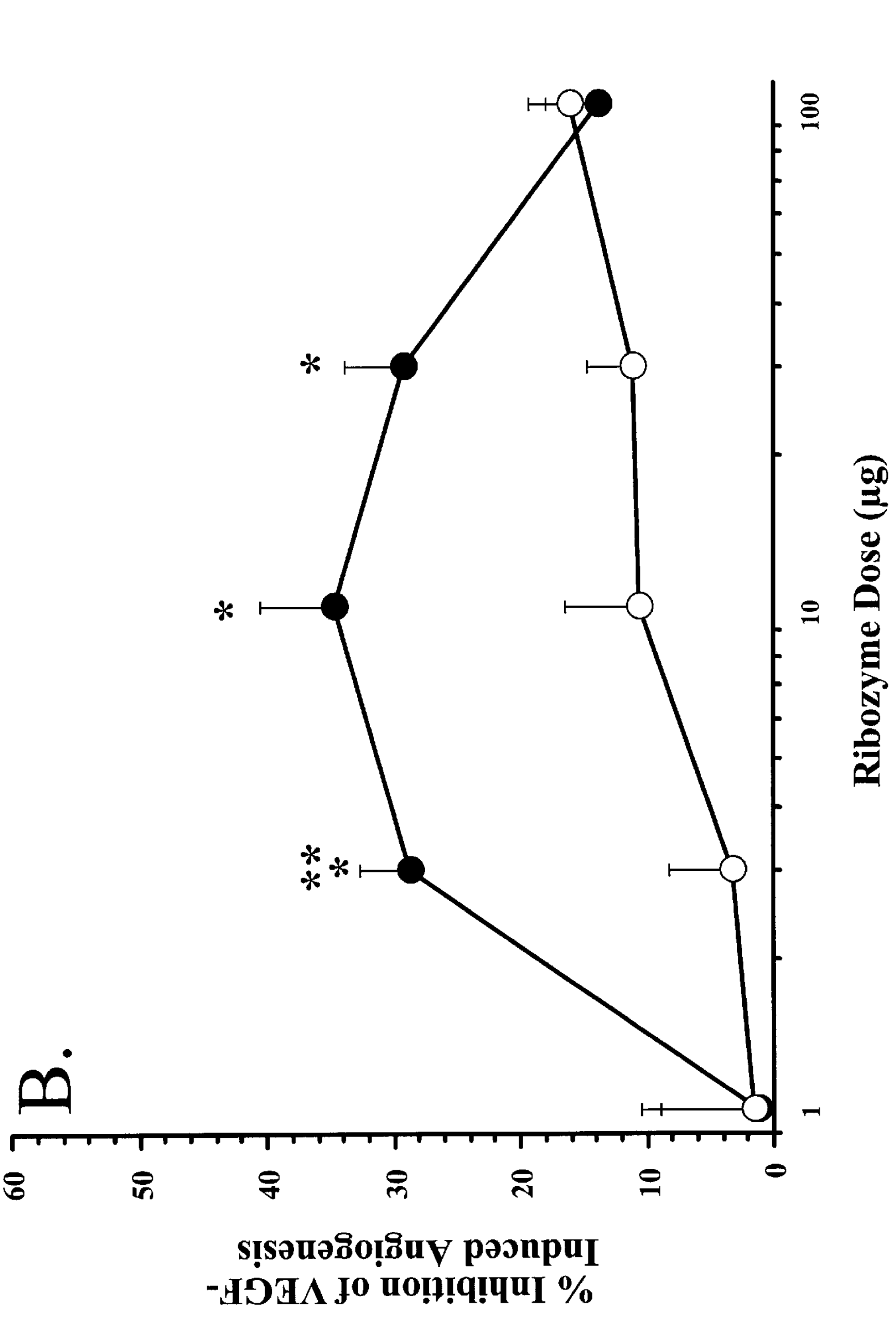

FIGS. 21 and 22 show antiangiogenic efficacy of ribozymes in the rat corneal model of VEGF-induced angiogenesis. The percent inhibition of VEGF-induced angiogenesis for locally administered FIG. 21, anti-Flt-1 (site 4229) and FIG. 22, anti-KDR (site 726) ribozymes (filled circles) and their attenuated controls (open circles) are plotted over the dose range tested. Pixels associated with background structures including the iris were subtracted from all treatment groups. Data are expressed as mean percent reduction in VEGF-induced angiogenesis ±SEM.*$p<0.05$ relative to VEGF/vehicle treated controls by Dunnett's, **$p<0.05$ relative to attenuated dose-matched controls by Tukey-Kramer.

Figure 23:
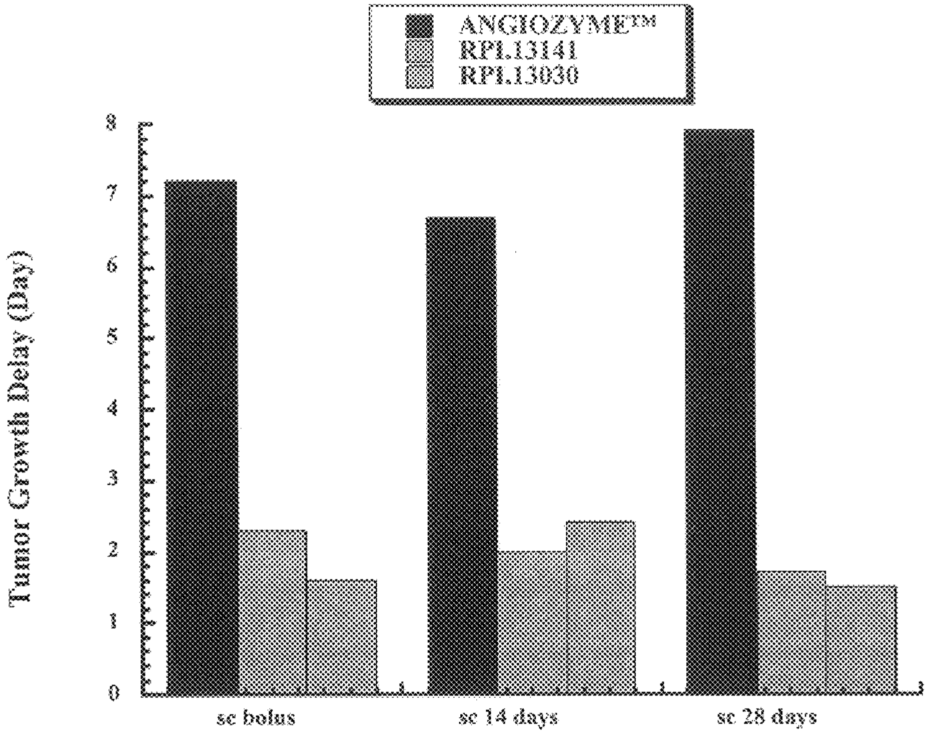

FIG. 23 shows the effect of subcutaneous bolus administration of ANGIOZYME™ in a mouse Lewis Lung Carcinoma (LLC) model.

Figure 24:
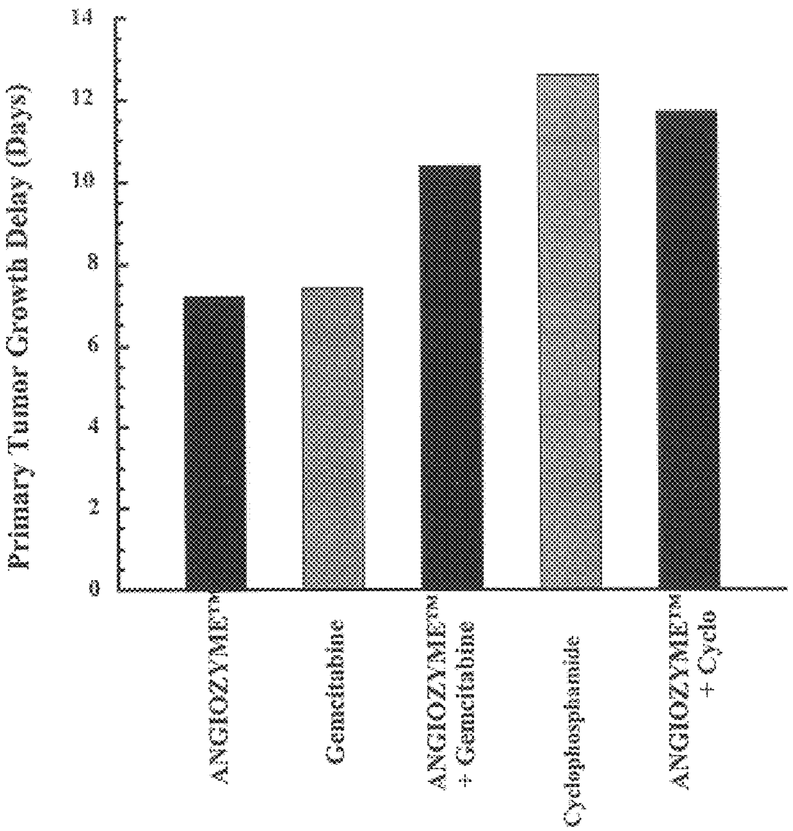

FIG. 24 shows the effect of ANGIOZYME™ in combination with gemcitabine or cyclophosphamide on primary tumor growth in the mouse LLC model.

Figure 25:
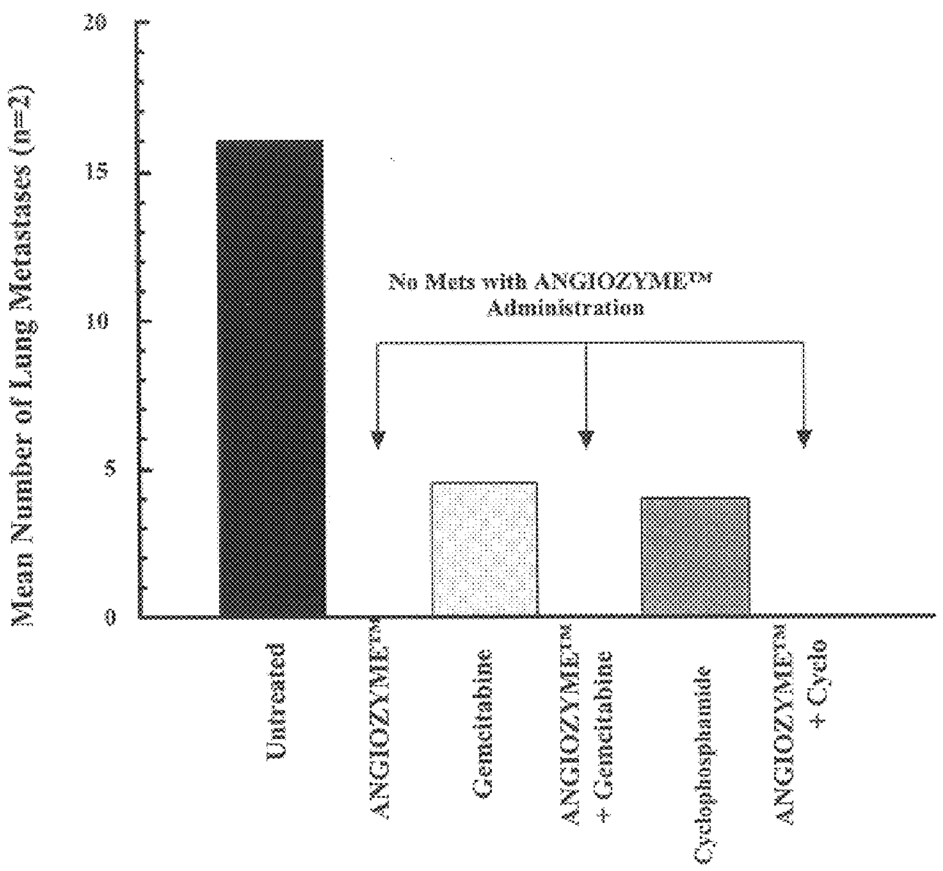

FIG. 25 shows the effect of ANGIOZYME™ in combination with gemcitabine or cyclophosphamide on tumor metastases in the mouse LLC model.

Figure 26:
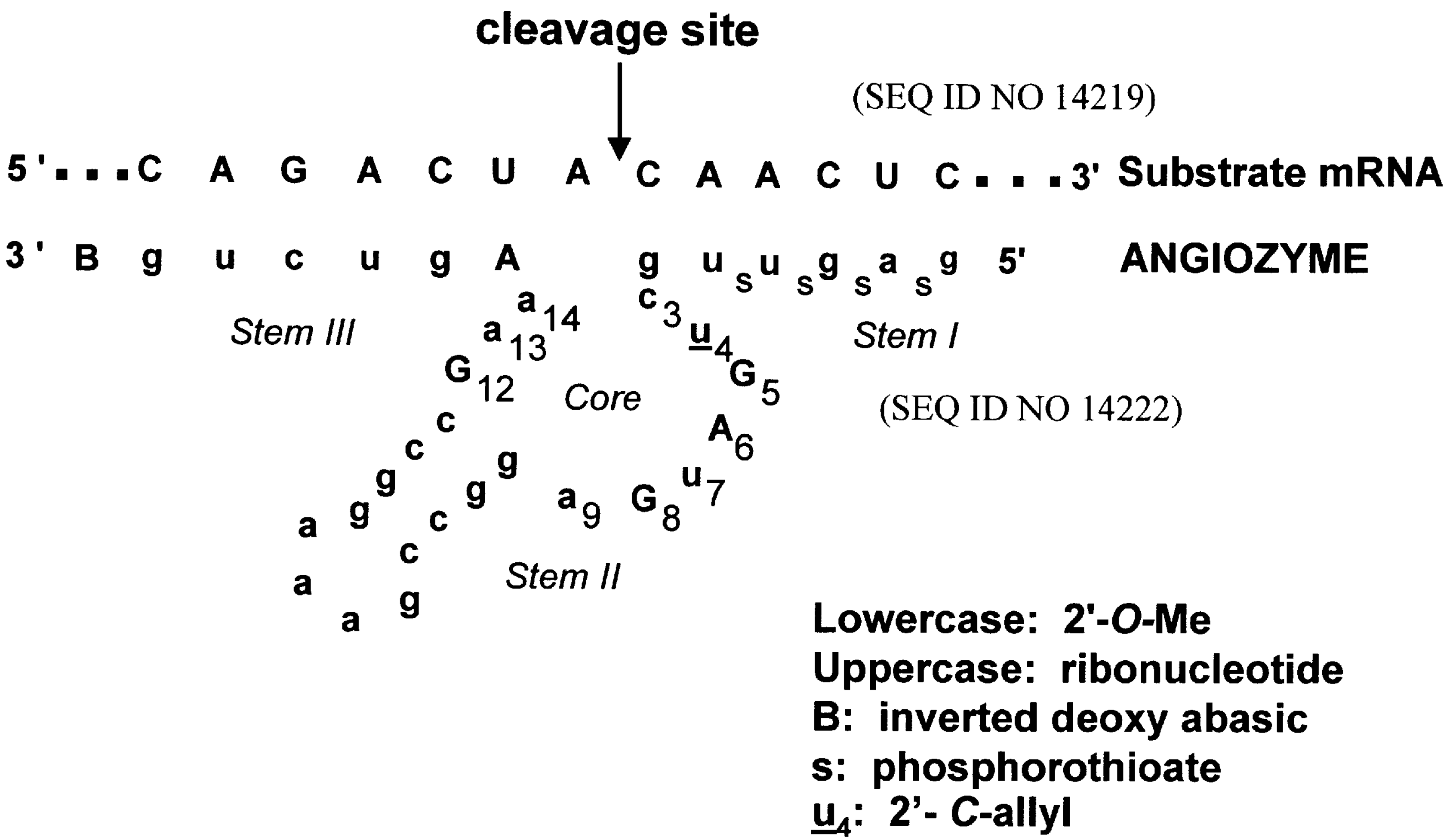

FIG. 26 shows a secondary structure model of ANGIOZYME™ ribozyme bound to its RNA target.

Figure 27:
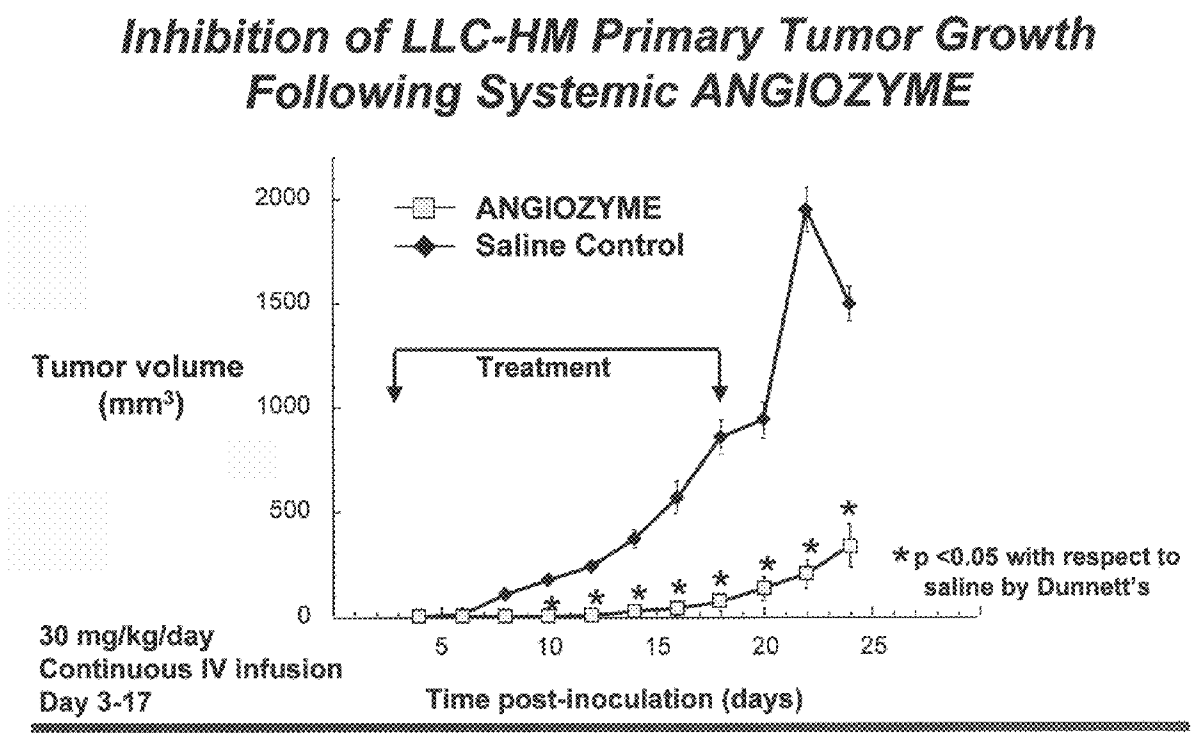

FIG. 27 shows a time course of inhibition of primary tumor growth following systemic administration of ANGIOZYME™ in the LLC mouse model.

Figure 28:
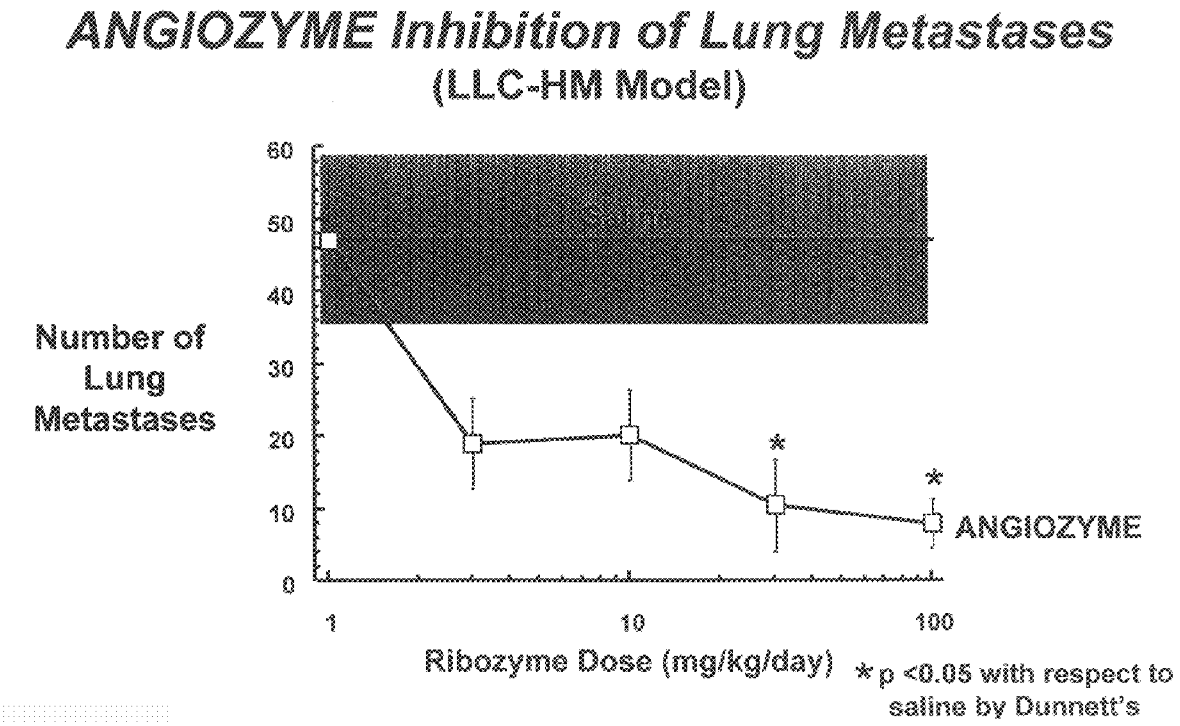

FIG. 28 shows inhibition of primary tumor growth following systemic administration of ANGIOZYME™ according to a certain dosing regimen in the LLC mouse model.

Figure 29:
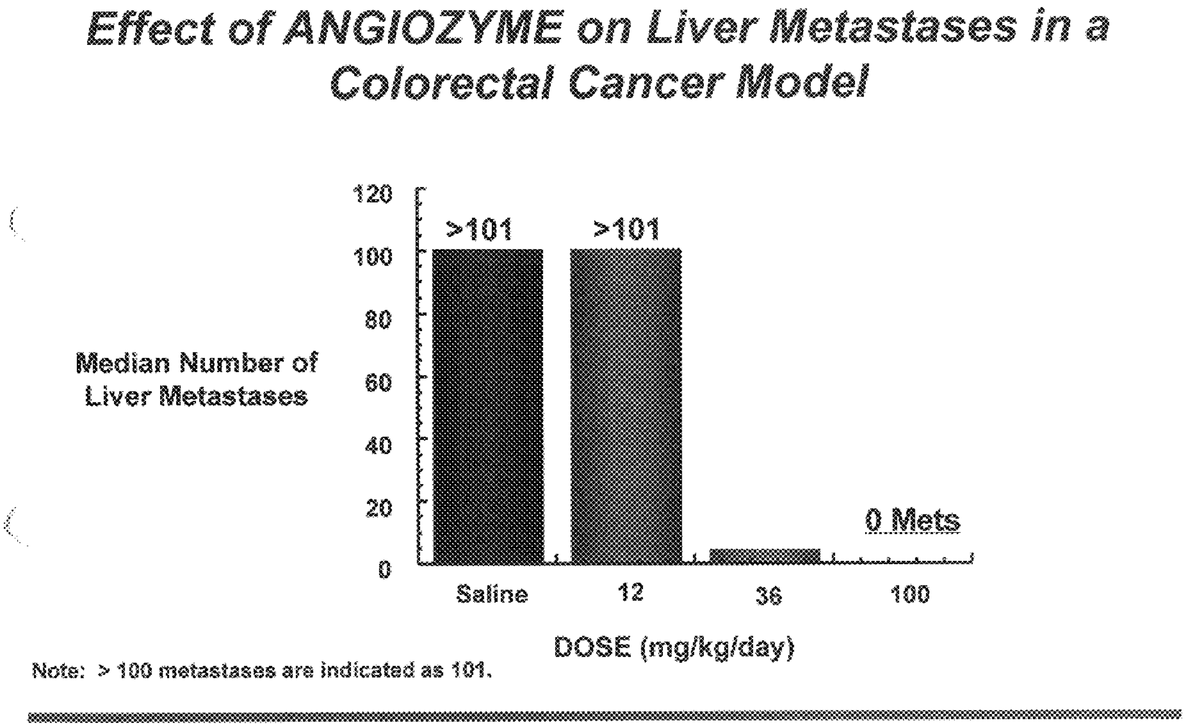

FIG. 29 shows a dose-dependent inhibition of tumor metastases following systemic administration of ANGIOZYME™ in a mouse colorectal model.

Figure 30:
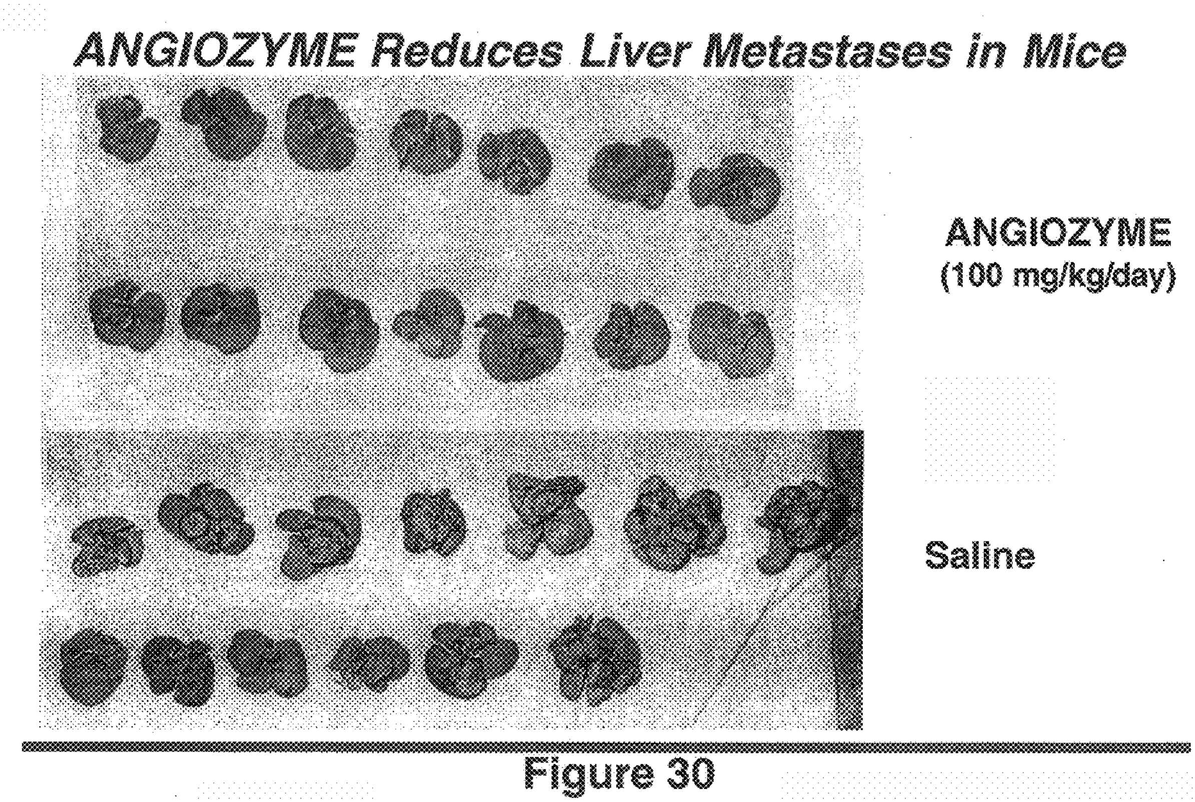

FIG. 30 shows inhibition of liver metastases following systemic administration of ANGIOZYME™ in a mouse colorectal model.

MECHANISM OF ACTION OF NUCLEIC ACID MOLECULES OF THE INVENTION

Antisense: Antisense molecules may be modified or unmodified RNA, DNA, or mixed polymer oligonucleotides and primarily function by specifically binding to matching sequences resulting in inhibition of peptide synthesis (Wu-Pong, November 1994, *BioPharm*, 20–33). The antisense oligonucleotide binds to target RNA by Watson Crick base-pairing and blocks gene expression by preventing ribosomal translation of the bound sequences either by steric blocking or by activating RNase H enzyme. Antisense molecules may also alter protein synthesis by interfering with RNA processing or transport from the nucleus into the cytoplasm (Mukhopadhyay & Roth, 1996, *Crit. Rev. in Oncogenesis* 7, 151–190).

In addition, binding of single stranded DNA to RNA may result in nuclease degradation of the heteroduplex (Wu-Pong, supra; Crooke, supra). To date, the only backbone modified DNA chemistry which will act as substrates for RNase H are phosphorothioates and phosphorodithioates. Recently it has been reported that 2'-arabino and 2'-fluoro arabino- containing oligos can also activate RNase H activity.

A number of antisense molecules have been described that utilize novel configurations of chemically modified nucleotides, secondary structure, and/or RNase H substrate domains (Woolf et al., International PCT Publication No. WO 98/13526; Thompson et al., U.S. Ser. No. 60/082,404 which was filed on Apr. 20, 1998; Hartmann et al., U.S. Ser. No. 60/101,174 which was filed on Sep. 21, 1998) all of these are incorporated by reference herein in their entirety.

Triplex Forming Oligonucleotides (TFO): Single stranded DNA may be designed to bind to genomic DNA in a sequence specific manner. TFOs are comprised of pyrimidine-rich oligonucleotides which bind DNA helices through Hoogsteen Base-pairing (Wu-Pong, supra). The resulting triple helix composed of the DNA sense, DNA antisense, and TFO disrupts RNA synthesis by RNA polymerase. The TFO mechanism may result in gene expression or cell death since binding may be irreversible (Mukhopadhyay & Roth, supra) 2-5A Antisense Chimera: The 2-5A system is an interferon mediated mechanism for RNA degradation found in higher vertebrates (Mitra et al., 1996, *Proc Nat Acad Sci USA* 93, 6780–6785). Two types of enzymes, 2-5A synthetase and RNase L, are required for RNA cleavage. The 2-5A synthetases require double stranded RNA to form 2'-5' oligoadenylates (2-5A). 2-5A then acts as an allosteric effector for utilizing RNase L which has the ability to cleave single stranded RNA. The ability to form 2-5A structures with double stranded RNA makes this system particularly useful for inhibition of viral replication. (2'-5') oligoadenylate structures may be covalently linked to antisense molecules to form chimeric oligonucleotides capable of RNA cleavage (Torrence, supra). These molecules putatively bind and activate a 2-5A dependent RNase, the oligonucleotide/enzyme complex then binds to a target RNA molecule which can then be cleaved by the RNase enzyme.

Enzymatic Nucleic Acid: Seven basic varieties of naturally-occurring enzymatic RNAs are presently known. In addition, several in vitro selection (evolution) strategies (Orgel, 1979, *Proc. R. Soc. London*, B 205, 435) have been used to evolve new nucleic acid catalysts capable of catalyzing cleavage and ligation of phosphodiester linkages (Joyce, 1989, *Gene*, 82, 83–87; Beaudry et al., 1992, *Science* 257, 635–641; Joyce, 1992, *Scientific American* 267, 90–97; Breaker et al., 1994, *TIBTECH* 12, 268; Bartel et al., 1993, *Science* 261:1411–1418; Szostak, 1993, *TIBS* 17, 89–93; Kumar et al., 1995, *FASEB J*., 9, 1183; Breaker, 1996, *Curr. Op. Biotech*., 7, 442; Santoro et al., 1997, *Proc. Natl. Acad. Sci*., 94, 4262; Tang et al., 1997, *RNA* 3, 914; Nakamaye & Eckstein, 1994, supra; Long & Uhlenbeck, 1994, supra; Ishizaka et al., 1995, supra; Vaish et al., 1997, *Biochemistry* 36, 6495; all of these are incorporated by reference herein). Each can catalyze a series of reactions including the hydrolysis of phosphodiester bonds in trans (and thus can cleave other RNA molecules) under physiological conditions.

Enzymatic nucleic acid molecules of this invention block to some extent VEGF-R (specifically flt-1 and flk-1/KDR) production and can be used to treat disease or diagnose such disease. Ribozymes will be delivered to cells in culture, to cells or tissues in animal models of angiogenesis and/or RA and to human cells or tissues ex vivo or in vivo. Ribozyme cleavage of VEGF-R RNAs (specifically RNAs that encode flt-1 and flk-1/KDR) in these systems may alleviate disease symptoms.

The enzymatic nature of a ribozyme has significant advantages, such as the concentration of ribozyme necessary to affect a therapeutic treatment is lower. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base-pairing mechanism of binding to the target RNA, but also on the mechanism of target RNA cleavage. Single mismatches, or base-substitutions, near the site of cleavage can be chosen to completely eliminate catalytic activity of a ribozyme.

Nucleic acid molecules having an endonuclease enzymatic activity are able to repeatedly cleave other separate RNA molecules in a nucleotide base sequence-specific manner. Such enzymatic nucleic acid molecules can be targeted to virtually any RNA transcript, and achieved efficient cleavage in vitro (Zaug et al., 324, *Nature* 429 1986; Uhlenbeck, 1987 *Nature* 328, 596; Kim et al., 84 *Proc. Natl. Acad. Sci. USA* 8788, 1987; Dreyfus, 1988, Einstein Quart. *J. Bio. Med*., 6, 92; Haseloff and Gerlach, 334 *Nature* 585, 1988; Cech, 260 *JAMA* 3030, 1988; =;and Jefferies et al., 17 *Nucleic Acids Research* 1371, 1989; Santoro et al., 1997 supra).

Because of their sequence specificity, trans-cleaving ribozymes show promise as therapeutic agents for human disease (Usman & McSwiggen, 1995 *Ann. Rep. Med. Chem*. 30, 285–294; Christoffersen and Marr, 1995 *J. Med. Chem*. 38, 2023–2037). Ribozymes can be designed to cleave specific RNA targets within the background of cellular RNA. Such a cleavage event renders the RNA non-functional and abrogates protein expression from that RNA. In this manner, synthesis of a protein associated with a disease state can be selectively inhibited.

Target Sites

Targets for useful ribozymes and antisense nucleic acids can be determined as disclosed in Draper et al., WO 93/23569; Sullivan et al., WO 93/23057; Thompson et al., WO 94/02595; Draper et al., WO 95/04818; McSwiggen et al., U.S. Pat. No. 5,525,468, and hereby incorporated by reference herein in totality. Other examples include the following PCT applications which concern inactivation of expression of disease-related genes: WO 95/23225, WO 95/13380, WO 94/02595, incorporated by reference herein. Rather than repeat the guidance provided in those documents here, below are provided specific examples of such methods, not limiting to those in the art. Ribozymes to such targets are designed as described in those applications and synthesized to be tested in vitro and in vivo, as also described.The sequence of human and mouse flt-1, KDR and/or flk-1 mRNAs were screened for optimal ribozyme target sites using a computer folding algorithm. Hammerhead, hairpin, NCH, or G-Cleaver ribozyme cleavage sites were identified. These sites are shown in Tables II to XVII (all sequences are 5' to 3' in the tables; X can be any base-paired sequence, the actual sequence is not relevant here). The nucleotide base position is noted in the Tables as that site to be cleaved by the designated type of ribozyme. While mouse and human sequences can be screened and ribozymes thereafter designed, the human targeted sequences are of most utility. However, as discussed in Stinchcomb et al., WO 95/23225, mouse targeted ribozymes may be useful to test efficacy of action of the ribozyme prior to testing in humans. The nucleotide base position is noted in the Tables as that site to be cleaved by the designated type of ribozyme.

Hammerhead or hairpin ribozymes were designed that could bind and cleave target RNA in a sequence-specific manner. The ribozymes were individually analyzed by computer folding jaeger et al., 1989 *Proc. Natl. Acad. Sci. USA*, 86, 7706) to assess whether the ribozyme sequences fold into the appropriate secondary structure. Those ribozymes with unfavorable intramolecular interactions between the binding arms and the catalytic core were eliminated from consideration. Varying binding arm lengths can be chosen to optimize activity.

Referring to FIG. 6, mRNA is screened for accessible cleavage sites by the method described generally in Draper et al., PCT WO93/23569, hereby incorporated by reference herein. Briefly, DNA oligonucleotides complementary to potential hammerhead or hairpin ribozyme cleavage sites were synthesized. A polymerase chain reaction is used to generate substrates for T7 RNA polymerase transcription from human and mouse flt-1, KDR and/or flk-1 cDNA clones. Labeled RNA transcripts are synthesized in vitro from the templates. The oligonucleotides and the labeled transcripts were annealed, RNAseH was added and the mixtures were incubated for the designated times at 37° C. Reactions are stopped and RNA separated on sequencing polyacrylamide gels. The percentage of the substrate cleaved is determined by autoradiographic quantitation using a PhosphorImaging system. From these data, antisense oligonucleotides, and ribozymes, such as hammerhead or hairpin ribozyme sites are chosen as the most accessible.

Ribozymes of the hammerhead or hairpin motif were designed to anneal to various sites in the mRNA message. The binding arms are complementary to the target site sequences described above. The ribozymes were chemically synthesized. The method of synthesis used follows the procedure for normal RNA synthesis as described below and in Usman et al., 1987 *J. Am. Chem. Soc.*, 109, 7845; Scaringe et al., 1990 *Nucleic Acids Res.*, 18, 5433; and Wincott et al., 1995 *Nucleic Acids Res.* 23, 2677–2684.

Synthesis of Nucleic Acid Molecules

Synthesis of nucleic acids greater than 100 nucleotides in length is difficult using automated methods, and the therapeutic cost of such molecules is prohibitive. In this invention, small nucleic acid motifs ("small refers to nucleic acid motifs no more than 100 nucleotides in length, preferably no more than 80 nucleotides in length, and most preferably no more than 50 nucleotides in length; e.g., antisense oligonucleotides, hammerhead or the hairpin ribozymes) are preferably used for exogenous delivery. The simple structure of these molecules increases the ability of the nucleic acid to invade targeted regions of RNA structure. Exemplary molecules of the instant invention were chemically synthesized, and others can similarly be synthesized. Oligodeoxyribonucleotides were synthesized using standard protocols as described in Caruthers et al., 1992*, Methods in Enzymology* 211,3–19, and is incorporated herein by reference.

The method of synthesis used for normal RNA including certain enzymatic nucleic acid molecules follows the procedure as described in Usman et al., 1987 *J. Am. Chem. Soc.,* 109, 7845; Scaringe et al., 1990 *Nucleic Acids Res.*, 18, 5433; and Wincott et al., 1995 *Nucleic Acids Res.* 23, 2677–2684 and makes use of common nucleic acid protecting and coupling groups, such as dimethoxytrityl at the 5'-end, and phosphoramidites at the 3'-end. In a non-limiting example, small scale syntheses were conducted on a 394 Applied Biosystems, Inc. synthesizer using a 0.2 μmol scale protocol with a 7.75 min coupling step for alkylsilyl protected nucleotides and a 2.5 min coupling step for 2'-O-methylated nucleotides. Table II outlines the amounts and the contact times of the reagents used in the synthesis cycle. Alternatively, syntheses at the 0.2 μmol scale can be done on a 96-well plate synthesizer, such as the instrument produced by Protogene (Palo Alto, Calif.) with minimal modification to the cycle. A 15-fold excess (31 μL of 0.1 M=3.1 μmol) of phosphoramidite and a 38.7-fold excess of S-ethyl tetrazole (31 μL of 0.25 M=7.75 μmol) relative to polymer-bound 5'-hydroxyl was used in each coupling cycle. Average coupling yields on the 394 Applied Biosystems, Inc. synthesizer, determined by colorimetric quantitation of the trityl fractions, were 97.5–99%. Other oligonucleotide synthesis reagents for the 394 Applied Biosystems, Inc. synthesizer; detritylation solution was 3% TCA in methylene chloride (ABI); capping was performed with 16% N-methyl imidazole in THF (ABI) and 10% acetic anhydride/10% 2,6-lutidine in THF (ABI); oxidation solution was 16.9 mM $I_2$, 49 mM pyridine, 9% water in THF (PERSEPTIVE™). Burdick & Jackson Synthesis Grade acetonitrile was used directly from the reagent bottle. S-Ethyltetrazole solution (0.25 M in acetonitrile) was made up from the solid obtained from American International Chemical, Inc.

Deprotection of the RNA was performed using either a two-pot or one-pot protocol. For the two-pot protocol, the polymer-bound trityl-on oligoribonucleotide was transferred to a 4 mL glass screw top vial and suspended in a solution of 40% aq. methylamine (1 mL) at 65° C. for 10 min. After cooling to −20° C., the supernatant was removed from the polymer support. The support was washed three times with 1.0 mL of EtOH:MeCN:H2O/3:1:1, vortexed and the supernatant was then added to the first supernatant. The combined supernatants, containing the oligoribonucleotide, were dried to a white powder. The base deprotected oligoribonucleotide was resuspended in anhydrous TEA/HF/NMP solution (300 μL of a solution of 1.5 mL N-methylpyrrolidinone, 750 μL TEA and 1 mL TEA·3HF to provide a 1.4 M HF concentration) and heated to 65° C. After 1.5 h, the oligomer was quenched with 1.5 M $NH_4HCO_3$.

Alternatively, for the one-pot protocol, the polymer-bound trityl-on oligoribonucleotide was transferred to a 4 mL glass screw top vial and suspended in a solution of 33% ethanolic methylamine/DMSO:1/1 (0.8 mL) at 65° C. for 15 min. The vial was brought to r.t. TEA·3HF (0.1 mL) was added and the vial was heated at 65° C. for 15 min. The sample was cooled at −20° C. and then quenched with 1.5 M $NH_4HCO_3$.

For purification of the trityl-on oligomers, the quenched $NH_4HCO_3$ solution was loaded onto a C-18 containing cartridge that had been prewashed with acetonitrile followed by 50 mM TEAA. After washing the loaded cartridge with water, the RNA was detritylated with 0.5% TFA for 13 min. The cartridge was then washed again with water, salt exchanged with 1 M NaCl and washed with water again. The oligonucleotide was then eluted with 30% acetonitrile.

Inactive hammerhead ribozymes or binding attenuated control (BAC) oligonucleotides) were synthesized by substituting a U for G5 and a U for A14 (numbering from Hertel, K. J., et al., 1992*, Nucleic Acids Res*., 20, 3252).

The average stepwise coupling yields were >98% (Wincott et al., 1995 *Nucleic Acids Res.* 23, 2677–2684). Those of ordinary skill in the art will recognize that the scale of synthesis can be adapted to be larger or smaller than the example described above including but not limited to 96 well format, all that is important is the ratio of chemicals used in the reaction.

Alternatively, the nucleic acid molecules of the present invention can be synthesized separately and joined together by ligation (Moore et al., 1992, *Science* 256, 9923; Draper et al., International PCT publication No. WO 93/23569; Shabarova et al., 1991*, Nucleic Acids Research* 19, 4247)

Ribozymes are modified extensively to enhance stability by modification with nuclease resistant groups, for example, 2'-amino, 2'-C-allyl, 2'-flouro, 2'-O-methyl, 2'-H (for a review see Usman and Cedergren, 1992 *TIBS* 17, 34; Usman et al., 1994 *Nucleic Acids Symp.* Ser. 31, 163). Ribozymes are purified by gel electrophoresis using general methods or are purified by high pressure liquid chromatography (HPLC; See Wincott et al., Supra, the totality of which is hereby incorporated herein by reference) and are resuspended in water.

The sequences of the ribozymes that are chemically synthesized, useful in this study, are shown in Tables II to XVII. Those in the art will recognize that these sequences are representative only of many more such sequences where the enzymatic portion of the ribozyme (all but the binding arms) is altered to affect activity. Stem-loop IV sequence of hairpin ribozymes listed in, for example, Table III (5'-CACGUUGUG-3') can be altered (substitution, deletion, and/or insertion) to contain any sequence, provided a minimum of two base-paired stem structure can form. Preferably, no more than 200 bases are inserted at these locations. The sequences listed in Tables II to XVII may be formed of ribonucleotides or other nucleotides or non-nucleotides. Such ribozymes with enzymatic activity are equivalent to the ribozymes described specifically in the Tables.

Optimizing Activity of the Nucleic Acid Molecule of the Invention.

Ribozyme activity can be optimized as described by Stinchcomb et al., supra. The details will not be repeated here, but include altering the length of the ribozyme binding arms (stems I and III, see FIG. 2*c*), or chemically synthesizing ribozymes with modifications that prevent their degradation by serum ribonucleases (see e.g., Eckstein et al., International Publication No. WO 92/07065; Perrault et al., 1990 *Nature* 344, 565; Pieken et al., 1991 *Science* 253, 314; Usman and Cedergren, 1992 Trends in *Biochem. Sci.* 17, 334; Usman et al., International Publication No. WO 93/15187; Rossi et al., International Publication No. WO 91/03162; Beigelman et al., 1995 *J. Biol Chem.* in press; as well as Sproat, U.S. Pat. No. 5,334,711 which describe various chemical modifications that can be made to the sugar moieties of enzymatic RNA molecules). Modifications which enhance their efficacy in cells, and removal of stem II bases to shorten RNA synthesis times and reduce chemical requirements are desired. (All these publications are hereby incorporated by reference herein).

There are several examples in the art describing sugar, base and phosphate modifications that can be introduced into enzymatic nucleic acid molecules without significantly effecting catalysis and with significant enhancement in their nuclease stability and efficacy. Ribozymes are modified to enhance stability and/or enhance catalytic activity by modification with nuclease resistant groups, for example, 2'-amino, 2'-C-allyl, 2'-fluoro, 2'-O-methyl, 2'-H, nucleotide base modifications (for a review see Usman and Cedergren, 1992 TIBS 17, 34; Usman et al., 1994 *Nucleic Acids Symp.* Ser. 31, 163; Burgin et al., 1996 *Biochemistry* 35, 14090). Sugar modification of enzymatic nucleic acid molecules have been extensively described in the art (see Eckstein et al., International Publication PCT No. WO 92/07065; Perrault et al. *Nature* 1990, 344, 565–568; Pieken et al. *Science* 1991, 253, 314–317; Usman and Cedergren, Trends in *Biochem. Sci.* 1992, 17, 334–339; Usman et al. International Publication PCT No. WO 93/15187; Sproat, U.S. Pat. No. 5,334,711 and Beigelman et al., 1995 *J. Biol. Chem.* 270, 25702; all of the references are hereby incorporated in their totality by reference herein). Such publications describe general methods and strategies to determine the location of incorporation of sugar, base and/or phosphate modifications and the like into ribozymes without inhibiting catalysis, and are incorporated by reference herein. In view of such teachings, similar modifications can be used as described herein to modify the nucleic acid catalysts of the instant invention.

Nucleic acid catalysts having chemical modifications which maintain or enhance enzymatic activity are provided. Such nucleic acid is also generally more resistant to nucleases than unmodified nucleic acid. Thus, in a cell and/or in vivo the activity may not be significantly lowered. As exemplified herein such ribozymes are useful in a cell and/or in vivo even if activity over all is reduced 10 fold (Burgin et al., 1996, *Biochemistry*, 35, 14090). Such ribozymes herein are said to "maintain" the enzymatic activity of an all RNA ribozyme.

Therapeutic nucleic acid molecules (e.g., enzymatic nucleic acid molecules and antisense nucleic acid molecules) delivered exogenously must optimally be stable within cells until translation of the target RNA has been inhibited long enough to reduce the levels of the undesirable protein. This period of time varies between hours to days depending upon the disease state. Clearly, these nucleic acid molecules must be resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

By "enhanced enzymatic activity" is meant to include activity measured in cells and/or in vivo where the activity is a reflection of both catalytic activity and ribozyme stability. In this invention, the product of these properties is increased or not significantly (less that 10 fold) decreased in vivo compared to an all RNA ribozyme.

In yet another preferred embodiment, nucleic acid catalysts having chemical modifications which maintain or enhance enzymatic activity is provided. Such nucleic acid is also generally more resistant to nucleases than unmodified nucleic acid. Thus, in a cell and/or in vivo the activity may not be significantly lowered. As exemplified herein such ribozymes are useful in a cell and/or in vivo even if activity over all is reduced 10 fold (Burgin et al., 1996*, Biochemistry,* 35, 14090). Such ribozymes herein are said to "maintain" the enzymatic activity on all RNA ribozyme.

In another aspect the nucleic acid molecules comprise a 5' and/or a 3'-cap structure.

By "cap structure" is meant chemical modifications, which have been incorporated at the terminus of the oligonucleotide (see for example Wincott et al., WO 97/26270, incorporated by reference herein). These terminal modifications protect the nucleic acid molecule from exonuclease degradation, and may help in delivery and/or localization within a cell. The cap may be present at the 5'-terminus (5'-cap) or at the 3'-terminus (3'-cap) or may be present on both terminus. In non-limiting examples: the 5'-cap is selected from the group comprising inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Beigelman et al., International PCT publication No. WO 97/26270, incorporated by reference herein). In yet another preferred embodiment the 3'-cap is selected from a group comprising, 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moeity; 5'-5'-inverted abasic moeity; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moeities (for more details see Beaucage and lyer, 1993, Tetrahedron 49, 1925; incorporated by reference herein). By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine.

By "nucleotide" as used herein is as recognized in the art to include natural bases (standard), and modified bases well known in the art. Such bases are generally located at the 1' position of a sugar moiety. A nucleotide generally comprises a base, sugar and a phosphate group. The nucleotide may also be abasic, i.e., lacking a base. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; all hereby incorporated by reference herein). Several examples of modified nucleic acid bases are known in the art and has recently been summarized by Limbach et al., 1994*, Nucleic Acids Res.* 22, 2183. Some of the non-limiting examples of base modifications that can be introduced into enzymatic nucleic acids without significantly effecting their catalytic activity include, inosine, purine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine) and others (Burgin et al., 1996*, Biochemistry*, 35, 14090). By "modified bases" in this aspect is meant nucleotide bases other than adenine, guanine, cytosine and uracil at 1' position or their equivalents; such bases may be used within the catalytic core of the enzyme and/or in the substrate-binding regions.

By "abasic" is meant sugar moieties lacking a base or having other chemical groups in place of a base at the 1' position.

By "unmodified nucleoside" is meant one of the bases adenine, cytosine, guanine, uracil joined to the 1' carbon of β-D-ribo-furanose.

By "modified nucleoside" is meant any nucleotide base which contains a modification in the chemical structure of an unmodified nucleotide base, sugar and/or phosphate.

In connection with 2'-modified nucleotides as described for the present invention, by "amino" is meant 2'-$NH_2$ or 2'-O- $NH_2$, which may be modified or unmodified. Such modified groups are described, for example, in Eckstein et al., U.S. Pat. No. 5,672,695 and Matulic-Adamic et al., WO 98/28317, respectively, which are both incorporated by reference in their entireties.

Various modifications to nucleic acid (e.g., antisense and ribozyme) structure can be made to enhance the utility of these molecules. Such modifications will enhance shelf-life, half-life in vitro, stability, and ease of introduction of such oligonucleotides to the target site, e.g., to enhance penetration of cellular membranes, and confer the ability to recognize and bind to targeted cells.

Use of these molecules will lead to better treatment of the disease progression by affording the possibility of combination therapies (e.g., multiple ribozymes targeted to different genes, ribozymes coupled with known small molecule inhibitors, or intermittent treatment with combinations of ribozymes (including different ribozyme motifs) and/or other chemical or biological molecules). The treatment of patients with nucleic acid molecules may also include combinations of different types of nucleic acid molecules. Therapies may be devised which include a mixture of ribozymes (including different ribozyme motifs), antisense and/or 2-5A chimera molecules to one or more targets to alleviate symptoms of a disease.

Administration of Nucleic Acid Molecules

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., supra which have been incorporated by reference herein.

Methods for the delivery of nucleic acid molecules is described in Akhtar et al., 1992*, Trends Cell Bio*., 2, 139; and *Delivery Strategies for Antisense Oligonucleotide Therapeutics*, ed. Akhtar, 1995 which are both incorporated herein by reference. Sullivan et al., PCT WO 94/02595, further describes the general methods for delivery of enzymatic RNA molecules . These protocols may be utilized for the delivery of virtually any nucleic acid molecule. Nucleic acid molecules may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, nucleic acid molecules may be directly delivered ex vivo to cells or tissues with or without the aforementioned vehicles. Alternatively, the nucleic acid/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of nucleic acid delivery and administration are provided in Sullivan et al., supra and Draper et al., PCT WO93/23569 which have been incorporated by reference herein.

The molecules of the instant invention can be used as pharmaceutical agents. Pharmaceutical agents prevent, inhibit the occurrence, or treat (alleviate a symptom to some extent, preferably all of the symptoms) of a disease state in a patient.

The negatively charged polynucleotides of the invention can be administered (e.g., RNA, DNA or protein) and introduced into a patient by any standard means, with or without stabilizers, buffers, and the like, to form a pharmaceutical composition. When it is desired to use a liposome delivery mechanism, standard protocols for formation of liposomes can be followed. The compositions of the present invention may also be formulated and used as tablets, capsules or elixirs for oral administration; suppositories for rectal administration; sterile solutions; suspensions for injectable administration; and the like.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or patient, preferably a human. Suitable forms, in part, depend upon the use or the route of entry, for example oral, transdermal, or by injection. Such forms should not prevent the composition or formulation to reach a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

By "systemic administration" is meant in vivo systemic absorption or accumulation of drugs in the blood stream followed by distribution throughout the entire body. Administration routes which lead to systemic absorption include, without limitations: intravenous, subcutaneous, intraperitoneal, inhalation, oral, intrapulmonary and intramuscular. Each of these administration routes expose the desired negatively charged polymers, e.g., nucleic acids, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful. This approach may provide enhanced delivery of the drug to target cells by taking advantage of the specificity of macrophage and lymphocyte immune recognition of abnormal cells, such as the cancer cells.

The invention also features the use of a composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev*. 1995, 95, 2601–2627; Ishiwata et al., *Chem. Pharm. Bull*. 1995, 43, 1005–101 1). Such liposomes have been shown to accumulate selectively in tumors, presumably by extravasation and capture in the neovascularized target tissues (Lasic et al., *Science* 1995, 267, 1275–1276; Oku et al., 1995*, Biochim. Biophys*. Acta, 1238, 86–90). Long-circulating liposomes enhance the pharmacokinetics and pharmacodynamics of DNA and RNA, particularly compared to conventional cationic liposomes which are known to accumulate in tissues of the MPS (Liu et al., *J. Biol. Chem*. 1995, 42, 24864–24870; Choi et al., International PCT Publication No. WO 96/10391; Ansell et al., International PCT Publication No. WO 96/10390; Holland et al., International PCT Publication No. WO 96/10392; all of these are incorporated by reference herein). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985) hereby incorporated by reference herein. For example, preservatives, stabilizers, dyes and flavoring agents may be provided. Id. at 1449. These include sodium benzoate, sorbic acid and esters of p-hydroxybenzoic acid. In addition, antioxidants and suspending agents may be used. Id.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 100 mg/kg body weight/day of active ingredients is administered dependent upon potency of the negatively charged polymer.

The nucleic acid molecules of the present invention may also be administered to a patient in combination with other therapeutic compounds to increase the overall therapeutic effect. The use of multiple compounds to treat an indication may increase the beneficial effects while reducing the presence of side effects.

Another means of accumulating high concentrations of a nucleic acid molecule of the invention (e.g., ribozyme) within cells is to incorporate the ribozyme-encoding sequences into a DNA or RNA expression vector. Transcription of the ribozyme sequences are driven from a promoter for eukaryotic RNA polymerase I (pol I), RNA polymerase II (pol II ), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. U S A*, 87, 6743–7; Gao and Huang 1993 *Nucleic Acids Res*., 21, 2867–72; Lieber et al., 1993 *Methods Enzymol*., 217, 47–66; Zhou et al., 1990 *Mol. Cell. Biol*., 10, 4529–37; Thompson et al., 1995 supra). Several investigators have demonstrated that ribozymes or antisese expressed from such promoters can function in mammalian cells (e.g. Izant and Weintraub, 1985 *Science* 229, 345; McGarry and Lindquist, 1986 *Proc. Natl. Acad. Sci. USA* 83, 399; Kashani-Sabet et al., 1992 *Antisense Res. Dev*., 2, 3–15; Ojwang et al., 1992 *Proc. Natl. Acad. Sci. U S A*, 89, 10802–6; Chen et al., 1992 *Nucleic Acids Res*., 20, 4581–9; Yu et al., 1993 *Proc. Natl. Acad. Sci. U S A*, 90, 6340–4; L'Huillier et al., 1992 *EMBO J*. 11,4411–8; Lisziewicz et al., 1993 *Proc*. 237/198 *Natl. Acad. Sci. U. S. A*., 90, 80004; Thompson et al., 1995 *Nucleic Acids Res*. 23, 2259). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors).

In a preferred embodiment of the invention, a transcription unit expressing a ribozyme that cleaves RNAs that encode flt-1, KDR and/or flk-1 are inserted into a plasmid DNA vector or an adenovirus or adeno-associated virus DNA viral vector or a retroviral RNA vector. Viral vectors have been used to transfer genes and lead to either transient or long term gene expression (Zabner et al., 1993 *Cell* 75, 207; Carter, 1992 *Curr. Opi. Biotech*. 3, 533). The adenovirus, AAV or retroviral vector is delivered as recombinant viral particles. The DNA may be delivered alone or complexed with vehicles (as described for RNA above). The recombinant adenovirus or AAV or retroviral particles are locally administered to the site of treatment, e.g. through incubation or inhalation in vivo or by direct application to cells or tissues ex vivo. Retroviral vectors have also been used to express ribozymes in mammalian cells (Ojwang et al., 1992 supra; Thompson et al., 1995 supra).

flt-1, KDR and/or flk-1 are attractive nucleic acid-based therapeutic targets by several criteria. The interaction between VEGF and VEGF-R is well-established. Efficacy can be tested in well-defined and predictive animal models. Finally, the disease conditions are serious and current therapies are inadequate. Whereas protein-based therapies would inhibit VEGF activity nucleic acid-based therapy provides a direct and elegant approach to directly modulate flt-1, KDR and/or flk-1 expression.

Because flt-1 and KDR mRNAs are highly homologous in certain regions, some ribozyme target sites are also homologous (see Table X). In this case, a single ribozyme will target both flt-1 and KDR mRNAs. At partially homologous sites, a single ribozyme can sometimes be designed to accommodate a site on both mRNAs by including G/U base pairing. For example, if there is a G present in a ribozyme target site in KDR mRNA at the same position there is an A in the flt-1 ribozyme target site, the ribozyme can be synthesized with a U at the complementary position and it will bind both to sites. The advantage of one ribozyme that targets both VEGF-R mRNAs is clear, especially in cases where both VEGF receptors may contribute to the progression of angiogenesis in the disease state. "Angiogenesis" refers to formation of new blood vessels which is an essential process in reproduction, development and wound repair. "Tumor angiogenesis" refers to the induction of the growth of blood vessels from surrounding tissue into a solid tumor. Tumor growth and tumor metastasis are dependent on angiogenesis (for a review see Folkman, 1985 supra; Folkman 1990 *J. Natl. Cancer Inst*., 82, 4; Folkman and Shing, 1992 *J. Biol. Chem*. 267, 10931).

Angiogenesis plays an important role in other diseases such as arthritis wherein new blood vessels have been shown to invade the joints and degrade cartilage (Folkman and Shing, supra). "Retinopathy" refers to inflammation of the retina and/or degenerative condition of the retina which may lead to occlusion of the retina and eventual blindness. In "diabetic retinopathy" angiogenesis causes the capillaries in the retina to invade the vitreous resulting in bleeding and blindness which is also seen in neonatal retinopathy (for a review see Folkman, 1985 supra; Folkman 1990 supra; Folkman and Shing, 1992 supra).

EXAMPLE 1 flt-1, KDR and/or flk-1 Ribozymes

By engineering ribozyme motifs applicant has designed several ribozymes directed against flt-1, KDR and/or flk-1 encoded mRNA sequences. These ribozymes were synthesized with modifications that improve their nuclease resistance (Beigelman et al., 1995 *J. Biol. Chem*. 270, 25702) and enhance their activity in cells. The ability of ribozymes to cleave target sequences in vitro was evaluated essentially as described in Thompson et al., PCT Publication No. WO 93/23057; Draper et al., PCT Publication No. WO 95/04818.

EXAMPLE 2

Effect of Ribozymes on the Binding of VEGF to flt-1, KDR and/or flk-1 Receptors

Several common human cell lines are available that express endogenous flt-1, KDR and/or flk-1. flt-1, KDR and/or flk-1 which can be detected easily with monoclonal antibodies. Use of appropriate fluorescent reagents and fluorescence-activated cell-sorting (FACS) will permit direct quantitation of surface flt-1, KDR and/or flk-1 on a cell-by-cell basis. Active ribozymes are expected to directly reduce flt-1, KDR and/or flk-1 expression and thereby reduce VEGF binding to the cells. In this example, human umbelical cord microvascular endothelial cells were used.

Cell Preparation

Plates are coated with 1.5% gelatin and allowed to stand for one hour. Cells (e.g., microvascular endothelial cells derived from human umbilical cord vein) are plated at 20,000 cells/well (24 well plate) in 200 $\mu$l growth media and incubated overnight (~1 doubling) to yield ~40,000 cells (75–80% confluent).

Ribozyme Treatment

Media is removed from cells and the cells are washed two times with 300 $\mu$l 1×PBS: $Ca^{2+}$: $Mg^{2+}$ mixture. A complex of 200–500 nM ribozyme and LipofectAMINE® (3:1 lipid:phosphate ratio) in 200 $\mu$l OptiMEM® (5% FBS) was added to the cells. The cells are incubated for 6 hr (equivalent to 2–3 VEGF-R turnovers).

$^{125}$I VEGF binding assay:

The assay is carried out on ice to inhibit internalization of VEGF during the experiment. The media containing the ribozyme is removed from the cells and the cells are washed twice with 300 $\mu$l 1×PBS: $Ca^{2+}$: $Mg^{2+}$ mixture containing 1% BSA. Appropriate $^{125}$I VEGF solution (100,000 cpm/well, +/−10×) cold 1×PBS, 1% BSA) was applied to the cells. The cells are incubated on ice for 1 h. $^{125}$I VEGF-containing solution is removed and the cells are washed three times with 300 $\mu$l 1×PBS: $Ca^{2+}$: $Mg^{2+}$ mixture containing 1% BSA. To each well 300 $\mu$l of 100 mM Tris-HCl, pH 8.0, 0.5% Triton X-100 was added and the mixture was incubated for 2 min. The $^{125}$I VEGF-binding was quantitated using standard scintillation counting techniques. Percent inhibition was calculated as follows:

Percent Inhibition= cpm $^{1251}$I VEGF Bound by the Ribozyme-treated Samples X100 cpm $^{125}$I VEGF Bound by the Control Sample

EXAMPLE 3

Effect of Hammerhead Ribozymes Targeted Against flt-1 Receptor on the Binding of VEGF Hammerhead ribozymes targeted to twenty sites within flt-1 RNA were synthesized as described above. The sequences of the ribozymes used are shown in Table II; the length of the stem 11 region is 3 bp. The hammerhead ribozymes were chemically modified such that the ribozyme consists of ribose residues at five positions; U4 and U7 positions contain 2'-$NH_2$ modifications, the remaining nucleotide positions contain 2'-O-methyl substitutions; four nucleotides at the 5' terminus contains phosphorothioate substitutions. Additionally, 3' end of the ribozyme contains a 3'-3' linked inverted abasic ribose.

Referring to FIG. 7, the effect of hammerhead ribozymes targeted against flt-1 receptor on the binding of VEGF to flt-1 on the surface of human microvascular endothelial cells is shown. The majority of the ribozymes tested were able to inhibit the expression of flt-1 and thereby were able to inhibit the binding of VEGF.

In order to determine the specificity of ribozymes targeted against flt-1 RNA, the effect of five anti-flt-1 ribozymes on the binding of VEGF, UPA (urokinase plasminogen activator) and FGF (fibroblast growth factor) to their corresponding receptors were assayed. As shown in FIG. 9, there was significant inhibition of VEGF binding to its receptors on cells treated with anti-flt-1 ribozymes. There was no specific inhibition of the binding of UPA and FGF to their corresponding receptors. These data strongly suggest that anti-flt-1 ribozymes specifically cleave flt-1 RNA and not RNAs encoding the receptors for UPA and FGF, resulting in the inhibition of flt-1 receptor expression on the surface of the cells. Thus the ribozymes are responsible for the inhibition of VEGF binding but not the binding of UPA and FGF.

EXAMPLE 4

Effect of Hammerhead Ribozymes Targeted Against KDR Receptor on the Binding of VEGF Hammerhead ribozymes targeted to twenty-one sites within KDR RNA were synthesized as described above. The sequences of the ribozymes used are shown in Table IV; the length of stem II region is 3 bp. The hammerhead ribozymes were chemically modified such that the ribozyme consists of ribose residues at five positions; U4 and U7 positions contain 2'-$NH_2$ modifications, the remaining nucleotide positions contain 2'-O-methyl substitutions; four nucleotides at the 5' terminus contains phosphorothioate substitutions. Additionally, the 3' end of the ribozyme contains a 3'-3' linked inverted abasic deoxyribose.

Referring to FIG. 8, the effect of hammerhead ribozymes targeted against KDR receptor on the binding of VEGF to KDR on the surface of human microvascular endothelial cells is shown. A majority of the ribozymes tested were able to inhibit the expression of KDR and thereby were able to inhibit the binding of VEGF. As a control, the cells were treated with a ribozyme that is not targeted towards KDR RNA (irrel. RZ); there was no specific inhibition of VEGF binding. The results from this control experiment strongly suggest that the inhibition of VEGF binding observed with anti-KDR ribozymes is a ribozyme-mediated inhibition.

EXAMPLE 5

Effect of Ribozymes Targeted Against VEGF Receptors on Cell Proliferation

Cell Preparation:

24-well plates are coated with 1.5% gelatin (porcine skin 300 bloom). After 1 hr, excess gelatin is washed off of the plate. Microvascular endothelial cells are 25 plated at 5,000 cells/well (24 well plate) in 200 $\mu$l growth media. The cells are allowed to grow for ~18 hr (~1 doubling) to yield ~10,000 cells (25–30% confluent).

Ribozyme Treatment:

Media is removed from the cells, and the cells are washed two times with 300 $\mu$l 1×PBS: $Ca^{2+}$: $Mg^{2+}$ mixture.

For anti-flt-1 HH ribozyme experiment (FIG. 12) a complex of 500 nM ribozyme; 15 $\mu$M LFA (3:1 lipid:phosphate ratio) in 200 $\mu$l OptiMEM (5% FCS) media was added to the cells. Incubation of cells is carried out for 6 hr (equivalent to 2–3 VEGF receptor turnovers).

For anti-KDR HH ribozyme experiment (FIG. 13) a complex of 200 nM ribozyme; 5.25 $\mu$M LFA (3:1 lipid:phosphate ratio) in 200 $\mu$l OptiMEM (5% FCS) media was added to the cells. Incubation of cells is carried out for 3 hr.

Proliferation:

After three or six hours, the media is removed from the cells and the cells are washed with 300 μl 1×PBS: $Ca^{2+}$: $Mg^{2+}$ mixture. Maintenance media (contains dialyzed 10% FBS) +/− VEGF or basic FGF at 10 ng/ml is added to the cells. The cells are incubated for 48 or 72 h. The cells are trypsinized and counted (Coulter counter). Trypan blue is added on one well of each treatment as a control.

Figure 12B:
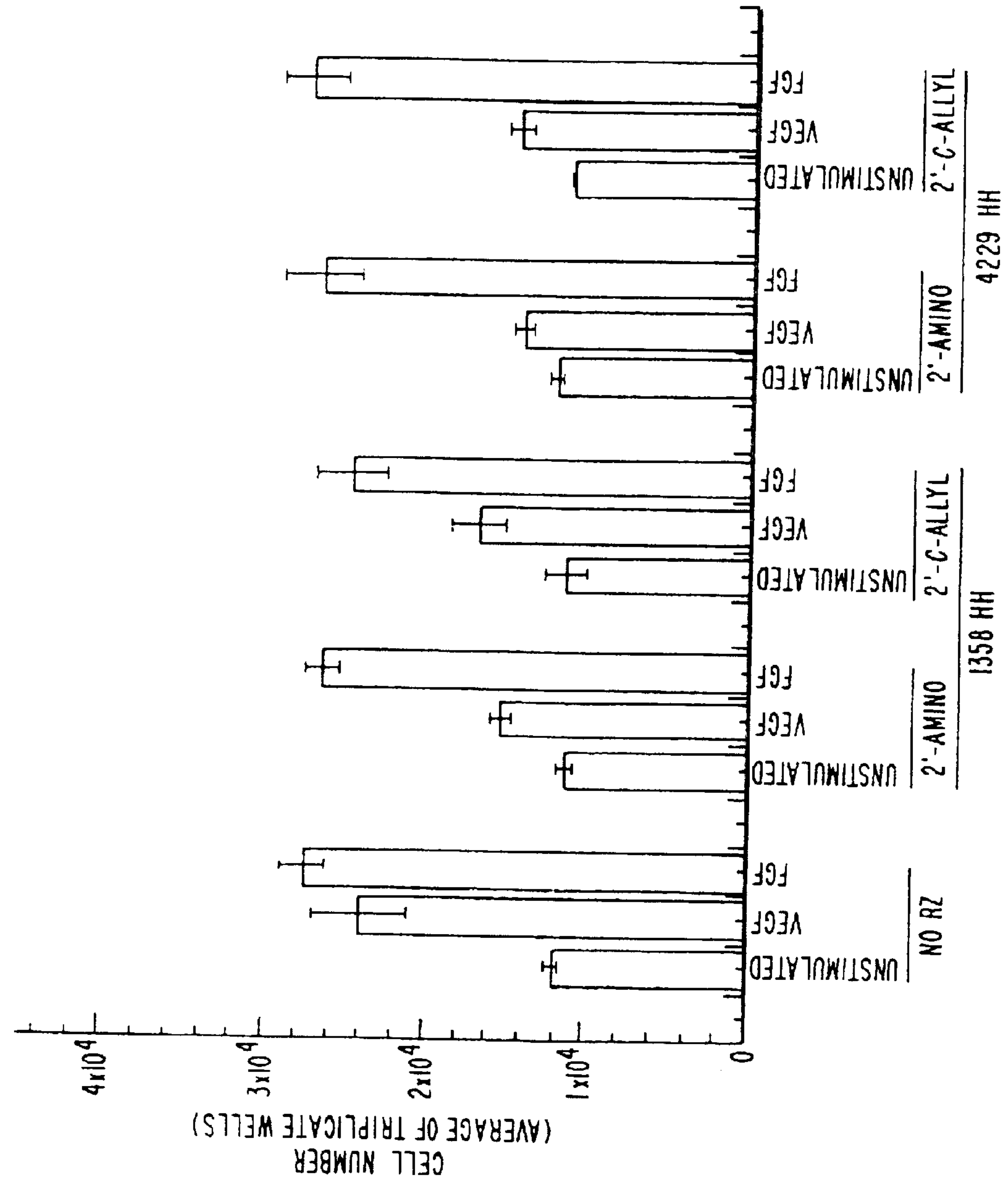

As shown in FIG. 12B, VEGF and basic FGF can stimulate human microvascular endothelial cell proliferation. However, treatment of cells with 1358 HH or 4229 HH ribozymes, targeted against flt-1 mRNA, results in a significant decrease in the ability of VEGF to stimulate endothelial cell proliferation. These ribozymes do not inhibit the FGF-mediated stimulation of endothelial cell proliferation.

Human microvascular endothelial cells were also treated with hammerhead ribozymes targeted against sites 527, 730, 3702 or 3950 within the KDR mRNA. As shown in FIG. 13, all four ribozymes caused significant inhibition of VEGF-mediated induction of cell proliferation. No significant inhibition of cell proliferation was observed when the cells were treated with a hammerhead ribozyme targeted to an irrelevant RNA. Additionally, none of the ribozymes inhibited FGF-mediated stimulation of cell proliferation.

These results strongly suggest that hammerhead ribozymes targeted against either flt-1 or KDR mRNA can specifically inhibit VEGF-mediated induction of endothelial cell proliferation.

EXAMPLE 6

Effect of Antisense Oligonucleotides Targeted Against VEGF Receptors on Cell Proliferation (Colorimetric Assay)

Following are some of the reagents used in the proliferation assay:

Cells: Human aortic endothelial cells (HAEC) from Clonetics®. Cells at early passage are preferably used.

Uptake Medium: EBM (from Clonetics®);1% L-Glutamine;20 mM Hepes;No serum;No antibiotics.

Growth Medium: EGM (from Clonetics®);FBS to 20%;1% L-Glutamine;20 mM Hepes.

Cell Plating: 96-well tissue culture plates are coated with 0.2% gelatin (50 μl/well). The gelatin is incubated in the wells at room temperature for 15–30 minutes. The gelatin is removed by aspiration and the wells are washed with PBS:$Ca^{2+}$: $Mg^{2+}$ mixture. PBS mixture is left in the wells until cells are ready to be added. HAEC cells were detached by trypsin treatment and resuspended at $1.25\times10^4$/ml in growth medium. PBS is removed from plates and 200 μl of cells (i.e. 2.5×103 cells/well) are added to each well. The cells are allowed to grow for 48 hours before the proliferation assay.

Assay: Growth medium is removed from the wells. The cells are washed twice with PBS:$Ca^{2+}$: $Mg^{2+}$ mixture without antibiotics. A formulation of lipidlantisense oligonucleotide (antisense oligonucleotide is used here as a non-limiting example) complex is added to each well (100 μl/well) in uptake medium. The cells are incubated for 2–3 hours at 37° C. in a $CO_2$ incubator. After uptake, 100 μl/well of growth medium is added (gives final FBS concentration of 10%). After approximately 72 hours, 40 μl MTS® stock solution (made as described by manufacturer) was added to each well and incubated at 37° C. for 1–3 hours, depending on the color development. (For this assay, 2 hours was sufficient). The intensity of color formation was determined on a plate reader at 490 nM.

Phosphorothioate-substituted antisense oligodeoxynucleotides were custom synthesized by The Midland Certified Reagent Company®, Midland, Tex. Following non-limiting antisense oligodeoxynucleotides targeted against KDR RNA were used in the proliferation assay: KDR 21 AS: 5'-GCA GCA CCT TGC TCT CCA TCC-3' (Seq ID No. 14208) SCRAMBLED CONTROL: 5'-CTG CCA ACT TCC CAT GCC TGC-3' (Seq ID No. 14209)

As shown in FIG. 10, proliferation of HAEC cells is specifically inhibited by increasing concentrations of the phosphorothioate anti-KDR-antisense oligodeoxynucleotide. The scrambled antisense oligonucleotide is not expected to bind the KDR RNA and therefore is not expected to inhibit KDR expression. As expected, there is no detectable inhibition of proliferation of HAEC cells treated with a phosphorothioate antisense oligonucleotide with scrambled sequence.

EXAMPLE 7

In Vitro Cleavage of flt-1 RNA by Hammerhead Ribozymes

Referring to FIG. 11A, hammerhead ribozymes (HH) targeted against sites 1358 and 4229 within the flt-1 RNA were synthesized as described above.

RNA Cleavage Assay in Vitro:

Substrate RNA was 5' end-labeled using [γ-$^{32}$P] ATP and T4 polynucleotide kinase (US Biochemicals). Cleavage reactions were carried out under ribozyme "excess" conditions. Trace amount (≦1 nM) of 5' end-labeled substrate and 40 nM unlabeled ribozyme were denatured and renatured separately by heating to 90° C. for 2 min and snap-cooling on ice for 10–15 min. The ribozyme and substrate were incubated, separately, at 37° C. for 10 min in a buffer containing 50 mM Tris-HCl and 10 mM $MgCl_2$. The reaction was initiated by mixing the ribozyme and substrate solutions and incubating at 37° C. Aliquots of 5 μl are taken at regular intervals of time and the reaction is quenched by mixing with equal volume of 2× formamide stop mix. The samples are resolved on 20% denaturing polyacrylamide gels. The results were quantified and percentage of target RNA cleaved is plotted as a function of time.

Referring to FIGS. 11B and 11C, hammerhead ribozymes targeted against sites 1358 and 4229 within the flt-1 RNA are capable of cleaving target RNA efficiently in vitro.

EXAMPLE 8

In Vitro Cleavage of KDR RNA by Hammerhead Ribozymes

In this non-limiting example, hammerhead ribozymes targeted against sites 726, 527, 3702 and 3950 within KDR RNA were synthesized as described above. RNA cleavage reactions were carried out in vitro essentially as described under EXAMPLE 7.

Referring to FIGS. 14 and 15, all four ribozymes were able to cleave their cognate target RNA efficiently in a sequence-specific manner.

EXAMPLE 9

In Vitro Cleavage of RNA by Hammerhead Ribozymes Targeted Against Cleavage Sites that are Homologous Between KDR and flt-1 mRNA Because flt-1 and KDR mRNAs are highly homologous in certain regions, some ribozyme target sites are also homologous (see Table X). In this case, a single ribozyme will target both flt-1 and KDR mRNAs. Hammerhead ribozyme (FLT/KDR-I) targeted against one of the homologous sites between flt-1 and KDR (flt-1 site 3388 and KDR site 3151) was synthesized as described above. Ribozymes with either a 3 bp stem II or a 4 bp stem II were synthesized. RNA cleavage reactions were carried out in vitro essentially as described under Example 7.

Referring to FIG. 16, FLT/KDR-I ribozyme with either a 3 or a 4 bp stem II was able to cleave its target RNA efficiently in vitro.

EXAMPLE 10

Effect of Multiple Ribozymes Targeted Against Both flt-1 and KDR RNA on Cell Proliferation Since both flt-1 and KDR receptors of VEGF are involved in angiogenesis, the inhibition of the expression of both of these genes may be an effective approach to inhibit angiogenesis.

Human microvascular endothalial cells were treated with hammerhead ribozymes targeted against sites flt-1 4229 alone, KDR 527 alone, KDR 726 alone, KDR 3950 alone, flt-1 4229+KDR 527, flt-1 4229+KDR 726 or flt-1 4229+KDR 3950. As shown in FIG. 17, all the combinations of active ribozymes (A) caused significant inhibition of VEGF-mediated induction of cell proliferation. No significant inhibition of cell proliferation was observed when the cells were treated with a catalytically inactive (I) hammerhead ribozymes. Additionally, cells treated with ribozymes targeted against both flt-1 and KDR RNAs- flt-1 4229 +KDR 527; flt-1 4229+KDR 726; flt-1 4229+KDR 3950, were able to cause a greater inhibition of VEGF-mediated induction of cell proliferation when compared with individual ribozymes targeted against either flt-1 or KDR RNA (see flt-1 4229 alone; KDR 527 alone; KDR 726 alone; KDR 3950 alone). This strongly suggests that treatment of cells with multiple ribozymes may be a more effective means of inhibition of gene expression.

Animal Models

There are several animal models in which the anti-angiogenesis effect of nucleic acids of the present invention, such as ribozymes, directed against VEGF-R mRNAs can be tested. Typically a corneal model has been used to study angiogenesis in rat and rabbit since recruitment of vessels can easily be followed in this normally avascular tissue (Pandey et al., 1995 *Science* 268: 567–569). In these models, a small Teflon or Hydron disk pretreated with an angiogenesis factor (e.g. bFGF or VEGF) is inserted into a pocket surgically created in the cornea. Angiogenesis is monitored 3 to 5 days later. Ribozymes directed against VEGF-R mRNAs would be delivered in the disk as well, or dropwise to the eye over the time course of the experiment. In another eye model, hypoxia has been shown to cause both increased expression of VEGF and neovascularization in the retina (Pierce et al., 1995 *Proc. Natl. Acad. Sci. USA*. 92: 905–909; Shweiki et al., 1992 *J. Clin. Invest*. 91: 2235–2243).

In human glioblastomas, it has been shown that VEGF is at least partially responsible for tumor angiogenesis (Plate et al., 1992 *Nature* 359, 845). Animal models have been developed in which glioblastoma cells are implanted subcutaneously into nude mice and the progress of tumor growth and angiogenesism is studied (Kim et al., 1993 supra; Millauer et al., 1994 supra).

Another animal model that addresses neovascularization involves Matrigel, an extract of basement membrane that becomes a solid gel when injected subcutaneously (Passaniti et al., 1992 *Lab. Invest*. 67: 519–528). When the Matrigel is supplemented with angiogenesis factors such as VEGF, vessels grow into the Matrigel over a period of 3 to 5 days and angiogenesis can be assessed. Again, ribozymes directed against VEGF-R mRNAs would be delivered in the Matrigel.

Several animal models exist for screening of anti-angiogenic agents. These include corneal vessel formation following corneal injury (Burger et al., 1985 *Cornea* 4: 35–41; Lepri, et al., 1994 *J. Ocular Pharmacol*. 10: 273–280; Ormerod et al., 1990 *Am. J. Pathol*. 137: 1243–1252) or intracorneal growth factor implant (Grant et al., 1993 *Diabetologia* 36: 282–291; Pandey et al. 1995 supra; Zieche et al., 1992 *Lab. Invest*. 67: 711–715), vessel growth into Matrigel matrix containing growth factors (Passaniti et al., 1992 supra), female reproductive organ neovascularization following hormonal manipulation (Shweiki et al., 1993 *Clin. Invest*. 91: 2235–2243), several models involving inhibition of tumor growth in highly vascularized solid tumors (O'Reilly et al., 1994 *Cell* 79: 315–328; Senger et al., 1993 *Cancer and Metas. Rev*. 12: 303–324; Takahasi et al., 1994 *Cancer Res*. 54: 4233–4237; Kim et al., 1993 supra), and transient hypoxia-induced neovascularization in the mouse retina (Pierce et al., 1995 *Proc. Natl. Acad. Sci. USA*. 92: 905–909).

The cornea model, described in Pandey et al. supra, is the most common and well characterized anti-angiogenic agent efficacy screening model. This model involves an avascular tissue into which vessels are recruited by a stimulating agent (growth factor, thermal or alkalai burn, endotoxin). The corneal model would utilize the intrastromal corneal implantation of a Teflon pellet soaked in a VEGF-Hydron solution to recruit blood vessels toward the pellet which can be quantitated using standard microscopic and image analysis techniques. To evaluate their anti-angiogenic efficacy, ribozymes are applied topically to the eye or bound within Hydron on the Teflon pellet itself. This avascular cornea as well as the Matrigel (see below) provide for low background assays. While the corneal model has been performed extensively in the rabbit, studies in the rat have also been conducted.

The mouse model (Passaniti et al., supra) is a non-tissue model which utilizes Matrigel, an extract of basement membrane (Kleinman et al., 1986) or Millipore® filter disk, which can be impregnated with growth factors and anti-angiogenic agents in a liquid form prior to injection. Upon subcutaneous administration at body temperature, the Matrigel or Millipore® filter disk forms a solid implant. VEGF embedded in the Matrigel or Millipore® filter disk would be used to recruit vessels within the matrix of the Matrigel or Millipore® filter disk which can be processed histologically for endothelial cell specific vWF (factor VIII antigen) immunohistochemistry, Trichrome-Masson stain, or hemoglobin content. Like the cornea, the Matrigel or Millipore® filter disk are avascular; however, it is not tissue. In the Matrigel or Millipore® filter disk model, ribozymes are administered within the matrix of the Matrigel or Millipore® filter disk to test their anti-angiogenic efficacy. Thus, delivery issues in this model, as with delivery of ribozymes by Hydron- coated Teflon pellets in the rat cornea model, may be less problematic due to the homogeneous presence of the ribozyme within the respective matrix.

These models offer a distinct advantage over several other angiogenic models listed previously. The ability to use VEGF as a pro-angiogenic stimulus in both models is highly desirable since ribozymes will target only VEGFr mRNA. In other words, the involvement of other non-specific types of stimuli in the cornea and Matrigel models is not advantageous from the standpoint of understanding the pharmacologic mechanism by which the anti-VEGFr mRNA ribozymes produce their effects. In addition, the models will allow for testing the specificity of the anti-VEGFr mRNA ribozymes by using either a- or bFGF as a pro-angiogenic factor. Vessel recruitment using FGF should not be affected in either model by anti-VEGFr mRNA ribozymes. Other models of angiogenesis including vessel formation in the female reproductive system using hormonal manipulation (Shweiki et al., 1993 supra); a variety of vascular solid tumor models which involve indirect correltations with angiogenesis (O'Reilly et al., 1994 supra; Senger et al., 1993 supra; Takahasi et al., 1994 supra; Kim et al., 1993 supra); and retinal neovascularization following transient hypoxia (Pierce et al., 1995 supra) were not selected for efficacy screening due to their non-specific nature, although there is a correlation between VEGF and angiogenesis in these models.

Other model systems to study tumor angiogenesis is reviewed by Folkman, 1985 *Adv. Cancer. Res.* 43, 175.

Use of Murine Models

For a typical systemic study involving 10 mice (20 g each) per dose group, 5 doses (1, 3, 10, 30 and 100 mg/kg daily over 14 days continuous administration), approximately 400 mg of ribozyme, formulated in saline would be used. A similar study in young adult rats (200 g) would require over 4 g. Parallel pharmacokinetic studies may involve the use of similar quantities of ribozymes further justifying the use of murine models. Ribozymes and Lewis lung carcinoma and B-16 melanoma murine models Identifying a common animal model for systemic efficacy testing of ribozymes is an efficient way of screening ribozymes for systemic efficacy.

The Lewis lung carcinoma and B-16 murine melanoma models are well accepted models of primary and metastatic cancer and are used for initial screening of anti-cancer agents. These murine models are not dependent upon the use of immunodeficient mice, are relatively inexpensive, and minimize housing concerns. Both the Lewis lung and B-16 melanoma models involve subcutaneous implantation of approximately $10^6$ tumor cells from metastatically aggressive tumor cell lines (Lewis lung lines 3LL or D122, LLc-LN7; B-16-BL6 melanoma) in C57BL/6J mice. Alternatively, the Lewis lung model can be produced by the surgical implantation of tumor spheres (approximately 0.8 mm in diameter). Metastasis also may be modeled by injecting the tumor cells directly i.v. In the Lewis lung model, microscopic metastases can be observed approximately 14 days following implantation with quantifiable macroscopic metastatic tumors developing within 21–25 days. The B-16 melanoma exhibits a similar time course with tumor neovascularization beginning 4 days following implantation. Since both primary and metastatic tumors exist in these models after 21–25 days in the same animal, multiple measurements can be taken as indices of efficacy. Primary tumor volume and growth latency as well as the number of micro- and macroscopic metastatic lung foci or number of animals exhibiting metastases can be quantitated. The percent increase in lifespan can also be measured. Thus, these models would provide suitable primary efficacy assays for screening systemically administered ribozymes/ribozyme formulations.

In the Lewis lung and B-16 melanoma models, systemic pharmacotherapy with a wide variety of agents usually begins 1–7 days following tumor implantation/inoculation with either continuous or multiple administration regimens. Concurrent pharmacokinetic studies can be performed to determine whether sufficient tissue levels of ribozymes can be achieved for pharmacodynamic effect to be expected. Furthermore, primary tumors and secondary lung metastases can be removed and subjected to a variety of in vitro studies (i.e. target RNA reduction).

flt-1, KDR and/or flk-1 protein levels can be measured clinically or experimentally by FACS analysis. flt-1, KDR and/or flk-1 encoded mRNA levels will be assessed by Northern analysis, RNase-protection, primer extension analysis and/or quantitative RT-PCR. Ribozymes that block flt-1, KDR and/or flk-1 protein encoding mRNAs and therefore result in decreased levels of flt-1, KDR and/or flk-1 activity by more than 20% in vitro will be identified.

Ribozymes and/or genes encoding them are delivered by either free delivery, liposome delivery, cationic lipid delivery, adeno-associated virus vector delivery, adenovirus vector delivery, retrovirus vector delivery or plasmid vector delivery in these animal model experiments (see above).

Patients can be treated by locally administering nucleic acids targeted against VEGF-R by direct injection. Routes of administration may include, but are not limited to, intravascular, intramuscular, subcutaneous, intraarticular, aerosol inhalation, oral (tablet, capsule or pill form), topical, systemic, ocular, intraperitoneal and/or intrathecal delivery.

EXAMPLE 11

Ribozyme-mediated Inhibition of Angiogenesis in vivo

The purpose ot this study was to assess the anti-angiogenic activity of hammerhead ribozymes targeted against flt-1 4229 site in the rat cornea model of VEGF induced angiogenesis (see above). These ribozymes have either active or inactive catalytic core and either bind and cleave or just bind to VEGF-R mRNA of the flt-1 subtype. The active ribozymes, that are able to bind and cleave the target RNA, have been shown to inhibit ($^{125}$1-labeled) VEGF binding in cultured endothelial cells and produce a dose-dependent decrease in VEGF induced endothelial cell proliferation in these cells (see Examples 3–5 above). The catalytically inactive forms of these ribozymes, wherein the ribozymes can only bind to the RNA but cannot catalyze RNA cleavage, fail to show these characteristics. The ribozymes and VEGF were co-delivered using the filter disk method: Nitrocellulose filter disks (Millipore®) of 0.057 diameter were immersed in appropriate solutions and were surgically implanted in rat cornea as described by Pandey et al., supra. This delivery method has been shown to deliver rhodamine-labeled free ribozyme to scleral cells and, in all likelihood cells of the pericorneal vascular plexus. Since the active ribozymes show cell culture efficacy and can be delivered to the target site using the disk method, it is essential that these ribozymes be assessed for in vivo anti-angiogenic activity. The stimulus for angiogenesis in this study was the treatment of the filter disk with 30 $\mu$M VEGF which is implanted within the cornea's stroma. This dose yields reproducible neovascularization stemming from the pericorneal vascular plexus growing toward the disk in a dose-response study 5 days following implant. Filter disks treated only with the vehicle for VEGF show no angiogenic response. The ribozymes was co-adminstered with VEGF on a disk in two different ribozyme concentrations. One concern with the simultaneous administration is that the ribozymes will not be able to inhibit angiogenesis since VEGF receptors can be stimulated. However, we have observed that in low VEGF doses, the neovascular response reverts to normal suggesting that the VEGF stimulus is essential for maintaining the angiogenic response. Blocking the production of VEGF receptors using simultaneous administration of anti-VEGF-R mRNA ribozymes could attenuate the normal neovascularization induced by the filter disk treated with VEGF.

MATERIALS AND METHODS

1. Stock Hammerhead Ribozyme Solutions:
   a. flt-1 4229 (786 μM)—Active
   b. flt-1 4229 (736 μM)—Inactive
2. Experimantal solutions/groups:

| | | |
|---|---|---|
| Group 1 | Solution 1 | Control VEGF solution: 30 μM in 82 μM Tris base |
| Group 2 | Solution 2 | flt-1 4229 (1 μg/μL) in 30 μM VEGF/82 mM Tris base |
| Group 3 | Solution 3 | flt-1 4229 (10 μg/μL) in 30 μM VEGF/82 mM Tris base |
| Group 4 | Solution 4 | No VEGF, flt-1 4229 (10 μg/μL) in 82 mM Tris base |
| Group 5 | Solution 5 | No VEGF, No ribozyme in 82 mM Tris base |

10 eyes per group, 5 animals (Since they have similar molecular weights, the molar concentrations should be essentially similar). Each solution (VEGF and RIBOZYMES) were prepared as a 2× solution for 1:1 mixing for final concentrations above, with the exception of solution 1 in which VEGF was 2× and diluted with ribozyme diluent (sterile water).

3. VEGF Solutions

The 2× VEGF solution (60 μM) was prepared from a stock of 0.82 μg/μL in 50 mM Tris base. 200 μL of VEGF stock was concentrated by speed vac to a final volume of 60.8 μL, for a final concentration of 2.7 μg/μL or 60 μM. Six 10 μL aliquots was prepared for daily mixing. 2X solutions for VEGF and Ribozyme was stored at 4° C. until the day of the surgery. Solutions were mixed for each day of surgery. Original 2X solutions was prepared on the day before the first day of the surgery.

4. Surgical Solutions:

Anesthesia:

stock ketamine hydrochloride 100 mg/mL stock xylazine hydrochloride 20 mg/mL stock acepromazine 10 mg/mL Final anesthesia solution: 50 mg/mL ketamine, 10 mg/mL xylazine, and 0.5 mg/mL acepromazine 5% povidone iodine for opthalmic surgical wash 2% lidocaine (sterile) for opthalmic administration (2 drops per eye) sterile 0.9% NaCl for opthalmic irrigation 5. Surgical Methods:

Standard surgical procedure as described in Pandey et al., supra. Filter disks were incubated in 1 μL of each solution for approximately 30 minutes prior to implantation.

6. Experimental Protocol: The animal cornea were treated with the treatment groups as described above. Animals were allowed to recover for 5 days after treatment with daily observation (scoring 0–3). On the fifth day animals were euthanized and digital images of each eye was obtained for quantitaion using Image Pro Plus. Quantitated neovascular surface area were analyzed by ANOVA followed by two post-hoc tests including Dunnets and Tukey-Kramer tests for significance at the 95% confidence level. Dunnets provide information on the significance between the differences within the means of treatments vs. controls while Tukey-Kramer provide information on the significance of differences within the means of each group.

Results are graphically represented in FIG. 18. As shown in the figure, flt-1 4229 active hammerhead ribozyme at both concentrations was effective at inhibiting angiogenesis while the inactive ribozyme did not show any significant reduction in angiogenesis. A statistically signifiant reduction in neovascular surface area was observed only with active ribozymes. This result clearly shows that the ribozymes are capable of significantly inhibiting angiogenesis in vivo . Specifically, the mechanism of inhibition appears to be by the binding and cleavage of target RNA by ribozymes.

EXAMPLE 12

Bioactivity of Anti-angiogenesis Ribozymes Targeting flt-1 and kdr RNA

MATERIALS AND METHODS

Ribozymes: Hammerhead ribozymes and controls designed to have attenuated activity (attenuated controls) were synthesized and purified as previously described above. The attenuated ribozyme controls maintain the binding arm sequence of the parent ribozyme and thus are still capable of binding to the mRNA target. However, they have two nucleotide changes in the core sequence that substantially reduce their ability to carry out the cleavage reaction. Ribozymes were designed to target Flt-1 or KDR mRNA sites conserved in human, mouse, and rat. In general, ribozymes with binding arms of seven nucleotides were designed and tested. If, however, only six nucleotides surrounding the cleavage site were conserved in all three species, six nucleotide binding arms were used. A subset of ribozyme and attenuated control sequences and modifications are listed in Table XII. Data are presented herein for 2'-$NH_2$ uridine modified ribozymes in cell proliferation studies and for 2'-C-allyl uridine modified ribozymes in RNAse protection, in vitro cleavage and corneal studies.

In vitro ribozyme cleavage assays: In vitro RNA cleavage rates on a 15 nucleotide synthetic RNA substrate were measured as previously described above.

Cell culture: Human dermal microvascular endothelial cells (HMVEC-d, Clonetics Corp.) were maintained at 37° C. in flasks or plates coated with 1.5% porcine skin gelatin (300 bloom, Sigma) in Growth medium (Clonetics Corp.) supplemented with 10–20% fetal bovine serum (FBS, Hyclone). Cells were grown to confluency and used up to the seventh passage. Stimulation medium consisted of 50% Sigma 99 media and 50% RPMI 1640 with L-glutamine and additional supplementation with 10 μg/mL Insulin-Transferrin-Selenium (Gibco BRL) and 10% FBS. Cell growth was stimulated by incubation in Stimulation medium supplemented with 20 ng/mL of either $VEGF_{165}$ or bFGF. $VEGF_{165}$, (165 amino acids) was selected for cell culture and animal studies because it is the predominant form of the four native forms of VEGF generated by alternative mRNA splicing. Cell culture assays were carried out in triplicate.

Ribozyme and Ribozyme/LIPOFECTAMINE™ Formulations

Cell culture: Ribozymes or attenuated controls (50–200 nM) were formulated for cell culture studies and used immediately. Formulations were carried out with LIPOFECTAMINE™ (Gibco BRL) at a 3:1 lipid to phosphate charge ratio in serum-free medium (OPTI-MEM™, Gibco BRL) by mixing for 20 min at room temperature. For example, a 3:1 lipid to phosphate charge ratio was established by complexing 200 nM ribozyme with 10.8 μg/μL LIPOFECTAMINE™ (13.5 μM DOSPA).

In vivo: For corneal studies, lyophilized ribozyme or attenuated controls were resuspended in sterile water at a final stock concentration of 170 μg/μL (highest dose). Lower doses (1.7–50 μ/μL) were prepared by serial dilution in sterile water.

Proliferation assay: HMVEC-d were seeded ($5\times10^3$ cells/well) in 48-well plates (Costar) and incubated 24–30 h in Growth medium at 37° C. After removal of the Growth medium, cells were treated with 50–200 nM LIPOFECTAMINE™ complexes of ribozyme or attenuated controls for 2 h in OPTI-MEM™. The ribozyme/control-containing medium was removed and the cells were washed extensively in 1× PBS. The medium was then replaced with Stimulation medium or Stimulation medium supplemented with 20 ng/mL $VEGF_{165}$ or bFGF. After 48 h, the cell number was determined using a Coulter™ cell counter. Data are presented as cell number per well following 48 h of VEGF stimulation.

RNAse protection assay: HMVEC-d were seeded ($2\times10^5$ cells/well) in 6-well plates (Costar) and allowed to grow 32–36 h in Growth medium at 37° C. Cells were treated with LIPOFECTAMINE™ complexes containing 200 nM ribozyme or attenuated control for 2 h as described under "Proliferation Assay" and then incubated in Growth medium containing 20 ng/mL $VEGF_{165}$ for 24 h. Cells were harvested and an RNAse protection assay was carried out using the Ambion Direct Protect kit and protocol with the exception that 50 mM EDTA was added to the lysis buffer to eliminate the possibility of ribozyme cleavage during sample preparation. Antisense RNA probes targeting portions of Flt-1 and KDR were prepared by transcription in the presence of [$^{32}$P]-UTP. Samples were analyzed on polyacrylamide gels and the level of protected RNA fragments was quantified using a Molecular Dynamics PhosphorImager. The levels of Flt-1 and KDR were normalized to the level of cyclophilin (human cyclophilin probe template, Ambion) in each sample. The coefficient of variation for cyclophilin levels was 11% [265940 cpm±29386 (SD)] for all conditions tested here (i.e. in the presence of either active ribozymes or attenuated controls). Thus, cyclophilin is useful as an internal standard in these studies.

Rat Corneal Pocket Assay of VEGF-induced Angiogenesis

Animal guidelines and anesthesia. Animal housing and experimentation adhered to standards outlined in the 1996 Guide for the Care and Use of Laboratory Animals (National Research Council). Male Sprague Dawley rats (250–300 g) were anesthetized with ketamine (50 mg/kg), xylazine (10 mg/kg), and acepromazine (0.5 mg/kg) administered intramuscularly (im). The level of anesthesia was monitored every 2–3 min by applying hind limb paw pressure and examining for limb withdrawal. Atropine (0.4 mg/kg, im) was also administered to prevent potential corneal reflex-induced bradycardia.

Preparation of VEGF soaked disk. For corneal implantation, 0.57 mm diameter nitrocellulose disks, prepared from 0.45 μm pore diameter nitrocellulose filter membranes (Millipore Corporation), were soaked for 30 min in 1 μL of 30 μM $VEGF_{165}$ in 82 mM Tris-HCl (pH 6.9) in covered petri dishes on ice.

Corneal surgery. The rat corneal model used in this study was a modified from Koch et al. Supra and Pandey et al., supra. Briefly, corneas were irrigated with 0.5% povidone iodine solution followed by normal saline and two drops of 2% lidocaine. Under a dissecting microscope (Leica MZ-6), a stromal pocket was created and a presoaked filter disk (see above) was inserted into the pocket such that its edge was 1 mm from the corneal limbus.

Intraconjunctival injection of test solutions. Immediately after disk insertion, the tip of a 40–50 μm OD injector (constructed in our laboratory) was inserted within the conjunctival tissue 1 mm away from the edge of the corneal limbus that was directly adjacent to the VEGF-soaked filter disk. Six hundred nanoliters of test solution (ribozyme, attenuated control or sterile water vehicle) were dispensed at a rate of 1.2 μL/min using a syringe pump (Kd Scientific). The injector was then removed, serially rinsed in 70% ethanol and sterile water and immersed in sterile water between each injection. Once the test solution was injected, closure of the eyelid was maintained using microaneurism clips until the animal began to recover gross motor activity. Following treatment, animals were warmed on a heating pad at 37° C.

Animal treatment groups/experimental protocol. Ribozymes targeting Flt-1 site 4229 and KDR mRNA site 726 were tested in the corneal model along with their attenuated controls. Five treatment groups were assigned to examine the effects of five doses of each test substance over a dose range of 1–100 μg on VEGF-stimulated angiogenesis. Negative (30 μM VEGF soaked filter disk and intraconjunctival injection of 600 nL sterile water) and no stimulus (Tris-soaked filter disk and intraconjunctival injection of sterile water) control groups were also included. Each group consisted of five animals (10 eyes) receiving the same treatment.

Quantitation of angiogenic response. Five days after disk implantation, animals were euthanized following im administration of 0.4 mg/kg atropine and corneas were digitally imaged. The neovascular surface area (NSA, expressed in pixels) was measured postmortem from blood-filled corneal vessels using computerized morphometry (Image Pro Plus, Media Cybernetics, v2.0). The individual mean NSA was determined in triplicate from three regions of identical size in the area of maximal neovascularization between the filter disk and the limbus. The number of pixels corresponding to the blood-filled corneal vessels in these regions was summated to produce an index of NSA. A group mean NSA was then calculated. Data from each treatment group were normalized to VEGF/ribozyme vehicle-treated control NSA and finally expressed as percent inhibition of VEGF-induced angiogenesis.

Statistics. After determining the normality of treatment group means, group mean percent inhibition of VEGF-induced angiogenesis was subjected to a one-way analysis of variance. This was followed by two post-hoc tests for significance including Dunnett's (comparison to VEGF control) and Tukey-Kramer (all other group mean comparisons) at alpha=0.05. Statistical analyses were performed using JMP v.3.1.6 (SAS Institute).

RESULTS

Figure 19:
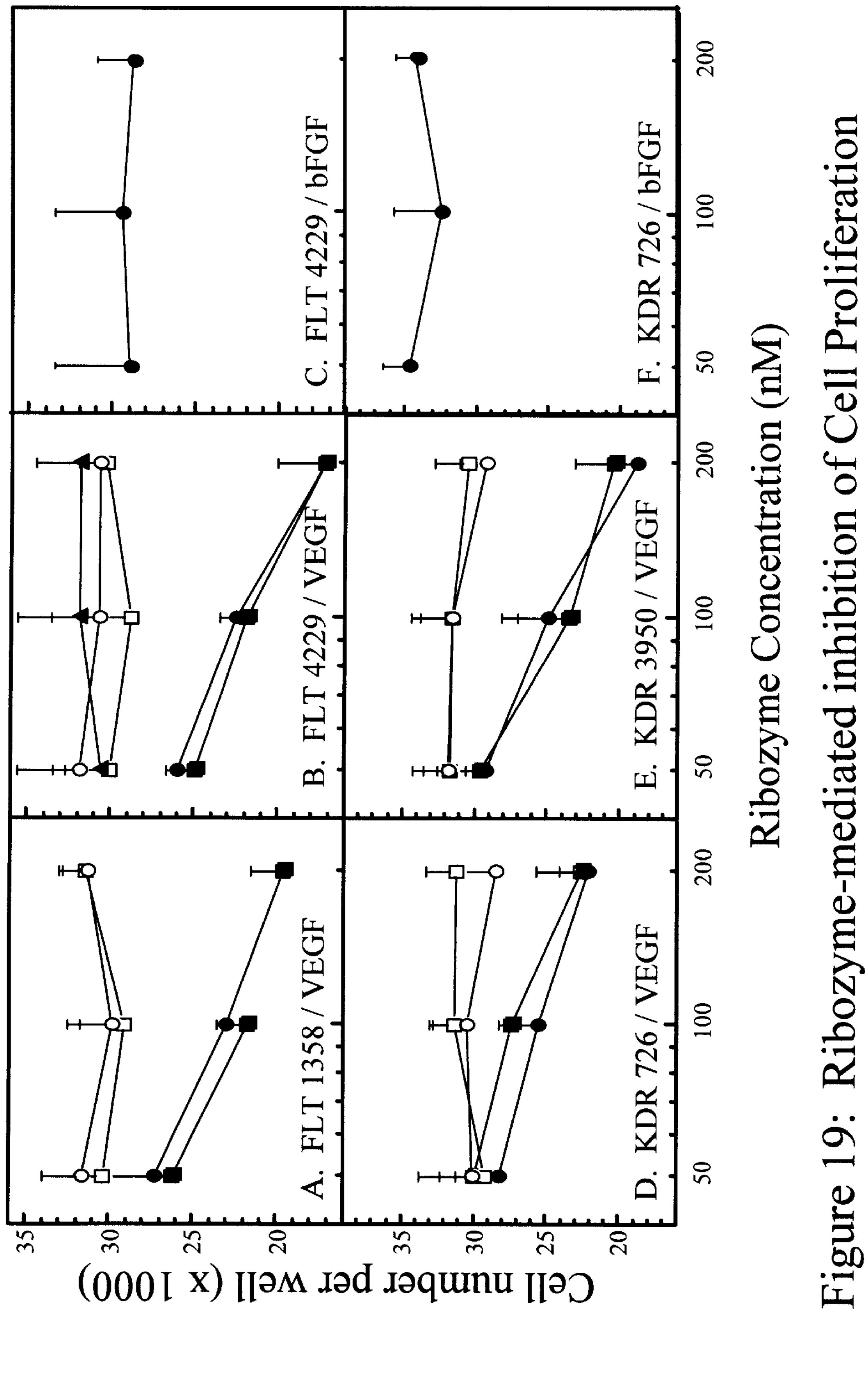

Ribozyme-mediated reduction of VEGF-induced cell proliferation: Ribozyme cleavage of Flt-1 or KDR mRNA should result in a decrease in the density of cell surface VEGF receptors. This decrease should limit VEGF binding and consequently interfere with the mitogenic signaling induced by VEGF. To determine if cell proliferation was impacted by anti-Flt-1 and/or anti-KDR ribozyme treatment, proliferation assays using cultured human microvascular cells were carried out. Ribozymes included in the proliferation assays were initially chosen by their ability to decrease the level of VEGF binding to treated cells (see FIG. 8). In these initial studies, ribozymes targeting 20 sites in the coding region of each mRNA were screened. The most effective ribozymes against two sites in each target (Table XII), Flt-1 sites 1358 and 4229 and KDR sites 726 and 3950, were included in the proliferation assays reported here (FIG. 19). In addition, attenuated analogs of each ribozyme were used as controls (Table XII ). These attenuated controls are still capable of binding to the mRNA target since the binding arm sequence is maintained. However, these controls have two nucleotide changes in the core sequence that substantially reduce their ability to carry out the cleavage reaction.

The antiproliferative effect of active ribozymes targeting two lead sites on each VEGF receptor mRNA is shown in FIG. 19. The active ribozymes tested decreased the relative proliferation of HMVEC-d after VEGF stimulation, an effect that increased with ribozyme concentration. This concentration dependency was not observed following treatment with the attenuated controls designed for these sites. In fact, little or no change in cell growth was noted following treatment with the attenuated controls, even though these controls can still bind to the specific target sequences. At 200 nM, there was a distinct "window" between the anti-proliferative effects of each ribozyme and its attenuated control; a trend also observed at lower doses. This window of inhibition of proliferation (56–77% based on total cells/well) reflects the contribution of ribozyme-mediated activity. In comparison, no effect of anti-Flt-1 or anti-KDR ribozymes was noted on bFGF-stimulated cell proliferation (FIGS. 19C, 19F). Moreover, an irrelevant, but active, ribozyme whose binding sequence is not found in either Flt-1 or KDR mRNA had no effect in this assay (FIG. 19B). These data are consistent with the basic ribozyme mechanism in which binding and cleavage are necessary components. Although the relative surface distribution of Flt-1 and KDR receptors in this cell type is not known, the antiproliferative effects of these ribozymes indicate that, at least in cell culture, both receptors are functionally coupled to proliferation.

Specific reduction of Flt-1 or KDR mRNA by ribozyme treatment: To confirm that anti-Flt-1 and anti-KDR ribozymes reduce their respective mRNA targets, cellular levels of Flt-1 or KDR were quantified using an RNAse protection assay with specific Flt-1 or KDR probes. For each target, one ribozyme/attenuated control pair was chosen for continued study. Data from a representative experiment are shown in FIG. 20. Exposure of HMVEC-d to active ribozyme targeting Flt-1 site 4229 decreased Flt-1 mRNA, but not KDR mRNA. Likewise, treatment with the active ribozyme targeting KDR site 726 decreased KDR, but not Flt-1 mRNA. Both ribozymes decreased the level of their respective target RNA by greater than 50%. The degree of reduction associated with the corresponding attenuated controls was not greater than 13%.

In vitro Activity of Anti-Flt and Anti-KDR Ribozymes.

To confirm further the necessity of an active ribozyme core, in vitro cleavage activities were determined for the Flt-1 site 4229 ribozyme and the KDR site 726 ribozyme as well as their paired attenuated controls. The first order rate constants calculated from the time-course of short substrate cleavage for the anti-Flt-1 ribozyme and its attenuated control were $0.081\pm0.0007$ $min^{-1}$ and $0.001\pm6\times10^{-5}$ $min^{-1}$, respectively. For the anti-KDR ribozyme and its paired control, the first order rate constants were $0.434\pm0.024$ $min^{-1}$ and $0.002\pm1\times10^{-4}$ $min^{-1}$, respectively. Although the attenuated controls retain a very slight level of cleavage activity under these optimized conditions, the decrease in in vitro cleavage activity between each active ribozyme and its paired attenuated control is about two orders of magnitude. Thus, an active core is essential for cleavage activity in vitro and is also necessary for ribozyme activity in cell culture.

Ribozyme-mediated reduction of VEGF-induced angiogenesis in vivo. To assess whether ribozymes targeting VEGF receptor mRNA could impact the complex process of angiogenesis, prototypic anti-Flt-1 and KDR ribozymes that were identified in cell culture studies were screened in a rat corneal pocket assay of VEGF-induced angiogenesis. In this assay, corneas implanted with VEGF-containing filter disks exhibited a robust neovascular response in the corneal region between the disk and the corneal limbus (from which the new vessels emerge). Disks containing a vehicle solution elicited no angiogenic response. In separate studies, intraconjunctival injections of sterile water vehicle did not affect the magnitude of the VEGF-induced angiogenic response. In addition, ribozyme. injections alone did not induce angiogenesis.

The dose-related effects of anti-Flt-1 or KDR ribozymes on the VEGF-induced angiogenic response were then examined. FIGS. 21 and 22 illustrates the quantified antiangiogenic effect of the anti-Flt-1 (site 4229) and KDR (site 726) ribozymes and their attenuated controls over a dose range from 1 to 100 μg, respectively. For both ribozymes, the maximal antiangiogenic response (48 and 36% for anti-Flt-1 and KDR ribozymes, respectively) was observed at a dose of 10 μg.

The anti-Flt-1 ribozyme produced a significantly greater antiangiogenic 30 response than its attenuated control at 3 and 10 μg ($p<0.05$; FIG. 21). Its attenuated control exhibited a small but significant antiangiogenic response at doses above 10 μg compared to vehicle treated VEGF controls ($p<0.05$; FIG. 21). At its maximum, this response was not significantly greater than that observed with the lowest dose of active anti-Flt-1 ribozyme. The anti-KDR ribozyme significantly inhibited angiogenesis from 3 to 30 μg ($p<0.05$; FIG. 22). The anti-KDR attenuated control had no significant effect at any dose tested.

EXAMPLE 13

In vivo Inhibition of Tumor Growth and Metastases by VEGF-R Ribozymes.

A. Lewis Lung Carcinoma Mouse Model: Ribozymes were chemically synthesized as described above. The sequence of ANGIOZYME™ bound to its target RNA is shown in FIG. 26.

The tumors in this study were derived from a cell line (LLC-HM) which gives rise to reproducible numbers of spontaneous lung metastases when propagated in vivo. The LLC-HM line was obtained from Dr. Michael O'Reilly, Harvard University. Tumor neovascularization in Lewis lung carcinoma has been shown to be VEGF-dependent. Tumors from mice bearing LLC-HM (selected for the highly metastatic phenotype by serial propagation) were harvested 20 days post-inoculation. A tumor brei suspension was prepared from these tumors according to standard protocols. On day 0 of the study, $0.5 \times 10^6$ viable LLC-HM tumor cells were injected subcutaneously (sc) into the dorsum or flank of previously untreated mice (100 $\mu$L injectate). Tumors were allowed to grow for a period of 3 days prior to initiating continuous intravenous administration of saline or 30 mg/kg/d ANGIOZYME™ via Alzet mini-pumps. One set of animals was dosed from days 3 to 17, inclusive. Tumor length and width measurements and volumes were calculated according to the formula: Volume=0.5(length)(width)$^2$. At post-inoculation day 25, animals were euthanized and lungs harvested. The number of lung macrometastatic nodules was counted. It should be noted that metastatic foci were quantified 8 days after the cessation of dosing. Ribozyme solutions were prepared to deliver to another set of animals 100, 10, 3, or 1 mg/kg/day of ANGIOZYME™ via Alzet mini-pumps. A total of 10 animals per dose or saline control group were surgically implanted on the left flank with osmotic mini-pumps pre-filled with the respective test solution three days following tumor inoculation. Pumps were attached to indwelling jugular vein catheters.

FIG. 27 shows the antitumor effects of ANGIOZYME™. There is a statistically significant inhibition ($p<0.05$) of primary LLC-HM tumor growth in tumors grown in the flank regions compared to saline control. ANGIOZYME™ significantly reduced ($p<0.05$) the number of lung metastatic foci in animals inoculated either in the flank regions. FIG. 28 illustrates the dose-dependent anti-metastatic effect of ANGIOZYME™ compared to saline control.

B. Mouse Colorectal Cancer Model. KM12L4a-16 is a human colorectal cancer cell line. On day 0 of the study, 0.5×106 KM12L4a-16 cells were implanted into the spleen of nude mice. Three days after tumor inoculation, Alzet minipumps were implanted and continuous subcutaneous delivery of either saline or 12, 36 or 100 mg/kg/day of ANGIOZYME™ was initiated. On day 5, the spleens containing the primary tumors were removed. On day 18, the Alzet minipumps were replaced with fresh pumps so that delivery of saline or ANGIOZYME™ was continuous over a 28 day period from day 3 to day 32. Animals were euthanized on day 41 and the liver tumor burden was evaluated.

Following treatment with 100 mg/kg/day of ANGIOZYME™, there was a significant reduction in the incidence and median number of liver metastasis (FIGS. 29 and 30). In saline-treated animals, the median number of metastases was 101. However, at the high dose of ANGIOZYME™ (100 mg/kg/day), the median number of metastases was zero.

EXAMPLE 14

Effect of ANGIOZYME™ Alone or in Combination with Chemotherapeutic Agents in the Mouse Lewis Lung Carcinoma Model Methods Tumor inoculations. Male C57BL6 mice, age 6 to 8 weeks, were inoculated subcutaneously in the flank with $5 \times 10^5$ LLC-HM cells from brei preparations made from tumors grown in mice.

Ribozymes and controls. The ribozyme and controls tested in this study are given in Table XIII. RPI.4610, also known as ANGIOZYME™, is an anti-Flt-1 ribozyme that targets site 4229 in the human Flt-1 receptor mRNA (EMBL accession no. X51602). The controls tested include RPI.13141, an attenuated version of RPI.4610 in which four nucleotides in the catalytic core are changed so that the cleavage activity is dramatically decreased. RPI.13141, however, maintains the base composition and binding arms of RPI.4610 and so is still capable of binding to the target site. The second control (RPI.13030) also has changes to the catalytic core (three) to inhibit cleavage activity, but in addition the sequence of the binding arms has been scrambled so that it can no longer bind to the target sequence. One nucleotide in the arm of RPI.13030 is also changed to maintain the same base composition as RPI.4610.

Ribozyme administrations. Ribozymes and controls were resuspended in normal saline. Administration was initiated seven days following tumor inoculation. Animals either received a daily subcutaneous injection (30 mg/kg test substance) from day 7 to day 20 or were instrumented with an Alzet osmotic minipump (12 $\mu$/day flow rate) containing a solution of ribozyme or control. Subcutaneous infusion pumps delivered the test substances (30 mg/kg/day) from day 7 to 20 (14-day pumps, 420 mg/kg total test substance) or days 7–34 (28-day pumps, 840 mg/kg total test substance). Where indicated, chemotherapeutic agents were given in combination with ribozyme treatment. Cyclophosphamide was given by ip administration on days 7, 9 and 11 (125 mg/kg). Gemcitabine was given by ip administration on days 8, 11 and 14 (125 mg/kg). Untreated, uninstrumented animals were used as comparison. Five animals were included in each group.

Results

The antiangiogenic ribozyme, ANGIOZYME™, was tested in a model of Lewis lung carcinoma alone and in combination with two chemotherapeutic agents. Previously (see above), 30 mg/kg/day ANGIOZYME™ alone was determined to inhibit both primary tumor growth and lung metastases in a highly metastatic variant of Lewis lung (continuous 14-day iv deliveryvia Alzet minipump, manuscript in preparation).

In this study, 30 mg/kg/day ANGIOZYME™ delivered either as a daily sc bolus injection or as a continuous infusion from an Alzet minipump resulted in a delay in tumor growth (FIG. 23). On average, tumor growth to 500 mm$^3$ was delayed by ~7 days in animals being treated with ANGIOZYME™ compared to an untreated group. Growth of tumors in animals being treated with either of two attenuated controls was delayed by only ~2 days. ANGIOZYME™ delivered by sc bolus was also tested in combination with either Gemcytabine or cyclophosphamide (Fig, 24). Tumor growth delay increased by about 3 days in the presence of combination therapy with ANGIOZYME™ and Gemcytabine over the effects of either treatment alone. The combination of ANGIOZYME™ and cyclophosphamide did not increase tumor growth delay over that of cyclophosphamide alone, however, suboptimal doses of cyclophosphamide were not included in this study. Neither of the attenuated controls increased the effect of the chemotherapeutic agents.

The effect of ANGIOZYME™ on metastases to the lung was also determined in the presence and absence of additional chemotherapeutic treatment. Macrometastases to the lungs were counted in two animals in each treatment group on day 20. Data for the daily sc administration of 30 mg/kg ANGIOZYME™ alone or with Gemcytabine or cyclophosphamide is given in FIG. 25. In the presence of ANGIOZYME™, with or without a chemotherapeutic agent, the lung metastases were reduced to zero. Treatment with either Gemcytabine or cyclophosphamide alone (mean number of metastases 4.5 and 4, respectively) were not as effective as ANGIOZYME™ alone or when used in combination with ANGIOZYME™. Neither of the attenuated controls increased the effect of the chemotherapeutic agents.

The effect on metastases to the lung was also determined following continuous treatment with ANGIOZYME™. At day 20, an average of ~8 macrometastases were noted in the treatment groups which had been instrumented with Alzet minipumps (either 14- or 28-day pumps). This is a decrease in metastases of ~50% from the untreated group. Since ANGIOZYME™ delivered by a daily sc bolus resulted in zero metastases (FIG. 4) in the two animals counted, it is possible that the additional burden of being instrumented with the minipump contributes to a slightly decreased response to ANGIOZYME™.

Gemcytabine and cyclophosphamide are non-limiting examples of chemotherapeutic agents that can be combined with or used in conjunction with the nucleic acid molecules (e.g. ribozymes and antisense molecules) of the instant invention. Those skilled in the art will recognize that other anti-angiogenic and/or anti-cancer compounds and therapies can be similarly be readily combined with the nucleic acid molecules of the instant invention (e.g. ribozymes and antisense molecules) are are hence within the scope of the instant invention. Such compounds and therapies are well known in the art (see for example *Cancer: Principles and Pranctice of Oncology*, Volumes 1 and 2, eds Devita, V. T., Hellman, S., and Rosenberg, S. A., J. B. Lippincott Company, Philadelphia, USA; incorporated herein by reference) and include, without limitations, antifolates; fluoropyrimidines; cytarabine; purine analogs; adenosine analogs; amsacrine; topoisomerase I inhibitors; anthrapyrazoles; retinoids; antibiotics such as bleomycin, anthacyclins, mitomycin C, dactinomycin, and mithramycin; hexamethylmelamine; dacarbazine; I-asperginase; platinum analogs; alkylating agents such as nitrogen mustard, melphalan, chlorambucil, busulfan, ifosfamide, 4-hydroperoxycyclophosphamide, nitrosoureas, thiotepa; plant derived compounds such as vinca alkaloids, epipodophyllotoxins, taxol; Tomaxifen; radiation therapy; surgery; nutritional supplements; gene therapy; radiotherapy such as 3D-CRT; immunotoxin therapy such as ricin, monoclonal antibodies herceptin; and the like.

Indications

1) Tumor angiogenesis: Angiogenesis has been shown to be necessary for tumors to grow into pathological size (Folkman, 1971, *PNAS* 76, 5217–5221; Wellstein & Czubayko, 1996, *Breast Cancer Res and Treatment* 38, 109–119). In addition, it allows tumor cells to travel through the circulatory system during metastasis. Increased levels of gene expression of a number of angiogenic factors such as vascular endothelial growth factor (VEGF) have been reported in vascularized and edema-associated brain tumors (Berkman et al., 1993 *J. Clini. Invest.* 91, 153). A more direct demostration of the role of VEGF in tumor angiogenesis was demonstrated by Jim Kim et al., 1993 *Nature* 362,841 wherein, monoclonal antibodies against VEGF were successfully used to inhibit the growth of rhabdomyosarcoma, glioblastoma multiforme cells in nude mice. Similarly, expression of a dominant negative mutated form of the flt-1 VEGF receptor inhibits vascularization induced by human glioblastoma cells in nude mice (Millauer et al., 1994, *Nature* 367, 576).

2) Ocular diseases: Neovascularization has been shown to cause or exacerbate ocular diseases including but not limited to, macular degeneration, neovascular glaucoma, diabetic retinopathy, myopic degeneration, and trachoma (Norrby, 1997, *APMIS* 105, 417437). Aiello et al., 1994 *New Engl. J. Med.* 331, 1480, showed that the ocular fluid, of a majority of patients suffering from diabetic retinopathy and other retinal disorders, contains a high concentration of VEGF. Miller et al., 1994 *Am. J. Pathol.* 145, 574, reported elevated levels of VEGF mRNA in patients suffering from retinal ischemia. These observations support a direct role for VEGF in ocular diseases. Other factors including those that stimulate VEGF synthesis may also contribute to these indications.

3) Dermatological Disorders: Many indications have been identified which may by angiogenesis dependent including but not limited to psoriasis, verruca vulgaris, angiofibroma of tuberous sclerosis, pot-wine stains, Sturge Weber syndrome, Kippel-Trenaunay-Weber syndrome, and Osler-Weber-Rendu syndrome (Norrby, supra). Intradermal injection of the angiogenic factor b-FGF demonstrated angiogenesis in nude mice (Weckbecker et al., 1992, *Angiogenesis: Key principles-Science-Technology-Medicine*, ed R. Steiner) Detmar et al., 1994 *J. Exp. Med.* 180, 1141 reported that VEGF and its receptors were over-expressed in psoriatic skin and psoriatic dermal microvessels, suggesting that VEGF plays a significant role in psoriasis.

4) Rheumatoid arthritis: Immunohistochemistry and in situ hybridization studies on tissues from the joints of patients suffering from rheumatoid arthritis show an increased level of VEGF and its receptors (Fava et al., 1994 *J. Exp. Med.* 180, 341). Additionally, Koch et al., 1994 *J. Immunol.* 152, 4149, found that VEGF-specific antibodies were able to significantly reduce the mitogenic activity of synovial tissues from patients suffering from rheumatoid arthritis. These observations support a direct role for VEGF in rheumatoid arthritis. Other angiogenic factors including those of -the present invention may also be involved in arthritis.

Diagnostic Uses

The nucleic acid molecules of this invention (e.g., ribozymes) may be used as diagnostic tools to examine genetic drift and mutations within diseased cells or to detect the presence of flt-1, KDR and/or flk-1 RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with flt-1, KDR and/or flk-1 related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., flt-1, KDR and/or flk-1) is adequate to establish risk. If probes of comparable, specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Additional Uses

Potential usefulness of sequence-specific enzymatic nucleic acid molecules of the instant invention might have many of the same applications for the study of RNA that DNA restriction endonucleases have for the study of DNA (Nathans et al., 1975 *Ann. Rev. Biochem.* 44:273). For example, the pattern of restriction fragments could be used to establish sequence relationships between two related RNAs, and large RNAs could be specifically cleaved to fragments of a size more useful for study. The ability to engineer sequence specificity of the enzymatic nucleic acid molecule is ideal for cleavage of RNAs of unknown sequence. Applicant describes the use of nucleic acid molecules to down-regulate gene expression of target genes in bacterial, microbial, fungal, viral, and eukaryotic systems including plant, or mammalian cells.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

RECEIVED
AUG 23 2001
TECH CENTER 1600/2900

71

OIPE JC48
AUG 15 2001
PATENT & TRADEMARK OFFICE

RECEIVED
AUG 24 2001
TECH CENTER 1600/2900

TABLE I

Characteristics of Ribozymes

Group I Introns
Size: ~200 to >1000 nucleotides.
Requires a U in the target sequence immediately 5' of the cleavage site.
Binds 4-6 nucleotides at 5' side of cleavage site.
Over 75 known members of this class. Found in *Tetrahymena thermophila* rRNA, fungal mitochondria, chloroplasts, phage T4, blue-green algae, and others.

RNAseP RNA (M1 RNA)
Size: ~290 to 400 nucleotides.
RNA portion of a ribonucleoprotein enzyme. Cleaves tRNA precursors to form mature tRNA.
Roughly 10 known members of this group all are bacterial in origin.

Hammerhead Ribozyme
Size: ~13 to 40 nucleotides.
Requires the target sequence UH immediately 5' of the cleavage site.
Binds a variable number of nucleotides on both sides of the cleavage site.
14 known members of this class. Found in a number of plant pathogens (virusoids) that use RNA as the infectious agent (Figure 1 and 2)

Hairpin Ribozyme
Size: ~50 nucleotides.
Requires the target sequence GUC immediately 3' of the cleavage site.
Binds 4-6 nucleotides at 5' side of the cleavage site and a variable number to the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent (Figure 3).

Hepatitis Delta Virus (HDV) Ribozyme
Size: 50 - 60 nucleotides (at present).
Sequence requirements not fully determined.
Binding sites and structural requirements not fully determined, although no sequences 5' of cleavage site are required.
Only 1 known member of this class. Found in human HDV (Figure 4).

***Neurospora* VS RNA Ribozyme**

Size: ~144 nucleotides (at present)

72

72

Cleavage of target RNAs recently demonstrated.
Sequence requirements not fully determined.
Binding sites and structural requirements not fully determined. Only 1 known member of this class. Found in *Neurospora* VS RNA (Figure 5).

**Table II: Human *flt*1 VEGF Receptor-Hammerhead Ribozyme and Substrate Sequence** 237.198

| nt. Position | HH Ribozyme | Rz Seq ID No. | Substrate | Seq ID No. |
|---|---|---|---|---|
| 10 | GCCGAGAG CUGAUGA GCCGUUAGGC GAA AGUGUCCG | 7143 | CGGACACUC CUCUCGGC | 1 |
| 13 | GGAGCCGA CUGAUGA GCCGUUAGGC GAA AGGAGUGU | 7144 | ACACUCCUC UCGGCUCC | 2 |
| 15 | GAGGAGCC CUGAUGA GCCGUUAGGC GAA AGAGGAGU | 7145 | ACUCCUCUC GGCUCCUC | 3 |
| 20 | CCGGGGAG CUGAUGA GCCGUUAGGC GAA AGCCGAGA | 7146 | UCUCGGCUC CUCCCCGG | 4 |
| 23 | CUGCCGGG CUGAUGA GCCGUUAGGC GAA AGGAGCCG | 7147 | CGGCUCCUC CCCGGCAG | 5 |
| 43 | CCCGCUCC CUGAUGA GCCGUUAGGC GAA AGCCGCCG | 7148 | CGGCGGCUC GGAGCGGG | 6 |
| 54 | GAGCCCCG CUGAUGA GCCGUUAGGC GAA AGCCCGCU | 7149 | AGCGGGCUC CGGGGCUC | 7 |
| 62 | CUGCACCC CUGAUGA GCCGUUAGGC GAA AGCCCCGG | 7150 | CCGGGGCUC GGGUGCAG | 8 |
| 97 | CCCCGGGU CUGAUGA GCCGUUAGGC GAA AUCCUCGC | 7151 | GCGAGGAUU ACCCGGGG | 9 |
| 98 | UCCCCGGG CUGAUGA GCCGUUAGGC GAA AAUCCUCG | 7152 | CGAGGAUUA CCCGGGGA | 10 |
| 113 | CAGGAGAC CUGAUGA GCCGUUAGGC GAA ACCACUUC | 7153 | GAAGUGGUU GUCUCCUG | 11 |
| 116 | AGCCAGGA CUGAUGA GCCGUUAGGC GAA ACAACCAC | 7154 | GUGGUUGUC UCCUGGCU | 12 |
| 118 | CCAGCCAG CUGAUGA GCCGUUAGGC GAA AGACAACC | 7155 | GGUUGUCUC CUGGCUGG | 13 |
| 145 | CGCGCCCU CUGAUGA GCCGUUAGGC GAA AGCGCCCG | 7156 | CGGGCGCUC AGGGCGCG | 14 |
| 185 | GGCCGCCA CUGAUGA GCCGUUAGGC GAA AGUCCGUC | 7157 | GACGGACUC UGGCGGCC | 15 |
| 198 | CGGCCAAC CUGAUGA GCCGUUAGGC GAA ACCCGGCC | 7158 | GGCCGGGUC GUUGGCCG | 16 |
| 201 | CCCCGGCC CUGAUGA GCCGUUAGGC GAA ACGACCCG | 7159 | CGGGUCGUU GGCCGGGG | 17 |
| 240 | GUGAGCGC CUGAUGA GCCGUUAGGC GAA ACGCGGCC | 7160 | GGCCGCGUC GCGCUCAC | 18 |
| 246 | ACCAUGGU CUGAUGA GCCGUUAGGC GAA AGCGCGAC | 7161 | GUCGCGCUC ACCAUGGU | 19 |
| 255 | CAGUAGCU CUGAUGA GCCGUUAGGC GAA ACCAUGGU | 7162 | ACCAUGGUC AGCUACUG | 20 |
| 260 | UGUCCCAG CUGAUGA GCCGUUAGGC GAA AGCUGACC | 7163 | GGUCAGCUA CUGGGACA | 21 |
| 276 | CACAGCAG CUGAUGA GCCGUUAGGC GAA ACCCCGGU | 7164 | ACCGGGGUC CUGCUGUG | 22 |
| 294 | AGACAGCU CUGAUGA GCCGUUAGGC GAA AGCAGCGC | 7165 | GCGCUGCUC AGCUGUCU | 23 |
| 301 | GAGAAGCA CUGAUGA GCCGUUAGGC GAA ACAGCUGA | 7166 | UCAGCUGUC UGCUUCUC | 24 |
| 306 | CCUGUGAG CUGAUGA GCCGUUAGGC GAA AGCAGACA | 7167 | UGUCUGCUU CUCACAGG | 25 |
| 307 | UCCUGUGA CUGAUGA GCCGUUAGGC GAA AAGCAGAC | 7168 | GUCUGCUUC UCACAGGA | 26 |
| 309 | GAUCCUGU CUGAUGA GCCGUUAGGC GAA AGAAGCAG | 7169 | CUGCUUCUC ACAGGAUC | 27 |
| 317 | CUGAACUA CUGAUGA GCCGUUAGGC GAA AUCCUGUG | 7170 | CACAGGAUC UAGUUCAG | 28 |
| 319 | ACCUGAAC CUGAUGA GCCGUUAGGC GAA AGAUCCUG | 7171 | CAGGAUCUA GUUCAGGU | 29 |

| | | | | |
|---|---|---|---|---|
| 322 | UGAACCUG CUGAUGA GCCGUUAGGC GAA ACUAGAUC | 7172 | GAUCUAGUU CAGGUUCA | 30 |
| 323 | UUGAACCU CUGAUGA GCCGUUAGGC GAA AACUAGAU | 7173 | AUCUAGUUC AGGUUCAA | 31 |
| 328 | UAAUUUUG CUGAUGA GCCGUUAGGC GAA ACCUGAAC | 7174 | GUUCAGGUU CAAAAUUA | 32 |
| 329 | UUAAUUUU CUGAUGA GCCGUUAGGC GAA AACCUGAA | 7175 | UUCAGGUUC AAAAUUAA | 33 |
| 335 | GAUCUUUU CUGAUGA GCCGUUAGGC GAA AUUUUGAA | 7176 | UUCAAAAUU AAAAGAUC | 34 |
| 336 | GGAUCUUU CUGAUGA GCCGUUAGGC GAA AAUUUUGA | 7177 | UCAAAAUUA AAAGAUCC | 35 |
| 343 | CAGUUCAG CUGAUGA GCCGUUAGGC GAA AUCUUUUA | 7178 | UAAAAGAUC CUGAACUG | 36 |
| 355 | GCCUUUUA CUGAUGA GCCGUUAGGC GAA ACUCAGUU | 7179 | AACUGAGUU UAAAAGGC | 37 |
| 356 | UGCCUUUU CUGAUGA GCCGUUAGGC GAA AACUCAGU | 7180 | ACUGAGUUU AAAAGGCA | 38 |
| 357 | GUGCCUUU CUGAUGA GCCGUUAGGC GAA AAACUCAG | 7181 | CUGAGUUUA AAAGGCAC | 39 |
| 375 | GCUUGCAU CUGAUGA GCCGUUAGGC GAA AUGUGCUG | 7182 | CAGCACAUC AUGCAAGC | 40 |
| 400 | GCAUUGGA CUGAUGA GCCGUUAGGC GAA AUGCAGUG | 7183 | CACUGCAUC UCCAAUGC | 41 |
| 402 | CUGCAUUG CUGAUGA GCCGUUAGGC GAA AGAUGCAG | 7184 | CUGCAUCUC CAAUGCAG | 42 |
| 427 | AGACCAUU CUGAUGA GCCGUUAGGC GAA AUGGGCUG | 7185 | CAGCCCAUA AAUGGUCU | 43 |
| 434 | CAGGCAAA CUGAUGA GCCGUUAGGC GAA ACCAUUUA | 7186 | UAAAUGGUC UUUGCCUG | 44 |
| 436 | UUCAGGCA CUGAUGA GCCGUUAGGC GAA AGACCAUU | 7187 | AAUGGUCUU UGCCUGAA | 45 |
| 437 | UUUCAGGC CUGAUGA GCCGUUAGGC GAA AAGACCAU | 7188 | AUGGUCUUU GCCUGAAA | 46 |
| 454 | GCUUUCCU CUGAUGA GCCGUUAGGC GAA ACUCACCA | 7189 | UGGUGAGUA AGGAAAGC | 47 |
| 477 | GAUUUAGU CUGAUGA GCCGUUAGGC GAA AUGCUCAG | 7190 | CUGAGCAUA ACUAAAUC | 48 |
| 481 | GGCAGAUU CUGAUGA GCCGUUAGGC GAA AGUUAUGC | 7191 | GCAUAACUA AAUCUGCC | 49 |
| 485 | CACAGGCA CUGAUGA GCCGUUAGGC GAA AUUUAGUU | 7192 | AACUAAAUC UGCCUGUG | 50 |
| 512 | UACUGCAG CUGAUGA GCCGUUAGGC GAA AUUGUUUG | 7193 | CAAACAAUU CUGCAGUA | 51 |
| 513 | GUACUGCA CUGAUGA GCCGUUAGGC GAA AAUUGUUU | 7194 | AAACAAUUC UGCAGUAC | 52 |
| 520 | GGUUAAAG CUGAUGA GCCGUUAGGC GAA ACUGCAGA | 7195 | UCUGCAGUA CUUUAACC | 53 |
| 523 | CAAGGUUA CUGAUGA GCCGUUAGGC GAA AGUACUGC | 7196 | GCAGUACUU UAACCUUG | 54 |
| 524 | UCAAGGUU CUGAUGA GCCGUUAGGC GAA AAGUACUG | 7197 | CAGUACUUU AACCUUGA | 55 |
| 525 | UUCAAGGU CUGAUGA GCCGUUAGGC GAA AAAGUACU | 7198 | AGUACUUUA ACCUUGAA | 56 |
| 530 | CUGUGUUC CUGAUGA GCCGUUAGGC GAA AGGUUAAA | 7199 | UUUAACCUU GAACACAG | 57 |
| 541 | GUUUGCUU CUGAUGA GCCGUUAGGC GAA AGCUGUGU | 7200 | ACACAGCUC AAGCAAAC | 58 |
| 560 | AGCUGUAG CUGAUGA GCCGUUAGGC GAA AGCCAGUG | 7201 | CACUGGCUU CUACAGCU | 59 |
| 561 | CAGCUGUA CUGAUGA GCCGUUAGGC GAA AAGCCAGU | 7202 | ACUGGCUUC UACAGCUG | 60 |
| 563 | UGCAGCUG CUGAUGA GCCGUUAGGC GAA AGAAGCCA | 7203 | UGGCUUCUA CAGCUGCA | 61 |
| 575 | CAGCUAGA CUGAUGA GCCGUUAGGC GAA AUUUGCAG | 7204 | CUGCAAAUA UCUAGCUG | 62 |

| | | | | |
|---|---|---|---|---|
| 577 | UACAGCUA CUGAUGA GCCGUUAGGC GAA AUAUUUGC | 7205 | GCAAAUAUC UAGCUGUA | 63 |
| 579 | GGUACAGC CUGAUGA GCCGUUAGGC GAA AGAUAUUU | 7206 | AAAUAUCUA GCUGUACC | 64 |
| 585 | GAAGUAGG CUGAUGA GCCGUUAGGC GAA ACAGCUAG | 7207 | CUAGCUGUA CCUACUUC | 65 |
| 589 | CUUUGAAG CUGAUGA GCCGUUAGGC GAA AGGUACAG | 7208 | CUGUACCUA CUUCAAAG | 66 |
| 592 | CUUCUUUG CUGAUGA GCCGUUAGGC GAA AGUAGGUA | 7209 | UACCUACUU CAAAGAAG | 67 |
| 593 | UCUUCUUU CUGAUGA GCCGUUAGGC GAA AAGUAGGU | 7210 | ACCUACUUC AAAGAAGA | 68 |
| 614 | AGAUUGCA CUGAUGA GCCGUUAGGC GAA AUUCUGUU | 7211 | AACAGAAUC UGCAAUCU | 69 |
| 621 | AAUAUAUA CUGAUGA GCCGUUAGGC GAA AUUGCAGA | 7212 | UCUGCAAUC UAUAUAUU | 70 |
| 623 | UAAAUAUA CUGAUGA GCCGUUAGGC GAA AGAUUGCA | 7213 | UGCAAUCUA UAUAUUUA | 71 |
| 625 | AAUAAAUA CUGAUGA GCCGUUAGGC GAA AUAGAUUG | 7214 | CAAUCUAUA UAUUUAUU | 72 |
| 627 | CUAAUAAA CUGAUGA GCCGUUAGGC GAA AUAUAGAU | 7215 | AUCUAUAUA UUUAUUAG | 73 |
| 629 | CACUAAUA CUGAUGA GCCGUUAGGC GAA AUAUAUAG | 7216 | CUAUAUAUU UAUUAGUG | 74 |
| 630 | UCACUAAU CUGAUGA GCCGUUAGGC GAA AAUAUAUA | 7217 | UAUAUAUUU AUUAGUGA | 75 |
| 631 | AUCACUAA CUGAUGA GCCGUUAGGC GAA AAAUAUAU | 7218 | AUAUAUUUA UUAGUGAU | 76 |
| 633 | GUAUCACU CUGAUGA GCCGUUAGGC GAA AUAAAUAU | 7219 | AUAUUUAUU AGUGAUAC | 77 |
| 634 | UGUAUCAC CUGAUGA GCCGUUAGGC GAA AAUAAAUA | 7220 | UAUUUAUUA GUGAUACA | 78 |
| 640 | UCUACCUG CUGAUGA GCCGUUAGGC GAA AUCACUAA | 7221 | UUAGUGAUA CAGGUAGA | 79 |
| 646 | GAAAGGUC CUGAUGA GCCGUUAGGC GAA ACCUGUAU | 7222 | AUACAGGUA GACCUUUC | 80 |
| 652 | CUCUACGA CUGAUGA GCCGUUAGGC GAA AGGUCUAC | 7223 | GUAGACCUU UCGUAGAG | 81 |
| 653 | UCUCUACG CUGAUGA GCCGUUAGGC GAA AAGGUCUA | 7224 | UAGACCUUU CGUAGAGA | 82 |
| 654 | AUCUCUAC CUGAUGA GCCGUUAGGC GAA AAAGGUCU | 7225 | AGACCUUUC GUAGAGAU | 83 |
| 657 | UACAUCUC CUGAUGA GCCGUUAGGC GAA ACGAAAGG | 7226 | CCUUUCGUA GAGAUGUA | 84 |
| 665 | UUUCACUG CUGAUGA GCCGUUAGGC GAA ACAUCUCU | 7227 | AGAGAUGUA CAGUGAAA | 85 |
| 675 | AUUUCGGG CUGAUGA GCCGUUAGGC GAA AUUUCACU | 7228 | AGUGAAAUC CCCGAAAU | 86 |
| 684 | AUGUGUAU CUGAUGA GCCGUUAGGC GAA AUUUCGGG | 7229 | CCCGAAAUU AUACACAU | 87 |
| 685 | CAUGUGUA CUGAUGA GCCGUUAGGC GAA AAUUUCGG | 7230 | CCGAAAUUA UACACAUG | 88 |
| 687 | GUCAUGUG CUGAUGA GCCGUUAGGC GAA AUAAUUUC | 7231 | GAAAUUAUA CACAUGAC | 89 |
| 711 | GGAAUGAC CUGAUGA GCCGUUAGGC GAA AGCUCCCU | 7232 | AGGGAGCUC GUCAUUCC | 90 |
| 714 | CAGGGAAU CUGAUGA GCCGUUAGGC GAA ACGAGCUC | 7233 | GAGCUCGUC AUUCCCUG | 91 |
| 717 | CGGCAGGG CUGAUGA GCCGUUAGGC GAA AUGACGAG | 7234 | CUCGUCAUU CCCUGCCG | 92 |
| 718 | CCGGCAGG CUGAUGA GCCGUUAGGC GAA AAUGACGA | 7235 | UCGUCAUUC CCUGCCGG | 93 |
| 729 | GGUGACGU CUGAUGA GCCGUUAGGC GAA ACCCGGCA | 7236 | UGCCGGGUU ACGUCACC | 94 |
| 730 | AGGUGACG CUGAUGA GCCGUUAGGC GAA AACCCGGC | 7237 | GCCGGGUUA CGUCACCU | 95 |

| | | | | |
|---|---|---|---|---|
| 734 | UGUUAGGU CUGAUGA GCCGUUAGGC GAA ACGUAACC | 7238 | GGUUACGUC ACCUAACA | 96 |
| 739 | AGUGAUGU CUGAUGA GCCGUUAGGC GAA AGGUGACG | 7239 | CGUCACCUA ACAUCACU | 97 |
| 744 | GUAACAGU CUGAUGA GCCGUUAGGC GAA AUGUUAGG | 7240 | CCUAACAUC ACUGUUAC | 98 |
| 750 | UUUAAAGU CUGAUGA GCCGUUAGGC GAA ACAGUGAU | 7241 | AUCACUGUU ACUUUAAA | 99 |
| 751 | UUUUAAAG CUGAUGA GCCGUUAGGC GAA AACAGUGA | 7242 | UCACUGUUA CUUUAAAA | 100 |
| 754 | CUUUUUUA CUGAUGA GCCGUUAGGC GAA AGUAACAG | 7243 | CUGUUACUU UAAAAAAG | 101 |
| 755 | ACUUUUUU CUGAUGA GCCGUUAGGC GAA AAGUAACA | 7244 | UGUUACUUU AAAAAAGU | 102 |
| 756 | AACUUUUU CUGAUGA GCCGUUAGGC GAA AAAGUAAC | 7245 | GUUACUUUA AAAAAGUU | 103 |
| 764 | CAAGUGGA CUGAUGA GCCGUUAGGC GAA ACUUUUUU | 7246 | AAAAAAGUU UCCACUUG | 104 |
| 765 | UCAAGUGG CUGAUGA GCCGUUAGGC GAA AACUUUUU | 7247 | AAAAAGUUU CCACUUGA | 105 |
| 766 | GUCAAGUG CUGAUGA GCCGUUAGGC GAA AAACUUUU | 7248 | AAAAGUUUC CACUUGAC | 106 |
| 771 | AAAGUGUC CUGAUGA GCCGUUAGGC GAA AGUGGAAA | 7249 | UUUCCACUU GACACUUU | 107 |
| 778 | AGGGAUCA CUGAUGA GCCGUUAGGC GAA AGUGUCAA | 7250 | UUGACACUU UGAUCCCU | 108 |
| 779 | CAGGGAUC CUGAUGA GCCGUUAGGC GAA AAGUGUCA | 7251 | UGACACUUU GAUCCCUG | 109 |
| 783 | CCAUCAGG CUGAUGA GCCGUUAGGC GAA AUCAAAGU | 7252 | ACUUUGAUC CCUGAUGG | 110 |
| 801 | UCCCAGAU CUGAUGA GCCGUUAGGC GAA AUGCGUUU | 7253 | AAACGCAUA AUCUGGGA | 111 |
| 804 | CUGUCCCA CUGAUGA GCCGUUAGGC GAA AUUAUGCG | 7254 | CGCAUAAUC UGGGACAG | 112 |
| 814 | GCCCUUUC CUGAUGA GCCGUUAGGC GAA ACUGUCCC | 7255 | GGGACAGUA GAAAGGGC | 113 |
| 824 | AUAUGAUG CUGAUGA GCCGUUAGGC GAA AGCCCUUU | 7256 | AAAGGGCUU CAUCAUAU | 114 |
| 825 | GAUAUGAU CUGAUGA GCCGUUAGGC GAA AAGCCCUU | 7257 | AAGGGCUUC AUCAUAUC | 115 |
| 828 | UUUGAUAU CUGAUGA GCCGUUAGGC GAA AUGAAGCC | 7258 | GGCUUCAUC AUAUCAAA | 116 |
| 831 | GCAUUUGA CUGAUGA GCCGUUAGGC GAA AUGAUGAA | 7259 | UUCAUCAUA UCAAAUGC | 117 |
| 833 | UUGCAUUU CUGAUGA GCCGUUAGGC GAA AUAUGAUG | 7260 | CAUCAUAUC AAAUGCAA | 118 |
| 845 | UUUCUUUG CUGAUGA GCCGUUAGGC GAA ACGUUGCA | 7261 | UGCAACGUA CAAAGAAA | 119 |
| 855 | AGAAGCCC CUGAUGA GCCGUUAGGC GAA AUUUCUUU | 7262 | AAAGAAAUA GGGCUUCU | 120 |
| 861 | CAGGUCAG CUGAUGA GCCGUUAGGC GAA AGCCCUAU | 7263 | AUAGGGCUU CUGACCUG | 121 |
| 862 | ACAGGUCA CUGAUGA GCCGUUAGGC GAA AAGCCCUA | 7264 | UAGGGCUUC UGACCUGU | 122 |
| 882 | UGCCCAUU CUGAUGA GCCGUUAGGC GAA ACUGUUGC | 7265 | GCAACAGUC AAUGGGCA | 123 |
| 892 | CUUAUACA CUGAUGA GCCGUUAGGC GAA AUGCCCAU | 7266 | AUGGGCAUU UGUAUAAG | 124 |
| 893 | UCUUAUAC CUGAUGA GCCGUUAGGC GAA AAUGCCCA | 7267 | UGGGCAUUU GUAUAAGA | 125 |
| 896 | UUGUCUUA CUGAUGA GCCGUUAGGC GAA ACAAAUGC | 7268 | GCAUUUGUA UAAGACAA | 126 |
| 898 | GUUUGUCU CUGAUGA GCCGUUAGGC GAA AUACAAAU | 7269 | AUUUGUAUA AGACAAAC | 127 |
| 908 | GUGUGAGA CUGAUGA GCCGUUAGGC GAA AGUUUGUC | 7270 | GACAAACUA UCUCACAC | 128 |

| | | | | |
|---|---|---|---|---|
| 910 | AUGUGUGA CUGAUGA GCCGUUAGGC GAA AUAGUUUG | 7271 | CAAACUAUC UCACACAU | 129 |
| 912 | CGAUGUGU CUGAUGA GCCGUUAGGC GAA AGAUAGUU | 7272 | AACUAUCUC ACACAUCG | 130 |
| 919 | GGUUUGUC CUGAUGA GCCGUUAGGC GAA AUGUGUGA | 7273 | UCACACAUC GACAAACC | 131 |
| 931 | UAUGAUUG CUGAUGA GCCGUUAGGC GAA AUUGGUUU | 7274 | AAACCAAUA CAAUCAUA | 132 |
| 936 | ACAUCUAU CUGAUGA GCCGUUAGGC GAA AUUGUAUU | 7275 | AAUACAAUC AUAGAUGU | 133 |
| 939 | UGGACAUC CUGAUGA GCCGUUAGGC GAA AUGAUUGU | 7276 | ACAAUCAUA GAUGUCCA | 134 |
| 945 | CUUAUUUG CUGAUGA GCCGUUAGGC GAA ACAUCUAU | 7277 | AUAGAUGUC CAAAUAAG | 135 |
| 951 | GGUGUGCU CUGAUGA GCCGUUAGGC GAA AUUUGGAC | 7278 | GUCCAAAUA AGCACACC | 136 |
| 969 | AGUAAUUU CUGAUGA GCCGUUAGGC GAA ACUGGGCG | 7279 | CGCCCAGUC AAAUUACU | 137 |
| 974 | CUCUAAGU CUGAUGA GCCGUUAGGC GAA AUUUGACU | 7280 | AGUCAAAUU ACUUAGAG | 138 |
| 975 | CCUCUAAG CUGAUGA GCCGUUAGGC GAA AAUUUGAC | 7281 | GUCAAAUUA CUUAGAGG | 139 |
| 978 | UGGCCUCU CUGAUGA GCCGUUAGGC GAA AGUAAUUU | 7282 | AAAUUACUU AGAGGCCA | 140 |
| 979 | AUGGCCUC CUGAUGA GCCGUUAGGC GAA AAGUAAUU | 7283 | AAUUACUUA GAGGCCAU | 141 |
| 988 | GACAAGAG CUGAUGA GCCGUUAGGC GAA AUGGCCUC | 7284 | GAGGCCAUA CUCUUGUC | 142 |
| 991 | GAGGACAA CUGAUGA GCCGUUAGGC GAA AGUAUGGC | 7285 | GCCAUACUC UUGUCCUC | 143 |
| 993 | UUGAGGAC CUGAUGA GCCGUUAGGC GAA AGAGUAUG | 7286 | CAUACUCUU GUCCUCAA | 144 |
| 996 | CAAUUGAG CUGAUGA GCCGUUAGGC GAA ACAAGAGU | 7287 | ACUCUUGUC CUCAAUUG | 145 |
| 999 | GUACAAUU CUGAUGA GCCGUUAGGC GAA AGGACAAG | 7288 | CUUGUCCUC AAUUGUAC | 146 |
| 1003 | AGCAGUAC CUGAUGA GCCGUUAGGC GAA AUUGAGGA | 7289 | UCCUCAAUU GUACUGCU | 147 |
| 1006 | GGUAGCAG CUGAUGA GCCGUUAGGC GAA ACAAUUGA | 7290 | UCAAUUGUA CUGCUACC | 148 |
| 1012 | GGGAGUGG CUGAUGA GCCGUUAGGC GAA AGCAGUAC | 7291 | GUACUGCUA CCACUCCC | 149 |
| 1018 | GUUCAAGG CUGAUGA GCCGUUAGGC GAA AGUGGUAG | 7292 | CUACCACUC CCUUGAAC | 150 |
| 1022 | UCGUGUUC CUGAUGA GCCGUUAGGC GAA AGGGAGUG | 7293 | CACUCCCUU GAACACGA | 151 |
| 1035 | GUCAUUUG CUGAUGA GCCGUUAGGC GAA ACUCUCGU | 7294 | ACGAGAGUU CAAAUGAC | 152 |
| 1036 | GGUCAUUU CUGAUGA GCCGUUAGGC GAA AACUCUCG | 7295 | CGAGAGUUC AAAUGACC | 153 |
| 1051 | AUCAGGGU CUGAUGA GCCGUUAGGC GAA ACUCCAGG | 7296 | CCUGGAGUU ACCCUGAU | 154 |
| 1052 | CAUCAGGG CUGAUGA GCCGUUAGGC GAA AACUCCAG | 7297 | CUGGAGUUA CCCUGAUG | 155 |
| 1069 | AGCUCUCU CUGAUGA GCCGUUAGGC GAA AUUUUUUU | 7298 | AAAAAAAUA AGAGAGCU | 156 |
| 1078 | CCUUACGG CUGAUGA GCCGUUAGGC GAA AGCUCUCU | 7299 | AGAGAGCUU CCGUAAGG | 157 |
| 1079 | GCCUUACG CUGAUGA GCCGUUAGGC GAA AAGCUCUC | 7300 | GAGAGCUUC CGUAAGGC | 158 |
| 1083 | CGUCGCCU CUGAUGA GCCGUUAGGC GAA ACGGAAGC | 7301 | GCUUCCGUA AGGCGACG | 159 |
| 1095 | CUUUGGUC CUGAUGA GCCGUUAGGC GAA AUUCGUCG | 7302 | CGACGAAUU GACCAAAG | 160 |
| 1108 | GGCAUGGG CUGAUGA GCCGUUAGGC GAA AUUGCUUU | 7303 | AAAGCAAUU CCCAUGCC | 161 |

78

| | | | | |
|---|---|---|---|---|
| 1109 | UGGCAUGG CUGAUGA GCCGUUAGGC GAA AAUUGCUU | 7304 | AAGCAAUUC CCAUGCCA | 162 |
| 1122 | CUGUAGAA CUGAUGA GCCGUUAGGC GAA AUGUUGGC | 7305 | GCCAACAUA UUCUACAG | 163 |
| 1124 | CACUGUAG CUGAUGA GCCGUUAGGC GAA AUAUGUUG | 7306 | CAACAUAUU CUACAGUG | 164 |
| 1125 | ACACUGUA CUGAUGA GCCGUUAGGC GAA AAUAUGUU | 7307 | AACAUAUUC UACAGUGU | 165 |
| 1127 | GAACACUG CUGAUGA GCCGUUAGGC GAA AGAAUAUG | 7308 | CAUAUUCUA CAGUGUUC | 166 |
| 1134 | AUAGUAAG CUGAUGA GCCGUUAGGC GAA ACACUGUA | 7309 | UACAGUGUU CUUACUAU | 167 |
| 1135 | AAUAGUAA CUGAUGA GCCGUUAGGC GAA AACACUGU | 7310 | ACAGUGUUC UUACUAUU | 168 |
| 1137 | UCAAUAGU CUGAUGA GCCGUUAGGC GAA AGAACACU | 7311 | AGUGUUCUU ACUAUUGA | 169 |
| 1138 | GUCAAUAG CUGAUGA GCCGUUAGGC GAA AAGAACAC | 7312 | GUGUUCUUA CUAUUGAC | 170 |
| 1141 | UUUGUCAA CUGAUGA GCCGUUAGGC GAA AGUAAGAA | 7313 | UUCUUACUA UUGACAAA | 171 |
| 1143 | AUUUUGUC CUGAUGA GCCGUUAGGC GAA AUAGUAAG | 7314 | CUUACUAUU GACAAAAU | 172 |
| 1173 | CAAGUAUA CUGAUGA GCCGUUAGGC GAA AGUCCUUU | 7315 | AAAGGACUU UAUACUUG | 173 |
| 1174 | ACAAGUAU CUGAUGA GCCGUUAGGC GAA AAGUCCUU | 7316 | AAGGACUUU AUACUUGU | 174 |
| 1175 | GACAAGUA CUGAUGA GCCGUUAGGC GAA AAAGUCCU | 7317 | AGGACUUUA UACUUGUC | 175 |
| 1177 | ACGACAAG CUGAUGA GCCGUUAGGC GAA AUAAAGUC | 7318 | GACUUUAUA CUUGUCGU | 176 |
| 1180 | UACACGAC CUGAUGA GCCGUUAGGC GAA AGUAUAAA | 7319 | UUUAUACUU GUCGUGUA | 177 |
| 1183 | CCUUACAC CUGAUGA GCCGUUAGGC GAA ACAAGUAU | 7320 | AUACUUGUC GUGUAAGG | 178 |
| 1188 | CCACUCCU CUGAUGA GCCGUUAGGC GAA ACACGACA | 7321 | UGUCGUGUA AGGAGUGG | 179 |
| 1202 | AUUUGAAU CUGAUGA GCCGUUAGGC GAA AUGGUCCA | 7322 | UGGACCAUC AUUCAAAU | 180 |
| 1205 | CAGAUUUG CUGAUGA GCCGUUAGGC GAA AUGAUGGU | 7323 | ACCAUCAUU CAAAUCUG | 181 |
| 1206 | ACAGAUUU CUGAUGA GCCGUUAGGC GAA AAUGAUGG | 7324 | CCAUCAUUC AAAUCUGU | 182 |
| 1211 | UGUUAACA CUGAUGA GCCGUUAGGC GAA AUUUGAAU | 7325 | AUUCAAAUC UGUUAACA | 183 |
| 1215 | GAGGUGUU CUGAUGA GCCGUUAGGC GAA ACAGAUUU | 7326 | AAAUCUGUU AACACCUC | 184 |
| 1216 | UGAGGUGU CUGAUGA GCCGUUAGGC GAA AACAGAUU | 7327 | AAUCUGUUA ACACCUCA | 185 |
| 1223 | UAUGCACU CUGAUGA GCCGUUAGGC GAA AGGUGUUA | 7328 | UAACACCUC AGUGCAUA | 186 |
| 1231 | AUCAUAUA CUGAUGA GCCGUUAGGC GAA AUGCACUG | 7329 | CAGUGCAUA UAUAUGAU | 187 |
| 1233 | UUAUCAUA CUGAUGA GCCGUUAGGC GAA AUAUGCAC | 7330 | GUGCAUAUA UAUGAUAA | 188 |
| 1235 | CUUUAUCA CUGAUGA GCCGUUAGGC GAA AUAUAUGC | 7331 | GCAUAUAUA UGAUAAAG | 189 |
| 1240 | GAAUGCUU CUGAUGA GCCGUUAGGC GAA AUCAUAUA | 7332 | UAUAUGAUA AAGCAUUC | 190 |
| 1247 | CAGUGAUG CUGAUGA GCCGUUAGGC GAA AUGCUUUA | 7333 | UAAAGCAUU CAUCACUG | 191 |
| 1248 | ACAGUGAU CUGAUGA GCCGUUAGGC GAA AAUGCUUU | 7334 | AAAGCAUUC AUCACUGU | 192 |
| 1251 | UUCACAGU CUGAUGA GCCGUUAGGC GAA AUGAAUGC | 7335 | GCAUUCAUC ACUGUGAA | 193 |
| 1264 | CUGUUUUC CUGAUGA GCCGUUAGGC GAA AUGUUUCA | 7336 | UGAAACAUC GAAAACAG | 194 |

79

| | | | | |
|---|---|---|---|---|
| 1281 | ACGGUUUC CUGAUGA GCCGUUAGGC GAA AGCACCUG | 7337 | CAGGUGCUU GAAACCGU | 195 |
| 1290 | UUGCCAGC CUGAUGA GCCGUUAGGC GAA ACGGUUUC | 7338 | GAAACCGUA GCUGGCAA | 196 |
| 1304 | GCCGGUAA CUGAUGA GCCGUUAGGC GAA ACCGCUUG | 7339 | CAAGCGGUC UUACCGGC | 197 |
| 1306 | GAGCCGGU CUGAUGA GCCGUUAGGC GAA AGACCGCU | 7340 | AGCGGUCUU ACCGGCUC | 198 |
| 1307 | AGAGCCGG CUGAUGA GCCGUUAGGC GAA AAGACCGC | 7341 | GCGGUCUUA CCGGCUCU | 199 |
| 1314 | UUCAUAGA CUGAUGA GCCGUUAGGC GAA AGCCGGUA | 7342 | UACCGGCUC UCUAUGAA | 200 |
| 1316 | CUUUCAUA CUGAUGA GCCGUUAGGC GAA AGAGCCGG | 7343 | CCGGCUCUC UAUGAAAG | 201 |
| 1318 | CACUUUCA CUGAUGA GCCGUUAGGC GAA AGAGAGCC | 7344 | GGCUCUCUA UGAAAGUG | 202 |
| 1334 | GCGAGGGA CUGAUGA GCCGUUAGGC GAA AUGCCUUC | 7345 | GAAGGCAUU UCCCUCGC | 203 |
| 1335 | GGCGAGGG CUGAUGA GCCGUUAGGC GAA AAUGCCUU | 7346 | AAGGCAUUU CCCUCGCC | 204 |
| 1336 | CGGCGAGG CUGAUGA GCCGUUAGGC GAA AAAUGCCU | 7347 | AGGCAUUUC CCUCGCCG | 205 |
| 1340 | CUUCCGGC CUGAUGA GCCGUUAGGC GAA AGGGAAAU | 7348 | AUUUCCCUC GCCGGAAG | 206 |
| 1350 | AACCAUAC CUGAUGA GCCGUUAGGC GAA ACUUCCGG | 7349 | CCGGAAGUU GUAUGGUU | 207 |
| 1353 | UUUAACCA CUGAUGA GCCGUUAGGC GAA ACAACUUC | 7350 | GAAGUUGUA UGGUUAAA | 208 |
| 1358 | CAUCUUUU CUGAUGA GCCGUUAGGC GAA ACCAUACA | 7351 | UGUAUGGUU AAAAGAUG | 209 |
| 1359 | CCAUCUUU CUGAUGA GCCGUUAGGC GAA AACCAUAC | 7352 | GUAUGGUUA AAAGAUGG | 210 |
| 1370 | UCGCAGGU CUGAUGA GCCGUUAGGC GAA ACCCAUCU | 7353 | AGAUGGGUU ACCUGCGA | 211 |
| 1371 | GUCGCAGG CUGAUGA GCCGUUAGGC GAA AACCCAUC | 7354 | GAUGGGUUA CCUGCGAC | 212 |
| 1388 | AGCGAGCA CUGAUGA GCCGUUAGGC GAA AUUUCUCA | 7355 | UGAGAAAUC UGCUCGCU | 213 |
| 1393 | CAAAUAGC CUGAUGA GCCGUUAGGC GAA AGCAGAUU | 7356 | AAUCUGCUC GCUAUUUG | 214 |
| 1397 | GAGUCAAA CUGAUGA GCCGUUAGGC GAA AGCGAGCA | 7357 | UGCUCGCUA UUUGACUC | 215 |
| 1399 | ACGAGUCA CUGAUGA GCCGUUAGGC GAA AUAGCGAG | 7358 | CUCGCUAUU UGACUCGU | 216 |
| 1400 | CACGAGUC CUGAUGA GCCGUUAGGC GAA AAUAGCGA | 7359 | UCGCUAUUU GACUCGUG | 217 |
| 1405 | GUAGCCAC CUGAUGA GCCGUUAGGC GAA AGUCAAAU | 7360 | AUUUGACUC GUGGCUAC | 218 |
| 1412 | UUAACGAG CUGAUGA GCCGUUAGGC GAA AGCCACGA | 7361 | UCGUGGCUA CUCGUUAA | 219 |
| 1415 | UAAUUAAC CUGAUGA GCCGUUAGGC GAA AGUAGCCA | 7362 | UGGCUACUC GUUAAUUA | 220 |
| 1418 | UGAUAAUU CUGAUGA GCCGUUAGGC GAA ACGAGUAG | 7363 | CUACUCGUU AAUUAUCA | 221 |
| 1419 | UUGAUAAU CUGAUGA GCCGUUAGGC GAA AACGAGUA | 7364 | UACUCGUUA AUUAUCAA | 222 |
| 1422 | UCCUUGAU CUGAUGA GCCGUUAGGC GAA AUUAACGA | 7365 | UCGUUAAUU AUCAAGGA | 223 |
| 1423 | GUCCUUGA CUGAUGA GCCGUUAGGC GAA AAUUAACG | 7366 | CGUUAAUUA UCAAGGAC | 224 |
| 1425 | ACGUCCUU CUGAUGA GCCGUUAGGC GAA AUAAUUAA | 7367 | UUAAUUAUC AAGGACGU | 225 |
| 1434 | UCUUCAGU CUGAUGA GCCGUUAGGC GAA ACGUCCUU | 7368 | AAGGACGUA ACUGAAGA | 226 |
| 1456 | GAUUGUAU CUGAUGA GCCGUUAGGC GAA AUUCCCUG | 7369 | CAGGGAAUU AUACAAUC | 227 |

80

| | | | | |
|---|---|---|---|---|
| 1457 | AGAUUGUA CUGAUGA GCCGUUAGGC GAA AAUUCCCU | 7370 | AGGGAAUUA UACAAUCU | 228 |
| 1459 | CAAGAUUG CUGAUGA GCCGUUAGGC GAA AUAAUUCC | 7371 | GGAAUUAUA CAAUCUUG | 229 |
| 1464 | CUCAGCAA CUGAUGA GCCGUUAGGC GAA AUUGUAUA | 7372 | UAUACAAUC UUGCUGAG | 230 |
| 1466 | UGCUCAGC CUGAUGA GCCGUUAGGC GAA AGAUUGUA | 7373 | UACAAUCUU GCUGAGCA | 231 |
| 1476 | GACUGUUU CUGAUGA GCCGUUAGGC GAA AUGCUCAG | 7374 | CUGAGCAUA AAACAGUC | 232 |
| 1484 | ACACAUUU CUGAUGA GCCGUUAGGC GAA ACUGUUUU | 7375 | AAAACAGUC AAAUGUGU | 233 |
| 1493 | GGUUUUUA CUGAUGA GCCGUUAGGC GAA ACACAUUU | 7376 | AAAUGUGUU UAAAAACC | 234 |
| 1494 | AGGUUUUU CUGAUGA GCCGUUAGGC GAA AACACAUU | 7377 | AAUGUGUUU AAAAACCU | 235 |
| 1495 | GAGGUUUU CUGAUGA GCCGUUAGGC GAA AAACACAU | 7378 | AUGUGUUUA AAAACCUC | 236 |
| 1503 | GUGGCAGU CUGAUGA GCCGUUAGGC GAA AGGUUUUU | 7379 | AAAAACCUC ACUGCCAC | 237 |
| 1513 | GACAAUUA CUGAUGA GCCGUUAGGC GAA AGUGGCAG | 7380 | CUGCCACUC UAAUUGUC | 238 |
| 1515 | UUGACAAU CUGAUGA GCCGUUAGGC GAA AGAGUGGC | 7381 | GCCACUCUA AUUGUCAA | 239 |
| 1518 | ACAUUGAC CUGAUGA GCCGUUAGGC GAA AUUAGAGU | 7382 | ACUCUAAUU GUCAAUGU | 240 |
| 1521 | UUCACAUU CUGAUGA GCCGUUAGGC GAA ACAAUUAG | 7383 | CUAAUUGUC AAUGUGAA | 241 |
| 1539 | UUUUCGUA CUGAUGA GCCGUUAGGC GAA AUCUGGGG | 7384 | CCCCAGAUU UACGAAAA | 242 |
| 1540 | CUUUUCGU CUGAUGA GCCGUUAGGC GAA AAUCUGGG | 7385 | CCCAGAUUU ACGAAAAG | 243 |
| 1541 | CCUUUUCG CUGAUGA GCCGUUAGGC GAA AAAUCUGG | 7386 | CCAGAUUUA CGAAAAGG | 244 |
| 1556 | GAAACGAU CUGAUGA GCCGUUAGGC GAA ACACGGCC | 7387 | GGCCGUGUC AUCGUUUC | 245 |
| 1559 | CUGGAAAC CUGAUGA GCCGUUAGGC GAA AUGACACG | 7388 | CGUGUCAUC GUUUCCAG | 246 |
| 1562 | GGUCUGGA CUGAUGA GCCGUUAGGC GAA ACGAUGAC | 7389 | GUCAUCGUU UCCAGACC | 247 |
| 1563 | GGGUCUGG CUGAUGA GCCGUUAGGC GAA AACGAUGA | 7390 | UCAUCGUUU CCAGACCC | 248 |
| 1564 | CGGGUCUG CUGAUGA GCCGUUAGGC GAA AAACGAUG | 7391 | CAUCGUUUC CAGACCCG | 249 |
| 1576 | UGGGUAGA CUGAUGA GCCGUUAGGC GAA AGCCGGGU | 7392 | ACCCGGCUC UCUACCCA | 250 |
| 1578 | AGUGGGUA CUGAUGA GCCGUUAGGC GAA AGAGCCGG | 7393 | CCGGCUCUC UACCCACU | 251 |
| 1580 | CCAGUGGG CUGAUGA GCCGUUAGGC GAA AGAGAGCC | 7394 | GGCUCUCUA CCCACUGG | 252 |
| 1602 | CAAGUCAG CUGAUGA GCCGUUAGGC GAA AUUUGUCU | 7395 | AGACAAAUC CUGACUUG | 253 |
| 1609 | UGCGGUAC CUGAUGA GCCGUUAGGC GAA AGUCAGGA | 7396 | UCCUGACUU GUACCGCA | 254 |
| 1612 | AUAUGCGG CUGAUGA GCCGUUAGGC GAA ACAAGUCA | 7397 | UGACUUGUA CCGCAUAU | 255 |
| 1619 | GGAUACCA CUGAUGA GCCGUUAGGC GAA AUGCGGUA | 7398 | UACCGCAUA UGGUAUCC | 256 |
| 1624 | UUGAGGGA CUGAUGA GCCGUUAGGC GAA ACCAUAUG | 7399 | CAUAUGGUA UCCCUCAA | 257 |
| 1626 | GGUUGAGG CUGAUGA GCCGUUAGGC GAA AUACCAUA | 7400 | UAUGGUAUC CCUCAACC | 258 |
| 1630 | UGUAGGUU CUGAUGA GCCGUUAGGC GAA AGGGAUAC | 7401 | GUAUCCCUC AACCUACA | 259 |
| 1636 | CUUGAUUG CUGAUGA GCCGUUAGGC GAA AGGUUGAG | 7402 | CUCAACCUA CAAUCAAG | 260 |

81

| | | | | |
|---|---|---|---|---|
| 1641 | AACCACUU CUGAUGA GCCGUUAGGC GAA AUUGUAGG | 7403 | CCUACAAUC AAGUGGUU | 261 |
| 1649 | GGUGCCAG CUGAUGA GCCGUUAGGC GAA ACCACUUG | 7404 | CAAGUGGUU CUGGCACC | 262 |
| 1650 | GGGUGCCA CUGAUGA GCCGUUAGGC GAA AACCACUU | 7405 | AAGUGGUUC UGGCACCC | 263 |
| 1663 | AUUAUGGU CUGAUGA GCCGUUAGGC GAA ACAGGGGU | 7406 | ACCCCUGUA ACCAUAAU | 264 |
| 1669 | GGAAUGAU CUGAUGA GCCGUUAGGC GAA AUGGUUAC | 7407 | GUAACCAUA AUCAUUCC | 265 |
| 1672 | UUCGGAAU CUGAUGA GCCGUUAGGC GAA AUUAUGGU | 7408 | ACCAUAAUC AUUCCGAA | 266 |
| 1675 | UGCUUCGG CUGAUGA GCCGUUAGGC GAA AUGAUUAU | 7409 | AUAAUCAUU CCGAAGCA | 267 |
| 1676 | UUGCUUCG CUGAUGA GCCGUUAGGC GAA AAUGAUUA | 7410 | UAAUCAUUC CGAAGCAA | 268 |
| 1694 | UGGAACAA CUGAUGA GCCGUUAGGC GAA AGUCACAC | 7411 | GUGUGACUU UUGUUCCA | 269 |
| 1695 | UUGGAACA CUGAUGA GCCGUUAGGC GAA AAGUCACA | 7412 | UGUGACUUU UGUUCCAA | 270 |
| 1696 | AUUGGAAC CUGAUGA GCCGUUAGGC GAA AAAGUCAC | 7413 | GUGACUUUU GUUCCAAU | 271 |
| 1699 | AUUAUUGG CUGAUGA GCCGUUAGGC GAA ACAAAAGU | 7414 | ACUUUUGUU CCAAUAAU | 272 |
| 1700 | CAUUAUUG CUGAUGA GCCGUUAGGC GAA AACAAAAG | 7415 | CUUUUGUUC CAAUAAUG | 273 |
| 1705 | CUCUUCAU CUGAUGA GCCGUUAGGC GAA AUUGGAAC | 7416 | GUUCCAAUA AUGAAGAG | 274 |
| 1715 | GGAUAAAG CUGAUGA GCCGUUAGGC GAA ACUCUUCA | 7417 | UGAAGAGUC CUUUAUCC | 275 |
| 1718 | CCAGGAUA CUGAUGA GCCGUUAGGC GAA AGGACUCU | 7418 | AGAGUCCUU UAUCCUGG | 276 |
| 1719 | UCCAGGAU CUGAUGA GCCGUUAGGC GAA AAGGACUC | 7419 | GAGUCCUUU AUCCUGGA | 277 |
| 1720 | AUCCAGGA CUGAUGA GCCGUUAGGC GAA AAAGGACU | 7420 | AGUCCUUUA UCCUGGAU | 278 |
| 1722 | GCAUCCAG CUGAUGA GCCGUUAGGC GAA AUAAAGGA | 7421 | UCCUUUAUC CUGGAUGC | 279 |
| 1755 | AUGCUCUC CUGAUGA GCCGUUAGGC GAA AUUCUGUU | 7422 | AACAGAAUU GAGAGCAU | 280 |
| 1764 | CGCUGAGU CUGAUGA GCCGUUAGGC GAA AUGCUCUC | 7423 | GAGAGCAUC ACUCAGCG | 281 |
| 1768 | CAUGCGCU CUGAUGA GCCGUUAGGC GAA AGUGAUGC | 7424 | GCAUCACUC AGCGCAUG | 282 |
| 1782 | CCUUCUAU CUGAUGA GCCGUUAGGC GAA AUUGCCAU | 7425 | AUGGCAAUA AUAGAAGG | 283 |
| 1785 | UUUCCUUC CUGAUGA GCCGUUAGGC GAA AUUAUUGC | 7426 | GCAAUAAUA GAAGGAAA | 284 |
| 1798 | AGCCAUCU CUGAUGA GCCGUUAGGC GAA AUUCUUUC | 7427 | GAAAGAAUA AGAUGGCU | 285 |
| 1807 | CAAGGUGC CUGAUGA GCCGUUAGGC GAA AGCCAUCU | 7428 | AGAUGGCUA GCACCUUG | 286 |
| 1814 | CCACAACC CUGAUGA GCCGUUAGGC GAA AGGUGCUA | 7429 | UAGCACCUU GGUUGUGG | 287 |
| 1818 | UCAGCCAC CUGAUGA GCCGUUAGGC GAA ACCAAGGU | 7430 | ACCUUGGUU GUGGCUGA | 288 |
| 1829 | AAAUUCUA CUGAUGA GCCGUUAGGC GAA AGUCAGCC | 7431 | GGCUGACUC UAGAAUUU | 289 |
| 1831 | AGAAAUUC CUGAUGA GCCGUUAGGC GAA AGAGUCAG | 7432 | CUGACUCUA GAAUUUCU | 290 |
| 1836 | AUUCCAGA CUGAUGA GCCGUUAGGC GAA AUUCUAGA | 7433 | UCUAGAAUU UCUGGAAU | 291 |
| 1837 | GAUUCCAG CUGAUGA GCCGUUAGGC GAA AAUUCUAG | 7434 | CUAGAAUUU CUGGAAUC | 292 |
| 1838 | AGAUUCCA CUGAUGA GCCGUUAGGC GAA AAAUUCUA | 7435 | UAGAAUUUC UGGAAUCU | 293 |

82

| | | | | |
|---|---|---|---|---|
| 1845 | CAAAUGUA CUGAUGA GCCGUUAGGC GAA AUUCCAGA | 7436 | UCUGGAAUC UACAUUUG | 294 |
| 1847 | UGCAAAUG CUGAUGA GCCGUUAGGC GAA AGAUUCCA | 7437 | UGGAAUCUA CAUUUGCA | 295 |
| 1851 | GCUAUGCA CUGAUGA GCCGUUAGGC GAA AUGUAGAU | 7438 | AUCUACAUU UGCAUAGC | 296 |
| 1852 | AGCUAUGC CUGAUGA GCCGUUAGGC GAA AAUGUAGA | 7439 | UCUACAUUU GCAUAGCU | 297 |
| 1857 | UUGGAAGC CUGAUGA GCCGUUAGGC GAA AUGCAAAU | 7440 | AUUUGCAUA GCUUCCAA | 298 |
| 1861 | UUUAUUGG CUGAUGA GCCGUUAGGC GAA AGCUAUGC | 7441 | GCAUAGCUU CCAAUAAA | 299 |
| 1862 | CUUUAUUG CUGAUGA GCCGUUAGGC GAA AAGCUAUG | 7442 | CAUAGCUUC CAAUAAAG | 300 |
| 1867 | CCCAACUU CUGAUGA GCCGUUAGGC GAA AUUGGAAG | 7443 | CUUCCAAUA AAGUUGGG | 301 |
| 1872 | ACAGUCCC CUGAUGA GCCGUUAGGC GAA ACUUUAUU | 7444 | AAUAAAGUU GGGACUGU | 302 |
| 1893 | UAAAAGCU CUGAUGA GCCGUUAGGC GAA AUGUUUCU | 7445 | AGAAACAUA AGCUUUUA | 303 |
| 1898 | UGAUAUAA CUGAUGA GCCGUUAGGC GAA AGCUUAUG | 7446 | CAUAAGCUU UUAUAUCA | 304 |
| 1899 | GUGAUAUA CUGAUGA GCCGUUAGGC GAA AAGCUUAU | 7447 | AUAAGCUUU UAUAUCAC | 305 |
| 1900 | UGUGAUAU CUGAUGA GCCGUUAGGC GAA AAAGCUUA | 7448 | UAAGCUUUU AUAUCACA | 306 |
| 1901 | CUGUGAUA CUGAUGA GCCGUUAGGC GAA AAAAGCUU | 7449 | AAGCUUUUA UAUCACAG | 307 |
| 1903 | AUCUGUGA CUGAUGA GCCGUUAGGC GAA AUAAAAGC | 7450 | GCUUUUAUA UCACAGAU | 308 |
| 1905 | ACAUCUGU CUGAUGA GCCGUUAGGC GAA AUAUAAAA | 7451 | UUUUAUAUC ACAGAUGU | 309 |
| 1925 | UAACAUGA CUGAUGA GCCGUUAGGC GAA ACCCAUUU | 7452 | AAAUGGGUU UCAUGUUA | 310 |
| 1926 | UUAACAUG CUGAUGA GCCGUUAGGC GAA AACCCAUU | 7453 | AAUGGGUUU CAUGUUAA | 311 |
| 1927 | GUUAACAU CUGAUGA GCCGUUAGGC GAA AAACCCAU | 7454 | AUGGGUUUC AUGUUAAC | 312 |
| 1932 | UCCAAGUU CUGAUGA GCCGUUAGGC GAA ACAUGAAA | 7455 | UUUCAUGUU AACUUGGA | 313 |
| 1933 | UUCCAAGU CUGAUGA GCCGUUAGGC GAA AACAUGAA | 7456 | UUCAUGUUA ACUUGGAA | 314 |
| 1937 | UUUUUUCC CUGAUGA GCCGUUAGGC GAA AGUUAACA | 7457 | UGUUAACUU GGAAAAAA | 315 |
| 1976 | CUGUGCAA CUGAUGA GCCGUUAGGC GAA ACAGUUUC | 7458 | GAAACUGUC UUGCACAG | 316 |
| 1978 | AACUGUGC CUGAUGA GCCGUUAGGC GAA AGACAGUU | 7459 | AACUGUCUU GCACAGUU | 317 |
| 1986 | AACUUGUU CUGAUGA GCCGUUAGGC GAA ACUGUGCA | 7460 | UGCACAGUU AACAAGUU | 318 |
| 1987 | GAACUUGU CUGAUGA GCCGUUAGGC GAA AACUGUGC | 7461 | GCACAGUUA ACAAGUUC | 319 |
| 1994 | UGUAUAAG CUGAUGA GCCGUUAGGC GAA ACUUGUUA | 7462 | UAACAAGUU CUUAUACA | 320 |
| 1995 | CUGUAUAA CUGAUGA GCCGUUAGGC GAA AACUUGUU | 7463 | AACAAGUUC UUAUACAG | 321 |
| 1997 | CUCUGUAU CUGAUGA GCCGUUAGGC GAA AGAACUUG | 7464 | CAAGUUCUU AUACAGAG | 322 |
| 1998 | UCUCUGUA CUGAUGA GCCGUUAGGC GAA AAGAACUU | 7465 | AAGUUCUUA UACAGAGA | 323 |
| 2000 | CGUCUCUG CUGAUGA GCCGUUAGGC GAA AUAAGAAC | 7466 | GUUCUUAUA CAGAGACG | 324 |
| 2010 | AUCCAAGU CUGAUGA GCCGUUAGGC GAA ACGUCUCU | 7467 | AGAGACGUU ACUUGGAU | 325 |
| 2011 | AAUCCAAG CUGAUGA GCCGUUAGGC GAA AACGUCUC | 7468 | GAGACGUUA CUUGGAUU | 326 |

83

| | | | | |
|---|---|---|---|---|
| 2014 | UAAAAUCC CUGAUGA GCCGUUAGGC GAA AGUAACGU | 7469 | ACGUUACUU GGAUUUUA | 327 |
| 2019 | CGCAGUAA CUGAUGA GCCGUUAGGC GAA AUCCAAGU | 7470 | ACUUGGAUU UUACUGCG | 328 |
| 2020 | CCGCAGUA CUGAUGA GCCGUUAGGC GAA AAUCCAAG | 7471 | CUUGGAUUU UACUGCGG | 329 |
| 2021 | UCCGCAGU CUGAUGA GCCGUUAGGC GAA AAAUCCAA | 7472 | UUGGAUUUU ACUGCGGA | 330 |
| 2022 | GUCCGCAG CUGAUGA GCCGUUAGGC GAA AAAAUCCA | 7473 | UGGAUUUUA CUGCGGAC | 331 |
| 2034 | CUGUUAUU CUGAUGA GCCGUUAGGC GAA ACUGUCCG | 7474 | CGGACAGUU AAUAACAG | 332 |
| 2035 | UCUGUUAU CUGAUGA GCCGUUAGGC GAA AACUGUCC | 7475 | GGACAGUUA AUAACAGA | 333 |
| 2038 | UGUUCUGU CUGAUGA GCCGUUAGGC GAA AUUAACUG | 7476 | CAGUUAAUA ACAGAACA | 334 |
| 2054 | UAAUACUG CUGAUGA GCCGUUAGGC GAA AGUGCAUU | 7477 | AAUGCACUA CAGUAUUA | 335 |
| 2059 | CUUGCUAA CUGAUGA GCCGUUAGGC GAA ACUGUAGU | 7478 | ACUACAGUA UUAGCAAG | 336 |
| 2061 | UGCUUGCU CUGAUGA GCCGUUAGGC GAA AUACUGUA | 7479 | UACAGUAUU AGCAAGCA | 337 |
| 2062 | UUGCUUGC CUGAUGA GCCGUUAGGC GAA AAUACUGU | 7480 | ACAGUAUUA GCAAGCAA | 338 |
| 2082 | UCCUUAGU CUGAUGA GCCGUUAGGC GAA AUGGCCAU | 7481 | AUGGCCAUC ACUAAGGA | 339 |
| 2086 | GUGCUCCU CUGAUGA GCCGUUAGGC GAA AGUGAUGG | 7482 | CCAUCACUA AGGAGCAC | 340 |
| 2096 | GAGUGAUG CUGAUGA GCCGUUAGGC GAA AGUGCUCC | 7483 | GGAGCACUC CAUCACUC | 341 |
| 2100 | UUAAGAGU CUGAUGA GCCGUUAGGC GAA AUGGAGUG | 7484 | CACUCCAUC ACUCUUAA | 342 |
| 2104 | AAGAUUAA CUGAUGA GCCGUUAGGC GAA AGUGAUGG | 7485 | CCAUCACUC UUAAUCUU | 343 |
| 2106 | GUAAGAUU CUGAUGA GCCGUUAGGC GAA AGAGUGAU | 7486 | AUCACUCUU AAUCUUAC | 344 |
| 2107 | GGUAAGAU CUGAUGA GCCGUUAGGC GAA AAGAGUGA | 7487 | UCACUCUUA AUCUUACC | 345 |
| 2110 | GAUGGUAA CUGAUGA GCCGUUAGGC GAA AUUAAGAG | 7488 | CUCUUAAUC UUACCAUC | 346 |
| 2112 | AUGAUGGU CUGAUGA GCCGUUAGGC GAA AGAUUAAG | 7489 | CUUAAUCUU ACCAUCAU | 347 |
| 2113 | CAUGAUGG CUGAUGA GCCGUUAGGC GAA AAGAUUAA | 7490 | UUAAUCUUA CCAUCAUG | 348 |
| 2118 | ACAUUCAU CUGAUGA GCCGUUAGGC GAA AUGGUAAG | 7491 | CUUACCAUC AUGAAUGU | 349 |
| 2127 | UGCAGGGA CUGAUGA GCCGUUAGGC GAA ACAUUCAU | 7492 | AUGAAUGUU UCCCUGCA | 350 |
| 2128 | UUGCAGGG CUGAUGA GCCGUUAGGC GAA AACAUUCA | 7493 | UGAAUGUUU CCCUGCAA | 351 |
| 2129 | CUUGCAGG CUGAUGA GCCGUUAGGC GAA AAACAUUC | 7494 | GAAUGUUUC CCUGCAAG | 352 |
| 2140 | GGUGCCUG CUGAUGA GCCGUUAGGC GAA AUCUUGCA | 7495 | UGCAAGAUU CAGGCACC | 353 |
| 2141 | AGGUGCCU CUGAUGA GCCGUUAGGC GAA AAUCUUGC | 7496 | GCAAGAUUC AGGCACCU | 354 |
| 2150 | UGCAGGCA CUGAUGA GCCGUUAGGC GAA AGGUGCCU | 7497 | AGGCACCUA UGCCUGCA | 355 |
| 2172 | CCUGUGUA CUGAUGA GCCGUUAGGC GAA ACAUUCCU | 7498 | AGGAAUGUA UACACAGG | 356 |
| 2174 | CCCCUGUG CUGAUGA GCCGUUAGGC GAA AUACAUUC | 7499 | GAAUGUAUA CACAGGGG | 357 |
| 2190 | UUCUGGAG CUGAUGA GCCGUUAGGC GAA AUUUCUUC | 7500 | GAAGAAAUC CUCCAGAA | 358 |
| 2193 | UUCUUCUG CUGAUGA GCCGUUAGGC GAA AGGAUUUC | 7501 | GAAAUCCUC CAGAAGAA | 359 |

84

| | | | | |
|---|---|---|---|---|
| 2208 | CUGAUUGU CUGAUGA GCCGUUAGGC GAA AUUUCUUU | 7502 | AAAGAAAUU ACAAUCAG | 360 |
| 2209 | UCUGAUUG CUGAUGA GCCGUUAGGC GAA AAUUUCUU | 7503 | AAGAAAUUA CAAUCAGA | 361 |
| 2214 | UGAUCUCU CUGAUGA GCCGUUAGGC GAA AUUGUAAU | 7504 | AUUACAAUC AGAGAUCA | 362 |
| 2221 | UGCUUCCU CUGAUGA GCCGUUAGGC GAA AUCUCUGA | 7505 | UCAGAGAUC AGGAAGCA | 363 |
| 2234 | GCAGGAGG CUGAUGA GCCGUUAGGC GAA AUGGUGCU | 7506 | AGCACCAUA CCUCCUGC | 364 |
| 2238 | UUUCGCAG CUGAUGA GCCGUUAGGC GAA AGGUAUGG | 7507 | CCAUACCUC CUGCGAAA | 365 |
| 2250 | UGAUCACU CUGAUGA GCCGUUAGGC GAA AGGUUUCG | 7508 | CGAAACCUC AGUGAUCA | 366 |
| 2257 | CACUGUGU CUGAUGA GCCGUUAGGC GAA AUCACUGA | 7509 | UCAGUGAUC ACACAGUG | 367 |
| 2271 | GAACUGCU CUGAUGA GCCGUUAGGC GAA AUGGCCAC | 7510 | GUGGCCAUC AGCAGUUC | 368 |
| 2278 | AGUGGUGG CUGAUGA GCCGUUAGGC GAA ACUGCUGA | 7511 | UCAGCAGUU CCACCACU | 369 |
| 2279 | AAGUGGUG CUGAUGA GCCGUUAGGC GAA AACUGCUG | 7512 | CAGCAGUUC CACCACUU | 370 |
| 2287 | ACAGUCUA CUGAUGA GCCGUUAGGC GAA AGUGGUGG | 7513 | CCACCACUU UAGACUGU | 371 |
| 2288 | GACAGUCU CUGAUGA GCCGUUAGGC GAA AAGUGGUG | 7514 | CACCACUUU AGACUGUC | 372 |
| 2289 | UGACAGUC CUGAUGA GCCGUUAGGC GAA AAAGUGGU | 7515 | ACCACUUUA GACUGUCA | 373 |
| 2296 | AUUAGCAU CUGAUGA GCCGUUAGGC GAA ACAGUCUA | 7516 | UAGACUGUC AUGCUAAU | 374 |
| 2302 | GACACCAU CUGAUGA GCCGUUAGGC GAA AGCAUGAC | 7517 | GUCAUGCUA AUGGUGUC | 375 |
| 2310 | GGCUCGGG CUGAUGA GCCGUUAGGC GAA ACACCAUU | 7518 | AAUGGUGUC CCCGAGCC | 376 |
| 2320 | AGUGAUCU CUGAUGA GCCGUUAGGC GAA AGGCUCGG | 7519 | CCGAGCCUC AGAUCACU | 377 |
| 2325 | AACCAAGU CUGAUGA GCCGUUAGGC GAA AUCUGAGG | 7520 | CCUCAGAUC ACUUGGUU | 378 |
| 2329 | UUUAAACC CUGAUGA GCCGUUAGGC GAA AGUGAUCU | 7521 | AGAUCACUU GGUUUAAA | 379 |
| 2333 | UGUUUUUA CUGAUGA GCCGUUAGGC GAA ACCAAGUG | 7522 | CACUUGGUU UAAAAACA | 380 |
| 2334 | UUGUUUUU CUGAUGA GCCGUUAGGC GAA AACCAAGU | 7523 | ACUUGGUUU AAAAACAA | 381 |
| 2335 | GUUGUUUU CUGAUGA GCCGUUAGGC GAA AAACCAAG | 7524 | CUUGGUUUA AAAACAAC | 382 |
| 2352 | UCUUGUUG CUGAUGA GCCGUUAGGC GAA AUUUUGUG | 7525 | CACAAAAUA CAACAAGA | 383 |
| 2370 | CCUAAAAU CUGAUGA GCCGUUAGGC GAA AUUCCAGG | 7526 | CCUGGAAUU AUUUUAGG | 384 |
| 2371 | UCCUAAAA CUGAUGA GCCGUUAGGC GAA AAUUCCAG | 7527 | CUGGAAUUA UUUUAGGA | 385 |
| 2373 | GGUCCUAA CUGAUGA GCCGUUAGGC GAA AUAAUUCC | 7528 | GGAAUUAUU UUAGGACC | 386 |
| 2374 | UGGUCCUA CUGAUGA GCCGUUAGGC GAA AAUAAUUC | 7529 | GAAUUAUUU UAGGACCA | 387 |
| 2375 | CUGGUCCU CUGAUGA GCCGUUAGGC GAA AAAUAAUU | 7530 | AAUUAUUUU AGGACCAG | 388 |
| 2376 | CCUGGUCC CUGAUGA GCCGUUAGGC GAA AAAAUAAU | 7531 | AUUAUUUUA GGACCAGG | 389 |
| 2399 | UUUCAAUA CUGAUGA GCCGUUAGGC GAA ACAGCGUG | 7532 | CACGCUGUU UAUUGAAA | 390 |
| 2400 | CUUUCAAU CUGAUGA GCCGUUAGGC GAA AACAGCGU | 7533 | ACGCUGUUU AUUGAAAG | 391 |
| 2401 | UCUUUCAA CUGAUGA GCCGUUAGGC GAA AAACAGCG | 7534 | CGCUGUUUA UUGAAAGA | 392 |

| | | | | |
|---|---|---|---|---|
| 2403 | ACUCUUUC CUGAUGA GCCGUUAGGC GAA AUAAACAG | 7535 | CUGUUUAUU GAAAGAGU | 393 |
| 2412 | UCUUCUGU CUGAUGA GCCGUUAGGC GAA ACUCUUUC | 7536 | GAAAGAGUC ACAGAAGA | 394 |
| 2433 | CAGUGAUA CUGAUGA GCCGUUAGGC GAA ACACCUUC | 7537 | GAAGGUGUC UAUCACUG | 395 |
| 2435 | UGCAGUGA CUGAUGA GCCGUUAGGC GAA AGACACCU | 7538 | AGGUGUCUA UCACUGCA | 396 |
| 2437 | UUUGCAGU CUGAUGA GCCGUUAGGC GAA AUAGACAC | 7539 | GUGUCUAUC ACUGCAAA | 397 |
| 2465 | UUUCCACA CUGAUGA GCCGUUAGGC GAA AGCCCUUC | 7540 | GAAGGGCUC UGUGGAAA | 398 |
| 2476 | GUAUGCUG CUGAUGA GCCGUUAGGC GAA ACUUUCCA | 7541 | UGGAAAGUU CAGCAUAC | 399 |
| 2477 | GGUAUGCU CUGAUGA GCCGUUAGGC GAA AACUUUCC | 7542 | GGAAAGUUC AGCAUACC | 400 |
| 2483 | CAGUGAGG CUGAUGA GCCGUUAGGC GAA AUGCUGAA | 7543 | UUCAGCAUA CCUCACUG | 401 |
| 2487 | UGAACAGU CUGAUGA GCCGUUAGGC GAA AGGUAUGC | 7544 | GCAUACCUC ACUGUUCA | 402 |
| 2493 | GUUCCUUG CUGAUGA GCCGUUAGGC GAA ACAGUGAG | 7545 | CUCACUGUU CAAGGAAC | 403 |
| 2494 | GGUUCCUU CUGAUGA GCCGUUAGGC GAA AACAGUGA | 7546 | UCACUGUUC AAGGAACC | 404 |
| 2504 | ACUUGUCC CUGAUGA GCCGUUAGGC GAA AGGUUCCU | 7547 | AGGAACCUC GGACAAGU | 405 |
| 2513 | CCAGAUUA CUGAUGA GCCGUUAGGC GAA ACUUGUCC | 7548 | GGACAAGUC UAAUCUGG | 406 |
| 2515 | CUCCAGAU CUGAUGA GCCGUUAGGC GAA AGACUUGU | 7549 | ACAAGUCUA AUCUGGAG | 407 |
| 2518 | CAGCUCCA CUGAUGA GCCGUUAGGC GAA AUUAGACU | 7550 | AGUCUAAUC UGGAGCUG | 408 |
| 2529 | GUUAGAGU CUGAUGA GCCGUUAGGC GAA AUCAGCUC | 7551 | GAGCUGAUC ACUCUAAC | 409 |
| 2533 | GCAUGUUA CUGAUGA GCCGUUAGGC GAA AGUGAUCA | 7552 | UGAUCACUC UAACAUGC | 410 |
| 2535 | GUGCAUGU CUGAUGA GCCGUUAGGC GAA AGAGUGAU | 7553 | AUCACUCUA ACAUGCAC | 411 |
| 2560 | CCAGAAGA CUGAUGA GCCGUUAGGC GAA AGUCGCAG | 7554 | CUGCGACUC UCUUCUGG | 412 |
| 2562 | AGCCAGAA CUGAUGA GCCGUUAGGC GAA AGAGUCGC | 7555 | GCGACUCUC UUCUGGCU | 413 |
| 2564 | GGAGCCAG CUGAUGA GCCGUUAGGC GAA AGAGAGUC | 7556 | GACUCUCUU CUGGCUCC | 414 |
| 2565 | AGGAGCCA CUGAUGA GCCGUUAGGC GAA AAGAGAGU | 7557 | ACUCUCUUC UGGCUCCU | 415 |
| 2571 | GUUAAUAG CUGAUGA GCCGUUAGGC GAA AGCCAGAA | 7558 | UUCUGGCUC CUAUUAAC | 416 |
| 2574 | AGGGUUAA CUGAUGA GCCGUUAGGC GAA AGGAGCCA | 7559 | UGGCUCCUA UUAACCCU | 417 |
| 2576 | GGAGGGUU CUGAUGA GCCGUUAGGC GAA AUAGGAGC | 7560 | GCUCCUAUU AACCCUCC | 418 |
| 2577 | AGGAGGGU CUGAUGA GCCGUUAGGC GAA AAUAGGAG | 7561 | CUCCUAUUA ACCCUCCU | 419 |
| 2583 | CGGAUAAG CUGAUGA GCCGUUAGGC GAA AGGGUUAA | 7562 | UUAACCCUC CUUAUCCG | 420 |
| 2586 | UUUCGGAU CUGAUGA GCCGUUAGGC GAA AGGAGGGU | 7563 | ACCCUCCUU AUCCGAAA | 421 |
| 2587 | UUUUCGGA CUGAUGA GCCGUUAGGC GAA AAGGAGGG | 7564 | CCCUCCUUA UCCGAAAA | 422 |
| 2589 | AUUUUUCG CUGAUGA GCCGUUAGGC GAA AUAAGGAG | 7565 | CUCCUUAUC CGAAAAAU | 423 |
| 2606 | CAGAAGAA CUGAUGA GCCGUUAGGC GAA ACCUUUUC | 7566 | GAAAAGGUC UUCUUCUG | 424 |
| 2608 | UUCAGAAG CUGAUGA GCCGUUAGGC GAA AGACCUUU | 7567 | AAAGGUCUU CUUCUGAA | 425 |

86

| | | | | |
|---|---|---|---|---|
| 2609 | UUUCAGAA CUGAUGA GCCGUUAGGC GAA AAGACCUU | 7568 | AAGGUCUUC UUCUGAAA | 426 |
| 2611 | UAUUUCAG CUGAUGA GCCGUUAGGC GAA AGAAGACC | 7569 | GGUCUUCUU CUGAAAUA | 427 |
| 2612 | UUAUUUCA CUGAUGA GCCGUUAGGC GAA AAGAAGAC | 7570 | GUCUUCUUC UGAAAUAA | 428 |
| 2619 | UCAGUCUU CUGAUGA GCCGUUAGGC GAA AUUUCAGA | 7571 | UCUGAAAUA AAGACUGA | 429 |
| 2630 | UUGAUAGG CUGAUGA GCCGUUAGGC GAA AGUCAGUC | 7572 | GACUGACUA CCUAUCAA | 430 |
| 2634 | AUAAUUGA CUGAUGA GCCGUUAGGC GAA AGGUAGUC | 7573 | GACUACCUA UCAAUUAU | 431 |
| 2636 | UUAUAAUU CUGAUGA GCCGUUAGGC GAA AUAGGUAG | 7574 | CUACCUAUC AAUUAUAA | 432 |
| 2640 | UCCAUUAU CUGAUGA GCCGUUAGGC GAA AUUGAUAG | 7575 | CUAUCAAUU AUAAUGGA | 433 |
| 2641 | GUCCAUUA CUGAUGA GCCGUUAGGC GAA AAUUGAUA | 7576 | UAUCAAUUA UAAUGGAC | 434 |
| 2643 | GGGUCCAU CUGAUGA GCCGUUAGGC GAA AUAAUUGA | 7577 | UCAAUUAUA AUGGACCC | 435 |
| 2661 | UCCAAAGG CUGAUGA GCCGUUAGGC GAA ACUUCAUC | 7578 | GAUGAAGUU CCUUUGGA | 436 |
| 2662 | AUCCAAAG CUGAUGA GCCGUUAGGC GAA AACUUCAU | 7579 | AUGAAGUUC CUUUGGAU | 437 |
| 2665 | CUCAUCCA CUGAUGA GCCGUUAGGC GAA AGGAACUU | 7580 | AAGUUCCUU UGGAUGAG | 438 |
| 2666 | GCUCAUCC CUGAUGA GCCGUUAGGC GAA AAGGAACU | 7581 | AGUUCCUUU GGAUGAGC | 439 |
| 2688 | UCAUAAGG CUGAUGA GCCGUUAGGC GAA AGCCGCUC | 7582 | GAGCGGCUC CCUUAUGA | 440 |
| 2692 | GGCAUCAU CUGAUGA GCCGUUAGGC GAA AGGGAGCC | 7583 | GGCUCCCUU AUGAUGCC | 441 |
| 2693 | UGGCAUCA CUGAUGA GCCGUUAGGC GAA AAGGGAGC | 7584 | GCUCCCUUA UGAUGCCA | 442 |
| 2714 | CCCGGGCA CUGAUGA GCCGUUAGGC GAA ACUCCCAC | 7585 | GUGGGAGUU UGCCCGGG | 443 |
| 2715 | UCCCGGGC CUGAUGA GCCGUUAGGC GAA AACUCCCA | 7586 | UGGGAGUUU GCCCGGGA | 444 |
| 2730 | CCCAGUUU CUGAUGA GCCGUUAGGC GAA AGUCUCUC | 7587 | GAGAGACUU AAACUGGG | 445 |
| 2731 | GCCCAGUU CUGAUGA GCCGUUAGGC GAA AAGUCUCU | 7588 | AGAGACUUA AACUGGGC | 446 |
| 2744 | UUCCAAGU CUGAUGA GCCGUUAGGC GAA AUUUGCCC | 7589 | GGGCAAAUC ACUUGGAA | 447 |
| 2748 | CCUCUUCC CUGAUGA GCCGUUAGGC GAA AGUGAUUU | 7590 | AAAUCACUU GGAAGAGG | 448 |
| 2761 | UUUUCCAA CUGAUGA GCCGUUAGGC GAA AGCCCCUC | 7591 | GAGGGGCUU UUGGAAAA | 449 |
| 2762 | CUUUUCCA CUGAUGA GCCGUUAGGC GAA AAGCCCCU | 7592 | AGGGGCUUU UGGAAAAG | 450 |
| 2763 | ACUUUUCC CUGAUGA GCCGUUAGGC GAA AAAGCCCC | 7593 | GGGGCUUUU GGAAAAGU | 451 |
| 2775 | GAUGCUUG CUGAUGA GCCGUUAGGC GAA ACCACUUU | 7594 | AAAGUGGUU CAAGCAUC | 452 |
| 2776 | UGAUGCUU CUGAUGA GCCGUUAGGC GAA AACCACUU | 7595 | AAGUGGUUC AAGCAUCA | 453 |
| 2783 | CAAAUGCU CUGAUGA GCCGUUAGGC GAA AUGCUUGA | 7596 | UCAAGCAUC AGCAUUUG | 454 |
| 2789 | UAAUGCCA CUGAUGA GCCGUUAGGC GAA AUGCUGAU | 7597 | AUCAGCAUU UGGCAUUA | 455 |
| 2790 | UUAAUGCC CUGAUGA GCCGUUAGGC GAA AAUGCUGA | 7598 | UCAGCAUUU GGCAUUAA | 456 |
| 2796 | GAUUUCUU CUGAUGA GCCGUUAGGC GAA AUGCCAAA | 7599 | UUUGGCAUU AAGAAAUC | 457 |
| 2797 | UGAUUUCU CUGAUGA GCCGUUAGGC GAA AAUGCCAA | 7600 | UUGGCAUUA AGAAAUCA | 458 |

87

| | | | | |
|---|---|---|---|---|
| 2804 | ACGUAGGU CUGAUGA GCCGUUAGGC GAA AUUUCUUA | 7601 | UAAGAAAUC ACCUACGU | 459 |
| 2809 | CCGGCACG CUGAUGA GCCGUUAGGC GAA AGGUGAUU | 7602 | AAUCACCUA CGUGCCGG | 460 |
| 2864 | GAGCUUUG CUGAUGA GCCGUUAGGC GAA ACUCGCUG | 7603 | CAGCGAGUA CAAAGCUC | 461 |
| 2872 | AGUCAUCA CUGAUGA GCCGUUAGGC GAA AGCUUUGU | 7604 | ACAAAGCUC UGAUGACU | 462 |
| 2886 | AAGAUUUU CUGAUGA GCCGUUAGGC GAA AGCUCAGU | 7605 | ACUGAGCUA AAAAUCUU | 463 |
| 2892 | UGGGUCAA CUGAUGA GCCGUUAGGC GAA AUUUUUAG | 7606 | CUAAAAAUC UUGACCCA | 464 |
| 2894 | UGUGGGUC CUGAUGA GCCGUUAGGC GAA AGAUUUUU | 7607 | AAAAAUCUU GACCCACA | 465 |
| 2904 | UGGUGGCC CUGAUGA GCCGUUAGGC GAA AUGUGGGU | 7608 | ACCCACAUU GGCCACCA | 466 |
| 2914 | CACGUUCA CUGAUGA GCCGUUAGGC GAA AUGGUGGC | 7609 | GCCACCAUC UGAACGUG | 467 |
| 2925 | AGCAGGUU CUGAUGA GCCGUUAGGC GAA ACCACGUU | 7610 | AACGUGGUU AACCUGCU | 468 |
| 2926 | CAGCAGGU CUGAUGA GCCGUUAGGC GAA AACCACGU | 7611 | ACGUGGUUA ACCUGCUG | 469 |
| 2962 | CACCAUCA CUGAUGA GCCGUUAGGC GAA AGGCCCUC | 7612 | GAGGGCCUC UGAUGGUG | 470 |
| 2973 | UAUUCAAC CUGAUGA GCCGUUAGGC GAA AUCACCAU | 7613 | AUGGUGAUU GUUGAAUA | 471 |
| 2976 | CAGUAUUC CUGAUGA GCCGUUAGGC GAA ACAAUCAC | 7614 | GUGAUUGUU GAAUACUG | 472 |
| 2981 | AUUUGCAG CUGAUGA GCCGUUAGGC GAA AUUCAACA | 7615 | UGUUGAAUA CUGCAAAU | 473 |
| 2990 | GAUUUCCA CUGAUGA GCCGUUAGGC GAA AUUUGCAG | 7616 | CUGCAAAUA UGGAAAUC | 474 |
| 2998 | GUUGGAGA CUGAUGA GCCGUUAGGC GAA AUUUCCAU | 7617 | AUGGAAAUC UCUCCAAC | 475 |
| 3000 | UAGUUGGA CUGAUGA GCCGUUAGGC GAA AGAUUUCC | 7618 | GGAAAUCUC UCCAACUA | 476 |
| 3002 | GGUAGUUG CUGAUGA GCCGUUAGGC GAA AGAGAUUU | 7619 | AAAUCUCUC CAACUACC | 477 |
| 3008 | UCUUGAGG CUGAUGA GCCGUUAGGC GAA AGUUGGAG | 7620 | CUCCAACUA CCUCAAGA | 478 |
| 3012 | UUGCUCUU CUGAUGA GCCGUUAGGC GAA AGGUAGUU | 7621 | AACUACCUC AAGAGCAA | 479 |
| 3029 | GAAAAAAU CUGAUGA GCCGUUAGGC GAA AGUCACGU | 7622 | ACGUGACUU AUUUUUUC | 480 |
| 3030 | AGAAAAAA CUGAUGA GCCGUUAGGC GAA AAGUCACG | 7623 | CGUGACUUA UUUUUUCU | 481 |
| 3032 | UGAGAAAA CUGAUGA GCCGUUAGGC GAA AUAAGUCA | 7624 | UGACUUAUU UUUUCUCA | 482 |
| 3033 | UUGAGAAA CUGAUGA GCCGUUAGGC GAA AAUAAGUC | 7625 | GACUUAUUU UUUCUCAA | 483 |
| 3034 | GUUGAGAA CUGAUGA GCCGUUAGGC GAA AAAUAAGU | 7626 | ACUUAUUUU UUCUCAAC | 484 |
| 3035 | UGUUGAGA CUGAUGA GCCGUUAGGC GAA AAAAUAAG | 7627 | CUUAUUUUU UCUCAACA | 485 |
| 3036 | UUGUUGAG CUGAUGA GCCGUUAGGC GAA AAAAAUAA | 7628 | UUAUUUUUU CUCAACAA | 486 |
| 3037 | CUUGUUGA CUGAUGA GCCGUUAGGC GAA AAAAAAUA | 7629 | UAUUUUUUC UCAACAAG | 487 |
| 3039 | UCCUUGUU CUGAUGA GCCGUUAGGC GAA AGAAAAAA | 7630 | UUUUUUCUC AACAAGGA | 488 |
| 3057 | UCCAUGUG CUGAUGA GCCGUUAGGC GAA AGUGCUGC | 7631 | GCAGCACUA CACAUGGA | 489 |
| 3070 | UUCUUUCU CUGAUGA GCCGUUAGGC GAA AGGCUCCA | 7632 | UGGAGCCUA AGAAAGAA | 490 |
| 3120 | ACGCUAUC CUGAUGA GCCGUUAGGC GAA AGUCUUGG | 7633 | CCAAGACUA GAUAGCGU | 491 |

| | | | | |
|---|---|---|---|---|
| 3124 | GGUGACGC CUGAUGA GCCGUUAGGC GAA AUCUAGUC | 7634 | GACUAGAUA GCGUCACC | 492 |
| 3129 | CUGCUGGU CUGAUGA GCCGUUAGGC GAA ACGCUAUC | 7635 | GAUAGCGUC ACCAGCAG | 493 |
| 3146 | AGCUCGCA CUGAUGA GCCGUUAGGC GAA AGCUUUCG | 7636 | CGAAAGCUU UGCGAGCU | 494 |
| 3147 | GAGCUCGC CUGAUGA GCCGUUAGGC GAA AAGCUUUC | 7637 | GAAAGCUUU GCGAGCUC | 495 |
| 3155 | GAAAGCCG CUGAUGA GCCGUUAGGC GAA AGCUCGCA | 7638 | UGCGAGCUC CGGCUUUC | 496 |
| 3161 | CUUCCUGA CUGAUGA GCCGUUAGGC GAA AGCCGGAG | 7639 | CUCCGGCUU UCAGGAAG | 497 |
| 3162 | UCUUCCUG CUGAUGA GCCGUUAGGC GAA AAGCCGGA | 7640 | UCCGGCUUU CAGGAAGA | 498 |
| 3163 | AUCUUCCU CUGAUGA GCCGUUAGGC GAA AAAGCCGG | 7641 | CCGGCUUUC AGGAAGAU | 499 |
| 3172 | CAGACUUU CUGAUGA GCCGUUAGGC GAA AUCUUCCU | 7642 | AGGAAGAUA AAAGUCUG | 500 |
| 3178 | AUCACUCA CUGAUGA GCCGUUAGGC GAA ACUUUUAU | 7643 | AUAAAAGUC UGAGUGAU | 501 |
| 3189 | UCUUCCUC CUGAUGA GCCGUUAGGC GAA ACAUCACU | 7644 | AGUGAUGUU GAGGAAGA | 502 |
| 3205 | ACCGUCAG CUGAUGA GCCGUUAGGC GAA AUCCUCCU | 7645 | AGGAGGAUU CUGACGGU | 503 |
| 3206 | AACCGUCA CUGAUGA GCCGUUAGGC GAA AAUCCUCC | 7646 | GGAGGAUUC UGACGGUU | 504 |
| 3214 | CUUGUAGA CUGAUGA GCCGUUAGGC GAA ACCGUCAG | 7647 | CUGACGGUU UCUACAAG | 505 |
| 3215 | CCUUGUAG CUGAUGA GCCGUUAGGC GAA AACCGUCA | 7648 | UGACGGUUU CUACAAGG | 506 |
| 3216 | UCCUUGUA CUGAUGA GCCGUUAGGC GAA AAACCGUC | 7649 | GACGGUUUC UACAAGGA | 507 |
| 3218 | GCUCCUUG CUGAUGA GCCGUUAGGC GAA AGAAACCG | 7650 | CGGUUUCUA CAAGGAGC | 508 |
| 3231 | UCCAUAGU CUGAUGA GCCGUUAGGC GAA AUGGGCUC | 7651 | GAGCCCAUC ACUAUGGA | 509 |
| 3235 | AUCUUCCA CUGAUGA GCCGUUAGGC GAA AGUGAUGG | 7652 | CCAUCACUA UGGAAGAU | 510 |
| 3244 | AGAAAUCA CUGAUGA GCCGUUAGGC GAA AUCUUCCA | 7653 | UGGAAGAUC UGAUUUCU | 511 |
| 3249 | CUGUAAGA CUGAUGA GCCGUUAGGC GAA AUCAGAUC | 7654 | GAUCUGAUU UCUUACAG | 512 |
| 3250 | ACUGUAAG CUGAUGA GCCGUUAGGC GAA AAUCAGAU | 7655 | AUCUGAUUU CUUACAGU | 513 |
| 3251 | AACUGUAA CUGAUGA GCCGUUAGGC GAA AAAUCAGA | 7656 | UCUGAUUUC UUACAGUU | 514 |
| 3253 | AAAACUGU CUGAUGA GCCGUUAGGC GAA AGAAAUCA | 7657 | UGAUUUCUU ACAGUUUU | 515 |
| 3254 | GAAAACUG CUGAUGA GCCGUUAGGC GAA AAGAAAUC | 7658 | GAUUUCUUA CAGUUUUC | 516 |
| 3259 | CACUUGAA CUGAUGA GCCGUUAGGC GAA ACUGUAAG | 7659 | CUUACAGUU UUCAAGUG | 517 |
| 3260 | CCACUUGA CUGAUGA GCCGUUAGGC GAA AACUGUAA | 7660 | UUACAGUUU UCAAGUGG | 518 |
| 3261 | GCCACUUG CUGAUGA GCCGUUAGGC GAA AAACUGUA | 7661 | UACAGUUUU CAAGUGGC | 519 |
| 3262 | GGCCACUU CUGAUGA GCCGUUAGGC GAA AAAACUGU | 7662 | ACAGUUUUC AAGUGGCC | 520 |
| 3284 | AAGACAGG CUGAUGA GCCGUUAGGC GAA ACUCCAUG | 7663 | CAUGGAGUU CCUGUCUU | 521 |
| 3285 | GAAGACAG CUGAUGA GCCGUUAGGC GAA AACUCCAU | 7664 | AUGGAGUUC CUGUCUUC | 522 |
| 3290 | UUCUGGAA CUGAUGA GCCGUUAGGC GAA ACAGGAAC | 7665 | GUUCCUGUC UUCCAGAA | 523 |
| 3292 | CUUUCUGG CUGAUGA GCCGUUAGGC GAA AGACAGGA | 7666 | UCCUGUCUU CCAGAAAG | 524 |

| | | | | |
|---|---|---|---|---|
| 3293 | ACUUUCUG CUGAUGA GCCGUUAGGC GAA AAGACAGG | 7667 | CCUGUCUUC CAGAAAGU | 525 |
| 3306 | UCCCGAUG CUGAUGA GCCGUUAGGC GAA AUGCACUU | 7668 | AAGUGCAUU CAUCGGGA | 526 |
| 3307 | GUCCCGAU CUGAUGA GCCGUUAGGC GAA AAUGCACU | 7669 | AGUGCAUUC AUCGGGAC | 527 |
| 3310 | CAGGUCCC CUGAUGA GCCGUUAGGC GAA AUGAAUGC | 7670 | GCAUUCAUC GGGACCUG | 528 |
| 3333 | GAUAAAAG CUGAUGA GCCGUUAGGC GAA AUGUUUCU | 7671 | AGAAACAUU CUUUUAUC | 529 |
| 3334 | AGAUAAAA CUGAUGA GCCGUUAGGC GAA AAUGUUUC | 7672 | GAAACAUUC UUUUAUCU | 530 |
| 3336 | UCAGAUAA CUGAUGA GCCGUUAGGC GAA AGAAUGUU | 7673 | AACAUUCUU UUAUCUGA | 531 |
| 3337 | CUCAGAUA CUGAUGA GCCGUUAGGC GAA AAGAAUGU | 7674 | ACAUUCUUU UAUCUGAG | 532 |
| 3338 | UCUCAGAU CUGAUGA GCCGUUAGGC GAA AAAGAAUG | 7675 | CAUUCUUUU AUCUGAGA | 533 |
| 3339 | UUCUCAGA CUGAUGA GCCGUUAGGC GAA AAAAGAAU | 7676 | AUUCUUUUA UCUGAGAA | 534 |
| 3341 | UGUUCUCA CUGAUGA GCCGUUAGGC GAA AUAAAAGA | 7677 | UCUUUUAUC UGAGAACA | 535 |
| 3363 | AAAUCACA CUGAUGA GCCGUUAGGC GAA AUCUUCAC | 7678 | GUGAAGAUU UGUGAUUU | 536 |
| 3364 | AAAAUCAC CUGAUGA GCCGUUAGGC GAA AAUCUUCA | 7679 | UGAAGAUUU GUGAUUUU | 537 |
| 3370 | AAGGCCAA CUGAUGA GCCGUUAGGC GAA AUCACAAA | 7680 | UUUGUGAUU UUGGCCUU | 538 |
| 3371 | CAAGGCCA CUGAUGA GCCGUUAGGC GAA AAUCACAA | 7681 | UUGUGAUUU UGGCCUUG | 539 |
| 3372 | GCAAGGCC CUGAUGA GCCGUUAGGC GAA AAAUCACA | 7682 | UGUGAUUUU GGCCUUGC | 540 |
| 3378 | UCCCGGGC CUGAUGA GCCGUUAGGC GAA AGGCCAAA | 7683 | UUUGGCCUU GCCCGGGA | 541 |
| 3388 | CUUAUAAA CUGAUGA GCCGUUAGGC GAA AUCCCGGG | 7684 | CCCGGGAUA UUUAUAAG | 542 |
| 3390 | UUCUUAUA CUGAUGA GCCGUUAGGC GAA AUAUCCCG | 7685 | CGGGAUAUU UAUAAGAA | 543 |
| 3391 | GUUCUUAU CUGAUGA GCCGUUAGGC GAA AAUAUCCC | 7686 | GGGAUAUUU AUAAGAAC | 544 |
| 3392 | GGUUCUUA CUGAUGA GCCGUUAGGC GAA AAAUAUCC | 7687 | GGAUAUUUA UAAGAACC | 545 |
| 3394 | GGGGUUCU CUGAUGA GCCGUUAGGC GAA AUAAAUAU | 7688 | AUAUUUAUA AGAACCCC | 546 |
| 3406 | UCUCACAU CUGAUGA GCCGUUAGGC GAA AUCGGGGU | 7689 | ACCCCGAUU AUGUGAGA | 547 |
| 3407 | UUCUCACA CUGAUGA GCCGUUAGGC GAA AAUCGGGG | 7690 | CCCCGAUUA UGUGAGAA | 548 |
| 3424 | AAGUCGAG CUGAUGA GCCGUUAGGC GAA AUCUCCUU | 7691 | AAGGAGAUA CUCGACUU | 549 |
| 3427 | AGGAAGUC CUGAUGA GCCGUUAGGC GAA AGUAUCUC | 7692 | GAGAUACUC GACUUCCU | 550 |
| 3432 | UUCAGAGG CUGAUGA GCCGUUAGGC GAA AGUCGAGU | 7693 | ACUCGACUU CCUCUGAA | 551 |
| 3433 | UUUCAGAG CUGAUGA GCCGUUAGGC GAA AAGUCGAG | 7694 | CUCGACUUC CUCUGAAA | 552 |
| 3436 | CCAUUUCA CUGAUGA GCCGUUAGGC GAA AGGAAGUC | 7695 | GACUUCCUC UGAAAUGG | 553 |
| 3451 | AGAUUCGG CUGAUGA GCCGUUAGGC GAA AGCCAUCC | 7696 | GGAUGGCUC CCGAAUCU | 554 |
| 3458 | CAAAGAUA CUGAUGA GCCGUUAGGC GAA AUUCGGGA | 7697 | UCCCGAAUC UAUCUUUG | 555 |
| 3460 | GUCAAAGA CUGAUGA GCCGUUAGGC GAA AGAUUCGG | 7698 | CCGAAUCUA UCUUUGAC | 556 |
| 3462 | UUGUCAAA CUGAUGA GCCGUUAGGC GAA AUAGAUUC | 7699 | GAAUCUAUC UUUGACAA | 557 |

| | | | | |
|---|---|---|---|---|
| 3464 | UUUUGUCA CUGAUGA GCCGUUAGGC GAA AGAUAGAU | 7700 | AUCUAUCUU UGACAAAA | 558 |
| 3465 | AUUUUGUC CUGAUGA GCCGUUAGGC GAA AAGAUAGA | 7701 | UCUAUCUUU GACAAAAU | 559 |
| 3474 | GUGCUGUA CUGAUGA GCCGUUAGGC GAA AUUUUGUC | 7702 | GACAAAAUC UACAGCAC | 560 |
| 3476 | UGGUGCUG CUGAUGA GCCGUUAGGC GAA AGAUUUUG | 7703 | CAAAAUCUA CAGCACCA | 561 |
| 3500 | CUCCGUAA CUGAUGA GCCGUUAGGC GAA ACCACACG | 7704 | CGUGUGGUC UUACGGAG | 562 |
| 3502 | UACUCCGU CUGAUGA GCCGUUAGGC GAA AGACCACA | 7705 | UGUGGUCUU ACGGAGUA | 563 |
| 3503 | AUACUCCG CUGAUGA GCCGUUAGGC GAA AAGACCAC | 7706 | GUGGUCUUA CGGAGUAU | 564 |
| 3510 | CACAGCAA CUGAUGA GCCGUUAGGC GAA ACUCCGUA | 7707 | UACGGAGUA UUGCUGUG | 565 |
| 3512 | CCCACAGC CUGAUGA GCCGUUAGGC GAA AUACUCCG | 7708 | CGGAGUAUU GCUGUGGG | 566 |
| 3525 | AAGGAGAA CUGAUGA GCCGUUAGGC GAA AUUUCCCA | 7709 | UGGGAAAUC UUCUCCUU | 567 |
| 3527 | CUAAGGAG CUGAUGA GCCGUUAGGC GAA AGAUUUCC | 7710 | GGAAAUCUU CUCCUUAG | 568 |
| 3528 | CCUAAGGA CUGAUGA GCCGUUAGGC GAA AAGAUUUC | 7711 | GAAAUCUUC UCCUUAGG | 569 |
| 3530 | CACCUAAG CUGAUGA GCCGUUAGGC GAA AGAAGAUU | 7712 | AAUCUUCUC CUUAGGUG | 570 |
| 3533 | ACCCACCU CUGAUGA GCCGUUAGGC GAA AGGAGAAG | 7713 | CUUCUCCUU AGGUGGGU | 571 |
| 3534 | GACCCACC CUGAUGA GCCGUUAGGC GAA AAGGAGAA | 7714 | UUCUCCUUA GGUGGGUC | 572 |
| 3542 | GGUAUGGA CUGAUGA GCCGUUAGGC GAA ACCCACCU | 7715 | AGGUGGGUC UCCAUACC | 573 |
| 3544 | UGGGUAUG CUGAUGA GCCGUUAGGC GAA AGACCCAC | 7716 | GUGGGUCUC CAUACCCA | 574 |
| 3548 | CUCCUGGG CUGAUGA GCCGUUAGGC GAA AUGGAGAC | 7717 | GUCUCCAUA CCCAGGAG | 575 |
| 3558 | UCCAUUUG CUGAUGA GCCGUUAGGC GAA ACUCCUGG | 7718 | CCAGGAGUA CAAAUGGA | 576 |
| 3575 | GACUGCAA CUGAUGA GCCGUUAGGC GAA AGUCCUCA | 7719 | UGAGGACUU UUGCAGUC | 577 |
| 3576 | CGACUGCA CUGAUGA GCCGUUAGGC GAA AAGUCCUC | 7720 | GAGGACUUU UGCAGUCG | 578 |
| 3577 | GCGACUGC CUGAUGA GCCGUUAGGC GAA AAAGUCCU | 7721 | AGGACUUUU GCAGUCGC | 579 |
| 3583 | CCUCAGGC CUGAUGA GCCGUUAGGC GAA ACUGCAAA | 7722 | UUUGCAGUC GCCUGAGG | 580 |
| 3613 | GUACUCAG CUGAUGA GCCGUUAGGC GAA AGCUCUCA | 7723 | UGAGAGCUC CUGAGUAC | 581 |
| 3620 | GAGUAGAG CUGAUGA GCCGUUAGGC GAA ACUCAGGA | 7724 | UCCUGAGUA CUCUACUC | 582 |
| 3623 | CAGGAGUA CUGAUGA GCCGUUAGGC GAA AGUACUCA | 7725 | UGAGUACUC UACUCCUG | 583 |
| 3625 | UUCAGGAG CUGAUGA GCCGUUAGGC GAA AGAGUACU | 7726 | AGUACUCUA CUCCUGAA | 584 |
| 3628 | GAUUUCAG CUGAUGA GCCGUUAGGC GAA AGUAGAGU | 7727 | ACUCUACUC CUGAAAUC | 585 |
| 3636 | AUCUGAUA CUGAUGA GCCGUUAGGC GAA AUUUCAGG | 7728 | CCUGAAAUC UAUCAGAU | 586 |
| 3638 | UGAUCUGA CUGAUGA GCCGUUAGGC GAA AGAUUUCA | 7729 | UGAAAUCUA UCAGAUCA | 587 |
| 3640 | CAUGAUCU CUGAUGA GCCGUUAGGC GAA AUAGAUUU | 7730 | AAAUCUAUC AGAUCAUG | 588 |
| 3645 | UCCAGCAU CUGAUGA GCCGUUAGGC GAA AUCUGAUA | 7731 | UAUCAGAUC AUGCUGGA | 589 |
| 3689 | GUUCUGCA CUGAUGA GCCGUUAGGC GAA AUCUUGGC | 7732 | GCCAAGAUU UGCAGAAC | 590 |

91

| | | | | |
|---|---|---|---|---|
| 3690 | AGUUCUGC CUGAUGA GCCGUUAGGC GAA AAUCUUGG | 7733 | CCAAGAUUU GCAGAACU | 591 |
| 3699 | UUUUCCAC CUGAUGA GCCGUUAGGC GAA AGUUCUGC | 7734 | GCAGAACUU GUGGAAAA | 592 |
| 3711 | AAAUCACC CUGAUGA GCCGUUAGGC GAA AGUUUUUC | 7735 | GAAAAACUA GGUGAUUU | 593 |
| 3718 | UUGAAGCA CUGAUGA GCCGUUAGGC GAA AUCACCUA | 7736 | UAGGUGAUU UGCUUCAA | 594 |
| 3719 | CUUGAAGC CUGAUGA GCCGUUAGGC GAA AAUCACCU | 7737 | AGGUGAUUU GCUUCAAG | 595 |
| 3723 | UUUGCUUG CUGAUGA GCCGUUAGGC GAA AGCAAAUC | 7738 | GAUUUGCUU CAAGCAAA | 596 |
| 3724 | AUUUGCUU CUGAUGA GCCGUUAGGC GAA AAGCAAAU | 7739 | AUUUGCUUC AAGCAAAU | 597 |
| 3735 | UCCUGUUG CUGAUGA GCCGUUAGGC GAA ACAUUUGC | 7740 | GCAAAUGUA CAACAGGA | 598 |
| 3748 | GUAGUCUU CUGAUGA GCCGUUAGGC GAA ACCAUCCU | 7741 | AGGAUGGUA AAGACUAC | 599 |
| 3755 | UUGGGAUG CUGAUGA GCCGUUAGGC GAA AGUCUUUA | 7742 | UAAAGACUA CAUCCCAA | 600 |
| 3759 | UUGAUUGG CUGAUGA GCCGUUAGGC GAA AUGUAGUC | 7743 | GACUACAUC CCAAUCAA | 601 |
| 3765 | AUGGCAUU CUGAUGA GCCGUUAGGC GAA AUUGGGAU | 7744 | AUCCCAAUC AAUGCCAU | 602 |
| 3774 | CCUGUCAG CUGAUGA GCCGUUAGGC GAA AUGGCAUU | 7745 | AAUGCCAUA CUGACAGG | 603 |
| 3787 | AAACCCAC CUGAUGA GCCGUUAGGC GAA AUUUCCUG | 7746 | CAGGAAAUA GUGGGUUU | 604 |
| 3794 | AGUAUGUA CUGAUGA GCCGUUAGGC GAA ACCCACUA | 7747 | UAGUGGGUU UACAUACU | 605 |
| 3795 | GAGUAUGU CUGAUGA GCCGUUAGGC GAA AACCCACU | 7748 | AGUGGGUUU ACAUACUC | 606 |
| 3796 | UGAGUAUG CUGAUGA GCCGUUAGGC GAA AAACCCAC | 7749 | GUGGGUUUA CAUACUCA | 607 |
| 3800 | GAGUUGAG CUGAUGA GCCGUUAGGC GAA AUGUAAAC | 7750 | GUUUACAUA CUCAACUC | 608 |
| 3803 | CAGGAGUU CUGAUGA GCCGUUAGGC GAA AGUAUGUA | 7751 | UACAUACUC AACUCCUG | 609 |
| 3808 | GAAGGCAG CUGAUGA GCCGUUAGGC GAA AGUUGAGU | 7752 | ACUCAACUC CUGCCUUC | 610 |
| 3815 | CCUCAGAG CUGAUGA GCCGUUAGGC GAA AGGCAGGA | 7753 | UCCUGCCUU CUCUGAGG | 611 |
| 3816 | UCCUCAGA CUGAUGA GCCGUUAGGC GAA AAGGCAGG | 7754 | CCUGCCUUC UCUGAGGA | 612 |
| 3818 | AGUCCUCA CUGAUGA GCCGUUAGGC GAA AGAAGGCA | 7755 | UGCCUUCUC UGAGGACU | 613 |
| 3827 | CCUUGAAG CUGAUGA GCCGUUAGGC GAA AGUCCUCA | 7756 | UGAGGACUU CUUCAAGG | 614 |
| 3828 | UCCUUGAA CUGAUGA GCCGUUAGGC GAA AAGUCCUC | 7757 | GAGGACUUC UUCAAGGA | 615 |
| 3830 | UUUCCUUG CUGAUGA GCCGUUAGGC GAA AGAAGUCC | 7758 | GGACUUCUU CAAGGAAA | 616 |
| 3831 | CUUUCCUU CUGAUGA GCCGUUAGGC GAA AAGAAGUC | 7759 | GACUUCUUC AAGGAAAG | 617 |
| 3841 | AGCUGAAA CUGAUGA GCCGUUAGGC GAA ACUUUCCU | 7760 | AGGAAAGUA UUUCAGCU | 618 |
| 3843 | GGAGCUGA CUGAUGA GCCGUUAGGC GAA AUACUUUC | 7761 | GAAAGUAUU UCAGCUCC | 619 |
| 3844 | CGGAGCUG CUGAUGA GCCGUUAGGC GAA AAUACUUU | 7762 | AAAGUAUUU CAGCUCCG | 620 |
| 3845 | UCGGAGCU CUGAUGA GCCGUUAGGC GAA AAAUACUU | 7763 | AAGUAUUUC AGCUCCGA | 621 |
| 3850 | AAACUUCG CUGAUGA GCCGUUAGGC GAA AGCUGAAA | 7764 | UUUCAGCUC CGAAGUUU | 622 |
| 3857 | CUGAAUUA CUGAUGA GCCGUUAGGC GAA ACUUCGGA | 7765 | UCCGAAGUU UAAUUCAG | 623 |

| | | | | |
|---|---|---|---|---|
| 3858 | CCUGAAUU CUGAUGA GCCGUUAGGC GAA AACUUCGG | 7766 | CCGAAGUUU AAUUCAGG | 624 |
| 3859 | UCCUGAAU CUGAUGA GCCGUUAGGC GAA AAACUUCG | 7767 | CGAAGUUUA AUUCAGGA | 625 |
| 3862 | GCUUCCUG CUGAUGA GCCGUUAGGC GAA AUUAAACU | 7768 | AGUUUAAUU CAGGAAGC | 626 |
| 3863 | AGCUUCCU CUGAUGA GCCGUUAGGC GAA AAUUAAAC | 7769 | GUUUAAUUC AGGAAGCU | 627 |
| 3872 | CAUCAUCA CUGAUGA GCCGUUAGGC GAA AGCUUCCU | 7770 | AGGAAGCUC UGAUGAUG | 628 |
| 3882 | ACAUAUCU CUGAUGA GCCGUUAGGC GAA ACAUCAUC | 7771 | GAUGAUGUC AGAUAUGU | 629 |
| 3887 | CAUUUACA CUGAUGA GCCGUUAGGC GAA AUCUGACA | 7772 | UGUCAGAUA UGUAAAUG | 630 |
| 3891 | AAAGCAUU CUGAUGA GCCGUUAGGC GAA ACAUAUCU | 7773 | AGAUAUGUA AAUGCUUU | 631 |
| 3898 | GAACUUGA CUGAUGA GCCGUUAGGC GAA AGCAUUUA | 7774 | UAAAUGCUU UCAAGUUC | 632 |
| 3899 | UGAACUUG CUGAUGA GCCGUUAGGC GAA AAGCAUUU | 7775 | AAAUGCUUU CAAGUUCA | 633 |
| 3900 | AUGAACUU CUGAUGA GCCGUUAGGC GAA AAAGCAUU | 7776 | AAUGCUUUC AAGUUCAU | 634 |
| 3905 | GGCUCAUG CUGAUGA GCCGUUAGGC GAA ACUUGAAA | 7777 | UUUCAAGUU CAUGAGCC | 635 |
| 3906 | AGGCUCAU CUGAUGA GCCGUUAGGC GAA AACUUGAA | 7778 | UUCAAGUUC AUGAGCCU | 636 |
| 3924 | AAGGUUUU CUGAUGA GCCGUUAGGC GAA AUUCUUUC | 7779 | GAAAGAAUC AAAACCUU | 637 |
| 3932 | GUUCUUCA CUGAUGA GCCGUUAGGC GAA AGGUUUUG | 7780 | CAAAACCUU UGAAGAAC | 638 |
| 3933 | AGUUCUUC CUGAUGA GCCGUUAGGC GAA AAGGUUUU | 7781 | AAAACCUUU GAAGAACU | 639 |
| 3942 | UUCGGUAA CUGAUGA GCCGUUAGGC GAA AGUUCUUC | 7782 | GAAGAACUU UUACCGAA | 640 |
| 3943 | AUUCGGUA CUGAUGA GCCGUUAGGC GAA AAGUUCUU | 7783 | AAGAACUUU UACCGAAU | 641 |
| 3944 | CAUUCGGU CUGAUGA GCCGUUAGGC GAA AAAGUUCU | 7784 | AGAACUUUU ACCGAAUG | 642 |
| 3945 | GCAUUCGG CUGAUGA GCCGUUAGGC GAA AAAAGUUC | 7785 | GAACUUUUA CCGAAUGC | 643 |
| 3959 | CAAACAUG CUGAUGA GCCGUUAGGC GAA AGGUGGCA | 7786 | UGCCACCUC CAUGUUUG | 644 |
| 3965 | AGUCAUCA CUGAUGA GCCGUUAGGC GAA ACAUGGAG | 7787 | CUCCAUGUU UGAUGACU | 645 |
| 3966 | UAGUCAUC CUGAUGA GCCGUUAGGC GAA AACAUGGA | 7788 | UCCAUGUUU GAUGACUA | 646 |
| 3974 | CGCCCUGG CUGAUGA GCCGUUAGGC GAA AGUCAUCA | 7789 | UGAUGACUA CCAGGGCG | 647 |
| 3994 | GGCCAACA CUGAUGA GCCGUUAGGC GAA AGUGCUGC | 7790 | GCAGCACUC UGUUGGCC | 648 |
| 3998 | GAGAGGCC CUGAUGA GCCGUUAGGC GAA ACAGAGUG | 7791 | CACUCUGUU GGCCUCUC | 649 |
| 4004 | GCAUGGGA CUGAUGA GCCGUUAGGC GAA AGGCCAAC | 7792 | GUUGGCCUC UCCCAUGC | 650 |
| 4006 | CAGCAUGG CUGAUGA GCCGUUAGGC GAA AGAGGCCA | 7793 | UGGCCUCUC CCAUGCUG | 651 |
| 4022 | UCCAGGUG CUGAUGA GCCGUUAGGC GAA AGCGCUUC | 7794 | GAAGCGCUU CACCUGGA | 652 |
| 4023 | GUCCAGGU CUGAUGA GCCGUUAGGC GAA AAGCGCUU | 7795 | AAGCGCUUC ACCUGGAC | 653 |
| 4052 | UCUUGAGC CUGAUGA GCCGUUAGGC GAA AGGCCUUG | 7796 | CAAGGCCUC GCUCAAGA | 654 |
| 4056 | UCAAUCUU CUGAUGA GCCGUUAGGC GAA AGCGAGGC | 7797 | GCCUCGCUC AAGAUUGA | 655 |
| 4062 | CUCAAGUC CUGAUGA GCCGUUAGGC GAA AUCUUGAG | 7798 | CUCAAGAUU GACUUGAG | 656 |

93

| | | | | |
|---|---|---|---|---|
| 4067 | UUACUCUC CUGAUGA GCCGUUAGGC GAA AGUCAAUC | 7799 | GAUUGACUU GAGAGUAA | 657 |
| 4074 | UUACUGGU CUGAUGA GCCGUUAGGC GAA ACUCUCAA | 7800 | UUGAGAGUA ACCAGUAA | 658 |
| 4081 | CUUACUUU CUGAUGA GCCGUUAGGC GAA ACUGGUUA | 7801 | UAACCAGUA AAAGUAAG | 659 |
| 4087 | CGACUCCU CUGAUGA GCCGUUAGGC GAA ACUUUUAC | 7802 | GUAAAAGUA AGGAGUCG | 660 |
| 4094 | ACAGCCCC CUGAUGA GCCGUUAGGC GAA ACUCCUUA | 7803 | UAAGGAGUC GGGGCUGU | 661 |
| 4103 | UGACAUCA CUGAUGA GCCGUUAGGC GAA ACAGCCCC | 7804 | GGGGCUGUC UGAUGUCA | 662 |
| 4110 | GGCCUGCU CUGAUGA GCCGUUAGGC GAA ACAUCAGA | 7805 | UCUGAUGUC AGCAGGCC | 663 |
| 4123 | AUGGCAGA CUGAUGA GCCGUUAGGC GAA ACUGGGCC | 7806 | GGCCCAGUU UCUGCCAU | 664 |
| 4124 | AAUGGCAG CUGAUGA GCCGUUAGGC GAA AACUGGGC | 7807 | GCCCAGUUU CUGCCAUU | 665 |
| 4125 | GAAUGGCA CUGAUGA GCCGUUAGGC GAA AAACUGGG | 7808 | CCCAGUUUC UGCCAUUC | 666 |
| 4132 | ACAGCUGG CUGAUGA GCCGUUAGGC GAA AUGGCAGA | 7809 | UCUGCCAUU CCAGCUGU | 667 |
| 4133 | CACAGCUG CUGAUGA GCCGUUAGGC GAA AAUGGCAG | 7810 | CUGCCAUUC CAGCUGUG | 668 |
| 4149 | CCUUCGCU CUGAUGA GCCGUUAGGC GAA ACGUGCCC | 7811 | GGGCACGUC AGCGAAGG | 669 |
| 4169 | CGUAGGUG CUGAUGA GCCGUUAGGC GAA ACCUGCGC | 7812 | GCGCAGGUU CACCUACG | 670 |
| 4170 | UCGUAGGU CUGAUGA GCCGUUAGGC GAA AACCUGCG | 7813 | CGCAGGUUC ACCUACGA | 671 |
| 4175 | CGUGGUCG CUGAUGA GCCGUUAGGC GAA AGGUGAAC | 7814 | GUUCACCUA CGACCACG | 672 |
| 4203 | CAGCACGC CUGAUGA GCCGUUAGGC GAA AUUUUCCU | 7815 | AGGAAAAUC GCGUGCUG | 673 |
| 4214 | GGGGCGGG CUGAUGA GCCGUUAGGC GAA AGCAGCAC | 7816 | GUGCUGCUC CCCGCCCC | 674 |
| 4229 | CCGAGUUG CUGAUGA GCCGUUAGGC GAA AGUCUGGG | 7817 | CCCAGACUA CAACUCGG | 675 |
| 4235 | GGACCACC CUGAUGA GCCGUUAGGC GAA AGUUGUAG | 7818 | CUACAACUC GGUGGUCC | 676 |
| 4242 | GAGUACAG CUGAUGA GCCGUUAGGC GAA ACCACCGA | 7819 | UCGGUGGUC CUGUACUC | 677 |
| 4247 | GGGUGGAG CUGAUGA GCCGUUAGGC GAA ACAGGACC | 7820 | GGUCCUGUA CUCCACCC | 678 |
| 4250 | GUGGGGUG CUGAUGA GCCGUUAGGC GAA AGUACAGG | 7821 | CCUGUACUC CACCCCAC | 679 |
| 4263 | AAACUCUA CUGAUGA GCCGUUAGGC GAA AUGGGUGG | 7822 | CCACCCAUC UAGAGUUU | 680 |
| 4265 | UCAAACUC CUGAUGA GCCGUUAGGC GAA AGAUGGGU | 7823 | ACCCAUCUA GAGUUUGA | 681 |
| 4270 | UCGUGUCA CUGAUGA GCCGUUAGGC GAA ACUCUAGA | 7824 | UCUAGAGUU UGACACGA | 682 |
| 4271 | UUCGUGUC CUGAUGA GCCGUUAGGC GAA AACUCUAG | 7825 | CUAGAGUUU GACACGAA | 683 |
| 4284 | CUAGAAAU CUGAUGA GCCGUUAGGC GAA AGGCUUCG | 7826 | CGAAGCCUU AUUUCUAG | 684 |
| 4285 | UCUAGAAA CUGAUGA GCCGUUAGGC GAA AAGGCUUC | 7827 | GAAGCCUUA UUUCUAGA | 685 |
| 4287 | CUUCUAGA CUGAUGA GCCGUUAGGC GAA AUAAGGCU | 7828 | AGCCUUAUU UCUAGAAG | 686 |
| 4288 | GCUUCUAG CUGAUGA GCCGUUAGGC GAA AAUAAGGC | 7829 | GCCUUAUUU CUAGAAGC | 687 |
| 4289 | UGCUUCUA CUGAUGA GCCGUUAGGC GAA AAAUAAGG | 7830 | CCUUAUUUC UAGAAGCA | 688 |
| 4291 | UGUGCUUC CUGAUGA GCCGUUAGGC GAA AGAAAUAA | 7831 | UUAUUUCUA GAAGCACA | 689 |

| | | | | |
|---|---|---|---|---|
| 4305 | GGUAUAAA CUGAUGA GCCGUUAGGC GAA ACACAUGU | 7832 | ACAUGUGUA UUUAUACC | 690 |
| 4307 | GGGGUAUA CUGAUGA GCCGUUAGGC GAA AUACACAU | 7833 | AUGUGUAUU UAUACCCC | 691 |
| 4308 | GGGGGUAU CUGAUGA GCCGUUAGGC GAA AAUACACA | 7834 | UGUGUAUUU AUACCCCC | 692 |
| 4309 | UGGGGGUA CUGAUGA GCCGUUAGGC GAA AAAUACAC | 7835 | GUGUAUUUA UACCCCCA | 693 |
| 4311 | CCUGGGGG CUGAUGA GCCGUUAGGC GAA AUAAAUAC | 7836 | GUAUUUAUA CCCCCAGG | 694 |
| 4325 | GCAAAAGC CUGAUGA GCCGUUAGGC GAA AGUUUCCU | 7837 | AGGAAACUA GCUUUUGC | 695 |
| 4329 | ACUGGCAA CUGAUGA GCCGUUAGGC GAA AGCUAGUU | 7838 | AACUAGCUU UUGCCAGU | 696 |
| 4330 | UACUGGCA CUGAUGA GCCGUUAGGC GAA AAGCUAGU | 7839 | ACUAGCUUU UGCCAGUA | 697 |
| 4331 | AUACUGGC CUGAUGA GCCGUUAGGC GAA AAAGCUAG | 7840 | CUAGCUUUU GCCAGUAU | 698 |
| 4338 | AUGCAUAA CUGAUGA GCCGUUAGGC GAA ACUGGCAA | 7841 | UUGCCAGUA UUAUGCAU | 699 |
| 4340 | AUAUGCAU CUGAUGA GCCGUUAGGC GAA AUACUGGC | 7842 | GCCAGUAUU AUGCAUAU | 700 |
| 4341 | UAUAUGCA CUGAUGA GCCGUUAGGC GAA AAUACUGG | 7843 | CCAGUAUUA UGCAUAUA | 701 |
| 4347 | AACUUAUA CUGAUGA GCCGUUAGGC GAA AUGCAUAA | 7844 | UUAUGCAUA UAUAAGUU | 702 |
| 4349 | UAAACUUA CUGAUGA GCCGUUAGGC GAA AUAUGCAU | 7845 | AUGCAUAUA UAAGUUUA | 703 |
| 4351 | UGUAAACU CUGAUGA GCCGUUAGGC GAA AUAUAUGC | 7846 | GCAUAUAUA AGUUUACA | 704 |
| 4355 | AAGGUGUA CUGAUGA GCCGUUAGGC GAA ACUUAUAU | 7847 | AUAUAAGUU UACACCUU | 705 |
| 4356 | AAAGGUGU CUGAUGA GCCGUUAGGC GAA AACUUAUA | 7848 | UAUAAGUUU ACACCUUU | 706 |
| 4357 | UAAAGGUG CUGAUGA GCCGUUAGGC GAA AAACUUAU | 7849 | AUAAGUUUA CACCUUUA | 707 |
| 4363 | GAAAGAUA CUGAUGA GCCGUUAGGC GAA AGGUGUAA | 7850 | UUACACCUU UAUCUUUC | 708 |
| 4364 | GGAAAGAU CUGAUGA GCCGUUAGGC GAA AAGGUGUA | 7851 | UACACCUUU AUCUUUCC | 709 |
| 4365 | UGGAAAGA CUGAUGA GCCGUUAGGC GAA AAAGGUGU | 7852 | ACACCUUUA UCUUUCCA | 710 |
| 4367 | CAUGGAAA CUGAUGA GCCGUUAGGC GAA AUAAAGGU | 7853 | ACCUUUAUC UUUCCAUG | 711 |
| 4369 | CCCAUGGA CUGAUGA GCCGUUAGGC GAA AGAUAAAG | 7854 | CUUUAUCUU UCCAUGGG | 712 |
| 4370 | UCCCAUGG CUGAUGA GCCGUUAGGC GAA AAGAUAAA | 7855 | UUUAUCUUU CCAUGGGA | 713 |
| 4371 | CUCCCAUG CUGAUGA GCCGUUAGGC GAA AAAGAUAA | 7856 | UUAUCUUUC CAUGGGAG | 714 |
| 4389 | AUCACAAA CUGAUGA GCCGUUAGGC GAA AGCAGCUG | 7857 | CAGCUGCUU UUUGUGAU | 715 |
| 4390 | AAUCACAA CUGAUGA GCCGUUAGGC GAA AAGCAGCU | 7858 | AGCUGCUUU UUGUGAUU | 716 |
| 4391 | AAAUCACA CUGAUGA GCCGUUAGGC GAA AAAGCAGC | 7859 | GCUGCUUUU UGUGAUUU | 717 |
| 4392 | AAAAUCAC CUGAUGA GCCGUUAGGC GAA AAAAGCAG | 7860 | CUGCUUUUU GUGAUUUU | 718 |
| 4398 | AUUAAAAA CUGAUGA GCCGUUAGGC GAA AUCACAAA | 7861 | UUUGUGAUU UUUUUAAU | 719 |
| 4399 | UAUUAAAA CUGAUGA GCCGUUAGGC GAA AAUCACAA | 7862 | UUGUGAUUU UUUUAAUA | 720 |
| 4400 | CUAUUAAA CUGAUGA GCCGUUAGGC GAA AAAUCACA | 7863 | UGUGAUUUU UUUAAUAG | 721 |
| 4401 | ACUAUUAA CUGAUGA GCCGUUAGGC GAA AAAAUCAC | 7864 | GUGAUUUUU UUAAUAGU | 722 |

| | | | | |
|---|---|---|---|---|
| 4402 | CACUAUUA CUGAUGA GCCGUUAGGC GAA AAAAAUCA | 7865 | UGAUUUUUU UAAUAGUG | 723 |
| 4403 | GCACUAUU CUGAUGA GCCGUUAGGC GAA AAAAAAUC | 7866 | GAUUUUUUU AAUAGUGC | 724 |
| 4404 | AGCACUAU CUGAUGA GCCGUUAGGC GAA AAAAAAAU | 7867 | AUUUUUUUA AUAGUGCU | 725 |
| 4407 | AAAAGCAC CUGAUGA GCCGUUAGGC GAA AUUAAAAA | 7868 | UUUUUAAUA GUGCUUUU | 726 |
| 4413 | AAAAAAAA CUGAUGA GCCGUUAGGC GAA AGCACUAU | 7869 | AUAGUGCUU UUUUUUUU | 727 |
| 4414 | AAAAAAAA CUGAUGA GCCGUUAGGC GAA AAGCACUA | 7870 | UAGUGCUUU UUUUUUUU | 728 |
| 4415 | CAAAAAAA CUGAUGA GCCGUUAGGC GAA AAAGCACU | 7871 | AGUGCUUUU UUUUUUUG | 729 |
| 4416 | UCAAAAAA CUGAUGA GCCGUUAGGC GAA AAAAGCAC | 7872 | GUGCUUUUU UUUUUUGA | 730 |
| 4417 | GUCAAAAA CUGAUGA GCCGUUAGGC GAA AAAAAGCA | 7873 | UGCUUUUUU UUUUUGAC | 731 |
| 4418 | AGUCAAAA CUGAUGA GCCGUUAGGC GAA AAAAAAGC | 7874 | GCUUUUUUU UUUUGACU | 732 |
| 4419 | UAGUCAAA CUGAUGA GCCGUUAGGC GAA AAAAAAAG | 7875 | CUUUUUUUU UUUGACUA | 733 |
| 4420 | UUAGUCAA CUGAUGA GCCGUUAGGC GAA AAAAAAAA | 7876 | UUUUUUUUU UUGACUAA | 734 |
| 4421 | GUUAGUCA CUGAUGA GCCGUUAGGC GAA AAAAAAAA | 7877 | UUUUUUUUU UGACUAAC | 735 |
| 4422 | UGUUAGUC CUGAUGA GCCGUUAGGC GAA AAAAAAAA | 7878 | UUUUUUUUU GACUAACA | 736 |
| 4427 | AUUCUUGU CUGAUGA GCCGUUAGGC GAA AGUCAAAA | 7879 | UUUUGACUA ACAAGAAU | 737 |
| 4438 | UCUGGAGU CUGAUGA GCCGUUAGGC GAA ACAUUCUU | 7880 | AAGAAUGUA ACUCCAGA | 738 |
| 4442 | UCUAUCUG CUGAUGA GCCGUUAGGC GAA AGUUACAU | 7881 | AUGUAACUC CAGAUAGA | 739 |
| 4448 | UAUUUCUC CUGAUGA GCCGUUAGGC GAA AUCUGGAG | 7882 | CUCCAGAUA GAGAAAUA | 740 |
| 4456 | CUUGUCAC CUGAUGA GCCGUUAGGC GAA AUUUCUCU | 7883 | AGAGAAAUA GUGACAAG | 741 |
| 4476 | UUUAGCAG CUGAUGA GCCGUUAGGC GAA AGUGUUCU | 7884 | AGAACACUA CUGCUAAA | 742 |
| 4482 | UGAGGAUU CUGAUGA GCCGUUAGGC GAA AGCAGUAG | 7885 | CUACUGCUA AAUCCUCA | 743 |
| 4486 | AACAUGAG CUGAUGA GCCGUUAGGC GAA AUUUAGCA | 7886 | UGCUAAAUC CUCAUGUU | 744 |
| 4489 | AGUAACAU CUGAUGA GCCGUUAGGC GAA AGGAUUUA | 7887 | UAAAUCCUC AUGUUACU | 745 |
| 4494 | CACUGAGU CUGAUGA GCCGUUAGGC GAA ACAUGAGG | 7888 | CCUCAUGUU ACUCAGUG | 746 |
| 4495 | ACACUGAG CUGAUGA GCCGUUAGGC GAA AACAUGAG | 7889 | CUCAUGUUA CUCAGUGU | 747 |
| 4498 | CUAACACU CUGAUGA GCCGUUAGGC GAA AGUAACAU | 7890 | AUGUUACUC AGUGUUAG | 748 |
| 4504 | AUUUCUCU CUGAUGA GCCGUUAGGC GAA ACACUGAG | 7891 | CUCAGUGUU AGAGAAAU | 749 |
| 4505 | GAUUUCUC CUGAUGA GCCGUUAGGC GAA AACACUGA | 7892 | UCAGUGUUA GAGAAAUC | 750 |
| 4513 | UUAGGAAG CUGAUGA GCCGUUAGGC GAA AUUUCUCU | 7893 | AGAGAAAUC CUUCCUAA | 751 |
| 4516 | GGUUUAGG CUGAUGA GCCGUUAGGC GAA AGGAUUUC | 7894 | GAAAUCCUU CCUAAACC | 752 |
| 4517 | GGGUUUAG CUGAUGA GCCGUUAGGC GAA AAGGAUUU | 7895 | AAAUCCUUC CUAAACCC | 753 |
| 4520 | AUUGGGUU CUGAUGA GCCGUUAGGC GAA AGGAAGGA | 7896 | UCCUUCCUA AACCCAAU | 754 |
| 4533 | GAGCAGGG CUGAUGA GCCGUUAGGC GAA AGUCAUUG | 7897 | CAAUGACUU CCCUGCUC | 755 |

| | | | | |
|---|---|---|---|---|
| 4534 | GGAGCAGG CUGAUGA GCCGUUAGGC GAA AAGUCAUU | 7898 | AAUGACUUC CCUGCUCC | 756 |
| 4541 | GGGGGUUG CUGAUGA GCCGUUAGGC GAA AGCAGGGA | 7899 | UCCCUGCUC CAACCCCC | 757 |
| 4557 | CGUGCCCU CUGAUGA GCCGUUAGGC GAA AGGUGGCG | 7900 | CGCCACCUC AGGGCACG | 758 |
| 4576 | CUCAAUCA CUGAUGA GCCGUUAGGC GAA ACUGGUCC | 7901 | GGACCAGUU UGAUUGAG | 759 |
| 4577 | CCUCAAUC CUGAUGA GCCGUUAGGC GAA AACUGGUC | 7902 | GACCAGUUU GAUUGAGG | 760 |
| 4581 | AGCUCCUC CUGAUGA GCCGUUAGGC GAA AUCAAACU | 7903 | AGUUUGAUU GAGGAGCU | 761 |
| 4598 | CAUUGGGU CUGAUGA GCCGUUAGGC GAA AUCAGUGC | 7904 | GCACUGAUC ACCCAAUG | 762 |
| 4610 | GGGUACGU CUGAUGA GCCGUUAGGC GAA AUGCAUUG | 7905 | CAAUGCAUC ACGUACCC | 763 |
| 4615 | CAGUGGGG CUGAUGA GCCGUUAGGC GAA ACGUGAUG | 7906 | CAUCACGUA CCCCACUG | 764 |
| 4664 | CUGGGGCU CUGAUGA GCCGUUAGGC GAA ACGGGCUU | 7907 | AAGCCCGUU AGCCCCAG | 765 |
| 4665 | CCUGGGGC CUGAUGA GCCGUUAGGC GAA AACGGGCU | 7908 | AGCCCGUUA GCCCCAGG | 766 |
| 4678 | CAGCCAGU CUGAUGA GCCGUUAGGC GAA AUCCCCUG | 7909 | CAGGGGAUC ACUGGCUG | 767 |
| 4700 | ACUCCCGA CUGAUGA GCCGUUAGGC GAA AUGUUGCU | 7910 | AGCAACAUC UCGGGAGU | 768 |
| 4702 | GGACUCCC CUGAUGA GCCGUUAGGC GAA AGAUGUUG | 7911 | CAACAUCUC GGGAGUCC | 769 |
| 4709 | UGCUAGAG CUGAUGA GCCGUUAGGC GAA ACUCCCGA | 7912 | UCGGGAGUC CUCUAGCA | 770 |
| 4712 | GCCUGCUA CUGAUGA GCCGUUAGGC GAA AGGACUCC | 7913 | GGAGUCCUC UAGCAGGC | 771 |
| 4714 | AGGCCUGC CUGAUGA GCCGUUAGGC GAA AGAGGACU | 7914 | AGUCCUCUA GCAGGCCU | 772 |
| 4723 | ACAUGUCU CUGAUGA GCCGUUAGGC GAA AGGCCUGC | 7915 | GCAGGCCUA AGACAUGU | 773 |
| 4802 | GCGUCUCA CUGAUGA GCCGUUAGGC GAA AUUCUUUC | 7916 | GAAAGAAUU UGAGACGC | 774 |
| 4803 | UGCGUCUC CUGAUGA GCCGUUAGGC GAA AAUUCUUU | 7917 | AAAGAAUUU GAGACGCA | 775 |
| 4840 | GCAUUGCU CUGAUGA GCCGUUAGGC GAA AGCCCCGU | 7918 | ACGGGGCUC AGCAAUGC | 776 |
| 4852 | GCCACUGA CUGAUGA GCCGUUAGGC GAA AUGGCAUU | 7919 | AAUGCCAUU UCAGUGGC | 777 |
| 4853 | AGCCACUG CUGAUGA GCCGUUAGGC GAA AAUGGCAU | 7920 | AUGCCAUUU CAGUGGCU | 778 |
| 4854 | AAGCCACU CUGAUGA GCCGUUAGGC GAA AAAUGGCA | 7921 | UGCCAUUUC AGUGGCUU | 779 |
| 4862 | GAGCUGGG CUGAUGA GCCGUUAGGC GAA AGCCACUG | 7922 | CAGUGGCUU CCCAGCUC | 780 |
| 4863 | AGAGCUGG CUGAUGA GCCGUUAGGC GAA AAGCCACU | 7923 | AGUGGCUUC CCAGCUCU | 781 |
| 4870 | AAGGGUCA CUGAUGA GCCGUUAGGC GAA AGCUGGGA | 7924 | UCCCAGCUC UGACCCUU | 782 |
| 4878 | AAAUGUAG CUGAUGA GCCGUUAGGC GAA AGGGUCAG | 7925 | CUGACCCUU CUACAUUU | 783 |
| 4879 | CAAAUGUA CUGAUGA GCCGUUAGGC GAA AAGGGUCA | 7926 | UGACCCUUC UACAUUUG | 784 |
| 4881 | CUCAAAUG CUGAUGA GCCGUUAGGC GAA AGAAGGGU | 7927 | ACCCUUCUA CAUUUGAG | 785 |
| 4885 | GGCCCUCA CUGAUGA GCCGUUAGGC GAA AUGUAGAA | 7928 | UUCUACAUU UGAGGGCC | 786 |
| 4886 | GGGCCCUC CUGAUGA GCCGUUAGGC GAA AAUGUAGA | 7929 | UCUACAUUU GAGGGCCC | 787 |
| 4929 | AUCCAGAA CUGAUGA GCCGUUAGGC GAA AUGUCCCC | 7930 | GGGGACAUU UUCUGGAU | 788 |

| | | | | |
|---|---|---|---|---|
| 4930 | AAUCCAGA CUGAUGA GCCGUUAGGC GAA AAUGUCCC | 7931 | GGGACAUUU UCUGGAUU | 789 |
| 4931 | GAAUCCAG CUGAUGA GCCGUUAGGC GAA AAAUGUCC | 7932 | GGACAUUUU CUGGAUUC | 790 |
| 4932 | AGAAUCCA CUGAUGA GCCGUUAGGC GAA AAAAUGUC | 7933 | GACAUUUUC UGGAUUCU | 791 |
| 4938 | CCUCCCAG CUGAUGA GCCGUUAGGC GAA AUCCAGAA | 7934 | UUCUGGAUU CUGGGAGG | 792 |
| 4939 | GCCUCCCA CUGAUGA GCCGUUAGGC GAA AAUCCAGA | 7935 | UCUGGAUUC UGGGAGGC | 793 |
| 4963 | AAAAAAGA CUGAUGA GCCGUUAGGC GAA AUUUGUCC | 7936 | GGACAAAUA UCUUUUUU | 794 |
| 4965 | CCAAAAAA CUGAUGA GCCGUUAGGC GAA AUAUUUGU | 7937 | ACAAAUAUC UUUUUUGG | 795 |
| 4967 | UUCCAAAA CUGAUGA GCCGUUAGGC GAA AGAUAUUU | 7938 | AAAUAUCUU UUUUGGAA | 796 |
| 4968 | GUUCCAAA CUGAUGA GCCGUUAGGC GAA AAGAUAUU | 7939 | AAUAUCUUU UUUGGAAC | 797 |
| 4969 | AGUUCCAA CUGAUGA GCCGUUAGGC GAA AAAGAUAU | 7940 | AUAUCUUUU UUGGAACU | 798 |
| 4970 | UAGUUCCA CUGAUGA GCCGUUAGGC GAA AAAAGAUA | 7941 | UAUCUUUUU UGGAACUA | 799 |
| 4971 | UUAGUUCC CUGAUGA GCCGUUAGGC GAA AAAAAGAU | 7942 | AUCUUUUUU GGAACUAA | 800 |
| 4978 | AUUUGCUU CUGAUGA GCCGUUAGGC GAA AGUUCCAA | 7943 | UUGGAACUA AAGCAAAU | 801 |
| 4987 | AGGUCUAA CUGAUGA GCCGUUAGGC GAA AUUUGCUU | 7944 | AAGCAAAUU UUAGACCU | 802 |
| 4988 | AAGGUCUA CUGAUGA GCCGUUAGGC GAA AAUUUGCU | 7945 | AGCAAAUUU UAGACCUU | 803 |
| 4989 | AAAGGUCU CUGAUGA GCCGUUAGGC GAA AAAUUUGC | 7946 | GCAAAUUUU AGACCUUU | 804 |
| 4990 | UAAAGGUC CUGAUGA GCCGUUAGGC GAA AAAAUUUG | 7947 | CAAAUUUUA GACCUUUA | 805 |
| 4996 | CAUAGGUA CUGAUGA GCCGUUAGGC GAA AGGUCUAA | 7948 | UUAGACCUU UACCUAUG | 806 |
| 4997 | CCAUAGGU CUGAUGA GCCGUUAGGC GAA AAGGUCUA | 7949 | UAGACCUUU ACCUAUGG | 807 |
| 4998 | UCCAUAGG CUGAUGA GCCGUUAGGC GAA AAAGGUCU | 7950 | AGACCUUUA CCUAUGGA | 808 |
| 5002 | CACUUCCA CUGAUGA GCCGUUAGGC GAA AGGUAAAG | 7951 | CUUUACCUA UGGAAGUG | 809 |
| 5013 | GGACAUAG CUGAUGA GCCGUUAGGC GAA ACCACUUC | 7952 | GAAGUGGUU CUAUGUCC | 810 |
| 5014 | UGGACAUA CUGAUGA GCCGUUAGGC GAA AACCACUU | 7953 | AAGUGGUUC UAUGUCCA | 811 |
| 5016 | AAUGGACA CUGAUGA GCCGUUAGGC GAA AGAACCAC | 7954 | GUGGUUCUA UGUCCAUU | 812 |
| 5020 | UGAGAAUG CUGAUGA GCCGUUAGGC GAA ACAUAGAA | 7955 | UUCUAUGUC CAUUCUCA | 813 |
| 5024 | CGAAUGAG CUGAUGA GCCGUUAGGC GAA AUGGACAU | 7956 | AUGUCCAUU CUCAUUCG | 814 |
| 5025 | ACGAAUGA CUGAUGA GCCGUUAGGC GAA AAUGGACA | 7957 | UGUCCAUUC UCAUUCGU | 815 |
| 5027 | CCACGAAU CUGAUGA GCCGUUAGGC GAA AGAAUGGA | 7958 | UCCAUUCUC AUUCGUGG | 816 |
| 5030 | AUGCCACG CUGAUGA GCCGUUAGGC GAA AUGAGAAU | 7959 | AUUCUCAUU CGUGGCAU | 817 |
| 5031 | CAUGCCAC CUGAUGA GCCGUUAGGC GAA AAUGAGAA | 7960 | UUCUCAUUC GUGGCAUG | 818 |
| 5041 | CAAAUCAA CUGAUGA GCCGUUAGGC GAA ACAUGCCA | 7961 | UGGCAUGUU UUGAUUUG | 819 |
| 5042 | ACAAAUCA CUGAUGA GCCGUUAGGC GAA AACAUGCC | 7962 | GGCAUGUUU UGAUUUGU | 820 |
| 5043 | UACAAAUC CUGAUGA GCCGUUAGGC GAA AAACAUGC | 7963 | GCAUGUUUU GAUUUGUA | 821 |

98

| | | | | |
|---|---|---|---|---|
| 5047 | GUGCUACA CUGAUGA GCCGUUAGGC GAA AUCAAAAC | 7964 | GUUUUGAUU UGUAGCAC | 822 |
| 5048 | AGUGCUAC CUGAUGA GCCGUUAGGC GAA AAUCAAAA | 7965 | UUUUGAUUU GUAGCACU | 823 |
| 5051 | CUCAGUGC CUGAUGA GCCGUUAGGC GAA ACAAAUCA | 7966 | UGAUUUGUA GCACUGAG | 824 |
| 5069 | UCAGAGUU CUGAUGA GCCGUUAGGC GAA AGUGCCAC | 7967 | GUGGCACUC AACUCUGA | 825 |
| 5074 | UGGGCUCA CUGAUGA GCCGUUAGGC GAA AGUUGAGU | 7968 | ACUCAACUC UGAGCCCA | 826 |
| 5084 | GCCAAAAG CUGAUGA GCCGUUAGGC GAA AUGGGCUC | 7969 | GAGCCCAUA CUUUUGGC | 827 |
| 5087 | GGAGCCAA CUGAUGA GCCGUUAGGC GAA AGUAUGGG | 7970 | CCCAUACUU UUGGCUCC | 828 |
| 5088 | AGGAGCCA CUGAUGA GCCGUUAGGC GAA AAGUAUGG | 7971 | CCAUACUUU UGGCUCCU | 829 |
| 5089 | GAGGAGCC CUGAUGA GCCGUUAGGC GAA AAAGUAUG | 7972 | CAUACUUUU GGCUCCUC | 830 |
| 5094 | UACUAGAG CUGAUGA GCCGUUAGGC GAA AGCCAAAA | 7973 | UUUUGGCUC CUCUAGUA | 831 |
| 5097 | UCUUACUA CUGAUGA GCCGUUAGGC GAA AGGAGCCA | 7974 | UGGCUCCUC UAGUAAGA | 832 |
| 5099 | CAUCUUAC CUGAUGA GCCGUUAGGC GAA AGAGGAGC | 7975 | GCUCCUCUA GUAAGAUG | 833 |
| 5102 | GUGCAUCU CUGAUGA GCCGUUAGGC GAA ACUAGAGG | 7976 | CCUCUAGUA AGAUGCAC | 834 |
| 5119 | CUCUGGCU CUGAUGA GCCGUUAGGC GAA AGUUUUCA | 7977 | UGAAAACUU AGCCAGAG | 835 |
| 5120 | ACUCUGGC CUGAUGA GCCGUUAGGC GAA AAGUUUUC | 7978 | GAAAACUUA GCCAGAGU | 836 |
| 5129 | GACAACCU CUGAUGA GCCGUUAGGC GAA ACUCUGGC | 7979 | GCCAGAGUU AGGUUGUC | 837 |
| 5130 | AGACAACC CUGAUGA GCCGUUAGGC GAA AACUCUGG | 7980 | CCAGAGUUA GGUUGUCU | 838 |
| 5134 | CUGGAGAC CUGAUGA GCCGUUAGGC GAA ACCUAACU | 7981 | AGUUAGGUU GUCUCCAG | 839 |
| 5137 | GGCCUGGA CUGAUGA GCCGUUAGGC GAA ACAACCUA | 7982 | UAGGUUGUC UCCAGGCC | 840 |
| 5139 | AUGGCCUG CUGAUGA GCCGUUAGGC GAA AGACAACC | 7983 | GGUUGUCUC CAGGCCAU | 841 |
| 5156 | UUCAGUGU CUGAUGA GCCGUUAGGC GAA AGGCCAUC | 7984 | GAUGGCCUU ACACUGAA | 842 |
| 5157 | UUUCAGUG CUGAUGA GCCGUUAGGC GAA AAGGCCAU | 7985 | AUGGCCUUA CACUGAAA | 843 |
| 5170 | UAGAAUGU CUGAUGA GCCGUUAGGC GAA ACAUUUUC | 7986 | GAAAAUGUC ACAUUCUA | 844 |
| 5175 | CAAAAUAG CUGAUGA GCCGUUAGGC GAA AUGUGACA | 7987 | UGUCACAUU CUAUUUUG | 845 |
| 5176 | CCAAAAUA CUGAUGA GCCGUUAGGC GAA AAUGUGAC | 7988 | GUCACAUUC UAUUUUGG | 846 |
| 5178 | ACCCAAAA CUGAUGA GCCGUUAGGC GAA AGAAUGUG | 7989 | CACAUUCUA UUUUGGGU | 847 |
| 5180 | AUACCCAA CUGAUGA GCCGUUAGGC GAA AUAGAAUG | 7990 | CAUUCUAUU UUGGGUAU | 848 |
| 5181 | AAUACCCA CUGAUGA GCCGUUAGGC GAA AAUAGAAU | 7991 | AUUCUAUUU UGGGUAUU | 849 |
| 5182 | UAAUACCC CUGAUGA GCCGUUAGGC GAA AAAUAGAA | 7992 | UUCUAUUUU GGGUAUUA | 850 |
| 5187 | UAUAUUAA CUGAUGA GCCGUUAGGC GAA ACCCAAAA | 7993 | UUUUGGGUA UUAAUAUA | 851 |
| 5189 | UAUAUAUU CUGAUGA GCCGUUAGGC GAA AUACCCAA | 7994 | UUGGGUAUU AAUAUAUA | 852 |
| 5190 | CUAUAUAU CUGAUGA GCCGUUAGGC GAA AAUACCCA | 7995 | UGGGUAUUA AUAUAUAG | 853 |
| 5193 | GGACUAUA CUGAUGA GCCGUUAGGC GAA AUUAAUAC | 7996 | GUAUUAAUA UAUAGUCC | 854 |

99

| | | | | |
|---|---|---|---|---|
| 5195 | CUGGACUA CUGAUGA GCCGUUAGGC GAA AUAUUAAU | 7997 | AUUAAUAUA UAGUCCAG | 855 |
| 5197 | GUCUGGAC CUGAUGA GCCGUUAGGC GAA AUAUAUUA | 7998 | UAAUAUAUA GUCCAGAC | 856 |
| 5200 | AGUGUCUG CUGAUGA GCCGUUAGGC GAA ACUAUAUA | 7999 | UAUAUAGUC CAGACACU | 857 |
| 5209 | AUUGAGUU CUGAUGA GCCGUUAGGC GAA AGUGUCUG | 8000 | CAGACACUU AACUCAAU | 858 |
| 5210 | AAUUGAGU CUGAUGA GCCGUUAGGC GAA AAGUGUCU | 8001 | AGACACUUA ACUCAAUU | 859 |
| 5214 | AAGAAAUU CUGAUGA GCCGUUAGGC GAA AGUUAAGU | 8002 | ACUUAACUC AAUUUCUU | 860 |
| 5218 | UACCAAGA CUGAUGA GCCGUUAGGC GAA AUUGAGUU | 8003 | AACUCAAUU UCUUGGUA | 861 |
| 5219 | AUACCAAG CUGAUGA GCCGUUAGGC GAA AAUUGAGU | 8004 | ACUCAAUUU CUUGGUAU | 862 |
| 5220 | AAUACCAA CUGAUGA GCCGUUAGGC GAA AAAUUGAG | 8005 | CUCAAUUUC UUGGUAUU | 863 |
| 5222 | AUAAUACC CUGAUGA GCCGUUAGGC GAA AGAAAUUG | 8006 | CAAUUUCUU GGUAUUAU | 864 |
| 5226 | CAGAAUAA CUGAUGA GCCGUUAGGC GAA ACCAAGAA | 8007 | UUCUUGGUA UUAUUCUG | 865 |
| 5228 | AACAGAAU CUGAUGA GCCGUUAGGC GAA AUACCAAG | 8008 | CUUGGUAUU AUUCUGUU | 866 |
| 5229 | AAACAGAA CUGAUGA GCCGUUAGGC GAA AAUACCAA | 8009 | UUGGUAUUA UUCUGUUU | 867 |
| 5231 | CAAAACAG CUGAUGA GCCGUUAGGC GAA AUAAUACC | 8010 | GGUAUUAUU CUGUUUUG | 868 |
| 5232 | GCAAAACA CUGAUGA GCCGUUAGGC GAA AAUAAUAC | 8011 | GUAUUAUUC UGUUUUGC | 869 |
| 5236 | CUGUGCAA CUGAUGA GCCGUUAGGC GAA ACAGAAUA | 8012 | UAUUCUGUU UUGCACAG | 870 |
| 5237 | ACUGUGCA CUGAUGA GCCGUUAGGC GAA AACAGAAU | 8013 | AUUCUGUUU UGCACAGU | 871 |
| 5238 | AACUGUGC CUGAUGA GCCGUUAGGC GAA AAACAGAA | 8014 | UUCUGUUUU GCACAGUU | 872 |
| 5246 | UCACAACU CUGAUGA GCCGUUAGGC GAA ACUGUGCA | 8015 | UGCACAGUU AGUUGUGA | 873 |
| 5247 | UUCACAAC CUGAUGA GCCGUUAGGC GAA AACUGUGC | 8016 | GCACAGUUA GUUGUGAA | 874 |
| 5250 | UCUUUCAC CUGAUGA GCCGUUAGGC GAA ACUAACUG | 8017 | CAGUUAGUU GUGAAAGA | 875 |
| 5284 | CUCCUCAG CUGAUGA GCCGUUAGGC GAA ACUGCAUU | 8018 | AAUGCAGUC CUGAGGAG | 876 |
| 5296 | AUGGAGAA CUGAUGA GCCGUUAGGC GAA ACUCUCCU | 8019 | AGGAGAGUU UUCUCCAU | 877 |
| 5297 | UAUGGAGA CUGAUGA GCCGUUAGGC GAA AACUCUCC | 8020 | GGAGAGUUU UCUCCAUA | 878 |
| 5298 | AUAUGGAG CUGAUGA GCCGUUAGGC GAA AAACUCUC | 8021 | GAGAGUUUU CUCCAUAU | 879 |
| 5299 | GAUAUGGA CUGAUGA GCCGUUAGGC GAA AAAACUCU | 8022 | AGAGUUUUC UCCAUAUC | 880 |
| 5301 | UUGAUAUG CUGAUGA GCCGUUAGGC GAA AGAAAACU | 8023 | AGUUUUCUC CAUAUCAA | 881 |
| 5305 | CGUUUUGA CUGAUGA GCCGUUAGGC GAA AUGGAGAA | 8024 | UUCUCCAUA UCAAAACG | 882 |
| 5307 | CUCGUUUU CUGAUGA GCCGUUAGGC GAA AUAUGGAG | 8025 | CUCCAUAUC AAAACGAG | 883 |
| 5336 | ACCUUAUU CUGAUGA GCCGUUAGGC GAA ACCUUUUU | 8026 | AAAAAGGUC AAUAAGGU | 884 |
| 5340 | CUUGACCU CUGAUGA GCCGUUAGGC GAA AUUGACCU | 8027 | AGGUCAAUA AGGUCAAG | 885 |
| 5345 | CUUCCCUU CUGAUGA GCCGUUAGGC GAA ACCUUAUU | 8028 | AAUAAGGUC AAGGGAAG | 886 |
| 5361 | GGUAUAGA CUGAUGA GCCGUUAGGC GAA ACGGGGUC | 8029 | GACCCCGUC UCUAUACC | 887 |

100

| | | | | |
|---|---|---|---|---|
| 5363 | UUGGUAUA CUGAUGA GCCGUUAGGC GAA AGACGGGG | 8030 | CCCCGUCUC UAUACCAA | 888 |
| 5365 | GGUUGGUA CUGAUGA GCCGUUAGGC GAA AGAGACGG | 8031 | CCGUCUCUA UACCAACC | 889 |
| 5367 | UUGGUUGG CUGAUGA GCCGUUAGGC GAA AUAGAGAC | 8032 | GUCUCUAUA CCAACCAA | 890 |
| 5382 | UGUUGGUG CUGAUGA GCCGUUAGGC GAA AUUGGUUU | 8033 | AAACCAAUU CACCAACA | 891 |
| 5383 | GUGUUGGU CUGAUGA GCCGUUAGGC GAA AAUUGGUU | 8034 | AACCAAUUC ACCAACAC | 892 |
| 5395 | UGGGUCCC CUGAUGA GCCGUUAGGC GAA ACUGUGUU | 8035 | AACACAGUU GGGACCCA | 893 |
| 5417 | ACGUGACU CUGAUGA GCCGUUAGGC GAA ACUUCCUG | 8036 | CAGGAAGUC AGUCACGU | 894 |
| 5421 | GGAAACGU CUGAUGA GCCGUUAGGC GAA ACUGACUU | 8037 | AAGUCAGUC ACGUUUCC | 895 |
| 5426 | GAAAAGGA CUGAUGA GCCGUUAGGC GAA ACGUGACU | 8038 | AGUCACGUU UCCUUUUC | 896 |
| 5427 | UGAAAAGG CUGAUGA GCCGUUAGGC GAA AACGUGAC | 8039 | GUCACGUUU CCUUUUCA | 897 |
| 5428 | AUGAAAAG CUGAUGA GCCGUUAGGC GAA AAACGUGA | 8040 | UCACGUUUC CUUUUCAU | 898 |
| 5431 | UAAAUGAA CUGAUGA GCCGUUAGGC GAA AGGAAACG | 8041 | CGUUUCCUU UUCAUUUA | 899 |
| 5432 | UUAAAUGA CUGAUGA GCCGUUAGGC GAA AAGGAAAC | 8042 | GUUUCCUUU UCAUUUAA | 900 |
| 5433 | AUUAAAUG CUGAUGA GCCGUUAGGC GAA AAAGGAAA | 8043 | UUUCCUUUU CAUUUAAU | 901 |
| 5434 | CAUUAAAU CUGAUGA GCCGUUAGGC GAA AAAAGGAA | 8044 | UUCCUUUUC AUUUAAUG | 902 |
| 5437 | CCCCAUUA CUGAUGA GCCGUUAGGC GAA AUGAAAAG | 8045 | CUUUUCAUU UAAUGGGG | 903 |
| 5438 | UCCCCAUU CUGAUGA GCCGUUAGGC GAA AAUGAAAA | 8046 | UUUUCAUUU AAUGGGGA | 904 |
| 5439 | AUCCCCAU CUGAUGA GCCGUUAGGC GAA AAAUGAAA | 8047 | UUUCAUUUA AUGGGGAU | 905 |
| 5448 | GAUAGUGG CUGAUGA GCCGUUAGGC GAA AUCCCCAU | 8048 | AUGGGGAUU CCACUAUC | 906 |
| 5449 | AGAUAGUG CUGAUGA GCCGUUAGGC GAA AAUCCCCA | 8049 | UGGGGAUUC CACUAUCU | 907 |
| 5454 | GUGUGAGA CUGAUGA GCCGUUAGGC GAA AGUGGAAU | 8050 | AUUCCACUA UCUCACAC | 908 |
| 5456 | UAGUGUGA CUGAUGA GCCGUUAGGC GAA AUAGUGGA | 8051 | UCCACUAUC UCACACUA | 909 |
| 5458 | AUUAGUGU CUGAUGA GCCGUUAGGC GAA AGAUAGUG | 8052 | CACUAUCUC ACACUAAU | 910 |
| 5464 | UUUCAGAU CUGAUGA GCCGUUAGGC GAA AGUGUGAG | 8053 | CUCACACUA AUCUGAAA | 911 |
| 5467 | UCCUUUCA CUGAUGA GCCGUUAGGC GAA AUUAGUGU | 8054 | ACACUAAUC UGAAAGGA | 912 |
| 5489 | CGCCAGCU CUGAUGA GCCGUUAGGC GAA AUGCUCUU | 8055 | AAGAGCAUU AGCUGGCG | 913 |
| 5490 | GCGCCAGC CUGAUGA GCCGUUAGGC GAA AAUGCUCU | 8056 | AGAGCAUUA GCUGGCGC | 914 |
| 5501 | GUGCUUAA CUGAUGA GCCGUUAGGC GAA AUGCGCCA | 8057 | UGGCGCAUA UUAAGCAC | 915 |
| 5503 | AAGUGCUU CUGAUGA GCCGUUAGGC GAA AUAUGCGC | 8058 | GCGCAUAUU AAGCACUU | 916 |
| 5504 | AAAGUGCU CUGAUGA GCCGUUAGGC GAA AAUAUGCG | 8059 | CGCAUAUUA AGCACUUU | 917 |
| 5511 | GGAGCUUA CUGAUGA GCCGUUAGGC GAA AGUGCUUA | 8060 | UAAGCACUU UAAGCUCC | 918 |
| 5512 | AGGAGCUU CUGAUGA GCCGUUAGGC GAA AAGUGCUU | 8061 | AAGCACUUU AAGCUCCU | 919 |
| 5513 | AAGGAGCU CUGAUGA GCCGUUAGGC GAA AAAGUGCU | 8062 | AGCACUUUA AGCUCCUU | 920 |

101

| | | | | |
|---|---|---|---|---|
| 5518 | UACUCAAG CUGAUGA GCCGUUAGGC GAA AGCUUAAA | 8063 | UUUAAGCUC CUUGAGUA | 921 |
| 5521 | UUUUACUC CUGAUGA GCCGUUAGGC GAA AGGAGCUU | 8064 | AAGCUCCUU GAGUAAAA | 922 |
| 5526 | CACCUUUU CUGAUGA GCCGUUAGGC GAA ACUCAAGG | 8065 | CCUUGAGUA AAAAGGUG | 923 |
| 5537 | AAAUUACA CUGAUGA GCCGUUAGGC GAA ACCACCUU | 8066 | AAGGUGGUA UGUAAUUU | 924 |
| 5541 | GCAUAAAU CUGAUGA GCCGUUAGGC GAA ACAUACCA | 8067 | UGGUAUGUA AUUUAUGC | 925 |
| 5544 | CUUGCAUA CUGAUGA GCCGUUAGGC GAA AUUACAUA | 8068 | UAUGUAAUU UAUGCAAG | 926 |
| 5545 | CCUUGCAU CUGAUGA GCCGUUAGGC GAA AAUUACAU | 8069 | AUGUAAUUU AUGCAAGG | 927 |
| 5546 | ACCUUGCA CUGAUGA GCCGUUAGGC GAA AAAUUACA | 8070 | UGUAAUUUA UGCAAGGU | 928 |
| 5555 | UGGAGAAA CUGAUGA GCCGUUAGGC GAA ACCUUGCA | 8071 | UGCAAGGUA UUUCUCCA | 929 |
| 5557 | ACUGGAGA CUGAUGA GCCGUUAGGC GAA AUACCUUG | 8072 | CAAGGUAUU UCUCCAGU | 930 |
| 5558 | AACUGGAG CUGAUGA GCCGUUAGGC GAA AAUACCUU | 8073 | AAGGUAUUU CUCCAGUU | 931 |
| 5559 | CAACUGGA CUGAUGA GCCGUUAGGC GAA AAAUACCU | 8074 | AGGUAUUUC UCCAGUUG | 932 |
| 5561 | CCCAACUG CUGAUGA GCCGUUAGGC GAA AGAAAUAC | 8075 | GUAUUUCUC CAGUUGGG | 933 |
| 5566 | UGAGUCCC CUGAUGA GCCGUUAGGC GAA ACUGGAGA | 8076 | UCUCCAGUU GGGACUCA | 934 |
| 5573 | AAUAUCCU CUGAUGA GCCGUUAGGC GAA AGUCCCAA | 8077 | UUGGGACUC AGGAUAUU | 935 |
| 5579 | UUAACUAA CUGAUGA GCCGUUAGGC GAA AUCCUGAG | 8078 | CUCAGGAUA UUAGUUAA | 936 |
| 5581 | CAUUAACU CUGAUGA GCCGUUAGGC GAA AUAUCCUG | 8079 | CAGGAUAUU AGUUAAUG | 937 |
| 5582 | UCAUUAAC CUGAUGA GCCGUUAGGC GAA AAUAUCCU | 8080 | AGGAUAUUA GUUAAUGA | 938 |
| 5585 | GGCUCAUU CUGAUGA GCCGUUAGGC GAA ACUAAUAU | 8081 | AUAUUAGUU AAUGAGCC | 939 |
| 5586 | UGGCUCAU CUGAUGA GCCGUUAGGC GAA AACUAAUA | 8082 | UAUUAGUUA AUGAGCCA | 940 |
| 5596 | CUUCUAGU CUGAUGA GCCGUUAGGC GAA AUGGCUCA | 8083 | UGAGCCAUC ACUAGAAG | 941 |
| 5600 | UUUUCUUC CUGAUGA GCCGUUAGGC GAA AGUGAUGG | 8084 | CCAUCACUA GAAGAAAA | 942 |
| 5615 | CAGUUGAA CUGAUGA GCCGUUAGGC GAA AUGGGCUU | 8085 | AAGCCCAUU UUCAACUG | 943 |
| 5616 | GCAGUUGA CUGAUGA GCCGUUAGGC GAA AAUGGGCU | 8086 | AGCCCAUUU UCAACUGC | 944 |
| 5617 | AGCAGUUG CUGAUGA GCCGUUAGGC GAA AAAUGGGC | 8087 | GCCCAUUUU CAACUGCU | 945 |
| 5618 | AAGCAGUU CUGAUGA GCCGUUAGGC GAA AAAAUGGG | 8088 | CCCAUUUUC AACUGCUU | 946 |
| 5626 | AAGUUUCA CUGAUGA GCCGUUAGGC GAA AGCAGUUG | 8089 | CAACUGCUU UGAAACUU | 947 |
| 5627 | CAAGUUUC CUGAUGA GCCGUUAGGC GAA AAGCAGUU | 8090 | AACUGCUUU GAAACUUG | 948 |
| 5634 | CCCCAGGC CUGAUGA GCCGUUAGGC GAA AGUUUCAA | 8091 | UUGAAACUU GCCUGGGG | 949 |
| 5644 | CAUGCUCA CUGAUGA GCCGUUAGGC GAA ACCCCAGG | 8092 | CCUGGGGUC UGAGCAUG | 950 |
| 5661 | UGUCUCCC CUGAUGA GCCGUUAGGC GAA AUUCCCAU | 8093 | AUGGGAAUA GGGAGACA | 951 |
| 5674 | CCCUUUCC CUGAUGA GCCGUUAGGC GAA ACCCUGUC | 8094 | GACAGGGUA GGAAAGGG | 952 |
| 5688 | CUGAAGAG CUGAUGA GCCGUUAGGC GAA AGGCGCCC | 8095 | GGGCGCCUA CUCUUCAG | 953 |

102

| | | | | |
|---|---|---|---|---|
| 5691 | ACCCUGAA CUGAUGA GCCGUUAGGC GAA AGUAGGCG | 8096 | CGCCUACUC UUCAGGGU | 954 |
| 5693 | AGACCCUG CUGAUGA GCCGUUAGGC GAA AGAGUAGG | 8097 | CCUACUCUU CAGGGUCU | 955 |
| 5694 | UAGACCCU CUGAUGA GCCGUUAGGC GAA AAGAGUAG | 8098 | CUACUCUUC AGGGUCUA | 956 |
| 5700 | GAUCUUUA CUGAUGA GCCGUUAGGC GAA ACCCUGAA | 8099 | UUCAGGGUC UAAAGAUC | 957 |
| 5702 | UUGAUCUU CUGAUGA GCCGUUAGGC GAA AGACCCUG | 8100 | CAGGGUCUA AAGAUCAA | 958 |
| 5708 | GCCCACUU CUGAUGA GCCGUUAGGC GAA AUCUUUAG | 8101 | CUAAAGAUC AAGUGGGC | 959 |
| 5719 | AGCGAUCC CUGAUGA GCCGUUAGGC GAA AGGCCCAC | 8102 | GUGGGCCUU GGAUCGCU | 960 |
| 5724 | AGCUUAGC CUGAUGA GCCGUUAGGC GAA AUCCAAGG | 8103 | CCUUGGAUC GCUAAGCU | 961 |
| 5728 | AGCCAGCU CUGAUGA GCCGUUAGGC GAA AGCGAUCC | 8104 | GGAUCGCUA AGCUGGCU | 962 |
| 5737 | AUCAAACA CUGAUGA GCCGUUAGGC GAA AGCCAGCU | 8105 | AGCUGGCUC UGUUUGAU | 963 |
| 5741 | UAGCAUCA CUGAUGA GCCGUUAGGC GAA ACAGAGCC | 8106 | GGCUCUGUU UGAUGCUA | 964 |
| 5742 | AUAGCAUC CUGAUGA GCCGUUAGGC GAA AACAGAGC | 8107 | GCUCUGUUU GAUGCUAU | 965 |
| 5749 | UGCAUAAA CUGAUGA GCCGUUAGGC GAA AGCAUCAA | 8108 | UUGAUGCUA UUUAUGCA | 966 |
| 5751 | CUUGCAUA CUGAUGA GCCGUUAGGC GAA AUAGCAUC | 8109 | GAUGCUAUU UAUGCAAG | 967 |
| 5752 | ACUUGCAU CUGAUGA GCCGUUAGGC GAA AAUAGCAU | 8110 | AUGCUAUUU AUGCAAGU | 968 |
| 5753 | AACUUGCA CUGAUGA GCCGUUAGGC GAA AAAUAGCA | 8111 | UGCUAUUUA UGCAAGUU | 969 |
| 5761 | UAGACCCU CUGAUGA GCCGUUAGGC GAA ACUUGCAU | 8112 | AUGCAAGUU AGGGUCUA | 970 |
| 5762 | AUAGACCC CUGAUGA GCCGUUAGGC GAA AACUUGCA | 8113 | UGCAAGUUA GGGUCUAU | 971 |
| 5767 | AAUACAUA CUGAUGA GCCGUUAGGC GAA ACCCUAAC | 8114 | GUUAGGGUC UAUGUAUU | 972 |
| 5769 | UAAAUACA CUGAUGA GCCGUUAGGC GAA AGACCCUA | 8115 | UAGGGUCUA UGUAUUUA | 973 |
| 5773 | AUCCUAAA CUGAUGA GCCGUUAGGC GAA ACAUAGAC | 8116 | GUCUAUGUA UUUAGGAU | 974 |
| 5775 | GCAUCCUA CUGAUGA GCCGUUAGGC GAA AUACAUAG | 8117 | CUAUGUAUU UAGGAUGC | 975 |
| 5776 | CGCAUCCU CUGAUGA GCCGUUAGGC GAA AAUACAUA | 8118 | UAUGUAUUU AGGAUGCG | 976 |
| 5777 | GCGCAUCC CUGAUGA GCCGUUAGGC GAA AAAUACAU | 8119 | AUGUAUUUA GGAUGCGC | 977 |
| 5788 | CUGAAGAG CUGAUGA GCCGUUAGGC GAA AGGCGCAU | 8120 | AUGCGCCUA CUCUUCAG | 978 |
| 5791 | ACCCUGAA CUGAUGA GCCGUUAGGC GAA AGUAGGCG | 8096 | CGCCUACUC UUCAGGGU | 954 |
| 5793 | AGACCCUG CUGAUGA GCCGUUAGGC GAA AGAGUAGG | 8097 | CCUACUCUU CAGGGUCU | 955 |
| 5794 | UAGACCCU CUGAUGA GCCGUUAGGC GAA AAGAGUAG | 8098 | CUACUCUUC AGGGUCUA | 956 |
| 5800 | GAUCUUUA CUGAUGA GCCGUUAGGC GAA ACCCUGAA | 8099 | UUCAGGGUC UAAAGAUC | 957 |
| 5802 | UUGAUCUU CUGAUGA GCCGUUAGGC GAA AGACCCUG | 8100 | CAGGGUCUA AAGAUCAA | 958 |
| 5808 | GCCCACUU CUGAUGA GCCGUUAGGC GAA AUCUUUAG | 8101 | CUAAAGAUC AAGUGGGC | 959 |
| 5819 | AGCGAUCC CUGAUGA GCCGUUAGGC GAA AGGCCCAC | 8102 | GUGGGCCUU GGAUCGCU | 960 |
| 5824 | AGCUUAGC CUGAUGA GCCGUUAGGC GAA AUCCAAGG | 8103 | CCUUGGAUC GCUAAGCU | 961 |

| | | | | |
|---|---|---|---|---|
| 5828 | AGCCAGCU CUGAUGA GCCGUUAGGC GAA AGCGAUCC | 8104 | GGAUCGCUA AGCUGGCU | 962 |
| 5837 | AUCAAACA CUGAUGA GCCGUUAGGC GAA AGCCAGCU | 8105 | AGCUGGCUC UGUUUGAU | 963 |
| 5841 | UAGCAUCA CUGAUGA GCCGUUAGGC GAA ACAGAGCC | 8106 | GGCUCUGUU UGAUGCUA | 964 |
| 5842 | AUAGCAUC CUGAUGA GCCGUUAGGC GAA AACAGAGC | 8107 | GCUCUGUUU GAUGCUAU | 965 |
| 5849 | UGCAUAAA CUGAUGA GCCGUUAGGC GAA AGCAUCAA | 8108 | UUGAUGCUA UUUAUGCA | 966 |
| 5851 | CUUGCAUA CUGAUGA GCCGUUAGGC GAA AUAGCAUC | 8109 | GAUGCUAUU UAUGCAAG | 967 |
| 5852 | ACUUGCAU CUGAUGA GCCGUUAGGC GAA AAUAGCAU | 8110 | AUGCUAUUU AUGCAAGU | 968 |
| 5853 | AACUUGCA CUGAUGA GCCGUUAGGC GAA AAAUAGCA | 8111 | UGCUAUUUA UGCAAGUU | 969 |
| 5861 | UAGACCCU CUGAUGA GCCGUUAGGC GAA ACUUGCAU | 8112 | AUGCAAGUU AGGGUCUA | 970 |
| 5862 | AUAGACCC CUGAUGA GCCGUUAGGC GAA AACUUGCA | 8113 | UGCAAGUUA GGGUCUAU | 971 |
| 5867 | AAUACAUA CUGAUGA GCCGUUAGGC GAA ACCCUAAC | 8114 | GUUAGGGUC UAUGUAUU | 972 |
| 5869 | UAAAUACA CUGAUGA GCCGUUAGGC GAA AGACCCUA | 8115 | UAGGGUCUA UGUAUUUA | 973 |
| 5873 | AUCCUAAA CUGAUGA GCCGUUAGGC GAA ACAUAGAC | 8116 | GUCUAUGUA UUUAGGAU | 974 |
| 5875 | ACAUCCUA CUGAUGA GCCGUUAGGC GAA AUACAUAG | 8121 | CUAUGUAUU UAGGAUGU | 979 |
| 5876 | GACAUCCU CUGAUGA GCCGUUAGGC GAA AAUACAUA | 8122 | UAUGUAUUU AGGAUGUC | 980 |
| 5877 | AGACAUCC CUGAUGA GCCGUUAGGC GAA AAAUACAU | 8123 | AUGUAUUUA GGAUGUCU | 981 |
| 5884 | AAGGUGCA CUGAUGA GCCGUUAGGC GAA ACAUCCUA | 8124 | UAGGAUGUC UGCACCUU | 982 |
| 5892 | GGCUGCAG CUGAUGA GCCGUUAGGC GAA AGGUGCAG | 8125 | CUGCACCUU CUGCAGCC | 983 |
| 5893 | UGGCUGCA CUGAUGA GCCGUUAGGC GAA AAGGUGCA | 8126 | UGCACCUUC UGCAGCCA | 984 |
| 5904 | CAGCUUCU CUGAUGA GCCGUUAGGC GAA ACUGGCUG | 8127 | CAGCCAGUC AGAAGCUG | 985 |
| 5930 | GAAGCAGC CUGAUGA GCCGUUAGGC GAA AUCCACUG | 8128 | CAGUGGAUU GCUGCUUC | 986 |
| 5937 | UCCCCAAG CUGAUGA GCCGUUAGGC GAA AGCAGCAA | 8129 | UUGCUGCUU CUUGGGGA | 987 |
| 5938 | CUCCCCAA CUGAUGA GCCGUUAGGC GAA AAGCAGCA | 8130 | UGCUGCUUC UUGGGGAG | 988 |
| 5940 | UUCUCCCC CUGAUGA GCCGUUAGGC GAA AGAAGCAG | 8131 | CUGCUUCUU GGGGAGAA | 989 |
| 5953 | AGGAAGCA CUGAUGA GCCGUUAGGC GAA ACUCUUCU | 8132 | AGAAGAGUA UGCUUCCU | 990 |
| 5958 | AUAAAAGG CUGAUGA GCCGUUAGGC GAA AGCAUACU | 8133 | AGUAUGCUU CCUUUUAU | 991 |
| 5959 | GAUAAAAG CUGAUGA GCCGUUAGGC GAA AAGCAUAC | 8134 | GUAUGCUUC CUUUUAUC | 992 |
| 5962 | AUGGAUAA CUGAUGA GCCGUUAGGC GAA AGGAAGCA | 8135 | UGCUUCCUU UUAUCCAU | 993 |
| 5963 | CAUGGAUA CUGAUGA GCCGUUAGGC GAA AAGGAAGC | 8136 | GCUUCCUUU UAUCCAUG | 994 |
| 5964 | ACAUGGAU CUGAUGA GCCGUUAGGC GAA AAAGGAAG | 8137 | CUUCCUUUU AUCCAUGU | 995 |
| 5965 | UACAUGGA CUGAUGA GCCGUUAGGC GAA AAAAGGAA | 8138 | UUCCUUUUA UCCAUGUA | 996 |
| 5967 | AUUACAUG CUGAUGA GCCGUUAGGC GAA AUAAAAGG | 8139 | CCUUUUAUC CAUGUAAU | 997 |
| 5973 | AGUUAAAU CUGAUGA GCCGUUAGGC GAA ACAUGGAU | 8140 | AUCCAUGUA AUUUAACU | 998 |

| | | | | |
|---|---|---|---|---|
| 5976 | UACAGUUA CUGAUGA GCCGUUAGGC GAA AUUACAUG | 8141 | CAUGUAAUU UAACUGUA | 999 |
| 5977 | CUACAGUU CUGAUGA GCCGUUAGGC GAA AAUUACAU | 8142 | AUGUAAUUU AACUGUAG | 1000 |
| 5978 | UCUACAGU CUGAUGA GCCGUUAGGC GAA AAAUUACA | 8143 | UGUAAUUUA ACUGUAGA | 1001 |
| 5984 | UCAGGUUC CUGAUGA GCCGUUAGGC GAA ACAGUUAA | 8144 | UUAACUGUA GAACCUGA | 1002 |
| 5996 | GUUACUUA CUGAUGA GCCGUUAGGC GAA AGCUCAGG | 8145 | CCUGAGCUC UAAGUAAC | 1003 |
| 5998 | CGGUUACU CUGAUGA GCCGUUAGGC GAA AGAGCUCA | 8146 | UGAGCUCUA AGUAACCG | 1004 |
| 6002 | UCUUCGGU CUGAUGA GCCGUUAGGC GAA ACUUAGAG | 8147 | CUCUAAGUA ACCGAAGA | 1005 |
| 6015 | CAGAGGCA CUGAUGA GCCGUUAGGC GAA ACAUUCUU | 8148 | AAGAAUGUA UGCCUCUG | 1006 |
| 6021 | UAAGAACA CUGAUGA GCCGUUAGGC GAA AGGCAUAC | 8149 | GUAUGCCUC UGUUCUUA | 1007 |
| 6025 | CACAUAAG CUGAUGA GCCGUUAGGC GAA ACAGAGGC | 8150 | GCCUCUGUU CUUAUGUG | 1008 |
| 6026 | GCACAUAA CUGAUGA GCCGUUAGGC GAA AACAGAGG | 8151 | CCUCUGUUC UUAUGUGC | 1009 |
| 6028 | UGGCACAU CUGAUGA GCCGUUAGGC GAA AGAACAGA | 8152 | UCUGUUCUU AUGUGCCA | 1010 |
| 6029 | GUGGCACA CUGAUGA GCCGUUAGGC GAA AAGAACAG | 8153 | CUGUUCUUA UGUGCCAC | 1011 |
| 6040 | UAAACAAG CUGAUGA GCCGUUAGGC GAA AUGUGGCA | 8154 | UGCCACAUC CUUGUUUA | 1012 |
| 6043 | CUUUAAAC CUGAUGA GCCGUUAGGC GAA AGGAUGUG | 8155 | CACAUCCUU GUUUAAAG | 1013 |
| 6046 | AGCCUUUA CUGAUGA GCCGUUAGGC GAA ACAAGGAU | 8156 | AUCCUUGUU UAAAGGCU | 1014 |
| 6047 | GAGCCUUU CUGAUGA GCCGUUAGGC GAA AACAAGGA | 8157 | UCCUUGUUU AAAGGCUC | 1015 |
| 6048 | AGAGCCUU CUGAUGA GCCGUUAGGC GAA AAACAAGG | 8158 | CCUUGUUUA AAGGCUCU | 1016 |
| 6055 | CAUACAGA CUGAUGA GCCGUUAGGC GAA AGCCUUUA | 8159 | UAAAGGCUC UCUGUAUG | 1017 |
| 6057 | UUCAUACA CUGAUGA GCCGUUAGGC GAA AGAGCCUU | 8160 | AAGGCUCUC UGUAUGAA | 1018 |
| 6061 | UCUCUUCA CUGAUGA GCCGUUAGGC GAA ACAGAGAG | 8161 | CUCUCUGUA UGAAGAGA | 1019 |
| 6079 | GUGCUGAU CUGAUGA GCCGUUAGGC GAA ACGGUCCC | 8162 | GGGACCGUC AUCAGCAC | 1020 |
| 6082 | AAUGUGCU CUGAUGA GCCGUUAGGC GAA AUGACGGU | 8163 | ACCGUCAUC AGCACAUU | 1021 |
| 6090 | CACUAGGG CUGAUGA GCCGUUAGGC GAA AUGUGCUG | 8164 | CAGCACAUU CCCUAGUG | 1022 |
| 6091 | UCACUAGG CUGAUGA GCCGUUAGGC GAA AAUGUGCU | 8165 | AGCACAUUC CCUAGUGA | 1023 |
| 6095 | AGGCUCAC CUGAUGA GCCGUUAGGC GAA AGGGAAUG | 8166 | CAUUCCCUA GUGAGCCU | 1024 |
| 6104 | GGAGCCAG CUGAUGA GCCGUUAGGC GAA AGGCUCAC | 8167 | GUGAGCCUA CUGGCUCC | 1025 |
| 6111 | GCUGCCAG CUGAUGA GCCGUUAGGC GAA AGCCAGUA | 8168 | UACUGGCUC CUGGCAGC | 1026 |
| 6124 | UUCCACAA CUGAUGA GCCGUUAGGC GAA AGCCGCUG | 8169 | CAGCGGCUU UUGUGGAA | 1027 |
| 6125 | CUUCCACA CUGAUGA GCCGUUAGGC GAA AAGCCGCU | 8170 | AGCGGCUUU UGUGGAAG | 1028 |
| 6126 | UCUUCCAC CUGAUGA GCCGUUAGGC GAA AAAGCCGC | 8171 | GCGGCUUUU GUGGAAGA | 1029 |
| 6137 | UGGCUAGU CUGAUGA GCCGUUAGGC GAA AGUCUUCC | 8172 | GGAAGACUC ACUAGCCA | 1030 |
| 6141 | CUUCUGGC CUGAUGA GCCGUUAGGC GAA AGUGAGUC | 8173 | GACUCACUA GCCAGAAG | 1031 |

| | | | | |
|---|---|---|---|---|
| 6166 | GUGGAGAG CUGAUGA GCCGUUAGGC GAA ACUGUCCC | 8174 | GGGACAGUC CUCUCCAC | 1032 |
| 6169 | UUGGUGGA CUGAUGA GCCGUUAGGC GAA AGGACUGU | 8175 | ACAGUCCUC UCCACCAA | 1033 |
| 6171 | UCUUGGUG CUGAUGA GCCGUUAGGC GAA AGAGGACU | 8176 | AGUCCUCUC CACCAAGA | 1034 |
| 6181 | UGGAUUUA CUGAUGA GCCGUUAGGC GAA AUCUUGGU | 8177 | ACCAAGAUC UAAAUCCA | 1035 |
| 6183 | UUUGGAUU CUGAUGA GCCGUUAGGC GAA AGAUCUUG | 8178 | CAAGAUCUA AAUCCAAA | 1036 |
| 6187 | UUUGUUUG CUGAUGA GCCGUUAGGC GAA AUUUAGAU | 8179 | AUCUAAAUC CAAACAAA | 1037 |
| 6204 | UCUGGCUC CUGAUGA GCCGUUAGGC GAA AGCCUGCU | 8180 | AGCAGGCUA GAGCCAGA | 1038 |
| 6226 | ACAACAAA CUGAUGA GCCGUUAGGC GAA AUUUGUCC | 8181 | GGACAAAUC UUUGUUGU | 1039 |
| 6228 | GAACAACA CUGAUGA GCCGUUAGGC GAA AGAUUUGU | 8182 | ACAAAUCUU UGUUGUUC | 1040 |
| 6229 | GGAACAAC CUGAUGA GCCGUUAGGC GAA AAGAUUUG | 8183 | CAAAUCUUU GUUGUUCC | 1041 |
| 6232 | AGAGGAAC CUGAUGA GCCGUUAGGC GAA ACAAAGAU | 8184 | AUCUUUGUU GUUCCUCU | 1042 |
| 6235 | AGAAGAGG CUGAUGA GCCGUUAGGC GAA ACAACAAA | 8185 | UUUGUUGUU CCUCUUCU | 1043 |
| 6236 | AAGAAGAG CUGAUGA GCCGUUAGGC GAA AACAACAA | 8186 | UUGUUGUUC CUCUUCUU | 1044 |
| 6239 | GUAAAGAA CUGAUGA GCCGUUAGGC GAA AGGAACAA | 8187 | UUGUUCCUC UUCUUUAC | 1045 |
| 6241 | GUGUAAAG CUGAUGA GCCGUUAGGC GAA AGAGGAAC | 8188 | GUUCCUCUU CUUUACAC | 1046 |
| 6242 | UGUGUAAA CUGAUGA GCCGUUAGGC GAA AAGAGGAA | 8189 | UUCCUCUUC UUUACACA | 1047 |
| 6244 | UAUGUGUA CUGAUGA GCCGUUAGGC GAA AGAAGAGG | 8190 | CCUCUUCUU UACACAUA | 1048 |
| 6245 | GUAUGUGU CUGAUGA GCCGUUAGGC GAA AAGAAGAG | 8191 | CUCUUCUUU ACACAUAC | 1049 |
| 6246 | CGUAUGUG CUGAUGA GCCGUUAGGC GAA AAAGAAGA | 8192 | UCUUCUUUA CACAUACG | 1050 |
| 6252 | GGUUUGCG CUGAUGA GCCGUUAGGC GAA AUGUGUAA | 8193 | UUACACAUA CGCAAACC | 1051 |
| 6280 | AUUUAUAA CUGAUGA GCCGUUAGGC GAA AUUGCCAG | 8194 | CUGGCAAUU UUAUAAAU | 1052 |
| 6281 | GAUUUAUA CUGAUGA GCCGUUAGGC GAA AAUUGCCA | 8195 | UGGCAAUUU UAUAAAUC | 1053 |
| 6282 | UGAUUUAU CUGAUGA GCCGUUAGGC GAA AAAUUGCC | 8196 | GGCAAUUUU AUAAAUCA | 1054 |
| 6283 | CUGAUUUA CUGAUGA GCCGUUAGGC GAA AAAAUUGC | 8197 | GCAAUUUUA UAAAUCAG | 1055 |
| 6285 | ACCUGAUU CUGAUGA GCCGUUAGGC GAA AUAAAAUU | 8198 | AAUUUUAUA AAUCAGGU | 1056 |
| 6289 | AGUUACCU CUGAUGA GCCGUUAGGC GAA AUUUAUAA | 8199 | UUAUAAAUC AGGUAACU | 1057 |
| 6294 | CUUCCAGU CUGAUGA GCCGUUAGGC GAA ACCUGAUU | 8200 | AAUCAGGUA ACUGGAAG | 1058 |
| 6308 | CUGAGUUU CUGAUGA GCCGUUAGGC GAA ACCUCCUU | 8201 | AAGGAGGUU AAACUCAG | 1059 |
| 6309 | UCUGAGUU CUGAUGA GCCGUUAGGC GAA AACCUCCU | 8202 | AGGAGGUUA AACUCAGA | 1060 |
| 6314 | UUUUUUCU CUGAUGA GCCGUUAGGC GAA AGUUUAAC | 8203 | GUUAAACUC AGAAAAAA | 1061 |
| 6331 | AAUUGACU CUGAUGA GCCGUUAGGC GAA AGGUCUUC | 8204 | GAAGACCUC AGUCAAUU | 1062 |
| 6335 | AGAGAAUU CUGAUGA GCCGUUAGGC GAA ACUGAGGU | 8205 | ACCUCAGUC AAUUCUCU | 1063 |
| 6339 | AAGUAGAG CUGAUGA GCCGUUAGGC GAA AUUGACUG | 8206 | CAGUCAAUU CUCUACUU | 1064 |

| | | | | |
|---|---|---|---|---|
| 6340 | AAAGUAGA CUGAUGA GCCGUUAGGC GAA AAUUGACU | 8207 | AGUCAAUUC UCUACUUU | 1065 |
| 6342 | AAAAAGUA CUGAUGA GCCGUUAGGC GAA AGAAUUGA | 8208 | UCAAUUCUC UACUUUUU | 1066 |
| 6344 | AAAAAAAG CUGAUGA GCCGUUAGGC GAA AGAGAAUU | 8209 | AAUUCUCUA CUUUUUUU | 1067 |
| 6347 | AAAAAAAA CUGAUGA GCCGUUAGGC GAA AGUAGAGA | 8210 | UCUCUACUU UUUUUUUU | 1068 |
| 6348 | AAAAAAAA CUGAUGA GCCGUUAGGC GAA AAGUAGAG | 8211 | CUCUACUUU UUUUUUUU | 1069 |
| 6349 | AAAAAAAA CUGAUGA GCCGUUAGGC GAA AAAGUAGA | 8212 | UCUACUUUU UUUUUUUU | 1070 |
| 6350 | AAAAAAAA CUGAUGA GCCGUUAGGC GAA AAAAGUAG | 8213 | CUACUUUUU UUUUUUUU | 1071 |
| 6351 | AAAAAAAA CUGAUGA GCCGUUAGGC GAA AAAAAGUA | 8214 | UACUUUUUU UUUUUUUU | 1072 |
| 6352 | AAAAAAAA CUGAUGA GCCGUUAGGC GAA AAAAAAGU | 8215 | ACUUUUUUU UUUUUUUU | 1073 |
| 6353 | AAAAAAAA CUGAUGA GCCGUUAGGC GAA AAAAAAAG | 8216 | CUUUUUUUU UUUUUUUU | 1074 |
| 6354 | GAAAAAAA CUGAUGA GCCGUUAGGC GAA AAAAAAAA | 8217 | UUUUUUUUU UUUUUUUC | 1075 |
| 6355 | GGAAAAAA CUGAUGA GCCGUUAGGC GAA AAAAAAAA | 8218 | UUUUUUUUU UUUUUUCC | 1076 |
| 6356 | UGGAAAAA CUGAUGA GCCGUUAGGC GAA AAAAAAAA | 8219 | UUUUUUUUU UUUUUCCA | 1077 |
| 6357 | UUGGAAAA CUGAUGA GCCGUUAGGC GAA AAAAAAAA | 8220 | UUUUUUUUU UUUUCCAA | 1078 |
| 6358 | UUUGGAAA CUGAUGA GCCGUUAGGC GAA AAAAAAAA | 8221 | UUUUUUUUU UUUCCAAA | 1079 |
| 6359 | AUUUGGAA CUGAUGA GCCGUUAGGC GAA AAAAAAAA | 8222 | UUUUUUUUU UUCCAAAU | 1080 |
| 6360 | GAUUUGGA CUGAUGA GCCGUUAGGC GAA AAAAAAAA | 8223 | UUUUUUUUU UCCAAAUC | 1081 |
| 6361 | UGAUUUGG CUGAUGA GCCGUUAGGC GAA AAAAAAAA | 8224 | UUUUUUUUU CCAAAUCA | 1082 |
| 6362 | CUGAUUUG CUGAUGA GCCGUUAGGC GAA AAAAAAAA | 8225 | UUUUUUUUC CAAAUCAG | 1083 |
| 6368 | UAUUAUCU CUGAUGA GCCGUUAGGC GAA AUUUGGAA | 8226 | UUCCAAAUC AGAUAAUA | 1084 |
| 6373 | UGGGCUAU CUGAUGA GCCGUUAGGC GAA AUCUGAUU | 8227 | AAUCAGAUA AUAGCCCA | 1085 |
| 6376 | UGCUGGGC CUGAUGA GCCGUUAGGC GAA AUUAUCUG | 8228 | CAGAUAAUA GCCCAGCA | 1086 |
| 6388 | GUUAUCAC CUGAUGA GCCGUUAGGC GAA AUUUGCUG | 8229 | CAGCAAAUA GUGAUAAC | 1087 |
| 6394 | UUAUUUGU CUGAUGA GCCGUUAGGC GAA AUCACUAU | 8230 | AUAGUGAUA ACAAAUAA | 1088 |
| 6401 | UAAGGUUU CUGAUGA GCCGUUAGGC GAA AUUUGUUA | 8231 | UAACAAAUA AAACCUUA | 1089 |
| 6408 | GAACAGCU CUGAUGA GCCGUUAGGC GAA AGGUUUUA | 8232 | UAAAACCUU AGCUGUUC | 1090 |
| 6409 | UGAACAGC CUGAUGA GCCGUUAGGC GAA AAGGUUUU | 8233 | AAAACCUUA GCUGUUCA | 1091 |
| 6415 | AAGACAUG CUGAUGA GCCGUUAGGC GAA ACAGCUAA | 8234 | UUAGCUGUU CAUGUCUU | 1092 |
| 6416 | CAAGACAU CUGAUGA GCCGUUAGGC GAA AACAGCUA | 8235 | UAGCUGUUC AUGUCUUG | 1093 |
| 6421 | GAAAUCAA CUGAUGA GCCGUUAGGC GAA ACAUGAAC | 8236 | GUUCAUGUC UUGAUUUC | 1094 |
| 6423 | UUGAAAUC CUGAUGA GCCGUUAGGC GAA AGACAUGA | 8237 | UCAUGUCUU GAUUUCAA | 1095 |
| 6427 | AUUAUUGA CUGAUGA GCCGUUAGGC GAA AUCAAGAC | 8238 | GUCUUGAUU UCAAUAAU | 1096 |
| 6428 | AAUUAUUG CUGAUGA GCCGUUAGGC GAA AAUCAAGA | 8239 | UCUUGAUUU CAAUAAUU | 1097 |

107

| | | | | |
|---|---|---|---|---|
| 6429 | UAAUUAUU CUGAUGA GCCGUUAGGC GAA AAAUCAAG | 8240 | CUUGAUUUC AAUAAUUA | 1098 |
| 6433 | GAAUUAAU CUGAUGA GCCGUUAGGC GAA AUUGAAAU | 8241 | AUUUCAAUA AUUAAUUC | 1099 |
| 6436 | UAAGAAUU CUGAUGA GCCGUUAGGC GAA AUUAUUGA | 8242 | UCAAUAAUU AAUUCUUA | 1100 |
| 6437 | UUAAGAAU CUGAUGA GCCGUUAGGC GAA AAUUAUUG | 8243 | CAAUAAUUA AUUCUUAA | 1101 |
| 6440 | UGAUUAAG CUGAUGA GCCGUUAGGC GAA AUUAAUUA | 8244 | UAAUUAAUU CUUAAUCA | 1102 |
| 6441 | AUGAUUAA CUGAUGA GCCGUUAGGC GAA AAUUAAUU | 8245 | AAUUAAUUC UUAAUCAU | 1103 |
| 6443 | UAAUGAUU CUGAUGA GCCGUUAGGC GAA AGAAUUAA | 8246 | UUAAUUCUU AAUCAUUA | 1104 |
| 6444 | UUAAUGAU CUGAUGA GCCGUUAGGC GAA AAGAAUUA | 8247 | UAAUUCUUA AUCAUUAA | 1105 |
| 6447 | CUCUUAAU CUGAUGA GCCGUUAGGC GAA AUUAAGAA | 8248 | UUCUUAAUC AUUAAGAG | 1106 |
| 6450 | GGUCUCUU CUGAUGA GCCGUUAGGC GAA AUGAUUAA | 8249 | UUAAUCAUU AAGAGACC | 1107 |
| 6451 | UGGUCUCU CUGAUGA GCCGUUAGGC GAA AAUGAUUA | 8250 | UAAUCAUUA AGAGACCA | 1108 |
| 6461 | GUAUUUAU CUGAUGA GCCGUUAGGC GAA AUGGUCUC | 8251 | GAGACCAUA AUAAAUAC | 1109 |
| 6464 | GGAGUAUU CUGAUGA GCCGUUAGGC GAA AUUAUGGU | 8252 | ACCAUAAUA AAUACUCC | 1110 |
| 6468 | AAAAGGAG CUGAUGA GCCGUUAGGC GAA AUUUAUUA | 8253 | UAAUAAAUA CUCCUUUU | 1111 |
| 6471 | UUGAAAAG CUGAUGA GCCGUUAGGC GAA AGUAUUUA | 8254 | UAAAUACUC CUUUUCAA | 1112 |
| 6474 | CUCUUGAA CUGAUGA GCCGUUAGGC GAA AGGAGUAU | 8255 | AUACUCCUU UUCAAGAG | 1113 |
| 6475 | UCUCUUGA CUGAUGA GCCGUUAGGC GAA AAGGAGUA | 8256 | UACUCCUUU UCAAGAGA | 1114 |
| 6476 | UUCUCUUG CUGAUGA GCCGUUAGGC GAA AAAGGAGU | 8257 | ACUCCUUUU CAAGAGAA | 1115 |
| 6477 | UUUCUCUU CUGAUGA GCCGUUAGGC GAA AAAAGGAG | 8258 | CUCCUUUUC AAGAGAAA | 1116 |
| 6497 | ACAAUUCU CUGAUGA GCCGUUAGGC GAA AUGGUUUU | 8259 | AAAACCAUU AGAAUUGU | 1117 |
| 6498 | AACAAUUC CUGAUGA GCCGUUAGGC GAA AAUGGUUU | 8260 | AAACCAUUA GAAUUGUU | 1118 |
| 6503 | UGAGUAAC CUGAUGA GCCGUUAGGC GAA AUUCUAAU | 8261 | AUUAGAAUU GUUACUCA | 1119 |
| 6506 | AGCUGAGU CUGAUGA GCCGUUAGGC GAA ACAAUUCU | 8262 | AGAAUUGUU ACUCAGCU | 1120 |
| 6507 | GAGCUGAG CUGAUGA GCCGUUAGGC GAA AACAAUUC | 8263 | GAAUUGUUA CUCAGCUC | 1121 |
| 6510 | AAGGAGCU CUGAUGA GCCGUUAGGC GAA AGUAACAA | 8264 | UUGUUACUC AGCUCCUU | 1122 |
| 6515 | GUUUGAAG CUGAUGA GCCGUUAGGC GAA AGCUGAGU | 8265 | ACUCAGCUC CUUCAAAC | 1123 |
| 6518 | UGAGUUUG CUGAUGA GCCGUUAGGC GAA AGGAGCUG | 8266 | CAGCUCCUU CAAACUCA | 1124 |
| 6519 | CUGAGUUU CUGAUGA GCCGUUAGGC GAA AAGGAGCU | 8267 | AGCUCCUUC AAACUCAG | 1125 |
| 6525 | ACAAACCU CUGAUGA GCCGUUAGGC GAA AGUUUGAA | 8268 | UUCAAACUC AGGUUUGU | 1126 |
| 6530 | AUGCUACA CUGAUGA GCCGUUAGGC GAA ACCUGAGU | 8269 | ACUCAGGUU UGUAGCAU | 1127 |
| 6531 | UAUGCUAC CUGAUGA GCCGUUAGGC GAA AACCUGAG | 8270 | CUCAGGUUU GUAGCAUA | 1128 |
| 6534 | AUGUAUGC CUGAUGA GCCGUUAGGC GAA ACAAACCU | 8271 | AGGUUUGUA GCAUACAU | 1129 |
| 6539 | GACUCAUG CUGAUGA GCCGUUAGGC GAA AUGCUACA | 8272 | UGUAGCAUA CAUGAGUC | 1130 |

108

| | | | | |
|---|---|---|---|---|
| 6547 | GAUGGAUG CUGAUGA GCCGUUAGGC GAA ACUCAUGU | 8273 | ACAUGAGUC CAUCCAUC | 1131 |
| 6551 | GACUGAUG CUGAUGA GCCGUUAGGC GAA AUGGACUC | 8274 | GAGUCCAUC CAUCAGUC | 1132 |
| 6555 | CUUUGACU CUGAUGA GCCGUUAGGC GAA AUGGAUGG | 8275 | CCAUCCAUC AGUCAAAG | 1133 |
| 6559 | CAUUCUUU CUGAUGA GCCGUUAGGC GAA ACUGAUGG | 8276 | CCAUCAGUC AAAGAAUG | 1134 |
| 6570 | CCAGAUGG CUGAUGA GCCGUUAGGC GAA ACCAUUCU | 8277 | AGAAUGGUU CCAUCUGG | 1135 |
| 6571 | UCCAGAUG CUGAUGA GCCGUUAGGC GAA AACCAUUC | 8278 | GAAUGGUUC CAUCUGGA | 1136 |
| 6575 | AGACUCCA CUGAUGA GCCGUUAGGC GAA AUGGAACC | 8279 | GGUUCCAUC UGGAGUCU | 1137 |
| 6582 | UACAUUAA CUGAUGA GCCGUUAGGC GAA ACUCCAGA | 8280 | UCUGGAGUC UUAAUGUA | 1138 |
| 6584 | UCUACAUU CUGAUGA GCCGUUAGGC GAA AGACUCCA | 8281 | UGGAGUCUU AAUGUAGA | 1139 |
| 6585 | UUCUACAU CUGAUGA GCCGUUAGGC GAA AAGACUCC | 8282 | GGAGUCUUA AUGUAGAA | 1140 |
| 6590 | UUUCUUUC CUGAUGA GCCGUUAGGC GAA ACAUUAAG | 8283 | CUUAAUGUA GAAAGAAA | 1141 |
| 6609 | AUUAUUAC CUGAUGA GCCGUUAGGC GAA AGUCUCCA | 8284 | UGGAGACUU GUAAUAAU | 1142 |
| 6612 | CUCAUUAU CUGAUGA GCCGUUAGGC GAA ACAAGUCU | 8285 | AGACUUGUA AUAAUGAG | 1143 |
| 6615 | UAGCUCAU CUGAUGA GCCGUUAGGC GAA AUUACAAG | 8286 | CUUGUAAUA AUGAGCUA | 1144 |
| 6623 | UUUGUAAC CUGAUGA GCCGUUAGGC GAA AGCUCAUU | 8287 | AAUGAGCUA GUUACAAA | 1145 |
| 6626 | CACUUUGU CUGAUGA GCCGUUAGGC GAA ACUAGCUC | 8288 | GAGCUAGUU ACAAAGUG | 1146 |
| 6627 | GCACUUUG CUGAUGA GCCGUUAGGC GAA AACUAGCU | 8289 | AGCUAGUUA CAAAGUGC | 1147 |
| 6637 | UAAUGAAC CUGAUGA GCCGUUAGGC GAA AGCACUUU | 8290 | AAAGUGCUU GUUCAUUA | 1148 |
| 6640 | UUUUAAUG CUGAUGA GCCGUUAGGC GAA ACAAGCAC | 8291 | GUGCUUGUU CAUUAAAA | 1149 |
| 6641 | AUUUUAAU CUGAUGA GCCGUUAGGC GAA AACAAGCA | 8292 | UGCUUGUUC AUUAAAAU | 1150 |
| 6644 | GCUAUUUU CUGAUGA GCCGUUAGGC GAA AUGAACAA | 8293 | UUGUUCAUU AAAAUAGC | 1151 |
| 6645 | UGCUAUUU CUGAUGA GCCGUUAGGC GAA AAUGAACA | 8294 | UGUUCAUUA AAAUAGCA | 1152 |
| 6650 | UUCAGUGC CUGAUGA GCCGUUAGGC GAA AUUUUAAU | 8295 | AUUAAAAUA GCACUGAA | 1153 |
| 6662 | CAUGUUUC CUGAUGA GCCGUUAGGC GAA AUUUUCAG | 8296 | CUGAAAAUU GAAACAUG | 1154 |
| 6674 | UAUCAGUU CUGAUGA GCCGUUAGGC GAA AUUCAUGU | 8297 | ACAUGAAUU AACUGAUA | 1155 |
| 6675 | UUAUCAGU CUGAUGA GCCGUUAGGC GAA AAUUCAUG | 8298 | CAUGAAUUA ACUGAUAA | 1156 |
| 6682 | UGGAAUAU CUGAUGA GCCGUUAGGC GAA AUCAGUUA | 8299 | UAACUGAUA AUAUUCCA | 1157 |
| 6685 | GAUUGGAA CUGAUGA GCCGUUAGGC GAA AUUAUCAG | 8300 | CUGAUAAUA UUCCAAUC | 1158 |
| 6687 | AUGAUUGG CUGAUGA GCCGUUAGGC GAA AUAUUAUC | 8301 | GAUAAUAUU CCAAUCAU | 1159 |
| 6688 | AAUGAUUG CUGAUGA GCCGUUAGGC GAA AAUAUUAU | 8302 | AUAAUAUUC CAAUCAUU | 1160 |
| 6693 | UGGCAAAU CUGAUGA GCCGUUAGGC GAA AUUGGAAU | 8303 | AUUCCAAUC AUUUGCCA | 1161 |
| 6696 | AAAUGGCA CUGAUGA GCCGUUAGGC GAA AUGAUUGG | 8304 | CCAAUCAUU UGCCAUUU | 1162 |
| 6697 | UAAAUGGC CUGAUGA GCCGUUAGGC GAA AAUGAUUG | 8305 | CAAUCAUUU GCCAUUUA | 1163 |

109

| | | | | |
|---|---|---|---|---|
| 6703 | UUGUCAUA CUGAUGA GCCGUUAGGC GAA AUGGCAAA | 8306 | UUUGCCAUU UAUGACAA | 1164 |
| 6704 | UUUGUCAU CUGAUGA GCCGUUAGGC GAA AAUGGCAA | 8307 | UUGCCAUUU AUGACAAA | 1165 |
| 6705 | UUUUGUCA CUGAUGA GCCGUUAGGC GAA AAAUGGCA | 8308 | UGCCAUUUA UGACAAAA | 1166 |
| 6719 | UUAGUGCC CUGAUGA GCCGUUAGGC GAA ACCAUUUU | 8309 | AAAAUGGUU GGCACUAA | 1167 |
| 6726 | UUCUUUGU CUGAUGA GCCGUUAGGC GAA AGUGCCAA | 8310 | UUGGCACUA ACAAAGAA | 1168 |
| 6743 | CUGAAAGG CUGAUGA GCCGUUAGGC GAA AGUGCUCG | 8311 | CGAGCACUU CCUUUCAG | 1169 |
| 6744 | UCUGAAAG CUGAUGA GCCGUUAGGC GAA AAGUGCUC | 8312 | GAGCACUUC CUUUCAGA | 1170 |
| 6747 | AACUCUGA CUGAUGA GCCGUUAGGC GAA AGGAAGUG | 8313 | CACUUCCUU UCAGAGUU | 1171 |
| 6748 | AAACUCUG CUGAUGA GCCGUUAGGC GAA AAGGAAGU | 8314 | ACUUCCUUU CAGAGUUU | 1172 |
| 6749 | GAAACUCU CUGAUGA GCCGUUAGGC GAA AAAGGAAG | 8315 | CUUCCUUUC AGAGUUUC | 1173 |
| 6755 | AUCUCAGA CUGAUGA GCCGUUAGGC GAA ACUCUGAA | 8316 | UUCAGAGUU UCUGAGAU | 1174 |
| 6756 | UAUCUCAG CUGAUGA GCCGUUAGGC GAA AACUCUGA | 8317 | UCAGAGUUU CUGAGAUA | 1175 |
| 6757 | UUAUCUCA CUGAUGA GCCGUUAGGC GAA AAACUCUG | 8318 | CAGAGUUUC UGAGAUAA | 1176 |
| 6764 | ACGUACAU CUGAUGA GCCGUUAGGC GAA AUCUCAGA | 8319 | UCUGAGAUA AUGUACGU | 1177 |
| 6769 | GUUCCACG CUGAUGA GCCGUUAGGC GAA ACAUUAUC | 8320 | GAUAAUGUA CGUGGAAC | 1178 |
| 6781 | UCCACCCA CUGAUGA GCCGUUAGGC GAA ACUGUUCC | 8321 | GGAACAGUC UGGGUGGA | 1179 |
| 6814 | AAGACACA CUGAUGA GCCGUUAGGC GAA ACUUGCAC | 8322 | GUGCAAGUC UGUGUCUU | 1180 |
| 6820 | ACUGACAA CUGAUGA GCCGUUAGGC GAA ACACAGAC | 8323 | GUCUGUGUC UUGUCAGU | 1181 |
| 6822 | GGACUGAC CUGAUGA GCCGUUAGGC GAA AGACACAG | 8324 | CUGUGUCUU GUCAGUCC | 1182 |
| 6825 | CUUGGACU CUGAUGA GCCGUUAGGC GAA ACAAGACA | 8325 | UGUCUUGUC AGUCCAAG | 1183 |
| 6829 | ACUUCUUG CUGAUGA GCCGUUAGGC GAA ACUGACAA | 8326 | UUGUCAGUC CAAGAAGU | 1184 |
| 6851 | CUAAAAUU CUGAUGA GCCGUUAGGC GAA ACAUCUCG | 8327 | CGAGAUGUU AAUUUUAG | 1185 |
| 6852 | CCUAAAAU CUGAUGA GCCGUUAGGC GAA AACAUCUC | 8328 | GAGAUGUUA AUUUUAGG | 1186 |
| 6855 | GUCCCUAA CUGAUGA GCCGUUAGGC GAA AUUAACAU | 8329 | AUGUUAAUU UUAGGGAC | 1187 |
| 6856 | GGUCCCUA CUGAUGA GCCGUUAGGC GAA AAUUAACA | 8330 | UGUUAAUUU UAGGGACC | 1188 |
| 6857 | GGGUCCCU CUGAUGA GCCGUUAGGC GAA AAAUUAAC | 8331 | GUUAAUUUU AGGGACCC | 1189 |
| 6858 | CGGGUCCC CUGAUGA GCCGUUAGGC GAA AAAAUUAA | 8332 | UUAAUUUUA GGGACCCG | 1190 |
| 6872 | UAGGAAAC CUGAUGA GCCGUUAGGC GAA AGGCACGG | 8333 | CCGUGCCUU GUUUCCUA | 1191 |
| 6875 | GGCUAGGA CUGAUGA GCCGUUAGGC GAA ACAAGGCA | 8334 | UGCCUUGUU UCCUAGCC | 1192 |
| 6876 | GGGCUAGG CUGAUGA GCCGUUAGGC GAA AACAAGGC | 8335 | GCCUUGUUU CCUAGCCC | 1193 |
| 6877 | UGGGCUAG CUGAUGA GCCGUUAGGC GAA AAACAAGG | 8336 | CCUUGUUUC CUAGCCCA | 1194 |
| 6880 | UUGUGGGC CUGAUGA GCCGUUAGGC GAA AGGAAACA | 8337 | UGUUUCCUA GCCCACAA | 1195 |
| 6901 | AUCUGUUU CUGAUGA GCCGUUAGGC GAA AUGUUUGC | 8338 | GCAAACAUC AAACAGAU | 1196 |

110

| | | | | |
|---|---|---|---|---|
| 6910 | CUAGCGAG CUGAUGA GCCGUUAGGC GAA AUCUGUUU | 8339 | AAACAGAUA CUCGCUAG | 1197 |
| 6913 | AGGCUAGC CUGAUGA GCCGUUAGGC GAA AGUAUCUG | 8340 | CAGAUACUC GCUAGCCU | 1198 |
| 6917 | AAUGAGGC CUGAUGA GCCGUUAGGC GAA AGCGAGUA | 8341 | UACUCGCUA GCCUCAUU | 1199 |
| 6922 | AUUUAAAU CUGAUGA GCCGUUAGGC GAA AGGCUAGC | 8342 | GCUAGCCUC AUUUAAAU | 1200 |
| 6925 | UCAAUUUA CUGAUGA GCCGUUAGGC GAA AUGAGGCU | 8343 | AGCCUCAUU UAAAUUGA | 1201 |
| 6926 | AUCAAUUU CUGAUGA GCCGUUAGGC GAA AAUGAGGC | 8344 | GCCUCAUUU AAAUUGAU | 1202 |
| 6927 | AAUCAAUU CUGAUGA GCCGUUAGGC GAA AAAUGAGG | 8345 | CCUCAUUUA AAUUGAUU | 1203 |
| 6931 | CUUUAAUC CUGAUGA GCCGUUAGGC GAA AUUUAAAU | 8346 | AUUUAAAUU GAUUAAAG | 1204 |
| 6935 | CCUCCUUU CUGAUGA GCCGUUAGGC GAA AUCAAUUU | 8347 | AAAUUGAUU AAAGGAGG | 1205 |
| 6936 | UCCUCCUU CUGAUGA GCCGUUAGGC GAA AAUCAAUU | 8348 | AAUUGAUUA AAGGAGGA | 1206 |
| 6951 | CGGCCAAA CUGAUGA GCCGUUAGGC GAA AUGCACUC | 8349 | GAGUGCAUC UUUGGCCG | 1207 |
| 6953 | GUCGGCCA CUGAUGA GCCGUUAGGC GAA AGAUGCAC | 8350 | GUGCAUCUU UGGCCGAC | 1208 |
| 6954 | UGUCGGCC CUGAUGA GCCGUUAGGC GAA AAGAUGCA | 8351 | UGCAUCUUU GGCCGACA | 1209 |
| 6970 | CACACAGU CUGAUGA GCCGUUAGGC GAA ACACCACU | 8352 | AGUGGUGUA ACUGUGUG | 1210 |
| 7026 | AACACACA CUGAUGA GCCGUUAGGC GAA ACACCCAC | 8353 | GUGGGUGUA UGUGUGUU | 1211 |
| 7034 | AUGCACAA CUGAUGA GCCGUUAGGC GAA ACACACAU | 8354 | AUGUGUGUU UUGUGCAU | 1212 |
| 7035 | UAUGCACA CUGAUGA GCCGUUAGGC GAA AACACACA | 8355 | UGUGUGUUU UGUGCAUA | 1213 |
| 7036 | UUAUGCAC CUGAUGA GCCGUUAGGC GAA AAACACAC | 8356 | GUGUGUUUU GUGCAUAA | 1214 |
| 7043 | UAAAUAGU CUGAUGA GCCGUUAGGC GAA AUGCACAA | 8357 | UUGUGCAUA ACUAUUUA | 1215 |
| 7047 | UCCUUAAA CUGAUGA GCCGUUAGGC GAA AGUUAUGC | 8358 | GCAUAACUA UUUAAGGA | 1216 |
| 7049 | UUUCCUUA CUGAUGA GCCGUUAGGC GAA AUAGUUAU | 8359 | AUAACUAUU UAAGGAAA | 1217 |
| 7050 | GUUUCCUU CUGAUGA GCCGUUAGGC GAA AAUAGUUA | 8360 | UAACUAUUU AAGGAAAC | 1218 |
| 7051 | AGUUUCCU CUGAUGA GCCGUUAGGC GAA AAAUAGUU | 8361 | AACUAUUUA AGGAAACU | 1219 |
| 7065 | AACUUUAA CUGAUGA GCCGUUAGGC GAA AUUCCAGU | 8362 | ACUGGAAUU UUAAAGUU | 1220 |
| 7066 | UAACUUUA CUGAUGA GCCGUUAGGC GAA AAUUCCAG | 8363 | CUGGAAUUU UAAAGUUA | 1221 |
| 7067 | GUAACUUU CUGAUGA GCCGUUAGGC GAA AAAUUCCA | 8364 | UGGAAUUUU AAAGUUAC | 1222 |
| 7068 | AGUAACUU CUGAUGA GCCGUUAGGC GAA AAAAUUCC | 8365 | GGAAUUUUA AAGUUACU | 1223 |
| 7073 | AUAAAAGU CUGAUGA GCCGUUAGGC GAA ACUUUAAA | 8366 | UUUAAAGUU ACUUUUAU | 1224 |
| 7074 | UAUAAAAG CUGAUGA GCCGUUAGGC GAA AACUUUAA | 8367 | UUAAAGUUA CUUUUAUA | 1225 |
| 7077 | UUGUAUAA CUGAUGA GCCGUUAGGC GAA AGUAACUU | 8368 | AAGUUACUU UUAUACAA | 1226 |
| 7078 | UUUGUAUA CUGAUGA GCCGUUAGGC GAA AAGUAACU | 8369 | AGUUACUUU UAUACAAA | 1227 |
| 7079 | GUUUGUAU CUGAUGA GCCGUUAGGC GAA AAAGUAAC | 8370 | GUUACUUUU AUACAAAC | 1228 |
| 7080 | GGUUUGUA CUGAUGA GCCGUUAGGC GAA AAAAGUAA | 8371 | UUACUUUUA UACAAACC | 1229 |

111

| | | | | |
|---|---|---|---|---|
| 7082 | UUGGUUUG CUGAUGA GCCGUUAGGC GAA AUAAAAGU | 8372 | ACUUUUAUA CAAACCAA | 1230 |
| 7095 | GUAGCAUA CUGAUGA GCCGUUAGGC GAA AUUCUUGG | 8373 | CCAAGAAUA UAUGCUAC | 1231 |
| 7097 | CUGUAGCA CUGAUGA GCCGUUAGGC GAA AUAUUCUU | 8374 | AAGAAUAUA UGCUACAG | 1232 |
| 7102 | UAUAUCUG CUGAUGA GCCGUUAGGC GAA AGCAUAUA | 8375 | UAUAUGCUA CAGAUAUA | 1233 |
| 7108 | CUGUCUUA CUGAUGA GCCGUUAGGC GAA AUCUGUAG | 8376 | CUACAGAUA UAAGACAG | 1234 |
| 7110 | GUCUGUCU CUGAUGA GCCGUUAGGC GAA AUAUCUGU | 8377 | ACAGAUAUA AGACAGAC | 1235 |
| 7124 | UAGGACCA CUGAUGA GCCGUUAGGC GAA ACCAUGUC | 8378 | GACAUGGUU UGGUCCUA | 1236 |
| 7125 | AUAGGACC CUGAUGA GCCGUUAGGC GAA AACCAUGU | 8379 | ACAUGGUUU GGUCCUAU | 1237 |
| 7129 | AAAUAUAG CUGAUGA GCCGUUAGGC GAA ACCAAACC | 8380 | GGUUUGGUC CUAUAUUU | 1238 |
| 7132 | UAGAAAUA CUGAUGA GCCGUUAGGC GAA AGGACCAA | 8381 | UUGGUCCUA UAUUUCUA | 1239 |
| 7134 | ACUAGAAA CUGAUGA GCCGUUAGGC GAA AUAGGACC | 8382 | GGUCCUAUA UUUCUAGU | 1240 |
| 7136 | UGACUAGA CUGAUGA GCCGUUAGGC GAA AUAUAGGA | 8383 | UCCUAUAUU UCUAGUCA | 1241 |
| 7137 | AUGACUAG CUGAUGA GCCGUUAGGC GAA AAUAUAGG | 8384 | CCUAUAUUU CUAGUCAU | 1242 |
| 7138 | CAUGACUA CUGAUGA GCCGUUAGGC GAA AAAUAUAG | 8385 | CUAUAUUUC UAGUCAUG | 1243 |
| 7140 | AUCAUGAC CUGAUGA GCCGUUAGGC GAA AGAAAUAU | 8386 | AUAUUUCUA GUCAUGAU | 1244 |
| 7143 | UUCAUCAU CUGAUGA GCCGUUAGGC GAA ACUAGAAA | 8387 | UUUCUAGUC AUGAUGAA | 1245 |
| 7155 | AUACAAAA CUGAUGA GCCGUUAGGC GAA ACAUUCAU | 8388 | AUGAAUGUA UUUUGUAU | 1246 |
| 7157 | GUAUACAA CUGAUGA GCCGUUAGGC GAA AUACAUUC | 8389 | GAAUGUAUU UUGUAUAC | 1247 |
| 7158 | GGUAUACA CUGAUGA GCCGUUAGGC GAA AAUACAUU | 8390 | AAUGUAUUU UGUAUACC | 1248 |
| 7159 | UGGUAUAC CUGAUGA GCCGUUAGGC GAA AAAUACAU | 8391 | AUGUAUUUU GUAUACCA | 1249 |
| 7162 | AGAUGGUA CUGAUGA GCCGUUAGGC GAA ACAAAAUA | 8392 | UAUUUUGUA UACCAUCU | 1250 |
| 7164 | GAAGAUGG CUGAUGA GCCGUUAGGC GAA AUACAAAA | 8393 | UUUUGUAUA CCAUCUUC | 1251 |
| 7169 | UAUAUGAA CUGAUGA GCCGUUAGGC GAA AUGGUAUA | 8394 | UAUACCAUC UUCAUAUA | 1252 |
| 7171 | AUUAUAUG CUGAUGA GCCGUUAGGC GAA AGAUGGUA | 8395 | UACCAUCUU CAUAUAAU | 1253 |
| 7172 | UAUUAUAU CUGAUGA GCCGUUAGGC GAA AAGAUGGU | 8396 | ACCAUCUUC AUAUAAUA | 1254 |
| 7175 | GUAUAUUA CUGAUGA GCCGUUAGGC GAA AUGAAGAU | 8397 | AUCUUCAUA UAAUAUAC | 1255 |
| 7177 | AAGUAUAU CUGAUGA GCCGUUAGGC GAA AUAUGAAG | 8398 | CUUCAUAUA AUAUACUU | 1256 |
| 7180 | UUUAAGUA CUGAUGA GCCGUUAGGC GAA AUUAUAUG | 8399 | CAUAUAAUA UACUUAAA | 1257 |
| 7182 | UUUUUAAG CUGAUGA GCCGUUAGGC GAA AUAUUAUA | 8400 | UAUAAUAUA CUUAAAAA | 1258 |
| 7185 | AUAUUUUU CUGAUGA GCCGUUAGGC GAA AGUAUAUU | 8401 | AAUAUACUU AAAAAUAU | 1259 |
| 7186 | AAUAUUUU CUGAUGA GCCGUUAGGC GAA AAGUAUAU | 8402 | AUAUACUUA AAAAUAUU | 1260 |
| 7192 | UUAAGAAA CUGAUGA GCCGUUAGGC GAA AUUUUUAA | 8403 | UUAAAAAUA UUUCUUAA | 1261 |
| 7194 | AAUUAAGA CUGAUGA GCCGUUAGGC GAA AUAUUUUU | 8404 | AAAAAUAUU UCUUAAUU | 1262 |

| | | | | |
|---|---|---|---|---|
| 7195 | CAAUUAAG CUGAUGA GCCGUUAGGC GAA AAUAUUUU | 8405 | AAAAUAUUU CUUAAUUG | 1263 |
| 7196 | CCAAUUAA CUGAUGA GCCGUUAGGC GAA AAAUAUUU | 8406 | AAAUAUUUC UUAAUUGG | 1264 |
| 7198 | UCCCAAUU CUGAUGA GCCGUUAGGC GAA AGAAAUAU | 8407 | AUAUUUCUU AAUUGGGA | 1265 |
| 7199 | AUCCCAAU CUGAUGA GCCGUUAGGC GAA AAGAAAUA | 8408 | UAUUUCUUA AUUGGGAU | 1266 |
| 7202 | CAAAUCCC CUGAUGA GCCGUUAGGC GAA AUUAAGAA | 8409 | UUCUUAAUU GGGAUUUG | 1267 |
| 7208 | CGAUUACA CUGAUGA GCCGUUAGGC GAA AUCCCAAU | 8410 | AUUGGGAUU UGUAAUCG | 1268 |
| 7209 | ACGAUUAC CUGAUGA GCCGUUAGGC GAA AAUCCCAA | 8411 | UUGGGAUUU GUAAUCGU | 1269 |
| 7212 | GGUACGAU CUGAUGA GCCGUUAGGC GAA ACAAAUCC | 8412 | GGAUUUGUA AUCGUACC | 1270 |
| 7215 | GUUGGUAC CUGAUGA GCCGUUAGGC GAA AUUACAAA | 8413 | UUUGUAAUC GUACCAAC | 1271 |
| 7218 | UAAGUUGG CUGAUGA GCCGUUAGGC GAA ACGAUUAC | 8414 | GUAAUCGUA CCAACUUA | 1272 |
| 7225 | UAUCAAUU CUGAUGA GCCGUUAGGC GAA AGUUGGUA | 8415 | UACCAACUU AAUUGAUA | 1273 |
| 7226 | UUAUCAAU CUGAUGA GCCGUUAGGC GAA AAGUUGGU | 8416 | ACCAACUUA AUUGAUAA | 1274 |
| 7229 | AGUUUAUC CUGAUGA GCCGUUAGGC GAA AUUAAGUU | 8417 | AACUUAAUU GAUAAACU | 1275 |
| 7233 | GCCAAGUU CUGAUGA GCCGUUAGGC GAA AUCAAUUA | 8418 | UAAUUGAUA AACUUGGC | 1276 |
| 7238 | CAGUUGCC CUGAUGA GCCGUUAGGC GAA AGUUUAUC | 8419 | GAUAAACUU GGCAACUG | 1277 |
| 7249 | GAACAUAA CUGAUGA GCCGUUAGGC GAA AGCAGUUG | 8420 | CAACUGCUU UUAUGUUC | 1278 |
| 7250 | AGAACAUA CUGAUGA GCCGUUAGGC GAA AAGCAGUU | 8421 | AACUGCUUU UAUGUUCU | 1279 |
| 7251 | CAGAACAU CUGAUGA GCCGUUAGGC GAA AAAGCAGU | 8422 | ACUGCUUUU AUGUUCUG | 1280 |
| 7252 | ACAGAACA CUGAUGA GCCGUUAGGC GAA AAAAGCAG | 8423 | CUGCUUUUA UGUUCUGU | 1281 |
| 7256 | GGAGACAG CUGAUGA GCCGUUAGGC GAA ACAUAAAA | 8424 | UUUUAUGUU CUGUCUCC | 1282 |
| 7257 | AGGAGACA CUGAUGA GCCGUUAGGC GAA AACAUAAA | 8425 | UUUAUGUUC UGUCUCCU | 1283 |
| 7261 | UGGAAGGA CUGAUGA GCCGUUAGGC GAA ACAGAACA | 8426 | UGUUCUGUC UCCUUCCA | 1284 |
| 7263 | UAUGGAAG CUGAUGA GCCGUUAGGC GAA AGACAGAA | 8427 | UUCUGUCUC CUUCCAUA | 1285 |
| 7266 | AUUUAUGG CUGAUGA GCCGUUAGGC GAA AGGAGACA | 8428 | UGUCUCCUU CCAUAAAU | 1286 |
| 7267 | AAUUUAUG CUGAUGA GCCGUUAGGC GAA AAGGAGAC | 8429 | GUCUCCUUC CAUAAAUU | 1287 |
| 7271 | GAAAAAUU CUGAUGA GCCGUUAGGC GAA AUGGAAGG | 8430 | CCUUCCAUA AAUUUUUC | 1288 |
| 7275 | UUUUGAAA CUGAUGA GCCGUUAGGC GAA AUUUAUGG | 8431 | CCAUAAAUU UUUCAAAA | 1289 |
| 7276 | AUUUUGAA CUGAUGA GCCGUUAGGC GAA AAUUUAUG | 8432 | CAUAAAUUU UUCAAAAU | 1290 |
| 7277 | UAUUUUGA CUGAUGA GCCGUUAGGC GAA AAAUUUAU | 8433 | AUAAAUUUU UCAAAAUA | 1291 |
| 7278 | GUAUUUUG CUGAUGA GCCGUUAGGC GAA AAAAUUUA | 8434 | UAAAUUUUU CAAAAUAC | 1292 |
| 7279 | AGUAUUUU CUGAUGA GCCGUUAGGC GAA AAAAAUUU | 8435 | AAAUUUUUC AAAAUACU | 1293 |
| 7285 | UGAAUUAG CUGAUGA GCCGUUAGGC GAA AUUUUGAA | 8436 | UUCAAAAUA CUAAUUCA | 1294 |
| 7288 | UGUUGAAU CUGAUGA GCCGUUAGGC GAA AGUAUUUU | 8437 | AAAAUACUA AUUCAACA | 1295 |

| | | | | |
|---|---|---|---|---|
| 7291 | CUUUGUUG CUGAUGA GCCGUUAGGC GAA AUUAGUAU | 8438 | AUACUAAUU CAACAAAG | 1296 |
| 7292 | UCUUUGUU CUGAUGA GCCGUUAGGC GAA AAUUAGUA | 8439 | UACUAAUUC AACAAAGA | 1297 |
| 7308 | AAAAAAAA CUGAUGA GCCGUUAGGC GAA AGCUUUUU | 8440 | AAAAAGCUC UUUUUUUU | 1298 |
| 7310 | GGAAAAAA CUGAUGA GCCGUUAGGC GAA AGAGCUUU | 8441 | AAAGCUCUU UUUUUUCC | 1299 |
| 7311 | AGGAAAAA CUGAUGA GCCGUUAGGC GAA AAGAGCUU | 8442 | AAGCUCUUU UUUUUCCU | 1300 |
| 7312 | UAGGAAAA CUGAUGA GCCGUUAGGC GAA AAAGAGCU | 8443 | AGCUCUUUU UUUUCCUA | 1301 |
| 7313 | UUAGGAAA CUGAUGA GCCGUUAGGC GAA AAAAGAGC | 8444 | GCUCUUUUU UUUCCUAA | 1302 |
| 7314 | UUUAGGAA CUGAUGA GCCGUUAGGC GAA AAAAAGAG | 8445 | CUCUUUUUU UUCCUAAA | 1303 |
| 7315 | UUUUAGGA CUGAUGA GCCGUUAGGC GAA AAAAAAGA | 8446 | UCUUUUUUU UCCUAAAA | 1304 |
| 7316 | AUUUUAGG CUGAUGA GCCGUUAGGC GAA AAAAAAAG | 8447 | CUUUUUUUU CCUAAAAU | 1305 |
| 7317 | UAUUUUAG CUGAUGA GCCGUUAGGC GAA AAAAAAAA | 8448 | UUUUUUUUC CUAAAAUA | 1306 |
| 7320 | GUUUAUUU CUGAUGA GCCGUUAGGC GAA AGGAAAAA | 8449 | UUUUUCCUA AAAUAAAC | 1307 |
| 7325 | UUUGAGUU CUGAUGA GCCGUUAGGC GAA AUUUUAGG | 8450 | CCUAAAAUA AACUCAAA | 1308 |
| 7330 | AUAAAUUU CUGAUGA GCCGUUAGGC GAA AGUUUAUU | 8451 | AAUAAACUC AAAUUUAU | 1309 |
| 7335 | CAAGGAUA CUGAUGA GCCGUUAGGC GAA AUUUGAGU | 8452 | ACUCAAAUU UAUCCUUG | 1310 |
| 7336 | ACAAGGAU CUGAUGA GCCGUUAGGC GAA AAUUUGAG | 8453 | CUCAAAUUU AUCCUUGU | 1311 |
| 7337 | AACAAGGA CUGAUGA GCCGUUAGGC GAA AAAUUUGA | 8454 | UCAAAUUUA UCCUUGUU | 1312 |
| 7339 | UAAACAAG CUGAUGA GCCGUUAGGC GAA AUAAAUUU | 8455 | AAAUUUAUC CUUGUUUA | 1313 |
| 7342 | CUCUAAAC CUGAUGA GCCGUUAGGC GAA AGGAUAAA | 8456 | UUUAUCCUU GUUUAGAG | 1314 |
| 7345 | CUGCUCUA CUGAUGA GCCGUUAGGC GAA ACAAGGAU | 8457 | AUCCUUGUU UAGAGCAG | 1315 |
| 7346 | UCUGCUCU CUGAUGA GCCGUUAGGC GAA AACAAGGA | 8458 | UCCUUGUUU AGAGCAGA | 1316 |
| 7347 | CUCUGCUC CUGAUGA GCCGUUAGGC GAA AAACAAGG | 8459 | CCUUGUUUA GAGCAGAG | 1317 |
| 7362 | UUUUUCUU CUGAUGA GCCGUUAGGC GAA AUUUUUCU | 8460 | AGAAAAAUU AAGAAAAA | 1318 |
| 7363 | GUUUUUCU CUGAUGA GCCGUUAGGC GAA AAUUUUUC | 8461 | GAAAAAUUA AGAAAAAC | 1319 |
| 7373 | CCAUUUCA CUGAUGA GCCGUUAGGC GAA AGUUUUUC | 8462 | GAAAAACUU UGAAAUGG | 1320 |
| 7374 | ACCAUUUC CUGAUGA GCCGUUAGGC GAA AAGUUUUU | 8463 | AAAAACUUU GAAAUGGU | 1321 |
| 7383 | UUUUUUGA CUGAUGA GCCGUUAGGC GAA ACCAUUUC | 8464 | GAAAUGGUC UCAAAAAA | 1322 |
| 7385 | AAUUUUUU CUGAUGA GCCGUUAGGC GAA AGACCAUU | 8465 | AAUGGUCUC AAAAAAUU | 1323 |
| 7393 | UAUUUAGC CUGAUGA GCCGUUAGGC GAA AUUUUUUG | 8466 | CAAAAAAUU GCUAAAUA | 1324 |
| 7397 | AAAAUAUU CUGAUGA GCCGUUAGGC GAA AGCAAUUU | 8467 | AAAUUGCUA AAUAUUUU | 1325 |
| 7401 | AUUGAAAA CUGAUGA GCCGUUAGGC GAA AUUUAGCA | 8468 | UGCUAAAUA UUUUCAAU | 1326 |
| 7403 | CCAUUGAA CUGAUGA GCCGUUAGGC GAA AUAUUUAG | 8469 | CUAAAUAUU UUCAAUGG | 1327 |
| 7404 | UCCAUUGA CUGAUGA GCCGUUAGGC GAA AAUAUUUA | 8470 | UAAAUAUUU UCAAUGGA | 1328 |

| | | | | |
|---|---|---|---|---|
| 7405 | UUCCAUUG CUGAUGA GCCGUUAGGC GAA AAAUAUUU | 8471 | AAAUAUUUU CAAUGGAA | 1329 |
| 7406 | UUUCCAUU CUGAUGA GCCGUUAGGC GAA AAAAUAUU | 8472 | AAUAUUUUC AAUGGAAA | 1330 |
| 7418 | CUAACAUU CUGAUGA GCCGUUAGGC GAA AGUUUUCC | 8473 | GGAAAACUA AAUGUUAG | 1331 |
| 7424 | GCUAAACU CUGAUGA GCCGUUAGGC GAA ACAUUUAG | 8474 | CUAAAUGUU AGUUUAGC | 1332 |
| 7425 | AGCUAAAC CUGAUGA GCCGUUAGGC GAA AACAUUUA | 8475 | UAAAUGUUA GUUUAGCU | 1333 |
| 7428 | AUCAGCUA CUGAUGA GCCGUUAGGC GAA ACUAACAU | 8476 | AUGUUAGUU UAGCUGAU | 1334 |
| 7429 | AAUCAGCU CUGAUGA GCCGUUAGGC GAA AACUAACA | 8477 | UGUUAGUUU AGCUGAUU | 1335 |
| 7430 | CAAUCAGC CUGAUGA GCCGUUAGGC GAA AAACUAAC | 8478 | GUUAGUUUA GCUGAUUG | 1336 |
| 7437 | CCCCAUAC CUGAUGA GCCGUUAGGC GAA AUCAGCUA | 8479 | UAGCUGAUU GUAUGGGG | 1337 |
| 7440 | AAACCCCA CUGAUGA GCCGUUAGGC GAA ACAAUCAG | 8480 | CUGAUUGUA UGGGGUUU | 1338 |
| 7447 | GGUUCGAA CUGAUGA GCCGUUAGGC GAA ACCCCAUA | 8481 | UAUGGGGUU UUCGAACC | 1339 |
| 7448 | AGGUUCGA CUGAUGA GCCGUUAGGC GAA AACCCCAU | 8482 | AUGGGGUUU UCGAACCU | 1340 |
| 7449 | AAGGUUCG CUGAUGA GCCGUUAGGC GAA AAACCCCA | 8483 | UGGGGUUUU CGAACCUU | 1341 |
| 7450 | AAAGGUUC CUGAUGA GCCGUUAGGC GAA AAAACCCC | 8484 | GGGGUUUUC GAACCUUU | 1342 |
| 7457 | AAAAGUGA CUGAUGA GCCGUUAGGC GAA AGGUUCGA | 8485 | UCGAACCUU UCACUUUU | 1343 |
| 7458 | AAAAAGUG CUGAUGA GCCGUUAGGC GAA AAGGUUCG | 8486 | CGAACCUUU CACUUUUU | 1344 |
| 7459 | CAAAAAGU CUGAUGA GCCGUUAGGC GAA AAAGGUUC | 8487 | GAACCUUUC ACUUUUUG | 1345 |
| 7463 | CAAACAAA CUGAUGA GCCGUUAGGC GAA AGUGAAAG | 8488 | CUUUCACUU UUUGUUUG | 1346 |
| 7464 | ACAAACAA CUGAUGA GCCGUUAGGC GAA AAGUGAAA | 8489 | UUUCACUUU UUGUUUGU | 1347 |
| 7465 | AACAAACA CUGAUGA GCCGUUAGGC GAA AAAGUGAA | 8490 | UUCACUUUU UGUUUGUU | 1348 |
| 7466 | AAACAAAC CUGAUGA GCCGUUAGGC GAA AAAAGUGA | 8491 | UCACUUUUU GUUUGUUU | 1349 |
| 7469 | GUAAAACA CUGAUGA GCCGUUAGGC GAA ACAAAAAG | 8492 | CUUUUUGUU UGUUUUAC | 1350 |
| 7470 | GGUAAAAC CUGAUGA GCCGUUAGGC GAA AACAAAAA | 8493 | UUUUUGUUU GUUUUACC | 1351 |
| 7473 | AUAGGUAA CUGAUGA GCCGUUAGGC GAA ACAAACAA | 8494 | UUGUUUGUU UUACCUAU | 1352 |
| 7474 | AAUAGGUA CUGAUGA GCCGUUAGGC GAA AACAAACA | 8495 | UGUUUGUUU UACCUAUU | 1353 |
| 7475 | AAAUAGGU CUGAUGA GCCGUUAGGC GAA AAACAAAC | 8496 | GUUUGUUUU ACCUAUUU | 1354 |
| 7476 | GAAAUAGG CUGAUGA GCCGUUAGGC GAA AAAACAAA | 8497 | UUUGUUUUA CCUAUUUC | 1355 |
| 7480 | UUGUGAAA CUGAUGA GCCGUUAGGC GAA AGGUAAAA | 8498 | UUUUACCUA UUUCACAA | 1356 |
| 7482 | AGUUGUGA CUGAUGA GCCGUUAGGC GAA AUAGGUAA | 8499 | UUACCUAUU UCACAACU | 1357 |
| 7483 | CAGUUGUG CUGAUGA GCCGUUAGGC GAA AAUAGGUA | 8500 | UACCUAUUU CACAACUG | 1358 |
| 7484 | ACAGUUGU CUGAUGA GCCGUUAGGC GAA AAAUAGGU | 8501 | ACCUAUUUC ACAACUGU | 1359 |
| 7495 | UGGCAAUU CUGAUGA GCCGUUAGGC GAA ACACAGUU | 8502 | AACUGUGUA AAUUGCCA | 1360 |
| 7499 | UUAUUGGC CUGAUGA GCCGUUAGGC GAA AUUUACAC | 8503 | GUGUAAAUU GCCAAUAA | 1361 |

115

| | | | | |
|---|---|---|---|---|
| 7506 | ACAGGAAU CUGAUGA GCCGUUAGGC GAA AUUGGCAA | 8504 | UUGCCAAUA AUUCCUGU | 1362 |
| 7509 | UGGACAGG CUGAUGA GCCGUUAGGC GAA AUUAUUGG | 8505 | CCAAUAAUU CCUGUCCA | 1363 |
| 7510 | AUGGACAG CUGAUGA GCCGUUAGGC GAA AAUUAUUG | 8506 | CAAUAAUUC CUGUCCAU | 1364 |
| 7515 | UUUUCAUG CUGAUGA GCCGUUAGGC GAA ACAGGAAU | 8507 | AUUCCUGUC CAUGAAAA | 1365 |
| 7531 | CACUGGAU CUGAUGA GCCGUUAGGC GAA AUUUGCAU | 8508 | AUGCAAAUU AUCCAGUG | 1366 |
| 7532 | ACACUGGA CUGAUGA GCCGUUAGGC GAA AAUUUGCA | 8509 | UGCAAAUUA UCCAGUGU | 1367 |
| 7534 | CUACACUG CUGAUGA GCCGUUAGGC GAA AUAAUUUG | 8510 | CAAAUUAUC CAGUGUAG | 1368 |
| 7541 | AAUAUAUC CUGAUGA GCCGUUAGGC GAA ACACUGGA | 8511 | UCCAGUGUA GAUAUAUU | 1369 |
| 7545 | GUCAAAUA CUGAUGA GCCGUUAGGC GAA AUCUACAC | 8512 | GUGUAGAUA UAUUUGAC | 1370 |
| 7547 | UGGUCAAA CUGAUGA GCCGUUAGGC GAA AUAUCUAC | 8513 | GUAGAUAUA UUUGACCA | 1371 |
| 7549 | GAUGGUCA CUGAUGA GCCGUUAGGC GAA AUAUAUCU | 8514 | AGAUAUAUU UGACCAUC | 1372 |
| 7550 | UGAUGGUC CUGAUGA GCCGUUAGGC GAA AAUAUAUC | 8515 | GAUAUAUUU GACCAUCA | 1373 |
| 7557 | CAUAGGGU CUGAUGA GCCGUUAGGC GAA AUGGUCAA | 8516 | UUGACCAUC ACCCUAUG | 1374 |
| 7563 | AAUAUCCA CUGAUGA GCCGUUAGGC GAA AGGGUGAU | 8517 | AUCACCCUA UGGAUAUU | 1375 |
| 7569 | CUAGCCAA CUGAUGA GCCGUUAGGC GAA AUCCAUAG | 8518 | CUAUGGAUA UUGGCUAG | 1376 |
| 7571 | AACUAGCC CUGAUGA GCCGUUAGGC GAA AUAUCCAU | 8519 | AUGGAUAUU GGCUAGUU | 1377 |
| 7576 | GGCAAAAC CUGAUGA GCCGUUAGGC GAA AGCCAAUA | 8520 | UAUUGGCUA GUUUUGCC | 1378 |
| 7579 | AAAGGCAA CUGAUGA GCCGUUAGGC GAA ACUAGCCA | 8521 | UGGCUAGUU UUGCCUUU | 1379 |
| 7580 | UAAAGGCA CUGAUGA GCCGUUAGGC GAA AACUAGCC | 8522 | GGCUAGUUU UGCCUUUA | 1380 |
| 7581 | AUAAAGGC CUGAUGA GCCGUUAGGC GAA AAACUAGC | 8523 | GCUAGUUUU GCCUUUAU | 1381 |
| 7586 | GCUUAAUA CUGAUGA GCCGUUAGGC GAA AGGCAAAA | 8524 | UUUUGCCUU UAUUAAGC | 1382 |
| 7587 | UGCUUAAU CUGAUGA GCCGUUAGGC GAA AAGGCAAA | 8525 | UUUGCCUUU AUUAAGCA | 1383 |
| 7588 | UUGCUUAA CUGAUGA GCCGUUAGGC GAA AAAGGCAA | 8526 | UUGCCUUUA UUAAGCAA | 1384 |
| 7590 | AUUUGCUU CUGAUGA GCCGUUAGGC GAA AUAAAGGC | 8527 | GCCUUUAUU AAGCAAAU | 1385 |
| 7591 | AAUUUGCU CUGAUGA GCCGUUAGGC GAA AAUAAAGG | 8528 | CCUUUAUUA AGCAAAUU | 1386 |
| 7599 | CUGAAAUG CUGAUGA GCCGUUAGGC GAA AUUUGCUU | 8529 | AAGCAAAUU CAUUUCAG | 1387 |
| 7600 | GCUGAAAU CUGAUGA GCCGUUAGGC GAA AAUUUGCU | 8530 | AGCAAAUUC AUUUCAGC | 1388 |
| 7603 | CAGGCUGA CUGAUGA GCCGUUAGGC GAA AUGAAUUU | 8531 | AAAUUCAUU UCAGCCUG | 1389 |
| 7604 | UCAGGCUG CUGAUGA GCCGUUAGGC GAA AAUGAAUU | 8532 | AAUUCAUUU CAGCCUGA | 1390 |
| 7605 | UUCAGGCU CUGAUGA GCCGUUAGGC GAA AAAUGAAU | 8533 | AUUCAUUUC AGCCUGAA | 1391 |
| 7617 | UAUAGGCA CUGAUGA GCCGUUAGGC GAA ACAUUCAG | 8534 | CUGAAUGUC UGCCUAUA | 1392 |
| 7623 | AGAAUAUA CUGAUGA GCCGUUAGGC GAA AGGCAGAC | 8535 | GUCUGCCUA UAUAUUCU | 1393 |
| 7625 | AGAGAAUA CUGAUGA GCCGUUAGGC GAA AUAGGCAG | 8536 | CUGCCUAUA UAUUCUCU | 1394 |

| | | | | |
|---|---|---|---|---|
| 7627 | GCAGAGAA CUGAUGA GCCGUUAGGC GAA AUAUAGGC | 8537 | GCCUAUAUA UUCUCUGC | 1395 |
| 7629 | GAGCAGAG CUGAUGA GCCGUUAGGC GAA AUAUAUAG | 8538 | CUAUAUAUU CUCUGCUC | 1396 |
| 7630 | AGAGCAGA CUGAUGA GCCGUUAGGC GAA AAUAUAUA | 8539 | UAUAUAUUC UCUGCUCU | 1397 |
| 7632 | AAAGAGCA CUGAUGA GCCGUUAGGC GAA AGAAUAUA | 8540 | UAUAUUCUC UGCUCUUU | 1398 |
| 7637 | AAUACAAA CUGAUGA GCCGUUAGGC GAA AGCAGAGA | 8541 | UCUCUGCUC UUUGUAUU | 1399 |
| 7639 | AGAAUACA CUGAUGA GCCGUUAGGC GAA AGAGCAGA | 8542 | UCUGCUCUU UGUAUUCU | 1400 |
| 7640 | GAGAAUAC CUGAUGA GCCGUUAGGC GAA AAGAGCAG | 8543 | CUGCUCUUU GUAUUCUC | 1401 |
| 7643 | AAGGAGAA CUGAUGA GCCGUUAGGC GAA ACAAAGAG | 8544 | CUCUUUGUA UUCUCCUU | 1402 |
| 7645 | CAAAGGAG CUGAUGA GCCGUUAGGC GAA AUACAAAG | 8545 | CUUUGUAUU CUCCUUUG | 1403 |
| 7646 | UCAAAGGA CUGAUGA GCCGUUAGGC GAA AAUACAAA | 8546 | UUUGUAUUC UCCUUUGA | 1404 |
| 7648 | GUUCAAAG CUGAUGA GCCGUUAGGC GAA AGAAUACA | 8547 | UGUAUUCUC CUUUGAAC | 1405 |
| 7651 | CGGGUUCA CUGAUGA GCCGUUAGGC GAA AGGAGAAU | 8548 | AUUCUCCUU UGAACCCG | 1406 |
| 7652 | ACGGGUUC CUGAUGA GCCGUUAGGC GAA AAGGAGAA | 8549 | UUCUCCUUU GAACCCGU | 1407 |
| 7661 | GAUGUUUU CUGAUGA GCCGUUAGGC GAA ACGGGUUC | 8550 | GAACCCGUU AAAACAUC | 1408 |
| 7662 | GGAUGUUU CUGAUGA GCCGUUAGGC GAA AACGGGUU | 8551 | AACCCGUUA AAACAUCC | 1409 |
| 7669 | UGCCACAG CUGAUGA GCCGUUAGGC GAA AUGUUUUA | 8552 | UAAAACAUC CUGUGGCA | 1410 |

Underlined region can be any X sequence or linker, as described herein.

117

**Table III: Human *flt*1 VEGF Receptor-Hairpin Ribozyme and Substrate sequence** 237.198

| nt. Position | HP Ribozyme Sequence | Rz Seq ID No. | Substrate | Seq ID No. |
|---|---|---|---|---|
| 16 | CGGGGAGG AGAA GAGAGG ACCAGAGAAACACACGUUGUGGUACAUUACCUGGUA | 8553 | CCUCUCG GCU CCUCCCCG | 1411 |
| 39 | CCGCUCCG AGAA GCCGCC ACCAGAGAAACACACGUUGUGGUACAUUACCUGGUA | 8554 | GGCGGCG GCU CGGAGCGG | 1412 |
| 180 | CCGCCAGA AGAA GUCCUC ACCAGAGAAACACACGUUGUGGUACAUUACCUGGUA | 8555 | GAGGACG GAC UCUGGCGG | 1413 |
| 190 | AACGACCC AGAA GCCAGA ACCAGAGAAACACACGUUGUGGUACAUUACCUGGUA | 8556 | UCUGGCG GCC GGGUCGUU | 1414 |
| 278 | GCGCGCAC AGAA GGACCC ACCAGAGAAACACACGUUGUGGUACAUUACCUGGUA | 8557 | GGGUCCU GCU GUGCGCGC | 1415 |
| 290 | GACAGCUG AGAA GCGCGC ACCAGAGAAACACACGUUGUGGUACAUUACCUGGUA | 8558 | GCGCGCU GCU CAGCUGUC | 1416 |
| 295 | AAGCAGAC AGAA GAGCAG ACCAGAGAAACACACGUUGUGGUACAUUACCUGGUA | 8559 | CUGCUCA GCU GUCUGCUU | 1417 |
| 298 | GAGAAGCA AGAA GCUGAG ACCAGAGAAACACACGUUGUGGUACAUUACCUGGUA | 8560 | CUCAGCU GUC UGCUUCUC | 1418 |
| 302 | CUGUGAGA AGAA GACAGC ACCAGAGAAACACACGUUGUGGUACAUUACCUGGUA | 8561 | GCUGUCU GCU UCUCACAG | 1419 |
| 420 | CAUUUAUG AGAA GCUUCC ACCAGAGAAACACACGUUGUGGUACAUUACCUGGUA | 8562 | GGAAGCA GCC CAUAAAUG | 1420 |
| 486 | CUUCCACA AGAA GAUUUA ACCAGAGAAACACACGUUGUGGUACAUUACCUGGUA | 8563 | UAAAUCU GCC UGUGGAAG | 1421 |
| 537 | UUUGCUUG AGAA GUGUUC ACCAGAGAAACACACGUUGUGGUACAUUACCUGGUA | 8564 | GAACACA GCU CAAGCAAA | 1422 |
| 565 | AUAUUUGC AGAA GUAGAA ACCAGAGAAACACACGUUGUGGUACAUUACCUGGUA | 8565 | UUCUACA GCU GCAAAUAU | 1423 |
| 721 | CGUAACCC AGAA GGGAAU ACCAGAGAAACACACGUUGUGGUACAUUACCUGGUA | 8566 | AUUCCCU GCC GGGUUACG | 1424 |
| 786 | CGUUUUCC AGAA GGGAUC ACCAGAGAAACACACGUUGUGGUACAUUACCUGGUA | 8567 | GAUCCCU GAU GGAAAACG | 1425 |
| 863 | CUUCACAG AGAA GAAGCC ACCAGAGAAACACACGUUGUGGUACAUUACCUGGUA | 8568 | GGCUUCU GAC CUGUGAAG | 1426 |
| 1056 | UUUUUUUC AGAA GGGUAA ACCAGAGAAACACACGUUGUGGUACAUUACCUGGUA | 8569 | UUACCCU GAU GAAAAAAA | 1427 |
| 1301 | GCCGGUAA AGAA GCUUGC ACCAGAGAAACACACGUUGUGGUACAUUACCUGGUA | 8570 | GCAAGCG GUC UUACCGGC | 1428 |
| 1310 | UCAUAGAG AGAA GGUAAG ACCAGAGAAACACACGUUGUGGUACAUUACCUGGUA | 8571 | CUUACCG GCU CUCUAUGA | 1429 |
| 1389 | AAAUAGCG AGAA GAUUUC ACCAGAGAAACACACGUUGUGGUACAUUACCUGGUA | 8572 | GAAAUCU GCU CGCUAUUU | 1430 |
| 1535 | UUUCGUAA AGAA GGGGUU ACCAGAGAAACACACGUUGUGGUACAUUACCUGGUA | 8573 | AACCCCA GAU UUACGAAA | 1431 |
| 1566 | AGAGCCGG AGAA GGAAAC ACCAGAGAAACACACGUUGUGGUACAUUACCUGGUA | 8574 | GUUUCCA GAC CCGGCUCU | 1432 |
| 1572 | GGGUAGAG AGAA GGGUCU ACCAGAGAAACACACGUUGUGGUACAUUACCUGGUA | 8575 | AGACCCG GCU CUCUACCC | 1433 |
| 1604 | CGGUACAA AGAA GGAUUU ACCAGAGAAACACACGUUGUGGUACAUUACCUGGUA | 8576 | AAAUCCU GAC UUGUACCG | 1434 |
| 1824 | AUUCUAGA AGAA GCCACA ACCAGAGAAACACACGUUGUGGUACAUUACCUGGUA | 8577 | UGUGGCU GAC UCUAGAAU | 1435 |
| 1908 | UUUGGCAC AGAA GUGAUA ACCAGAGAAACACACGUUGUGGUACAUUACCUGGUA | 8578 | UAUCACA GAU GUGCCAAA | 1436 |
| 1949 | CUCCUUCC AGAA GCAUUU ACCAGAGAAACACACGUUGUGGUACAUUACCUGGUA | 8579 | AAAUGCC GAC GGAAGGAG | 1437 |
| 1973 | CUGUGCAA AGAA GUUUCA ACCAGAGAAACACACGUUGUGGUACAUUACCUGGUA | 8580 | UGAAACU GUC UUGCACAG | 1438 |
| 2275 | AGUGGUGG AGAA GCUGAU ACCAGAGAAACACACGUUGUGGUACAUUACCUGGUA | 8581 | AUCAGCA GUU CCACCACU | 1439 |
| 2321 | ACCAAGUG AGAA GAGGCU ACCAGAGAAACACACGUUGUGGUACAUUACCUGGUA | 8582 | AGCCUCA GAU CACUUGGU | 1440 |
| 2396 | UUUCAAUA AGAA GCGUGC ACCAGAGAAACACACGUUGUGGUACAUUACCUGGUA | 8583 | GCACGCU GUU UAUUGAAA | 1441 |
| 2490 | GUUCCUUG AGAA GUGAGG ACCAGAGAAACACACGUUGUGGUACAUUACCUGGUA | 8584 | CCUCACU GUU CAAGGAAC | 1442 |

| | | | | |
|---|---|---|---|---|
| 2525 | UUAGAGUG AGAA GCUCCA ACCAGAGAAACACACGUUGUGGUACAUUACCUGGUA | 8585 | UGGAGCU GAU CACUCUAA | 1443 |
| 2625 | GAUAGGUA AGAA GUCUUU ACCAGAGAAACACACGUUGUGGUACAUUACCUGGUA | 8586 | AAAGACU GAC UACCUAUC | 1444 |
| 2652 | GGAACUUC AGAA GGGUCC ACCAGAGAAACACACGUUGUGGUACAUUACCUGGUA | 8587 | GGACCCA GAU GAAGUUCC | 1445 |
| 2684 | CAUAAGGG AGAA GCUCAC ACCAGAGAAACACACGUUGUGGUACAUUACCUGGUA | 8588 | GUGAGCG GCU CCCUUAUG | 1446 |
| 2816 | CAGCCACA AGAA GGCACG ACCAGAGAAACACACGUUGUGGUACAUUACCUGGUA | 8589 | CGUGCCG GAC UGUGGCUG | 1447 |
| 2873 | GCUCAGUC AGAA GAGCUU ACCAGAGAAACACACGUUGUGGUACAUUACCUGGUA | 8590 | AAGCUCU GAU GACUGAGC | 1448 |
| 2930 | AGGCUCCC AGAA GGUUAA ACCAGAGAAACACACGUUGUGGUACAUUACCUGGUA | 8591 | UUAACCU GCU GGGAGCCU | 1449 |
| 2963 | CAAUCACC AGAA GAGGCC ACCAGAGAAACACACGUUGUGGUACAUUACCUGGUA | 8592 | GGCCUCU GAU GGUGAUUG | 1450 |
| 3157 | UUCCUGAA AGAA GGAGCU ACCAGAGAAACACACGUUGUGGUACAUUACCUGGUA | 8593 | AGCUCCG GCU UUCAGGAA | 1451 |
| 3207 | UAGAAACC AGAA GAAUCC ACCAGAGAAACACACGUUGUGGUACAUUACCUGGUA | 8594 | GGAUUCU GAC GGUUUCUA | 1452 |
| 3211 | CUUGUAGA AGAA GUCAGA ACCAGAGAAACACACGUUGUGGUACAUUACCUGGUA | 8595 | UCUGACG GUU UCUACAAG | 1453 |
| 3245 | UGUAAGAA AGAA GAUCUU ACCAGAGAAACACACGUUGUGGUACAUUACCUGGUA | 8596 | AAGAUCU GAU UUCUUACA | 1454 |
| 3256 | CACUUGAA AGAA GUAAGA ACCAGAGAAACACACGUUGUGGUACAUUACCUGGUA | 8597 | UCUUACA GUU UUCAAGUG | 1455 |
| 3287 | UUCUGGAA AGAA GGAACU ACCAGAGAAACACACGUUGUGGUACAUUACCUGGUA | 8598 | AGUUCCU GUC UUCCAGAA | 1456 |
| 3402 | CUCACAUA AGAA GGGUUC ACCAGAGAAACACACGUUGUGGUACAUUACCUGGUA | 8599 | GAACCCC GAU UAUGUGAG | 1457 |
| 3580 | CCUCAGGC AGAA GCAAAA ACCAGAGAAACACACGUUGUGGUACAUUACCUGGUA | 8600 | UUUUGCA GUC GCCUGAGG | 1458 |
| 3641 | CCAGCAUG AGAA GAUAGA ACCAGAGAAACACACGUUGUGGUACAUUACCUGGUA | 8601 | UCUAUCA GAU CAUGCUGG | 1459 |
| 3655 | UCUGUGCC AGAA GUCCAG ACCAGAGAAACACACGUUGUGGUACAUUACCUGGUA | 8602 | CUGGACU GCU GGCACAGA | 1460 |
| 3810 | UCAGAGAA AGAA GGAGUU ACCAGAGAAACACACGUUGUGGUACAUUACCUGGUA | 8603 | AACUCCU GCC UUCUCUGA | 1461 |
| 3846 | AACUUCGG AGAA GAAAUA ACCAGAGAAACACACGUUGUGGUACAUUACCUGGUA | 8604 | UAUUUCA GCU CCGAAGUU | 1462 |
| 3873 | CUGACAUC AGAA GAGCUU ACCAGAGAAACACACGUUGUGGUACAUUACCUGGUA | 8605 | AAGCUCU GAU GAUGUCAG | 1463 |
| 3995 | GAGAGGCC AGAA GAGUGC ACCAGAGAAACACACGUUGUGGUACAUUACCUGGUA | 8606 | GCACUCU GUU GGCCUCUC | 1464 |
| 4100 | UGACAUCA AGAA GCCCCG ACCAGAGAAACACACGUUGUGGUACAUUACCUGGUA | 8607 | CGGGGCU GUC UGAUGUCA | 1465 |
| 4104 | CUGCUGAC AGAA GACAGC ACCAGAGAAACACACGUUGUGGUACAUUACCUGGUA | 8608 | GCUGUCU GAU GUCAGCAG | 1466 |
| 4120 | AUGGCAGA AGAA GGGCCU ACCAGAGAAACACACGUUGUGGUACAUUACCUGGUA | 8609 | AGGCCCA GUU UCUGCCAU | 1467 |
| 4135 | GUGCCCAC AGAA GGAAUG ACCAGAGAAACACACGUUGUGGUACAUUACCUGGUA | 8610 | CAUUCCA GCU GUGGGCAC | 1468 |
| 4210 | GGGCGGGG AGAA GCACGC ACCAGAGAAACACACGUUGUGGUACAUUACCUGGUA | 8611 | GCGUGCU GCU CCCCGCCC | 1469 |
| 4217 | AGUCUGGG AGAA GGGAGC ACCAGAGAAACACACGUUGUGGUACAUUACCUGGUA | 8612 | GCUCCCC GCC CCCAGACU | 1470 |
| 4224 | GAGUUGUA AGAA GGGGGC ACCAGAGAAACACACGUUGUGGUACAUUACCUGGUA | 8613 | GCCCCCA GAC UACAACUC | 1471 |
| 4382 | CAAAAAGC AGAA GGCUCC ACCAGAGAAACACACGUUGUGGUACAUUACCUGGUA | 8614 | GGAGCCA GCU GCUUUUUG | 1472 |
| 4385 | UCACAAAA AGAA GCUGGC ACCAGAGAAACACACGUUGUGGUACAUUACCUGGUA | 8615 | GCCAGCU GCU UUUUGUGA | 1473 |
| 4537 | GGGGUUGG AGAA GGGAAG ACCAGAGAAACACACGUUGUGGUACAUUACCUGGUA | 8616 | CUUCCCU GCU CCAACCCC | 1474 |
| 4573 | CUCAAUCA AGAA GGUCCU ACCAGAGAAACACACGUUGUGGUACAUUACCUGGUA | 8617 | AGGACCA GUU UGAUUGAG | 1475 |
| 4594 | AUUGGGUG AGAA GUGCAG ACCAGAGAAACACACGUUGUGGUACAUUACCUGGUA | 8618 | CUGCACU GAU CACCCAAU | 1476 |
| 4628 | GGCUGCAG AGAA GGCCCA ACCAGAGAAACACACGUUGUGGUACAUUACCUGGUA | 8619 | UGGGCCA GCC CUGCAGCC | 1477 |
| 4636 | GGGUUUUG AGAA GCAGGG ACCAGAGAAACACACGUUGUGGUACAUUACCUGGUA | 8620 | CCCUGCA GCC CAAAACCC | 1478 |

| | | | | |
|---|---|---|---|---|
| 4866 | AGGGUCAG AGAA GGGAAG ACCAGAGAAACACACGUUGUGGUACAUUACCUGGUA | 8621 | CUUCCCA GCU CUGACCCU | 1479 |
| 4871 | GUAGAAGG AGAA GAGCUG ACCAGAGAAACACACGUUGUGGUACAUUACCUGGUA | 8622 | CAGCUCU GAC CCUUCUAC | 1480 |
| 4905 | CGCUGUCC AGAA GCUCCU ACCAGAGAAACACACGUUGUGGUACAUUACCUGGUA | 8623 | AGGAGCA GAU GGACAGCG | 1481 |
| 5233 | CUGUGCAA AGAA GAAUAA ACCAGAGAAACACACGUUGUGGUACAUUACCUGGUA | 8624 | UUAUUCU GUU UUGCACAG | 1482 |
| 5281 | CUCCUCAG AGAA GCAUUU ACCAGAGAAACACACGUUGUGGUACAUUACCUGGUA | 8625 | AAAUGCA GUC CUGAGGAG | 1483 |
| 5319 | UUUCCUCC AGAA GCCCUC ACCAGAGAAACACACGUUGUGGUACAUUACCUGGUA | 8626 | GAGGGCU GAU GGAGGAAA | 1484 |
| 5358 | GGUAUAGA AGAA GGGUCU ACCAGAGAAACACACGUUGUGGUACAUUACCUGGUA | 8627 | AGACCCC GUC UCUAUACC | 1485 |
| 5392 | UGGGUCCC AGAA GUGUUG ACCAGAGAAACACACGUUGUGGUACAUUACCUGGUA | 8628 | CAACACA GUU GGGACCCA | 1486 |
| 5563 | UGAGUCCC AGAA GGAGAA ACCAGAGAAACACACGUUGUGGUACAUUACCUGGUA | 8629 | UUCUCCA GUU GGGACUCA | 1487 |
| 5622 | AGUUUCAA AGAA GUUGAA ACCAGAGAAACACACGUUGUGGUACAUUACCUGGUA | 8630 | UUCAACU GCU UUGAAACU | 1488 |
| 5738 | UAGCAUCA AGAA GAGCCA ACCAGAGAAACACACGUUGUGGUACAUUACCUGGUA | 8631 | UGGCUCU GUU UGAUGCUA | 1489 |
| 5838 | UAGCAUCA AGAA GAGCCA ACCAGAGAAACACACGUUGUGGUACAUUACCUGGUA | 8631 | UGGCUCU GUU UGAUGCUA | 1489 |
| 5933 | CCCCAAGA AGAA GCAAUC ACCAGAGAAACACACGUUGUGGUACAUUACCUGGUA | 8632 | GAUUGCU GCU UCUUGGGG | 1490 |
| 6022 | CACAUAAG AGAA GAGGCA ACCAGAGAAACACACGUUGUGGUACAUUACCUGGUA | 8633 | UGCCUCU GUU CUUAUGUG | 1491 |
| 6120 | UCCACAAA AGAA GCUGCC ACCAGAGAAACACACGUUGUGGUACAUUACCUGGUA | 8634 | GGCAGCG GCU UUUGUGGA | 1492 |
| 6163 | GUGGAGAG AGAA GUCCCA ACCAGAGAAACACACGUUGUGGUACAUUACCUGGUA | 8635 | UGGGACA GUC CUCUCCAC | 1493 |
| 6270 | AAAUUGCC AGAA GUCACA ACCAGAGAAACACACGUUGUGGUACAUUACCUGGUA | 8636 | UGUGACA GCU GGCAAUUU | 1494 |
| 6412 | AAGACAUG AGAA GCUAAG ACCAGAGAAACACACGUUGUGGUACAUUACCUGGUA | 8637 | CUUAGCU GUU CAUGUCUU | 1495 |
| 6511 | UUUGAAGG AGAA GAGUAA ACCAGAGAAACACACGUUGUGGUACAUUACCUGGUA | 8638 | UUACUCA GCU CCUUCAAA | 1496 |
| 6778 | UCCACCCA AGAA GUUCCA ACCAGAGAAACACACGUUGUGGUACAUUACCUGGUA | 8639 | UGGAACA GUC UGGGUGGA | 1497 |
| 6826 | ACUUCUUG AGAA GACAAG ACCAGAGAAACACACGUUGUGGUACAUUACCUGGUA | 8640 | CUUGUCA GUC CAAGAAGU | 1498 |
| 7245 | AACAUAAA AGAA GUUGCC ACCAGAGAAACACACGUUGUGGUACAUUACCUGGUA | 8641 | GGCAACU GCU UUUAUGUU | 1499 |
| 7258 | UGGAAGGA AGAA GAACAU ACCAGAGAAACACACGUUGUGGUACAUUACCUGGUA | 8642 | AUGUUCU GUC UCCUUCCA | 1500 |
| 7433 | CCCAUACA AGAA GCUAAA ACCAGAGAAACACACGUUGUGGUACAUUACCUGGUA | 8643 | UUUAGCU GAU UGUAUGGG | 1501 |
| 7512 | UUUUCAUG AGAA GGAAUU ACCAGAGAAACACACGUUGUGGUACAUUACCUGGUA | 8644 | AAUUCCU GUC CAUGAAAA | 1502 |
| 7606 | GACAUUCA AGAA GAAAUG ACCAGAGAAACACACGUUGUGGUACAUUACCUGGUA | 8645 | CAUUUCA GCC UGAAUGUC | 1503 |
| 7618 | AAUAUAUA AGAA GACAUU ACCAGAGAAACACACGUUGUGGUACAUUACCUGGUA | 8646 | AAUGUCU GCC UAUAUAUU | 1504 |
| 7633 | AUACAAAG AGAA GAGAAU ACCAGAGAAACACACGUUGUGGUACAUUACCUGGUA | 8647 | AUUCUCU GCU CUUUGUAU | 1505 |

Table IV: Human KDR VEGF Receptor-Hammerhead Ribozyme and Substrate Sequence 237.198

| nt. Position | HH Ribozyme Sequence | Seq ID No. | Substrate | Rz Seq ID No. |
|---|---|---|---|---|
| 21 | CACAGGGC CUGAUGA GCCGUUAGGC GAA ACGGCCAG | 8648 | CUGGCCGUC GCCCUGUG | 1506 |
| 33 | UCCACGCA CUGAUGA GCCGUUAGGC GAA AGCCACAG | 8649 | CUGUGGCUC UGCGUGGA | 1507 |
| 56 | AACCCACA CUGAUGA GCCGUUAGGC GAA AGGCGGCC | 8650 | GGCCGCCUC UGUGGGUU | 1508 |
| 64 | ACUAGGCA CUGAUGA GCCGUUAGGC GAA ACCCACAG | 8651 | CUGUGGGUU UGCCUAGU | 1509 |
| 65 | CACUAGGC CUGAUGA GCCGUUAGGC GAA AACCCACA | 8652 | UGUGGGUUU GCCUAGUG | 1510 |
| 70 | AGAAACAC CUGAUGA GCCGUUAGGC GAA AGGCAAAC | 8653 | GUUUGCCUA GUGUUUCU | 1511 |
| 75 | UCAAGAGA CUGAUGA GCCGUUAGGC GAA ACACUAGG | 8654 | CCUAGUGUU UCUCUUGA | 1512 |
| 76 | AUCAAGAG CUGAUGA GCCGUUAGGC GAA AACACUAG | 8655 | CUAGUGUUU CUCUUGAU | 1513 |
| 77 | GAUCAAGA CUGAUGA GCCGUUAGGC GAA AAACACUA | 8656 | UAGUGUUUC UCUUGAUC | 1514 |
| 79 | CAGAUCAA CUGAUGA GCCGUUAGGC GAA AGAAACAC | 8657 | GUGUUUCUC UUGAUCUG | 1515 |
| 81 | GGCAGAUC CUGAUGA GCCGUUAGGC GAA AGAGAAAC | 8658 | GUUUCUCUU GAUCUGCC | 1516 |
| 85 | CCUGGGCA CUGAUGA GCCGUUAGGC GAA AUCAAGAG | 8659 | CUCUUGAUC UGCCCAGG | 1517 |
| 96 | UGUAUGCU CUGAUGA GCCGUUAGGC GAA AGCCUGGG | 8660 | CCCAGGCUC AGCAUACA | 1518 |
| 102 | UCUUUUUG CUGAUGA GCCGUUAGGC GAA AUGCUGAG | 8661 | CUCAGCAUA CAAAAAGA | 1519 |
| 114 | AUUGUAAG CUGAUGA GCCGUUAGGC GAA AUGUCUUU | 8662 | AAAGACAUA CUUACAAU | 1520 |
| 117 | UUAAUUGU CUGAUGA GCCGUUAGGC GAA AGUAUGUC | 8663 | GACAUACUU ACAAUUAA | 1521 |
| 118 | CUUAAUUG CUGAUGA GCCGUUAGGC GAA AAGUAUGU | 8664 | ACAUACUUA CAAUUAAG | 1522 |
| 123 | UUAGCCUU CUGAUGA GCCGUUAGGC GAA AUUGUAAG | 8665 | CUUACAAUU AAGGCUAA | 1523 |
| 124 | AUUAGCCU CUGAUGA GCCGUUAGGC GAA AAUUGUAA | 8666 | UUACAAUUA AGGCUAAU | 1524 |
| 130 | AGUUGUAU CUGAUGA GCCGUUAGGC GAA AGCCUUAA | 8667 | UUAAGGCUA AUACAACU | 1525 |
| 133 | AAGAGUUG CUGAUGA GCCGUUAGGC GAA AUUAGCCU | 8668 | AGGCUAAUA CAACUCUU | 1526 |
| 139 | AAUUUGAA CUGAUGA GCCGUUAGGC GAA AGUUGUAU | 8669 | AUACAACUC UUCAAAUU | 1527 |
| 141 | GUAAUUUG CUGAUGA GCCGUUAGGC GAA AGAGUUGU | 8670 | ACAACUCUU CAAAUUAC | 1528 |
| 142 | AGUAAUUU CUGAUGA GCCGUUAGGC GAA AAGAGUUG | 8671 | CAACUCUUC AAAUUACU | 1529 |
| 147 | CUGCAAGU CUGAUGA GCCGUUAGGC GAA AUUUGAAG | 8672 | CUUCAAAUU ACUUGCAG | 1530 |
| 148 | CCUGCAAG CUGAUGA GCCGUUAGGC GAA AAUUUGAA | 8673 | UUCAAAUUA CUUGCAGG | 1531 |
| 151 | UCCCCUGC CUGAUGA GCCGUUAGGC GAA AGUAAUUU | 8674 | AAAUUACUU GCAGGGGA | 1532 |
| 170 | GCCAGUCC CUGAUGA GCCGUUAGGC GAA AGUCCCUC | 8675 | GAGGGACUU GGACUGGC | 1533 |
| 180 | UUGGGCCA CUGAUGA GCCGUUAGGC GAA AGCCAGUC | 8676 | GACUGGCUU UGGCCCAA | 1534 |
| 181 | AUUGGGCC CUGAUGA GCCGUUAGGC GAA AAGCCAGU | 8677 | ACUGGCUUU GGCCCAAU | 1535 |
| 190 | ACUCUGAU CUGAUGA GCCGUUAGGC GAA AUUGGGCC | 8678 | GGCCCAAUA AUCAGAGU | 1536 |

121

| | | | | |
|---|---|---|---|---|
| 193 | GCCACUCU CUGAUGA GCCGUUAGGC GAA AUUAUUGG | 8679 | CCAAUAAUC AGAGUGGC | 1537 |
| 243 | UUACAGAA CUGAUGA GCCGUUAGGC GAA AGGCCAUC | 8680 | GAUGGCCUC UUCUGUAA | 1538 |
| 245 | UCUUACAG CUGAUGA GCCGUUAGGC GAA AGAGGCCA | 8681 | UGGCCUCUU CUGUAAGA | 1539 |
| 246 | GUCUUACA CUGAUGA GCCGUUAGGC GAA AAGAGGCC | 8682 | GGCCUCUUC UGUAAGAC | 1540 |
| 250 | GAGUGUCU CUGAUGA GCCGUUAGGC GAA ACAGAAGA | 8683 | UCUUCUGUA AGACACUC | 1541 |
| 258 | GGAAUUGU CUGAUGA GCCGUUAGGC GAA AGUGUCUU | 8684 | AAGACACUC ACAAUUCC | 1542 |
| 264 | ACUUUUGG CUGAUGA GCCGUUAGGC GAA AUUGUGAG | 8685 | CUCACAAUU CCAAAAGU | 1543 |
| 265 | CACUUUUG CUGAUGA GCCGUUAGGC GAA AAUUGUGA | 8686 | UCACAAUUC CAAAAGUG | 1544 |
| 276 | UCAUUUCC CUGAUGA GCCGUUAGGC GAA AUCACUUU | 8687 | AAAGUGAUC GGAAAUGA | 1545 |
| 296 | AGCACUUG CUGAUGA GCCGUUAGGC GAA AGGCUCCA | 8688 | UGGAGCCUA CAAGUGCU | 1546 |
| 305 | CCCGGUAG CUGAUGA GCCGUUAGGC GAA AGCACUUG | 8689 | CAAGUGCUU CUACCGGG | 1547 |
| 306 | UCCCGGUA CUGAUGA GCCGUUAGGC GAA AAGCACUU | 8690 | AAGUGCUUC UACCGGGA | 1548 |
| 308 | UUUCCCGG CUGAUGA GCCGUUAGGC GAA AGAAGCAC | 8691 | GUGCUUCUA CCGGGAAA | 1549 |
| 323 | CCGAGGCC CUGAUGA GCCGUUAGGC GAA AGUCAGUU | 8692 | AACUGACUU GGCCUCGG | 1550 |
| 329 | AAAUGACC CUGAUGA GCCGUUAGGC GAA AGGCCAAG | 8693 | CUUGGCCUC GGUCAUUU | 1551 |
| 333 | ACAUAAAU CUGAUGA GCCGUUAGGC GAA ACCGAGGC | 8694 | GCCUCGGUC AUUUAUGU | 1552 |
| 336 | UAGACAUA CUGAUGA GCCGUUAGGC GAA AUGACCGA | 8695 | UCGGUCAUU UAUGUCUA | 1553 |
| 337 | AUAGACAU CUGAUGA GCCGUUAGGC GAA AAUGACCG | 8696 | CGGUCAUUU AUGUCUAU | 1554 |
| 338 | CAUAGACA CUGAUGA GCCGUUAGGC GAA AAAUGACC | 8697 | GGUCAUUUA UGUCUAUG | 1555 |
| 342 | UGAACAUA CUGAUGA GCCGUUAGGC GAA ACAUAAAU | 8698 | AUUUAUGUC UAUGUUCA | 1556 |
| 344 | CUUGAACA CUGAUGA GCCGUUAGGC GAA AGACAUAA | 8699 | UUAUGUCUA UGUUCAAG | 1557 |
| 348 | UAAUCUUG CUGAUGA GCCGUUAGGC GAA ACAUAGAC | 8700 | GUCUAUGUU CAAGAUUA | 1558 |
| 349 | GUAAUCUU CUGAUGA GCCGUUAGGC GAA AACAUAGA | 8701 | UCUAUGUUC AAGAUUAC | 1559 |
| 355 | AGAUCUGU CUGAUGA GCCGUUAGGC GAA AUCUUGAA | 8702 | UUCAAGAUU ACAGAUCU | 1560 |
| 356 | GAGAUCUG CUGAUGA GCCGUUAGGC GAA AAUCUUGA | 8703 | UCAAGAUUA CAGAUCUC | 1561 |
| 362 | UAAAUGGA CUGAUGA GCCGUUAGGC GAA AUCUGUAA | 8704 | UUACAGAUC UCCAUUUA | 1562 |
| 364 | AAUAAAUG CUGAUGA GCCGUUAGGC GAA AGAUCUGU | 8705 | ACAGAUCUC CAUUUAUU | 1563 |
| 368 | AAGCAAUA CUGAUGA GCCGUUAGGC GAA AUGGAGAU | 8706 | AUCUCCAUU UAUUGCUU | 1564 |
| 369 | GAAGCAAU CUGAUGA GCCGUUAGGC GAA AAUGGAGA | 8707 | UCUCCAUUU AUUGCUUC | 1565 |
| 370 | AGAAGCAA CUGAUGA GCCGUUAGGC GAA AAAUGGAG | 8708 | CUCCAUUUA UUGCUUCU | 1566 |
| 372 | ACAGAAGC CUGAUGA GCCGUUAGGC GAA AUAAAUGG | 8709 | CCAUUUAUU GCUUCUGU | 1567 |
| 376 | ACUAACAG CUGAUGA GCCGUUAGGC GAA AGCAAUAA | 8710 | UUAUUGCUU CUGUUAGU | 1568 |
| 377 | CACUAACA CUGAUGA GCCGUUAGGC GAA AAGCAAUA | 8711 | UAUUGCUUC UGUUAGUG | 1569 |
| 381 | UGGUCACU CUGAUGA GCCGUUAGGC GAA ACAGAAGC | 8712 | GCUUCUGUU AGUGACCA | 1570 |
| 382 | UUGGUCAC CUGAUGA GCCGUUAGGC GAA AACAGAAG | 8713 | CUUCUGUUA GUGACCAA | 1571 |

| | | | | |
|---|---|---|---|---|
| 399 | AUGUACAC CUGAUGA GCCGUUAGGC GAA ACUCCAUG | 8714 | CAUGGAGUC GUGUACAU | 1572 |
| 404 | CAGUAAUG CUGAUGA GCCGUUAGGC GAA ACACGACU | 8715 | AGUCGUGUA CAUUACUG | 1573 |
| 408 | UUCUCAGU CUGAUGA GCCGUUAGGC GAA AUGUACAC | 8716 | GUGUACAUU ACUGAGAA | 1574 |
| 409 | GUUCUCAG CUGAUGA GCCGUUAGGC GAA AAUGUACA | 8717 | UGUACAUUA CUGAGAAC | 1575 |
| 438 | AGACAUGG CUGAUGA GCCGUUAGGC GAA AUCACCAC | 8718 | GUGGUGAUU CCAUGUCU | 1576 |
| 439 | GAGACAUG CUGAUGA GCCGUUAGGC GAA AAUCACCA | 8719 | UGGUGAUUC CAUGUCUC | 1577 |
| 445 | GGACCCGA CUGAUGA GCCGUUAGGC GAA ACAUGGAA | 8720 | UUCCAUGUC UCGGGUCC | 1578 |
| 447 | AUGGACCC CUGAUGA GCCGUUAGGC GAA AGACAUGG | 8721 | CCAUGUCUC GGGUCCAU | 1579 |
| 452 | UUGAAAUG CUGAUGA GCCGUUAGGC GAA ACCCGAGA | 8722 | UCUCGGGUC CAUUUCAA | 1580 |
| 456 | AGAUUUGA CUGAUGA GCCGUUAGGC GAA AUGGACCC | 8723 | GGGUCCAUU UCAAAUCU | 1581 |
| 457 | GAGAUUUG CUGAUGA GCCGUUAGGC GAA AAUGGACC | 8724 | GGUCCAUUU CAAAUCUC | 1582 |
| 458 | UGAGAUUU CUGAUGA GCCGUUAGGC GAA AAAUGGAC | 8725 | GUCCAUUUC AAAUCUCA | 1583 |
| 463 | CACGUUGA CUGAUGA GCCGUUAGGC GAA AUUUGAAA | 8726 | UUUCAAAUC UCAACGUG | 1584 |
| 465 | GACACGUU CUGAUGA GCCGUUAGGC GAA AGAUUUGA | 8727 | UCAAAUCUC AACGUGUC | 1585 |
| 473 | CACAAAGU CUGAUGA GCCGUUAGGC GAA ACACGUUG | 8728 | CAACGUGUC ACUUUGUG | 1586 |
| 477 | CUUGCACA CUGAUGA GCCGUUAGGC GAA AGUGACAC | 8729 | GUGUCACUU UGUGCAAG | 1587 |
| 478 | UCUUGCAC CUGAUGA GCCGUUAGGC GAA AAGUGACA | 8730 | UGUCACUUU GUGCAAGA | 1588 |
| 488 | UUUCUGGG CUGAUGA GCCGUUAGGC GAA AUCUUGCA | 8731 | UGCAAGAUA CCCAGAAA | 1589 |
| 503 | CAGGAACA CUGAUGA GCCGUUAGGC GAA AUCUCUUU | 8732 | AAAGAGAUU UGUUCCUG | 1590 |
| 504 | UCAGGAAC CUGAUGA GCCGUUAGGC GAA AAUCUCUU | 8733 | AAGAGAUUU GUUCCUGA | 1591 |
| 507 | CCAUCAGG CUGAUGA GCCGUUAGGC GAA ACAAAUCU | 8734 | AGAUUUGUU CCUGAUGG | 1592 |
| 508 | ACCAUCAG CUGAUGA GCCGUUAGGC GAA AACAAAUC | 8735 | GAUUUGUUC CUGAUGGU | 1593 |
| 517 | AAUUCUGU CUGAUGA GCCGUUAGGC GAA ACCAUCAG | 8736 | CUGAUGGUA ACAGAAUU | 1594 |
| 525 | UCCCAGGA CUGAUGA GCCGUUAGGC GAA AUUCUGUU | 8737 | AACAGAAUU UCCUGGGA | 1595 |
| 526 | GUCCCAGG CUGAUGA GCCGUUAGGC GAA AAUUCUGU | 8738 | ACAGAAUUU CCUGGGAC | 1596 |
| 527 | UGUCCCAG CUGAUGA GCCGUUAGGC GAA AAAUUCUG | 8739 | CAGAAUUUC CUGGGACA | 1597 |
| 548 | GAAUAGUA CUGAUGA GCCGUUAGGC GAA AGCCCUUC | 8740 | GAAGGGCUU UACUAUUC | 1598 |
| 549 | GGAAUAGU CUGAUGA GCCGUUAGGC GAA AAGCCCUU | 8741 | AAGGGCUUU ACUAUUCC | 1599 |
| 550 | GGGAAUAG CUGAUGA GCCGUUAGGC GAA AAAGCCCU | 8742 | AGGGCUUUA CUAUUCCC | 1600 |
| 553 | GCUGGGAA CUGAUGA GCCGUUAGGC GAA AGUAAAGC | 8743 | GCUUUACUA UUCCCAGC | 1601 |
| 555 | UAGCUGGG CUGAUGA GCCGUUAGGC GAA AUAGUAAA | 8744 | UUUACUAUU CCCAGCUA | 1602 |
| 556 | GUAGCUGG CUGAUGA GCCGUUAGGC GAA AAUAGUAA | 8745 | UUACUAUUC CCAGCUAC | 1603 |
| 563 | UGAUCAUG CUGAUGA GCCGUUAGGC GAA AGCUGGGA | 8746 | UCCCAGCUA CAUGAUCA | 1604 |
| 570 | GCAUAGCU CUGAUGA GCCGUUAGGC GAA AUCAUGUA | 8747 | UACAUGAUC AGCUAUGC | 1605 |
| 575 | UGCCAGCA CUGAUGA GCCGUUAGGC GAA AGCUGAUC | 8748 | GAUCAGCUA UGCUGGCA | 1606 |

123

| | | | | |
|---|---|---|---|---|
| 588 | UCACAGAA CUGAUGA GCCGUUAGGC GAA ACCAUGCC | 8749 | GGCAUGGUC UUCUGUGA | 1607 |
| 590 | CUUCACAG CUGAUGA GCCGUUAGGC GAA AGACCAUG | 8750 | CAUGGUCUU CUGUGAAG | 1608 |
| 591 | GCUUCACA CUGAUGA GCCGUUAGGC GAA AAGACCAU | 8751 | AUGGUCUUC UGUGAAGC | 1609 |
| 606 | UCAUCAUU CUGAUGA GCCGUUAGGC GAA AUUUUUGC | 8752 | GCAAAAAUU AAUGAUGA | 1610 |
| 607 | UUCAUCAU CUGAUGA GCCGUUAGGC GAA AAUUUUUG | 8753 | CAAAAAUUA AUGAUGAA | 1611 |
| 619 | AGACUGGU CUGAUGA GCCGUUAGGC GAA ACUUUCAU | 8754 | AUGAAAGUU ACCAGUCU | 1612 |
| 620 | UAGACUGG CUGAUGA GCCGUUAGGC GAA AACUUUCA | 8755 | UGAAAGUUA CCAGUCUA | 1613 |
| 626 | ACAUAAUA CUGAUGA GCCGUUAGGC GAA ACUGGUAA | 8756 | UUACCAGUC UAUUAUGU | 1614 |
| 628 | GUACAUAA CUGAUGA GCCGUUAGGC GAA AGACUGGU | 8757 | ACCAGUCUA UUAUGUAC | 1615 |
| 630 | AUGUACAU CUGAUGA GCCGUUAGGC GAA AUAGACUG | 8758 | CAGUCUAUU AUGUACAU | 1616 |
| 631 | UAUGUACA CUGAUGA GCCGUUAGGC GAA AAUAGACU | 8759 | AGUCUAUUA UGUACAUA | 1617 |
| 635 | CAACUAUG CUGAUGA GCCGUUAGGC GAA ACAUAAUA | 8760 | UAUUAUGUA CAUAGUUG | 1618 |
| 639 | ACGACAAC CUGAUGA GCCGUUAGGC GAA AUGUACAU | 8761 | AUGUACAUA GUUGUCGU | 1619 |
| 642 | ACAACGAC CUGAUGA GCCGUUAGGC GAA ACUAUGUA | 8762 | UACAUAGUU GUCGUUGU | 1620 |
| 645 | CCUACAAC CUGAUGA GCCGUUAGGC GAA ACAACUAU | 8763 | AUAGUUGUC GUUGUAGG | 1621 |
| 648 | UACCCUAC CUGAUGA GCCGUUAGGC GAA ACGACAAC | 8764 | GUUGUCGUU GUAGGGUA | 1622 |
| 651 | CUAUACCC CUGAUGA GCCGUUAGGC GAA ACAACGAC | 8765 | GUCGUUGUA GGGUAUAG | 1623 |
| 656 | AAAUCCUA CUGAUGA GCCGUUAGGC GAA ACCCUACA | 8766 | UGUAGGGUA UAGGAUUU | 1624 |
| 658 | AUAAAUCC CUGAUGA GCCGUUAGGC GAA AUACCCUA | 8767 | UAGGGUAUA GGAUUUAU | 1625 |
| 663 | ACAUCAUA CUGAUGA GCCGUUAGGC GAA AUCCUAUA | 8768 | UAUAGGAUU UAUGAUGU | 1626 |
| 664 | CACAUCAU CUGAUGA GCCGUUAGGC GAA AAUCCUAU | 8769 | AUAGGAUUU AUGAUGUG | 1627 |
| 665 | CCACAUCA CUGAUGA GCCGUUAGGC GAA AAAUCCUA | 8770 | UAGGAUUUA UGAUGUGG | 1628 |
| 675 | GGACUCAG CUGAUGA GCCGUUAGGC GAA ACCACAUC | 8771 | GAUGUGGUU CUGAGUCC | 1629 |
| 676 | CGGACUCA CUGAUGA GCCGUUAGGC GAA AACCACAU | 8772 | AUGUGGUUC UGAGUCCG | 1630 |
| 682 | AUGAGACG CUGAUGA GCCGUUAGGC GAA ACUCAGAA | 8773 | UUCUGAGUC CGUCUCAU | 1631 |
| 686 | UUCCAUGA CUGAUGA GCCGUUAGGC GAA ACGGACUC | 8774 | GAGUCCGUC UCAUGGAA | 1632 |
| 688 | AAUUCCAU CUGAUGA GCCGUUAGGC GAA AGACGGAC | 8775 | GUCCGUCUC AUGGAAUU | 1633 |
| 696 | GAUAGUUC CUGAUGA GCCGUUAGGC GAA AUUCCAUG | 8776 | CAUGGAAUU GAACUAUC | 1634 |
| 702 | CCAACAGA CUGAUGA GCCGUUAGGC GAA AGUUCAAU | 8777 | AUUGAACUA UCUGUUGG | 1635 |
| 704 | CUCCAACA CUGAUGA GCCGUUAGGC GAA AUAGUUCA | 8778 | UGAACUAUC UGUUGGAG | 1636 |
| 708 | UUUUCUCC CUGAUGA GCCGUUAGGC GAA ACAGAUAG | 8779 | CUAUCUGUU GGAGAAAA | 1637 |
| 720 | UUUAAGAC CUGAUGA GCCGUUAGGC GAA AGCUUUUC | 8780 | GAAAAGCUU GUCUUAAA | 1638 |
| 723 | CAAUUUAA CUGAUGA GCCGUUAGGC GAA ACAAGCUU | 8781 | AAGCUUGUC UUAAAUUG | 1639 |
| 725 | UACAAUUU CUGAUGA GCCGUUAGGC GAA AGACAAGC | 8782 | GCUUGUCUU AAAUUGUA | 1640 |
| 726 | GUACAAUU CUGAUGA GCCGUUAGGC GAA AAGACAAG | 8783 | CUUGUCUUA AAUUGUAC | 1641 |

124

| | | | | |
|---|---|---|---|---|
| 730 | UGCUGUAC CUGAUGA GCCGUUAGGC GAA AUUUAAGA | 8784 | UCUUAAAUU GUACAGCA | 1642 |
| 733 | UCUUGCUG CUGAUGA GCCGUUAGGC GAA ACAAUUUA | 8785 | UAAAUUGUA CAGCAAGA | 1643 |
| 750 | CCCACAUU CUGAUGA GCCGUUAGGC GAA AGUUCAGU | 8786 | ACUGAACUA AAUGUGGG | 1644 |
| 762 | UUGAAGUC CUGAUGA GCCGUUAGGC GAA AUCCCCAC | 8787 | GUGGGGAUU GACUUCAA | 1645 |
| 767 | CCCAGUUG CUGAUGA GCCGUUAGGC GAA AGUCAAUC | 8788 | GAUUGACUU CAACUGGG | 1646 |
| 768 | UCCCAGUU CUGAUGA GCCGUUAGGC GAA AAGUCAAU | 8789 | AUUGACUUC AACUGGGA | 1647 |
| 779 | AAGAAGGG CUGAUGA GCCGUUAGGC GAA AUUCCCAG | 8790 | CUGGGAAUA CCCUUCUU | 1648 |
| 784 | CUUCGAAG CUGAUGA GCCGUUAGGC GAA AGGGUAUU | 8791 | AAUACCCUU CUUCGAAG | 1649 |
| 785 | GCUUCGAA CUGAUGA GCCGUUAGGC GAA AAGGGUAU | 8792 | AUACCCUUC UUCGAAGC | 1650 |
| 787 | AUGCUUCG CUGAUGA GCCGUUAGGC GAA AGAAGGGU | 8793 | ACCCUUCUU CGAAGCAU | 1651 |
| 788 | GAUGCUUC CUGAUGA GCCGUUAGGC GAA AAGAAGGG | 8794 | CCCUUCUUC GAAGCAUC | 1652 |
| 796 | CUUAUGCU CUGAUGA GCCGUUAGGC GAA AUGCUUCG | 8795 | CGAAGCAUC AGCAUAAG | 1653 |
| 802 | AAGUUUCU CUGAUGA GCCGUUAGGC GAA AUGCUGAU | 8796 | AUCAGCAUA AGAAACUU | 1654 |
| 810 | CGGUUUAC CUGAUGA GCCGUUAGGC GAA AGUUUCUU | 8797 | AAGAAACUU GUAAACCG | 1655 |
| 813 | UCUCGGUU CUGAUGA GCCGUUAGGC GAA ACAAGUUU | 8798 | AAACUUGUA AACCGAGA | 1656 |
| 825 | UGGGUUUU CUGAUGA GCCGUUAGGC GAA AGGUCUCG | 8799 | CGAGACCUA AAAACCCA | 1657 |
| 836 | CACUCCCA CUGAUGA GCCGUUAGGC GAA ACUGGGUU | 8800 | AACCCAGUC UGGGAGUG | 1658 |
| 857 | UGCUCAAA CUGAUGA GCCGUUAGGC GAA AUUUCUUC | 8801 | GAAGAAAUU UUUGAGCA | 1659 |
| 858 | GUGCUCAA CUGAUGA GCCGUUAGGC GAA AAUUUCUU | 8802 | AAGAAAUUU UUGAGCAC | 1660 |
| 859 | GGUGCUCA CUGAUGA GCCGUUAGGC GAA AAAUUUCU | 8803 | AGAAAUUUU UGAGCACC | 1661 |
| 860 | AGGUGCUC CUGAUGA GCCGUUAGGC GAA AAAAUUUC | 8804 | GAAAUUUUU GAGCACCU | 1662 |
| 869 | CUAUAGUU CUGAUGA GCCGUUAGGC GAA AGGUGCUC | 8805 | GAGCACCUU AACUAUAG | 1663 |
| 870 | UCUAUAGU CUGAUGA GCCGUUAGGC GAA AAGGUGCU | 8806 | AGCACCUUA ACUAUAGA | 1664 |
| 874 | ACCAUCUA CUGAUGA GCCGUUAGGC GAA AGUUAAGG | 8807 | CCUUAACUA UAGAUGGU | 1665 |
| 876 | ACACCAUC CUGAUGA GCCGUUAGGC GAA AUAGUUAA | 8808 | UUAACUAUA GAUGGUGU | 1666 |
| 885 | CUCCGGGU CUGAUGA GCCGUUAGGC GAA ACACCAUC | 8809 | GAUGGUGUA ACCCGGAG | 1667 |
| 905 | AGGUGUAC CUGAUGA GCCGUUAGGC GAA AUCCUUGG | 8810 | CCAAGGAUU GUACACCU | 1668 |
| 908 | CACAGGUG CUGAUGA GCCGUUAGGC GAA ACAAUCCU | 8811 | AGGAUUGUA CACCUGUG | 1669 |
| 923 | GCCCACUG CUGAUGA GCCGUUAGGC GAA AUGCUGCA | 8812 | UGCAGCAUC CAGUGGGC | 1670 |
| 956 | CCCUGACA CUGAUGA GCCGUUAGGC GAA AUGUGCUG | 8813 | CAGCACAUU UGUCAGGG | 1671 |
| 957 | ACCCUGAC CUGAUGA GCCGUUAGGC GAA AAUGUGCU | 8814 | AGCACAUUU GUCAGGGU | 1672 |
| 960 | UGGACCCU CUGAUGA GCCGUUAGGC GAA ACAAAUGU | 8815 | ACAUUUGUC AGGGUCCA | 1673 |
| 966 | UUUUCAUG CUGAUGA GCCGUUAGGC GAA ACCCUGAC | 8816 | GUCAGGGUC CAUGAAAA | 1674 |
| 979 | AGCAACAA CUGAUGA GCCGUUAGGC GAA AGGUUUUU | 8817 | AAAAACCUU UUGUUGCU | 1675 |
| 980 | AAGCAACA CUGAUGA GCCGUUAGGC GAA AAGGUUUU | 8818 | AAAACCUUU UGUUGCUU | 1676 |

| | | | | |
|---|---|---|---|---|
| 981 | AAAGCAAC CUGAUGA GCCGUUAGGC GAA AAAGGUUU | 8819 | AAACCUUUU GUUGCUUU | 1677 |
| 984 | CCAAAAGC CUGAUGA GCCGUUAGGC GAA ACAAAAGG | 8820 | CCUUUUGUU GCUUUUGG | 1678 |
| 988 | ACUUCCAA CUGAUGA GCCGUUAGGC GAA AGCAACAA | 8821 | UUGUUGCUU UUGGAAGU | 1679 |
| 989 | CACUUCCA CUGAUGA GCCGUUAGGC GAA AAGCAACA | 8822 | UGUUGCUUU UGGAAGUG | 1680 |
| 990 | CCACUUCC CUGAUGA GCCGUUAGGC GAA AAAGCAAC | 8823 | GUUGCUUUU GGAAGUGG | 1681 |
| 1007 | CCACCAGA CUGAUGA GCCGUUAGGC GAA AUUCCAUG | 8824 | CAUGGAAUC UCUGGUGG | 1682 |
| 1009 | UUCCACCA CUGAUGA GCCGUUAGGC GAA AGAUUCCA | 8825 | UGGAAUCUC UGGUGGAA | 1683 |
| 1038 | GGGAUUCU CUGAUGA GCCGUUAGGC GAA ACACGCUC | 8826 | GAGCGUGUC AGAAUCCC | 1684 |
| 1044 | UUCGCAGG CUGAUGA GCCGUUAGGC GAA AUUCUGAC | 8827 | GUCAGAAUC CCUGCGAA | 1685 |
| 1055 | AACCAAGG CUGAUGA GCCGUUAGGC GAA ACUUCGCA | 8828 | UGCGAAGUA CCUUGGUU | 1686 |
| 1059 | GGGUAACC CUGAUGA GCCGUUAGGC GAA AGGUACUU | 8829 | AAGUACCUU GGUUACCC | 1687 |
| 1063 | GGGUGGGU CUGAUGA GCCGUUAGGC GAA ACCAAGGU | 8830 | ACCUUGGUU ACCCACCC | 1688 |
| 1064 | GGGGUGGG CUGAUGA GCCGUUAGGC GAA AACCAAGG | 8831 | CCUUGGUUA CCCACCCC | 1689 |
| 1080 | UACCAUUU CUGAUGA GCCGUUAGGC GAA AUUUCUGG | 8832 | CCAGAAAUA AAAUGGUA | 1690 |
| 1088 | CAUUUUUA CUGAUGA GCCGUUAGGC GAA ACCAUUUU | 8833 | AAAAUGGUA UAAAAAUG | 1691 |
| 1090 | UCCAUUUU CUGAUGA GCCGUUAGGC GAA AUACCAUU | 8834 | AAUGGUAUA AAAAUGGA | 1692 |
| 1101 | UCAAGGGG CUGAUGA GCCGUUAGGC GAA AUUCCAUU | 8835 | AAUGGAAUA CCCCUUGA | 1693 |
| 1107 | UUGGACUC CUGAUGA GCCGUUAGGC GAA AGGGGUAU | 8836 | AUACCCCUU GAGUCCAA | 1694 |
| 1112 | UGUGAUUG CUGAUGA GCCGUUAGGC GAA ACUCAAGG | 8837 | CCUUGAGUC CAAUCACA | 1695 |
| 1117 | AAUUGUGU CUGAUGA GCCGUUAGGC GAA AUUGGACU | 8838 | AGUCCAAUC ACACAAUU | 1696 |
| 1125 | CCCGCUUU CUGAUGA GCCGUUAGGC GAA AUUGUGUG | 8839 | CACACAAUU AAAGCGGG | 1697 |
| 1126 | CCCCGCUU CUGAUGA GCCGUUAGGC GAA AAUUGUGU | 8840 | ACACAAUUA AAGCGGGG | 1698 |
| 1140 | AUCGUCAG CUGAUGA GCCGUUAGGC GAA ACAUGCCC | 8841 | GGGCAUGUA CUGACGAU | 1699 |
| 1149 | ACUUCCAU CUGAUGA GCCGUUAGGC GAA AUCGUCAG | 8842 | CUGACGAUU AUGGAAGU | 1700 |
| 1150 | CACUUCCA CUGAUGA GCCGUUAGGC GAA AAUCGUCA | 8843 | UGACGAUUA UGGAAGUG | 1701 |
| 1180 | GACAGUGU CUGAUGA GCCGUUAGGC GAA AUUUCCUG | 8844 | CAGGAAAUU ACACUGUC | 1702 |
| 1181 | UGACAGUG CUGAUGA GCCGUUAGGC GAA AAUUUCCU | 8845 | AGGAAAUUA CACUGUCA | 1703 |
| 1188 | GUAAGGAU CUGAUGA GCCGUUAGGC GAA ACAGUGUA | 8846 | UACACUGUC AUCCUUAC | 1704 |
| 1191 | UUGGUAAG CUGAUGA GCCGUUAGGC GAA AUGACAGU | 8847 | ACUGUCAUC CUUACCAA | 1705 |
| 1194 | GGAUUGGU CUGAUGA GCCGUUAGGC GAA AGGAUGAC | 8848 | GUCAUCCUU ACCAAUCC | 1706 |
| 1195 | GGGAUUGG CUGAUGA GCCGUUAGGC GAA AAGGAUGA | 8849 | UCAUCCUUA CCAAUCCC | 1707 |
| 1201 | UGAAAUGG CUGAUGA GCCGUUAGGC GAA AUUGGUAA | 8850 | UUACCAAUC CCAUUUCA | 1708 |
| 1206 | UCCUUUGA CUGAUGA GCCGUUAGGC GAA AUGGGAUU | 8851 | AAUCCCAUU UCAAAGGA | 1709 |
| 1207 | CUCCUUUG CUGAUGA GCCGUUAGGC GAA AAUGGGAU | 8852 | AUCCCAUUU CAAAGGAG | 1710 |
| 1208 | UCUCCUUU CUGAUGA GCCGUUAGGC GAA AAAUGGGA | 8853 | UCCCAUUUC AAAGGAGA | 1711 |

| | | | | | |
|---|---|---|---|---|---|
| 1233 | ACCAGAGA CUGAUGA GCCGUUAGGC GAA ACCACAUG | 8854 | CAUGUGGUC UCUCUGGU | 1712 |
| 1235 | CAACCAGA CUGAUGA GCCGUUAGGC GAA AGACCACA | 8855 | UGUGGUCUC UCUGGUUG | 1713 |
| 1237 | CACAACCA CUGAUGA GCCGUUAGGC GAA AGAGACCA | 8856 | UGGUCUCUC UGGUUGUG | 1714 |
| 1242 | ACAUACAC CUGAUGA GCCGUUAGGC GAA ACCAGAGA | 8857 | UCUCUGGUU GUGUAUGU | 1715 |
| 1247 | GUGGGACA CUGAUGA GCCGUUAGGC GAA ACACAACC | 8858 | GGUUGUGUA UGUCCCAC | 1716 |
| 1251 | UGGGGUGG CUGAUGA GCCGUUAGGC GAA ACAUACAC | 8859 | GUGUAUGUC CCACCCCA | 1717 |
| 1263 | UUCUCACC CUGAUGA GCCGUUAGGC GAA AUCUGGGG | 8860 | CCCCAGAUU GGUGAGAA | 1718 |
| 1274 | AGAUUAGA CUGAUGA GCCGUUAGGC GAA AUUUCUCA | 8861 | UGAGAAAUC UCUAAUCU | 1719 |
| 1276 | AGAGAUUA CUGAUGA GCCGUUAGGC GAA AGAUUUCU | 8862 | AGAAAUCUC UAAUCUCU | 1720 |
| 1278 | GGAGAGAU CUGAUGA GCCGUUAGGC GAA AGAGAUUU | 8863 | AAAUCUCUA AUCUCUCC | 1721 |
| 1281 | ACAGGAGA CUGAUGA GCCGUUAGGC GAA AUUAGAGA | 8864 | UCUCUAAUC UCUCCUGU | 1722 |
| 1283 | CCACAGGA CUGAUGA GCCGUUAGGC GAA AGAUUAGA | 8865 | UCUAAUCUC UCCUGUGG | 1723 |
| 1285 | AUCCACAG CUGAUGA GCCGUUAGGC GAA AGAGAUUA | 8866 | UAAUCUCUC CUGUGGAU | 1724 |
| 1294 | CUGGUAGG CUGAUGA GCCGUUAGGC GAA AUCCACAG | 8867 | CUGUGGAUU CCUACCAG | 1725 |
| 1295 | ACUGGUAG CUGAUGA GCCGUUAGGC GAA AAUCCACA | 8868 | UGUGGAUUC CUACCAGU | 1726 |
| 1298 | CGUACUGG CUGAUGA GCCGUUAGGC GAA AGGAAUCC | 8869 | GGAUUCCUA CCAGUACG | 1727 |
| 1304 | UGGUGCCG CUGAUGA GCCGUUAGGC GAA ACUGGUAG | 8870 | CUACCAGUA CGGCACCA | 1728 |
| 1315 | CAGCGUUU CUGAUGA GCCGUUAGGC GAA AGUGGUGC | 8871 | GCACCACUC AAACGCUG | 1729 |
| 1330 | AUAGACCG CUGAUGA GCCGUUAGGC GAA ACAUGUCA | 8872 | UGACAUGUA CGGUCUAU | 1730 |
| 1335 | AUGGCAUA CUGAUGA GCCGUUAGGC GAA ACCGUACA | 8873 | UGUACGGUC UAUGCCAU | 1731 |
| 1337 | GAAUGGCA CUGAUGA GCCGUUAGGC GAA AGACCGUA | 8874 | UACGGUCUA UGCCAUUC | 1732 |
| 1344 | GGGGGAGG CUGAUGA GCCGUUAGGC GAA AUGGCAUA | 8875 | UAUGCCAUU CCUCCCCC | 1733 |
| 1345 | CGGGGGAG CUGAUGA GCCGUUAGGC GAA AAUGGCAU | 8876 | AUGCCAUUC CUCCCCCG | 1734 |
| 1348 | AUGCGGGG CUGAUGA GCCGUUAGGC GAA AGGAAUGG | 8877 | CCAUUCCUC CCCCGCAU | 1735 |
| 1357 | GUGGAUGU CUGAUGA GCCGUUAGGC GAA AUGCGGGG | 8878 | CCCCGCAUC ACAUCCAC | 1736 |
| 1362 | UACCAGUG CUGAUGA GCCGUUAGGC GAA AUGUGAUG | 8879 | CAUCACAUC CACUGGUA | 1737 |
| 1370 | ACUGCCAA CUGAUGA GCCGUUAGGC GAA ACCAGUGG | 8880 | CCACUGGUA UUGGCAGU | 1738 |
| 1372 | CAACUGCC CUGAUGA GCCGUUAGGC GAA AUACCAGU | 8881 | ACUGGUAUU GGCAGUUG | 1739 |
| 1379 | CUUCCUCC CUGAUGA GCCGUUAGGC GAA ACUGCCAA | 8882 | UUGGCAGUU GGAGGAAG | 1740 |
| 1416 | GUCACUGA CUGAUGA GCCGUUAGGC GAA ACAGCUUG | 8883 | CAAGCUGUC UCAGUGAC | 1741 |
| 1418 | UUGUCACU CUGAUGA GCCGUUAGGC GAA AGACAGCU | 8884 | AGCUGUCUC AGUGACAA | 1742 |
| 1433 | CACAAGGG CUGAUGA GCCGUUAGGC GAA AUGGGUUU | 8885 | AAACCCAUA CCCUUGUG | 1743 |
| 1438 | UUCUUCAC CUGAUGA GCCGUUAGGC GAA AGGGUAUG | 8886 | CAUACCCUU GUGAAGAA | 1744 |
| 1466 | CUCCCUGG CUGAUGA GCCGUUAGGC GAA AGUCCUCC | 8887 | GGAGGACUU CCAGGGAG | 1745 |
| 1467 | CCUCCCUG CUGAUGA GCCGUUAGGC GAA AAGUCCUC | 8888 | GAGGACUUC CAGGGAGG | 1746 |

127

| | | | | |
|---|---|---|---|---|
| 1480 | UUCAAUUU CUGAUGA GCCGUUAGGC GAA AUUUCCUC | 8889 | GAGGAAAUA AAAUUGAA | 1747 |
| 1485 | UUAACUUC CUGAUGA GCCGUUAGGC GAA AUUUUAUU | 8890 | AAUAAAAUU GAAGUUAA | 1748 |
| 1491 | UUUUUAUU CUGAUGA GCCGUUAGGC GAA ACUUCAAU | 8891 | AUUGAAGUU AAUAAAAA | 1749 |
| 1492 | AUUUUUAU CUGAUGA GCCGUUAGGC GAA AACUUCAA | 8892 | UUGAAGUUA AUAAAAAU | 1750 |
| 1495 | UUGAUUUU CUGAUGA GCCGUUAGGC GAA AUUAACUU | 8893 | AAGUUAAUA AAAAUCAA | 1751 |
| 1501 | AGCAAAUU CUGAUGA GCCGUUAGGC GAA AUUUUUAU | 8894 | AUAAAAAUC AAUUUGCU | 1752 |
| 1505 | UUAGAGCA CUGAUGA GCCGUUAGGC GAA AUUGAUUU | 8895 | AAAUCAAUU UGCUCUAA | 1753 |
| 1506 | AUUAGAGC CUGAUGA GCCGUUAGGC GAA AAUUGAUU | 8896 | AAUCAAUUU GCUCUAAU | 1754 |
| 1510 | UUCAAUUA CUGAUGA GCCGUUAGGC GAA AGCAAAUU | 8897 | AAUUUGCUC UAAUUGAA | 1755 |
| 1512 | CCUUCAAU CUGAUGA GCCGUUAGGC GAA AGAGCAAA | 8898 | UUUGCUCUA AUUGAAGG | 1756 |
| 1515 | UUUCCUUC CUGAUGA GCCGUUAGGC GAA AUUAGAGC | 8899 | GCUCUAAUU GAAGGAAA | 1757 |
| 1536 | AGGGUACU CUGAUGA GCCGUUAGGC GAA ACAGUUUU | 8900 | AAAACUGUA AGUACCCU | 1758 |
| 1540 | AACAAGGG CUGAUGA GCCGUUAGGC GAA ACUUACAG | 8901 | CUGUAAGUA CCCUUGUU | 1759 |
| 1545 | UGGAUAAC CUGAUGA GCCGUUAGGC GAA AGGGUACU | 8902 | AGUACCCUU GUUAUCCA | 1760 |
| 1548 | GCUUGGAU CUGAUGA GCCGUUAGGC GAA ACAAGGGU | 8903 | ACCCUUGUU AUCCAAGC | 1761 |
| 1549 | CGCUUGGA CUGAUGA GCCGUUAGGC GAA AACAAGGG | 8904 | CCCUUGUUA UCCAAGCG | 1762 |
| 1551 | GCCGCUUG CUGAUGA GCCGUUAGGC GAA AUAACAAG | 8905 | CUUGUUAUC CAAGCGGC | 1763 |
| 1568 | ACAAAGCU CUGAUGA GCCGUUAGGC GAA ACACAUUU | 8906 | AAAUGUGUC AGCUUUGU | 1764 |
| 1573 | UUUGUACA CUGAUGA GCCGUUAGGC GAA AGCUGACA | 8907 | UGUCAGCUU UGUACAAA | 1765 |
| 1574 | AUUUGUAC CUGAUGA GCCGUUAGGC GAA AAGCUGAC | 8908 | GUCAGCUUU GUACAAAU | 1766 |
| 1577 | CACAUUUG CUGAUGA GCCGUUAGGC GAA ACAAAGCU | 8909 | AGCUUUGUA CAAAUGUG | 1767 |
| 1593 | ACUUUGUU CUGAUGA GCCGUUAGGC GAA ACCGCUUC | 8910 | GAAGCGGUC AACAAAGU | 1768 |
| 1602 | CCUCUCCC CUGAUGA GCCGUUAGGC GAA ACUUUGUU | 8911 | AACAAAGUC GGGAGAGG | 1769 |
| 1623 | UGGAAGGA CUGAUGA GCCGUUAGGC GAA AUCACCCU | 8912 | AGGGUGAUC UCCUUCCA | 1770 |
| 1625 | CGUGGAAG CUGAUGA GCCGUUAGGC GAA AGAUCACC | 8913 | GGUGAUCUC CUUCCACG | 1771 |
| 1628 | UCACGUGG CUGAUGA GCCGUUAGGC GAA AGGAGAUC | 8914 | GAUCUCCUU CCACGUGA | 1772 |
| 1629 | GUCACGUG CUGAUGA GCCGUUAGGC GAA AAGGAGAU | 8915 | AUCUCCUUC CACGUGAC | 1773 |
| 1645 | AAUUUCAG CUGAUGA GCCGUUAGGC GAA ACCCCUGG | 8916 | CCAGGGGUC CUGAAAUU | 1774 |
| 1653 | UGCAAAGU CUGAUGA GCCGUUAGGC GAA AUUUCAGG | 8917 | CCUGAAAUU ACUUUGCA | 1775 |
| 1654 | UUGCAAAG CUGAUGA GCCGUUAGGC GAA AAUUUCAG | 8918 | CUGAAAUUA CUUUGCAA | 1776 |
| 1657 | AGGUUGCA CUGAUGA GCCGUUAGGC GAA AGUAAUUU | 8919 | AAAUUACUU UGCAACCU | 1777 |
| 1658 | CAGGUUGC CUGAUGA GCCGUUAGGC GAA AAGUAAUU | 8920 | AAUUACUUU GCAACCUG | 1778 |
| 1697 | ACCACAAA CUGAUGA GCCGUUAGGC GAA ACACGCUC | 8921 | GAGCGUGUC UUUGUGGU | 1779 |
| 1699 | GCACCACA CUGAUGA GCCGUUAGGC GAA AGACACGC | 8922 | GCGUGUCUU UGUGGUGC | 1780 |
| 1700 | UGCACCAC CUGAUGA GCCGUUAGGC GAA AAGACACG | 8923 | CGUGUCUUU GUGGUGCA | 1781 |

| | | | | |
|---|---|---|---|---|
| 1721 | CAAACGUA CUGAUGA GCCGUUAGGC GAA AUCUGUCU | 8924 | AGACAGAUC UACGUUUG | 1782 |
| 1723 | CUCAAACG CUGAUGA GCCGUUAGGC GAA AGAUCUGU | 8925 | ACAGAUCUA CGUUUGAG | 1783 |
| 1727 | GGUUCUCA CUGAUGA GCCGUUAGGC GAA ACGUAGAU | 8926 | AUCUACGUU UGAGAACC | 1784 |
| 1728 | AGGUUCUC CUGAUGA GCCGUUAGGC GAA AACGUAGA | 8927 | UCUACGUUU GAGAACCU | 1785 |
| 1737 | UACCAUGU CUGAUGA GCCGUUAGGC GAA AGGUUCUC | 8928 | GAGAACCUC ACAUGGUA | 1786 |
| 1745 | CAAGCUUG CUGAUGA GCCGUUAGGC GAA ACCAUGUG | 8929 | CACAUGGUA CAAGCUUG | 1787 |
| 1752 | UGUGGGCC CUGAUGA GCCGUUAGGC GAA AGCUUGUA | 8930 | UACAAGCUU GGCCCACA | 1788 |
| 1765 | GAUUGGCA CUGAUGA GCCGUUAGGC GAA AGGCUGUG | 8931 | CACAGCCUC UGCCAAUC | 1789 |
| 1773 | CCCACAUG CUGAUGA GCCGUUAGGC GAA AUUGGCAG | 8932 | CUGCCAAUC CAUGUGGG | 1790 |
| 1787 | GUGUGGGC CUGAUGA GCCGUUAGGC GAA ACUCUCCC | 8933 | GGGAGAGUU GCCCACAC | 1791 |
| 1800 | UUCUUGCA CUGAUGA GCCGUUAGGC GAA ACAGGUGU | 8934 | ACACCUGUU UGCAAGAA | 1792 |
| 1801 | GUUCUUGC CUGAUGA GCCGUUAGGC GAA AACAGGUG | 8935 | CACCUGUUU GCAAGAAC | 1793 |
| 1811 | GAGUAUCC CUGAUGA GCCGUUAGGC GAA AGUUCUUG | 8936 | CAAGAACUU GGAUACUC | 1794 |
| 1816 | CCAAAGAG CUGAUGA GCCGUUAGGC GAA AUCCAAGU | 8937 | ACUUGGAUA CUCUUUGG | 1795 |
| 1819 | UUUCCAAA CUGAUGA GCCGUUAGGC GAA AGUAUCCA | 8938 | UGGAUACUC UUUGGAAA | 1796 |
| 1821 | AAUUUCCA CUGAUGA GCCGUUAGGC GAA AGAGUAUC | 8939 | GAUACUCUU UGGAAAUU | 1797 |
| 1822 | CAAUUUCC CUGAUGA GCCGUUAGGC GAA AAGAGUAU | 8940 | AUACUCUUU GGAAAUUG | 1798 |
| 1829 | UGGCAUUC CUGAUGA GCCGUUAGGC GAA AUUUCCAA | 8941 | UUGGAAAUU GAAUGCCA | 1799 |
| 1844 | UAUUAGAG CUGAUGA GCCGUUAGGC GAA ACAUGGUG | 8942 | CACCAUGUU CUCUAAUA | 1800 |
| 1845 | CUAUUAGA CUGAUGA GCCGUUAGGC GAA AACAUGGU | 8943 | ACCAUGUUC UCUAAUAG | 1801 |
| 1847 | UGCUAUUA CUGAUGA GCCGUUAGGC GAA AGAACAUG | 8944 | CAUGUUCUC UAAUAGCA | 1802 |
| 1849 | UGUGCUAU CUGAUGA GCCGUUAGGC GAA AGAGAACA | 8945 | UGUUCUCUA AUAGCACA | 1803 |
| 1852 | AUUUGUGC CUGAUGA GCCGUUAGGC GAA AUUAGAGA | 8946 | UCUCUAAUA GCACAAAU | 1804 |
| 1866 | AUGAUCAA CUGAUGA GCCGUUAGGC GAA AUGUCAUU | 8947 | AAUGACAUU UUGAUCAU | 1805 |
| 1867 | CAUGAUCA CUGAUGA GCCGUUAGGC GAA AAUGUCAU | 8948 | AUGACAUUU UGAUCAUG | 1806 |
| 1868 | CCAUGAUC CUGAUGA GCCGUUAGGC GAA AAAUGUCA | 8949 | UGACAUUUU GAUCAUGG | 1807 |
| 1872 | AGCUCCAU CUGAUGA GCCGUUAGGC GAA AUCAAAAU | 8950 | AUUUUGAUC AUGGAGCU | 1808 |
| 1881 | GCAUUCUU CUGAUGA GCCGUUAGGC GAA AGCUCCAU | 8951 | AUGGAGCUU AAGAAUGC | 1809 |
| 1882 | UGCAUUCU CUGAUGA GCCGUUAGGC GAA AAGCUCCA | 8952 | UGGAGCUUA AGAAUGCA | 1810 |
| 1892 | CCUGCAAG CUGAUGA GCCGUUAGGC GAA AUGCAUUC | 8953 | GAAUGCAUC CUUGCAGG | 1811 |
| 1895 | GGUCCUGC CUGAUGA GCCGUUAGGC GAA AGGAUGCA | 8954 | UGCAUCCUU GCAGGACC | 1812 |
| 1913 | GGCAGACA CUGAUGA GCCGUUAGGC GAA AGUCUCCU | 8955 | AGGAGACUA UGUCUGCC | 1813 |
| 1917 | GCAAGGCA CUGAUGA GCCGUUAGGC GAA ACAUAGUC | 8956 | GACUAUGUC UGCCUUGC | 1814 |
| 1923 | UCUUGAGC CUGAUGA GCCGUUAGGC GAA AGGCAGAC | 8957 | GUCUGCCUU GCUCAAGA | 1815 |
| 1927 | CCUGUCUU CUGAUGA GCCGUUAGGC GAA AGCAAGGC | 8958 | GCCUUGCUC AAGACAGG | 1816 |

129

| | | | | |
|---|---|---|---|---|
| 1954 | GACCACGC CUGAUGA GCCGUUAGGC GAA AUGUCUUU | 8959 | AAAGACAUU GCGUGGUC | 1817 |
| 1962 | AGCUGCCU CUGAUGA GCCGUUAGGC GAA ACCACGCA | 8960 | UGCGUGGUC AGGCAGCU | 1818 |
| 1971 | AGGACUGU CUGAUGA GCCGUUAGGC GAA AGCUGCCU | 8961 | AGGCAGCUC ACAGUCCU | 1819 |
| 1977 | CGCUCUAG CUGAUGA GCCGUUAGGC GAA ACUGUGAG | 8962 | CUCACAGUC CUAGAGCG | 1820 |
| 1980 | ACACGCUC CUGAUGA GCCGUUAGGC GAA AGGACUGU | 8963 | ACAGUCCUA GAGCGUGU | 1821 |
| 2001 | UUUCCUGU CUGAUGA GCCGUUAGGC GAA AUCGUGGG | 8964 | CCCACGAUC ACAGGAAA | 1822 |
| 2020 | UGUCGUCU CUGAUGA GCCGUUAGGC GAA AUUCUCCA | 8965 | UGGAGAAUC AGACGACA | 1823 |
| 2032 | UUCCCCAA CUGAUGA GCCGUUAGGC GAA ACUUGUCG | 8966 | CGACAAGUA UUGGGGAA | 1824 |
| 2034 | CUUUCCCC CUGAUGA GCCGUUAGGC GAA AUACUUGU | 8967 | ACAAGUAUU GGGGAAAG | 1825 |
| 2046 | GAGACUUC CUGAUGA GCCGUUAGGC GAA AUGCUUUC | 8968 | GAAAGCAUC GAAGUCUC | 1826 |
| 2052 | GUGCAUGA CUGAUGA GCCGUUAGGC GAA ACUUCGAU | 8969 | AUCGAAGUC UCAUGCAC | 1827 |
| 2054 | CCGUGCAU CUGAUGA GCCGUUAGGC GAA AGACUUCG | 8970 | CGAAGUCUC AUGCACGG | 1828 |
| 2066 | GAUUCCCA CUGAUGA GCCGUUAGGC GAA AUGCCGUG | 8971 | CACGGCAUC UGGGAAUC | 1829 |
| 2074 | UGGAGGGG CUGAUGA GCCGUUAGGC GAA AUUCCCAG | 8972 | CUGGGAAUC CCCCUCCA | 1830 |
| 2080 | GAUCUGUG CUGAUGA GCCGUUAGGC GAA AGGGGGAU | 8973 | AUCCCCCUC CACAGAUC | 1831 |
| 2088 | AACCACAU CUGAUGA GCCGUUAGGC GAA AUCUGUGG | 8974 | CCACAGAUC AUGUGGUU | 1832 |
| 2096 | UAUCUUUA CUGAUGA GCCGUUAGGC GAA ACCACAUG | 8975 | CAUGUGGUU UAAAGAUA | 1833 |
| 2097 | UUAUCUUU CUGAUGA GCCGUUAGGC GAA AACCACAU | 8976 | AUGUGGUUU AAAGAUAA | 1834 |
| 2098 | AUUAUCUU CUGAUGA GCCGUUAGGC GAA AAACCACA | 8977 | UGUGGUUUA AAGAUAAU | 1835 |
| 2104 | GGUCUCAU CUGAUGA GCCGUUAGGC GAA AUCUUUAA | 8978 | UUAAAGAUA AUGAGACC | 1836 |
| 2115 | UCUUCUAC CUGAUGA GCCGUUAGGC GAA AGGGUCUC | 8979 | GAGACCCUU GUAGAAGA | 1837 |
| 2118 | GAGUCUUC CUGAUGA GCCGUUAGGC GAA ACAAGGGU | 8980 | ACCCUUGUA GAAGACUC | 1838 |
| 2126 | CAAUGCCU CUGAUGA GCCGUUAGGC GAA AGUCUUCU | 8981 | AGAAGACUC AGGCAUUG | 1839 |
| 2133 | UUCAAUAC CUGAUGA GCCGUUAGGC GAA AUGCCUGA | 8982 | UCAGGCAUU GUAUUGAA | 1840 |
| 2136 | UCCUUCAA CUGAUGA GCCGUUAGGC GAA ACAAUGCC | 8983 | GGCAUUGUA UUGAAGGA | 1841 |
| 2138 | CAUCCUUC CUGAUGA GCCGUUAGGC GAA AUACAAUG | 8984 | CAUUGUAUU GAAGGAUG | 1842 |
| 2160 | CGGAUAGU CUGAUGA GCCGUUAGGC GAA AGGUUCCG | 8985 | CGGAACCUC ACUAUCCG | 1843 |
| 2164 | UCUGCGGA CUGAUGA GCCGUUAGGC GAA AGUGAGGU | 8986 | ACCUCACUA UCCGCAGA | 1844 |
| 2166 | ACUCUGCG CUGAUGA GCCGUUAGGC GAA AUAGUGAG | 8987 | CUCACUAUC CGCAGAGU | 1845 |
| 2196 | CAGGUGUA CUGAUGA GCCGUUAGGC GAA AGGCCUUC | 8988 | GAAGGCCUC UACACCUG | 1846 |
| 2198 | GGCAGGUG CUGAUGA GCCGUUAGGC GAA AGAGGCCU | 8989 | AGGCCUCUA CACCUGCC | 1847 |
| 2220 | CAGCCAAG CUGAUGA GCCGUUAGGC GAA ACACUGCA | 8990 | UGCAGUGUU CUUGGCUG | 1848 |
| 2221 | ACAGCCAA CUGAUGA GCCGUUAGGC GAA AACACUGC | 8991 | GCAGUGUUC UUGGCUGU | 1849 |
| 2223 | GCACAGCC CUGAUGA GCCGUUAGGC GAA AGAACACU | 8992 | AGUGUUCUU GGCUGUGC | 1850 |
| 2246 | UUAUGAAA CUGAUGA GCCGUUAGGC GAA AUGCCUCC | 8993 | GGAGGCAUU UUUCAUAA | 1851 |

130

| | | | | |
|---|---|---|---|---|
| 2247 | AUUAUGAA CUGAUGA GCCGUUAGGC GAA AAUGCCUC | 8994 | GAGGCAUUU UUCAUAAU | 1852 |
| 2248 | UAUUAUGA CUGAUGA GCCGUUAGGC GAA AAAUGCCU | 8995 | AGGCAUUUU UCAUAAUA | 1853 |
| 2249 | CUAUUAUG CUGAUGA GCCGUUAGGC GAA AAAAUGCC | 8996 | GGCAUUUUU CAUAAUAG | 1854 |
| 2250 | UCUAUUAU CUGAUGA GCCGUUAGGC GAA AAAAAUGC | 8997 | GCAUUUUUC AUAAUAGA | 1855 |
| 2253 | CCUUCUAU CUGAUGA GCCGUUAGGC GAA AUGAAAAA | 8998 | UUUUUCAUA AUAGAAGG | 1856 |
| 2256 | GCACCUUC CUGAUGA GCCGUUAGGC GAA AUUAUGAA | 8999 | UUCAUAAUA GAAGGUGC | 1857 |
| 2282 | UGAUUUCC CUGAUGA GCCGUUAGGC GAA AGUUCGUC | 9000 | GACGAACUU GGAAAUCA | 1858 |
| 2289 | AGAAUAAU CUGAUGA GCCGUUAGGC GAA AUUUCCAA | 9001 | UUGGAAAUC AUUAUUCU | 1859 |
| 2292 | ACUAGAAU CUGAUGA GCCGUUAGGC GAA AUGAUUUC | 9002 | GAAAUCAUU AUUCUAGU | 1860 |
| 2293 | UACUAGAA CUGAUGA GCCGUUAGGC GAA AAUGAUUU | 9003 | AAAUCAUUA UUCUAGUA | 1861 |
| 2295 | CCUACUAG CUGAUGA GCCGUUAGGC GAA AUAAUGAU | 9004 | AUCAUUAUU CUAGUAGG | 1862 |
| 2296 | GCCUACUA CUGAUGA GCCGUUAGGC GAA AAUAAUGA | 9005 | UCAUUAUUC UAGUAGGC | 1863 |
| 2298 | GUGCCUAC CUGAUGA GCCGUUAGGC GAA AGAAUAAU | 9006 | AUUAUUCUA GUAGGCAC | 1864 |
| 2301 | GUCGUGCC CUGAUGA GCCGUUAGGC GAA ACUAGAAU | 9007 | AUUCUAGUA GGCACGAC | 1865 |
| 2316 | AACAUGGC CUGAUGA GCCGUUAGGC GAA AUCACCGU | 9008 | ACGGUGAUU GCCAUGUU | 1866 |
| 2324 | GCCAGAAG CUGAUGA GCCGUUAGGC GAA ACAUGGCA | 9009 | UGCCAUGUU CUUCUGGC | 1867 |
| 2325 | AGCCAGAA CUGAUGA GCCGUUAGGC GAA AACAUGGC | 9010 | GCCAUGUUC UUCUGGCU | 1868 |
| 2327 | GUAGCCAG CUGAUGA GCCGUUAGGC GAA AGAACAUG | 9011 | CAUGUUCUU CUGGCUAC | 1869 |
| 2328 | AGUAGCCA CUGAUGA GCCGUUAGGC GAA AAGAACAU | 9012 | AUGUUCUUC UGGCUACU | 1870 |
| 2334 | ACAAGAAG CUGAUGA GCCGUUAGGC GAA AGCCAGAA | 9013 | UUCUGGCUA CUUCUUGU | 1871 |
| 2337 | AUGACAAG CUGAUGA GCCGUUAGGC GAA AGUAGCCA | 9014 | UGGCUACUU CUUGUCAU | 1872 |
| 2338 | GAUGACAA CUGAUGA GCCGUUAGGC GAA AAGUAGCC | 9015 | GGCUACUUC UUGUCAUC | 1873 |
| 2340 | AUGAUGAC CUGAUGA GCCGUUAGGC GAA AGAAGUAG | 9016 | CUACUUCUU GUCAUCAU | 1874 |
| 2343 | AGGAUGAU CUGAUGA GCCGUUAGGC GAA ACAAGAAG | 9017 | CUUCUUGUC AUCAUCCU | 1875 |
| 2346 | CCUAGGAU CUGAUGA GCCGUUAGGC GAA AUGACAAG | 9018 | CUUGUCAUC AUCCUAGG | 1876 |
| 2349 | GUCCCUAG CUGAUGA GCCGUUAGGC GAA AUGAUGAC | 9019 | GUCAUCAUC CUAGGGAC | 1877 |
| 2352 | ACGGUCCC CUGAUGA GCCGUUAGGC GAA AGGAUGAU | 9020 | AUCAUCCUA GGGACCGU | 1878 |
| 2361 | GCCCGCUU CUGAUGA GCCGUUAGGC GAA ACGGUCCC | 9021 | GGGACCGUU AAGCGGGC | 1879 |
| 2362 | GGCCCGCU CUGAUGA GCCGUUAGGC GAA AACGGUCC | 9022 | GGACCGUUA AGCGGGCC | 1880 |
| 2396 | UGGACAAG CUGAUGA GCCGUUAGGC GAA AGCCUGUC | 9023 | GACAGGCUA CUUGUCCA | 1881 |
| 2399 | CGAUGGAC CUGAUGA GCCGUUAGGC GAA AGUAGCCU | 9024 | AGGCUACUU GUCCAUCG | 1882 |
| 2402 | UGACGAUG CUGAUGA GCCGUUAGGC GAA ACAAGUAG | 9025 | CUACUUGUC CAUCGUCA | 1883 |
| 2406 | UCCAUGAC CUGAUGA GCCGUUAGGC GAA AUGGACAA | 9026 | UUGUCCAUC GUCAUGGA | 1884 |
| 2409 | GGAUCCAU CUGAUGA GCCGUUAGGC GAA ACGAUGGA | 9027 | UCCAUCGUC AUGGAUCC | 1885 |
| 2416 | UUCAUCUG CUGAUGA GCCGUUAGGC GAA AUCCAUGA | 9028 | UCAUGGAUC CAGAUGAA | 1886 |

| | | | | |
|---|---|---|---|---|
| 2427 | UCCAAUGG CUGAUGA GCCGUUAGGC GAA AGUUCAUC | 9029 | GAUGAACUC CCAUUGGA | 1887 |
| 2432 | GUUCAUCC CUGAUGA GCCGUUAGGC GAA AUGGGAGU | 9030 | ACUCCCAUU GGAUGAAC | 1888 |
| 2443 | UCGUUCAC CUGAUGA GCCGUUAGGC GAA AUGUUCAU | 9031 | AUGAACAUU GUGAACGA | 1889 |
| 2458 | GGCAUCAU CUGAUGA GCCGUUAGGC GAA AGGCAGUC | 9032 | GACUGCCUU AUGAUGCC | 1890 |
| 2459 | UGGCAUCA CUGAUGA GCCGUUAGGC GAA AAGGCAGU | 9033 | ACUGCCUUA UGAUGCCA | 1891 |
| 2480 | CUCUGGGG CUGAUGA GCCGUUAGGC GAA AUUCCCAU | 9034 | AUGGGAAUU CCCCAGAG | 1892 |
| 2481 | UCUCUGGG CUGAUGA GCCGUUAGGC GAA AAUUCCCA | 9035 | UGGGAAUUC CCCAGAGA | 1893 |
| 2502 | GGCUUACC CUGAUGA GCCGUUAGGC GAA AGGUUCAG | 9036 | CUGAACCUA GGUAAGCC | 1894 |
| 2506 | AAGAGGCU CUGAUGA GCCGUUAGGC GAA ACCUAGGU | 9037 | ACCUAGGUA AGCCUCUU | 1895 |
| 2512 | ACGGCCAA CUGAUGA GCCGUUAGGC GAA AGGCUUAC | 9038 | GUAAGCCUC UUGGCCGU | 1896 |
| 2514 | CCACGGCC CUGAUGA GCCGUUAGGC GAA AGAGGCUU | 9039 | AAGCCUCUU GGCCGUGG | 1897 |
| 2528 | CUUGGCCA CUGAUGA GCCGUUAGGC GAA AGGCACCA | 9040 | UGGUGCCUU UGGCCAAG | 1898 |
| 2529 | UCUUGGCC CUGAUGA GCCGUUAGGC GAA AAGGCACC | 9041 | GGUGCCUUU GGCCAAGA | 1899 |
| 2541 | UCUGCUUC CUGAUGA GCCGUUAGGC GAA AUCUCUUG | 9042 | CAAGAGAUU GAAGCAGA | 1900 |
| 2555 | CAAUUCCA CUGAUGA GCCGUUAGGC GAA AGGCAUCU | 9043 | AGAUGCCUU UGGAAUUG | 1901 |
| 2556 | UCAAUUCC CUGAUGA GCCGUUAGGC GAA AAGGCAUC | 9044 | GAUGCCUUU GGAAUUGA | 1902 |
| 2562 | GUCUUGUC CUGAUGA GCCGUUAGGC GAA AUUCCAAA | 9045 | UUUGGAAUU GACAAGAC | 1903 |
| 2578 | UGUCCUGC CUGAUGA GCCGUUAGGC GAA AGUUGCUG | 9046 | CAGCAACUU GCAGGACA | 1904 |
| 2589 | UUGACUGC CUGAUGA GCCGUUAGGC GAA ACUGUCCU | 9047 | AGGACAGUA GCAGUCAA | 1905 |
| 2595 | AACAUUUU CUGAUGA GCCGUUAGGC GAA ACUGCUAC | 9048 | GUAGCAGUC AAAAUGUU | 1906 |
| 2603 | CUUCUUUC CUGAUGA GCCGUUAGGC GAA ACAUUUUG | 9049 | CAAAAUGUU GAAAGAAG | 1907 |
| 2632 | GAGAGCUC CUGAUGA GCCGUUAGGC GAA AUGCUCAC | 9050 | GUGAGCAUC GAGCUCUC | 1908 |
| 2638 | AGACAUGA CUGAUGA GCCGUUAGGC GAA AGCUCGAU | 9051 | AUCGAGCUC UCAUGUCU | 1909 |
| 2640 | UCAGACAU CUGAUGA GCCGUUAGGC GAA AGAGCUCG | 9052 | CGAGCUCUC AUGUCUGA | 1910 |
| 2645 | UGAGUUCA CUGAUGA GCCGUUAGGC GAA ACAUGAGA | 9053 | UCUCAUGUC UGAACUCA | 1911 |
| 2652 | AGGAUCUU CUGAUGA GCCGUUAGGC GAA AGUUCAGA | 9054 | UCUGAACUC AAGAUCCU | 1912 |
| 2658 | UGAAUGAG CUGAUGA GCCGUUAGGC GAA AUCUUGAG | 9055 | CUCAAGAUC CUCAUUCA | 1913 |
| 2661 | AUAUGAAU CUGAUGA GCCGUUAGGC GAA AGGAUCUU | 9056 | AAGAUCCUC AUUCAUAU | 1914 |
| 2664 | CCAAUAUG CUGAUGA GCCGUUAGGC GAA AUGAGGAU | 9057 | AUCCUCAUU CAUAUUGG | 1915 |
| 2665 | ACCAAUAU CUGAUGA GCCGUUAGGC GAA AAUGAGGA | 9058 | UCCUCAUUC AUAUUGGU | 1916 |
| 2668 | GUGACCAA CUGAUGA GCCGUUAGGC GAA AUGAAUGA | 9059 | UCAUUCAUA UUGGUCAC | 1917 |
| 2670 | UGGUGACC CUGAUGA GCCGUUAGGC GAA AUAUGAAU | 9060 | AUUCAUAUU GGUCACCA | 1918 |
| 2674 | GAGAUGGU CUGAUGA GCCGUUAGGC GAA ACCAAUAU | 9061 | AUAUUGGUC ACCAUCUC | 1919 |
| 2680 | CACAUUGA CUGAUGA GCCGUUAGGC GAA AUGGUGAC | 9062 | GUCACCAUC UCAAUGUG | 1920 |
| 2682 | ACCACAUU CUGAUGA GCCGUUAGGC GAA AGAUGGUG | 9063 | CACCAUCUC AAUGUGGU | 1921 |

132

| | | | | |
|---|---|---|---|---|
| 2691 | AGAAGGUU CUGAUGA GCCGUUAGGC GAA ACCACAUU | 9064 | AAUGUGGUC AACCUUCU | 1922 |
| 2697 | GCACCUAG CUGAUGA GCCGUUAGGC GAA AGGUUGAC | 9065 | GUCAACCUU CUAGGUGC | 1923 |
| 2698 | GGCACCUA CUGAUGA GCCGUUAGGC GAA AAGGUUGA | 9066 | UCAACCUUC UAGGUGCC | 1924 |
| 2700 | CAGGCACC CUGAUGA GCCGUUAGGC GAA AGAAGGUU | 9067 | AACCUUCUA GGUGCCUG | 1925 |
| 2710 | UGGCUUGG CUGAUGA GCCGUUAGGC GAA ACAGGCAC | 9068 | GUGCCUGUA CCAAGCCA | 1926 |
| 2730 | AUCACCAU CUGAUGA GCCGUUAGGC GAA AGUGGCCC | 9069 | GGGCCACUC AUGGUGAU | 1927 |
| 2739 | AAUUCCAC CUGAUGA GCCGUUAGGC GAA AUCACCAU | 9070 | AUGGUGAUU GUGGAAUU | 1928 |
| 2747 | AUUUGCAG CUGAUGA GCCGUUAGGC GAA AUUCCACA | 9071 | UGUGGAAUU CUGCAAAU | 1929 |
| 2748 | AAUUUGCA CUGAUGA GCCGUUAGGC GAA AAUUCCAC | 9072 | GUGGAAUUC UGCAAAUU | 1930 |
| 2756 | GGUUUCCA CUGAUGA GCCGUUAGGC GAA AUUUGCAG | 9073 | CUGCAAAUU UGGAAACC | 1931 |
| 2757 | AGGUUUCC CUGAUGA GCCGUUAGGC GAA AAUUUGCA | 9074 | UGCAAAUUU GGAAACCU | 1932 |
| 2768 | GGUAAGUG CUGAUGA GCCGUUAGGC GAA ACAGGUUU | 9075 | AAACCUGUC CACUUACC | 1933 |
| 2773 | CCUCAGGU CUGAUGA GCCGUUAGGC GAA AGUGGACA | 9076 | UGUCCACUU ACCUGAGG | 1934 |
| 2774 | UCCUCAGG CUGAUGA GCCGUUAGGC GAA AAGUGGAC | 9077 | GUCCACUUA CCUGAGGA | 1935 |
| 2798 | AGGGGACA CUGAUGA GCCGUUAGGC GAA AUUCAUUU | 9078 | AAAUGAAUU UGUCCCCU | 1936 |
| 2799 | UAGGGGAC CUGAUGA GCCGUUAGGC GAA AAUUCAUU | 9079 | AAUGAAUUU GUCCCCUA | 1937 |
| 2802 | UUGUAGGG CUGAUGA GCCGUUAGGC GAA ACAAAUUC | 9080 | GAAUUUGUC CCCUACAA | 1938 |
| 2807 | UGGUCUUG CUGAUGA GCCGUUAGGC GAA AGGGGACA | 9081 | UGUCCCCUA CAAGACCA | 1939 |
| 2828 | CUUGACGG CUGAUGA GCCGUUAGGC GAA AUCGUGCC | 9082 | GGCACGAUU CCGUCAAG | 1940 |
| 2829 | CCUUGACG CUGAUGA GCCGUUAGGC GAA AAUCGUGC | 9083 | GCACGAUUC CGUCAAGG | 1941 |
| 2833 | UUUCCCUU CUGAUGA GCCGUUAGGC GAA ACGGAAUC | 9084 | GAUUCCGUC AAGGGAAA | 1942 |
| 2846 | CUCCAACG CUGAUGA GCCGUUAGGC GAA AGUCUUUC | 9085 | GAAAGACUA CGUUGGAG | 1943 |
| 2850 | AUUGCUCC CUGAUGA GCCGUUAGGC GAA ACGUAGUC | 9086 | GACUACGUU GGAGCAAU | 1944 |
| 2859 | UCCACAGG CUGAUGA GCCGUUAGGC GAA AUUGCUCC | 9087 | GGAGCAAUC CCUGUGGA | 1945 |
| 2869 | CCGUUUCA CUGAUGA GCCGUUAGGC GAA AUCCACAG | 9088 | CUGUGGAUC UGAAACGG | 1946 |
| 2882 | UGCUGUCC CUGAUGA GCCGUUAGGC GAA AGCGCCGU | 9089 | ACGGCGCUU GGACAGCA | 1947 |
| 2892 | CUACUGGU CUGAUGA GCCGUUAGGC GAA AUGCUGUC | 9090 | GACAGCAUC ACCAGUAG | 1948 |
| 2899 | GCUCUGGC CUGAUGA GCCGUUAGGC GAA ACUGGUGA | 9091 | UCACCAGUA GCCAGAGC | 1949 |
| 2909 | AGCUGGCU CUGAUGA GCCGUUAGGC GAA AGCUCUGG | 9092 | CCAGAGCUC AGCCAGCU | 1950 |
| 2918 | CAAAUCCA CUGAUGA GCCGUUAGGC GAA AGCUGGCU | 9093 | AGCCAGCUC UGGAUUUG | 1951 |
| 2924 | CCUCCACA CUGAUGA GCCGUUAGGC GAA AUCCAGAG | 9094 | CUCUGGAUU UGUGGAGG | 1952 |
| 2925 | UCCUCCAC CUGAUGA GCCGUUAGGC GAA AAUCCAGA | 9095 | UCUGGAUUU GUGGAGGA | 1953 |
| 2939 | CACUGAGG CUGAUGA GCCGUUAGGC GAA ACUUCUCC | 9096 | GGAGAAGUC CCUCAGUG | 1954 |
| 2943 | ACAUCACU CUGAUGA GCCGUUAGGC GAA AGGGACUU | 9097 | AAGUCCCUC AGUGAUGU | 1955 |
| 2952 | UCUUCUUC CUGAUGA GCCGUUAGGC GAA ACAUCACU | 9098 | AGUGAUGUA GAAGAAGA | 1956 |

| | | | | |
|---|---|---|---|---|
| 2968 | AUCUUCAG CUGAUGA GCCGUUAGGC GAA AGCUUCCU | 9099 | AGGAAGCUC CUGAAGAU | 1957 |
| 2977 | CUUAUACA CUGAUGA GCCGUUAGGC GAA AUCUUCAG | 9100 | CUGAAGAUC UGUAUAAG | 1958 |
| 2981 | AGUCCUUA CUGAUGA GCCGUUAGGC GAA ACAGAUCU | 9101 | AGAUCUGUA UAAGGACU | 1959 |
| 2983 | GAAGUCCU CUGAUGA GCCGUUAGGC GAA AUACAGAU | 9102 | AUCUGUAUA AGGACUUC | 1960 |
| 2990 | AGGUCAGG CUGAUGA GCCGUUAGGC GAA AGUCCUUA | 9103 | UAAGGACUU CCUGACCU | 1961 |
| 2991 | AAGGUCAG CUGAUGA GCCGUUAGGC GAA AAGUCCUU | 9104 | AAGGACUUC CUGACCUU | 1962 |
| 2999 | GAUGCUCC CUGAUGA GCCGUUAGGC GAA AGGUCAGG | 9105 | CCUGACCUU GGAGCAUC | 1963 |
| 3007 | ACAGAUGA CUGAUGA GCCGUUAGGC GAA AUGCUCCA | 9106 | UGGAGCAUC UCAUCUGU | 1964 |
| 3009 | UAACAGAU CUGAUGA GCCGUUAGGC GAA AGAUGCUC | 9107 | GAGCAUCUC AUCUGUUA | 1965 |
| 3012 | CUGUAACA CUGAUGA GCCGUUAGGC GAA AUGAGAUG | 9108 | CAUCUCAUC UGUUACAG | 1966 |
| 3016 | GAAGCUGU CUGAUGA GCCGUUAGGC GAA ACAGAUGA | 9109 | UCAUCUGUU ACAGCUUC | 1967 |
| 3017 | GGAAGCUG CUGAUGA GCCGUUAGGC GAA AACAGAUG | 9110 | CAUCUGUUA CAGCUUCC | 1968 |
| 3023 | CCACUUGG CUGAUGA GCCGUUAGGC GAA AGCUGUAA | 9111 | UUACAGCUU CCAAGUGG | 1969 |
| 3024 | GCCACUUG CUGAUGA GCCGUUAGGC GAA AAGCUGUA | 9112 | UACAGCUUC CAAGUGGC | 1970 |
| 3034 | CAUGCCCU CUGAUGA GCCGUUAGGC GAA AGCCACUU | 9113 | AAGUGGCUA AGGGCAUG | 1971 |
| 3047 | AUGCCAAG CUGAUGA GCCGUUAGGC GAA ACUCCAUG | 9114 | CAUGGAGUU CUUGGCAU | 1972 |
| 3048 | GAUGCCAA CUGAUGA GCCGUUAGGC GAA AACUCCAU | 9115 | AUGGAGUUC UUGGCAUC | 1973 |
| 3050 | GCGAUGCC CUGAUGA GCCGUUAGGC GAA AGAACUCC | 9116 | GGAGUUCUU GGCAUCGC | 1974 |
| 3056 | ACUUUCGC CUGAUGA GCCGUUAGGC GAA AUGCCAAG | 9117 | CUUGGCAUC GCGAAAGU | 1975 |
| 3067 | CCUGUGGA CUGAUGA GCCGUUAGGC GAA ACACUUUC | 9118 | GAAAGUGUA UCCACAGG | 1976 |
| 3069 | UCCCUGUG CUGAUGA GCCGUUAGGC GAA AUACACUU | 9119 | AAGUGUAUC CACAGGGA | 1977 |
| 3094 | UAAGAGGA CUGAUGA GCCGUUAGGC GAA AUUUCGUG | 9120 | CACGAAAUA UCCUCUUA | 1978 |
| 3096 | GAUAAGAG CUGAUGA GCCGUUAGGC GAA AUAUUUCG | 9121 | CGAAAUAUC CUCUUAUC | 1979 |
| 3099 | UCCGAUAA CUGAUGA GCCGUUAGGC GAA AGGAUAUU | 9122 | AAUAUCCUC UUAUCGGA | 1980 |
| 3101 | UCUCCGAU CUGAUGA GCCGUUAGGC GAA AGAGGAUA | 9123 | UAUCCUCUU AUCGGAGA | 1981 |
| 3102 | UUCUCCGA CUGAUGA GCCGUUAGGC GAA AAGAGGAU | 9124 | AUCCUCUUA UCGGAGAA | 1982 |
| 3104 | UCUUCUCC CUGAUGA GCCGUUAGGC GAA AUAAGAGG | 9125 | CCUCUUAUC GGAGAAGA | 1983 |
| 3120 | CAGAUUUU CUGAUGA GCCGUUAGGC GAA ACCACGUU | 9126 | AACGUGGUU AAAAUCUG | 1984 |
| 3121 | ACAGAUUU CUGAUGA GCCGUUAGGC GAA AACCACGU | 9127 | ACGUGGUUA AAAUCUGU | 1985 |
| 3126 | AAGUCACA CUGAUGA GCCGUUAGGC GAA AUUUUAAC | 9128 | GUUAAAAUC UGUGACUU | 1986 |
| 3134 | CCAAGCCA CUGAUGA GCCGUUAGGC GAA AGUCACAG | 9129 | CUGUGACUU UGGCUUGG | 1987 |
| 3135 | GCCAAGCC CUGAUGA GCCGUUAGGC GAA AAGUCACA | 9130 | UGUGACUUU GGCUUGGC | 1988 |
| 3140 | CCCGGGCC CUGAUGA GCCGUUAGGC GAA AGCCAAAG | 9131 | CUUUGGCUU GGCCCGGG | 1989 |
| 3151 | UUUAUAAA CUGAUGA GCCGUUAGGC GAA AUCCCGGG | 9132 | CCCGGGAUA UUUAUAAA | 1990 |
| 3153 | UCUUUAUA CUGAUGA GCCGUUAGGC GAA AUAUCCCG | 9133 | CGGGAUAUU UAUAAAGA | 1991 |

134

| | | | | |
|---|---|---|---|---|
| 3154 | AUCUUUAU CUGAUGA GCCGUUAGGC GAA AAUAUCCC | 9134 | GGGAUAUUU AUAAAGAU | 1992 |
| 3155 | GAUCUUUA CUGAUGA GCCGUUAGGC GAA AAAUAUCC | 9135 | GGAUAUUUA UAAAGAUC | 1993 |
| 3157 | UGGAUCUU CUGAUGA GCCGUUAGGC GAA AUAAAUAU | 9136 | AUAUUUAUA AAGAUCCA | 1994 |
| 3163 | AUAAUCUG CUGAUGA GCCGUUAGGC GAA AUCUUUAU | 9137 | AUAAAGAUC CAGAUUAU | 1995 |
| 3169 | UCUGACAU CUGAUGA GCCGUUAGGC GAA AUCUGGAU | 9138 | AUCCAGAUU AUGUCAGA | 1996 |
| 3170 | UUCUGACA CUGAUGA GCCGUUAGGC GAA AAUCUGGA | 9139 | UCCAGAUUA UGUCAGAA | 1997 |
| 3174 | CCUUUUCU CUGAUGA GCCGUUAGGC GAA ACAUAAUC | 9140 | GAUUAUGUC AGAAAAGG | 1998 |
| 3190 | AGGGAGGC CUGAUGA GCCGUUAGGC GAA AGCAUCUC | 9141 | GAGAUGCUC GCCUCCCU | 1999 |
| 3195 | UUCAAAGG CUGAUGA GCCGUUAGGC GAA AGGCGAGC | 9142 | GCUCGCCUC CCUUUGAA | 2000 |
| 3199 | CCAUUUCA CUGAUGA GCCGUUAGGC GAA AGGGAGGC | 9143 | GCCUCCCUU UGAAAUGG | 2001 |
| 3200 | UCCAUUUC CUGAUGA GCCGUUAGGC GAA AAGGGAGG | 9144 | CCUCCCUUU GAAAUGGA | 2002 |
| 3225 | CUGUCAAA CUGAUGA GCCGUUAGGC GAA AUUGUUUC | 9145 | GAAACAAUU UUUGACAG | 2003 |
| 3226 | UCUGUCAA CUGAUGA GCCGUUAGGC GAA AAUUGUUU | 9146 | AAACAAUUU UUGACAGA | 2004 |
| 3227 | CUCUGUCA CUGAUGA GCCGUUAGGC GAA AAAUUGUU | 9147 | AACAAUUUU UGACAGAG | 2005 |
| 3228 | ACUCUGUC CUGAUGA GCCGUUAGGC GAA AAAAUUGU | 9148 | ACAAUUUUU GACAGAGU | 2006 |
| 3239 | GGAUUGUG CUGAUGA GCCGUUAGGC GAA ACACUCUG | 9149 | CAGAGUGUA CACAAUCC | 2007 |
| 3246 | UCACUCUG CUGAUGA GCCGUUAGGC GAA AUUGUGUA | 9150 | UACACAAUC CAGAGUGA | 2008 |
| 3258 | AAAGACCA CUGAUGA GCCGUUAGGC GAA ACGUCACU | 9151 | AGUGACGUC UGGUCUUU | 2009 |
| 3263 | CACCAAAA CUGAUGA GCCGUUAGGC GAA ACCAGACG | 9152 | CGUCUGGUC UUUUGGUG | 2010 |
| 3265 | AACACCAA CUGAUGA GCCGUUAGGC GAA AGACCAGA | 9153 | UCUGGUCUU UUGGUGUU | 2011 |
| 3266 | AAACACCA CUGAUGA GCCGUUAGGC GAA AAGACCAG | 9154 | CUGGUCUUU UGGUGUUU | 2012 |
| 3267 | AAAACACC CUGAUGA GCCGUUAGGC GAA AAAGACCA | 9155 | UGGUCUUUU GGUGUUUU | 2013 |
| 3273 | CACAGCAA CUGAUGA GCCGUUAGGC GAA ACACCAAA | 9156 | UUUGGUGUU UUGCUGUG | 2014 |
| 3274 | CCACAGCA CUGAUGA GCCGUUAGGC GAA AACACCAA | 9157 | UUGGUGUUU UGCUGUGG | 2015 |
| 3275 | CCCACAGC CUGAUGA GCCGUUAGGC GAA AAACACCA | 9158 | UGGUGUUUU GCUGUGGG | 2016 |
| 3288 | AAGGAAAA CUGAUGA GCCGUUAGGC GAA AUUUCCCA | 9159 | UGGGAAAUA UUUUCCUU | 2017 |
| 3290 | CUAAGGAA CUGAUGA GCCGUUAGGC GAA AUAUUUCC | 9160 | GGAAAUAUU UUCCUUAG | 2018 |
| 3291 | CCUAAGGA CUGAUGA GCCGUUAGGC GAA AAUAUUUC | 9161 | GAAAUAUUU UCCUUAGG | 2019 |
| 3292 | ACCUAAGG CUGAUGA GCCGUUAGGC GAA AAAUAUUU | 9162 | AAAUAUUUU CCUUAGGU | 2020 |
| 3293 | CACCUAAG CUGAUGA GCCGUUAGGC GAA AAAAUAUU | 9163 | AAUAUUUUC CUUAGGUG | 2021 |
| 3296 | AAGCACCU CUGAUGA GCCGUUAGGC GAA AGGAAAAU | 9164 | AUUUUCCUU AGGUGCUU | 2022 |
| 3297 | GAAGCACC CUGAUGA GCCGUUAGGC GAA AAGGAAAA | 9165 | UUUUCCUUA GGUGCUUC | 2023 |
| 3304 | AUAUGGAG CUGAUGA GCCGUUAGGC GAA AGCACCUA | 9166 | UAGGUGCUU CUCCAUAU | 2024 |
| 3305 | GAUAUGGA CUGAUGA GCCGUUAGGC GAA AAGCACCU | 9167 | AGGUGCUUC UCCAUAUC | 2025 |
| 3307 | AGGAUAUG CUGAUGA GCCGUUAGGC GAA AGAAGCAC | 9168 | GUGCUUCUC CAUAUCCU | 2026 |

135

| | | | | |
|---|---|---|---|---|
| 3311 | CCCCAGGA CUGAUGA GCCGUUAGGC GAA AUGGAGAA | 9169 | UUCUCCAUA UCCUGGGG | 2027 |
| 3313 | UACCCCAG CUGAUGA GCCGUUAGGC GAA AUAUGGAG | 9170 | CUCCAUAUC CUGGGGUA | 2028 |
| 3321 | UCAAUCUU CUGAUGA GCCGUUAGGC GAA ACCCCAGG | 9171 | CCUGGGGUA AAGAUUGA | 2029 |
| 3327 | UCUUCAUC CUGAUGA GCCGUUAGGC GAA AUCUUUAC | 9172 | GUAAAGAUU GAUGAAGA | 2030 |
| 3338 | GCCUACAA CUGAUGA GCCGUUAGGC GAA AUUCUUCA | 9173 | UGAAGAAUU UUGUAGGC | 2031 |
| 3339 | CGCCUACA CUGAUGA GCCGUUAGGC GAA AAUUCUUC | 9174 | GAAGAAUUU UGUAGGCG | 2032 |
| 3340 | UCGCCUAC CUGAUGA GCCGUUAGGC GAA AAAUUCUU | 9175 | AAGAAUUUU GUAGGCGA | 2033 |
| 3343 | CAAUCGCC CUGAUGA GCCGUUAGGC GAA ACAAAAUU | 9176 | AAUUUUGUA GGCGAUUG | 2034 |
| 3350 | CUUCUUUC CUGAUGA GCCGUUAGGC GAA AUCGCCUA | 9177 | UAGGCGAUU GAAAGAAG | 2035 |
| 3364 | CCUCAUUC CUGAUGA GCCGUUAGGC GAA AGUUCCUU | 9178 | AAGGAACUA GAAUGAGG | 2036 |
| 3382 | UGUAGUAU CUGAUGA GCCGUUAGGC GAA AUCAGGGG | 9179 | CCCCUGAUU AUACUACA | 2037 |
| 3383 | GUGUAGUA CUGAUGA GCCGUUAGGC GAA AAUCAGGG | 9180 | CCCUGAUUA UACUACAC | 2038 |
| 3385 | UGGUGUAG CUGAUGA GCCGUUAGGC GAA AUAAUCAG | 9181 | CUGAUUAUA CUACACCA | 2039 |
| 3388 | UUCUGGUG CUGAUGA GCCGUUAGGC GAA AGUAUAAU | 9182 | AUUAUACUA CACCAGAA | 2040 |
| 3401 | UGGUCUGG CUGAUGA GCCGUUAGGC GAA ACAUUUCU | 9183 | AGAAAUGUA CCAGACCA | 2041 |
| 3439 | GGGUCUCU CUGAUGA GCCGUUAGGC GAA ACUGGGCU | 9184 | AGCCCAGUC AGAGACCC | 2042 |
| 3452 | ACUCUGAA CUGAUGA GCCGUUAGGC GAA ACGUGGGU | 9185 | ACCCACGUU UUCAGAGU | 2043 |
| 3453 | AACUCUGA CUGAUGA GCCGUUAGGC GAA AACGUGGG | 9186 | CCCACGUUU UCAGAGUU | 2044 |
| 3454 | CAACUCUG CUGAUGA GCCGUUAGGC GAA AAACGUGG | 9187 | CCACGUUUU CAGAGUUG | 2045 |
| 3455 | CCAACUCU CUGAUGA GCCGUUAGGC GAA AAAACGUG | 9188 | CACGUUUUC AGAGUUGG | 2046 |
| 3461 | GUUCCACC CUGAUGA GCCGUUAGGC GAA ACUCUGAA | 9189 | UUCAGAGUU GGUGGAAC | 2047 |
| 3472 | AUUUCCCA CUGAUGA GCCGUUAGGC GAA AUGUUCCA | 9190 | UGGAACAUU UGGGAAAU | 2048 |
| 3473 | GAUUUCCC CUGAUGA GCCGUUAGGC GAA AAUGUUCC | 9191 | GGAACAUUU GGGAAAUC | 2049 |
| 3481 | UUGCAAGA CUGAUGA GCCGUUAGGC GAA AUUUCCCA | 9192 | UGGGAAAUC UCUUGCAA | 2050 |
| 3483 | GCUUGCAA CUGAUGA GCCGUUAGGC GAA AGAUUUCC | 9193 | GGAAAUCUC UUGCAAGC | 2051 |
| 3485 | UAGCUUGC CUGAUGA GCCGUUAGGC GAA AGAGAUUU | 9194 | AAAUCUCUU GCAAGCUA | 2052 |
| 3493 | CUGAGCAU CUGAUGA GCCGUUAGGC GAA AGCUUGCA | 9195 | UGCAAGCUA AUGCUCAG | 2053 |
| 3499 | AUCCUGCU CUGAUGA GCCGUUAGGC GAA AGCAUUAG | 9196 | CUAAUGCUC AGCAGGAU | 2054 |
| 3518 | GAACAAUG CUGAUGA GCCGUUAGGC GAA AGUCUUUG | 9197 | CAAAGACUA CAUUGUUC | 2055 |
| 3522 | GGAAGAAC CUGAUGA GCCGUUAGGC GAA AUGUAGUC | 9198 | GACUACAUU GUUCUUCC | 2056 |
| 3525 | AUCGGAAG CUGAUGA GCCGUUAGGC GAA ACAAUGUA | 9199 | UACAUUGUU CUUCCGAU | 2057 |
| 3526 | UAUCGGAA CUGAUGA GCCGUUAGGC GAA AACAAUGU | 9200 | ACAUUGUUC UUCCGAUA | 2058 |
| 3528 | GAUAUCGG CUGAUGA GCCGUUAGGC GAA AGAACAAU | 9201 | AUUGUUCUU CCGAUAUC | 2059 |
| 3529 | UGAUAUCG CUGAUGA GCCGUUAGGC GAA AAGAACAA | 9202 | UUGUUCUUC CGAUAUCA | 2060 |
| 3534 | GUCUCUGA CUGAUGA GCCGUUAGGC GAA AUCGGAAG | 9203 | CUUCCGAUA UCAGAGAC | 2061 |

136

| | | | | |
|---|---|---|---|---|
| 3536 | AAGUCUCU CUGAUGA GCCGUUAGGC GAA AUAUCGGA | 9204 | UCCGAUAUC AGAGACUU | 2062 |
| 3544 | CAUGCUCA CUGAUGA GCCGUUAGGC GAA AGUCUCUG | 9205 | CAGAGACUU UGAGCAUG | 2063 |
| 3545 | CCAUGCUC CUGAUGA GCCGUUAGGC GAA AAGUCUCU | 9206 | AGAGACUUU GAGCAUGG | 2064 |
| 3562 | GAGUCCAG CUGAUGA GCCGUUAGGC GAA AUCCUCUU | 9207 | AAGAGGAUU CUGGACUC | 2065 |
| 3563 | AGAGUCCA CUGAUGA GCCGUUAGGC GAA AAUCCUCU | 9208 | AGAGGAUUC UGGACUCU | 2066 |
| 3570 | GGCAGAGA CUGAUGA GCCGUUAGGC GAA AGUCCAGA | 9209 | UCUGGACUC UCUCUGCC | 2067 |
| 3572 | UAGGCAGA CUGAUGA GCCGUUAGGC GAA AGAGUCCA | 9210 | UGGACUCUC UCUGCCUA | 2068 |
| 3574 | GGUAGGCA CUGAUGA GCCGUUAGGC GAA AGAGAGUC | 9211 | GACUCUCUC UGCCUACC | 2069 |
| 3580 | AGGUGAGG CUGAUGA GCCGUUAGGC GAA AGGCAGAG | 9212 | CUCUGCCUA CCUCACCU | 2070 |
| 3584 | AAACAGGU CUGAUGA GCCGUUAGGC GAA AGGUAGGC | 9213 | GCCUACCUC ACCUGUUU | 2071 |
| 3591 | AUACAGGA CUGAUGA GCCGUUAGGC GAA ACAGGUGA | 9214 | UCACCUGUU UCCUGUAU | 2072 |
| 3592 | CAUACAGG CUGAUGA GCCGUUAGGC GAA AACAGGUG | 9215 | CACCUGUUU CCUGUAUG | 2073 |
| 3593 | CCAUACAG CUGAUGA GCCGUUAGGC GAA AAACAGGU | 9216 | ACCUGUUUC CUGUAUGG | 2074 |
| 3598 | CUCCUCCA CUGAUGA GCCGUUAGGC GAA ACAGGAAA | 9217 | UUUCCUGUA UGGAGGAG | 2075 |
| 3615 | GGGUCACA CUGAUGA GCCGUUAGGC GAA ACUUCCUC | 9218 | GAGGAAGUA UGUGACCC | 2076 |
| 3629 | CAUAAUGG CUGAUGA GCCGUUAGGC GAA AUUUGGGG | 9219 | CCCCAAAUU CCAUUAUG | 2077 |
| 3630 | UCAUAAUG CUGAUGA GCCGUUAGGC GAA AAUUUGGG | 9220 | CCCAAAUUC CAUUAUGA | 2078 |
| 3634 | GUUGUCAU CUGAUGA GCCGUUAGGC GAA AUGGAAUU | 9221 | AAUUCCAUU AUGACAAC | 2079 |
| 3635 | UGUUGUCA CUGAUGA GCCGUUAGGC GAA AAUGGAAU | 9222 | AUUCCAUUA UGACAACA | 2080 |
| 3654 | UACUGACU CUGAUGA GCCGUUAGGC GAA AUUCCUGC | 9223 | GCAGGAAUC AGUCAGUA | 2081 |
| 3658 | CAGAUACU CUGAUGA GCCGUUAGGC GAA ACUGAUUC | 9224 | GAAUCAGUC AGUAUCUG | 2082 |
| 3662 | UCUGCAGA CUGAUGA GCCGUUAGGC GAA ACUGACUG | 9225 | CAGUCAGUA UCUGCAGA | 2083 |
| 3664 | GUUCUGCA CUGAUGA GCCGUUAGGC GAA AUACUGAC | 9226 | GUCAGUAUC UGCAGAAC | 2084 |
| 3676 | CUUUCGCU CUGAUGA GCCGUUAGGC GAA ACUGUUCU | 9227 | AGAACAGUA AGCGAAAG | 2085 |
| 3702 | AAUGUUUU CUGAUGA GCCGUUAGGC GAA ACACUCAC | 9228 | GUGAGUGUA AAAACAUU | 2086 |
| 3710 | UAUCUUCA CUGAUGA GCCGUUAGGC GAA AUGUUUUU | 9229 | AAAAACAUU UGAAGAUA | 2087 |
| 3711 | AUAUCUUC CUGAUGA GCCGUUAGGC GAA AAUGUUUU | 9230 | AAAACAUUU GAAGAUAU | 2088 |
| 3718 | UAACGGGA CUGAUGA GCCGUUAGGC GAA AUCUUCAA | 9231 | UUGAAGAUA UCCCGUUA | 2089 |
| 3720 | UCUAACGG CUGAUGA GCCGUUAGGC GAA AUAUCUUC | 9232 | GAAGAUAUC CCGUUAGA | 2090 |
| 3725 | GUUCUUCU CUGAUGA GCCGUUAGGC GAA ACGGGAUA | 9233 | UAUCCCGUU AGAAGAAC | 2091 |
| 3726 | GGUUCUUC CUGAUGA GCCGUUAGGC GAA AACGGGAU | 9234 | AUCCCGUUA GAAGAACC | 2092 |
| 3741 | AUUACUUU CUGAUGA GCCGUUAGGC GAA ACUUCUGG | 9235 | CCAGAAGUA AAAGUAAU | 2093 |
| 3747 | UCUGGGAU CUGAUGA GCCGUUAGGC GAA ACUUUUAC | 9236 | GUAAAAGUA AUCCCAGA | 2094 |
| 3750 | UCAUCUGG CUGAUGA GCCGUUAGGC GAA AUUACUUU | 9237 | AAAGUAAUC CCAGAUGA | 2095 |
| 3778 | AAGAACCA CUGAUGA GCCGUUAGGC GAA ACCACUGU | 9238 | ACAGUGGUA UGGUUCUU | 2096 |

137

| | | | | |
|---|---|---|---|---|
| 3783 | GAGGCAAG CUGAUGA GCCGUUAGGC GAA ACCAUACC | 9239 | GGUAUGGUU CUUGCCUC | 2097 |
| 3784 | UGAGGCAA CUGAUGA GCCGUUAGGC GAA AACCAUAC | 9240 | GUAUGGUUC UUGCCUCA | 2098 |
| 3786 | UCUGAGGC CUGAUGA GCCGUUAGGC GAA AGAACCAU | 9241 | AUGGUUCUU GCCUCAGA | 2099 |
| 3791 | GCUCUUCU CUGAUGA GCCGUUAGGC GAA AGGCAAGA | 9242 | UCUUGCCUC AGAAGAGC | 2100 |
| 3808 | GUCUUCCA CUGAUGA GCCGUUAGGC GAA AGUUUUCA | 9243 | UGAAAACUU UGGAAGAC | 2101 |
| 3809 | UGUCUUCC CUGAUGA GCCGUUAGGC GAA AAGUUUUC | 9244 | GAAAACUUU GGAAGACA | 2102 |
| 3827 | AUGGAGAU CUGAUGA GCCGUUAGGC GAA AUUUGGUU | 9245 | AACCAAAUU AUCUCCAU | 2103 |
| 3828 | GAUGGAGA CUGAUGA GCCGUUAGGC GAA AAUUUGGU | 9246 | ACCAAAUUA UCUCCAUC | 2104 |
| 3830 | AAGAUGGA CUGAUGA GCCGUUAGGC GAA AUAAUUUG | 9247 | CAAAUUAUC UCCAUCUU | 2105 |
| 3832 | AAAAGAUG CUGAUGA GCCGUUAGGC GAA AGAUAAUU | 9248 | AAUUAUCUC CAUCUUUU | 2106 |
| 3836 | CACCAAAA CUGAUGA GCCGUUAGGC GAA AUGGAGAU | 9249 | AUCUCCAUC UUUUGGUG | 2107 |
| 3838 | UCCACCAA CUGAUGA GCCGUUAGGC GAA AGAUGGAG | 9250 | CUCCAUCUU UUGGUGGA | 2108 |
| 3839 | UUCCACCA CUGAUGA GCCGUUAGGC GAA AAGAUGGA | 9251 | UCCAUCUUU UGGUGGAA | 2109 |
| 3840 | AUUCCACC CUGAUGA GCCGUUAGGC GAA AAAGAUGG | 9252 | CCAUCUUUU GGUGGAAU | 2110 |
| 3872 | AUGCCACA CUGAUGA GCCGUUAGGC GAA ACUCCCUG | 9253 | CAGGGAGUC UGUGGCAU | 2111 |
| 3881 | AGCCUUCA CUGAUGA GCCGUUAGGC GAA AUGCCACA | 9254 | UGUGGCAUC UGAAGGCU | 2112 |
| 3890 | UCUGGUUU CUGAUGA GCCGUUAGGC GAA AGCCUUCA | 9255 | UGAAGGCUC AAACCAGA | 2113 |
| 3908 | CGGACUGG CUGAUGA GCCGUUAGGC GAA AGCCGCUU | 9256 | AAGCGGCUA CCAGUCCG | 2114 |
| 3914 | GAUAUCCG CUGAUGA GCCGUUAGGC GAA ACUGGUAG | 9257 | CUACCAGUC CGGAUAUC | 2115 |
| 3920 | CGGAGUGA CUGAUGA GCCGUUAGGC GAA AUCCGGAC | 9258 | GUCCGGAUA UCACUCCG | 2116 |
| 3922 | AUCGGAGU CUGAUGA GCCGUUAGGC GAA AUAUCCGG | 9259 | CCGGAUAUC ACUCCGAU | 2117 |
| 3926 | UGUCAUCG CUGAUGA GCCGUUAGGC GAA AGUGAUAU | 9260 | AUAUCACUC CGAUGACA | 2118 |
| 3950 | CACUGGAG CUGAUGA GCCGUUAGGC GAA ACACGGUG | 9261 | CACCGUGUA CUCCAGUG | 2119 |
| 3953 | CCUCACUG CUGAUGA GCCGUUAGGC GAA AGUACACG | 9262 | CGUGUACUC CAGUGAGG | 2120 |
| 3972 | AGCUUUAA CUGAUGA GCCGUUAGGC GAA AGUUCUGC | 9263 | GCAGAACUU UUAAAGCU | 2121 |
| 3973 | CAGCUUUA CUGAUGA GCCGUUAGGC GAA AAGUUCUG | 9264 | CAGAACUUU UAAAGCUG | 2122 |
| 3974 | UCAGCUUU CUGAUGA GCCGUUAGGC GAA AAAGUUCU | 9265 | AGAACUUUU AAAGCUGA | 2123 |
| 3975 | AUCAGCUU CUGAUGA GCCGUUAGGC GAA AAAAGUUC | 9266 | GAACUUUUA AAGCUGAU | 2124 |
| 3984 | CCAAUCUC CUGAUGA GCCGUUAGGC GAA AUCAGCUU | 9267 | AAGCUGAUA GAGAUUGG | 2125 |
| 3990 | UGCACUCC CUGAUGA GCCGUUAGGC GAA AUCUCUAU | 9268 | AUAGAGAUU GGAGUGCA | 2126 |
| 4006 | GGCUGUGC CUGAUGA GCCGUUAGGC GAA ACCGGUUU | 9269 | AAACCGGUA GCACAGCC | 2127 |
| 4020 | GGCUGGAG CUGAUGA GCCGUUAGGC GAA AUCUGGGC | 9270 | GCCCAGAUU CUCCAGCC | 2128 |
| 4021 | AGGCUGGA CUGAUGA GCCGUUAGGC GAA AAUCUGGG | 9271 | CCCAGAUUC UCCAGCCU | 2129 |
| 4023 | UCAGGCUG CUGAUGA GCCGUUAGGC GAA AGAAUCUG | 9272 | CAGAUUCUC CAGCCUGA | 2130 |
| 4052 | CAGGAGGA CUGAUGA GCCGUUAGGC GAA AGCUCAGU | 9273 | ACUGAGCUC UCCUCCUG | 2131 |

| | | | | |
|---|---|---|---|---|
| 4054 | AACAGGAG CUGAUGA GCCGUUAGGC GAA AGAGCUCA | 9274 | UGAGCUCUC CUCCUGUU | 2132 |
| 4057 | UUAAACAG CUGAUGA GCCGUUAGGC GAA AGGAGAGC | 9275 | GCUCUCCUC CUGUUUAA | 2133 |
| 4062 | UCCUUUUA CUGAUGA GCCGUUAGGC GAA ACAGGAGG | 9276 | CCUCCUGUU UAAAAGGA | 2134 |
| 4063 | UUCCUUUU CUGAUGA GCCGUUAGGC GAA AACAGGAG | 9277 | CUCCUGUUU AAAAGGAA | 2135 |
| 4064 | CUUCCUUU CUGAUGA GCCGUUAGGC GAA AAACAGGA | 9278 | UCCUGUUUA AAAGGAAG | 2136 |
| 4076 | GGGGUGUG CUGAUGA GCCGUUAGGC GAA AUGCUUCC | 9279 | GGAAGCAUC CACACCCC | 2137 |
| 4089 | AUGUCCGG CUGAUGA GCCGUUAGGC GAA AGUUGGGG | 9280 | CCCCAACUC CCGGACAU | 2138 |
| 4098 | UCUCAUGU CUGAUGA GCCGUUAGGC GAA AUGUCCGG | 9281 | CCGGACAUC ACAUGAGA | 2139 |
| 4110 | UCUGAGCA CUGAUGA GCCGUUAGGC GAA ACCUCUCA | 9282 | UGAGAGGUC UGCUCAGA | 2140 |
| 4115 | CAAAAUCU CUGAUGA GCCGUUAGGC GAA AGCAGACC | 9283 | GGUCUGCUC AGAUUUUG | 2141 |
| 4120 | CACUUCAA CUGAUGA GCCGUUAGGC GAA AUCUGAGC | 9284 | GCUCAGAUU UUGAAGUG | 2142 |
| 4121 | ACACUUCA CUGAUGA GCCGUUAGGC GAA AAUCUGAG | 9285 | CUCAGAUUU UGAAGUGU | 2143 |
| 4122 | AACACUUC CUGAUGA GCCGUUAGGC GAA AAAUCUGA | 9286 | UCAGAUUUU GAAGUGUU | 2144 |
| 4130 | GAAAGAAC CUGAUGA GCCGUUAGGC GAA ACACUUCA | 9287 | UGAAGUGUU GUUCUUUC | 2145 |
| 4133 | GUGGAAAG CUGAUGA GCCGUUAGGC GAA ACAACACU | 9288 | AGUGUUGUU CUUUCCAC | 2146 |
| 4134 | GGUGGAAA CUGAUGA GCCGUUAGGC GAA AACAACAC | 9289 | GUGUUGUUC UUUCCACC | 2147 |
| 4136 | CUGGUGGA CUGAUGA GCCGUUAGGC GAA AGAACAAC | 9290 | GUUGUUCUU UCCACCAG | 2148 |
| 4137 | GCUGGUGG CUGAUGA GCCGUUAGGC GAA AAGAACAA | 9291 | UUGUUCUUU CCACCAGC | 2149 |
| 4138 | UGCUGGUG CUGAUGA GCCGUUAGGC GAA AAAGAACA | 9292 | UGUUCUUUC CACCAGCA | 2150 |
| 4153 | AAUGCGGC CUGAUGA GCCGUUAGGC GAA ACUUCCUG | 9293 | CAGGAAGUA GCCGCAUU | 2151 |
| 4161 | GAAAAUCA CUGAUGA GCCGUUAGGC GAA AUGCGGCU | 9294 | AGCCGCAUU UGAUUUUC | 2152 |
| 4162 | UGAAAAUC CUGAUGA GCCGUUAGGC GAA AAUGCGGC | 9295 | GCCGCAUUU GAUUUUCA | 2153 |
| 4166 | GAAAUGAA CUGAUGA GCCGUUAGGC GAA AUCAAAUG | 9296 | CAUUUGAUU UUCAUUUC | 2154 |
| 4167 | CGAAAUGA CUGAUGA GCCGUUAGGC GAA AAUCAAAU | 9297 | AUUUGAUUU UCAUUUCG | 2155 |
| 4168 | UCGAAAUG CUGAUGA GCCGUUAGGC GAA AAAUCAAA | 9298 | UUUGAUUUU CAUUUCGA | 2156 |
| 4169 | GUCGAAAU CUGAUGA GCCGUUAGGC GAA AAAAUCAA | 9299 | UUGAUUUUC AUUUCGAC | 2157 |
| 4172 | GUUGUCGA CUGAUGA GCCGUUAGGC GAA AUGAAAAU | 9300 | AUUUUCAUU UCGACAAC | 2158 |
| 4173 | UGUUGUCG CUGAUGA GCCGUUAGGC GAA AAUGAAAA | 9301 | UUUUCAUUU CGACAACA | 2159 |
| 4174 | CUGUUGUC CUGAUGA GCCGUUAGGC GAA AAAUGAAA | 9302 | UUUCAUUUC GACAACAG | 2160 |
| 4194 | UGCAGUCC CUGAUGA GCCGUUAGGC GAA AGGUCCUU | 9303 | AAGGACCUC GGACUGCA | 2161 |
| 4214 | GCCUAGAA CUGAUGA GCCGUUAGGC GAA AGCUGGCU | 9304 | AGCCAGCUC UUCUAGGC | 2162 |
| 4216 | AAGCCUAG CUGAUGA GCCGUUAGGC GAA AGAGCUGG | 9305 | CCAGCUCUU CUAGGCUU | 2163 |
| 4217 | CAAGCCUA CUGAUGA GCCGUUAGGC GAA AAGAGCUG | 9306 | CAGCUCUUC UAGGCUUG | 2164 |
| 4219 | CACAAGCC CUGAUGA GCCGUUAGGC GAA AGAAGAGC | 9307 | GCUCUUCUA GGCUUGUG | 2165 |

Underlined region can be any X sequence or linker, as described herein.

139

Table V: Human KDR VEGF Receptor-Hairpin Ribozyme and Substrate Sequences 237.198

| nt. Position | Hairpin Ribozyme Sequence | Rz Seq ID No. | Substrate | Seq ID No. |
|---|---|---|---|---|
| 11 | CGACGGCC AGAA GCACCU ACCAGAGAAACACACGUUGUGGUACAUUACCUGGUA | 9308 | AGGUGCU GCU GGCCGUCG | 2166 |
| 18 | CACAGGGC AGAA GCCAGC ACCAGAGAAACACACGUUGUGGUACAUUACCUGGUA | 9309 | GCUGGCC GUC GCCCUGUG | 2167 |
| 51 | CCCACAGA AGAA GCCCGG ACCAGAGAAACACACGUUGUGGUACAUUACCUGGUA | 9310 | CCGGGCC GCC UCUGUGGG | 2168 |
| 86 | UGAGCCUG AGAA GAUCAA ACCAGAGAAACACACGUUGUGGUACAUUACCUGGUA | 9311 | UUGAUCU GCC CAGGCUCA | 2169 |
| 318 | GAGGCCAA AGAA GUUUCC ACCAGAGAAACACACGUUGUGGUACAUUACCUGGUA | 9312 | GGAAACU GAC UUGGCCUC | 2170 |
| 358 | AAAUGGAG AGAA GUAAUC ACCAGAGAAACACACGUUGUGGUACAUUACCUGGUA | 9313 | GAUUACA GAU CUCCAUUU | 2171 |
| 510 | CUGUUACC AGAA GGAACA ACCAGAGAAACACACGUUGUGGUACAUUACCUGGUA | 9314 | UGUUCCU GAU GGUAACAG | 2172 |
| 623 | ACAUAAUA AGAA GGUAAC ACCAGAGAAACACACGUUGUGGUACAUUACCUGGUA | 9315 | GUUACCA GUC UAUUAUGU | 2173 |
| 683 | UUCCAUGA AGAA GACUCA ACCAGAGAAACACACGUUGUGGUACAUUACCUGGUA | 9316 | UGAGUCC GUC UCAUGGAA | 2174 |
| 705 | UUUUCUCC AGAA GAUAGU ACCAGAGAAACACACGUUGUGGUACAUUACCUGGUA | 9317 | ACUAUCU GUU GGAGAAAA | 2175 |
| 833 | CACUCCCA AGAA GGGUUU ACCAGAGAAACACACGUUGUGGUACAUUACCUGGUA | 9318 | AAACCCA GUC UGGGAGUG | 2176 |
| 932 | UCUUGGUC AGAA GCCCAC ACCAGAGAAACACACGUUGUGGUACAUUACCUGGUA | 9319 | GUGGGCU GAU GACCAAGA | 2177 |
| 1142 | CCAUAAUC AGAA GUACAU ACCAGAGAAACACACGUUGUGGUACAUUACCUGGUA | 9320 | AUGUACU GAC GAUUAUGG | 2178 |
| 1259 | UCUCACCA AGAA GGGGUG ACCAGAGAAACACACGUUGUGGUACAUUACCUGGUA | 9321 | CACCCCA GAU UGGUGAGA | 2179 |
| 1332 | AUGGCAUA AGAA GUACAU ACCAGAGAAACACACGUUGUGGUACAUUACCUGGUA | 9322 | AUGUACG GUC UAUGCCAU | 2180 |
| 1376 | CUUCCUCC AGAA GCCAAU ACCAGAGAAACACACGUUGUGGUACAUUACCUGGUA | 9323 | AUUGGCA GUU GGAGGAAG | 2181 |
| 1413 | GUCACUGA AGAA GCUUGG ACCAGAGAAACACACGUUGUGGUACAUUACCUGGUA | 9324 | CCAAGCU GUC UCAGUGAC | 2182 |
| 1569 | UUGUACAA AGAA GACACA ACCAGAGAAACACACGUUGUGGUACAUUACCUGGUA | 9325 | UGUGUCA GCU UUGUACAA | 2183 |
| 1673 | GCUCAGUG AGAA GCAUGU ACCAGAGAAACACACGUUGUGGUACAUUACCUGGUA | 9326 | ACAUGCA GCC CACUGAGC | 2184 |
| 1717 | AAACGUAG AGAA GUCUGC ACCAGAGAAACACACGUUGUGGUACAUUACCUGGUA | 9327 | GCAGACA GAU CUACGUUU | 2185 |
| 1760 | UUGGCAGA AGAA GUGGGC ACCAGAGAAACACACGUUGUGGUACAUUACCUGGUA | 9328 | GCCCACA GCC UCUGCCAA | 2186 |
| 1797 | UUCUUGCA AGAA GGUGUG ACCAGAGAAACACACGUUGUGGUACAUUACCUGGUA | 9329 | CACACCU GUU UGCAAGAA | 2187 |
| 1918 | UUGAGCAA AGAA GACAUA ACCAGAGAAACACACGUUGUGGUACAUUACCUGGUA | 9330 | UAUGUCU GCC UUGCUCAA | 2188 |
| 1967 | GGACUGUG AGAA GCCUGA ACCAGAGAAACACACGUUGUGGUACAUUACCUGGUA | 9331 | UCAGGCA GCU CACAGUCC | 2189 |
| 1974 | CGCUCUAG AGAA GUGAGC ACCAGAGAAACACACGUUGUGGUACAUUACCUGGUA | 9332 | GCUCACA GUC CUAGAGCG | 2190 |
| 2021 | UACUUGUC AGAA GAUUCU ACCAGAGAAACACACGUUGUGGUACAUUACCUGGUA | 9333 | AGAAUCA GAC GACAAGUA | 2191 |
| 2084 | ACCACAUG AGAA GUGGAG ACCAGAGAAACACACGUUGUGGUACAUUACCUGGUA | 9334 | CUCCACA GAU CAUGUGGU | 2192 |
| 2418 | GGGAGUUC AGAA GGAUCC ACCAGAGAAACACACGUUGUGGUACAUUACCUGGUA | 9335 | GGAUCCA GAU GAACUCCC | 2193 |
| 2453 | CAUCAUAA AGAA GUCGUU ACCAGAGAAACACACGUUGUGGUACAUUACCUGGUA | 9336 | AACGACU GCC UUAUGAUG | 2194 |
| 2492 | CUAGGUUC AGAA GGUCUC ACCAGAGAAACACACGUUGUGGUACAUUACCUGGUA | 9337 | GAGACCG GCU GAACCUAG | 2195 |
| 2547 | CCAAAGGC AGAA GCUUCA ACCAGAGAAACACACGUUGUGGUACAUUACCUGGUA | 9338 | UGAAGCA GAU GCCUUUGG | 2196 |

| | | | | |
|---|---|---|---|---|
| 2765 | GGUAAGUG AGAA GGUUUC ACCAGAGAAACACACGUUGUGGUACAUUACCUGGUA | 9339 | GAAACCU GUC CACUUACC | 2197 |
| 2914 | AAAUCCAG AGAA GGCUGA ACCAGAGAAACACACGUUGUGGUACAUUACCUGGUA | 9340 | UCAGCCA GCU CUGGAUUU | 2198 |
| 2993 | GCUCCAAG AGAA GGAAGU ACCAGAGAAACACACGUUGUGGUACAUUACCUGGUA | 9341 | ACUUCCU GAC CUUGGAGC | 2199 |
| 3019 | CACUUGGA AGAA GUAACA ACCAGAGAAACACACGUUGUGGUACAUUACCUGGUA | 9342 | UGUUACA GCU UCCAAGUG | 2200 |
| 3165 | CUGACAUA AGAA GGAUCU ACCAGAGAAACACACGUUGUGGUACAUUACCUGGUA | 9343 | AGAUCCA GAU UAUGUCAG | 2201 |
| 3378 | GUAGUAUA AGAA GGGGCC ACCAGAGAAACACACGUUGUGGUACAUUACCUGGUA | 9344 | GGCCCCU GAU UAUACUAC | 2202 |
| 3404 | CCAGCAUG AGAA GGUACA ACCAGAGAAACACACGUUGUGGUACAUUACCUGGUA | 9345 | UGUACCA GAC CAUGCUGG | 2203 |
| 3418 | CCCGUGCC AGAA GUCCAG ACCAGAGAAACACACGUUGUGGUACAUUACCUGGUA | 9346 | CUGGACU GCU GGCACGGG | 2204 |
| 3575 | GUGAGGUA AGAA GAGAGA ACCAGAGAAACACACGUUGUGGUACAUUACCUGGUA | 9347 | UCUCUCU GCC UACCUCAC | 2205 |
| 3588 | AUACAGGA AGAA GGUGAG ACCAGAGAAACACACGUUGUGGUACAUUACCUGGUA | 9348 | CUCACCU GUU UCCUGUAU | 2206 |
| 3689 | CACUCACA AGAA GGCUCU ACCAGAGAAACACACGUUGUGGUACAUUACCUGGUA | 9349 | AGAGCCG GCC UGUGAGUG | 2207 |
| 3753 | UGGUUGUC AGAA GGGAUU ACCAGAGAAACACACGUUGUGGUACAUUACCUGGUA | 9350 | AAUCCCA GAU GACAACCA | 2208 |
| 3764 | CACUGUCC AGAA GGUUGU ACCAGAGAAACACACGUUGUGGUACAUUACCUGGUA | 9351 | ACAACCA GAC GGACAGUG | 2209 |
| 3911 | GAUAUCCG AGAA GGUAGC ACCAGAGAAACACACGUUGUGGUACAUUACCUGGUA | 9352 | GCUACCA GUC CGGAUAUC | 2210 |
| 3927 | UCUGUGUC AGAA GAGUGA ACCAGAGAAACACACGUUGUGGUACAUUACCUGGUA | 9353 | UCACUCC GAU GACACAGA | 2211 |
| 4011 | AGAAUCUG AGAA GUGCUA ACCAGAGAAACACACGUUGUGGUACAUUACCUGGUA | 9354 | UAGCACA GCC CAGAUUCU | 2212 |
| 4016 | GCUGGAGA AGAA GGGCUG ACCAGAGAAACACACGUUGUGGUACAUUACCUGGUA | 9355 | CAGCCCA GAU UCUCCAGC | 2213 |
| 4025 | CCGUGUCA AGAA GGAGAA ACCAGAGAAACACACGUUGUGGUACAUUACCUGGUA | 9356 | UUCUCCA GCC UGACACGG | 2214 |
| 4059 | UCCUUUUA AGAA GGAGGA ACCAGAGAAACACACGUUGUGGUACAUUACCUGGUA | 9357 | UCCUCCU GUU UAAAAGGA | 2215 |
| 4111 | AAAAUCUG AGAA GACCUC ACCAGAGAAACACACGUUGUGGUACAUUACCUGGUA | 9358 | GAGGUCU GCU CAGAUUUU | 2216 |
| 4116 | ACUUCAAA AGAA GAGCAG ACCAGAGAAACACACGUUGUGGUACAUUACCUGGUA | 9359 | CUGCUCA GAU UUUGAAGU | 2217 |
| 4195 | UCCCUGCA AGAA GAGGUC ACCAGAGAAACACACGUUGUGGUACAUUACCUGGUA | 9360 | GACCUCG GAC UGCAGGGA | 2218 |
| 4210 | CCUAGAAG AGAA GGCUCC ACCAGAGAAACACACGUUGUGGUACAUUACCUGGUA | 9361 | GGAGCCA GCU CUUCUAGG | 2219 |

Table VI: Mouse *flk*-1 VEGF Receptor-Hammerhead Ribozyme and Substrate sequence 237.198

| nt. Position | HH Ribozyme Sequence | Rz Seq ID No. | Substrate | Seq ID No. |
|---|---|---|---|---|
| 13 | CCGUACCC CUGAUGA GCCGUUAGGC GAA AUUCGCCC | 9362 | GGGCGAAUU GGGUACGG | 2220 |
| 18 | GGGUCCCG CUGAUGA GCCGUUAGGC GAA ACCCAAUU | 9363 | AAUUGGGUA CGGGACCC | 2221 |
| 31 | UCGACCUC CUGAUGA GCCGUUAGGC GAA AGGGGGGU | 9364 | ACCCCCCUC GAGGUCGA | 2222 |
| 37 | AUACCGUC CUGAUGA GCCGUUAGGC GAA ACCUCGAG | 9365 | CUCGAGGUC GACGGUAU | 2223 |
| 44 | CUUAUCGA CUGAUGA GCCGUUAGGC GAA ACCGUCGA | 9366 | UCGACGGUA UCGAUAAG | 2224 |
| 46 | AGCUUAUC CUGAUGA GCCGUUAGGC GAA AUACCGUC | 9367 | GACGGUAUC GAUAAGCU | 2225 |
| 50 | AUCAAGCU CUGAUGA GCCGUUAGGC GAA AUCGAUAC | 9368 | GUAUCGAUA AGCUUGAU | 2226 |
| 55 | UCGAUAUC CUGAUGA GCCGUUAGGC GAA AGCUUAUC | 9369 | GAUAAGCUU GAUAUCGA | 2227 |
| 59 | GAAUUCGA CUGAUGA GCCGUUAGGC GAA AUCAAGCU | 9370 | AGCUUGAUA UCGAAUUC | 2228 |
| 61 | CCGAAUUC CUGAUGA GCCGUUAGGC GAA AUAUCAAG | 9371 | CUUGAUAUC GAAUUCGG | 2229 |
| 66 | UGGGCCCG CUGAUGA GCCGUUAGGC GAA AUUCGAUA | 9372 | UAUCGAAUU CGGGCCCA | 2230 |
| 67 | CUGGGCCC CUGAUGA GCCGUUAGGC GAA AAUUCGAU | 9373 | AUCGAAUUC GGGCCCAG | 2231 |
| 83 | GGCUGCGG CUGAUGA GCCGUUAGGC GAA ACACAGUC | 9374 | GACUGUGUC CCGCAGCC | 2232 |
| 97 | AGCCAGGU CUGAUGA GCCGUUAGGC GAA AUCCCGGC | 9375 | GCCGGGAUA ACCUGGCU | 2233 |
| 114 | GUCCGCGG CUGAUGA GCCGUUAGGC GAA AUCGGGUC | 9376 | GACCCGAUU CCGCGGAC | 2234 |
| 115 | UGUCCGCG CUGAUGA GCCGUUAGGC GAA AAUCGGGU | 9377 | ACCCGAUUC CGCGGACA | 2235 |
| 169 | ACCGGGGA CUGAUGA GCCGUUAGGC GAA AGCGCGGG | 9378 | CCCGCGCUC UCCCCGGU | 2236 |
| 171 | AGACCGGG CUGAUGA GCCGUUAGGC GAA AGAGCGCG | 9379 | CGCGCUCUC CCCGGUCU | 2237 |
| 178 | CAGCGCAA CUGAUGA GCCGUUAGGC GAA ACCGGGGA | 9380 | UCCCCGGUC UUGCGCUG | 2238 |
| 180 | CGCAGCGC CUGAUGA GCCGUUAGGC GAA AGACCGGG | 9381 | CCCGGUCUU GCGCUGCG | 2239 |
| 197 | AGAGGCGG CUGAUGA GCCGUUAGGC GAA AUGGCCCC | 9382 | GGGGCCAUA CCGCCUCU | 2240 |
| 204 | AAGUCACA CUGAUGA GCCGUUAGGC GAA AGGCGGUA | 9383 | UACCGCCUC UGUGACUU | 2241 |
| 212 | CCGCAAAG CUGAUGA GCCGUUAGGC GAA AGUCACAG | 9384 | CUGUGACUU CUUUGCGG | 2242 |
| 213 | CCCGCAAA CUGAUGA GCCGUUAGGC GAA AAGUCACA | 9385 | UGUGACUUC UUUGCGGG | 2243 |
| 215 | GGCCCGCA CUGAUGA GCCGUUAGGC GAA AGAAGUCA | 9386 | UGACUUCUU UGCGGGCC | 2244 |
| 216 | UGGCCCGC CUGAUGA GCCGUUAGGC GAA AAGAAGUC | 9387 | GACUUCUUU GCGGGCCA | 2245 |
| 241 | CAGGCACA CUGAUGA GCCGUUAGGC GAA ACUCCUUC | 9388 | GAAGGAGUC UGUGCCUG | 2246 |
| 262 | UGGGCACA CUGAUGA GCCGUUAGGC GAA AGCCCAGU | 9389 | ACUGGGCUC UGUGCCCA | 2247 |
| 306 | GCGACAGC CUGAUGA GCCGUUAGGC GAA AGCAGCGC | 9390 | GCGCUGCUA GCUGUCGC | 2248 |
| 312 | CACAGAGC CUGAUGA GCCGUUAGGC GAA ACAGCUAG | 9391 | CUAGCUGUC GCUCUGUG | 2249 |
| 316 | GAACCACA CUGAUGA GCCGUUAGGC GAA AGCGACAG | 9392 | CUGUCGCUC UGUGGUUC | 2250 |
| 323 | CCACGCAG CUGAUGA GCCGUUAGGC GAA ACCACAGA | 9393 | UCUGUGGUU CUGCGUGG | 2251 |
| 324 | UCCACGCA CUGAUGA GCCGUUAGGC GAA AACCACAG | 9394 | CUGUGGUUC UGCGUGGA | 2252 |
| 347 | AACCCACA CUGAUGA GCCGUUAGGC GAA AGGCGGCU | 9395 | AGCCGCCUC UGUGGGUU | 2253 |
| 355 | GCCAGUCA CUGAUGA GCCGUUAGGC GAA ACCCACAG | 9396 | CUGUGGGUU UGACUGGC | 2254 |

142

| | | | | |
|---|---|---|---|---|
| 356 | CGCCAGUC CUGAUGA GCCGUUAGGC GAA AACCCACA | 9397 | UGUGGGUUU GACUGGCG | 2255 |
| 367 | AUGGAGAA CUGAUGA GCCGUUAGGC GAA AUCGCCAG | 9398 | CUGGCGAUU UUCUCCAU | 2256 |
| 368 | GAUGGAGA CUGAUGA GCCGUUAGGC GAA AAUCGCCA | 9399 | UGGCGAUUU UCUCCAUC | 2257 |
| 369 | GGAUGGAG CUGAUGA GCCGUUAGGC GAA AAAUCGCC | 9400 | GGCGAUUUU CUCCAUCC | 2258 |
| 370 | GGGAUGGA CUGAUGA GCCGUUAGGC GAA AAAAUCGC | 9401 | GCGAUUUUC UCCAUCCC | 2259 |
| 372 | GGGGGAUG CUGAUGA GCCGUUAGGC GAA AGAAAAUC | 9402 | GAUUUUCUC CAUCCCCC | 2260 |
| 376 | CUUGGGGG CUGAUGA GCCGUUAGGC GAA AUGGAGAA | 9403 | UUCUCCAUC CCCCCAAG | 2261 |
| 387 | UGUGUGCU CUGAUGA GCCGUUAGGC GAA AGCUUGGG | 9404 | CCCAAGCUC AGCACACA | 2262 |
| 405 | AUUGUCAG CUGAUGA GCCGUUAGGC GAA AUGUCUUU | 9405 | AAAGACAUA CUGACAAU | 2263 |
| 414 | UUUGCCAA CUGAUGA GCCGUUAGGC GAA AUUGUCAG | 9406 | CUGACAAUU UUGGCAAA | 2264 |
| 415 | AUUUGCCA CUGAUGA GCCGUUAGGC GAA AAUUGUCA | 9407 | UGACAAUUU UGGCAAAU | 2265 |
| 416 | UAUUUGCC CUGAUGA GCCGUUAGGC GAA AAAUUGUC | 9408 | GACAAUUUU GGCAAAUA | 2266 |
| 424 | AAGGGUUG CUGAUGA GCCGUUAGGC GAA AUUUGCCA | 9409 | UGGCAAAUA CAACCCUU | 2267 |
| 432 | GUAAUCUG CUGAUGA GCCGUUAGGC GAA AGGGUUGU | 9410 | ACAACCCUU CAGAUUAC | 2268 |
| 433 | AGUAAUCU CUGAUGA GCCGUUAGGC GAA AAGGGUUG | 9411 | CAACCCUUC AGAUUACU | 2269 |
| 438 | CUGCAAGU CUGAUGA GCCGUUAGGC GAA AUCUGAAG | 9412 | CUUCAGAUU ACUUGCAG | 2270 |
| 439 | CCUGCAAG CUGAUGA GCCGUUAGGC GAA AAUCUGAA | 9413 | UUCAGAUUA CUUGCAGG | 2271 |
| 442 | UCCCCUGC CUGAUGA GCCGUUAGGC GAA AGUAAUCU | 9414 | AGAUUACUU GCAGGGGA | 2272 |
| 471 | UUGGGCCA CUGAUGA GCCGUUAGGC GAA AGCCAGUC | 8676 | GACUGGCUU UGGCCCAA | 1534 |
| 472 | AUUGGGCC CUGAUGA GCCGUUAGGC GAA AAGCCAGU | 8677 | ACUGGCUUU GGCCCAAU | 1535 |
| 484 | AUCACGCU CUGAUGA GCCGUUAGGC GAA AGCAUUGG | 9415 | CCAAUGCUC AGCGUGAU | 2273 |
| 493 | UUCCUCAG CUGAUGA GCCGUUAGGC GAA AUCACGCU | 9416 | AGCGUGAUU CUGAGGAA | 2274 |
| 494 | UUUCCUCA CUGAUGA GCCGUUAGGC GAA AAUCACGC | 9417 | GCGUGAUUC UGAGGAAA | 2275 |
| 507 | GUCACCAA CUGAUGA GCCGUUAGGC GAA ACCCUUUC | 9418 | GAAAGGGUA UUGGUGAC | 2276 |
| 509 | CAGUCACC CUGAUGA GCCGUUAGGC GAA AUACCCUU | 9419 | AAGGGUAUU GGUGACUG | 2277 |
| 538 | GCAGAAGA CUGAUGA GCCGUUAGGC GAA ACUGUCAC | 9420 | GUGACAGUA UCUUCUGC | 2278 |
| 540 | UUGCAGAA CUGAUGA GCCGUUAGGC GAA AUACUGUC | 9421 | GACAGUAUC UUCUGCAA | 2279 |
| 542 | UUUUGCAG CUGAUGA GCCGUUAGGC GAA AGAUACUG | 9422 | CAGUAUCUU CUGCAAAA | 2280 |
| 543 | GUUUUGCA CUGAUGA GCCGUUAGGC GAA AAGAUACU | 9423 | AGUAUCUUC UGCAAAAC | 2281 |
| 555 | GGAAUGGU CUGAUGA GCCGUUAGGC GAA AGUGUUUU | 9424 | AAAACACUC ACCAUUCC | 2282 |
| 561 | ACCCUGGG CUGAUGA GCCGUUAGGC GAA AUGGUGAG | 9425 | CUCACCAUU CCCAGGGU | 2283 |
| 562 | CACCCUGG CUGAUGA GCCGUUAGGC GAA AAUGGUGA | 9426 | UCACCAUUC CCAGGGUG | 2284 |
| 573 | UCAUUUCC CUGAUGA GCCGUUAGGC GAA ACCACCCU | 9427 | AGGGUGGUU GGAAAUGA | 2285 |
| 583 | GGCUCCAG CUGAUGA GCCGUUAGGC GAA AUCAUUUC | 9428 | GAAAUGAUA CUGGAGCC | 2286 |
| 593 | AGCACUUG CUGAUGA GCCGUUAGGC GAA AGGCUCCA | 8688 | UGGAGCCUA CAAGUGCU | 1546 |
| 602 | CCCGGUAC CUGAUGA GCCGUUAGGC GAA AGCACUUG | 9429 | CAAGUGCUC GUACCGGG | 2287 |
| 605 | CGUCCCGG CUGAUGA GCCGUUAGGC GAA ACGAGCAC | 9430 | GUGCUCGUA CCGGGACG | 2288 |
| 615 | GCUAUGUC CUGAUGA GCCGUUAGGC GAA ACGUCCCG | 9431 | CGGGACGUC GACAUAGC | 2289 |
| 621 | GUGGAGGC CUGAUGA GCCGUUAGGC GAA AUGUCGAC | 9432 | GUCGACAUA GCCUCCAC | 2290 |

| | | | | |
|---|---|---|---|---|
| 626 | AAACAGUG CUGAUGA GCCGUUAGGC GAA AGGCUAUG | 9433 | CAUAGCCUC CACUGUUU | 2291 |
| 633 | UAGACAUA CUGAUGA GCCGUUAGGC GAA ACAGUGGA | 9434 | UCCACUGUU UAUGUCUA | 2292 |
| 634 | AUAGACAU CUGAUGA GCCGUUAGGC GAA AACAGUGG | 9435 | CCACUGUUU AUGUCUAU | 2293 |
| 635 | CAUAGACA CUGAUGA GCCGUUAGGC GAA AAACAGUG | 9436 | CACUGUUUA UGUCUAUG | 2294 |
| 639 | CGAACAUA CUGAUGA GCCGUUAGGC GAA ACAUAAAC | 9437 | GUUUAUGUC UAUGUUCG | 2295 |
| 641 | CUCGAACA CUGAUGA GCCGUUAGGC GAA AGACAUAA | 9438 | UUAUGUCUA UGUUCGAG | 2296 |
| 645 | UAAUCUCG CUGAUGA GCCGUUAGGC GAA ACAUAGAC | 9439 | GUCUAUGUU CGAGAUUA | 2297 |
| 646 | GUAAUCUC CUGAUGA GCCGUUAGGC GAA AACAUAGA | 9440 | UCUAUGUUC GAGAUUAC | 2298 |
| 652 | UGAUCUGU CUGAUGA GCCGUUAGGC GAA AUCUCGAA | 9441 | UUCGAGAUU ACAGAUCA | 2299 |
| 653 | GUGAUCUG CUGAUGA GCCGUUAGGC GAA AAUCUCGA | 9442 | UCGAGAUUA CAGAUCAC | 2300 |
| 659 | UGAAUGGU CUGAUGA GCCGUUAGGC GAA AUCUGUAA | 9443 | UUACAGAUC ACCAUUCA | 2301 |
| 665 | AGGCGAUG CUGAUGA GCCGUUAGGC GAA AUGGUGAU | 9444 | AUCACCAUU CAUCGCCU | 2302 |
| 666 | GAGGCGAU CUGAUGA GCCGUUAGGC GAA AAUGGUGA | 9445 | UCACCAUUC AUCGCCUC | 2303 |
| 669 | ACAGAGGC CUGAUGA GCCGUUAGGC GAA AUGAAUGG | 9446 | CCAUUCAUC GCCUCUGU | 2304 |
| 674 | CACUGACA CUGAUGA GCCGUUAGGC GAA AGGCGAUG | 9447 | CAUCGCCUC UGUCAGUG | 2305 |
| 678 | UGGUCACU CUGAUGA GCCGUUAGGC GAA ACAGAGGC | 9448 | GCCUCUGUC AGUGACCA | 2306 |
| 696 | AUGUACAC CUGAUGA GCCGUUAGGC GAA AUGCCAUG | 9449 | CAUGGCAUC GUGUACAU | 2307 |
| 701 | CGGUGAUG CUGAUGA GCCGUUAGGC GAA ACACGAUG | 9450 | CAUCGUGUA CAUCACCG | 2308 |
| 705 | UUCUCGGU CUGAUGA GCCGUUAGGC GAA AUGUACAC | 9451 | GUGUACAUC ACCGAGAA | 2309 |
| 735 | CGGCAGGG CUGAUGA GCCGUUAGGC GAA AUCACCAC | 9452 | GUGGUGAUC CCCUGCCG | 2310 |
| 749 | UUGAAAUC CUGAUGA GCCGUUAGGC GAA ACCCUCGG | 9453 | CCGAGGGUC GAUUUCAA | 2311 |
| 753 | AGGUUUGA CUGAUGA GCCGUUAGGC GAA AUCGACCC | 9454 | GGGUCGAUU UCAAACCU | 2312 |
| 754 | GAGGUUUG CUGAUGA GCCGUUAGGC GAA AAUCGACC | 9455 | GGUCGAUUU CAAACCUC | 2313 |
| 755 | UGAGGUUU CUGAUGA GCCGUUAGGC GAA AAAUCGAC | 9456 | GUCGAUUUC AAACCUCA | 2314 |
| 762 | GACACAUU CUGAUGA GCCGUUAGGC GAA AGGUUUGA | 9457 | UCAAACCUC AAUGUGUC | 2315 |
| 770 | CGCAAAGA CUGAUGA GCCGUUAGGC GAA ACACAUUG | 9458 | CAAUGUGUC UCUUUGCG | 2316 |
| 772 | AGCGCAAA CUGAUGA GCCGUUAGGC GAA AGACACAU | 9459 | AUGUGUCUC UUUGCGCU | 2317 |
| 774 | CUAGCGCA CUGAUGA GCCGUUAGGC GAA AGAGACAC | 9460 | GUGUCUCUU UGCGCUAG | 2318 |
| 775 | CCUAGCGC CUGAUGA GCCGUUAGGC GAA AAGAGACA | 9461 | UGUCUCUUU GCGCUAGG | 2319 |
| 781 | UGGAUACC CUGAUGA GCCGUUAGGC GAA AGCGCAAA | 9462 | UUUGCGCUA GGUAUCCA | 2320 |
| 785 | UUUCUGGA CUGAUGA GCCGUUAGGC GAA ACCUAGCG | 9463 | CGCUAGGUA UCCAGAAA | 2321 |
| 787 | CUUUUCUG CUGAUGA GCCGUUAGGC GAA AUACCUAG | 9464 | CUAGGUAUC CAGAAAAG | 2322 |
| 800 | CCGGAACA CUGAUGA GCCGUUAGGC GAA AUCUCUUU | 9465 | AAAGAGAUU UGUUCCGG | 2323 |
| 801 | UCCGGAAC CUGAUGA GCCGUUAGGC GAA AAUCUCUU | 9466 | AAGAGAUUU GUUCCGGA | 2324 |
| 804 | CCAUCCGG CUGAUGA GCCGUUAGGC GAA ACAAAUCU | 9467 | AGAUUUGUU CCGGAUGG | 2325 |
| 805 | UCCAUCCG CUGAUGA GCCGUUAGGC GAA AACAAAUC | 9468 | GAUUUGUUC CGGAUGGA | 2326 |
| 822 | UCCCAGGA CUGAUGA GCCGUUAGGC GAA AUUCUGUU | 8737 | AACAGAAUU UCCUGGGA | 1595 |
| 823 | GUCCCAGG CUGAUGA GCCGUUAGGC GAA AAUUCUGU | 8738 | ACAGAAUUU CCUGGGAC | 1596 |
| 824 | UGUCCCAG CUGAUGA GCCGUUAGGC GAA AAAUUCUG | 8739 | CAGAAUUUC CUGGGACA | 1597 |

144

| | | | | |
|---|---|---|---|---|
| 840 | GUAAAGCC CUGAUGA GCCGUUAGGC GAA AUCUCGCU | 9469 | AGCGAGAUA GGCUUUAC | 2327 |
| 845 | GGAGAGUA CUGAUGA GCCGUUAGGC GAA AGCCUAUC | 9470 | GAUAGGCUU UACUCUCC | 2328 |
| 846 | GGGAGAGU CUGAUGA GCCGUUAGGC GAA AAGCCUAU | 9471 | AUAGGCUUU ACUCUCCC | 2329 |
| 847 | GGGGAGAG CUGAUGA GCCGUUAGGC GAA AAAGCCUA | 9472 | UAGGCUUUA CUCUCCCC | 2330 |
| 850 | ACUGGGGA CUGAUGA GCCGUUAGGC GAA AGUAAAGC | 9473 | GCUUUACUC UCCCCAGU | 2331 |
| 852 | UAACUGGG CUGAUGA GCCGUUAGGC GAA AGAGUAAA | 9474 | UUUACUCUC CCCAGUUA | 2332 |
| 859 | GAUCAUGU CUGAUGA GCCGUUAGGC GAA ACUGGGGA | 9475 | UCCCCAGUU ACAUGAUC | 2333 |
| 860 | UGAUCAUG CUGAUGA GCCGUUAGGC GAA AACUGGGG | 9476 | CCCCAGUUA CAUGAUCA | 2334 |
| 867 | GCAUAGCU CUGAUGA GCCGUUAGGC GAA AUCAUGUA | 8747 | UACAUGAUC AGCUAUGC | 1605 |
| 872 | UGCCGGCA CUGAUGA GCCGUUAGGC GAA AGCUGAUC | 9477 | GAUCAGCUA UGCCGGCA | 2335 |
| 885 | UCACAGAA CUGAUGA GCCGUUAGGC GAA ACCAUGCC | 8749 | GGCAUGGUC UUCUGUGA | 1607 |
| 887 | CCUCACAG CUGAUGA GCCGUUAGGC GAA AGACCAUG | 9478 | CAUGGUCUU CUGUGAGG | 2336 |
| 888 | GCCUCACA CUGAUGA GCCGUUAGGC GAA AAGACCAU | 9479 | AUGGUCUUC UGUGAGGC | 2337 |
| 903 | UCAUCAUU CUGAUGA GCCGUUAGGC GAA AUCUUUGC | 9480 | GCAAAGAUC AAUGAUGA | 2338 |
| 917 | UAGACUGA CUGAUGA GCCGUUAGGC GAA AGGUUUCA | 9481 | UGAAACCUA UCAGUCUA | 2339 |
| 919 | GAUAGACU CUGAUGA GCCGUUAGGC GAA AUAGGUUU | 9482 | AAACCUAUC AGUCUAUC | 2340 |
| 923 | ACAUGAUA CUGAUGA GCCGUUAGGC GAA ACUGAUAG | 9483 | CUAUCAGUC UAUCAUGU | 2341 |
| 925 | GUACAUGA CUGAUGA GCCGUUAGGC GAA AGACUGAU | 9484 | AUCAGUCUA UCAUGUAC | 2342 |
| 927 | AUGUACAU CUGAUGA GCCGUUAGGC GAA AUAGACUG | 8758 | CAGUCUAUC AUGUACAU | 2343 |
| 932 | CAACUAUG CUGAUGA GCCGUUAGGC GAA ACAUGAUA | 9485 | UAUCAUGUA CAUAGUUG | 2344 |
| 936 | ACCACAAC CUGAUGA GCCGUUAGGC GAA AUGUACAU | 9486 | AUGUACAUA GUUGUGGU | 2345 |
| 939 | ACAACCAC CUGAUGA GCCGUUAGGC GAA ACUAUGUA | 9487 | UACAUAGUU GUGGUUGU | 2346 |
| 945 | UAUCCUAC CUGAUGA GCCGUUAGGC GAA ACCACAAC | 9488 | GUUGUGGUU GUAGGAUA | 2347 |
| 948 | CUAUAUCC CUGAUGA GCCGUUAGGC GAA ACAACCAC | 9489 | GUGGUUGUA GGAUAUAG | 2348 |
| 953 | AAAUCCUA CUGAUGA GCCGUUAGGC GAA AUCCUACA | 9490 | UGUAGGAUA UAGGAUUU | 2349 |
| 955 | AUAAAUCC CUGAUGA GCCGUUAGGC GAA AUAUCCUA | 9491 | UAGGAUAUA GGAUUUAU | 2350 |
| 960 | ACAUCAUA CUGAUGA GCCGUUAGGC GAA AUCCUAUA | 8768 | UAUAGGAUU UAUGAUGU | 1626 |
| 961 | CACAUCAU CUGAUGA GCCGUUAGGC GAA AAUCCUAU | 8769 | AUAGGAUUU AUGAUGUG | 1627 |
| 962 | UCACAUCA CUGAUGA GCCGUUAGGC GAA AAAUCCUA | 9492 | UAGGAUUUA UGAUGUGA | 2351 |
| 972 | GGGCUCAG CUGAUGA GCCGUUAGGC GAA AUCACAUC | 9493 | GAUGUGAUU CUGAGCCC | 2352 |
| 973 | GGGGCUCA CUGAUGA GCCGUUAGGC GAA AAUCACAU | 9494 | AUGUGAUUC UGAGCCCC | 2353 |
| 993 | GAUAGCUC CUGAUGA GCCGUUAGGC GAA AUUUCAUG | 9495 | CAUGAAAUU GAGCUAUC | 2354 |
| 999 | CCGGCAGA CUGAUGA GCCGUUAGGC GAA AGCUCAAU | 9496 | AUUGAGCUA UCUGCCGG | 2355 |
| 1001 | CUCCGGCA CUGAUGA GCCGUUAGGC GAA AUAGCUCA | 9497 | UGAGCUAUC UGCCGGAG | 2356 |
| 1017 | UUUAAGAC CUGAUGA GCCGUUAGGC GAA AGUUUUUC | 9498 | GAAAAACUU GUCUUAAA | 2357 |
| 1020 | CAAUUUAA CUGAUGA GCCGUUAGGC GAA ACAAGUUU | 9499 | AAACUUGUC UUAAAUUG | 2358 |
| 1022 | UACAAUUU CUGAUGA GCCGUUAGGC GAA AGACAAGU | 9500 | ACUUGUCUU AAAUUGUA | 2359 |
| 1023 | GUACAAUU CUGAUGA GCCGUUAGGC GAA AAGACAAG | 8783 | CUUGUCUUA AAUUGUAC | 1641 |
| 1027 | CGCUGUAC CUGAUGA GCCGUUAGGC GAA AUUUAAGA | 9501 | UCUUAAAUU GUACAGCG | 2360 |

145

| | | | | |
|---|---|---|---|---|
| 1030 | UCUCGCUG CUGAUGA GCCGUUAGGC GAA ACAAUUUA | 9502 | UAAAUUGUA CAGCGAGA | 2361 |
| 1047 | CCCACAUU CUGAUGA GCCGUUAGGC GAA AGCUCUGU | 9503 | ACAGAGCUC AAUGUGGG | 2362 |
| 1059 | GUGAAAUC CUGAUGA GCCGUUAGGC GAA AGCCCCAC | 9504 | GUGGGGCUU GAUUUCAC | 2363 |
| 1063 | CCAGGUGA CUGAUGA GCCGUUAGGC GAA AUCAAGCC | 9505 | GGCUUGAUU UCACCUGG | 2364 |
| 1064 | GCCAGGUG CUGAUGA GCCGUUAGGC GAA AAUCAAGC | 9506 | GCUUGAUUU CACCUGGC | 2365 |
| 1065 | UGCCAGGU CUGAUGA GCCGUUAGGC GAA AAAUCAAG | 9507 | CUUGAUUUC ACCUGGCA | 2366 |
| 1076 | AAGGUGGA CUGAUGA GCCGUUAGGC GAA AGUGCCAG | 9508 | CUGGCACUC UCCACCUU | 2367 |
| 1078 | UGAAGGUG CUGAUGA GCCGUUAGGC GAA AGAGUGCC | 9509 | GGCACUCUC CACCUUCA | 2368 |
| 1084 | AGACUUUG CUGAUGA GCCGUUAGGC GAA AGGUGGAG | 9510 | CUCCACCUU CAAAGUCU | 2369 |
| 1085 | GAGACUUU CUGAUGA GCCGUUAGGC GAA AAGGUGGA | 9511 | UCCACCUUC AAAGUCUC | 2370 |
| 1091 | UAUGAUGA CUGAUGA GCCGUUAGGC GAA ACUUUGAA | 9512 | UUCAAAGUC UCAUCAUA | 2371 |
| 1093 | CUUAUGAU CUGAUGA GCCGUUAGGC GAA AGACUUUG | 9513 | CAAAGUCUC AUCAUAAG | 2372 |
| 1096 | CUUCUUAU CUGAUGA GCCGUUAGGC GAA AUGAGACU | 9514 | AGUCUCAUC AUAAGAAG | 2373 |
| 1099 | AAUCUUCU CUGAUGA GCCGUUAGGC GAA AUGAUGAG | 9515 | CUCAUCAUA AGAAGAUU | 2374 |
| 1107 | CGGUUUAC CUGAUGA GCCGUUAGGC GAA AUCUUCUU | 9516 | AAGAAGAUU GUAAACCG | 2375 |
| 1110 | UCCCGGUU CUGAUGA GCCGUUAGGC GAA ACAAUCUU | 9517 | AAGAUUGUA AACCGGGA | 2376 |
| 1130 | UCCCAGGA CUGAUGA GCCGUUAGGC GAA AGGGUUUC | 9518 | GAAACCCUU UCCUGGGA | 2377 |
| 1131 | GUCCCAGG CUGAUGA GCCGUUAGGC GAA AAGGGUUU | 9519 | AAACCCUUU CCUGGGAC | 2378 |
| 1132 | AGUCCCAG CUGAUGA GCCGUUAGGC GAA AAAGGGUU | 9520 | AACCCUUUC CUGGGACU | 2379 |
| 1154 | UGCUCAAA CUGAUGA GCCGUUAGGC GAA ACAUCUUC | 9521 | GAAGAUGUU UUUGAGCA | 2380 |
| 1155 | GUGCUCAA CUGAUGA GCCGUUAGGC GAA AACAUCUU | 9522 | AAGAUGUUU UUGAGCAC | 2381 |
| 1156 | GGUGCUCA CUGAUGA GCCGUUAGGC GAA AAACAUCU | 9523 | AGAUGUUUU UGAGCACC | 2382 |
| 1157 | AGGUGCUC CUGAUGA GCCGUUAGGC GAA AAAACAUC | 9524 | GAUGUUUUU GAGCACCU | 2383 |
| 1166 | CUAUUGUC CUGAUGA GCCGUUAGGC GAA AGGUGCUC | 9525 | GAGCACCUU GACAAUAG | 2384 |
| 1173 | ACACUUUC CUGAUGA GCCGUUAGGC GAA AUUGUCAA | 9526 | UUGACAAUA GAAAGUGU | 2385 |
| 1205 | CACAGGUG CUGAUGA GCCGUUAGGC GAA AUUCCCCU | 9527 | AGGGGAAUA CACCUGUG | 2386 |
| 1215 | CUGGACGC CUGAUGA GCCGUUAGGC GAA ACACAGGU | 9528 | ACCUGUGUA GCGUCCAG | 2387 |
| 1220 | GUCCACUG CUGAUGA GCCGUUAGGC GAA ACGCUACA | 9529 | UGUAGCGUC CAGUGGAC | 2388 |
| 1236 | UUUCUCUU CUGAUGA GCCGUUAGGC GAA AUCAUCCG | 9530 | CGGAUGAUC AAGAGAAA | 2389 |
| 1246 | AAAUGUUC CUGAUGA GCCGUUAGGC GAA AUUUCUCU | 9531 | AGAGAAAUA GAACAUUU | 2390 |
| 1253 | CUCGGACA CUGAUGA GCCGUUAGGC GAA AUGUUCUA | 9532 | UAGAACAUU UGUCCGAG | 2391 |
| 1254 | ACUCGGAC CUGAUGA GCCGUUAGGC GAA AAUGUUCU | 9533 | AGAACAUUU GUCCGAGU | 2392 |
| 1257 | UGAACUCG CUGAUGA GCCGUUAGGC GAA ACAAAUGU | 9534 | ACAUUUGUC CGAGUUCA | 2393 |
| 1263 | UUUGUGUG CUGAUGA GCCGUUAGGC GAA ACUCGGAC | 9535 | GUCCGAGUU CACACAAA | 2394 |
| 1264 | CUUUGUGU CUGAUGA GCCGUUAGGC GAA AACUCGGA | 9536 | UCCGAGUUC ACACAAAG | 2395 |
| 1276 | AGCAAUAA CUGAUGA GCCGUUAGGC GAA AGGCUUUG | 9537 | CAAAGCCUU UUAUUGCU | 2396 |
| 1277 | AAGCAAUA CUGAUGA GCCGUUAGGC GAA AAGGCUUU | 9538 | AAAGCCUUU UAUUGCUU | 2397 |
| 1278 | AAAGCAAU CUGAUGA GCCGUUAGGC GAA AAAGGCUU | 9539 | AAGCCUUUU AUUGCUUU | 2398 |
| 1279 | GAAAGCAA CUGAUGA GCCGUUAGGC GAA AAAAGGCU | 9540 | AGCCUUUUA UUGCUUUC | 2399 |

| | | | | |
|---|---|---|---|---|
| 1281 | CCGAAAGC CUGAUGA GCCGUUAGGC GAA AUAAAAGG | 9541 | CCUUUUAUU GCUUUCGG | 2400 |
| 1285 | ACUACCGA CUGAUGA GCCGUUAGGC GAA AGCAAUAA | 9542 | UUAUUGCUU UCGGUAGU | 2401 |
| 1286 | CACUACCG CUGAUGA GCCGUUAGGC GAA AAGCAAUA | 9543 | UAUUGCUUU CGGUAGUG | 2402 |
| 1287 | CCACUACC CUGAUGA GCCGUUAGGC GAA AAAGCAAU | 9544 | AUUGCUUUC GGUAGUGG | 2403 |
| 1291 | CAUCCCAC CUGAUGA GCCGUUAGGC GAA ACCGAAAG | 9545 | CUUUCGGUA GUGGGAUG | 2404 |
| 1304 | CCACCAAA CUGAUGA GCCGUUAGGC GAA AUUUCAUC | 9546 | GAUGAAAUC UUUGGUGG | 2405 |
| 1306 | UUCCACCA CUGAUGA GCCGUUAGGC GAA AGAUUUCA | 9547 | UGAAAUCUU UGGUGGAA | 2406 |
| 1307 | CUUCCACC CUGAUGA GCCGUUAGGC GAA AAGAUUUC | 9548 | GAAAUCUUU GGUGGAAG | 2407 |
| 1330 | UCGGACUU CUGAUGA GCCGUUAGGC GAA ACUGCCCA | 9549 | UGGGCAGUC AAGUCCGA | 2408 |
| 1335 | GGGAUUCG CUGAUGA GCCGUUAGGC GAA ACUUGACU | 9550 | AGUCAAGUC CGAAUCCC | 2409 |
| 1341 | UUCACAGG CUGAUGA GCCGUUAGGC GAA AUUCGGAC | 9551 | GUCCGAAUC CCUGUGAA | 2410 |
| 1352 | AACUGAGA CUGAUGA GCCGUUAGGC GAA ACUUCACA | 9552 | UGUGAAGUA UCUCAGUU | 2411 |
| 1354 | GUAACUGA CUGAUGA GCCGUUAGGC GAA AUACUUCA | 9553 | UGAAGUAUC UCAGUUAC | 2412 |
| 1356 | GGGUAACU CUGAUGA GCCGUUAGGC GAA AGAUACUU | 9554 | AAGUAUCUC AGUUACCC | 2413 |
| 1360 | AGCUGGGU CUGAUGA GCCGUUAGGC GAA ACUGAGAU | 9555 | AUCUCAGUU ACCCAGCU | 2414 |
| 1361 | GAGCUGGG CUGAUGA GCCGUUAGGC GAA AACUGAGA | 9556 | UCUCAGUUA CCCAGCUC | 2415 |
| 1369 | GAUAUCAG CUGAUGA GCCGUUAGGC GAA AGCUGGGU | 9557 | ACCCAGCUC CUGAUAUC | 2416 |
| 1375 | CCAUUUGA CUGAUGA GCCGUUAGGC GAA AUCAGGAG | 9558 | CUCCUGAUA UCAAAUGG | 2417 |
| 1377 | UACCAUUU CUGAUGA GCCGUUAGGC GAA AUAUCAGG | 9559 | CCUGAUAUC AAAUGGUA | 2418 |
| 1385 | CAUUUCUG CUGAUGA GCCGUUAGGC GAA ACCAUUUG | 9560 | CAAAUGGUA CAGAAAUG | 2419 |
| 1404 | UUGGACUC CUGAUGA GCCGUUAGGC GAA AUGGGCCU | 9561 | AGGCCCAUU GAGUCCAA | 2420 |
| 1409 | UGUAGUUG CUGAUGA GCCGUUAGGC GAA ACUCAAUG | 9562 | CAUUGAGUC CAACUACA | 2421 |
| 1415 | UCAUUGUG CUGAUGA GCCGUUAGGC GAA AGUUGGAC | 9563 | GUCCAACUA CACAAUGA | 2422 |
| 1425 | UCGCCAAC CUGAUGA GCCGUUAGGC GAA AUCAUUGU | 9564 | ACAAUGAUU GUUGGCGA | 2423 |
| 1428 | UCAUCGCC CUGAUGA GCCGUUAGGC GAA ACAAUCAU | 9565 | AUGAUUGUU GGCGAUGA | 2424 |
| 1440 | AUGAUGGU CUGAUGA GCCGUUAGGC GAA AGUUCAUC | 9566 | GAUGAACUC ACCAUCAU | 2425 |
| 1446 | ACUUCCAU CUGAUGA GCCGUUAGGC GAA AUGGUGAG | 9567 | CUCACCAUC AUGGAAGU | 2426 |
| 1478 | UGACCGUG CUGAUGA GCCGUUAGGC GAA AGUUUCCU | 9568 | AGGAAACUA CACGGUCA | 2427 |
| 1485 | GUGAGGAU CUGAUGA GCCGUUAGGC GAA ACCGUGUA | 9569 | UACACGGUC AUCCUCAC | 2428 |
| 1488 | UUGGUGAG CUGAUGA GCCGUUAGGC GAA AUGACCGU | 9570 | ACGGUCAUC CUCACCAA | 2429 |
| 1491 | GGGUUGGU CUGAUGA GCCGUUAGGC GAA AGGAUGAC | 9571 | GUCAUCCUC ACCAACCC | 2430 |
| 1503 | UCCAUUGA CUGAUGA GCCGUUAGGC GAA AUGGGGUU | 9572 | AACCCCAUU UCAAUGGA | 2431 |
| 1504 | CUCCAUUG CUGAUGA GCCGUUAGGC GAA AAUGGGGU | 9573 | ACCCCAUUU CAAUGGAG | 2432 |
| 1505 | UCUCCAUU CUGAUGA GCCGUUAGGC GAA AAAUGGGG | 9574 | CCCCAUUUC AAUGGAGA | 2433 |
| 1530 | ACCAGAGA CUGAUGA GCCGUUAGGC GAA ACCAUGUG | 9575 | CACAUGGUC UCUCUGGU | 2434 |
| 1532 | CAACCAGA CUGAUGA GCCGUUAGGC GAA AGACCAUG | 9576 | CAUGGUCUC UCUGGUUG | 2435 |
| 1534 | CACAACCA CUGAUGA GCCGUUAGGC GAA AGAGACCA | 8856 | UGGUCUCUC UGGUUGUG | 1714 |
| 1539 | ACAUUCAC CUGAUGA GCCGUUAGGC GAA ACCAGAGA | 9577 | UCUCUGGUU GUGAAUGU | 2436 |
| 1548 | UGGGGUGG CUGAUGA GCCGUUAGGC GAA ACAUUCAC | 9578 | GUGAAUGUC CCACCCCA | 2437 |

147

| | | | | |
|---|---|---|---|---|
| 1560 | UUCUCACC CUGAUGA GCCGUUAGGC GAA AUCUGGGG | 8860 | CCCCAGAUC GGUGAGAA | 2438 |
| 1574 | GCGAGAUC CUGAUGA GCCGUUAGGC GAA AGGCUUUC | 9579 | GAAAGCCUU GAUCUCGC | 2439 |
| 1578 | AUAGGCGA CUGAUGA GCCGUUAGGC GAA AUCAAGGC | 9580 | GCCUUGAUC UCGCCUAU | 2440 |
| 1580 | CCAUAGGC CUGAUGA GCCGUUAGGC GAA AGAUCAAG | 9581 | CUUGAUCUC GCCUAUGG | 2441 |
| 1585 | GGAAUCCA CUGAUGA GCCGUUAGGC GAA AGGCGAGA | 9582 | UCUCGCCUA UGGAUUCC | 2442 |
| 1591 | CUGGUAGG CUGAUGA GCCGUUAGGC GAA AUCCAUAG | 9583 | CUAUGGAUU CCUACCAG | 2443 |
| 1592 | ACUGGUAG CUGAUGA GCCGUUAGGC GAA AAUCCAUA | 9584 | UAUGGAUUC CUACCAGU | 2444 |
| 1595 | CAUACUGG CUGAUGA GCCGUUAGGC GAA AGGAAUCC | 9585 | GGAUUCCUA CCAGUAUG | 2445 |
| 1601 | UGGUCCCA CUGAUGA GCCGUUAGGC GAA ACUGGUAG | 9586 | CUACCAGUA UGGGACCA | 2446 |
| 1619 | UGCAUGUC CUGAUGA GCCGUUAGGC GAA AUGUCUGC | 9587 | GCAGACAUU GACAUGCA | 2447 |
| 1632 | UUGGCGUA CUGAUGA GCCGUUAGGC GAA ACUGUGCA | 9588 | UGCACAGUC UACGCCAA | 2448 |
| 1634 | GGUUGGCG CUGAUGA GCCGUUAGGC GAA AGACUGUG | 9589 | CACAGUCUA CGCCAACC | 2449 |
| 1645 | GUGCAGGG CUGAUGA GCCGUUAGGC GAA AGGGUUGG | 9590 | CCAACCCUC CCCUGCAC | 2450 |
| 1659 | UACCACUG CUGAUGA GCCGUUAGGC GAA AUGUGGUG | 9591 | CACCACAUC CAGUGGUA | 2451 |
| 1667 | GCUGCCAG CUGAUGA GCCGUUAGGC GAA ACCACUGG | 9592 | CCAGUGGUA CUGGCAGC | 2452 |
| 1677 | GCUUCUUC CUGAUGA GCCGUUAGGC GAA AGCUGCCA | 9593 | UGGCAGCUA GAAGAAGC | 2453 |
| 1691 | GUCUGUAG CUGAUGA GCCGUUAGGC GAA AGCAGGCU | 9594 | AGCCUGCUC CUACAGAC | 2454 |
| 1694 | CGGGUCUG CUGAUGA GCCGUUAGGC GAA AGGAGCAG | 9595 | CUGCUCCUA CAGACCCG | 2455 |
| 1718 | UACAAGCA CUGAUGA GCCGUUAGGC GAA ACGGGCUU | 9596 | AAGCCCGUA UGCUUGUA | 2456 |
| 1723 | UUCUUUAC CUGAUGA GCCGUUAGGC GAA AGCAUACG | 9597 | CGUAUGCUU GUAAAGAA | 2457 |
| 1726 | CCAUUCUU CUGAUGA GCCGUUAGGC GAA ACAAGCAU | 9598 | AUGCUUGUA AAGAAUGG | 2458 |
| 1750 | CCCCUGGA CUGAUGA GCCGUUAGGC GAA AUCCUCCA | 9599 | UGGAGGAUU UCCAGGGG | 2459 |
| 1751 | CCCCCUGG CUGAUGA GCCGUUAGGC GAA AAUCCUCC | 9600 | GGAGGAUUU CCAGGGGG | 2460 |
| 1752 | CCCCCCUG CUGAUGA GCCGUUAGGC GAA AAAUCCUC | 9601 | GAGGAUUUC CAGGGGGG | 2461 |
| 1770 | GUGACUUC CUGAUGA GCCGUUAGGC GAA AUCUUGUU | 9602 | AACAAGAUC GAAGUCAC | 2462 |
| 1776 | UUUUUGGU CUGAUGA GCCGUUAGGC GAA ACUUCGAU | 9603 | AUCGAAGUC ACCAAAAA | 2463 |
| 1790 | UCAGGGCA CUGAUGA GCCGUUAGGC GAA AUUGGUUU | 9604 | AAACCAAUA UGCCCUGA | 2464 |
| 1800 | UUUCCUUC CUGAUGA GCCGUUAGGC GAA AUCAGGGC | 9605 | GCCCUGAUU GAAGGAAA | 2465 |
| 1821 | AGCGUACU CUGAUGA GCCGUUAGGC GAA ACAGUUUU | 9606 | AAAACUGUA AGUACGCU | 2466 |
| 1825 | GACCAGCG CUGAUGA GCCGUUAGGC GAA ACUUACAG | 9607 | CUGUAAGUA CGCUGGUC | 2467 |
| 1833 | GCUUGGAU CUGAUGA GCCGUUAGGC GAA ACCAGCGU | 9608 | ACGCUGGUC AUCCAAGC | 2468 |
| 1836 | GCAGCUUG CUGAUGA GCCGUUAGGC GAA AUGACCAG | 9609 | CUGGUCAUC CAAGCUGC | 2469 |
| 1853 | ACAACGCU CUGAUGA GCCGUUAGGC GAA ACACGUUG | 9610 | CAACGUGUC AGCGUUGU | 2470 |
| 1859 | AUUUGUAC CUGAUGA GCCGUUAGGC GAA ACGCUGAC | 9611 | GUCAGCGUU GUACAAAU | 2471 |
| 1862 | CACAUUUG CUGAUGA GCCGUUAGGC GAA ACAACGCU | 9612 | AGCGUUGUA CAAAUGUG | 2472 |
| 1878 | GCUUUGUU CUGAUGA GCCGUUAGGC GAA AUGGCUUC | 9613 | GAAGCCAUC AACAAAGC | 2473 |
| 1905 | AAGGAGAU CUGAUGA GCCGUUAGGC GAA ACCCUCUC | 9614 | GAGAGGGUC AUCUCCUU | 2474 |
| 1908 | UGGAAGGA CUGAUGA GCCGUUAGGC GAA AUGACCCU | 9615 | AGGGUCAUC UCCUUCCA | 2475 |
| 1910 | CAUGGAAG CUGAUGA GCCGUUAGGC GAA AGAUGACC | 9616 | GGUCAUCUC CUUCCAUG | 2476 |

148

| | | | | |
|---|---|---|---|---|
| 1913 | UCACAUGG CUGAUGA GCCGUUAGGC GAA AGGAGAUG | 9617 | CAUCUCCUU CCAUGUGA | 2477 |
| 1914 | AUCACAUG CUGAUGA GCCGUUAGGC GAA AAGGAGAU | 9618 | AUCUCCUUC CAUGUGAU | 2478 |
| 1923 | GGACCCCU CUGAUGA GCCGUUAGGC GAA AUCACAUG | 9619 | CAUGUGAUC AGGGGUCC | 2479 |
| 1930 | AAUUUCAG CUGAUGA GCCGUUAGGC GAA ACCCCUGA | 9620 | UCAGGGGUC CUGAAAUU | 2480 |
| 1938 | UGCACAGU CUGAUGA GCCGUUAGGC GAA AUUUCAGG | 9621 | CCUGAAAUU ACUGUGCA | 2481 |
| 1939 | UUGCACAG CUGAUGA GCCGUUAGGC GAA AAUUUCAG | 9622 | CUGAAAUUA CUGUGCAA | 2482 |
| 1982 | ACAACAGG CUGAUGA GCCGUUAGGC GAA ACACACUC | 9623 | GAGUGUGUC CCUGUUGU | 2483 |
| 1988 | CAGUGCAC CUGAUGA GCCGUUAGGC GAA ACAGGGAC | 9624 | GUCCCUGUU GUGCACUG | 2484 |
| 2008 | CUCAAACG CUGAUGA GCCGUUAGGC GAA AUUUCUGU | 9625 | ACAGAAAUA CGUUUGAG | 2485 |
| 2012 | GGUUCUCA CUGAUGA GCCGUUAGGC GAA ACGUAUUU | 9626 | AAAUACGUU UGAGAACC | 2486 |
| 2013 | AGGUUCUC CUGAUGA GCCGUUAGGC GAA AACGUAUU | 9627 | AAUACGUUU GAGAACCU | 2487 |
| 2022 | UACCACGU CUGAUGA GCCGUUAGGC GAA AGGUUCUC | 9628 | GAGAACCUC ACGUGGUA | 2488 |
| 2030 | CAAGCUUG CUGAUGA GCCGUUAGGC GAA ACCACGUG | 9629 | CACGUGGUA CAAGCUUG | 2489 |
| 2037 | UGUGAGCC CUGAUGA GCCGUUAGGC GAA AGCUUGUA | 9630 | UACAAGCUU GGCUCACA | 2490 |
| 2042 | UUGCCUGU CUGAUGA GCCGUUAGGC GAA AGCCAAGC | 9631 | GCUUGGCUC ACAGGCAA | 2491 |
| 2054 | UGUGGACC CUGAUGA GCCGUUAGGC GAA AUGUUGCC | 9632 | GGCAACAUC GGUCCACA | 2492 |
| 2058 | CCCAUGUG CUGAUGA GCCGUUAGGC GAA ACCGAUGU | 9633 | ACAUCGGUC CACAUGGG | 2493 |
| 2072 | GUGUGAGU CUGAUGA GCCGUUAGGC GAA AUUCGCCC | 9634 | GGGCGAAUC ACUCACAC | 2494 |
| 2076 | ACUGGUGU CUGAUGA GCCGUUAGGC GAA AGUGAUUC | 9635 | GAAUCACUC ACACCAGU | 2495 |
| 2085 | UUCUUGCA CUGAUGA GCCGUUAGGC GAA ACUGGUGU | 9636 | ACACCAGUU UGCAAGAA | 2496 |
| 2086 | GUUCUUGC CUGAUGA GCCGUUAGGC GAA AACUGGUG | 9637 | CACCAGUUU GCAAGAAC | 2497 |
| 2096 | GAGCAUCC CUGAUGA GCCGUUAGGC GAA AGUUCUUG | 9638 | CAAGAACUU GGAUGCUC | 2498 |
| 2104 | UUUCCAAA CUGAUGA GCCGUUAGGC GAA AGCAUCCA | 9639 | UGGAUGCUC UUUGGAAA | 2499 |
| 2106 | AGUUUCCA CUGAUGA GCCGUUAGGC GAA AGAGCAUC | 9640 | GAUGCUCUU UGGAAACU | 2500 |
| 2107 | CAGUUUCC CUGAUGA GCCGUUAGGC GAA AAGAGCAU | 9641 | AUGCUCUUU GGAAACUG | 2501 |
| 2129 | UGUUAGAA CUGAUGA GCCGUUAGGC GAA ACAUGGUG | 9642 | CACCAUGUU UUCUAACA | 2502 |
| 2130 | CUGUUAGA CUGAUGA GCCGUUAGGC GAA AACAUGGU | 9643 | ACCAUGUUU UCUAACAG | 2503 |
| 2131 | GCUGUUAG CUGAUGA GCCGUUAGGC GAA AAACAUGG | 9644 | CCAUGUUUU CUAACAGC | 2504 |
| 2132 | UGCUGUUA CUGAUGA GCCGUUAGGC GAA AAAACAUG | 9645 | CAUGUUUUC UAACAGCA | 2505 |
| 2134 | UGUGCUGU CUGAUGA GCCGUUAGGC GAA AGAAAACA | 9646 | UGUUUUCUA ACAGCACA | 2506 |
| 2151 | ACAAUCAA CUGAUGA GCCGUUAGGC GAA AUGUCAUU | 9647 | AAUGACAUC UUGAUUGU | 2507 |
| 2153 | CCACAAUC CUGAUGA GCCGUUAGGC GAA AGAUGUCA | 9648 | UGACAUCUU GAUUGUGG | 2508 |
| 2157 | AAUGCCAC CUGAUGA GCCGUUAGGC GAA AUCAAGAU | 9649 | AUCUUGAUU GUGGCAUU | 2509 |
| 2165 | CAUUCUGA CUGAUGA GCCGUUAGGC GAA AUGCCACA | 9650 | UGUGGCAUU UCAGAAUG | 2510 |
| 2166 | GCAUUCUG CUGAUGA GCCGUUAGGC GAA AAUGCCAC | 9651 | GUGGCAUUU CAGAAUGC | 2511 |
| 2167 | GGCAUUCU CUGAUGA GCCGUUAGGC GAA AAAUGCCA | 9652 | UGGCAUUUC AGAAUGCC | 2512 |
| 2177 | CCUGCAGA CUGAUGA GCCGUUAGGC GAA AGGCAUUC | 9653 | GAAUGCCUC UCUGCAGG | 2513 |
| 2179 | GUCCUGCA CUGAUGA GCCGUUAGGC GAA AGAGGCAU | 9654 | AUGCCUCUC UGCAGGAC | 2514 |
| 2198 | AGCAAACA CUGAUGA GCCGUUAGGC GAA AGUCGCCU | 9655 | AGGCGACUA UGUUUGCU | 2515 |

| | | | | |
|---|---|---|---|---|
| 2202 | GCAGAGCA CUGAUGA GCCGUUAGGC GAA ACAUAGUC | 9656 | GACUAUGUU UGCUCUGC | 2516 |
| 2203 | AGCAGAGC CUGAUGA GCCGUUAGGC GAA AACAUAGU | 9657 | ACUAUGUUU GCUCUGCU | 2517 |
| 2207 | CUUGAGCA CUGAUGA GCCGUUAGGC GAA AGCAAACA | 9658 | UGUUUGCUC UGCUCAAG | 2518 |
| 2212 | CUUAUCUU CUGAUGA GCCGUUAGGC GAA AGCAGAGC | 9659 | GCUCUGCUC AAGAUAAG | 2519 |
| 2218 | GGUCUUCU CUGAUGA GCCGUUAGGC GAA AUCUUGAG | 9660 | CUCAAGAUA AGAAGACC | 2520 |
| 2239 | GACCAGGC CUGAUGA GCCGUUAGGC GAA AUGUCUUU | 9661 | AAAGACAUU GCCUGGUC | 2521 |
| 2247 | AGCUGUUU CUGAUGA GCCGUUAGGC GAA ACCAGGCA | 9662 | UGCCUGGUC AAACAGCU | 2522 |
| 2256 | AGGAUGAU CUGAUGA GCCGUUAGGC GAA AGCUGUUU | 9663 | AAACAGCUC AUCAUCCU | 2523 |
| 2259 | UCUAGGAU CUGAUGA GCCGUUAGGC GAA AUGAGCUG | 9664 | CAGCUCAUC AUCCUAGA | 2524 |
| 2262 | CGCUCUAG CUGAUGA GCCGUUAGGC GAA AUGAUGAG | 9665 | CUCAUCAUC CUAGAGCG | 2525 |
| 2265 | AUGCGCUC CUGAUGA GCCGUUAGGC GAA AGGAUGAU | 9666 | AUCAUCCUA GAGCGCAU | 2526 |
| 2286 | UUUCCGGU CUGAUGA GCCGUUAGGC GAA AUCAUGGG | 9667 | CCCAUGAUC ACCGGAAA | 2527 |
| 2296 | AUUCUCCA CUGAUGA GCCGUUAGGC GAA AUUUCCGG | 9668 | CCGGAAAUC UGGAGAAU | 2528 |
| 2305 | UGUUGUCU CUGAUGA GCCGUUAGGC GAA AUUCUCCA | 9669 | UGGAGAAUC AGACAACA | 2529 |
| 2319 | GUCUCGCC CUGAUGA GCCGUUAGGC GAA AUGGUUGU | 9670 | ACAACCAUU GGCGAGAC | 2530 |
| 2331 | GUCACUUC CUGAUGA GCCGUUAGGC GAA AUGGUCUC | 9671 | GAGACCAUU GAAGUGAC | 2531 |
| 2341 | UGCUGGGC CUGAUGA GCCGUUAGGC GAA AGUCACUU | 9672 | AAGUGACUU GCCCAGCA | 2532 |
| 2351 | GAUUUCCA CUGAUGA GCCGUUAGGC GAA AUGCUGGG | 9673 | CCCAGCAUC UGGAAAUC | 2533 |
| 2359 | UGGGGUAG CUGAUGA GCCGUUAGGC GAA AUUUCCAG | 9674 | CUGGAAAUC CUACCCCA | 2534 |
| 2362 | GUGUGGGG CUGAUGA GCCGUUAGGC GAA AGGAUUUC | 9675 | GAAAUCCUA CCCCACAC | 2535 |
| 2373 | AACCAUGU CUGAUGA GCCGUUAGGC GAA AUGUGUGG | 9676 | CCACACAUU ACAUGGUU | 2536 |
| 2374 | GAACCAUG CUGAUGA GCCGUUAGGC GAA AAUGUGUG | 9677 | CACACAUUA CAUGGUUC | 2537 |
| 2381 | UGUCUUUG CUGAUGA GCCGUUAGGC GAA ACCAUGUA | 9678 | UACAUGGUU CAAAGACA | 2538 |
| 2382 | UUGUCUUU CUGAUGA GCCGUUAGGC GAA AACCAUGU | 9679 | ACAUGGUUC AAAGACAA | 2539 |
| 2403 | GAAUCUUC CUGAUGA GCCGUUAGGC GAA ACCAGGGU | 9680 | ACCCUGGUA GAAGAUUC | 2540 |
| 2410 | AAUGCCUG CUGAUGA GCCGUUAGGC GAA AUCUUCUA | 9681 | UAGAAGAUU CAGGCAUU | 2541 |
| 2411 | CAAUGCCU CUGAUGA GCCGUUAGGC GAA AAUCUUCU | 9682 | AGAAGAUUC AGGCAUUG | 2542 |
| 2418 | CUCAGUAC CUGAUGA GCCGUUAGGC GAA AUGCCUGA | 9683 | UCAGGCAUU GUACUGAG | 2543 |
| 2421 | UCUCUCAG CUGAUGA GCCGUUAGGC GAA ACAAUGCC | 9684 | GGCAUUGUA CUGAGAGA | 2544 |
| 2449 | CCUGCGGA CUGAUGA GCCGUUAGGC GAA AGUCAGGU | 9685 | ACCUGACUA UCCGCAGG | 2545 |
| 2451 | ACCCUGCG CUGAUGA GCCGUUAGGC GAA AUAGUCAG | 9686 | CUGACUAUC CGCAGGGU | 2546 |
| 2481 | CAGGUGUA CUGAUGA GCCGUUAGGC GAA AGGCCUCC | 9687 | GGAGGCCUC UACACCUG | 2547 |
| 2483 | GGCAGGUG CUGAUGA GCCGUUAGGC GAA AGAGGCCU | 8989 | AGGCCUCUA CACCUGCC | 1847 |
| 2505 | CAGCCAAG CUGAUGA GCCGUUAGGC GAA ACAUUGCA | 9688 | UGCAAUGUC CUUGGCUG | 2548 |
| 2508 | GCACAGCC CUGAUGA GCCGUUAGGC GAA AGGACAUU | 9689 | AAUGUCCUU GGCUGUGC | 2549 |
| 2532 | AUUAUGAA CUGAUGA GCCGUUAGGC GAA AGCGUCUC | 9690 | GAGACGCUC UUCAUAAU | 2550 |
| 2534 | CUAUUAUG CUGAUGA GCCGUUAGGC GAA AGAGCGUC | 9691 | GACGCUCUU CAUAAUAG | 2551 |
| 2535 | UCUAUUAU CUGAUGA GCCGUUAGGC GAA AAGAGCGU | 9692 | ACGCUCUUC AUAAUAGA | 2552 |
| 2538 | CCUUCUAU CUGAUGA GCCGUUAGGC GAA AUGAAGAG | 9693 | CUCUUCAUA AUAGAAGG | 2553 |

| | | | | |
|---|---|---|---|---|
| 2541 | GCACCUUC CUGAUGA GCCGUUAGGC GAA AUUAUGAA | 8999 | UUCAUAAUA GAAGGUGC | 1857 |
| 2567 | UGACUUCC CUGAUGA GCCGUUAGGC GAA AGUUGGUC | 9694 | GACCAACUU GGAAGUCA | 2554 |
| 2574 | AGGAUAAU CUGAUGA GCCGUUAGGC GAA ACUUCCAA | 9695 | UUGGAAGUC AUUAUCCU | 2555 |
| 2577 | ACGAGGAU CUGAUGA GCCGUUAGGC GAA AUGACUUC | 9696 | GAAGUCAUU AUCCUCGU | 2556 |
| 2578 | GACGAGGA CUGAUGA GCCGUUAGGC GAA AAUGACUU | 9697 | AAGUCAUUA UCCUCGUC | 2557 |
| 2580 | CCGACGAG CUGAUGA GCCGUUAGGC GAA AUAAUGAC | 9698 | GUCAUUAUC CUCGUCGG | 2558 |
| 2583 | GUGCCGAC CUGAUGA GCCGUUAGGC GAA AGGAUAAU | 9699 | AUUAUCCUC GUCGGCAC | 2559 |
| 2586 | GCAGUGCC CUGAUGA GCCGUUAGGC GAA ACGAGGAU | 9700 | AUCCUCGUC GGCACUGC | 2560 |
| 2601 | AACAUGGC CUGAUGA GCCGUUAGGC GAA AUCACUGC | 9701 | GCAGUGAUU GCCAUGUU | 2561 |
| 2609 | GCCAGAAG CUGAUGA GCCGUUAGGC GAA ACAUGGCA | 9009 | UGCCAUGUU CUUCUGGC | 1867 |
| 2610 | AGCCAGAA CUGAUGA GCCGUUAGGC GAA AACAUGGC | 9010 | GCCAUGUUC UUCUGGCU | 1868 |
| 2612 | GGAGCCAG CUGAUGA GCCGUUAGGC GAA AGAACAUG | 9702 | CAUGUUCUU CUGGCUCC | 2562 |
| 2613 | AGGAGCCA CUGAUGA GCCGUUAGGC GAA AAGAACAU | 9703 | AUGUUCUUC UGGCUCCU | 2563 |
| 2619 | ACAAGAAG CUGAUGA GCCGUUAGGC GAA AGCCAGAA | 9013 | UUCUGGCUC CUUCUUGU | 2564 |
| 2622 | AUGACAAG CUGAUGA GCCGUUAGGC GAA AGGAGCCA | 9704 | UGGCUCCUU CUUGUCAU | 2565 |
| 2623 | AAUGACAA CUGAUGA GCCGUUAGGC GAA AAGGAGCC | 9705 | GGCUCCUUC UUGUCAUU | 2566 |
| 2625 | ACAAUGAC CUGAUGA GCCGUUAGGC GAA AGAAGGAG | 9706 | CUCCUUCUU GUCAUUGU | 2567 |
| 2628 | AGGACAAU CUGAUGA GCCGUUAGGC GAA ACAAGAAG | 9707 | CUUCUUGUC AUUGUCCU | 2568 |
| 2631 | CGUAGGAC CUGAUGA GCCGUUAGGC GAA AUGACAAG | 9708 | CUUGUCAUU GUCCUACG | 2569 |
| 2634 | GUCCGUAG CUGAUGA GCCGUUAGGC GAA ACAAUGAC | 9709 | GUCAUUGUC CUACGGAC | 2570 |
| 2637 | ACGGUCCG CUGAUGA GCCGUUAGGC GAA AGGACAAU | 9710 | AUUGUCCUA CGGACCGU | 2571 |
| 2646 | GCCCGCUU CUGAUGA GCCGUUAGGC GAA ACGGUCCG | 9711 | CGGACCGUU AAGCGGGC | 2572 |
| 2647 | GGCCCGCU CUGAUGA GCCGUUAGGC GAA AACGGUCC | 9022 | GGACCGUUA AGCGGGCC | 1880 |
| 2681 | UAGACAAG CUGAUGA GCCGUUAGGC GAA AGCCUGUC | 9712 | GACAGGCUA CUUGUCUA | 2573 |
| 2684 | CAAUAGAC CUGAUGA GCCGUUAGGC GAA AGUAGCCU | 9713 | AGGCUACUU GUCUAUUG | 2574 |
| 2687 | UGACAAUA CUGAUGA GCCGUUAGGC GAA ACAAGUAG | 9714 | CUACUUGUC UAUUGUCA | 2575 |
| 2689 | CAUGACAA CUGAUGA GCCGUUAGGC GAA AGACAAGU | 9715 | ACUUGUCUA UUGUCAUG | 2576 |
| 2691 | UCCAUGAC CUGAUGA GCCGUUAGGC GAA AUAGACAA | 9716 | UUGUCUAUU GUCAUGGA | 2577 |
| 2694 | GGAUCCAU CUGAUGA GCCGUUAGGC GAA ACAAUAGA | 9717 | UCUAUUGUC AUGGAUCC | 2578 |
| 2701 | UUCAUCUG CUGAUGA GCCGUUAGGC GAA AUCCAUGA | 9028 | UCAUGGAUC CAGAUGAA | 1886 |
| 2711 | CCAAGGGC CUGAUGA GCCGUUAGGC GAA AUUCAUCU | 9718 | AGAUGAAUU GCCCUUGG | 2579 |
| 2717 | GCUCAUCC CUGAUGA GCCGUUAGGC GAA AGGGCAAU | 9719 | AUUGCCCUU GGAUGAGC | 2580 |
| 2738 | CAUAAGGC CUGAUGA GCCGUUAGGC GAA AGCGUUCA | 9720 | UGAACGCUU GCCUUAUG | 2581 |
| 2743 | GGCAUCAU CUGAUGA GCCGUUAGGC GAA AGGCAAGC | 9721 | GCUUGCCUU AUGAUGCC | 2582 |
| 2744 | UGGCAUCA CUGAUGA GCCGUUAGGC GAA AAGGCAAG | 9722 | CUUGCCUUA UGAUGCCA | 2583 |
| 2765 | CCCUGGGG CUGAUGA GCCGUUAGGC GAA AUUCCCAC | 9723 | GUGGGAAUU CCCCAGGG | 2584 |
| 2766 | UCCCUGGG CUGAUGA GCCGUUAGGC GAA AAUUCCCA | 9724 | UGGGAAUUC CCCAGGGA | 2585 |
| 2787 | GGUUUUCC CUGAUGA GCCGUUAGGC GAA AGUUUCAG | 9725 | CUGAAACUA GGAAAACC | 2586 |
| 2797 | GCGGCCAA CUGAUGA GCCGUUAGGC GAA AGGUUUUC | 9726 | GAAAACCUC UUGGCCGC | 2587 |

| | | | | |
|---|---|---|---|---|
| 2799 | CCGCGGCC CUGAUGA GCCGUUAGGC GAA AGAGGUUU | 9727 | AAACCUCUU GGCCGCGG | 2588 |
| 2813 | CUUGGCCG CUGAUGA GCCGUUAGGC GAA AGGCACCG | 9728 | CGGUGCCUU CGGCCAAG | 2589 |
| 2814 | ACUUGGCC CUGAUGA GCCGUUAGGC GAA AAGGCACC | 9729 | GGUGCCUUC GGCCAAGU | 2590 |
| 2826 | UCUGCCUC CUGAUGA GCCGUUAGGC GAA AUCACUUG | 9730 | CAAGUGAUU GAGGCAGA | 2591 |
| 2839 | AAUUCCAA CUGAUGA GCCGUUAGGC GAA AGCGUCUG | 9731 | CAGACGCUU UUGGAAUU | 2592 |
| 2840 | CAAUUCCA CUGAUGA GCCGUUAGGC GAA AAGCGUCU | 9732 | AGACGCUUU UGGAAUUG | 2593 |
| 2841 | UCAAUUCC CUGAUGA GCCGUUAGGC GAA AAAGCGUC | 9733 | GACGCUUUU GGAAUUGA | 2594 |
| 2847 | GUCUUGUC CUGAUGA GCCGUUAGGC GAA AUUCCAAA | 9045 | UUUGGAAUU GACAAGAC | 1903 |
| 2863 | UGUUUUGC CUGAUGA GCCGUUAGGC GAA AGUCGCUG | 9734 | CAGCGACUU GCAAAACA | 2595 |
| 2874 | UUGACGGC CUGAUGA GCCGUUAGGC GAA ACUGUUUU | 9735 | AAAACAGUA GCCGUCAA | 2596 |
| 2880 | AACAUCUU CUGAUGA GCCGUUAGGC GAA ACGGCUAC | 9736 | GUAGCCGUC AAGAUGUU | 2597 |
| 2888 | CUUCUUUC CUGAUGA GCCGUUAGGC GAA ACAUCUUG | 9737 | CAAGAUGUU GAAAGAAG | 2598 |
| 2917 | GAGGGCUC CUGAUGA GCCGUUAGGC GAA AUGCUCGC | 9738 | GCGAGCAUC GAGCCCUC | 2599 |
| 2925 | UCAGACAU CUGAUGA GCCGUUAGGC GAA AGGGCUCG | 9739 | CGAGCCCUC AUGUCUGA | 2600 |
| 2930 | UGAGUUCA CUGAUGA GCCGUUAGGC GAA ACAUGAGG | 9740 | CCUCAUGUC UGAACUCA | 2601 |
| 2937 | AGGAUCUU CUGAUGA GCCGUUAGGC GAA AGUUCAGA | 9054 | UCUGAACUC AAGAUCCU | 1912 |
| 2943 | UGGAUGAG CUGAUGA GCCGUUAGGC GAA AUCUUGAG | 9741 | CUCAAGAUC CUCAUCCA | 2602 |
| 2946 | AUGUGGAU CUGAUGA GCCGUUAGGC GAA AGGAUCUU | 9742 | AAGAUCCUC AUCCACAU | 2603 |
| 2949 | CCAAUGUG CUGAUGA GCCGUUAGGC GAA AUGAGGAU | 9743 | AUCCUCAUC CACAUUGG | 2604 |
| 2955 | UGGUGACC CUGAUGA GCCGUUAGGC GAA AUGUGGAU | 9744 | AUCCACAUU GGUCACCA | 2605 |
| 2959 | GAGAUGGU CUGAUGA GCCGUUAGGC GAA ACCAAUGU | 9745 | ACAUUGGUC ACCAUCUC | 2606 |
| 2965 | CACAUUGA CUGAUGA GCCGUUAGGC GAA AUGGUGAC | 9062 | GUCACCAUC UCAAUGUG | 1920 |
| 2967 | ACCACAUU CUGAUGA GCCGUUAGGC GAA AGAUGGUG | 9063 | CACCAUCUC AAUGUGGU | 1921 |
| 2982 | GCGCCUAG CUGAUGA GCCGUUAGGC GAA AGGUUCAC | 9746 | GUGAACCUC CUAGGCGC | 2607 |
| 2985 | CAGGCGCC CUGAUGA GCCGUUAGGC GAA AGGAGGUU | 9747 | AACCUCCUA GGCGCCUG | 2608 |
| 3013 | CACCAUGA CUGAUGA GCCGUUAGGC GAA AGGCCCUC | 9748 | GAGGGCCUC UCAUGGUG | 2609 |
| 3015 | AUCACCAU CUGAUGA GCCGUUAGGC GAA AGAGGCCC | 9749 | GGGCCUCUC AUGGUGAU | 2610 |
| 3024 | AAUUCCAC CUGAUGA GCCGUUAGGC GAA AUCACCAU | 9070 | AUGGUGAUU GUGGAAUU | 1928 |
| 3032 | ACUUGCAG CUGAUGA GCCGUUAGGC GAA AUUCCACA | 9750 | UGUGGAAUU CUGCAAGU | 2611 |
| 3033 | AACUUGCA CUGAUGA GCCGUUAGGC GAA AAUUCCAC | 9751 | GUGGAAUUC UGCAAGUU | 2612 |
| 3041 | GGUUUCCA CUGAUGA GCCGUUAGGC GAA ACUUGCAG | 9752 | CUGCAAGUU UGGAAACC | 2613 |
| 3042 | AGGUUUCC CUGAUGA GCCGUUAGGC GAA AACUUGCA | 9753 | UGCAAGUUU GGAAACCU | 2614 |
| 3051 | UAAGUUGA CUGAUGA GCCGUUAGGC GAA AGGUUUCC | 9754 | GGAAACCUA UCAACUUA | 2615 |
| 3053 | AGUAAGUU CUGAUGA GCCGUUAGGC GAA AUAGGUUU | 9755 | AAACCUAUC AACUUACU | 2616 |
| 3058 | CCGUAAGU CUGAUGA GCCGUUAGGC GAA AGUUGAUA | 9756 | UAUCAACUU ACUUACGG | 2617 |
| 3059 | CCCGUAAG CUGAUGA GCCGUUAGGC GAA AAGUUGAU | 9757 | AUCAACUUA CUUACGGG | 2618 |
| 3062 | UGCCCCGU CUGAUGA GCCGUUAGGC GAA AGUAAGUU | 9758 | AACUUACUU ACGGGGCA | 2619 |
| 3063 | UUGCCCCG CUGAUGA GCCGUUAGGC GAA AAGUAAGU | 9759 | ACUUACUUA CGGGGCAA | 2620 |
| 3083 | AGGGAACA CUGAUGA GCCGUUAGGC GAA AUUCAUUU | 9760 | AAAUGAAUU UGUUCCCU | 2621 |

| | | | | |
|---|---|---|---|---|
| 3084 | UAGGGAAC CUGAUGA GCCGUUAGGC GAA AAUUCAUU | 9761 | AAUGAAUUU GUUCCCUA | 2622 |
| 3087 | UUAUAGGG CUGAUGA GCCGUUAGGC GAA ACAAAUUC | 9762 | GAAUUUGUU CCCUAUAA | 2623 |
| 3088 | CUUAUAGG CUGAUGA GCCGUUAGGC GAA AACAAAUU | 9763 | AAUUUGUUC CCUAUAAG | 2624 |
| 3092 | UGCUCUUA CUGAUGA GCCGUUAGGC GAA AGGGAACA | 9764 | UGUUCCCUA UAAGAGCA | 2625 |
| 3094 | UUUGCUCU CUGAUGA GCCGUUAGGC GAA AUAGGGAA | 9765 | UUCCCUAUA AGAGCAAA | 2626 |
| 3113 | CCUGGCGG CUGAUGA GCCGUUAGGC GAA AGCGUGCC | 9766 | GGCACGCUU CCGCCAGG | 2627 |
| 3114 | CCCUGGCG CUGAUGA GCCGUUAGGC GAA AAGCGUGC | 9767 | GCACGCUUC CGCCAGGG | 2628 |
| 3131 | CCCCAACG CUGAUGA GCCGUUAGGC GAA AGUCCUUG | 9768 | CAAGGACUA CGUUGGGG | 2629 |
| 3135 | AGCUCCCC CUGAUGA GCCGUUAGGC GAA ACGUAGUC | 9769 | GACUACGUU GGGGAGCU | 2630 |
| 3144 | UCCACGGA CUGAUGA GCCGUUAGGC GAA AGCUCCCC | 9770 | GGGGAGCUC UCCGUGGA | 2631 |
| 3146 | GAUCCACG CUGAUGA GCCGUUAGGC GAA AGAGCUCC | 9771 | GGAGCUCUC CGUGGAUC | 2632 |
| 3154 | UCUUUUCA CUGAUGA GCCGUUAGGC GAA AUCCACGG | 9772 | CCGUGGAUC UGAAAAGA | 2633 |
| 3167 | UGCUGUCC CUGAUGA GCCGUUAGGC GAA AGCGUCUU | 9773 | AAGACGCUU GGACAGCA | 2634 |
| 3177 | CUGCUGGU CUGAUGA GCCGUUAGGC GAA AUGCUGUC | 9774 | GACAGCAUC ACCAGCAG | 2635 |
| 3194 | AGCUGGCA CUGAUGA GCCGUUAGGC GAA AGCUCUGG | 9775 | CCAGAGCUC UGCCAGCU | 2636 |
| 3203 | CAAAGCCU CUGAUGA GCCGUUAGGC GAA AGCUGGCA | 9776 | UGCCAGCUC AGGCUUUG | 2637 |
| 3209 | CCUCAACA CUGAUGA GCCGUUAGGC GAA AGCCUGAG | 9777 | CUCAGGCUU UGUUGAGG | 2638 |
| 3210 | UCCUCAAC CUGAUGA GCCGUUAGGC GAA AAGCCUGA | 9778 | UCAGGCUUU GUUGAGGA | 2639 |
| 3213 | UUCUCCUC CUGAUGA GCCGUUAGGC GAA ACAAAGCC | 9779 | GGCUUUGUU GAGGAGAA | 2640 |
| 3224 | CACUGAGC CUGAUGA GCCGUUAGGC GAA AUUUCUCC | 9780 | GGAGAAAUC GCUCAGUG | 2641 |
| 3228 | ACAUCACU CUGAUGA GCCGUUAGGC GAA AGCGAUUU | 9781 | AAAUCGCUC AGUGAUGU | 2642 |
| 3237 | UCUUCCUC CUGAUGA GCCGUUAGGC GAA ACAUCACU | 7644 | AGUGAUGUA GAGGAAGA | 2643 |
| 3253 | UUCUUCAG CUGAUGA GCCGUUAGGC GAA AGCUUCUU | 9782 | AAGAAGCUU CUGAAGAA | 2644 |
| 3254 | GUUCUUCA CUGAUGA GCCGUUAGGC GAA AAGCUUCU | 9783 | AGAAGCUUC UGAAGAAC | 2645 |
| 3266 | AGUCCUUG CUGAUGA GCCGUUAGGC GAA ACAGUUCU | 9784 | AGAACUGUA CAAGGACU | 2646 |
| 3275 | AGGUCAGG CUGAUGA GCCGUUAGGC GAA AGUCCUUG | 9785 | CAAGGACUU CCUGACCU | 2647 |
| 3276 | AAGGUCAG CUGAUGA GCCGUUAGGC GAA AAGUCCUU | 9104 | AAGGACUUC CUGACCUU | 1962 |
| 3284 | GAUGCUCC CUGAUGA GCCGUUAGGC GAA AGGUCAGG | 9105 | CCUGACCUU GGAGCAUC | 1963 |
| 3292 | ACAGAUGA CUGAUGA GCCGUUAGGC GAA AUGCUCCA | 9106 | UGGAGCAUC UCAUCUGU | 1964 |
| 3294 | UAACAGAU CUGAUGA GCCGUUAGGC GAA AGAUGCUC | 9107 | GAGCAUCUC AUCUGUUA | 1965 |
| 3297 | CUGUAACA CUGAUGA GCCGUUAGGC GAA AUGAGAUG | 9108 | CAUCUCAUC UGUUACAG | 1966 |
| 3301 | GAAGCUGU CUGAUGA GCCGUUAGGC GAA ACAGAUGA | 9109 | UCAUCUGUU ACAGCUUC | 1967 |
| 3302 | GGAAGCUG CUGAUGA GCCGUUAGGC GAA AACAGAUG | 9110 | CAUCUGUUA CAGCUUCC | 1968 |
| 3308 | CCACUUGG CUGAUGA GCCGUUAGGC GAA AGCUGUAA | 9111 | UUACAGCUU CCAAGUGG | 1969 |
| 3309 | GCCACUUG CUGAUGA GCCGUUAGGC GAA AAGCUGUA | 9112 | UACAGCUUC CAAGUGGC | 1970 |
| 3319 | CAUGCCCU CUGAUGA GCCGUUAGGC GAA AGCCACUU | 9113 | AAGUGGCUA AGGGCAUG | 1971 |
| 3332 | AUGCCAAG CUGAUGA GCCGUUAGGC GAA ACUCCAUG | 9114 | CAUGGAGUU CUUGGCAU | 1972 |
| 3333 | GAUGCCAA CUGAUGA GCCGUUAGGC GAA AACUCCAU | 9115 | AUGGAGUUC UUGGCAUC | 1973 |
| 3335 | UUGAUGCC CUGAUGA GCCGUUAGGC GAA AGAACUCC | 9786 | GGAGUUCUU GGCAUCAA | 2648 |

153

| | | | | |
|---|---|---|---|---|
| 3341 | ACUUCCUU CUGAUGA GCCGUUAGGC GAA AUGCCAAG | 9787 | CUUGGCAUC AAGGAAGU | 2649 |
| 3352 | CCUGUGGA CUGAUGA GCCGUUAGGC GAA ACACUUCC | 9788 | GGAAGUGUA UCCACAGG | 2650 |
| 3354 | UCCCUGUG CUGAUGA GCCGUUAGGC GAA AUACACUU | 9119 | AAGUGUAUC CACAGGGA | 1977 |
| 3381 | GAUAGGAG CUGAUGA GCCGUUAGGC GAA AUGUUUCG | 9789 | CGAAACAUU CUCCUAUC | 2651 |
| 3382 | CGAUAGGA CUGAUGA GCCGUUAGGC GAA AAUGUUUC | 9790 | GAAACAUUC UCCUAUCG | 2652 |
| 3384 | UCCGAUAG CUGAUGA GCCGUUAGGC GAA AGAAUGUU | 9791 | AACAUUCUC CUAUCGGA | 2653 |
| 3387 | UUCUCCGA CUGAUGA GCCGUUAGGC GAA AGGAGAAU | 9792 | AUUCUCCUA UCGGAGAA | 2654 |
| 3389 | UCUUCUCC CUGAUGA GCCGUUAGGC GAA AUAGGAGA | 9793 | UCUCCUAUC GGAGAAGA | 2655 |
| 3405 | CAGAUCUU CUGAUGA GCCGUUAGGC GAA ACCACAUU | 9794 | AAUGUGGUU AAGAUCUG | 2656 |
| 3406 | ACAGAUCU CUGAUGA GCCGUUAGGC GAA AACCACAU | 9795 | AUGUGGUUA AGAUCUGU | 2657 |
| 3411 | AAGUCACA CUGAUGA GCCGUUAGGC GAA AUCUUAAC | 9796 | GUUAAGAUC UGUGACUU | 2658 |
| 3419 | CCAAGCCG CUGAUGA GCCGUUAGGC GAA AGUCACAG | 9797 | CUGUGACUU CGGCUUGG | 2659 |
| 3420 | GCCAAGCC CUGAUGA GCCGUUAGGC GAA AAGUCACA | 9130 | UGUGACUUC GGCUUGGC | 2660 |
| 3425 | CCCGGGCC CUGAUGA GCCGUUAGGC GAA AGCCGAAG | 9798 | CUUCGGCUU GGCCCGGG | 2661 |
| 3438 | UCUUUAUA CUGAUGA GCCGUUAGGC GAA AUGUCCCG | 9799 | CGGGACAUU UAUAAAGA | 2662 |
| 3439 | GUCUUUAU CUGAUGA GCCGUUAGGC GAA AAUGUCCC | 9800 | GGGACAUUU AUAAAGAC | 2663 |
| 3440 | GGUCUUUA CUGAUGA GCCGUUAGGC GAA AAAUGUCC | 9801 | GGACAUUUA UAAAGACC | 2664 |
| 3442 | CGGGUCUU CUGAUGA GCCGUUAGGC GAA AUAAAUGU | 9802 | ACAUUUAUA AAGACCCG | 2665 |
| 3454 | UCUGACAU CUGAUGA GCCGUUAGGC GAA AUCCGGGU | 9803 | ACCCGGAUU AUGUCAGA | 2666 |
| 3455 | UUCUGACA CUGAUGA GCCGUUAGGC GAA AAUCCGGG | 9804 | CCCGGAUUA UGUCAGAA | 2667 |
| 3459 | CCUUUUCU CUGAUGA GCCGUUAGGC GAA ACAUAAUC | 9140 | GAUUAUGUC AGAAAAGG | 1998 |
| 3480 | UUCAAAGG CUGAUGA GCCGUUAGGC GAA AGUCGGGC | 9805 | GCCCGACUC CCUUUGAA | 2668 |
| 3484 | CCACUUCA CUGAUGA GCCGUUAGGC GAA AGGGAGUC | 9806 | GACUCCCUU UGAAGUGG | 2669 |
| 3485 | UCCACUUC CUGAUGA GCCGUUAGGC GAA AAGGGAGU | 9807 | ACUCCCUUU GAAGUGGA | 2670 |
| 3510 | CUGUCAAA CUGAUGA GCCGUUAGGC GAA AUGGUUUC | 9808 | GAAACCAUU UUUGACAG | 2671 |
| 3511 | UCUGUCAA CUGAUGA GCCGUUAGGC GAA AAUGGUUU | 9809 | AAACCAUUU UUGACAGA | 2672 |
| 3512 | CUCUGUCA CUGAUGA GCCGUUAGGC GAA AAAUGGUU | 9810 | AACCAUUUU UGACAGAG | 2673 |
| 3513 | ACUCUGUC CUGAUGA GCCGUUAGGC GAA AAAAUGGU | 9811 | ACCAUUUUU GACAGAGU | 2674 |
| 3522 | AUUGUGUA CUGAUGA GCCGUUAGGC GAA ACUCUGUC | 9812 | GACAGAGUA UACACAAU | 2675 |
| 3524 | GAAUUGUG CUGAUGA GCCGUUAGGC GAA AUACUCUG | 9813 | CAGAGUAUA CACAAUUC | 2676 |
| 3531 | UCGCUCUG CUGAUGA GCCGUUAGGC GAA AUUGUGUA | 9814 | UACACAAUU CAGAGCGA | 2677 |
| 3532 | AUCGCUCU CUGAUGA GCCGUUAGGC GAA AAUUGUGU | 9815 | ACACAAUUC AGAGCGAU | 2678 |
| 3548 | CACCGAAA CUGAUGA GCCGUUAGGC GAA ACCACACA | 9816 | UGUGUGGUC UUUCGGUG | 2679 |
| 3550 | CACACCGA CUGAUGA GCCGUUAGGC GAA AGACCACA | 9817 | UGUGGUCUU UCGGUGUG | 2680 |
| 3551 | ACACACCG CUGAUGA GCCGUUAGGC GAA AAGACCAC | 9818 | GUGGUCUUU CGGUGUGU | 2681 |
| 3552 | AACACACC CUGAUGA GCCGUUAGGC GAA AAAGACCA | 9819 | UGGUCUUUC GGUGUGUU | 2682 |
| 3560 | CCCAGAGC CUGAUGA GCCGUUAGGC GAA ACACACCG | 9820 | CGGUGUGUU GCUCUGGG | 2683 |
| 3564 | AUUUCCCA CUGAUGA GCCGUUAGGC GAA AGCAACAC | 9821 | GUGUUGCUC UGGGAAAU | 2684 |
| 3573 | AAGGAAAA CUGAUGA GCCGUUAGGC GAA AUUUCCCA | 9159 | UGGGAAAUA UUUUCCUU | 2017 |

154

| | | | | |
|---|---|---|---|---|
| 3575 | CUAAGGAA CUGAUGA GCCGUUAGGC GAA AUAUUUCC | 9160 | GGAAAUAUU UUCCUUAG | 2018 |
| 3576 | CCUAAGGA CUGAUGA GCCGUUAGGC GAA AAUAUUUC | 9161 | GAAAUAUUU UCCUUAGG | 2019 |
| 3577 | ACCUAAGG CUGAUGA GCCGUUAGGC GAA AAAUAUUU | 9162 | AAAUAUUUU CCUUAGGU | 2020 |
| 3578 | CACCUAAG CUGAUGA GCCGUUAGGC GAA AAAAUAUU | 9163 | AAUAUUUUC CUUAGGUG | 2021 |
| 3581 | AGGCACCU CUGAUGA GCCGUUAGGC GAA AGGAAAAU | 9822 | AUUUUCCUU AGGUGCCU | 2685 |
| 3582 | GAGGCACC CUGAUGA GCCGUUAGGC GAA AAGGAAAA | 9823 | UUUUCCUUA GGUGCCUC | 2686 |
| 3590 | GGUAUGGG CUGAUGA GCCGUUAGGC GAA AGGCACCU | 9824 | AGGUGCCUC CCCAUACC | 2687 |
| 3596 | CCCCAGGG CUGAUGA GCCGUUAGGC GAA AUGGGGAG | 9825 | CUCCCCAUA CCCUGGGG | 2688 |
| 3606 | UCAAUCUU CUGAUGA GCCGUUAGGC GAA ACCCCAGG | 9171 | CCUGGGGUC AAGAUUGA | 2689 |
| 3612 | UCUUCAUC CUGAUGA GCCGUUAGGC GAA AUCUUGAC | 9826 | GUCAAGAUU GAUGAAGA | 2690 |
| 3623 | UCCUACAA CUGAUGA GCCGUUAGGC GAA AUUCUUCA | 9827 | UGAAGAAUU UUGUAGGA | 2691 |
| 3624 | CUCCUACA CUGAUGA GCCGUUAGGC GAA AAUUCUUC | 9828 | GAAGAAUUU UGUAGGAG | 2692 |
| 3625 | UCUCCUAC CUGAUGA GCCGUUAGGC GAA AAAUUCUU | 9829 | AAGAAUUUU GUAGGAGA | 2693 |
| 3628 | CAAUCUCC CUGAUGA GCCGUUAGGC GAA ACAAAAUU | 9830 | AAUUUUGUA GGAGAUUG | 2694 |
| 3635 | CUUCUUUC CUGAUGA GCCGUUAGGC GAA AUCUCCUA | 9831 | UAGGAGAUU GAAAGAAG | 2695 |
| 3649 | CCGCAUUC CUGAUGA GCCGUUAGGC GAA AGUUCCUU | 9832 | AAGGAACUA GAAUGCGG | 2696 |
| 3661 | GUAGUCAG CUGAUGA GCCGUUAGGC GAA AGCCCGCA | 9833 | UGCGGGCUC CUGACUAC | 2697 |
| 3668 | GGGUAGUG CUGAUGA GCCGUUAGGC GAA AGUCAGGA | 9834 | UCCUGACUA CACUACCC | 2698 |
| 3673 | UUCUGGGG CUGAUGA GCCGUUAGGC GAA AGUGUAGU | 9835 | ACUACACUA CCCCAGAA | 2699 |
| 3686 | UGGUCUGG CUGAUGA GCCGUUAGGC GAA ACAUUUCU | 9183 | AGAAAUGUA CCAGACCA | 2041 |
| 3734 | CUGAAAAC CUGAUGA GCCGUUAGGC GAA AGGGUCUC | 9836 | GAGACCCUC GUUUUCAG | 2700 |
| 3737 | ACUCUGAA CUGAUGA GCCGUUAGGC GAA ACGAGGGU | 9837 | ACCCUCGUU UUCAGAGU | 2701 |
| 3738 | AACUCUGA CUGAUGA GCCGUUAGGC GAA AACGAGGG | 9838 | CCCUCGUUU UCAGAGUU | 2702 |
| 3739 | CAACUCUG CUGAUGA GCCGUUAGGC GAA AAACGAGG | 9839 | CCUCGUUUU CAGAGUUG | 2703 |
| 3740 | CCAACUCU CUGAUGA GCCGUUAGGC GAA AAAACGAG | 9840 | CUCGUUUUC AGAGUUGG | 2704 |
| 3746 | GCUCCACC CUGAUGA GCCGUUAGGC GAA ACUCUGAA | 9841 | UUCAGAGUU GGUGGAGC | 2705 |
| 3757 | GUUUCCCA CUGAUGA GCCGUUAGGC GAA AUGCUCCA | 9842 | UGGAGCAUU UGGGAAAC | 2706 |
| 3758 | GGUUUCCC CUGAUGA GCCGUUAGGC GAA AAUGCUCC | 9843 | GGAGCAUUU GGGAAACC | 2707 |
| 3768 | GCUUGCAG CUGAUGA GCCGUUAGGC GAA AGGUUUCC | 9844 | GGAAACCUC CUGCAAGC | 2708 |
| 3803 | GAACAAUA CUGAUGA GCCGUUAGGC GAA AGUCUUUG | 9845 | CAAAGACUA UAUUGUUC | 2709 |
| 3805 | AAGAACAA CUGAUGA GCCGUUAGGC GAA AUAGUCUU | 9846 | AAGACUAUA UUGUUCUU | 2710 |
| 3807 | GGAAGAAC CUGAUGA GCCGUUAGGC GAA AUAUAGUC | 9847 | GACUAUAUU GUUCUUCC | 2711 |
| 3810 | AUUGGAAG CUGAUGA GCCGUUAGGC GAA ACAAUAUA | 9848 | UAUAUUGUU CUUCCAAU | 2712 |
| 3811 | CAUUGGAA CUGAUGA GCCGUUAGGC GAA AACAAUAU | 9849 | AUAUUGUUC UUCCAAUG | 2713 |
| 3813 | GACAUUGG CUGAUGA GCCGUUAGGC GAA AGAACAAU | 9850 | AUUGUUCUU CCAAUGUC | 2714 |
| 3814 | UGACAUUG CUGAUGA GCCGUUAGGC GAA AAGAACAA | 9851 | UUGUUCUUC CAAUGUCA | 2715 |
| 3821 | GUGUCUCU CUGAUGA GCCGUUAGGC GAA ACAUUGGA | 9852 | UCCAAUGUC AGAGACAC | 2716 |
| 3847 | GAGUCCAG CUGAUGA GCCGUUAGGC GAA AUCCUCUU | 9207 | AAGAGGAUU CUGGACUC | 2065 |
| 3848 | AGAGUCCA CUGAUGA GCCGUUAGGC GAA AAUCCUCU | 9208 | AGAGGAUUC UGGACUCU | 2066 |

155

| | | | | |
|---|---|---|---|---|
| 3855 | GGCAGGGA CUGAUGA GCCGUUAGGC GAA AGUCCAGA | 9853 | UCUGGACUC UCCCUGCC | 2717 |
| 3857 | UAGGCAGG CUGAUGA GCCGUUAGGC GAA AGAGUCCA | 9854 | UGGACUCUC CCUGCCUA | 2718 |
| 3865 | AGGUGAGG CUGAUGA GCCGUUAGGC GAA AGGCAGGG | 9855 | CCCUGCCUA CCUCACCU | 2719 |
| 3869 | AAACAGGU CUGAUGA GCCGUUAGGC GAA AGGUAGGC | 9213 | GCCUACCUC ACCUGUUU | 2071 |
| 3876 | AUACAGGA CUGAUGA GCCGUUAGGC GAA ACAGGUGA | 9214 | UCACCUGUU UCCUGUAU | 2072 |
| 3877 | CAUACAGG CUGAUGA GCCGUUAGGC GAA AACAGGUG | 9215 | CACCUGUUU CCUGUAUG | 2073 |
| 3878 | CCAUACAG CUGAUGA GCCGUUAGGC GAA AAACAGGU | 9216 | ACCUGUUUC CUGUAUGG | 2074 |
| 3883 | UUCCUCCA CUGAUGA GCCGUUAGGC GAA ACAGGAAA | 9856 | UUUCCUGUA UGGAGGAA | 2720 |
| 3914 | CAUAAUGG CUGAUGA GCCGUUAGGC GAA AUUUGGGG | 9219 | CCCCAAAUU CCAUUAUG | 2077 |
| 3915 | UCAUAAUG CUGAUGA GCCGUUAGGC GAA AAUUUGGG | 9220 | CCCAAAUUC CAUUAUGA | 2078 |
| 3919 | GUUGUCAU CUGAUGA GCCGUUAGGC GAA AUGGAAUU | 9221 | AAUUCCAUU AUGACAAC | 2079 |
| 3920 | UGUUGUCA CUGAUGA GCCGUUAGGC GAA AAUGGAAU | 9222 | AUUCCAUUA UGACAACA | 2080 |
| 3939 | UAAUGACU CUGAUGA GCCGUUAGGC GAA AUUCCUGC | 9857 | GCAGGAAUC AGUCAUUA | 2721 |
| 3943 | GAGAUAAU CUGAUGA GCCGUUAGGC GAA ACUGAUUC | 9858 | GAAUCAGUC AUUAUCUC | 2722 |
| 3946 | CUGGAGAU CUGAUGA GCCGUUAGGC GAA AUGACUGA | 9859 | UCAGUCAUU AUCUCCAG | 2723 |
| 3947 | UCUGGAGA CUGAUGA GCCGUUAGGC GAA AAUGACUG | 9860 | CAGUCAUUA UCUCCAGA | 2724 |
| 3949 | GUUCUGGA CUGAUGA GCCGUUAGGC GAA AUAAUGAC | 9861 | GUCAUUAUC UCCAGAAC | 2725 |
| 3951 | CUGUUCUG CUGAUGA GCCGUUAGGC GAA AGAUAAUG | 9862 | CAUUAUCUC CAGAACAG | 2726 |
| 3961 | CUUUCGCU CUGAUGA GCCGUUAGGC GAA ACUGUUCU | 9227 | AGAACAGUA AGCGAAAG | 2085 |
| 3987 | AAUGUUUU CUGAUGA GCCGUUAGGC GAA ACACUCAC | 9228 | GUGAGUGUA AAAACAUU | 2086 |
| 3995 | UAUCUUCA CUGAUGA GCCGUUAGGC GAA AUGUUUUU | 9229 | AAAAACAUU UGAAGAUA | 2087 |
| 3996 | AUAUCUUC CUGAUGA GCCGUUAGGC GAA AAUGUUUU | 9230 | AAAACAUUU GAAGAUAU | 2088 |
| 4003 | CAAUGGGA CUGAUGA GCCGUUAGGC GAA AUCUUCAA | 9863 | UUGAAGAUA UCCCAUUG | 2727 |
| 4005 | UCCAAUGG CUGAUGA GCCGUUAGGC GAA AUAUCUUC | 9864 | GAAGAUAUC CCAUUGGA | 2728 |
| 4010 | GUUCCUCC CUGAUGA GCCGUUAGGC GAA AUGGGAUA | 9865 | UAUCCCAUU GGAGGAAC | 2729 |
| 4026 | AUCACUUU CUGAUGA GCCGUUAGGC GAA ACUUCUGG | 9866 | CCAGAAGUA AAAGUGAU | 2730 |
| 4035 | UCAUCUGG CUGAUGA GCCGUUAGGC GAA AUCACUUU | 9867 | AAAGUGAUC CCAGAUGA | 2731 |
| 4068 | GAUGCAAG CUGAUGA GCCGUUAGGC GAA ACCAUCCC | 9868 | GGGAUGGUC CUUGCAUC | 2732 |
| 4071 | UCUGAUGC CUGAUGA GCCGUUAGGC GAA AGGACCAU | 9869 | AUGGUCCUU GCAUCAGA | 2733 |
| 4076 | GCUCUUCU CUGAUGA GCCGUUAGGC GAA AUGCAAGG | 9870 | CCUUGCAUC AGAAGAGC | 2734 |
| 4093 | GUCUUCCA CUGAUGA GCCGUUAGGC GAA AGUUUUCA | 9243 | UGAAAACUC UGGAAGAC | 2735 |
| 4112 | AUGGAGAU CUGAUGA GCCGUUAGGC GAA AUUUGUUC | 9871 | GAACAAAUU AUCUCCAU | 2736 |
| 4113 | GAUGGAGA CUGAUGA GCCGUUAGGC GAA AAUUUGUU | 9872 | AACAAAUUA UCUCCAUC | 2737 |
| 4115 | AAGAUGGA CUGAUGA GCCGUUAGGC GAA AUAAUUUG | 9247 | CAAAUUAUC UCCAUCUU | 2105 |
| 4117 | AAAAGAUG CUGAUGA GCCGUUAGGC GAA AGAUAAUU | 9248 | AAUUAUCUC CAUCUUUU | 2106 |
| 4121 | CACCAAAA CUGAUGA GCCGUUAGGC GAA AUGGAGAU | 9249 | AUCUCCAUC UUUUGGUG | 2107 |
| 4123 | UCCACCAA CUGAUGA GCCGUUAGGC GAA AGAUGGAG | 9250 | CUCCAUCUU UUGGUGGA | 2108 |
| 4124 | UUCCACCA CUGAUGA GCCGUUAGGC GAA AAGAUGGA | 9251 | UCCAUCUUU UGGUGGAA | 2109 |
| 4125 | AUUCCACC CUGAUGA GCCGUUAGGC GAA AAAGAUGG | 9252 | CCAUCUUUU GGUGGAAU | 2110 |

| | | | | |
|---|---|---|---|---|
| 4144 | CCUGCUUU CUGAUGA GCCGUUAGGC GAA ACUGGGCA | 9873 | UGCCCAGUA AAAGCAGG | 2738 |
| 4157 | AGGCCACA CUGAUGA GCCGUUAGGC GAA ACUCCCUG | 9874 | CAGGGAGUC UGUGGCCU | 2739 |
| 4166 | AGCCUUCC CUGAUGA GCCGUUAGGC GAA AGGCCACA | 9875 | UGUGGCCUC GGAAGGCU | 2740 |
| 4175 | UCUGGUUG CUGAUGA GCCGUUAGGC GAA AGCCUUCC | 9876 | GGAAGGCUC CAACCAGA | 2741 |
| 4193 | CAGACUGG CUGAUGA GCCGUUAGGC GAA AGCCACUG | 9877 | CAGUGGCUA CCAGUCUG | 2742 |
| 4199 | GAUACCCA CUGAUGA GCCGUUAGGC GAA ACUGGUAG | 9878 | CUACCAGUC UGGGUAUC | 2743 |
| 4205 | CUGAGUGA CUGAUGA GCCGUUAGGC GAA ACCCAGAC | 9879 | GUCUGGGUA UCACUCAG | 2744 |
| 4207 | AUCUGAGU CUGAUGA GCCGUUAGGC GAA AUACCCAG | 9880 | CUGGGUAUC ACUCAGAU | 2745 |
| 4211 | UGUCAUCU CUGAUGA GCCGUUAGGC GAA AGUGAUAC | 9881 | GUAUCACUC AGAUGACA | 2746 |
| 4235 | CGCUGGAG CUGAUGA GCCGUUAGGC GAA ACACGGUG | 9882 | CACCGUGUA CUCCAGCG | 2747 |
| 4238 | CGUCGCUG CUGAUGA GCCGUUAGGC GAA AGUACACG | 9883 | CGUGUACUC CAGCGACG | 2748 |
| 4257 | AUCUUUAA CUGAUGA GCCGUUAGGC GAA AGUCCUGC | 9884 | GCAGGACUU UUAAAGAU | 2749 |
| 4258 | CAUCUUUA CUGAUGA GCCGUUAGGC GAA AAGUCCUG | 9885 | CAGGACUUU UAAAGAUG | 2750 |
| 4259 | CCAUCUUU CUGAUGA GCCGUUAGGC GAA AAAGUCCU | 9886 | AGGACUUUU AAAGAUGG | 2751 |
| 4260 | ACCAUCUU CUGAUGA GCCGUUAGGC GAA AAAAGUCC | 9887 | GGACUUUUA AAGAUGGU | 2752 |
| 4281 | UCAGCGUG CUGAUGA GCCGUUAGGC GAA ACUGCAGC | 9888 | GCUGCAGUU CACGCUGA | 2753 |
| 4282 | GUCAGCGU CUGAUGA GCCGUUAGGC GAA AACUGCAG | 9889 | CUGCAGUUC ACGCUGAC | 2754 |
| 4292 | UGGUCCCU CUGAUGA GCCGUUAGGC GAA AGUCAGCG | 9890 | CGCUGACUC AGGGACCA | 2755 |
| 4311 | CAGGAGGU CUGAUGA GCCGUUAGGC GAA AGCUGCAG | 9891 | CUGCAGCUC ACCUCCUG | 2756 |
| 4316 | UUAAACAG CUGAUGA GCCGUUAGGC GAA AGGUGAGC | 9892 | GCUCACCUC CUGUUUAA | 2757 |
| 4321 | UCCAUUUA CUGAUGA GCCGUUAGGC GAA ACAGGAGG | 9893 | CCUCCUGUU UAAAUGGA | 2758 |
| 4322 | UUCCAUUU CUGAUGA GCCGUUAGGC GAA AACAGGAG | 9894 | CUCCUGUUU AAAUGGAA | 2759 |
| 4323 | CUUCCAUU CUGAUGA GCCGUUAGGC GAA AAACAGGA | 9895 | UCCUGUUUA AAUGGAAG | 2760 |
| 4336 | CGGGACAG CUGAUGA GCCGUUAGGC GAA ACCACUUC | 9896 | GAAGUGGUC CUGUCCCG | 2761 |
| 4341 | GGAGCCGG CUGAUGA GCCGUUAGGC GAA ACAGGACC | 9897 | GGUCCUGUC CCGGCUCC | 2762 |
| 4348 | UGGGGGCG CUGAUGA GCCGUUAGGC GAA AGCCGGGA | 9898 | UCCCGGCUC CGCCCCCA | 2763 |
| 4360 | AUUUCCAG CUGAUGA GCCGUUAGGC GAA AGUUGGGG | 9899 | CCCCAACUC CUGGAAAU | 2764 |
| 4369 | UCUCUCGU CUGAUGA GCCGUUAGGC GAA AUUUCCAG | 9900 | CUGGAAAUC ACGAGAGA | 2765 |
| 4387 | GAAAAUCU CUGAUGA GCCGUUAGGC GAA AGCAGCAC | 9901 | GUGCUGCUU AGAUUUUC | 2766 |
| 4388 | UGAAAAUC CUGAUGA GCCGUUAGGC GAA AAGCAGCA | 9902 | UGCUGCUUA GAUUUUCA | 2767 |
| 4392 | CACUUGAA CUGAUGA GCCGUUAGGC GAA AUCUAAGC | 9903 | GCUUAGAUU UUCAAGUG | 2768 |
| 4393 | ACACUUGA CUGAUGA GCCGUUAGGC GAA AAUCUAAG | 9904 | CUUAGAUUU UCAAGUGU | 2769 |
| 4394 | AACACUUG CUGAUGA GCCGUUAGGC GAA AAAUCUAA | 9905 | UUAGAUUUU CAAGUGUU | 2770 |
| 4395 | CAACACUU CUGAUGA GCCGUUAGGC GAA AAAAUCUA | 9906 | UAGAUUUUC AAGUGUUG | 2771 |
| 4402 | GAAAGAAC CUGAUGA GCCGUUAGGC GAA ACACUUGA | 9907 | UCAAGUGUU GUUCUUUC | 2772 |
| 4405 | GUGGAAAG CUGAUGA GCCGUUAGGC GAA ACAACACU | 9288 | AGUGUUGUU CUUUCCAC | 2146 |
| 4406 | GGUGGAAA CUGAUGA GCCGUUAGGC GAA AACAACAC | 9289 | GUGUUGUUC UUUCCACC | 2147 |
| 4408 | GUGGUGGA CUGAUGA GCCGUUAGGC GAA AGAACAAC | 9908 | GUUGUUCUU UCCACCAC | 2773 |
| 4409 | GGUGGUGG CUGAUGA GCCGUUAGGC GAA AAGAACAA | 9909 | UUGUUCUUU CCACCACC | 2774 |

157

| | | | | |
|---|---|---|---|---|
| 4410 | GGGUGGUG CUGAUGA GCCGUUAGGC GAA AAAGAACA | 9910 | UGUUCUUUC CACCACCC | 2775 |
| 4425 | AAUGUGGC CUGAUGA GCCGUUAGGC GAA ACUUCCGG | 9911 | CCGGAAGUA GCCACAUU | 2776 |
| 4433 | GAAAAUCA CUGAUGA GCCGUUAGGC GAA AUGUGGCU | 9912 | AGCCACAUU UGAUUUUC | 2777 |
| 4434 | UGAAAAUC CUGAUGA GCCGUUAGGC GAA AAUGUGGC | 9913 | GCCACAUUU GAUUUUCA | 2778 |
| 4438 | AAAAUGAA CUGAUGA GCCGUUAGGC GAA AUCAAAUG | 9914 | CAUUUGAUU UUCAUUUU | 2779 |
| 4439 | AAAAAUGA CUGAUGA GCCGUUAGGC GAA AAUCAAAU | 9915 | AUUUGAUUU UCAUUUUU | 2780 |
| 4440 | CAAAAAUG CUGAUGA GCCGUUAGGC GAA AAAUCAAA | 9916 | UUUGAUUUU CAUUUUUG | 2781 |
| 4441 | CCAAAAAU CUGAUGA GCCGUUAGGC GAA AAAAUCAA | 9917 | UUGAUUUUC AUUUUUGG | 2782 |
| 4444 | CCUCCAAA CUGAUGA GCCGUUAGGC GAA AUGAAAAU | 9918 | AUUUUCAUU UUUGGAGG | 2783 |
| 4445 | UCCUCCAA CUGAUGA GCCGUUAGGC GAA AAUGAAAA | 9919 | UUUUCAUUU UUGGAGGA | 2784 |
| 4446 | CUCCUCCA CUGAUGA GCCGUUAGGC GAA AAAUGAAA | 9920 | UUUCAUUUU UGGAGGAG | 2785 |
| 4447 | CCUCCUCC CUGAUGA GCCGUUAGGC GAA AAAAUGAA | 9921 | UUCAUUUUU GGAGGAGG | 2786 |
| 4461 | UGCAGUCU CUGAUGA GCCGUUAGGC GAA AGGUCCCU | 9922 | AGGGACCUC AGACUGCA | 2787 |
| 4477 | CUGAGGAC CUGAUGA GCCGUUAGGC GAA AGCUCCUU | 9923 | AAGGAGCUU GUCCUCAG | 2788 |
| 4480 | GCCCUGAG CUGAUGA GCCGUUAGGC GAA ACAAGCUC | 9924 | GAGCUUGUC CUCAGGGC | 2789 |
| 4483 | AAUGCCCU CUGAUGA GCCGUUAGGC GAA AGGACAAG | 9925 | CUUGUCCUC AGGGCAUU | 2790 |
| 4491 | UCUCUGGA CUGAUGA GCCGUUAGGC GAA AUGCCCUG | 9926 | CAGGGCAUU UCCAGAGA | 2791 |
| 4492 | UUCUCUGG CUGAUGA GCCGUUAGGC GAA AAUGCCCU | 9927 | AGGGCAUUU CCAGAGAA | 2792 |
| 4493 | CUUCUCUG CUGAUGA GCCGUUAGGC GAA AAAUGCCC | 9928 | GGGCAUUUC CAGAGAAG | 2793 |
| 4525 | GUAGAGUC CUGAUGA GCCGUUAGGC GAA ACACAUUC | 9929 | GAAUGUGUU GACUCUAC | 2794 |
| 4530 | AGAGAGUA CUGAUGA GCCGUUAGGC GAA AGUCAACA | 9930 | UGUUGACUC UACUCUCU | 2795 |
| 4532 | AAAGAGAG CUGAUGA GCCGUUAGGC GAA AGAGUCAA | 9931 | UUGACUCUA CUCUCUUU | 2796 |
| 4535 | GGAAAAGA CUGAUGA GCCGUUAGGC GAA AGUAGAGU | 9932 | ACUCUACUC UCUUUUCC | 2797 |
| 4537 | AUGGAAAA CUGAUGA GCCGUUAGGC GAA AGAGUAGA | 9933 | UCUACUCUC UUUUCCAU | 2798 |
| 4539 | GAAUGGAA CUGAUGA GCCGUUAGGC GAA AGAGAGUA | 9934 | UACUCUCUU UUCCAUUC | 2799 |
| 4540 | UGAAUGGA CUGAUGA GCCGUUAGGC GAA AAGAGAGU | 9935 | ACUCUCUUU UCCAUUCA | 2800 |
| 4541 | AUGAAUGG CUGAUGA GCCGUUAGGC GAA AAAGAGAG | 9936 | CUCUCUUUU CCAUUCAU | 2801 |
| 4542 | AAUGAAUG CUGAUGA GCCGUUAGGC GAA AAAAGAGA | 9937 | UCUCUUUUC CAUUCAUU | 2802 |
| 4546 | UUUAAAUG CUGAUGA GCCGUUAGGC GAA AUGGAAAA | 9938 | UUUUCCAUU CAUUUAAA | 2803 |
| 4547 | UUUUAAAU CUGAUGA GCCGUUAGGC GAA AAUGGAAA | 9939 | UUUCCAUUC AUUUAAAA | 2804 |
| 4550 | GACUUUUA CUGAUGA GCCGUUAGGC GAA AUGAAUGG | 9940 | CCAUUCAUU UAAAAGUC | 2805 |
| 4551 | GGACUUUU CUGAUGA GCCGUUAGGC GAA AAUGAAUG | 9941 | CAUUCAUUU AAAAGUCC | 2806 |
| 4552 | AGGACUUU CUGAUGA GCCGUUAGGC GAA AAAUGAAU | 9942 | AUUCAUUUA AAAGUCCU | 2807 |
| 4558 | UUAUAUAG CUGAUGA GCCGUUAGGC GAA ACUUUUAA | 9943 | UUAAAAGUC CUAUAUAA | 2808 |
| 4561 | ACAUUAUA CUGAUGA GCCGUUAGGC GAA AGGACUUU | 9944 | AAAGUCCUA UAUAAUGU | 2809 |
| 4563 | GCACAUUA CUGAUGA GCCGUUAGGC GAA AUAGGACU | 9945 | AGUCCUAUA UAAUGUGC | 2810 |
| 4565 | GGGCACAU CUGAUGA GCCGUUAGGC GAA AUAUAGGA | 9946 | UCCUAUAUA AUGUGCCC | 2811 |
| 4583 | GGUAGUGA CUGAUGA GCCGUUAGGC GAA ACCACAGC | 9947 | GCUGUGGUC UCACUACC | 2812 |
| 4585 | CUGGUAGU CUGAUGA GCCGUUAGGC GAA AGACCACA | 9948 | UGUGGUCUC ACUACCAG | 2813 |

158

| | | | | |
|---|---|---|---|---|
| 4589 | UUAACUGG CUGAUGA GCCGUUAGGC GAA AGUGAGAC | 9949 | GUCUCACUA CCAGUUAA | 2814 |
| 4595 | UUUGCUUU CUGAUGA GCCGUUAGGC GAA ACUGGUAG | 9950 | CUACCAGUU AAAGCAAA | 2815 |
| 4596 | UUUUGCUU CUGAUGA GCCGUUAGGC GAA AACUGGUA | 9951 | UACCAGUUA AAGCAAAA | 2816 |
| 4609 | GUGUUUGA CUGAUGA GCCGUUAGGC GAA AGUCUUUU | 9952 | AAAAGACUU UCAAACAC | 2817 |
| 4610 | CGUGUUUG CUGAUGA GCCGUUAGGC GAA AAGUCUUU | 9953 | AAAGACUUU CAAACACG | 2818 |
| 4611 | ACGUGUUU CUGAUGA GCCGUUAGGC GAA AAAGUCUU | 9954 | AAGACUUUC AAACACGU | 2819 |
| 4625 | GGAGGACA CUGAUGA GCCGUUAGGC GAA AGUCCACG | 9955 | CGUGGACUC UGUCCUCC | 2820 |
| 4629 | UCUUGGAG CUGAUGA GCCGUUAGGC GAA ACAGAGUC | 9956 | GACUCUGUC CUCCAAGA | 2821 |
| 4632 | ACUUCUUG CUGAUGA GCCGUUAGGC GAA AGGACAGA | 9957 | UCUGUCCUC CAAGAAGU | 2822 |
| 4654 | GUUUCACA CUGAUGA GCCGUUAGGC GAA AGGUGCCG | 9958 | CGGCACCUC UGUGAAAC | 2823 |
| 4668 | GCCCAUUC CUGAUGA GCCGUUAGGC GAA AUCCAGUU | 9959 | AACUGGAUC GAAUGGGC | 2824 |
| 4683 | AACACACA CUGAUGA GCCGUUAGGC GAA AGCAUUGC | 9960 | GCAAUGCUU UGUGUGUU | 2825 |
| 4684 | CAACACAC CUGAUGA GCCGUUAGGC GAA AAGCAUUG | 9961 | CAAUGCUUU GUGUGUUG | 2826 |
| 4691 | CCAUCCUC CUGAUGA GCCGUUAGGC GAA ACACACAA | 9962 | UUGUGUGUU GAGGAUGG | 2827 |
| 4709 | GGCCCUGG CUGAUGA GCCGUUAGGC GAA ACAUCUCA | 9963 | UGAGAUGUC CCAGGGCC | 2828 |
| 4722 | GGUAGACA CUGAUGA GCCGUUAGGC GAA ACUCGGCC | 9964 | GGCCGAGUC UGUCUACC | 2829 |
| 4726 | CCAAGGUA CUGAUGA GCCGUUAGGC GAA ACAGACUC | 9965 | GAGUCUGUC UACCUUGG | 2830 |
| 4728 | CUCCAAGG CUGAUGA GCCGUUAGGC GAA AGACAGAC | 9966 | GUCUGUCUA CCUUGGAG | 2831 |
| 4732 | AAGCCUCC CUGAUGA GCCGUUAGGC GAA AGGUAGAC | 9967 | GUCUACCUU GGAGGCUU | 2832 |
| 4740 | CCUCCACA CUGAUGA GCCGUUAGGC GAA AGCCUCCA | 9968 | UGGAGGCUU UGUGGAGG | 2833 |
| 4741 | UCCUCCAC CUGAUGA GCCGUUAGGC GAA AAGCCUCC | 9969 | GGAGGCUUU GUGGAGGA | 2834 |
| 4758 | UUGGCUCA CUGAUGA GCCGUUAGGC GAA AGCCCGCA | 9970 | UGCGGGCUA UGAGCCAA | 2835 |
| 4771 | CCACACUU CUGAUGA GCCGUUAGGC GAA ACACUUGG | 9971 | CCAAGUGUU AAGUGUGG | 2836 |
| 4772 | CCCACACU CUGAUGA GCCGUUAGGC GAA AACACUUG | 9972 | CAAGUGUUA AGUGUGGG | 2837 |
| 4811 | CUCCGAGC CUGAUGA GCCGUUAGGC GAA ACUUGCGC | 9973 | GCGCAAGUC GCUCGGAG | 2838 |
| 4815 | CGCUCUCC CUGAUGA GCCGUUAGGC GAA AGCGACUU | 9974 | AAGUCGCUC GGAGAGCG | 2839 |
| 4826 | CAGGCUCC CUGAUGA GCCGUUAGGC GAA ACCGCUCU | 9975 | AGAGCGGUU GGAGCCUG | 2840 |
| 4844 | GCCAGCAC CUGAUGA GCCGUUAGGC GAA AUGCAUCU | 9976 | AGAUGCAUU GUGCUGGC | 2841 |
| 4854 | CUCCACCA CUGAUGA GCCGUUAGGC GAA AGCCAGCA | 9977 | UGCUGGCUC UGGUGGAG | 2842 |
| 4870 | CAGGCCAC CUGAUGA GCCGUUAGGC GAA AGCCCACC | 9978 | GGUGGGCUU GUGGCCUG | 2843 |
| 4880 | CGUUUCCU CUGAUGA GCCGUUAGGC GAA ACAGGCCA | 9979 | UGGCCUGUC AGGAAACG | 2844 |
| 4908 | CAAAACCA CUGAUGA GCCGUUAGGC GAA ACCCUGCC | 9980 | GGCAGGGUU UGGUUUUG | 2845 |
| 4909 | CCAAAACC CUGAUGA GCCGUUAGGC GAA AACCCUGC | 9981 | GCAGGGUUU GGUUUUGG | 2846 |
| 4913 | CCUUCCAA CUGAUGA GCCGUUAGGC GAA ACCAAACC | 9982 | GGUUUGGUU UUGGAAGG | 2847 |
| 4914 | ACCUUCCA CUGAUGA GCCGUUAGGC GAA AACCAAAC | 9983 | GUUUGGUUU UGGAAGGU | 2848 |
| 4915 | AACCUUCC CUGAUGA GCCGUUAGGC GAA AAACCAAA | 9984 | UUUGGUUUU GGAAGGUU | 2849 |
| 4923 | AGCACGCA CUGAUGA GCCGUUAGGC GAA ACCUUCCA | 9985 | UGGAAGGUU UGCGUGCU | 2850 |
| 4924 | GAGCACGC CUGAUGA GCCGUUAGGC GAA AACCUUCC | 9986 | GGAAGGUUU GCGUGCUC | 2851 |
| 4932 | ACUGUGAA CUGAUGA GCCGUUAGGC GAA AGCACGCA | 9987 | UGCGUGCUC UUCACAGU | 2852 |

| | | | | |
|---|---|---|---|---|
| 4934 | CGACUGUG CUGAUGA GCCGUUAGGC GAA AGAGCACG | 9988 | CGUGCUCUU CACAGUCG | 2853 |
| 4935 | CCGACUGU CUGAUGA GCCGUUAGGC GAA AAGAGCAC | 9989 | GUGCUCUUC ACAGUCGG | 2854 |
| 4941 | UGUAACCC CUGAUGA GCCGUUAGGC GAA ACUGUGAA | 9990 | UUCACAGUC GGGUUACA | 2855 |
| 4946 | UCGCCUGU CUGAUGA GCCGUUAGGC GAA ACCCGACU | 9991 | AGUCGGGUU ACAGGCGA | 2856 |
| 4947 | CUCGCCUG CUGAUGA GCCGUUAGGC GAA AACCCGAC | 9992 | GUCGGGUUA CAGGCGAG | 2857 |
| 4957 | CCACAGGG CUGAUGA GCCGUUAGGC GAA ACUCGCCU | 9993 | AGGCGAGUU CCCUGUGG | 2858 |
| 4958 | GCCACAGG CUGAUGA GCCGUUAGGC GAA AACUCGCC | 9994 | GGCGAGUUC CCUGUGGC | 2859 |
| 4969 | GAGUAGGA CUGAUGA GCCGUUAGGC GAA ACGCCACA | 9995 | UGUGGCGUU UCCUACUC | 2860 |
| 4970 | GGAGUAGG CUGAUGA GCCGUUAGGC GAA AACGCCAC | 9996 | GUGGCGUUU CCUACUCC | 2861 |
| 4971 | AGGAGUAG CUGAUGA GCCGUUAGGC GAA AAACGCCA | 9997 | UGGCGUUUC CUACUCCU | 2862 |
| 4974 | AUUAGGAG CUGAUGA GCCGUUAGGC GAA AGGAAACG | 9998 | CGUUUCCUA CUCCUAAU | 2863 |
| 4977 | CUCAUUAG CUGAUGA GCCGUUAGGC GAA AGUAGGAA | 9999 | UUCCUACUC CUAAUGAG | 2864 |
| 4980 | ACUCUCAU CUGAUGA GCCGUUAGGC GAA AGGAGUAG | 10000 | CUACUCCUA AUGAGAGU | 2865 |
| 4989 | CCGGAAGG CUGAUGA GCCGUUAGGC GAA ACUCUCAU | 10001 | AUGAGAGUU CCUUCCGG | 2866 |
| 4990 | UCCGGAAG CUGAUGA GCCGUUAGGC GAA AACUCUCA | 10002 | UGAGAGUUC CUUCCGGA | 2867 |
| 4993 | GAGUCCGG CUGAUGA GCCGUUAGGC GAA AGGAACUC | 10003 | GAGUUCCUU CCGGACUC | 2868 |
| 4994 | AGAGUCCG CUGAUGA GCCGUUAGGC GAA AAGGAACU | 10004 | AGUUCCUUC CGGACUCU | 2869 |
| 5001 | ACACGUAA CUGAUGA GCCGUUAGGC GAA AGUCCGGA | 10005 | UCCGGACUC UUACGUGU | 2870 |
| 5003 | AGACACGU CUGAUGA GCCGUUAGGC GAA AGAGUCCG | 10006 | CGGACUCUU ACGUGUCU | 2871 |
| 5004 | GAGACACG CUGAUGA GCCGUUAGGC GAA AAGAGUCC | 10007 | GGACUCUUA CGUGUCUC | 2872 |
| 5010 | GGCCAGGA CUGAUGA GCCGUUAGGC GAA ACACGUAA | 10008 | UUACGUGUC UCCUGGCC | 2873 |
| 5012 | CAGGCCAG CUGAUGA GCCGUUAGGC GAA AGACACGU | 10009 | ACGUGUCUC CUGGCCUG | 2874 |
| 5046 | GAAGGAGC CUGAUGA GCCGUUAGGC GAA AGCUGCAU | 10010 | AUGCAGCUU GCUCCUUC | 2875 |
| 5050 | UGAGGAAG CUGAUGA GCCGUUAGGC GAA AGCAAGCU | 10011 | AGCUUGCUC CUUCCUCA | 2876 |
| 5053 | AGAUGAGG CUGAUGA GCCGUUAGGC GAA AGGAGCAA | 10012 | UUGCUCCUU CCUCAUCU | 2877 |
| 5054 | GAGAUGAG CUGAUGA GCCGUUAGGC GAA AAGGAGCA | 10013 | UGCUCCUUC CUCAUCUC | 2878 |
| 5057 | UGAGAGAU CUGAUGA GCCGUUAGGC GAA AGGAAGGA | 10014 | UCCUUCCUC AUCUCUCA | 2879 |
| 5060 | GCCUGAGA CUGAUGA GCCGUUAGGC GAA AUGAGGAA | 10015 | UUCCUCAUC UCUCAGGC | 2880 |
| 5062 | CAGCCUGA CUGAUGA GCCGUUAGGC GAA AGAUGAGG | 10016 | CCUCAUCUC UCAGGCUG | 2881 |
| 5064 | CACAGCCU CUGAUGA GCCGUUAGGC GAA AGAGAUGA | 10017 | UCAUCUCUC AGGCUGUG | 2882 |
| 5076 | UCUGAAUU CUGAUGA GCCGUUAGGC GAA AGGCACAG | 10018 | CUGUGCCUU AAUUCAGA | 2883 |
| 5077 | UUCUGAAU CUGAUGA GCCGUUAGGC GAA AAGGCACA | 10019 | UGUGCCUUA AUUCAGAA | 2884 |
| 5080 | GUGUUCUG CUGAUGA GCCGUUAGGC GAA AUUAAGGC | 10020 | GCCUUAAUU CAGAACAC | 2885 |
| 5081 | GGUGUUCU CUGAUGA GCCGUUAGGC GAA AAUUAAGG | 10021 | CCUUAAUUC AGAACACC | 2886 |
| 5105 | CCUCUGCC CUGAUGA GCCGUUAGGC GAA ACGUUCCU | 10022 | AGGAACGUC GGCAGAGG | 2887 |
| 5116 | CCCGUCAG CUGAUGA GCCGUUAGGC GAA AGCCUCUG | 10023 | CAGAGGCUC CUGACGGG | 2888 |
| 5135 | GUUCUCAC CUGAUGA GCCGUUAGGC GAA AUUCUUCG | 10024 | CGAAGAAUU GUGAGAAC | 2889 |
| 5156 | GAAACCCU CUGAUGA GCCGUUAGGC GAA AGUUUCUG | 10025 | CAGAAACUC AGGGUUUC | 2890 |
| 5162 | CCAGCAGA CUGAUGA GCCGUUAGGC GAA ACCCUGAG | 10026 | CUCAGGGUU UCUGCUGG | 2891 |

160

| | | | | |
|---|---|---|---|---|
| 5163 | CCCAGCAG CUGAUGA GCCGUUAGGC GAA AACCCUGA | 10027 | UCAGGGUUU CUGCUGGG | 2892 |
| 5164 | ACCCAGCA CUGAUGA GCCGUUAGGC GAA AAACCCUG | 10028 | CAGGGUUUC UGCUGGGU | 2893 |
| 5203 | AACCCUCA CUGAUGA GCCGUUAGGC GAA ACCUGCCA | 10029 | UGGCAGGUC UGAGGGUU | 2894 |
| 5211 | UGACAGAG CUGAUGA GCCGUUAGGC GAA ACCCUCAG | 10030 | CUGAGGGUU CUCUGUCA | 2895 |
| 5212 | UUGACAGA CUGAUGA GCCGUUAGGC GAA AACCCUCA | 10031 | UGAGGGUUC UCUGUCAA | 2896 |
| 5214 | ACUUGACA CUGAUGA GCCGUUAGGC GAA AGAACCCU | 10032 | AGGGUUCUC UGUCAAGU | 2897 |
| 5218 | CGCCACUU CUGAUGA GCCGUUAGGC GAA ACAGAGAA | 10033 | UUCUCUGUC AAGUGGCG | 2898 |
| 5229 | UGAGCCUU CUGAUGA GCCGUUAGGC GAA ACCGCCAC | 10034 | GUGGCGGUA AAGGCUCA | 2899 |
| 5236 | ACCAGCCU CUGAUGA GCCGUUAGGC GAA AGCCUUUA | 10035 | UAAAGGCUC AGGCUGGU | 2900 |
| 5247 | AGAGGAAG CUGAUGA GCCGUUAGGC GAA ACACCAGC | 10036 | GCUGGUGUU CUUCCUCU | 2901 |
| 5248 | UAGAGGAA CUGAUGA GCCGUUAGGC GAA AACACCAG | 10037 | CUGGUGUUC UUCCUCUA | 2902 |
| 5250 | GAUAGAGG CUGAUGA GCCGUUAGGC GAA AGAACACC | 10038 | GGUGUUCUU CCUCUAUC | 2903 |
| 5251 | AGAUAGAG CUGAUGA GCCGUUAGGC GAA AAGAACAC | 10039 | GUGUUCUUC CUCUAUCU | 2904 |
| 5254 | UGGAGAUA CUGAUGA GCCGUUAGGC GAA AGGAAGAA | 10040 | UUCUUCCUC UAUCUCCA | 2905 |
| 5256 | AGUGGAGA CUGAUGA GCCGUUAGGC GAA AGAGGAAG | 10041 | CUUCCUCUA UCUCCACU | 2906 |
| 5258 | GGAGUGGA CUGAUGA GCCGUUAGGC GAA AUAGAGGA | 10042 | UCCUCUAUC UCCACUCC | 2907 |
| 5260 | CAGGAGUG CUGAUGA GCCGUUAGGC GAA AGAUAGAG | 10043 | CUCUAUCUC CACUCCUG | 2908 |
| 5265 | CCUGACAG CUGAUGA GCCGUUAGGC GAA AGUGGAGA | 10044 | UCUCCACUC CUGUCAGG | 2909 |
| 5270 | GGGGGCCU CUGAUGA GCCGUUAGGC GAA ACAGGAGU | 10045 | ACUCCUGUC AGGCCCCC | 2910 |
| 5283 | AUACUGAG CUGAUGA GCCGUUAGGC GAA ACUUGGGG | 10046 | CCCCAAGUC CUCAGUAU | 2911 |
| 5286 | AAAAUACU CUGAUGA GCCGUUAGGC GAA AGGACUUG | 10047 | CAAGUCCUC AGUAUUUU | 2912 |
| 5290 | AGCUAAAA CUGAUGA GCCGUUAGGC GAA ACUGAGGA | 10048 | UCCUCAGUA UUUUAGCU | 2913 |
| 5292 | AAAGCUAA CUGAUGA GCCGUUAGGC GAA AUACUGAG | 10049 | CUCAGUAUU UUAGCUUU | 2914 |
| 5293 | CAAAGCUA CUGAUGA GCCGUUAGGC GAA AAUACUGA | 10050 | UCAGUAUUU UAGCUUUG | 2915 |
| 5294 | ACAAAGCU CUGAUGA GCCGUUAGGC GAA AAAUACUG | 10051 | CAGUAUUUU AGCUUUGU | 2916 |
| 5295 | CACAAAGC CUGAUGA GCCGUUAGGC GAA AAAAUACU | 10052 | AGUAUUUUA GCUUUGUG | 2917 |
| 5299 | AAGCCACA CUGAUGA GCCGUUAGGC GAA AGCUAAAA | 10053 | UUUUAGCUU UGUGGCUU | 2918 |
| 5300 | GAAGCCAC CUGAUGA GCCGUUAGGC GAA AAGCUAAA | 10054 | UUUAGCUUU GUGGCUUC | 2919 |
| 5307 | CCAUCAGG CUGAUGA GCCGUUAGGC GAA AGCCACAA | 10055 | UUGUGGCUU CCUGAUGG | 2920 |
| 5308 | GCCAUCAG CUGAUGA GCCGUUAGGC GAA AAGCCACA | 10056 | UGUGGCUUC CUGAUGGC | 2921 |
| 5325 | CCAAUUAA CUGAUGA GCCGUUAGGC GAA AUUUUUCU | 10057 | AGAAAAAUC UUAAUUGG | 2922 |
| 5327 | AACCAAUU CUGAUGA GCCGUUAGGC GAA AGAUUUUU | 10058 | AAAAAUCUU AAUUGGUU | 2923 |
| 5328 | CAACCAAU CUGAUGA GCCGUUAGGC GAA AAGAUUUU | 10059 | AAAAUCUUA AUUGGUUG | 2924 |
| 5331 | AACCAACC CUGAUGA GCCGUUAGGC GAA AUUAAGAU | 10060 | AUCUUAAUU GGUUGGUU | 2925 |
| 5335 | AGCAAACC CUGAUGA GCCGUUAGGC GAA ACCAAUUA | 10061 | UAAUUGGUU GGUUUGCU | 2926 |
| 5339 | GGAGAGCA CUGAUGA GCCGUUAGGC GAA ACCAACCA | 10062 | UGGUUGGUU UGCUCUCC | 2927 |
| 5340 | UGGAGAGC CUGAUGA GCCGUUAGGC GAA AACCAACC | 10063 | GGUUGGUUU GCUCUCCA | 2928 |
| 5344 | UAUCUGGA CUGAUGA GCCGUUAGGC GAA AGCAAACC | 10064 | GGUUUGCUC UCCAGAUA | 2929 |
| 5346 | AUUAUCUG CUGAUGA GCCGUUAGGC GAA AGAGCAAA | 10065 | UUUGCUCUC CAGAUAAU | 2930 |

161

| | | | | |
|---|---|---|---|---|
| 5352 | CUAGUGAU CUGAUGA GCCGUUAGGC GAA AUCUGGAG | 10066 | CUCCAGAUA AUCACUAG | 2931 |
| 5355 | UGGCUAGU CUGAUGA GCCGUUAGGC GAA AUUAUCUG | 10067 | CAGAUAAUC ACUAGCCA | 2932 |
| 5359 | AAUCUGGC CUGAUGA GCCGUUAGGC GAA AGUGAUUA | 10068 | UAAUCACUA GCCAGAUU | 2933 |
| 5367 | AAUUUCGA CUGAUGA GCCGUUAGGC GAA AUCUGGCU | 10069 | AGCCAGAUU UCGAAAUU | 2934 |
| 5368 | UAAUUUCG CUGAUGA GCCGUUAGGC GAA AAUCUGGC | 10070 | GCCAGAUUU CGAAAUUA | 2935 |
| 5369 | GUAAUUUC CUGAUGA GCCGUUAGGC GAA AAAUCUGG | 10071 | CCAGAUUUC GAAAUUAC | 2936 |
| 5375 | UAAAAAGU CUGAUGA GCCGUUAGGC GAA AUUUCGAA | 10072 | UUCGAAAUU ACUUUUUA | 2937 |
| 5376 | CUAAAAAG CUGAUGA GCCGUUAGGC GAA AAUUUCGA | 10073 | UCGAAAUUA CUUUUUAG | 2938 |
| 5379 | CGGCUAAA CUGAUGA GCCGUUAGGC GAA AGUAAUUU | 10074 | AAAUUACUU UUUAGCCG | 2939 |
| 5380 | UCGGCUAA CUGAUGA GCCGUUAGGC GAA AAGUAAUU | 10075 | AAUUACUUU UUAGCCGA | 2940 |
| 5381 | CUCGGCUA CUGAUGA GCCGUUAGGC GAA AAAGUAAU | 10076 | AUUACUUUU UAGCCGAG | 2941 |
| 5382 | CCUCGGCU CUGAUGA GCCGUUAGGC GAA AAAAGUAA | 10077 | UUACUUUUU AGCCGAGG | 2942 |
| 5383 | ACCUCGGC CUGAUGA GCCGUUAGGC GAA AAAAAGUA | 10078 | UACUUUUUA GCCGAGGU | 2943 |
| 5392 | GUUAUCAU CUGAUGA GCCGUUAGGC GAA ACCUCGGC | 10079 | GCCGAGGUU AUGAUAAC | 2944 |
| 5393 | UGUUAUCA CUGAUGA GCCGUUAGGC GAA AACCUCGG | 10080 | CCGAGGUUA UGAUAACA | 2945 |
| 5398 | GUAGAUGU CUGAUGA GCCGUUAGGC GAA AUCAUAAC | 10081 | GUUAUGAUA ACAUCUAC | 2946 |
| 5403 | AUACAGUA CUGAUGA GCCGUUAGGC GAA AUGUUAUC | 10082 | GAUAACAUC UACUGUAU | 2947 |
| 5405 | GGAUACAG CUGAUGA GCCGUUAGGC GAA AGAUGUUA | 10083 | UAACAUCUA CUGUAUCC | 2948 |
| 5410 | CUAAAGGA CUGAUGA GCCGUUAGGC GAA ACAGUAGA | 10084 | UCUACUGUA UCCUUUAG | 2949 |
| 5412 | UUCUAAAG CUGAUGA GCCGUUAGGC GAA AUACAGUA | 10085 | UACUGUAUC CUUUAGAA | 2950 |
| 5415 | AAAUUCUA CUGAUGA GCCGUUAGGC GAA AGGAUACA | 10086 | UGUAUCCUU UAGAAUUU | 2951 |
| 5416 | AAAAUUCU CUGAUGA GCCGUUAGGC GAA AAGGAUAC | 10087 | GUAUCCUUU AGAAUUUU | 2952 |
| 5417 | UAAAAUUC CUGAUGA GCCGUUAGGC GAA AAAGGAUA | 10088 | UAUCCUUUA GAAUUUUA | 2953 |
| 5422 | UAGGUUAA CUGAUGA GCCGUUAGGC GAA AUUCUAAA | 10089 | UUUAGAAUU UUAACCUA | 2954 |
| 5423 | AUAGGUUA CUGAUGA GCCGUUAGGC GAA AAUUCUAA | 10090 | UUAGAAUUU UAACCUAU | 2955 |
| 5424 | UAUAGGUU CUGAUGA GCCGUUAGGC GAA AAAUUCUA | 10091 | UAGAAUUUU AACCUAUA | 2956 |
| 5425 | UUAUAGGU CUGAUGA GCCGUUAGGC GAA AAAAUUCU | 10092 | AGAAUUUUA ACCUAUAA | 2957 |
| 5430 | UAGUUUUA CUGAUGA GCCGUUAGGC GAA AGGUUAAA | 10093 | UUUAACCUA UAAAACUA | 2958 |
| 5432 | CAUAGUUU CUGAUGA GCCGUUAGGC GAA AUAGGUUA | 10094 | UAACCUAUA AAACUAUG | 2959 |
| 5438 | AGUAGACA CUGAUGA GCCGUUAGGC GAA AGUUUUAU | 10095 | AUAAAACUA UGUCUACU | 2960 |
| 5442 | AACCAGUA CUGAUGA GCCGUUAGGC GAA ACAUAGUU | 10096 | AACUAUGUC UACUGGUU | 2961 |
| 5444 | GAAACCAG CUGAUGA GCCGUUAGGC GAA AGACAUAG | 10097 | CUAUGUCUA CUGGUUUC | 2962 |
| 5450 | CAGGCAGA CUGAUGA GCCGUUAGGC GAA ACCAGUAG | 10098 | CUACUGGUU UCUGCCUG | 2963 |
| 5451 | ACAGGCAG CUGAUGA GCCGUUAGGC GAA AACCAGUA | 10099 | UACUGGUUU CUGCCUGU | 2964 |
| 5452 | CACAGGCA CUGAUGA GCCGUUAGGC GAA AAACCAGU | 10100 | ACUGGUUUC UGCCUGUG | 2965 |

Underlined region can be any X sequence or linker, as described herein.

Table VII: Mouse *flk*-1 VEGF Receptor-Hairpin Ribozyme and Substrate Sequences 237.198

| nt. Position | HP Ribozyme Sequences | Rz Seq ID No. | Substrate | Seq ID No. |
|---|---|---|---|---|
| 74 | GGGACACA AGAA GGGCCC ACCAGAGAAACACACGUUGUGGUACAUUACCUGGUA | 10101 | GGGCCCA GAC UGUGUCCC | 2966 |
| 88 | GUUAUCCC AGAA GCGGGA ACCAGAGAAACACACGUUGUGGUACAUUACCUGGUA | 10102 | UCCCGCA GCC GGGAUAAC | 2967 |
| 105 | GGAAUCGG AGAA GCCAGG ACCAGAGAAACACACGUUGUGGUACAUUACCUGGUA | 10103 | CCUGGCU GAC CCGAUUCC | 2968 |
| 110 | UCCGCGGA AGAA GGUCAG ACCAGAGAAACACACGUUGUGGUACAUUACCUGGUA | 10104 | CUGACCC GAU UCCGCGGA | 2969 |
| 125 | CGGCUGUC AGAA GUGUCC ACCAGAGAAACACACGUUGUGGUACAUUACCUGGUA | 10105 | GGACACC GCU GACAGCCG | 2970 |
| 132 | CCAGCCGC AGAA GUCAGC ACCAGAGAAACACACGUUGUGGUACAUUACCUGGUA | 10106 | GCUGACA GCC GCGGCUGG | 2971 |
| 138 | CUGGCUCC AGAA GCGGCU ACCAGAGAAACACACGUUGUGGUACAUUACCUGGUA | 10107 | AGCCGCG GCU GGAGCCAG | 2972 |
| 175 | CAGCGCAA AGAA GGGGAG ACCAGAGAAACACACGUUGUGGUACAUUACCUGGUA | 10108 | CUCCCCG GUC UUGCGCUG | 2973 |
| 199 | GUCACAGA AGAA GUAUGG ACCAGAGAAACACACGUUGUGGUACAUUACCUGGUA | 10109 | CCAUACC GCC UCUGUGAC | 2974 |
| 309 | CACAGAGC AGAA GCUAGC ACCAGAGAAACACACGUUGUGGUACAUUACCUGGUA | 10110 | GCUAGCU GUC GCUCUGUG | 2975 |
| 342 | CCCACAGA AGAA GCUCGG ACCAGAGAAACACACGUUGUGGUACAUUACCUGGUA | 10111 | CCGAGCC GCC UCUGUGGG | 2976 |
| 434 | UGCAAGUA AGAA GAAGGG ACCAGAGAAACACACGUUGUGGUACAUUACCUGGUA | 10112 | CCCUUCA GAU UACUUGCA | 2977 |
| 630 | UAGACAUA AGAA GUGGAG ACCAGAGAAACACACGUUGUGGUACAUUACCUGGUA | 10113 | CUCCACU GUU UAUGUCUA | 2978 |
| 655 | GAAUGGUG AGAA GUAAUC ACCAGAGAAACACACGUUGUGGUACAUUACCUGGUA | 10114 | GAUUACA GAU CACCAUUC | 2979 |
| 739 | CGACCCUC AGAA GGGGAU ACCAGAGAAACACACGUUGUGGUACAUUACCUGGUA | 10115 | AUCCCCU GCC GAGGGUCG | 2980 |
| 807 | CUGUUUCC AGAA GGAACA ACCAGAGAAACACACGUUGUGGUACAUUACCUGGUA | 10116 | UGUUCCG GAU GGAAACAG | 2981 |
| 920 | ACAUGAUA AGAA GAUAGG ACCAGAGAAACACACGUUGUGGUACAUUACCUGGUA | 10117 | CCUAUCA GUC UAUCAUGU | 2982 |
| 1002 | UUUUCUCC AGAA GAUAGC ACCAGAGAAACACACGUUGUGGUACAUUACCUGGUA | 10118 | GCUAUCU GCC GGAGAAAA | 2983 |
| 1229 | UCUUGAUC AGAA GUCCAC ACCAGAGAAACACACGUUGUGGUACAUUACCUGGUA | 10119 | GUGGACG GAU GAUCAAGA | 2984 |
| 1365 | AUAUCAGG AGAA GGGUAA ACCAGAGAAACACACGUUGUGGUACAUUACCUGGUA | 10120 | UUACCCA GCU CCUGAUAU | 2985 |
| 1556 | UCUCACCG AGAA GGGGUG ACCAGAGAAACACACGUUGUGGUACAUUACCUGGUA | 10121 | CACCCCA GAU CGGUGAGA | 2986 |
| 1629 | UUGGCGUA AGAA GUGCAU ACCAGAGAAACACACGUUGUGGUACAUUACCUGGUA | 10122 | AUGCACA GUC UACGCCAA | 2987 |
| 1687 | UCUGUAGG AGAA GGCUUC ACCAGAGAAACACACGUUGUGGUACAUUACCUGGUA | 10123 | GAAGCCU GCU CCUACAGA | 2988 |
| 1696 | UUGGCCGG AGAA GUAGGA ACCAGAGAAACACACGUUGUGGUACAUUACCUGGUA | 10124 | UCCUACA GAC CCGGCCAA | 2989 |
| 1796 | UUCCUUCA AGAA GGGCAU ACCAGAGAAACACACGUUGUGGUACAUUACCUGGUA | 10125 | AUGCCCU GAU UGAAGGAA | 2990 |
| 1950 | GGCUGGGC AGAA GGUUGC ACCAGAGAAACACACGUUGUGGUACAUUACCUGGUA | 10126 | GCAACCU GCU GCCCAGCC | 2991 |
| 1953 | GUUGGCUG AGAA GCAGGU ACCAGAGAAACACACGUUGUGGUACAUUACCUGGUA | 10127 | ACCUGCU GCC CAGCCAAC | 2992 |
| 1985 | CAGUGCAC AGAA GGGACA ACCAGAGAAACACACGUUGUGGUACAUUACCUGGUA | 10128 | UGUCCCU GUU GUGCACUG | 2993 |
| 2055 | CCCAUGUG AGAA GAUGUU ACCAGAGAAACACACGUUGUGGUACAUUACCUGGUA | 10129 | AACAUCG GUC CACAUGGG | 2994 |
| 2082 | UUCUUGCA AGAA GGUGUG ACCAGAGAAACACACGUUGUGGUACAUUACCUGGUA | 9329 | CACACCA GUU UGCAAGAA | 2995 |
| 2208 | UUAUCUUG AGAA GAGCAA ACCAGAGAAACACACGUUGUGGUACAUUACCUGGUA | 10130 | UUGCUCU GCU CAAGAUAA | 2996 |

163

| | | | | |
|---|---|---|---|---|
| 2252 | GGAUGAUG AGAA GUUUGA ACCAGAGAAACACACGUUGUGGUACAUUACCUGGUA | 10131 | UCAAACA GCU CAUCAUCC | 2997 |
| 2444 | UGCGGAUA AGAA GGUUCC ACCAGAGAAACACACGUUGUGGUACAUUACCUGGUA | 10132 | GGAACCU GAC UAUCCGCA | 2998 |
| 2639 | GCUUAACG AGAA GUAGGA ACCAGAGAAACACACGUUGUGGUACAUUACCUGGUA | 10133 | UCCUACG GAC CGUUAAGC | 2999 |
| 2703 | GGCAAUUC AGAA GGAUCC ACCAGAGAAACACACGUUGUGGUACAUUACCUGGUA | 10134 | GGAUCCA GAU GAAUUGCC | 3000 |
| 2777 | CUAGUUUC AGAA GGUCCC ACCAGAGAAACACACGUUGUGGUACAUUACCUGGUA | 10135 | GGGACCG GCU GAAACUAG | 3001 |
| 2832 | CCAAAAGC AGAA GCCUCA ACCAGAGAAACACACGUUGUGGUACAUUACCUGGUA | 10136 | UGAGGCA GAC GCUUUUGG | 3002 |
| 3199 | AAAGCCUG AGAA GGCAGA ACCAGAGAAACACACGUUGUGGUACAUUACCUGGUA | 10137 | UCUGCCA GCU CAGGCUUU | 3003 |
| 3278 | GCUCCAAG AGAA GGAAGU ACCAGAGAAACACACGUUGUGGUACAUUACCUGGUA | 9341 | ACUUCCU GAC CUUGGAGC | 2199 |
| 3304 | CACUUGGA AGAA GUAACA ACCAGAGAAACACACGUUGUGGUACAUUACCUGGUA | 9342 | UGUUACA GCU UCCAAGUG | 2200 |
| 3421 | CCGGGCCA AGAA GAAGUC ACCAGAGAAACACACGUUGUGGUACAUUACCUGGUA | 10138 | GACUUCG GCU UGGCCCGG | 3004 |
| 3450 | CUGACAUA AGAA GGGUCU ACCAGAGAAACACACGUUGUGGUACAUUACCUGGUA | 10139 | AGACCCG GAU UAUGUCAG | 3005 |
| 3475 | CAAAGGGA AGAA GGCAUC ACCAGAGAAACACACGUUGUGGUACAUUACCUGGUA | 10140 | GAUGCCC GAC UCCCUUUG | 3006 |
| 3663 | GUAGUGUA AGAA GGAGCC ACCAGAGAAACACACGUUGUGGUACAUUACCUGGUA | 10141 | GGCUCCU GAC UACACUAC | 3007 |
| 3689 | CCAGCAUG AGAA GGUACA ACCAGAGAAACACACGUUGUGGUACAUUACCUGGUA | 9345 | UGUACCA GAC CAUGCUGG | 2203 |
| 3703 | CUCAUGCC AGAA GUCCAG ACCAGAGAAACACACGUUGUGGUACAUUACCUGGUA | 10142 | CUGGACU GCU GGCAUGAG | 3008 |
| 3860 | GUGAGGUA AGAA GGGAGA ACCAGAGAAACACACGUUGUGGUACAUUACCUGGUA | 10143 | UCUCCCU GCC UACCUCAC | 3009 |
| 3873 | AUACAGGA AGAA GGUGAG ACCAGAGAAACACACGUUGUGGUACAUUACCUGGUA | 9348 | CUCACCU GUU UCCUGUAU | 2206 |
| 4038 | UGGCUGUC AGAA GGGAUC ACCAGAGAAACACACGUUGUGGUACAUUACCUGGUA | 10144 | GAUCCCA GAU GACAGCCA | 3010 |
| 4181 | AGCCACUG AGAA GGUUGG ACCAGAGAAACACACGUUGUGGUACAUUACCUGGUA | 10145 | CCAACCA GAC CAGUGGCU | 3011 |
| 4196 | GAUACCCA AGAA GGUAGC ACCAGAGAAACACACGUUGUGGUACAUUACCUGGUA | 10146 | GCUACCA GUC UGGGUAUC | 3012 |
| 4212 | UCUGUGUC AGAA GAGUGA ACCAGAGAAACACACGUUGUGGUACAUUACCUGGUA | 9353 | UCACUCA GAU GACACAGA | 3013 |
| 4278 | UCAGCGUG AGAA GCAGCA ACCAGAGAAACACACGUUGUGGUACAUUACCUGGUA | 10147 | UGCUGCA GUU CACGCUGA | 3014 |
| 4287 | GUCCCUGA AGAA GCGUGA ACCAGAGAAACACACGUUGUGGUACAUUACCUGGUA | 10148 | UCACGCU GAC UCAGGGAC | 3015 |
| 4307 | AGGAGGUG AGAA GCAGUG ACCAGAGAAACACACGUUGUGGUACAUUACCUGGUA | 10149 | CACUGCA GCU CACCUCCU | 3016 |
| 4318 | UCCAUUUA AGAA GGAGGU ACCAGAGAAACACACGUUGUGGUACAUUACCUGGUA | 10150 | ACCUCCU GUU UAAAUGGA | 3017 |
| 4338 | GGAGCCGG AGAA GGACCA ACCAGAGAAACACACGUUGUGGUACAUUACCUGGUA | 10151 | UGGUCCU GUC CCGGCUCC | 3018 |
| 4344 | GGGGGCGG AGAA GGGACA ACCAGAGAAACACACGUUGUGGUACAUUACCUGGUA | 10152 | UGUCCCG GCU CCGCCCCC | 3019 |
| 4349 | GAGUUGGG AGAA GAGCCG ACCAGAGAAACACACGUUGUGGUACAUUACCUGGUA | 10153 | CGGCUCC GCC CCCAACUC | 3020 |
| 4383 | AAAAUCUA AGAA GCACCU ACCAGAGAAACACACGUUGUGGUACAUUACCUGGUA | 10154 | AGGUGCU GCU UAGAUUUU | 3021 |
| 4462 | UCCUUGCA AGAA GAGGUC ACCAGAGAAACACACGUUGUGGUACAUUACCUGGUA | 10155 | GACCUCA GAC UGCAAGGA | 3022 |
| 4574 | GAGACCAC AGAA GGGCAC ACCAGAGAAACACACGUUGUGGUACAUUACCUGGUA | 10156 | GUGCCCU GCU GUGGUCUC | 3023 |
| 4626 | UCUUGGAG AGAA GAGUCC ACCAGAGAAACACACGUUGUGGUACAUUACCUGGUA | 10157 | GGACUCU GUC CUCCAAGA | 3024 |
| 4723 | CCAAGGUA AGAA GACUCG ACCAGAGAAACACACGUUGUGGUACAUUACCUGGUA | 10158 | CGAGUCU GUC UACCUUGG | 3025 |
| 4823 | CAGGCUCC AGAA GCUCUC ACCAGAGAAACACACGUUGUGGUACAUUACCUGGUA | 10159 | GAGAGCG GUU GGAGCCUG | 3026 |
| 4836 | CACAAUGC AGAA GCAGGC ACCAGAGAAACACACGUUGUGGUACAUUACCUGGUA | 10160 | GCCUGCA GAU GCAUUGUG | 3027 |

164

| | | | | |
|---|---|---|---|---|
| 4896 | ACCCUGCC AGAA GCCUUU ACCAGAGAAACACACGUUGUGGUACAUUACCUGGUA | 10161 | AAAGGCG GCC GGCAGGGU | 3028 |
| 4938 | UGUAACCC AGAA GUGAAG ACCAGAGAAACACACGUUGUGGUACAUUACCUGGUA | 10162 | CUUCACA GUC GGGUUACA | 3029 |
| 4996 | ACGUAAGA AGAA GGAAGG ACCAGAGAAACACACGUUGUGGUACAUUACCUGGUA | 10163 | CCUUCCG GAC UCUUACGU | 3030 |
| 5042 | AAGGAGCA AGAA GCAUCA ACCAGAGAAACACACGUUGUGGUACAUUACCUGGUA | 10164 | UGAUGCA GCU UGCUCCUU | 3031 |
| 5118 | UCGGCCCC AGAA GGAGCC ACCAGAGAAACACACGUUGUGGUACAUUACCUGGUA | 10165 | GGCUCCU GAC GGGGCCGA | 3032 |
| 5165 | CUCCACCC AGAA GAAACC ACCAGAGAAACACACGUUGUGGUACAUUACCUGGUA | 10166 | GGUUUCU GCU GGGUGGAG | 3033 |
| 5310 | UUUCUGCC AGAA GGAAGC ACCAGAGAAACACACGUUGUGGUACAUUACCUGGUA | 10167 | GCUUCCU GAU GGCAGAAA | 3034 |
| 5363 | AUUUCGAA AGAA GGCUAG ACCAGAGAAACACACGUUGUGGUACAUUACCUGGUA | 10168 | CUAGCCA GAU UUCGAAAU | 3035 |
| 5453 | AGCACACA AGAA GAAACC ACCAGAGAAACACACGUUGUGGUACAUUACCUGGUA | 10169 | GGUUUCU GCC UGUGUGCU | 3036 |

165

Table VIII: Mouse *flt*-1 VEGF Receptor-Hammerhead Ribozyme and Substrate Sequence 237.198

| nt. Position | HH Ribozyme Sequence | Rz Seq ID No. | Substrate | Seq ID No. |
|---|---|---|---|---|
| 17 | GUGAGCAA CUGAUGA GCCGUUAGGC GAA ACGCGGCC | 10170 | GGCCGCGUC UUGCUCAC | 3037 |
| 19 | UGGUGAGC CUGAUGA GCCGUUAGGC GAA AGACGCGG | 10171 | CCGCGUCUU GCUCACCA | 3038 |
| 23 | ACCAUGGU CUGAUGA GCCGUUAGGC GAA AGCAAGAC | 10172 | GUCUUGCUC ACCAUGGU | 3039 |
| 32 | CAGCAGCU CUGAUGA GCCGUUAGGC GAA ACCAUGGU | 10173 | ACCAUGGUC AGCUGCUG | 3040 |
| 53 | UAAGGCAA CUGAUGA GCCGUUAGGC GAA ACCGCGGU | 10174 | ACCGCGGUC UUGCCUUA | 3041 |
| 55 | CGUAAGGC CUGAUGA GCCGUUAGGC GAA AGACCGCG | 10175 | CGCGGUCUU GCCUUACG | 3042 |
| 60 | CAGCGCGU CUGAUGA GCCGUUAGGC GAA AGGCAAGA | 10176 | UCUUGCCUU ACGCGCUG | 3043 |
| 61 | GCAGCGCG CUGAUGA GCCGUUAGGC GAA AAGGCAAG | 10177 | CUUGCCUUA CGCGCUGC | 3044 |
| 71 | AGACACCC CUGAUGA GCCGUUAGGC GAA AGCAGCGC | 10178 | GCGCUGCUC GGGUGUCU | 3045 |
| 78 | GAGAAGCA CUGAUGA GCCGUUAGGC GAA ACACCCGA | 10179 | UCGGGUGUC UGCUUCUC | 3046 |
| 83 | CCUGUGAG CUGAUGA GCCGUUAGGC GAA AGCAGACA | 7167 | UGUCUGCUU CUCACAGG | 25 |
| 84 | UCCUGUGA CUGAUGA GCCGUUAGGC GAA AAGCAGAC | 7168 | GUCUGCUUC UCACAGGA | 26 |
| 86 | UAUCCUGU CUGAUGA GCCGUUAGGC GAA AGAAGCAG | 10180 | CUGCUUCUC ACAGGAUA | 3047 |
| 94 | CUGAGCCA CUGAUGA GCCGUUAGGC GAA AUCCUGUG | 10181 | CACAGGAUA UGGCUCAG | 3048 |
| 100 | UCGACCCU CUGAUGA GCCGUUAGGC GAA AGCCAUAU | 10182 | AUAUGGCUC AGGGUCGA | 3049 |
| 106 | UUAACUUC CUGAUGA GCCGUUAGGC GAA ACCCUGAG | 10183 | CUCAGGGUC GAAGUUAA | 3050 |
| 112 | GCACUUUU CUGAUGA GCCGUUAGGC GAA ACUUCGAC | 10184 | GUCGAAGUU AAAAGUGC | 3051 |
| 113 | GGCACUUU CUGAUGA GCCGUUAGGC GAA AACUUCGA | 10185 | UCGAAGUUA AAAGUGCC | 3052 |
| 132 | GCCUUUUA CUGAUGA GCCGUUAGGC GAA ACUCAGUU | 7179 | AACUGAGUU UAAAAGGC | 37 |
| 133 | UGCCUUUU CUGAUGA GCCGUUAGGC GAA AACUCAGU | 7180 | ACUGAGUUU AAAAGGCA | 38 |
| 134 | GUGCCUUU CUGAUGA GCCGUUAGGC GAA AAACUCAG | 7181 | CUGAGUUUA AAAGGCAC | 39 |
| 152 | GCUUGCAU CUGAUGA GCCGUUAGGC GAA ACAUGCUG | 10186 | CAGCAUGUC AUGCAAGC | 3053 |
| 171 | GAGAAAGA CUGAUGA GCCGUUAGGC GAA AGUCUGGC | 10187 | GCCAGACUC UCUUUCUC | 3054 |
| 173 | UUGAGAAA CUGAUGA GCCGUUAGGC GAA AGAGUCUG | 10188 | CAGACUCUC UUUCUCAA | 3055 |
| 175 | ACUUGAGA CUGAUGA GCCGUUAGGC GAA AGAGAGUC | 10189 | GACUCUCUU UCUCAAGU | 3056 |
| 176 | CACUUGAG CUGAUGA GCCGUUAGGC GAA AAGAGAGU | 10190 | ACUCUCUUU CUCAAGUG | 3057 |
| 177 | GCACUUGA CUGAUGA GCCGUUAGGC GAA AAAGAGAG | 10191 | CUCUCUUUC UCAAGUGC | 3058 |
| 179 | CUGCACUU CUGAUGA GCCGUUAGGC GAA AGAAAGAG | 10192 | CUCUUUCUC AAGUGCAG | 3059 |
| 205 | GAGACCAU CUGAUGA GCCGUUAGGC GAA AGUGGGCU | 10193 | AGCCCACUC AUGGUCUC | 3060 |
| 211 | UGGGCAGA CUGAUGA GCCGUUAGGC GAA ACCAUGAG | 10194 | CUCAUGGUC UCUGCCCA | 3061 |
| 213 | CGUGGGCA CUGAUGA GCCGUUAGGC GAA AGACCAUG | 10195 | CAUGGUCUC UGCCCACG | 3062 |

166

| | | | | |
|---|---|---|---|---|
| 254 | GGGGGAGU CUGAUGA GCCGUUAGGC GAA AUGCUCAG | 10196 | CUGAGCAUC ACUCCCCC | 3063 |
| 258 | CGAUGGGG CUGAUGA GCCGUUAGGC GAA AGUGAUGC | 10197 | GCAUCACUC CCCCAUCG | 3064 |
| 265 | CACAGGCC CUGAUGA GCCGUUAGGC GAA AUGGGGGA | 10198 | UCCCCCAUC GGCCUGUG | 3065 |
| 282 | UUGCCUGU CUGAUGA GCCGUUAGGC GAA AUCCCUCC | 10199 | GGAGGGAUA ACAGGCAA | 3066 |
| 292 | UGCUGCAG CUGAUGA GCCGUUAGGC GAA AUUGCCUG | 10200 | CAGGCAAUU CUGCAGCA | 3067 |
| 293 | GUGCUGCA CUGAUGA GCCGUUAGGC GAA AAUUGCCU | 10201 | AGGCAAUUC UGCAGCAC | 3068 |
| 304 | CCAAGGUC CUGAUGA GCCGUUAGGC GAA AGGUGCUG | 10202 | CAGCACCUU GACCUUGG | 3069 |
| 310 | CCGUGUCC CUGAUGA GCCGUUAGGC GAA AGGUCAAG | 10203 | CUUGACCUU GGACACGG | 3070 |
| 341 | CAGGUGUA CUGAUGA GCCGUUAGGC GAA AGGCCCGU | 10204 | ACGGGCCUC UACACCUG | 3071 |
| 343 | UACAGGUG CUGAUGA GCCGUUAGGC GAA AGAGGCCC | 10205 | GGGCCUCUA CACCUGUA | 3072 |
| 351 | GAGGUAUC CUGAUGA GCCGUUAGGC GAA ACAGGUGU | 10206 | ACACCUGUA GAUACCUC | 3073 |
| 355 | UAGGGAGG CUGAUGA GCCGUUAGGC GAA AUCUACAG | 10207 | CUGUAGAUA CCUCCCUA | 3074 |
| 359 | GAUGUAGG CUGAUGA GCCGUUAGGC GAA AGGUAUCU | 10208 | AGAUACCUC CCUACAUC | 3075 |
| 363 | AGUAGAUG CUGAUGA GCCGUUAGGC GAA AGGGAGGU | 10209 | ACCUCCCUA CAUCUACU | 3076 |
| 367 | UCGAAGUA CUGAUGA GCCGUUAGGC GAA AUGUAGGG | 10210 | CCCUACAUC UACUUCGA | 3077 |
| 369 | CUUCGAAG CUGAUGA GCCGUUAGGC GAA AGAUGUAG | 10211 | CUACAUCUA CUUCGAAG | 3078 |
| 372 | UUUCUUCG CUGAUGA GCCGUUAGGC GAA AGUAGAUG | 10212 | CAUCUACUU CGAAGAAA | 3079 |
| 373 | UUUUCUUC CUGAUGA GCCGUUAGGC GAA AAGUAGAU | 10213 | AUCUACUUC GAAGAAAA | 3080 |
| 394 | AGAUUGAA CUGAUGA GCCGUUAGGC GAA AUUCCGCU | 10214 | AGCGGAAUC UUCAAUCU | 3081 |
| 396 | GUAGAUUG CUGAUGA GCCGUUAGGC GAA AGAUUCCG | 10215 | CGGAAUCUU CAAUCUAC | 3082 |
| 397 | UGUAGAUU CUGAUGA GCCGUUAGGC GAA AAGAUUCC | 10216 | GGAAUCUUC AAUCUACA | 3083 |
| 401 | AAUAUGUA CUGAUGA GCCGUUAGGC GAA AUUGAAGA | 10217 | UCUUCAAUC UACAUAUU | 3084 |
| 403 | CAAAUAUG CUGAUGA GCCGUUAGGC GAA AGAUUGAA | 10218 | UUCAAUCUA CAUAUUUG | 3085 |
| 407 | CUAACAAA CUGAUGA GCCGUUAGGC GAA AUGUAGAU | 10219 | AUCUACAUA UUUGUUAG | 3086 |
| 409 | CACUAACA CUGAUGA GCCGUUAGGC GAA AUAUGUAG | 10220 | CUACAUAUU UGUUAGUG | 3087 |
| 410 | UCACUAAC CUGAUGA GCCGUUAGGC GAA AAUAUGUA | 10221 | UACAUAUUU GUUAGUGA | 3088 |
| 413 | GCAUCACU CUGAUGA GCCGUUAGGC GAA ACAAAUAU | 10222 | AUAUUUGUU AGUGAUGC | 3089 |
| 414 | UGCAUCAC CUGAUGA GCCGUUAGGC GAA AACAAAUA | 10223 | UAUUUGUUA GUGAUGCA | 3090 |
| 429 | UAUGAAAG CUGAUGA GCCGUUAGGC GAA ACUCCCUG | 10224 | CAGGGAGUC CUUUCAUA | 3091 |
| 432 | CUCUAUGA CUGAUGA GCCGUUAGGC GAA AGGACUCC | 10225 | GGAGUCCUU UCAUAGAG | 3092 |
| 433 | UCUCUAUG CUGAUGA GCCGUUAGGC GAA AAGGACUC | 10226 | GAGUCCUUU CAUAGAGA | 3093 |
| 434 | AUCUCUAU CUGAUGA GCCGUUAGGC GAA AAAGGACU | 10227 | AGUCCUUUC AUAGAGAU | 3094 |
| 437 | UGCAUCUC CUGAUGA GCCGUUAGGC GAA AUGAAAGG | 10228 | CCUUUCAUA GAGAUGCA | 3095 |
| 455 | AGUUUGGG CUGAUGA GCCGUUAGGC GAA AUGUCAGU | 10229 | ACUGACAUA CCCAAACU | 3096 |
| 464 | AUGUGCAC CUGAUGA GCCGUUAGGC GAA AGUUUGGG | 10230 | CCCAAACUU GUGCACAU | 3097 |

167

| | | | | |
|---|---|---|---|---|
| 491 | GGGAUGAU CUGAUGA GCCGUUAGGC GAA AGCUGUCU | 10231 | AGACAGCUC AUCAUCCC | 3098 |
| 494 | CAGGGGAU CUGAUGA GCCGUUAGGC GAA AUGAGCUG | 10232 | CAGCUCAUC AUCCCCUG | 3099 |
| 497 | CGGCAGGG CUGAUGA GCCGUUAGGC GAA AUGAUGAG | 10233 | CUCAUCAUC CCCUGCCG | 3100 |
| 514 | CGUUGGGU CUGAUGA GCCGUUAGGC GAA ACGUCACC | 10234 | GGUGACGUC ACCCAACG | 3101 |
| 524 | GUGACUGU CUGAUGA GCCGUUAGGC GAA ACGUUGGG | 10235 | CCCAACGUC ACAGUCAC | 3102 |
| 530 | UUUAGGGU CUGAUGA GCCGUUAGGC GAA ACUGUGAC | 10236 | GUCACAGUC ACCCUAAA | 3103 |
| 536 | AACUUUUU CUGAUGA GCCGUUAGGC GAA AGGGUGAC | 10237 | GUCACCCUA AAAAAGUU | 3104 |
| 544 | CAAAUGGA CUGAUGA GCCGUUAGGC GAA ACUUUUUU | 10238 | AAAAAAGUU UCCAUUUG | 3105 |
| 545 | UCAAAUGG CUGAUGA GCCGUUAGGC GAA AACUUUUU | 10239 | AAAAAGUUU CCAUUUGA | 3106 |
| 546 | AUCAAAUG CUGAUGA GCCGUUAGGC GAA AAACUUUU | 10240 | AAAAGUUUC CAUUUGAU | 3107 |
| 550 | GAGUAUCA CUGAUGA GCCGUUAGGC GAA AUGGAAAC | 10241 | GUUUCCAUU UGAUACUC | 3108 |
| 551 | AGAGUAUC CUGAUGA GCCGUUAGGC GAA AAUGGAAA | 10242 | UUUCCAUUU GAUACUCU | 3109 |
| 555 | GGUAAGAG CUGAUGA GCCGUUAGGC GAA AUCAAAUG | 10243 | CAUUUGAUA CUCUUACC | 3110 |
| 558 | AGGGGUAA CUGAUGA GCCGUUAGGC GAA AGUAUCAA | 10244 | UUGAUACUC UUACCCCU | 3111 |
| 560 | UCAGGGGU CUGAUGA GCCGUUAGGC GAA AGAGUAUC | 10245 | GAUACUCUU ACCCCUGA | 3112 |
| 561 | AUCAGGGG CUGAUGA GCCGUUAGGC GAA AAGAGUAU | 10246 | AUACUCUUA CCCCUGAU | 3113 |
| 581 | UCCCAUGU CUGAUGA GCCGUUAGGC GAA AUUCUUUG | 10247 | CAAAGAAUA ACAUGGGA | 3114 |
| 594 | GCCUCUCC CUGAUGA GCCGUUAGGC GAA ACUGUCCC | 10248 | GGGACAGUA GGAGAGGC | 3115 |
| 604 | CUAUUAUA CUGAUGA GCCGUUAGGC GAA AGCCUCUC | 10249 | GAGAGGCUU UAUAAUAG | 3116 |
| 605 | GCUAUUAU CUGAUGA GCCGUUAGGC GAA AAGCCUCU | 10250 | AGAGGCUUU AUAAUAGC | 3117 |
| 606 | UGCUAUUA CUGAUGA GCCGUUAGGC GAA AAAGCCUC | 10251 | GAGGCUUUA UAAUAGCA | 3118 |
| 608 | UUUGCUAU CUGAUGA GCCGUUAGGC GAA AUAAAGCC | 10252 | GGCUUUAUA AUAGCAAA | 3119 |
| 611 | GCAUUUGC CUGAUGA GCCGUUAGGC GAA AUUAUAAA | 10253 | UUUAUAAUA GCAAAUGC | 3120 |
| 625 | UCUCUUUG CUGAUGA GCCGUUAGGC GAA ACGUUGCA | 10254 | UGCAACGUA CAAAGAGA | 3121 |
| 635 | AGCAGUCC CUGAUGA GCCGUUAGGC GAA AUCUCUUU | 10255 | AAAGAGAUA GGACUGCU | 3122 |
| 662 | UGCCCGUU CUGAUGA GCCGUUAGGC GAA ACGGUGGC | 10256 | GCCACCGUC AACGGGCA | 3123 |
| 676 | UUGUCUGG CUGAUGA GCCGUUAGGC GAA ACAGGUGC | 10257 | GCACCUGUA CCAGACAA | 3124 |
| 688 | GGGUCAGA CUGAUGA GCCGUUAGGC GAA AGUUUGUC | 10258 | GACAAACUA UCUGACCC | 3125 |
| 690 | AUGGGUCA CUGAUGA GCCGUUAGGC GAA AUAGUUUG | 10259 | CAAACUAUC UGACCCAU | 3126 |
| 699 | GGUCUGCC CUGAUGA GCCGUUAGGC GAA AUGGGUCA | 10260 | UGACCCAUC GGCAGACC | 3127 |
| 711 | UAGGAUUG CUGAUGA GCCGUUAGGC GAA AUUGGUCU | 10261 | AGACCAAUA CAAUCCUA | 3128 |
| 716 | ACAUCUAG CUGAUGA GCCGUUAGGC GAA AUUGUAUU | 10262 | AAUACAAUC CUAGAUGU | 3129 |
| 719 | UGGACAUC CUGAUGA GCCGUUAGGC GAA AGGAUUGU | 10263 | ACAAUCCUA GAUGUCCA | 3130 |
| 725 | CGUAUUUG CUGAUGA GCCGUUAGGC GAA ACAUCUAG | 10264 | CUAGAUGUC CAAAUACG | 3131 |
| 731 | GGCGGGCG CUGAUGA GCCGUUAGGC GAA AUUUGGAC | 10265 | GUCCAAAUA CGCCCGCC | 3132 |

168

| | | | | |
|---|---|---|---|---|
| 758 | UGCCCGUG CUGAUGA GCCGUUAGGC GAA AGCAGUCU | 10266 | AGACUGCUC CACGGGCA | 3133 |
| 771 | GAGGACAA CUGAUGA GCCGUUAGGC GAA AGUCUGCC | 10267 | GGCAGACUC UUGUCCUC | 3134 |
| 773 | UUGAGGAC CUGAUGA GCCGUUAGGC GAA AGAGUCUG | 10268 | CAGACUCUU GUCCUCAA | 3135 |
| 776 | CAGUUGAG CUGAUGA GCCGUUAGGC GAA ACAAGAGU | 10269 | ACUCUUGUC CUCAACUG | 3136 |
| 779 | GUGCAGUU CUGAUGA GCCGUUAGGC GAA AGGACAAG | 10270 | CUUGUCCUC AACUGCAC | 3137 |
| 803 | CUCGUAUU CUGAUGA GCCGUUAGGC GAA AGCUCCGU | 10271 | ACGGAGCUC AAUACGAG | 3138 |
| 807 | CACCCUCG CUGAUGA GCCGUUAGGC GAA AUUGAGCU | 10272 | AGCUCAAUA CGAGGGUG | 3139 |
| 831 | ACCAGGGU CUGAUGA GCCGUUAGGC GAA AUUCCAGC | 10273 | GCUGGAAUU ACCCUGGU | 3140 |
| 832 | UACCAGGG CUGAUGA GCCGUUAGGC GAA AAUUCCAG | 10274 | CUGGAAUUA CCCUGGUA | 3141 |
| 840 | AGUUGCUU CUGAUGA GCCGUUAGGC GAA ACCAGGGU | 10275 | ACCCUGGUA AAGCAACU | 3142 |
| 849 | UGCUCUCU CUGAUGA GCCGUUAGGC GAA AGUUGCUU | 10276 | AAGCAACUA AGAGAGCA | 3143 |
| 859 | GCCUUAUA CUGAUGA GCCGUUAGGC GAA AUGCUCUC | 10277 | GAGAGCAUC UAUAAGGC | 3144 |
| 861 | CUGCCUUA CUGAUGA GCCGUUAGGC GAA AGAUGCUC | 10278 | GAGCAUCUA UAAGGCAG | 3145 |
| 863 | CGCUGCCU CUGAUGA GCCGUUAGGC GAA AUAGAUGC | 10279 | GCAUCUAUA AGGCAGCG | 3146 |
| 875 | CUCCGGUC CUGAUGA GCCGUUAGGC GAA AUCCGCUG | 10280 | CAGCGGAUU GACCGGAG | 3147 |
| 888 | GUUGUGGG CUGAUGA GCCGUUAGGC GAA AUGGCUCC | 10281 | GGAGCCAUU CCCACAAC | 3148 |
| 889 | UGUUGUGG CUGAUGA GCCGUUAGGC GAA AAUGGCUC | 10282 | GAGCCAUUC CCACAACA | 3149 |
| 904 | CACUGUGG CUGAUGA GCCGUUAGGC GAA ACACAUUG | 10283 | CAAUGUGUU CCACAGUG | 3150 |
| 905 | ACACUGUG CUGAUGA GCCGUUAGGC GAA AACACAUU | 10284 | AAUGUGUUC CACAGUGU | 3151 |
| 914 | AUCUUAAG CUGAUGA GCCGUUAGGC GAA ACACUGUG | 10285 | CACAGUGUU CUUAAGAU | 3152 |
| 915 | GAUCUUAA CUGAUGA GCCGUUAGGC GAA AACACUGU | 10286 | ACAGUGUUC UUAAGAUC | 3153 |
| 917 | UUGAUCUU CUGAUGA GCCGUUAGGC GAA AGAACACU | 10287 | AGUGUUCUU AAGAUCAA | 3154 |
| 918 | GUUGAUCU CUGAUGA GCCGUUAGGC GAA AAGAACAC | 10288 | GUGUUCUUA AGAUCAAC | 3155 |
| 923 | ACAUUGUU CUGAUGA GCCGUUAGGC GAA AUCUUAAG | 10289 | CUUAAGAUC AACAAUGU | 3156 |
| 953 | CAGGUGUA CUGAUGA GCCGUUAGGC GAA AGCCCCUU | 10290 | AAGGGGCUC UACACCUG | 3157 |
| 955 | GACAGGUG CUGAUGA GCCGUUAGGC GAA AGAGCCCC | 10291 | GGGGCUCUA CACCUGUC | 3158 |
| 963 | CUUCACGC CUGAUGA GCCGUUAGGC GAA ACAGGUGU | 10292 | ACACCUGUC GCGUGAAG | 3159 |
| 979 | GGAACGAG CUGAUGA GCCGUUAGGC GAA ACCCACUC | 10293 | GAGUGGGUC CUCGUUCC | 3160 |
| 982 | ACUGGAAC CUGAUGA GCCGUUAGGC GAA AGGACCCA | 10294 | UGGGUCCUC GUUCCAGU | 3161 |
| 985 | AAGACUGG CUGAUGA GCCGUUAGGC GAA ACGAGGAC | 10295 | GUCCUCGUU CCAGUCUU | 3162 |
| 986 | AAAGACUG CUGAUGA GCCGUUAGGC GAA AACGAGGA | 10296 | UCCUCGUUC CAGUCUUU | 3163 |
| 991 | UGUUGAAA CUGAUGA GCCGUUAGGC GAA ACUGGAAC | 10297 | GUUCCAGUC UUUCAACA | 3164 |
| 993 | GGUGUUGA CUGAUGA GCCGUUAGGC GAA AGACUGGA | 10298 | UCCAGUCUU UCAACACC | 3165 |
| 994 | AGGUGUUG CUGAUGA GCCGUUAGGC GAA AAGACUGG | 10299 | CCAGUCUUU CAACACCU | 3166 |
| 995 | GAGGUGUU CUGAUGA GCCGUUAGGC GAA AAAGACUG | 10300 | CAGUCUUUC AACACCUC | 3167 |

| | | | | |
|---|---|---|---|---|
| 1003 | CAUGCACG CUGAUGA GCCGUUAGGC GAA AGGUGUUG | 10301 | CAACACCUC CGUGCAUG | 3168 |
| 1015 | CUUUUUCA CUGAUGA GCCGUUAGGC GAA ACACAUGC | 10302 | GCAUGUGUA UGAAAAAG | 3169 |
| 1027 | CACUGAUG CUGAUGA GCCGUUAGGC GAA AUCCUUUU | 10303 | AAAAGGAUU CAUCAGUG | 3170 |
| 1028 | ACACUGAU CUGAUGA GCCGUUAGGC GAA AAUCCUUU | 10304 | AAAGGAUUC AUCAGUGU | 3171 |
| 1031 | UUCACACU CUGAUGA GCCGUUAGGC GAA AUGAAUCC | 10305 | GGAUUCAUC AGUGUGAA | 3172 |
| 1044 | CUGCUUCC CUGAUGA GCCGUUAGGC GAA AUGUUUCA | 10306 | UGAAACAUC GGAAGCAG | 3173 |
| 1084 | GCCGAUAG CUGAUGA GCCGUUAGGC GAA ACCGUCUU | 10307 | AAGACGGUC CUAUCGGC | 3174 |
| 1087 | ACAGCCGA CUGAUGA GCCGUUAGGC GAA AGGACCGU | 10308 | ACGGUCCUA UCGGCUGU | 3175 |
| 1089 | GGACAGCC CUGAUGA GCCGUUAGGC GAA AUAGGACC | 10309 | GGUCCUAUC GGCUGUCC | 3176 |
| 1096 | CUUUCAUG CUGAUGA GCCGUUAGGC GAA ACAGCCGA | 10310 | UCGGCUGUC CAUGAAAG | 3177 |
| 1114 | GGGAGGGG CUGAUGA GCCGUUAGGC GAA AGGCCUUC | 10311 | GAAGGCCUU CCCCUCCC | 3178 |
| 1115 | GGGGAGGG CUGAUGA GCCGUUAGGC GAA AAGGCCUU | 10312 | AAGGCCUUC CCCUCCCC | 3179 |
| 1120 | UUUCUGGG CUGAUGA GCCGUUAGGC GAA AGGGGAAG | 10313 | CUUCCCCUC CCCAGAAA | 3180 |
| 1130 | AACCAUAC CUGAUGA GCCGUUAGGC GAA AUUUCUGG | 10314 | CCAGAAAUC GUAUGGUU | 3181 |
| 1133 | UUUAACCA CUGAUGA GCCGUUAGGC GAA ACGAUUUC | 10315 | GAAAUCGUA UGGUUAAA | 3182 |
| 1138 | CAUCUUUU CUGAUGA GCCGUUAGGC GAA ACCAUACG | 10316 | CGUAUGGUU AAAAGAUG | 3183 |
| 1139 | CCAUCUUU CUGAUGA GCCGUUAGGC GAA AACCAUAC | 7352 | GUAUGGUUA AAAGAUGG | 210 |
| 1150 | UUGCAGGC CUGAUGA GCCGUUAGGC GAA AGCCAUCU | 10317 | AGAUGGCUC GCCUGCAA | 3184 |
| 1162 | CAGACUUC CUGAUGA GCCGUUAGGC GAA AUGUUGCA | 10318 | UGCAACAUU GAAGUCUG | 3185 |
| 1168 | AGCGAGCA CUGAUGA GCCGUUAGGC GAA ACUUCAAU | 10319 | AUUGAAGUC UGCUCGCU | 3186 |
| 1173 | CAAAUAGC CUGAUGA GCCGUUAGGC GAA AGCAGACU | 10320 | AGUCUGCUC GCUAUUUG | 3187 |
| 1177 | GUACCAAA CUGAUGA GCCGUUAGGC GAA AGCGAGCA | 10321 | UGCUCGCUA UUUGGUAC | 3188 |
| 1179 | AUGUACCA CUGAUGA GCCGUUAGGC GAA AUAGCGAG | 10322 | CUCGCUAUU UGGUACAU | 3189 |
| 1180 | CAUGUACC CUGAUGA GCCGUUAGGC GAA AAUAGCGA | 10323 | UCGCUAUUU GGUACAUG | 3190 |
| 1184 | UAGCCAUG CUGAUGA GCCGUUAGGC GAA ACCAAAUA | 10324 | UAUUUGGUA CAUGGCUA | 3191 |
| 1192 | UUAAUGAG CUGAUGA GCCGUUAGGC GAA AGCCAUGU | 10325 | ACAUGGCUA CUCAUUAA | 3192 |
| 1195 | UAAUUAAU CUGAUGA GCCGUUAGGC GAA AGUAGCCA | 10326 | UGGCUACUC AUUAAUUA | 3193 |
| 1198 | UGAUAAUU CUGAUGA GCCGUUAGGC GAA AUGAGUAG | 10327 | CUACUCAUU AAUUAUCA | 3194 |
| 1199 | UUGAUAAU CUGAUGA GCCGUUAGGC GAA AAUGAGUA | 10328 | UACUCAUUA AUUAUCAA | 3195 |
| 1202 | UCUUUGAU CUGAUGA GCCGUUAGGC GAA AUUAAUGA | 10329 | UCAUUAAUU AUCAAAGA | 3196 |
| 1203 | AUCUUUGA CUGAUGA GCCGUUAGGC GAA AAUUAAUG | 10330 | CAUUAAUUA UCAAAGAU | 3197 |
| 1205 | ACAUCUUU CUGAUGA GCCGUUAGGC GAA AUAAUUAA | 10331 | UUAAUUAUC AAAGAUGU | 3198 |
| 1237 | AGAUCGUA CUGAUGA GCCGUUAGGC GAA AGUCCCCU | 10332 | AGGGGACUA UACGAUCU | 3199 |
| 1239 | CAAGAUCG CUGAUGA GCCGUUAGGC GAA AUAGUCCC | 10333 | GGGACUAUA CGAUCUUG | 3200 |
| 1244 | CCCAGCAA CUGAUGA GCCGUUAGGC GAA AUCGUAUA | 10334 | UAUACGAUC UUGCUGGG | 3201 |

170

| | | | | |
|---|---|---|---|---|
| 1246 | UGCCCAGC CUGAUGA GCCGUUAGGC GAA AGAUCGUA | 10335 | UACGAUCUU GCUGGGCA | 3202 |
| 1256 | GACUGCUU CUGAUGA GCCGUUAGGC GAA AUGCCCAG | 10336 | CUGGGCAUA AAGCAGUC | 3203 |
| 1264 | AUAGCCUU CUGAUGA GCCGUUAGGC GAA ACUGCUUU | 10337 | AAAGCAGUC AAGGCUAU | 3204 |
| 1271 | UUUUUAAA CUGAUGA GCCGUUAGGC GAA AGCCUUGA | 10338 | UCAAGGCUA UUUAAAAA | 3205 |
| 1273 | GGUUUUUA CUGAUGA GCCGUUAGGC GAA AUAGCCUU | 10339 | AAGGCUAUU UAAAAACC | 3206 |
| 1274 | AGGUUUUU CUGAUGA GCCGUUAGGC GAA AAUAGCCU | 10340 | AGGCUAUUU AAAAACCU | 3207 |
| 1275 | GAGGUUUU CUGAUGA GCCGUUAGGC GAA AAAUAGCC | 10341 | GGCUAUUUA AAAACCUC | 3208 |
| 1283 | GUGGCAGU CUGAUGA GCCGUUAGGC GAA AGGUUUUU | 7379 | AAAAACCUC ACUGCCAC | 237 |
| 1293 | UACAAUGA CUGAUGA GCCGUUAGGC GAA AGUGGCAG | 10342 | CUGCCACUC UCAUUGUA | 3209 |
| 1295 | UUUACAAU CUGAUGA GCCGUUAGGC GAA AGAGUGGC | 10343 | GCCACUCUC AUUGUAAA | 3210 |
| 1298 | ACGUUUAC CUGAUGA GCCGUUAGGC GAA AUGAGAGU | 10344 | ACUCUCAUU GUAAACGU | 3211 |
| 1301 | UUCACGUU CUGAUGA GCCGUUAGGC GAA ACAAUGAG | 10345 | CUCAUUGUA AACGUGAA | 3212 |
| 1314 | GUAGAUCU CUGAUGA GCCGUUAGGC GAA AGGUUUCA | 10346 | UGAAACCUC AGAUCUAC | 3213 |
| 1319 | UUUUCGUA CUGAUGA GCCGUUAGGC GAA AUCUGAGG | 10347 | CCUCAGAUC UACGAAAA | 3214 |
| 1321 | ACUUUUCG CUGAUGA GCCGUUAGGC GAA AGAUCUGA | 10348 | UCAGAUCUA CGAAAAGU | 3215 |
| 1330 | AGGACACG CUGAUGA GCCGUUAGGC GAA ACUUUUCG | 10349 | CGAAAAGUC CGUGUCCU | 3216 |
| 1336 | GAAGCGAG CUGAUGA GCCGUUAGGC GAA ACACGGAC | 10350 | GUCCGUGUC CUCGCUUC | 3217 |
| 1339 | UUGGAAGC CUGAUGA GCCGUUAGGC GAA AGGACACG | 10351 | CGUGUCCUC GCUUCCAA | 3218 |
| 1343 | GGGCUUGG CUGAUGA GCCGUUAGGC GAA AGCGAGGA | 10352 | UCCUCGCUU CCAAGCCC | 3219 |
| 1344 | UGGGCUUG CUGAUGA GCCGUUAGGC GAA AAGCGAGG | 10353 | CCUCGCUUC CAAGCCCA | 3220 |
| 1356 | CGGAUAGA CUGAUGA GCCGUUAGGC GAA AGGUGGGC | 10354 | GCCCACCUC UCUAUCCG | 3221 |
| 1358 | AGCGGAUA CUGAUGA GCCGUUAGGC GAA AGAGGUGG | 10355 | CCACCUCUC UAUCCGCU | 3222 |
| 1360 | CCAGCGGA CUGAUGA GCCGUUAGGC GAA AGAGAGGU | 10356 | ACCUCUCUA UCCGCUGG | 3223 |
| 1362 | GCCCAGCG CUGAUGA GCCGUUAGGC GAA AUAGAGAG | 10357 | CUCUCUAUC CGCUGGGC | 3224 |
| 1382 | CAAGUGAG CUGAUGA GCCGUUAGGC GAA ACUUGUCU | 10358 | AGACAAGUC CUCACUUG | 3225 |
| 1385 | GUGCAAGU CUGAUGA GCCGUUAGGC GAA AGGACUUG | 10359 | CAAGUCCUC ACUUGCAC | 3226 |
| 1389 | CACGGUGC CUGAUGA GCCGUUAGGC GAA AGUGAGGA | 10360 | UCCUCACUU GCACCGUG | 3227 |
| 1399 | GGAUGCCA CUGAUGA GCCGUUAGGC GAA ACACGGUG | 10361 | CACCGUGUA UGGCAUCC | 3228 |
| 1406 | GGCCGAGG CUGAUGA GCCGUUAGGC GAA AUGCCAUA | 10362 | UAUGGCAUC CCUCGGCC | 3229 |
| 1410 | UGUUGGCC CUGAUGA GCCGUUAGGC GAA AGGGAUGC | 10363 | GCAUCCCUC GGCCAACA | 3230 |
| 1421 | AGCCACGU CUGAUGA GCCGUUAGGC GAA AUUGUUGG | 10364 | CCAACAAUC ACGUGGCU | 3231 |
| 1430 | GGGUGCCA CUGAUGA GCCGUUAGGC GAA AGCCACGU | 10365 | ACGUGGCUC UGGCACCC | 3232 |
| 1443 | AUUGUGGU CUGAUGA GCCGUUAGGC GAA ACAGGGGU | 10366 | ACCCCUGUC ACCACAAU | 3233 |
| 1452 | UUUGGAGU CUGAUGA GCCGUUAGGC GAA AUUGUGGU | 10367 | ACCACAAUC ACUCCAAA | 3234 |
| 1456 | UUUCUUUG CUGAUGA GCCGUUAGGC GAA AGUGAUUG | 10368 | CAAUCACUC CAAAGAAA | 3235 |

171

| | | | | |
|---|---|---|---|---|
| 1468 | AGAAGUCA CUGAUGA GCCGUUAGGC GAA ACCUUUCU | 10369 | AGAAAGGUA UGACUUCU | 3236 |
| 1474 | CAGUGCAG CUGAUGA GCCGUUAGGC GAA AGUCAUAC | 10370 | GUAUGACUU CUGCACUG | 3237 |
| 1475 | UCAGUGCA CUGAUGA GCCGUUAGGC GAA AAGUCAUA | 10371 | UAUGACUUC UGCACUGA | 3238 |
| 1495 | GGAUAAAG CUGAUGA GCCGUUAGGC GAA AUUCUUCA | 10372 | UGAAGAAUC CUUUAUCC | 3239 |
| 1498 | CCAGGAUA CUGAUGA GCCGUUAGGC GAA AGGAUUCU | 10373 | AGAAUCCUU UAUCCUGG | 3240 |
| 1499 | UCCAGGAU CUGAUGA GCCGUUAGGC GAA AAGGAUUC | 10374 | GAAUCCUUU AUCCUGGA | 3241 |
| 1500 | AUCCAGGA CUGAUGA GCCGUUAGGC GAA AAAGGAUU | 10375 | AAUCCUUUA UCCUGGAU | 3242 |
| 1502 | GGAUCCAG CUGAUGA GCCGUUAGGC GAA AUAAAGGA | 10376 | UCCUUUAUC CUGGAUCC | 3243 |
| 1509 | GCUGCUGG CUGAUGA GCCGUUAGGC GAA AUCCAGGA | 10377 | UCCUGGAUC CCAGCAGC | 3244 |
| 1522 | UGUUUCCU CUGAUGA GCCGUUAGGC GAA AGUUGCUG | 10378 | CAGCAACUU AGGAAACA | 3245 |
| 1523 | CUGUUUCC CUGAUGA GCCGUUAGGC GAA AAGUUGCU | 10379 | AGCAACUUA GGAAACAG | 3246 |
| 1535 | AUGCUCUC CUGAUGA GCCGUUAGGC GAA AUUCUGUU | 7422 | AACAGAAUU GAGAGCAU | 280 |
| 1544 | CGCUGAGA CUGAUGA GCCGUUAGGC GAA AUGCUCUC | 10380 | GAGAGCAUC UCUCAGCG | 3247 |
| 1546 | UGCGCUGA CUGAUGA GCCGUUAGGC GAA AGAUGCUC | 10381 | GAGCAUCUC UCAGCGCA | 3248 |
| 1548 | CAUGCGCU CUGAUGA GCCGUUAGGC GAA AGAGAUGC | 10382 | GCAUCUCUC AGCGCAUG | 3249 |
| 1562 | CCUUCUAU CUGAUGA GCCGUUAGGC GAA ACCGUCAU | 10383 | AUGACGGUC AUAGAAGG | 3250 |
| 1565 | GUUCCUUC CUGAUGA GCCGUUAGGC GAA AUGACCGU | 10384 | ACGGUCAUA GAAGGAAC | 3251 |
| 1578 | AACCGUCU CUGAUGA GCCGUUAGGC GAA AUUUGUUC | 10385 | GAACAAAUA AGACGGUU | 3252 |
| 1586 | AAUGUGCU CUGAUGA GCCGUUAGGC GAA ACCGUCUU | 10386 | AAGACGGUU AGCACAUU | 3253 |
| 1587 | CAAUGUGC CUGAUGA GCCGUUAGGC GAA AACCGUCU | 10387 | AGACGGUUA GCACAUUG | 3254 |
| 1594 | CCACCACC CUGAUGA GCCGUUAGGC GAA AUGUGCUA | 10388 | UAGCACAUU GGUGGUGG | 3255 |
| 1609 | GGGUCUGA CUGAUGA GCCGUUAGGC GAA AGUCAGCC | 10389 | GGCUGACUC UCAGACCC | 3256 |
| 1611 | AGGGGUCU CUGAUGA GCCGUUAGGC GAA AGAGUCAG | 10390 | CUGACUCUC AGACCCCU | 3257 |
| 1625 | CAGCUGUA CUGAUGA GCCGUUAGGC GAA AUUCCAGG | 10391 | CCUGGAAUC UACAGCUG | 3258 |
| 1627 | GGCAGCUG CUGAUGA GCCGUUAGGC GAA AGAUUCCA | 10392 | UGGAAUCUA CAGCUGCC | 3259 |
| 1642 | UUUUAUUG CUGAUGA GCCGUUAGGC GAA AGGCCCGG | 10393 | CCGGGCCUU CAAUAAAA | 3260 |
| 1643 | AUUUUAUU CUGAUGA GCCGUUAGGC GAA AAGGCCCG | 10394 | CGGGCCUUC AAUAAAAU | 3261 |
| 1647 | CCCUAUUU CUGAUGA GCCGUUAGGC GAA AUUGAAGG | 10395 | CCUUCAAUA AAAUAGGG | 3262 |
| 1652 | ACAGUCCC CUGAUGA GCCGUUAGGC GAA AUUUUAUU | 10396 | AAUAAAAUA GGGACUGU | 3263 |
| 1673 | UAAAAUUU CUGAUGA GCCGUUAGGC GAA AUGUUUCU | 10397 | AGAAACAUA AAAUUUUA | 3264 |
| 1678 | UGACAUAA CUGAUGA GCCGUUAGGC GAA AUUUUAUG | 10398 | CAUAAAAUU UUAUGUCA | 3265 |
| 1679 | GUGACAUA CUGAUGA GCCGUUAGGC GAA AAUUUUAU | 10399 | AUAAAAUUU UAUGUCAC | 3266 |
| 1680 | UGUGACAU CUGAUGA GCCGUUAGGC GAA AAAUUUUA | 10400 | UAAAAUUUU AUGUCACA | 3267 |
| 1681 | CUGUGACA CUGAUGA GCCGUUAGGC GAA AAAAUUUU | 10401 | AAAAUUUUA UGUCACAG | 3268 |
| 1685 | ACAUCUGU CUGAUGA GCCGUUAGGC GAA ACAUAAAA | 10402 | UUUUAUGUC ACAGAUGU | 3269 |

172

| | | | | |
|---|---|---|---|---|
| 1705 | AAACGUGA CUGAUGA GCCGUUAGGC GAA AGCCAUUC | 10403 | GAAUGGCUU UCACGUUU | 3270 |
| 1706 | GAAACGUG CUGAUGA GCCGUUAGGC GAA AAGCCAUU | 10404 | AAUGGCUUU CACGUUUC | 3271 |
| 1707 | GGAAACGU CUGAUGA GCCGUUAGGC GAA AAAGCCAU | 10405 | AUGGCUUUC ACGUUUCC | 3272 |
| 1712 | UCCAAGGA CUGAUGA GCCGUUAGGC GAA ACGUGAAA | 10406 | UUUCACGUU UCCUUGGA | 3273 |
| 1713 | UUCCAAGG CUGAUGA GCCGUUAGGC GAA AACGUGAA | 10407 | UUCACGUUU CCUUGGAA | 3274 |
| 1714 | UUUCCAAG CUGAUGA GCCGUUAGGC GAA AAACGUGA | 10408 | UCACGUUUC CUUGGAAA | 3275 |
| 1717 | UCUUUUCC CUGAUGA GCCGUUAGGC GAA AGGAAACG | 10409 | CGUUUCCUU GGAAAAGA | 3276 |
| 1756 | CCACACAG CUGAUGA GCCGUUAGGC GAA ACAGUUUC | 10410 | GAAACUGUC CUGUGUGG | 3277 |
| 1766 | AAUUUAUU CUGAUGA GCCGUUAGGC GAA ACCACACA | 10411 | UGUGUGGUC AAUAAAUU | 3278 |
| 1770 | CAGGAAUU CUGAUGA GCCGUUAGGC GAA AUUGACCA | 10412 | UGGUCAAUA AAUUCCUG | 3279 |
| 1774 | UGUACAGG CUGAUGA GCCGUUAGGC GAA AUUUAUUG | 10413 | CAAUAAAUU CCUGUACA | 3280 |
| 1775 | CUGUACAG CUGAUGA GCCGUUAGGC GAA AAUUUAUU | 10414 | AAUAAAUUC CUGUACAG | 3281 |
| 1780 | UGUCUCUG CUGAUGA GCCGUUAGGC GAA ACAGGAAU | 10415 | AUUCCUGUA CAGAGACA | 3282 |
| 1790 | AUCCAGGU CUGAUGA GCCGUUAGGC GAA AUGUCUCU | 10416 | AGAGACAUU ACCUGGAU | 3283 |
| 1791 | AAUCCAGG CUGAUGA GCCGUUAGGC GAA AAUGUCUC | 10417 | GAGACAUUA CCUGGAUU | 3284 |
| 1799 | CGUAGCAG CUGAUGA GCCGUUAGGC GAA AUCCAGGU | 10418 | ACCUGGAUU CUGCUACG | 3285 |
| 1800 | CCGUAGCA CUGAUGA GCCGUUAGGC GAA AAUCCAGG | 10419 | CCUGGAUUC UGCUACGG | 3286 |
| 1805 | ACUGUCCG CUGAUGA GCCGUUAGGC GAA AGCAGAAU | 10420 | AUUCUGCUA CGGACAGU | 3287 |
| 1814 | CUGUUGUU CUGAUGA GCCGUUAGGC GAA ACUGUCCG | 10421 | CGGACAGUU AACAACAG | 3288 |
| 1815 | UCUGUUGU CUGAUGA GCCGUUAGGC GAA AACUGUCC | 10422 | GGACAGUUA ACAACAGA | 3289 |
| 1836 | GCUGAUAC CUGAUGA GCCGUUAGGC GAA AUGGUGCA | 10423 | UGCACCAUA GUAUCAGC | 3290 |
| 1839 | CUUGCUGA CUGAUGA GCCGUUAGGC GAA ACUAUGGU | 10424 | ACCAUAGUA UCAGCAAG | 3291 |
| 1841 | UGCUUGCU CUGAUGA GCCGUUAGGC GAA AUACUAUG | 10425 | CAUAGUAUC AGCAAGCA | 3292 |
| 1866 | GUAAUCUU CUGAUGA GCCGUUAGGC GAA AGUGGUGG | 10426 | CCACCACUC AAGAUUAC | 3293 |
| 1872 | GAUGGAGU CUGAUGA GCCGUUAGGC GAA AUCUUGAG | 10427 | CUCAAGAUU ACUCCAUC | 3294 |
| 1873 | UGAUGGAG CUGAUGA GCCGUUAGGC GAA AAUCUUGA | 10428 | UCAAGAUUA CUCCAUCA | 3295 |
| 1876 | GAGUGAUG CUGAUGA GCCGUUAGGC GAA AGUAAUCU | 10429 | AGAUUACUC CAUCACUC | 3296 |
| 1880 | UUCAGAGU CUGAUGA GCCGUUAGGC GAA AUGGAGUA | 10430 | UACUCCAUC ACUCUGAA | 3297 |
| 1884 | AAGGUUCA CUGAUGA GCCGUUAGGC GAA AGUGAUGG | 10431 | CCAUCACUC UGAACCUU | 3298 |
| 1892 | UUGAUGAC CUGAUGA GCCGUUAGGC GAA AGGUUCAG | 10432 | CUGAACCUU GUCAUCAA | 3299 |
| 1895 | UUCUUGAU CUGAUGA GCCGUUAGGC GAA ACAAGGUU | 10433 | AACCUUGUC AUCAAGAA | 3300 |
| 1898 | ACGUUCUU CUGAUGA GCCGUUAGGC GAA AUGACAAG | 10434 | CUUGUCAUC AAGAACGU | 3301 |
| 1909 | CUUCUAGA CUGAUGA GCCGUUAGGC GAA ACACGUUC | 10435 | GAACGUGUC UCUAGAAG | 3302 |
| 1911 | GUCUUCUA CUGAUGA GCCGUUAGGC GAA AGACACGU | 10436 | ACGUGUCUC UAGAAGAC | 3303 |
| 1913 | GAGUCUUC CUGAUGA GCCGUUAGGC GAA AGAGACAC | 10437 | GUGUCUCUA GAAGACUC | 3304 |

| | | | | |
|---|---|---|---|---|
| 1921 | AGGUGCCC CUGAUGA GCCGUUAGGC GAA AGUCUUCU | 10438 | AGAAGACUC GGGCACCU | 3305 |
| 1930 | UGCACGCA CUGAUGA GCCGUUAGGC GAA AGGUGCCC | 10439 | GGGCACCUA UGCGUGCA | 3306 |
| 1952 | CCUGUGUA CUGAUGA GCCGUUAGGC GAA AUGUUCCU | 10440 | AGGAACAUA UACACAGG | 3307 |
| 1954 | CCCCUGUG CUGAUGA GCCGUUAGGC GAA AUAUGUUC | 10441 | GAACAUAUA CACAGGGG | 3308 |
| 1970 | UUCCGAAG CUGAUGA GCCGUUAGGC GAA AUGUCUUC | 10442 | GAAGACAUC CUUCGGAA | 3309 |
| 1973 | GUCUUCCG CUGAUGA GCCGUUAGGC GAA AGGAUGUC | 10443 | GACAUCCUU CGGAAGAC | 3310 |
| 1974 | UGUCUUCC CUGAUGA GCCGUUAGGC GAA AAGGAUGU | 10444 | ACAUCCUUC GGAAGACA | 3311 |
| 1988 | CUAACGAG CUGAUGA GCCGUUAGGC GAA ACUUCUGU | 10445 | ACAGAAGUU CUCGUUAG | 3312 |
| 1989 | UCUAACGA CUGAUGA GCCGUUAGGC GAA AACUUCUG | 10446 | CAGAAGUUC UCGUUAGA | 3313 |
| 1991 | UCUCUAAC CUGAUGA GCCGUUAGGC GAA AGAACUUC | 10447 | GAAGUUCUC GUUAGAGA | 3314 |
| 1994 | GAAUCUCU CUGAUGA GCCGUUAGGC GAA ACGAGAAC | 10448 | GUUCUCGUU AGAGAUUC | 3315 |
| 1995 | CGAAUCUC CUGAUGA GCCGUUAGGC GAA AACGAGAA | 10449 | UUCUCGUUA GAGAUUCG | 3316 |
| 2001 | CGCUUCCG CUGAUGA GCCGUUAGGC GAA AUCUCUAA | 10450 | UUAGAGAUU CGGAAGCG | 3317 |
| 2002 | GCGCUUCC CUGAUGA GCCGUUAGGC GAA AAUCUCUA | 10451 | UAGAGAUUC GGAAGCGC | 3318 |
| 2021 | AGGUUUUG CUGAUGA GCCGUUAGGC GAA AGCAGGUG | 10452 | CACCUGCUU CAAAACCU | 3319 |
| 2022 | GAGGUUUU CUGAUGA GCCGUUAGGC GAA AAGCAGGU | 10453 | ACCUGCUUC AAAACCUC | 3320 |
| 2030 | UAGUCACU CUGAUGA GCCGUUAGGC GAA AGGUUUUG | 10454 | CAAAACCUC AGUGACUA | 3321 |
| 2038 | AGACCUCG CUGAUGA GCCGUUAGGC GAA AGUCACUG | 10455 | CAGUGACUA CGAGGUCU | 3322 |
| 2045 | CUGAUGGA CUGAUGA GCCGUUAGGC GAA ACCUCGUA | 10456 | UACGAGGUC UCCAUCAG | 3323 |
| 2047 | CACUGAUG CUGAUGA GCCGUUAGGC GAA AGACCUCG | 10457 | CGAGGUCUC CAUCAGUG | 3324 |
| 2051 | GAGCCACU CUGAUGA GCCGUUAGGC GAA AUGGAGAC | 10458 | GUCUCCAUC AGUGGCUC | 3325 |
| 2059 | AGGUCGUA CUGAUGA GCCGUUAGGC GAA AGCCACUG | 10459 | CAGUGGCUC UACGACCU | 3326 |
| 2061 | UAAGGUCG CUGAUGA GCCGUUAGGC GAA AGAGCCAC | 10460 | GUGGCUCUA CGACCUUA | 3327 |
| 2068 | GACAGUCU CUGAUGA GCCGUUAGGC GAA AGGUCGUA | 10461 | UACGACCUU AGACUGUC | 3328 |
| 2069 | UGACAGUC CUGAUGA GCCGUUAGGC GAA AAGGUCGU | 10462 | ACGACCUUA GACUGUCA | 3329 |
| 2076 | UCUAGCUU CUGAUGA GCCGUUAGGC GAA ACAGUCUA | 10463 | UAGACUGUC AAGCUAGA | 3330 |
| 2082 | GACACCUC CUGAUGA GCCGUUAGGC GAA AGCUUGAC | 10464 | GUCAAGCUA GAGGUGUC | 3331 |
| 2090 | GGCGCGGG CUGAUGA GCCGUUAGGC GAA ACACCUCU | 10465 | AGAGGUGUC CCCGCGCC | 3332 |
| 2100 | AGUGAUCU CUGAUGA GCCGUUAGGC GAA AGGCGCGG | 10466 | CCGCGCCUC AGAUCACU | 3333 |
| 2105 | AACCAAGU CUGAUGA GCCGUUAGGC GAA AUCUGAGG | 7520 | CCUCAGAUC ACUUGGUU | 378 |
| 2109 | UUUGAACC CUGAUGA GCCGUUAGGC GAA AGUGAUCU | 10467 | AGAUCACUU GGUUCAAA | 3334 |
| 2113 | UGUUUUUG CUGAUGA GCCGUUAGGC GAA ACCAAGUG | 10468 | CACUUGGUU CAAAAACA | 3335 |
| 2114 | UUGUUUUU CUGAUGA GCCGUUAGGC GAA AACCAAGU | 7523 | ACUUGGUUC AAAAACAA | 3336 |
| 2132 | UCUUGUUG CUGAUGA GCCGUUAGGC GAA AUUUUGUG | 7525 | CACAAAAUA CAACAAGA | 383 |
| 2150 | CCUAAAAU CUGAUGA GCCGUUAGGC GAA AUUCCCGG | 10469 | CCGGGAAUU AUUUUAGG | 3337 |

174

| | | | | |
|---|---|---|---|---|
| 2151 | UCCUAAAA CUGAUGA GCCGUUAGGC GAA AAUUCCCG | 10470 | CGGGAAUUA UUUUAGGA | 3338 |
| 2153 | GGUCCUAA CUGAUGA GCCGUUAGGC GAA AUAAUUCC | 7528 | GGAAUUAUU UUAGGACC | 386 |
| 2154 | UGGUCCUA CUGAUGA GCCGUUAGGC GAA AAUAAUUC | 7529 | GAAUUAUUU UAGGACCA | 387 |
| 2155 | CUGGUCCU CUGAUGA GCCGUUAGGC GAA AAAUAAUU | 7530 | AAUUAUUUU AGGACCAG | 388 |
| 2156 | CCUGGUCC CUGAUGA GCCGUUAGGC GAA AAAAUAAU | 7531 | AUUAUUUUA GGACCAGG | 389 |
| 2179 | UUUCAAUA CUGAUGA GCCGUUAGGC GAA ACAGCGUG | 7532 | CACGCUGUU UAUUGAAA | 390 |
| 2180 | CUUUCAAU CUGAUGA GCCGUUAGGC GAA AACAGCGU | 7533 | ACGCUGUUU AUUGAAAG | 391 |
| 2181 | UCUUUCAA CUGAUGA GCCGUUAGGC GAA AAACAGCG | 7534 | CGCUGUUUA UUGAAAGA | 392 |
| 2183 | ACUCUUUC CUGAUGA GCCGUUAGGC GAA AUAAACAG | 7535 | CUGUUUAUU GAAAGAGU | 393 |
| 2192 | UCCUCUGU CUGAUGA GCCGUUAGGC GAA ACUCUUUC | 10471 | GAAAGAGUC ACAGAGGA | 3339 |
| 2213 | CACCUAUA CUGAUGA GCCGUUAGGC GAA ACACCCUC | 10472 | GAGGGUGUC UAUAGGUG | 3340 |
| 2215 | GGCACCUA CUGAUGA GCCGUUAGGC GAA AGACACCC | 10473 | GGGUGUCUA UAGGUGCC | 3341 |
| 2217 | UCGGCACC CUGAUGA GCCGUUAGGC GAA AUAGACAC | 10474 | GUGUCUAUA GGUGCCGA | 3342 |
| 2263 | CGGUGAGG CUGAUGA GCCGUUAGGC GAA AGGCUGCG | 10475 | CGCAGCCUA CCUCACCG | 3343 |
| 2267 | UGCACGGU CUGAUGA GCCGUUAGGC GAA AGGUAGGC | 10476 | GCCUACCUC ACCGUGCA | 3344 |
| 2284 | ACUUGUCU CUGAUGA GCCGUUAGGC GAA AGGUUCCU | 10477 | AGGAACCUC AGACAAGU | 3345 |
| 2293 | CCAGGUUU CUGAUGA GCCGUUAGGC GAA ACUUGUCU | 10478 | AGACAAGUC AAACCUGG | 3346 |
| 2309 | GUGAGCGU CUGAUGA GCCGUUAGGC GAA AUCAGCUC | 10479 | GAGCUGAUC ACGCUCAC | 3347 |
| 2315 | GUGCACGU CUGAUGA GCCGUUAGGC GAA AGCGUGAU | 10480 | AUCACGCUC ACGUGCAC | 3348 |
| 2342 | AGCCAAAA CUGAUGA GCCGUUAGGC GAA AGGGUCGC | 10481 | GCGACCCUC UUUUGGCU | 3349 |
| 2344 | GGAGCCAA CUGAUGA GCCGUUAGGC GAA AGAGGGUC | 10482 | GACCCUCUU UUGGCUCC | 3350 |
| 2345 | AGGAGCCA CUGAUGA GCCGUUAGGC GAA AAGAGGGU | 10483 | ACCCUCUUU UGGCUCCU | 3351 |
| 2346 | AAGGAGCC CUGAUGA GCCGUUAGGC GAA AAAGAGGG | 10484 | CCCUCUUUU GGCUCCUU | 3352 |
| 2351 | GUUAGAAG CUGAUGA GCCGUUAGGC GAA AGCCAAAA | 10485 | UUUUGGCUC CUUCUAAC | 3353 |
| 2354 | AGAGUUAG CUGAUGA GCCGUUAGGC GAA AGGAGCCA | 10486 | UGGCUCCUU CUAACUCU | 3354 |
| 2355 | GAGAGUUA CUGAUGA GCCGUUAGGC GAA AAGGAGCC | 10487 | GGCUCCUUC UAACUCUC | 3355 |
| 2357 | AAGAGAGU CUGAUGA GCCGUUAGGC GAA AGAAGGAG | 10488 | CUCCUUCUA ACUCUCUU | 3356 |
| 2361 | GAUGAAGA CUGAUGA GCCGUUAGGC GAA AGUUAGAA | 10489 | UUCUAACUC UCUUCAUC | 3357 |
| 2363 | CUGAUGAA CUGAUGA GCCGUUAGGC GAA AGAGUUAG | 10490 | CUAACUCUC UUCAUCAG | 3358 |
| 2365 | UUCUGAUG CUGAUGA GCCGUUAGGC GAA AGAGAGUU | 10491 | AACUCUCUU CAUCAGAA | 3359 |
| 2366 | UUUCUGAU CUGAUGA GCCGUUAGGC GAA AAGAGAGU | 10492 | ACUCUCUUC AUCAGAAA | 3360 |
| 2369 | AGUUUUCU CUGAUGA GCCGUUAGGC GAA AUGAAGAG | 10493 | CUCUUCAUC AGAAAACU | 3361 |
| 2386 | CGGAAGAA CUGAUGA GCCGUUAGGC GAA ACCGCUUC | 10494 | GAAGCGGUC UUCUUCCG | 3362 |
| 2388 | UUCGGAAG CUGAUGA GCCGUUAGGC GAA AGACCGCU | 10495 | AGCGGUCUU CUUCCGAA | 3363 |
| 2389 | CUUCGGAA CUGAUGA GCCGUUAGGC GAA AAGACCGC | 10496 | GCGGUCUUC UUCCGAAG | 3364 |

175

| | | | | |
|---|---|---|---|---|
| 2391 | UACUUCGG CUGAUGA GCCGUUAGGC GAA AGAAGACC | 10497 | GGUCUUCUU CCGAAGUA | 3365 |
| 2392 | UUACUUCG CUGAUGA GCCGUUAGGC GAA AAGAAGAC | 10498 | GUCUUCUUC CGAAGUAA | 3366 |
| 2399 | UCUGUCUU CUGAUGA GCCGUUAGGC GAA ACUUCGGA | 10499 | UCCGAAGUA AAGACAGA | 3367 |
| 2410 | UUGACAGG CUGAUGA GCCGUUAGGC GAA AGUCUGUC | 10500 | GACAGACUA CCUGUCAA | 3368 |
| 2416 | UAAUGAUU CUGAUGA GCCGUUAGGC GAA ACAGGUAG | 10501 | CUACCUGUC AAUCAUUA | 3369 |
| 2420 | UCCAUAAU CUGAUGA GCCGUUAGGC GAA AUUGACAG | 10502 | CUGUCAAUC AUUAUGGA | 3370 |
| 2423 | GGGUCCAU CUGAUGA GCCGUUAGGC GAA AUGAUUGA | 10503 | UCAAUCAUU AUGGACCC | 3371 |
| 2424 | UGGGUCCA CUGAUGA GCCGUUAGGC GAA AAUGAUUG | 10504 | CAAUCAUUA UGGACCCA | 3372 |
| 2441 | UCCAGGGG CUGAUGA GCCGUUAGGC GAA ACUUCAUC | 10505 | GAUGAAGUU CCCCUGGA | 3373 |
| 2442 | AUCCAGGG CUGAUGA GCCGUUAGGC GAA AACUUCAU | 10506 | AUGAAGUUC CCCUGGAU | 3374 |
| 2473 | UGGCAUCA CUGAUGA GCCGUUAGGC GAA AGGGCAGC | 10507 | GCUGCCCUA UGAUGCCA | 3375 |
| 2494 | CCCGUGCA CUGAUGA GCCGUUAGGC GAA ACUCCCAC | 10508 | GUGGGAGUU UGCACGGG | 3376 |
| 2495 | UCCCGUGC CUGAUGA GCCGUUAGGC GAA AACUCCCA | 10509 | UGGGAGUUU GCACGGGA | 3377 |
| 2516 | GAUUUGCC CUGAUGA GCCGUUAGGC GAA AGUUUCAG | 10510 | CUGAAACUA GGCAAAUC | 3378 |
| 2524 | UUCCGAGC CUGAUGA GCCGUUAGGC GAA AUUUGCCU | 10511 | AGGCAAAUC GCUCGGAA | 3379 |
| 2528 | CCUCUUCC CUGAUGA GCCGUUAGGC GAA AGCGAUUU | 10512 | AAAUCGCUC GGAAGAGG | 3380 |
| 2541 | UUUCCCAA CUGAUGA GCCGUUAGGC GAA AGCCCCUC | 10513 | GAGGGGCUU UUGGGAAA | 3381 |
| 2542 | CUUUCCCA CUGAUGA GCCGUUAGGC GAA AAGCCCCU | 10514 | AGGGGCUUU UGGGAAAG | 3382 |
| 2543 | ACUUUCCC CUGAUGA GCCGUUAGGC GAA AAAGCCCC | 10515 | GGGGCUUUU GGGAAAGU | 3383 |
| 2552 | GCUUGAAC CUGAUGA GCCGUUAGGC GAA ACUUUCCC | 10516 | GGGAAAGUC GUUCAAGC | 3384 |
| 2555 | GAGGCUUG CUGAUGA GCCGUUAGGC GAA ACGACUUU | 10517 | AAAGUCGUU CAAGCCUC | 3385 |
| 2556 | AGAGGCUU CUGAUGA GCCGUUAGGC GAA AACGACUU | 10518 | AAGUCGUUC AAGCCUCU | 3386 |
| 2563 | CAAAUGCA CUGAUGA GCCGUUAGGC GAA AGGCUUGA | 10519 | UCAAGCCUC UGCAUUUG | 3387 |
| 2569 | UAAUGCCA CUGAUGA GCCGUUAGGC GAA AUGCAGAG | 10520 | CUCUGCAUU UGGCAUUA | 3388 |
| 2570 | UUAAUGCC CUGAUGA GCCGUUAGGC GAA AAUGCAGA | 10521 | UCUGCAUUU GGCAUUAA | 3389 |
| 2576 | GAUUUCUU CUGAUGA GCCGUUAGGC GAA AUGCCAAA | 7599 | UUUGGCAUU AAGAAAUC | 457 |
| 2577 | UGAUUUCU CUGAUGA GCCGUUAGGC GAA AAUGCCAA | 7600 | UUGGCAUUA AGAAAUCA | 458 |
| 2584 | AGGUGGGU CUGAUGA GCCGUUAGGC GAA AUUUCUUA | 10522 | UAAGAAAUC ACCCACCU | 3390 |
| 2617 | CCUCUUUC CUGAUGA GCCGUUAGGC GAA ACAUCUUC | 10523 | GAAGAUGUU GAAAGAGG | 3391 |
| 2644 | GAGCUUUG CUGAUGA GCCGUUAGGC GAA ACUCACUG | 10524 | CAGUGAGUA CAAAGCUC | 3392 |
| 2652 | GGUCAUCA CUGAUGA GCCGUUAGGC GAA AGCUUUGU | 10525 | ACAAAGCUC UGAUGACC | 3393 |
| 2666 | AAGAUCUU CUGAUGA GCCGUUAGGC GAA AGUUCGGU | 10526 | ACCGAACUC AAGAUCUU | 3394 |
| 2672 | UGGGUCAA CUGAUGA GCCGUUAGGC GAA AUCUUGAG | 10527 | CUCAAGAUC UUGACCCA | 3395 |
| 2674 | UGUGGGUC CUGAUGA GCCGUUAGGC GAA AGAUCUUG | 10528 | CAAGAUCUU GACCCACA | 3396 |
| 2684 | UGAUGGCC CUGAUGA GCCGUUAGGC GAA AUGUGGGU | 10529 | ACCCACAUC GGCCAUCA | 3397 |

176

| | | | | |
|---|---|---|---|---|
| 2691 | AUUCAGAU CUGAUGA GCCGUUAGGC GAA AUGGCCGA | 10530 | UCGGCCAUC AUCUGAAU | 3398 |
| 2694 | CACAUUCA CUGAUGA GCCGUUAGGC GAA AUGAUGGC | 10531 | GCCAUCAUC UGAAUGUG | 3399 |
| 2705 | AGGAGGUU CUGAUGA GCCGUUAGGC GAA ACCACAUU | 10532 | AAUGUGGUU AACCUCCU | 3400 |
| 2706 | CAGGAGGU CUGAUGA GCCGUUAGGC GAA AACCACAU | 10533 | AUGUGGUUA ACCUCCUG | 3401 |
| 2711 | GCUCCCAG CUGAUGA GCCGUUAGGC GAA AGGUUAAC | 10534 | GUUAACCUC CUGGGAGC | 3402 |
| 2742 | CACCAUCA CUGAUGA GCCGUUAGGC GAA AGGCCCUC | 7612 | GAGGGCCUC UGAUGGUG | 470 |
| 2753 | UAUUCCAC CUGAUGA GCCGUUAGGC GAA AUCACCAU | 10535 | AUGGUGAUC GUGGAAUA | 3403 |
| 2761 | AUUUGCAG CUGAUGA GCCGUUAGGC GAA AUUCCACG | 10536 | CGUGGAAUA CUGCAAAU | 3404 |
| 2770 | GGUUUCCG CUGAUGA GCCGUUAGGC GAA AUUUGCAG | 10537 | CUGCAAAUA CGGAAACC | 3405 |
| 2782 | GGUAGUUG CUGAUGA GCCGUUAGGC GAA ACAGGUUU | 10538 | AAACCUGUC CAACUACC | 3406 |
| 2788 | UCUUGAGG CUGAUGA GCCGUUAGGC GAA AGUUGGAC | 10539 | GUCCAACUA CCUCAAGA | 3407 |
| 2792 | UUGCUCUU CUGAUGA GCCGUUAGGC GAA AGGUAGUU | 7621 | AACUACCUC AAGAGCAA | 479 |
| 2809 | GACAGAAU CUGAUGA GCCGUUAGGC GAA AGUCACGU | 10540 | ACGUGACUU AUUCUGUC | 3408 |
| 2810 | AGACAGAA CUGAUGA GCCGUUAGGC GAA AAGUCACG | 10541 | CGUGACUUA UUCUGUCU | 3409 |
| 2812 | UGAGACAG CUGAUGA GCCGUUAGGC GAA AUAAGUCA | 10542 | UGACUUAUU CUGUCUCA | 3410 |
| 2813 | UUGAGACA CUGAUGA GCCGUUAGGC GAA AAUAAGUC | 10543 | GACUUAUUC UGUCUCAA | 3411 |
| 2817 | CUUGUUGA CUGAUGA GCCGUUAGGC GAA ACAGAAUA | 10544 | UAUUCUGUC UCAACAAG | 3412 |
| 2819 | UCCUUGUU CUGAUGA GCCGUUAGGC GAA AGACAGAA | 10545 | UUCUGUCUC AACAAGGA | 3413 |
| 2836 | CCAUAUGC CUGAUGA GCCGUUAGGC GAA AGGCUGCG | 10546 | CGCAGCCUU GCAUAUGG | 3414 |
| 2841 | GAGCUCCA CUGAUGA GCCGUUAGGC GAA AUGCAAGG | 10547 | CCUUGCAUA UGGAGCUC | 3415 |
| 2849 | UCUUUCUU CUGAUGA GCCGUUAGGC GAA AGCUCCAU | 10548 | AUGGAGCUC AAGAAAGA | 3416 |
| 2900 | ACACUGUC CUGAUGA GCCGUUAGGC GAA AGGCGGGG | 10549 | CCCCGCCUA GACAGUGU | 3417 |
| 2909 | GAGCUGCU CUGAUGA GCCGUUAGGC GAA ACACUGUC | 10550 | GACAGUGUC AGCAGCUC | 3418 |
| 2917 | UGACACUU CUGAUGA GCCGUUAGGC GAA AGCUGCUG | 10551 | CAGCAGCUC AAGUGUCA | 3419 |
| 2924 | GAGCUGGU CUGAUGA GCCGUUAGGC GAA ACACUUGA | 10552 | UCAAGUGUC ACCAGCUC | 3420 |
| 2932 | GGAAGCUG CUGAUGA GCCGUUAGGC GAA AGCUGGUG | 10553 | CACCAGCUC CAGCUUCC | 3421 |
| 2938 | CUUCAGGG CUGAUGA GCCGUUAGGC GAA AGCUGGAG | 10554 | CUCCAGCUU CCCUGAAG | 3422 |
| 2939 | UCUUCAGG CUGAUGA GCCGUUAGGC GAA AAGCUGGA | 10555 | UCCAGCUUC CCUGAAGA | 3423 |
| 2982 | CUCACUGU CUGAUGA GCCGUUAGGC GAA AUCCUCGU | 10556 | ACGAGGAUU ACAGUGAG | 3424 |
| 2983 | UCUCACUG CUGAUGA GCCGUUAGGC GAA AAUCCUCG | 10557 | CGAGGAUUA CAGUGAGA | 3425 |
| 2993 | UGCUUGGA CUGAUGA GCCGUUAGGC GAA AUCUCACU | 10558 | AGUGAGAUC UCCAAGCA | 3426 |
| 2995 | GCUGCUUG CUGAUGA GCCGUUAGGC GAA AGAUCUCA | 10559 | UGAGAUCUC CAAGCAGC | 3427 |
| 3008 | UCCAUGGU CUGAUGA GCCGUUAGGC GAA AGGGGCUG | 10560 | CAGCCCCUC ACCAUGGA | 3428 |
| 3026 | CUGUAGGA CUGAUGA GCCGUUAGGC GAA AUCAGGUC | 10561 | GACCUGAUU UCCUACAG | 3429 |
| 3027 | ACUGUAGG CUGAUGA GCCGUUAGGC GAA AAUCAGGU | 10562 | ACCUGAUUU CCUACAGU | 3430 |

177

| | | | | |
|---|---|---|---|---|
| 3028 | AACUGUAG CUGAUGA GCCGUUAGGC GAA AAAUCAGG | 10563 | CCUGAUUUC CUACAGUU | 3431 |
| 3031 | GGAAACUG CUGAUGA GCCGUUAGGC GAA AGGAAAUC | 10564 | GAUUUCCUA CAGUUUCC | 3432 |
| 3036 | CACUUGGA CUGAUGA GCCGUUAGGC GAA ACUGUAGG | 10565 | CCUACAGUU UCCAAGUG | 3433 |
| 3037 | CCACUUGG CUGAUGA GCCGUUAGGC GAA AACUGUAG | 10566 | CUACAGUUU CCAAGUGG | 3434 |
| 3038 | GCCACUUG CUGAUGA GCCGUUAGGC GAA AAACUGUA | 7661 | UACAGUUUC CAAGUGGC | 3435 |
| 3061 | AGGACAGA CUGAUGA GCCGUUAGGC GAA ACUCCAUG | 10567 | CAUGGAGUU UCUGUCCU | 3436 |
| 3062 | GAGGACAG CUGAUGA GCCGUUAGGC GAA AACUCCAU | 10568 | AUGGAGUUU CUGUCCUC | 3437 |
| 3063 | GGAGGACA CUGAUGA GCCGUUAGGC GAA AAACUCCA | 10569 | UGGAGUUUC UGUCCUCC | 3438 |
| 3067 | UUCUGGAG CUGAUGA GCCGUUAGGC GAA ACAGAAAC | 10570 | GUUUCUGUC CUCCAGAA | 3439 |
| 3070 | ACUUUCUG CUGAUGA GCCGUUAGGC GAA AGGACAGA | 10571 | UCUGUCCUC CAGAAAGU | 3440 |
| 3083 | UCCCGAUG CUGAUGA GCCGUUAGGC GAA AUGCACUU | 7668 | AAGUGCAUU CAUCGGGA | 526 |
| 3084 | GUCCCGAU CUGAUGA GCCGUUAGGC GAA AAUGCACU | 7669 | AGUGCAUUC AUCGGGAC | 527 |
| 3087 | CAGGUCCC CUGAUGA GCCGUUAGGC GAA AUGAAUGC | 7670 | GCAUUCAUC GGGACCUG | 528 |
| 3110 | GAUAAAAG CUGAUGA GCCGUUAGGC GAA AUGUUUCU | 7671 | AGAAACAUC CUUUUAUC | 3441 |
| 3113 | UCAGAUAA CUGAUGA GCCGUUAGGC GAA AGGAUGUU | 10572 | AACAUCCUU UUAUCUGA | 3442 |
| 3114 | CUCAGAUA CUGAUGA GCCGUUAGGC GAA AAGGAUGU | 10573 | ACAUCCUUU UAUCUGAG | 3443 |
| 3115 | UCUCAGAU CUGAUGA GCCGUUAGGC GAA AAAGGAUG | 10574 | CAUCCUUUU AUCUGAGA | 3444 |
| 3116 | UUCUCAGA CUGAUGA GCCGUUAGGC GAA AAAAGGAU | 10575 | AUCCUUUUA UCUGAGAA | 3445 |
| 3118 | UGUUCUCA CUGAUGA GCCGUUAGGC GAA AUAAAAGG | 10576 | CCUUUUAUC UGAGAACA | 3446 |
| 3140 | AAGUCGCA CUGAUGA GCCGUUAGGC GAA AUCUUCAC | 10577 | GUGAAGAUU UGCGACUU | 3447 |
| 3141 | AAAGUCGC CUGAUGA GCCGUUAGGC GAA AAUCUUCA | 10578 | UGAAGAUUU GCGACUUU | 3448 |
| 3148 | CCAGGCCA CUGAUGA GCCGUUAGGC GAA AGUCGCAA | 10579 | UUGCGACUU UGGCCUGG | 3449 |
| 3149 | GCCAGGCC CUGAUGA GCCGUUAGGC GAA AAGUCGCA | 10580 | UGCGACUUU GGCCUGGC | 3450 |
| 3165 | CUUAUAAA CUGAUGA GCCGUUAGGC GAA AUCCCGGG | 7684 | CCCGGGAUA UUUAUAAG | 542 |
| 3167 | UUCUUAUA CUGAUGA GCCGUUAGGC GAA AUAUCCCG | 7685 | CGGGAUAUU UAUAAGAA | 543 |
| 3168 | GUUCUUAU CUGAUGA GCCGUUAGGC GAA AAUAUCCC | 7686 | GGGAUAUUU AUAAGAAC | 544 |
| 3169 | GGUUCUUA CUGAUGA GCCGUUAGGC GAA AAAUAUCC | 7687 | GGAUAUUUA UAAGAACC | 545 |
| 3171 | AGGGUUCU CUGAUGA GCCGUUAGGC GAA AUAAAUAU | 10581 | AUAUUUAUA AGAACCCU | 3451 |
| 3183 | CCUCACAU CUGAUGA GCCGUUAGGC GAA AUCAGGGU | 10582 | ACCCUGAUU AUGUGAGG | 3452 |
| 3184 | UCCUCACA CUGAUGA GCCGUUAGGC GAA AAUCAGGG | 10583 | CCCUGAUUA UGUGAGGA | 3453 |
| 3201 | AAGUCGAG CUGAUGA GCCGUUAGGC GAA AUCUCCUC | 10584 | GAGGAGAUA CUCGACUU | 3454 |
| 3204 | GGGAAGUC CUGAUGA GCCGUUAGGC GAA AGUAUCUC | 10585 | GAGAUACUC GACUUCCC | 3455 |
| 3209 | UUUAGGGG CUGAUGA GCCGUUAGGC GAA AGUCGAGU | 10586 | ACUCGACUU CCCCUAAA | 3456 |
| 3210 | UUUUAGGG CUGAUGA GCCGUUAGGC GAA AAGUCGAG | 10587 | CUCGACUUC CCCUAAAA | 3457 |
| 3215 | AUCCAUUU CUGAUGA GCCGUUAGGC GAA AGGGGAAG | 10588 | CUUCCCCUA AAAUGGAU | 3458 |

178

| | | | | |
|---|---|---|---|---|
| 3228 | GGAUUCAG CUGAUGA GCCGUUAGGC GAA AGCCAUCC | 10589 | GGAUGGCUC CUGAAUCC | 3459 |
| 3235 | CAAAGAUG CUGAUGA GCCGUUAGGC GAA AUUCAGGA | 10590 | UCCUGAAUC CAUCUUUG | 3460 |
| 3239 | UUGUCAAA CUGAUGA GCCGUUAGGC GAA AUGGAUUC | 10591 | GAAUCCAUC UUUGACAA | 3461 |
| 3241 | CCUUGUCA CUGAUGA GCCGUUAGGC GAA AGAUGGAU | 10592 | AUCCAUCUU UGACAAGG | 3462 |
| 3242 | ACCUUGUC CUGAUGA GCCGUUAGGC GAA AAGAUGGA | 10593 | UCCAUCUUU GACAAGGU | 3463 |
| 3251 | GUGCUGUA CUGAUGA GCCGUUAGGC GAA ACCUUGUC | 10594 | GACAAGGUC UACAGCAC | 3464 |
| 3253 | UGGUGCUG CUGAUGA GCCGUUAGGC GAA AGACCUUG | 10595 | CAAGGUCUA CAGCACCA | 3465 |
| 3277 | CGCCAUAG CUGAUGA GCCGUUAGGC GAA ACCACACA | 10596 | UGUGUGGUC CUAUGGCG | 3466 |
| 3280 | ACACGCCA CUGAUGA GCCGUUAGGC GAA AGGACCAC | 10597 | GUGGUCCUA UGGCGUGU | 3467 |
| 3289 | CCCACAGC CUGAUGA GCCGUUAGGC GAA ACACGCCA | 10598 | UGGCGUGUU GCUGUGGG | 3468 |
| 3302 | AAGGAGAA CUGAUGA GCCGUUAGGC GAA AUCUCCCA | 10599 | UGGGAGAUC UUCUCCUU | 3469 |
| 3304 | CUAAGGAG CUGAUGA GCCGUUAGGC GAA AGAUCUCC | 10600 | GGAGAUCUU CUCCUUAG | 3470 |
| 3305 | CCUAAGGA CUGAUGA GCCGUUAGGC GAA AAGAUCUC | 10601 | GAGAUCUUC UCCUUAGG | 3471 |
| 3307 | CCCCUAAG CUGAUGA GCCGUUAGGC GAA AGAAGAUC | 10602 | GAUCUUCUC CUUAGGGG | 3472 |
| 3310 | AACCCCCU CUGAUGA GCCGUUAGGC GAA AGGAGAAG | 10603 | CUUCUCCUU AGGGGGUU | 3473 |
| 3311 | GAACCCCC CUGAUGA GCCGUUAGGC GAA AAGGAGAA | 10604 | UUCUCCUUA GGGGGUUC | 3474 |
| 3318 | GUAUGGAG CUGAUGA GCCGUUAGGC GAA ACCCCCUA | 10605 | UAGGGGGUU CUCCAUAC | 3475 |
| 3319 | GGUAUGGA CUGAUGA GCCGUUAGGC GAA AACCCCCU | 10606 | AGGGGGUUC UCCAUACC | 3476 |
| 3321 | UGGGUAUG CUGAUGA GCCGUUAGGC GAA AGAACCCC | 10607 | GGGGUUCUC CAUACCCA | 3477 |
| 3325 | CUCCUGGG CUGAUGA GCCGUUAGGC GAA AUGGAGAA | 10608 | UUCUCCAUA CCCAGGAG | 3478 |
| 3352 | GGCUGCAG CUGAUGA GCCGUUAGGC GAA AGUCUUCA | 10609 | UGAAGACUU CUGCAGCC | 3479 |
| 3353 | CGGCUGCA CUGAUGA GCCGUUAGGC GAA AAGUCUUC | 10610 | GAAGACUUC UGCAGCCG | 3480 |
| 3397 | GUGUGGCA CUGAUGA GCCGUUAGGC GAA ACUCCGGG | 10611 | CCCGGAGUA UGCCACAC | 3481 |
| 3413 | AUUUGGUA CUGAUGA GCCGUUAGGC GAA AUUUCAGG | 10612 | CCUGAAAUC UACCAAAU | 3482 |
| 3415 | UGAUUUGG CUGAUGA GCCGUUAGGC GAA AGAUUUCA | 10613 | UGAAAUCUA CCAAAUCA | 3483 |
| 3422 | UCCAACAU CUGAUGA GCCGUUAGGC GAA AUUUGGUA | 10614 | UACCAAAUC AUGUUGGA | 3484 |
| 3427 | AGCAAUCC CUGAUGA GCCGUUAGGC GAA ACAUGAUU | 10615 | AAUCAUGUU GGAUUGCU | 3485 |
| 3432 | GUGCCAGC CUGAUGA GCCGUUAGGC GAA AUCCAACA | 10616 | UGUUGGAUU GCUGGCAC | 3486 |
| 3466 | GUUCAGCA CUGAUGA GCCGUUAGGC GAA ACCGGGGC | 10617 | GCCCCGGUU UGCUGAAC | 3487 |
| 3467 | AGUUCAGC CUGAUGA GCCGUUAGGC GAA AACCGGGG | 10618 | CCCCGGUUU GCUGAACU | 3488 |
| 3476 | UUCUCCAC CUGAUGA GCCGUUAGGC GAA AGUUCAGC | 10619 | GCUGAACUU GUGGAGAA | 3489 |
| 3488 | AGGUCACC CUGAUGA GCCGUUAGGC GAA AGUUUCUC | 10620 | GAGAAACUU GGUGACCU | 3490 |
| 3500 | UUGGCUUG CUGAUGA GCCGUUAGGC GAA AGCAGGUC | 10621 | GACCUGCUU CAAGCCAA | 3491 |
| 3501 | GUUGGCUU CUGAUGA GCCGUUAGGC GAA AAGCAGGU | 10622 | ACCUGCUUC AAGCCAAC | 3492 |
| 3512 | UCCUGUUG CUGAUGA GCCGUUAGGC GAA ACGUUGGC | 10623 | GCCAACGUC CAACAGGA | 3493 |

179

| | | | | |
|---|---|---|---|---|
| 3531 | GGGGAUGU CUGAUGA GCCGUUAGGC GAA AUCUUUCC | 10624 | GGAAAGAUU ACAUCCCC | 3494 |
| 3532 | GGGGGAUG CUGAUGA GCCGUUAGGC GAA AAUCUUUC | 10625 | GAAAGAUUA CAUCCCCC | 3495 |
| 3536 | UUGAGGGG CUGAUGA GCCGUUAGGC GAA AUGUAAUC | 10626 | GAUUACAUC CCCCUCAA | 3496 |
| 3542 | AUGGCAUU CUGAUGA GCCGUUAGGC GAA AGGGGGAU | 10627 | AUCCCCCUC AAUGCCAU | 3497 |
| 3551 | CUAGUCAG CUGAUGA GCCGUUAGGC GAA AUGGCAUU | 10628 | AAUGCCAUA CUGACUAG | 3498 |
| 3558 | ACUGUUUC CUGAUGA GCCGUUAGGC GAA AGUCAGUA | 10629 | UACUGACUA GAAACAGU | 3499 |
| 3567 | UGUGAAGC CUGAUGA GCCGUUAGGC GAA ACUGUUUC | 10630 | GAAACAGUA GCUUCACA | 3500 |
| 3571 | AGUAUGUG CUGAUGA GCCGUUAGGC GAA AGCUACUG | 10631 | CAGUAGCUU CACAUACU | 3501 |
| 3572 | GAGUAUGU CUGAUGA GCCGUUAGGC GAA AAGCUACU | 10632 | AGUAGCUUC ACAUACUC | 3502 |
| 3577 | GGGUCGAG CUGAUGA GCCGUUAGGC GAA AUGUGAAG | 10633 | CUUCACAUA CUCGACCC | 3503 |
| 3580 | UGGGGGUC CUGAUGA GCCGUUAGGC GAA AGUAUGUG | 10634 | CACAUACUC GACCCCCA | 3504 |
| 3592 | CCUCAGAG CUGAUGA GCCGUUAGGC GAA AGGUGGGG | 10635 | CCCCACCUU CUCUGAGG | 3505 |
| 3593 | UCCUCAGA CUGAUGA GCCGUUAGGC GAA AAGGUGGG | 10636 | CCCACCUUC UCUGAGGA | 3506 |
| 3595 | GGUCCUCA CUGAUGA GCCGUUAGGC GAA AGAAGGUG | 10637 | CACCUUCUC UGAGGACC | 3507 |
| 3605 | UCCUUGAA CUGAUGA GCCGUUAGGC GAA AGGUCCUC | 10638 | GAGGACCUU UUCAAGGA | 3508 |
| 3606 | GUCCUUGA CUGAUGA GCCGUUAGGC GAA AAGGUCCU | 10639 | AGGACCUUU UCAAGGAC | 3509 |
| 3607 | CGUCCUUG CUGAUGA GCCGUUAGGC GAA AAAGGUCC | 10640 | GGACCUUUU CAAGGACG | 3510 |
| 3608 | CCGUCCUU CUGAUGA GCCGUUAGGC GAA AAAAGGUC | 10641 | GACCUUUUC AAGGACGG | 3511 |
| 3619 | GAUCUGCA CUGAUGA GCCGUUAGGC GAA AGCCGUCC | 10642 | GGACGGCUU UGCAGAUC | 3512 |
| 3620 | GGAUCUGC CUGAUGA GCCGUUAGGC GAA AAGCCGUC | 10643 | GACGGCUUU GCAGAUCC | 3513 |
| 3627 | AAAAUGUG CUGAUGA GCCGUUAGGC GAA AUCUGCAA | 10644 | UUGCAGAUC CACAUUUU | 3514 |
| 3633 | GGAAUGAA CUGAUGA GCCGUUAGGC GAA AUGUGGAU | 10645 | AUCCACAUU UUCAUUCC | 3515 |
| 3634 | CGGAAUGA CUGAUGA GCCGUUAGGC GAA AAUGUGGA | 10646 | UCCACAUUU UCAUUCCG | 3516 |
| 3635 | CCGGAAUG CUGAUGA GCCGUUAGGC GAA AAAUGUGG | 10647 | CCACAUUUU CAUUCCGG | 3517 |
| 3636 | UCCGGAAU CUGAUGA GCCGUUAGGC GAA AAAAUGUG | 10648 | CACAUUUUC AUUCCGGA | 3518 |
| 3639 | GCUUCCGG CUGAUGA GCCGUUAGGC GAA AUGAAAAU | 10649 | AUUUUCAUU CCGGAAGC | 3519 |
| 3640 | AGCUUCCG CUGAUGA GCCGUUAGGC GAA AAUGAAAA | 10650 | UUUUCAUUC CGGAAGCU | 3520 |
| 3649 | CAUCAUCA CUGAUGA GCCGUUAGGC GAA AGCUUCCG | 10651 | CGGAAGCUC UGAUGAUG | 3521 |
| 3664 | CGUUUACA CUGAUGA GCCGUUAGGC GAA AUCUCACA | 10652 | UGUGAGAUA UGUAAACG | 3522 |
| 3668 | AAAGCGUU CUGAUGA GCCGUUAGGC GAA ACAUAUCU | 10653 | AGAUAUGUA AACGCUUU | 3523 |
| 3675 | GAAUUUGA CUGAUGA GCCGUUAGGC GAA AGCGUUUA | 10654 | UAAACGCUU UCAAAUUC | 3524 |
| 3676 | UGAAUUUG CUGAUGA GCCGUUAGGC GAA AAGCGUUU | 10655 | AAACGCUUU CAAAUUCA | 3525 |
| 3677 | AUGAAUUU CUGAUGA GCCGUUAGGC GAA AAAGCGUU | 10656 | AACGCUUUC AAAUUCAU | 3526 |
| 3682 | GGCUCAUG CUGAUGA GCCGUUAGGC GAA AUUUGAAA | 10657 | UUUCAAAUU CAUGAGCC | 3527 |
| 3683 | AGGCUCAU CUGAUGA GCCGUUAGGC GAA AAUUUGAA | 10658 | UUCAAAUUC AUGAGCCU | 3528 |

180

| | | | | |
|---|---|---|---|---|
| 3701 | AAGGUUUU CUGAUGA GCCGUUAGGC GAA AUUCUUUC | 7779 | GAAAGAAUC AAAACCUU | 637 |
| 3709 | GCUCCUCA CUGAUGA GCCGUUAGGC GAA AGGUUUUG | 10659 | CAAAACCUU UGAGGAGC | 3529 |
| 3710 | AGCUCCUC CUGAUGA GCCGUUAGGC GAA AAGGUUUU | 10660 | AAAACCUUU GAGGAGCU | 3530 |
| 3719 | UUCGGUGA CUGAUGA GCCGUUAGGC GAA AGCUCCUC | 10661 | GAGGAGCUU UCACCGAA | 3531 |
| 3720 | GUUCGGUG CUGAUGA GCCGUUAGGC GAA AAGCUCCU | 10662 | AGGAGCUUU CACCGAAC | 3532 |
| 3721 | AGUUCGGU CUGAUGA GCCGUUAGGC GAA AAAGCUCC | 10663 | GGAGCUUUC ACCGAACU | 3533 |
| 3730 | UGGAGGUG CUGAUGA GCCGUUAGGC GAA AGUUCGGU | 10664 | ACCGAACUC CACCUCCA | 3534 |
| 3736 | CAAACAUG CUGAUGA GCCGUUAGGC GAA AGGUGGAG | 10665 | CUCCACCUC CAUGUUUG | 3535 |
| 3742 | AGUCCUCA CUGAUGA GCCGUUAGGC GAA ACAUGGAG | 10666 | CUCCAUGUU UGAGGACU | 3536 |
| 3743 | UAGUCCUC CUGAUGA GCCGUUAGGC GAA AACAUGGA | 10667 | UCCAUGUUU GAGGACUA | 3537 |
| 3751 | CCAGCUGA CUGAUGA GCCGUUAGGC GAA AGUCCUCA | 10668 | UGAGGACUA UCAGCUGG | 3538 |
| 3753 | GUCCAGCU CUGAUGA GCCGUUAGGC GAA AUAGUCCU | 10669 | AGGACUAUC AGCUGGAC | 3539 |
| 3765 | CAGAGUGC CUGAUGA GCCGUUAGGC GAA AGUGUCCA | 10670 | UGGACACUA GCACUCUG | 3540 |
| 3771 | GCCCAGCA CUGAUGA GCCGUUAGGC GAA AGUGCUAG | 10671 | CUAGCACUC UGCUGGGC | 3541 |
| 3781 | GCAAGGGG CUGAUGA GCCGUUAGGC GAA AGCCCAGC | 10672 | GCUGGGCUC CCCCUUGC | 3542 |
| 3787 | GCUUCAGC CUGAUGA GCCGUUAGGC GAA AGGGGGAG | 10673 | CUCCCCCUU GCUGAAGC | 3543 |
| 3799 | UCCAGGUG CUGAUGA GCCGUUAGGC GAA ACCGCUUC | 10674 | GAAGCGGUU CACCUGGA | 3544 |
| 3800 | GUCCAGGU CUGAUGA GCCGUUAGGC GAA AACCGCUU | 10675 | AAGCGGUUC ACCUGGAC | 3545 |
| 3829 | UCUUCAUG CUGAUGA GCCGUUAGGC GAA AGGCCUUG | 10676 | CAAGGCCUC CAUGAAGA | 3546 |
| 3839 | CUCAAGUC CUGAUGA GCCGUUAGGC GAA AUCUUCAU | 10677 | AUGAAGAUA GACUUGAG | 3547 |
| 3844 | CUAUUCUC CUGAUGA GCCGUUAGGC GAA AGUCUAUC | 10678 | GAUAGACUU GAGAAUAG | 3548 |
| 3851 | UUACUCGC CUGAUGA GCCGUUAGGC GAA AUUCUCAA | 10679 | UUGAGAAUA GCGAGUAA | 3549 |
| 3858 | CUUGCUUU CUGAUGA GCCGUUAGGC GAA ACUCGCUA | 10680 | UAGCGAGUA AAAGCAAG | 3550 |
| 3878 | AGAUCGGA CUGAUGA GCCGUUAGGC GAA AGUCCCGC | 10681 | GCGGGACUU UCCGAUCU | 3551 |
| 3879 | CAGAUCGG CUGAUGA GCCGUUAGGC GAA AAGUCCCG | 10682 | CGGGACUUU CCGAUCUG | 3552 |
| 3880 | GCAGAUCG CUGAUGA GCCGUUAGGC GAA AAAGUCCC | 10683 | GGGACUUUC CGAUCUGC | 3553 |
| 3885 | CCUCGGCA CUGAUGA GCCGUUAGGC GAA AUCGGAAA | 10684 | UUUCCGAUC UGCCGAGG | 3554 |
| 3901 | AGAAGCAG CUGAUGA GCCGUUAGGC GAA AGCUGGGC | 10685 | GCCCAGCUU CUGCUUCU | 3555 |
| 3902 | GAGAAGCA CUGAUGA GCCGUUAGGC GAA AAGCUGGG | 10686 | CCCAGCUUC UGCUUCUC | 3556 |
| 3907 | AGCUGGAG CUGAUGA GCCGUUAGGC GAA AGCAGAAG | 10687 | CUUCUGCUU CUCCAGCU | 3557 |
| 3908 | CAGCUGGA CUGAUGA GCCGUUAGGC GAA AAGCAGAA | 10688 | UUCUGCUUC UCCAGCUG | 3558 |
| 3910 | CACAGCUG CUGAUGA GCCGUUAGGC GAA AGAAGCAG | 10689 | CUGCUUCUC CAGCUGUG | 3559 |
| 3926 | ACGGGCCU CUGAUGA GCCGUUAGGC GAA AUGUGGCC | 10690 | GGCCACAUC AGGCCCGU | 3560 |
| 3949 | CCAGCUCA CUGAUGA GCCGUUAGGC GAA AUUCAUCG | 10691 | CGAUGAAUC UGAGCUGG | 3561 |
| 3967 | AACAGCAG CUGAUGA GCCGUUAGGC GAA ACUCCUUU | 10692 | AAAGGAGUC CUGCUGUU | 3562 |

181

| | | | | |
|---|---|---|---|---|
| 3975 | GGGUGGAG CUGAUGA GCCGUUAGGC GAA ACAGCAGG | 10693 | CCUGCUGUU CUCCACCC | 3563 |
| 3976 | GGGGUGGA CUGAUGA GCCGUUAGGC GAA AACAGCAG | 10694 | CUGCUGUUC UCCACCCC | 3564 |
| 3978 | UGGGGGUG CUGAUGA GCCGUUAGGC GAA AGAACAGC | 10695 | GCUGUUCUC CACCCCCA | 3565 |
| 3991 | CGGAGUUG CUGAUGA GCCGUUAGGC GAA AGUCUGGG | 10696 | CCCAGACUA CAACUCCG | 3566 |
| 3997 | ACACCACG CUGAUGA GCCGUUAGGC GAA AGUUGUAG | 10697 | CUACAACUC CGUGGUGU | 3567 |
| 4006 | AGGAGUAC CUGAUGA GCCGUUAGGC GAA ACACCACG | 10698 | CGUGGUGUU GUACUCCU | 3568 |
| 4009 | GGGAGGAG CUGAUGA GCCGUUAGGC GAA ACAACACC | 10699 | GGUGUUGUA CUCCUCCC | 3569 |
| 4012 | GCGGGGAG CUGAUGA GCCGUUAGGC GAA AGUACAAC | 10700 | GUUGUACUC CUCCCCGC | 3570 |
| 4015 | CGGGCGGG CUGAUGA GCCGUUAGGC GAA AGGAGUAC | 10701 | GUACUCCUC CCCGCCCG | 3571 |
| 4027 | AGAAGCUU CUGAUGA GCCGUUAGGC GAA AGGCGGGC | 10702 | GCCCGCCUA AAGCUUCU | 3572 |
| 4033 | CUGGUGAG CUGAUGA GCCGUUAGGC GAA AGCUUUAG | 10703 | CUAAAGCUU CUCACCAG | 3573 |
| 4034 | GCUGGUGA CUGAUGA GCCGUUAGGC GAA AAGCUUUA | 10704 | UAAAGCUUC UCACCAGC | 3574 |
| 4036 | GGGCUGGU CUGAUGA GCCGUUAGGC GAA AGAAGCUU | 10705 | AAGCUUCUC ACCAGCCC | 3575 |
| 4066 | AUGUAUAA CUGAUGA GCCGUUAGGC GAA ACUGUCAG | 10706 | CUGACAGUA UUAUACAU | 3576 |
| 4068 | AGAUGUAU CUGAUGA GCCGUUAGGC GAA AUACUGUC | 10707 | GACAGUAUU AUACAUCU | 3577 |
| 4069 | UAGAUGUA CUGAUGA GCCGUUAGGC GAA AAUACUGU | 10708 | ACAGUAUUA UACAUCUA | 3578 |
| 4071 | CAUAGAUG CUGAUGA GCCGUUAGGC GAA AUAAUACU | 10709 | AGUAUUAUA CAUCUAUG | 3579 |
| 4075 | AACUCAUA CUGAUGA GCCGUUAGGC GAA AUGUAUAA | 10710 | UUAUACAUC UAUGAGUU | 3580 |
| 4077 | UAAACUCA CUGAUGA GCCGUUAGGC GAA AGAUGUAU | 10711 | AUACAUCUA UGAGUUUA | 3581 |
| 4083 | UAGGUGUA CUGAUGA GCCGUUAGGC GAA ACUCAUAG | 10712 | CUAUGAGUU UACACCUA | 3582 |
| 4084 | AUAGGUGU CUGAUGA GCCGUUAGGC GAA AACUCAUA | 10713 | UAUGAGUUU ACACCUAU | 3583 |
| 4085 | AAUAGGUG CUGAUGA GCCGUUAGGC GAA AAACUCAU | 10714 | AUGAGUUUA CACCUAUU | 3584 |
| 4091 | GAGCGGAA CUGAUGA GCCGUUAGGC GAA AGGUGUAA | 10715 | UUACACCUA UUCCGCUC | 3585 |
| 4093 | UGGAGCGG CUGAUGA GCCGUUAGGC GAA AUAGGUGU | 10716 | ACACCUAUU CCGCUCCA | 3586 |
| 4094 | GUGGAGCG CUGAUGA GCCGUUAGGC GAA AAUAGGUG | 10717 | CACCUAUUC CGCUCCAC | 3587 |
| 4099 | CUCCUGUG CUGAUGA GCCGUUAGGC GAA AGCGGAAU | 10718 | AUUCCGCUC CACAGGAG | 3588 |
| 4117 | GUCACGAA CUGAUGA GCCGUUAGGC GAA AGCAGCUG | 10719 | CAGCUGCUU UUCGUGAC | 3589 |
| 4118 | GGUCACGA CUGAUGA GCCGUUAGGC GAA AAGCAGCU | 10720 | AGCUGCUUU UCGUGACC | 3590 |
| 4119 | AGGUCACG CUGAUGA GCCGUUAGGC GAA AAAGCAGC | 10721 | GCUGCUUUU CGUGACCU | 3591 |
| 4120 | AAGGUCAC CUGAUGA GCCGUUAGGC GAA AAAAGCAG | 10722 | CUGCUUUUC GUGACCUU | 3592 |
| 4128 | CACGAUUA CUGAUGA GCCGUUAGGC GAA AGGUCACG | 10723 | CGUGACCUU UAAUCGUG | 3593 |
| 4129 | GCACGAUU CUGAUGA GCCGUUAGGC GAA AAGGUCAC | 10724 | GUGACCUUU AAUCGUGC | 3594 |
| 4130 | AGCACGAU CUGAUGA GCCGUUAGGC GAA AAAGGUCA | 10725 | UGACCUUUA AUCGUGCU | 3595 |
| 4133 | AAAAGCAC CUGAUGA GCCGUUAGGC GAA AUUAAAGG | 10726 | CCUUUAAUC GUGCUUUU | 3596 |
| 4139 | AAACAAAA CUGAUGA GCCGUUAGGC GAA AGCACGAU | 10727 | AUCGUGCUU UUUUGUUU | 3597 |

| | | | | |
|---|---|---|---|---|
| 4140 | AAAACAAA CUGAUGA GCCGUUAGGC GAA AAGCACGA | 10728 | UCGUGCUUU UUUGUUUU | 3598 |
| 4141 | AAAAACAA CUGAUGA GCCGUUAGGC GAA AAAGCACG | 10729 | CGUGCUUUU UUGUUUUU | 3599 |
| 4142 | AAAAAACA CUGAUGA GCCGUUAGGC GAA AAAAGCAC | 10730 | GUGCUUUUU UGUUUUUU | 3600 |
| 4143 | CAAAAAAC CUGAUGA GCCGUUAGGC GAA AAAAAGCA | 10731 | UGCUUUUUU GUUUUUUG | 3601 |
| 4146 | AAACAAAA CUGAUGA GCCGUUAGGC GAA ACAAAAAA | 10732 | UUUUUUGUU UUUUGUUU | 3602 |
| 4147 | AAAACAAA CUGAUGA GCCGUUAGGC GAA AACAAAAA | 10733 | UUUUUGUUU UUUGUUUU | 3603 |
| 4148 | CAAAACAA CUGAUGA GCCGUUAGGC GAA AAACAAAA | 10734 | UUUUGUUUU UUGUUUUG | 3604 |
| 4149 | ACAAAACA CUGAUGA GCCGUUAGGC GAA AAAACAAA | 10735 | UUUGUUUUU UGUUUUGU | 3605 |
| 4150 | AACAAAAC CUGAUGA GCCGUUAGGC GAA AAAAACAA | 10736 | UUGUUUUUU GUUUUGUU | 3606 |
| 4153 | ACAAACAA CUGAUGA GCCGUUAGGC GAA ACAAAAAA | 10737 | UUUUUUGUU UUGUUUGU | 3607 |
| 4154 | AACAAACA CUGAUGA GCCGUUAGGC GAA AACAAAAA | 10738 | UUUUUGUUU UGUUUGUU | 3608 |
| 4155 | CAACAAAC CUGAUGA GCCGUUAGGC GAA AAACAAAA | 10739 | UUUUGUUUU GUUUGUUG | 3609 |
| 4158 | CAACAACA CUGAUGA GCCGUUAGGC GAA ACAAAACA | 10740 | UGUUUUGUU UGUUGUUG | 3610 |
| 4159 | GCAACAAC CUGAUGA GCCGUUAGGC GAA AACAAAAC | 10741 | GUUUUGUUU GUUGUUGC | 3611 |
| 4162 | ACAGCAAC CUGAUGA GCCGUUAGGC GAA ACAAACAA | 10742 | UUGUUUGUU GUUGCUGU | 3612 |
| 4165 | AAAACAGC CUGAUGA GCCGUUAGGC GAA ACAACAAA | 10743 | UUUGUUGUU GCUGUUUU | 3613 |
| 4171 | UUAGUCAA CUGAUGA GCCGUUAGGC GAA ACAGCAAC | 10744 | GUUGCUGUU UUGACUAA | 3614 |
| 4172 | GUUAGUCA CUGAUGA GCCGUUAGGC GAA AACAGCAA | 10745 | UUGCUGUUU UGACUAAC | 3615 |
| 4173 | UGUUAGUC CUGAUGA GCCGUUAGGC GAA AAACAGCA | 10746 | UGCUGUUUU GACUAACA | 3616 |
| 4178 | AUUCUUGU CUGAUGA GCCGUUAGGC GAA AGUCAAAA | 7879 | UUUUGACUA ACAAGAAU | 737 |
| 4189 | ACUGGGGU CUGAUGA GCCGUUAGGC GAA ACAUUCUU | 10747 | AAGAAUGUA ACCCCAGU | 3617 |
| 4198 | ACGUCACU CUGAUGA GCCGUUAGGC GAA ACUGGGGU | 10748 | ACCCCAGUU AGUGACGU | 3618 |
| 4199 | CACGUCAC CUGAUGA GCCGUUAGGC GAA AACUGGGG | 10749 | CCCCAGUUA GUGACGUG | 3619 |
| 4216 | AACAAUAG CUGAUGA GCCGUUAGGC GAA AUUCUUCA | 10750 | UGAAGAAUA CUAUUGUU | 3620 |
| 4219 | UCUAACAA CUGAUGA GCCGUUAGGC GAA AGUAUUCU | 10751 | AGAAUACUA UUGUUAGA | 3621 |
| 4221 | UCUCUAAC CUGAUGA GCCGUUAGGC GAA AUAGUAUU | 10752 | AAUACUAUU GUUAGAGA | 3622 |
| 4224 | AUUUCUCU CUGAUGA GCCGUUAGGC GAA ACAAUAGU | 10753 | ACUAUUGUU AGAGAAAU | 3623 |
| 4225 | GAUUUCUC CUGAUGA GCCGUUAGGC GAA AACAAUAG | 10754 | CUAUUGUUA GAGAAAUC | 3624 |
| 4233 | GCGGGGGG CUGAUGA GCCGUUAGGC GAA AUUUCUCU | 10755 | AGAGAAAUC CCCCCCGC | 3625 |
| 4249 | GUUACCCU CUGAUGA GCCGUUAGGC GAA AGGCUUUG | 10756 | CAAAGCCUC AGGGUAAC | 3626 |
| 4255 | GUCCAGGU CUGAUGA GCCGUUAGGC GAA ACCCUGAG | 10757 | CUCAGGGUA ACCUGGAC | 3627 |
| 4282 | GGUCGCCA CUGAUGA GCCGUUAGGC GAA AGGCACCU | 10758 | AGGUGCCUC UGGCGACC | 3628 |
| 4323 | GCUGCAGG CUGAUGA GCCGUUAGGC GAA AGGGUGGG | 10759 | CCCACCCUC CCUGCAGC | 3629 |
| 4341 | ACUGCCUC CUGAUGA GCCGUUAGGC GAA AGUCCCAC | 10760 | GUGGGACUA GAGGCAGU | 3630 |
| 4350 | AAUGGGCU CUGAUGA GCCGUUAGGC GAA ACUGCCUC | 10761 | GAGGCAGUA AGCCCAUU | 3631 |

| | | | | |
|---|---|---|---|---|
| 4358 | CAUGAGCU CUGAUGA GCCGUUAGGC GAA AUGGGCUU | 10762 | AAGCCCAUU AGCUCAUG | 3632 |
| 4359 | CCAUGAGC CUGAUGA GCCGUUAGGC GAA AAUGGGCU | 10763 | AGCCCAUUA GCUCAUGG | 3633 |
| 4363 | GCAGCCAU CUGAUGA GCCGUUAGGC GAA AGCUAAUG | 10764 | CAUUAGCUC AUGGCUGC | 3634 |
| 4387 | GAGAGACA CUGAUGA GCCGUUAGGC GAA AGCAGGUC | 10765 | GACCUGCUC UGUCUCUC | 3635 |
| 4391 | AUAAGAGA CUGAUGA GCCGUUAGGC GAA ACAGAGCA | 10766 | UGCUCUGUC UCUCUUAU | 3636 |
| 4393 | CCAUAAGA CUGAUGA GCCGUUAGGC GAA AGACAGAG | 10767 | CUCUGUCUC UCUUAUGG | 3637 |
| 4395 | CUCCAUAA CUGAUGA GCCGUUAGGC GAA AGAGACAG | 10768 | CUGUCUCUC UUAUGGAG | 3638 |
| 4397 | UCCUCCAU CUGAUGA GCCGUUAGGC GAA AGAGAGAC | 10769 | GUCUCUCUU AUGGAGGA | 3639 |
| 4398 | UUCCUCCA CUGAUGA GCCGUUAGGC GAA AAGAGAGA | 10770 | UCUCUCUUA UGGAGGAA | 3640 |
| 4445 | GCAUCCCA CUGAUGA GCCGUUAGGC GAA AGCCUUUU | 10771 | AAAAGGCUU UGGGAUGC | 3641 |
| 4446 | CGCAUCCC CUGAUGA GCCGUUAGGC GAA AAGCCUUU | 10772 | AAAGGCUUU GGGAUGCG | 3642 |
| 4456 | ACAGGACG CUGAUGA GCCGUUAGGC GAA ACGCAUCC | 10773 | GGAUGCGUC CGUCCUGU | 3643 |
| 4460 | CUCCACAG CUGAUGA GCCGUUAGGC GAA ACGGACGC | 10774 | GCGUCCGUC CUGUGGAG | 3644 |
| 4487 | GCAUAGCG CUGAUGA GCCGUUAGGC GAA AGCCCCCU | 10775 | AGGGGGCUC CGCUAUGC | 3645 |
| 4492 | AAGUGGCA CUGAUGA GCCGUUAGGC GAA AGCGGAGC | 10776 | GCUCCGCUA UGCCACUU | 3646 |
| 4500 | AGUCACUG CUGAUGA GCCGUUAGGC GAA AGUGGCAU | 10777 | AUGCCACUU CAGUGACU | 3647 |
| 4501 | AAGUCACU CUGAUGA GCCGUUAGGC GAA AAGUGGCA | 10778 | UGCCACUUC AGUGACUU | 3648 |
| 4509 | GGAGUGAG CUGAUGA GCCGUUAGGC GAA AGUCACUG | 10779 | CAGUGACUU CUCACUCC | 3649 |
| 4510 | AGGAGUGA CUGAUGA GCCGUUAGGC GAA AAGUCACU | 10780 | AGUGACUUC UCACUCCU | 3650 |
| 4512 | CCAGGAGU CUGAUGA GCCGUUAGGC GAA AGAAGUCA | 10781 | UGACUUCUC ACUCCUGG | 3651 |
| 4516 | GAGGCCAG CUGAUGA GCCGUUAGGC GAA AGUGAGAA | 10782 | UUCUCACUC CUGGCCUC | 3652 |
| 4524 | AAACAGCG CUGAUGA GCCGUUAGGC GAA AGGCCAGG | 10783 | CCUGGCCUC CGCUGUUU | 3653 |
| 4531 | GGGCCCGA CUGAUGA GCCGUUAGGC GAA ACAGCGGA | 10784 | UCCGCUGUU UCGGGCCC | 3654 |
| 4532 | GGGGCCCG CUGAUGA GCCGUUAGGC GAA AACAGCGG | 10785 | CCGCUGUUU CGGGCCCC | 3655 |
| 4533 | GGGGGCCC CUGAUGA GCCGUUAGGC GAA AAACAGCG | 10786 | CGCUGUUUC GGGCCCCC | 3656 |
| 4543 | CCUCUUGG CUGAUGA GCCGUUAGGC GAA AGGGGGCC | 10787 | GGCCCCCUU CCAAGAGG | 3657 |
| 4544 | ACCUCUUG CUGAUGA GCCGUUAGGC GAA AAGGGGGC | 10788 | GCCCCCUUC CAAGAGGU | 3658 |
| 4553 | UGCUCUGA CUGAUGA GCCGUUAGGC GAA ACCUCUUG | 10789 | CAAGAGGUA UCAGAGCA | 3659 |
| 4555 | UCUGCUCU CUGAUGA GCCGUUAGGC GAA AUACCUCU | 10790 | AGAGGUAUC AGAGCAGA | 3660 |
| 4577 | GUCUAGGA CUGAUGA GCCGUUAGGC GAA ACGUCCCU | 10791 | AGGGACGUU UCCUAGAC | 3661 |
| 4578 | GGUCUAGG CUGAUGA GCCGUUAGGC GAA AACGUCCC | 10792 | GGGACGUUU CCUAGACC | 3662 |
| 4579 | UGGUCUAG CUGAUGA GCCGUUAGGC GAA AAACGUCC | 10793 | GGACGUUUC CUAGACCA | 3663 |
| 4582 | CCCUGGUC CUGAUGA GCCGUUAGGC GAA AGGAAACG | 10794 | CGUUUCCUA GACCAGGG | 3664 |
| 4598 | UUCCCGAG CUGAUGA GCCGUUAGGC GAA ACAUGUGC | 10795 | GCACAUGUU CUCGGGAA | 3665 |
| 4599 | GUUCCCGA CUGAUGA GCCGUUAGGC GAA AACAUGUG | 10796 | CACAUGUUC UCGGGAAC | 3666 |

184

| | | | | |
|---|---|---|---|---|
| 4601 | UGGUUCCC CUGAUGA GCCGUUAGGC GAA AGAACAUG | 10797 | CAUGUUCUC GGGAACCA | 3667 |
| 4614 | UUAAGAUU CUGAUGA GCCGUUAGGC GAA ACUGUGGU | 10798 | ACCACAGUU AAUCUUAA | 3668 |
| 4615 | UUUAAGAU CUGAUGA GCCGUUAGGC GAA AACUGUGG | 10799 | CCACAGUUA AUCUUAAA | 3669 |
| 4618 | AGAUUUAA CUGAUGA GCCGUUAGGC GAA AUUAACUG | 10800 | CAGUUAAUC UUAAAUCU | 3670 |
| 4620 | AAAGAUUU CUGAUGA GCCGUUAGGC GAA AGAUUAAC | 10801 | GUUAAUCUU AAAUCUUU | 3671 |
| 4621 | AAAAGAUU CUGAUGA GCCGUUAGGC GAA AAGAUUAA | 10802 | UUAAUCUUA AAUCUUUU | 3672 |
| 4625 | CGGGAAAA CUGAUGA GCCGUUAGGC GAA AUUUAAGA | 10803 | UCUUAAAUC UUUUCCCG | 3673 |
| 4627 | CCCGGGAA CUGAUGA GCCGUUAGGC GAA AGAUUUAA | 10804 | UUAAAUCUU UUCCCGGG | 3674 |
| 4628 | UCCCGGGA CUGAUGA GCCGUUAGGC GAA AAGAUUUA | 10805 | UAAAUCUUU UCCCGGGA | 3675 |
| 4629 | CUCCCGGG CUGAUGA GCCGUUAGGC GAA AAAGAUUU | 10806 | AAAUCUUUU CCCGGGAG | 3676 |
| 4630 | ACUCCCGG CUGAUGA GCCGUUAGGC GAA AAAAGAUU | 10807 | AAUCUUUUC CCGGGAGU | 3677 |
| 4639 | CAACAGAA CUGAUGA GCCGUUAGGC GAA ACUCCCGG | 10808 | CCGGGAGUC UUCUGUUG | 3678 |
| 4641 | GACAACAG CUGAUGA GCCGUUAGGC GAA AGACUCCC | 10809 | GGGAGUCUU CUGUUGUC | 3679 |
| 4642 | AGACAACA CUGAUGA GCCGUUAGGC GAA AAGACUCC | 10810 | GGAGUCUUC UGUUGUCU | 3680 |
| 4646 | AAACAGAC CUGAUGA GCCGUUAGGC GAA ACAGAAGA | 10811 | UCUUCUGUU GUCUGUUU | 3681 |
| 4649 | GGUAAACA CUGAUGA GCCGUUAGGC GAA ACAACAGA | 10812 | UCUGUUGUC UGUUUACC | 3682 |
| 4653 | GGAUGGUA CUGAUGA GCCGUUAGGC GAA ACAGACAA | 10813 | UUGUCUGUU UACCAUCC | 3683 |
| 4654 | UGGAUGGU CUGAUGA GCCGUUAGGC GAA AACAGACA | 10814 | UGUCUGUUU ACCAUCCA | 3684 |
| 4655 | UUGGAUGG CUGAUGA GCCGUUAGGC GAA AAACAGAC | 10815 | GUCUGUUUA CCAUCCAA | 3685 |
| 4660 | AUGCUUUG CUGAUGA GCCGUUAGGC GAA AUGGUAAA | 10816 | UUUACCAUC CAAAGCAU | 3686 |
| 4669 | AUGUUAAA CUGAUGA GCCGUUAGGC GAA AUGCUUUG | 10817 | CAAAGCAUA UUUAACAU | 3687 |
| 4671 | ACAUGUUA CUGAUGA GCCGUUAGGC GAA AUAUGCUU | 10818 | AAGCAUAUU UAACAUGU | 3688 |
| 4672 | CACAUGUU CUGAUGA GCCGUUAGGC GAA AAUAUGCU | 10819 | AGCAUAUUU AACAUGUG | 3689 |
| 4673 | ACACAUGU CUGAUGA GCCGUUAGGC GAA AAAUAUGC | 10820 | GCAUAUUUA ACAUGUGU | 3690 |
| 4682 | CCCCCACU CUGAUGA GCCGUUAGGC GAA ACACAUGU | 10821 | ACAUGUGUC AGUGGGGG | 3691 |
| 4698 | CAGAAGCC CUGAUGA GCCGUUAGGC GAA AGCGCCAC | 10822 | GUGGCGCUU GGCUUCUG | 3692 |
| 4703 | GGCCUCAG CUGAUGA GCCGUUAGGC GAA AGCCAAGC | 10823 | GCUUGGCUU CUGAGGCC | 3693 |
| 4704 | UGGCCUCA CUGAUGA GCCGUUAGGC GAA AAGCCAAG | 10824 | CUUGGCUUC UGAGGCCA | 3694 |
| 4720 | GAACUGAU CUGAUGA GCCGUUAGGC GAA AUGGCUCU | 10825 | AGAGCCAUC AUCAGUUC | 3695 |
| 4723 | GAGGAACU CUGAUGA GCCGUUAGGC GAA AUGAUGGC | 10826 | GCCAUCAUC AGUUCCUC | 3696 |
| 4727 | ACUAGAGG CUGAUGA GCCGUUAGGC GAA ACUGAUGA | 10827 | UCAUCAGUU CCUCUAGU | 3697 |
| 4728 | CACUAGAG CUGAUGA GCCGUUAGGC GAA AACUGAUG | 10828 | CAUCAGUUC CUCUAGUG | 3698 |
| 4731 | UCUCACUA CUGAUGA GCCGUUAGGC GAA AGGAACUG | 10829 | CAGUUCCUC UAGUGAGA | 3699 |
| 4733 | CAUCUCAC CUGAUGA GCCGUUAGGC GAA AGAGGAAC | 10830 | GUUCCUCUA GUGAGAUG | 3700 |
| 4745 | AUGACCUC CUGAUGA GCCGUUAGGC GAA AUGCAUCU | 10831 | AGAUGCAUU GAGGUCAU | 3701 |

| | | | | |
|---|---|---|---|---|
| 4751 | UUGGGUAU CUGAUGA GCCGUUAGGC GAA ACCUCAAU | 10832 | AUUGAGGUC AUACCCAA | 3702 |
| 4754 | AGCUUGGG CUGAUGA GCCGUUAGGC GAA AUGACCUC | 10833 | GAGGUCAUA CCCAAGCU | 3703 |
| 4763 | AGGCCUGC CUGAUGA GCCGUUAGGC GAA AGCUUGGG | 10834 | CCCAAGCUU GCAGGCCU | 3704 |
| 4777 | AGUAUGCG CUGAUGA GCCGUUAGGC GAA AGGUCAGG | 10835 | CCUGACCUU CGCAUACU | 3705 |
| 4778 | CAGUAUGC CUGAUGA GCCGUUAGGC GAA AAGGUCAG | 10836 | CUGACCUUC GCAUACUG | 3706 |
| 4783 | GUGAGCAG CUGAUGA GCCGUUAGGC GAA AUGCGAAG | 10837 | CUUCGCAUA CUGCUCAC | 3707 |
| 4789 | CUCCCCGU CUGAUGA GCCGUUAGGC GAA AGCAGUAU | 10838 | AUACUGCUC ACGGGGAG | 3708 |
| 4799 | GACCACUU CUGAUGA GCCGUUAGGC GAA ACUCCCCG | 10839 | CGGGGAGUU AAGUGGUC | 3709 |
| 4800 | GGACCACU CUGAUGA GCCGUUAGGC GAA AACUCCCC | 10840 | GGGGAGUUA AGUGGUCC | 3710 |
| 4807 | CCAAACUG CUGAUGA GCCGUUAGGC GAA ACCACUUA | 10841 | UAAGUGGUC CAGUUUGG | 3711 |
| 4812 | CUAGGCCA CUGAUGA GCCGUUAGGC GAA ACUGGACC | 10842 | GGUCCAGUU UGGCCUAG | 3712 |
| 4813 | ACUAGGCC CUGAUGA GCCGUUAGGC GAA AACUGGAC | 10843 | GUCCAGUUU GGCCUAGU | 3713 |
| 4819 | AACCUUAC CUGAUGA GCCGUUAGGC GAA AGGCCAAA | 10844 | UUUGGCCUA GUAAGGUU | 3714 |
| 4822 | GGCAACCU CUGAUGA GCCGUUAGGC GAA ACUAGGCC | 10845 | GGCCUAGUA AGGUUGCC | 3715 |
| 4827 | CAGUAGGC CUGAUGA GCCGUUAGGC GAA ACCUUACU | 10846 | AGUAAGGUU GCCUACUG | 3716 |
| 4832 | CCCAUCAG CUGAUGA GCCGUUAGGC GAA AGGCAACC | 10847 | GGUUGCCUA CUGAUGGG | 3717 |
| 4843 | UGGCUUUU CUGAUGA GCCGUUAGGC GAA AGCCCAUC | 10848 | GAUGGGCUC AAAAGCCA | 3718 |
| 4855 | CUGUUUAA CUGAUGA GCCGUUAGGC GAA AUGUGGCU | 10849 | AGCCACAUU UUAAACAG | 3719 |
| 4856 | CCUGUUUA CUGAUGA GCCGUUAGGC GAA AAUGUGGC | 10850 | GCCACAUUU UAAACAGG | 3720 |
| 4857 | ACCUGUUU CUGAUGA GCCGUUAGGC GAA AAAUGUGG | 10851 | CCACAUUUU AAACAGGU | 3721 |
| 4858 | AACCUGUU CUGAUGA GCCGUUAGGC GAA AAAAUGUG | 10852 | CACAUUUUA AACAGGUU | 3722 |
| 4866 | UGAGAUAA CUGAUGA GCCGUUAGGC GAA ACCUGUUU | 10853 | AAACAGGUU UUAUCUCA | 3723 |
| 4867 | UUGAGAUA CUGAUGA GCCGUUAGGC GAA AACCUGUU | 10854 | AACAGGUUU UAUCUCAA | 3724 |
| 4868 | CUUGAGAU CUGAUGA GCCGUUAGGC GAA AAACCUGU | 10855 | ACAGGUUUU AUCUCAAG | 3725 |
| 4869 | ACUUGAGA CUGAUGA GCCGUUAGGC GAA AAAACCUG | 10856 | CAGGUUUUA UCUCAAGU | 3726 |
| 4871 | AUACUUGA CUGAUGA GCCGUUAGGC GAA AUAAAACC | 10857 | GGUUUUAUC UCAAGUAU | 3727 |
| 4873 | UAAUACUU CUGAUGA GCCGUUAGGC GAA AGAUAAAA | 10858 | UUUUAUCUC AAGUAUUA | 3728 |
| 4878 | UAUAUUAA CUGAUGA GCCGUUAGGC GAA ACUUGAGA | 10859 | UCUCAAGUA UUAAUAUA | 3729 |
| 4880 | UAUAUAUU CUGAUGA GCCGUUAGGC GAA AUACUUGA | 10860 | UCAAGUAUU AAUAUAUA | 3730 |
| 4881 | CUAUAUAU CUGAUGA GCCGUUAGGC GAA AAUACUUG | 10861 | CAAGUAUUA AUAUAUAG | 3731 |
| 4884 | UGUCUAUA CUGAUGA GCCGUUAGGC GAA AUUAAUAC | 10862 | GUAUUAAUA UAUAGACA | 3732 |
| 4886 | CUUGUCUA CUGAUGA GCCGUUAGGC GAA AUAUUAAU | 10863 | AUUAAUAUA UAGACAAG | 3733 |
| 4888 | GUCUUGUC CUGAUGA GCCGUUAGGC GAA AUAUAUUA | 10864 | UAAUAUAUA GACAAGAC | 3734 |
| 4900 | UAAUGCAU CUGAUGA GCCGUUAGGC GAA AGUGUCUU | 10865 | AAGACACUU AUGCAUUA | 3735 |
| 4901 | AUAAUGCA CUGAUGA GCCGUUAGGC GAA AAGUGUCU | 10866 | AGACACUUA UGCAUUAU | 3736 |

| | | | | |
|---|---|---|---|---|
| 4907 | AACAGGAU CUGAUGA GCCGUUAGGC GAA AUGCAUAA | 10867 | UUAUGCAUU AUCCUGUU | 3737 |
| 4908 | AAACAGGA CUGAUGA GCCGUUAGGC GAA AAUGCAUA | 10868 | UAUGCAUUA UCCUGUUU | 3738 |
| 4910 | UAAAACAG CUGAUGA GCCGUUAGGC GAA AUAAUGCA | 10869 | UGCAUUAUC CUGUUUUA | 3739 |
| 4915 | AUAUAUAA CUGAUGA GCCGUUAGGC GAA ACAGGAUA | 10870 | UAUCCUGUU UUAUAUAU | 3740 |
| 4916 | GAUAUAUA CUGAUGA GCCGUUAGGC GAA AACAGGAU | 10871 | AUCCUGUUU UAUAUAUC | 3741 |
| 4917 | GGAUAUAU CUGAUGA GCCGUUAGGC GAA AAACAGGA | 10872 | UCCUGUUUU AUAUAUCC | 3742 |
| 4918 | UGGAUAUA CUGAUGA GCCGUUAGGC GAA AAAACAGG | 10873 | CCUGUUUUA UAUAUCCA | 3743 |
| 4920 | AUUGGAUA CUGAUGA GCCGUUAGGC GAA AUAAAACA | 10874 | UGUUUUAUA UAUCCAAU | 3744 |
| 4922 | UCAUUGGA CUGAUGA GCCGUUAGGC GAA AUAUAAAA | 10875 | UUUUAUAUA UCCAAUGA | 3745 |
| 4924 | AUUCAUUG CUGAUGA GCCGUUAGGC GAA AUAUAUAA | 10876 | UUAUAUAUC CAAUGAAU | 3746 |
| 4933 | CCCAGUUA CUGAUGA GCCGUUAGGC GAA AUUCAUUG | 10877 | CAAUGAAUA UAACUGGG | 3747 |
| 4935 | GCCCCAGU CUGAUGA GCCGUUAGGC GAA AUAUUCAU | 10878 | AUGAAUAUA ACUGGGGC | 3748 |
| 4948 | UGACUCUU CUGAUGA GCCGUUAGGC GAA ACUCGCCC | 10879 | GGGCGAGUU AAGAGUCA | 3749 |
| 4949 | AUGACUCU CUGAUGA GCCGUUAGGC GAA AACUCGCC | 10880 | GGCGAGUUA AGAGUCAU | 3750 |
| 4955 | UAGACCAU CUGAUGA GCCGUUAGGC GAA ACUCUUAA | 10881 | UUAAGAGUC AUGGUCUA | 3751 |
| 4961 | CUUUUCUA CUGAUGA GCCGUUAGGC GAA ACCAUGAC | 10882 | GUCAUGGUC UAGAAAAG | 3752 |
| 4963 | CCCUUUUC CUGAUGA GCCGUUAGGC GAA AGACCAUG | 10883 | CAUGGUCUA GAAAAGGG | 3753 |
| 4974 | UACAGAGA CUGAUGA GCCGUUAGGC GAA ACCCCUUU | 10884 | AAAGGGGUU UCUCUGUA | 3754 |
| 4975 | GUACAGAG CUGAUGA GCCGUUAGGC GAA AACCCCUU | 10885 | AAGGGGUUU CUCUGUAC | 3755 |
| 4976 | GGUACAGA CUGAUGA GCCGUUAGGC GAA AAACCCCU | 10886 | AGGGGUUUC UCUGUACC | 3756 |
| 4978 | UGGGUACA CUGAUGA GCCGUUAGGC GAA AGAAACCC | 10887 | GGGUUUCUC UGUACCCA | 3757 |
| 4982 | GAUUUGGG CUGAUGA GCCGUUAGGC GAA ACAGAGAA | 10888 | UUCUCUGUA CCCAAAUC | 3758 |
| 4990 | ACCAGCCC CUGAUGA GCCGUUAGGC GAA AUUUGGGU | 10889 | ACCCAAAUC GGGCUGGU | 3759 |
| 4999 | CUUGGUCC CUGAUGA GCCGUUAGGC GAA ACCAGCCC | 10890 | GGGCUGGUU GGACCAAG | 3760 |
| 5029 | GCUGGGAC CUGAUGA GCCGUUAGGC GAA ACCACUCU | 10891 | AGAGUGGUU GUCCCAGC | 3761 |
| 5032 | AUAGCUGG CUGAUGA GCCGUUAGGC GAA ACAACCAC | 10892 | GUGGUUGUC CCAGCUAU | 3762 |
| 5039 | AGUAACUA CUGAUGA GCCGUUAGGC GAA AGCUGGGA | 10893 | UCCCAGCUA UAGUUACU | 3763 |
| 5041 | UUAGUAAC CUGAUGA GCCGUUAGGC GAA AUAGCUGG | 10894 | CCAGCUAUA GUUACUAA | 3764 |
| 5044 | AGUUUAGU CUGAUGA GCCGUUAGGC GAA ACUAUAGC | 10895 | GCUAUAGUU ACUAAACU | 3765 |
| 5045 | UAGUUUAG CUGAUGA GCCGUUAGGC GAA AACUAUAG | 10896 | CUAUAGUUA CUAAACUA | 3766 |
| 5048 | GAGUAGUU CUGAUGA GCCGUUAGGC GAA AGUAACUA | 10897 | UAGUUACUA AACUACUC | 3767 |
| 5053 | UGGGUGAG CUGAUGA GCCGUUAGGC GAA AGUUUAGU | 10898 | ACUAAACUA CUCACCCA | 3768 |
| 5056 | CUUUGGGU CUGAUGA GCCGUUAGGC GAA AGUAGUUU | 10899 | AAACUACUC ACCCAAAG | 3769 |
| 5066 | GAGGUCCC CUGAUGA GCCGUUAGGC GAA ACUUUGGG | 10900 | CCCAAAGUU GGGACCUC | 3770 |
| 5074 | AAGCCAGU CUGAUGA GCCGUUAGGC GAA AGGUCCCA | 10901 | UGGGACCUC ACUGGCUU | 3771 |

187

| | | | | |
|---|---|---|---|---|
| 5082 | GUAAAGAG CUGAUGA GCCGUUAGGC GAA AGCCAGUG | 10902 | CACUGGCUU CUCUUUAC | 3772 |
| 5083 | AGUAAAGA CUGAUGA GCCGUUAGGC GAA AAGCCAGU | 10903 | ACUGGCUUC UCUUUACU | 3773 |
| 5085 | GAAGUAAA CUGAUGA GCCGUUAGGC GAA AGAAGCCA | 10904 | UGGCUUCUC UUUACUUC | 3774 |
| 5087 | AUGAAGUA CUGAUGA GCCGUUAGGC GAA AGAGAAGC | 10905 | GCUUCUCUU UACUUCAU | 3775 |
| 5088 | GAUGAAGU CUGAUGA GCCGUUAGGC GAA AAGAGAAG | 10906 | CUUCUCUUU ACUUCAUC | 3776 |
| 5089 | UGAUGAAG CUGAUGA GCCGUUAGGC GAA AAAGAGAA | 10907 | UUCUCUUUA CUUCAUCA | 3777 |
| 5092 | CCAUGAUG CUGAUGA GCCGUUAGGC GAA AGUAAAGA | 10908 | UCUUUACUU CAUCAUGG | 3778 |
| 5093 | UCCAUGAU CUGAUGA GCCGUUAGGC GAA AAGUAAAG | 10909 | CUUUACUUC AUCAUGGA | 3779 |
| 5096 | AAAUCCAU CUGAUGA GCCGUUAGGC GAA AUGAAGUA | 10910 | UACUUCAUC AUGGAUUU | 3780 |
| 5103 | GAUGGUGA CUGAUGA GCCGUUAGGC GAA AUCCAUGA | 10911 | UCAUGGAUU UCACCAUC | 3781 |
| 5104 | GGAUGGUG CUGAUGA GCCGUUAGGC GAA AAUCCAUG | 10912 | CAUGGAUUU CACCAUCC | 3782 |
| 5105 | GGGAUGGU CUGAUGA GCCGUUAGGC GAA AAAUCCAU | 10913 | AUGGAUUUC ACCAUCCC | 3783 |
| 5111 | UGCCUUGG CUGAUGA GCCGUUAGGC GAA AUGGUGAA | 10914 | UUCACCAUC CCAAGGCA | 3784 |
| 5122 | UCCUCUCA CUGAUGA GCCGUUAGGC GAA ACUGCCUU | 10915 | AAGGCAGUC UGAGAGGA | 3785 |
| 5134 | AUACUCUU CUGAUGA GCCGUUAGGC GAA AGCUCCUC | 10916 | GAGGAGCUA AAGAGUAU | 3786 |
| 5141 | UGGGCUGA CUGAUGA GCCGUUAGGC GAA ACUCUUUA | 10917 | UAAAGAGUA UCAGCCCA | 3787 |
| 5143 | UAUGGGCU CUGAUGA GCCGUUAGGC GAA AUACUCUU | 10918 | AAGAGUAUC AGCCCAUA | 3788 |
| 5151 | UUAAUAAA CUGAUGA GCCGUUAGGC GAA AUGGGCUG | 10919 | CAGCCCAUA UUUAUUAA | 3789 |
| 5153 | GCUUAAUA CUGAUGA GCCGUUAGGC GAA AUAUGGGC | 10920 | GCCCAUAUU UAUUAAGC | 3790 |
| 5154 | UGCUUAAU CUGAUGA GCCGUUAGGC GAA AAUAUGGG | 10921 | CCCAUAUUU AUUAAGCA | 3791 |
| 5155 | GUGCUUAA CUGAUGA GCCGUUAGGC GAA AAAUAUGG | 10922 | CCAUAUUUA UUAAGCAC | 3792 |
| 5157 | AAGUGCUU CUGAUGA GCCGUUAGGC GAA AUAAAUAU | 10923 | AUAUUUAUU AAGCACUU | 3793 |
| 5158 | AAAGUGCU CUGAUGA GCCGUUAGGC GAA AAUAAAUA | 10924 | UAUUUAUUA AGCACUUU | 3794 |
| 5165 | GGAGCAUA CUGAUGA GCCGUUAGGC GAA AGUGCUUA | 10925 | UAAGCACUU UAUGCUCC | 3795 |
| 5166 | AGGAGCAU CUGAUGA GCCGUUAGGC GAA AAGUGCUU | 10926 | AAGCACUUU AUGCUCCU | 3796 |
| 5167 | AAGGAGCA CUGAUGA GCCGUUAGGC GAA AAAGUGCU | 10927 | AGCACUUUA UGCUCCUU | 3797 |
| 5172 | GUGCCAAG CUGAUGA GCCGUUAGGC GAA AGCAUAAA | 10928 | UUUAUGCUC CUUGGCAC | 3798 |
| 5175 | GCUGUGCC CUGAUGA GCCGUUAGGC GAA AGGAGCAU | 10929 | AUGCUCCUU GGCACAGC | 3799 |
| 5195 | GCAUAAAU CUGAUGA GCCGUUAGGC GAA ACACAUCA | 10930 | UGAUGUGUA AUUUAUGC | 3800 |
| 5198 | CUUGCAUA CUGAUGA GCCGUUAGGC GAA AUUACACA | 10931 | UGUGUAAUU UAUGCAAG | 3801 |
| 5199 | GCUUGCAU CUGAUGA GCCGUUAGGC GAA AAUUACAC | 10932 | GUGUAAUUU AUGCAAGC | 3802 |
| 5200 | AGCUUGCA CUGAUGA GCCGUUAGGC GAA AAAUUACA | 10933 | UGUAAUUUA UGCAAGCU | 3803 |
| 5209 | UGGAGAGG CUGAUGA GCCGUUAGGC GAA AGCUUGCA | 10934 | UGCAAGCUC CCUCUCCA | 3804 |
| 5213 | UAGCUGGA CUGAUGA GCCGUUAGGC GAA AGGGAGCU | 10935 | AGCUCCCUC UCCAGCUA | 3805 |
| 5215 | CCUAGCUG CUGAUGA GCCGUUAGGC GAA AGAGGGAG | 10936 | CUCCCUCUC CAGCUAGG | 3806 |

| | | | | |
|---|---|---|---|---|
| 5221 | CUGAGUCC CUGAUGA GCCGUUAGGC GAA AGCUGGAG | 10937 | CUCCAGCUA GGACUCAG | 3807 |
| 5227 | AAUAUCCU CUGAUGA GCCGUUAGGC GAA AGUCCUAG | 10938 | CUAGGACUC AGGAUAUU | 3808 |
| 5233 | UUGACUAA CUGAUGA GCCGUUAGGC GAA AUCCUGAG | 10939 | CUCAGGAUA UUAGUCAA | 3809 |
| 5235 | CAUUGACU CUGAUGA GCCGUUAGGC GAA AUAUCCUG | 10940 | CAGGAUAUU AGUCAAUG | 3810 |
| 5236 | UCAUUGAC CUGAUGA GCCGUUAGGC GAA AAUAUCCU | 10941 | AGGAUAUUA GUCAAUGA | 3811 |
| 5239 | GGCUCAUU CUGAUGA GCCGUUAGGC GAA ACUAAUAU | 8081 | AUAUUAGUC AAUGAGCC | 3812 |
| 5250 | UUCCUUUU CUGAUGA GCCGUUAGGC GAA AUGGCUCA | 10942 | UGAGCCAUC AAAAGGAA | 3813 |
| 5273 | AAAUAAGA CUGAUGA GCCGUUAGGC GAA AGGUUUUU | 10943 | AAAAACCUA UCUUAUUU | 3814 |
| 5275 | GAAAAUAA CUGAUGA GCCGUUAGGC GAA AUAGGUUU | 10944 | AAACCUAUC UUAUUUUC | 3815 |
| 5277 | AUGAAAAU CUGAUGA GCCGUUAGGC GAA AGAUAGGU | 10945 | ACCUAUCUU AUUUUCAU | 3816 |
| 5278 | GAUGAAAA CUGAUGA GCCGUUAGGC GAA AAGAUAGG | 10946 | CCUAUCUUA UUUUCAUC | 3817 |
| 5280 | CAGAUGAA CUGAUGA GCCGUUAGGC GAA AUAAGAUA | 10947 | UAUCUUAUU UUCAUCUG | 3818 |
| 5281 | ACAGAUGA CUGAUGA GCCGUUAGGC GAA AAUAAGAU | 10948 | AUCUUAUUU UCAUCUGU | 3819 |
| 5282 | AACAGAUG CUGAUGA GCCGUUAGGC GAA AAAUAAGA | 10949 | UCUUAUUUU CAUCUGUU | 3820 |
| 5283 | AAACAGAU CUGAUGA GCCGUUAGGC GAA AAAAUAAG | 10950 | CUUAUUUUC AUCUGUUU | 3821 |
| 5286 | AUGAAACA CUGAUGA GCCGUUAGGC GAA AUGAAAAU | 10951 | AUUUUCAUC UGUUUCAU | 3822 |
| 5290 | AGGUAUGA CUGAUGA GCCGUUAGGC GAA ACAGAUGA | 10952 | UCAUCUGUU UCAUACCU | 3823 |
| 5291 | AAGGUAUG CUGAUGA GCCGUUAGGC GAA AACAGAUG | 10953 | CAUCUGUUU CAUACCUU | 3824 |
| 5292 | CAAGGUAU CUGAUGA GCCGUUAGGC GAA AAACAGAU | 10954 | AUCUGUUUC AUACCUUG | 3825 |
| 5295 | AGACAAGG CUGAUGA GCCGUUAGGC GAA AUGAAACA | 10955 | UGUUUCAUA CCUUGUCU | 3826 |
| 5299 | CCCCAGAC CUGAUGA GCCGUUAGGC GAA AGGUAUGA | 10956 | UCAUACCUU GUCUGGGG | 3827 |
| 5302 | AGACCCCA CUGAUGA GCCGUUAGGC GAA ACAAGGUA | 10957 | UACCUUGUC UGGGGUCU | 3828 |
| 5309 | CGUCAUUA CUGAUGA GCCGUUAGGC GAA ACCCCAGA | 10958 | UCUGGGGUC UAAUGACG | 3829 |
| 5311 | AUCGUCAU CUGAUGA GCCGUUAGGC GAA AGACCCCA | 10959 | UGGGGUCUA AUGACGAU | 3830 |
| 5331 | CCCAUGUC CUGAUGA GCCGUUAGGC GAA ACCCUGUU | 10960 | AACAGGGUA GACAUGGG | 3831 |
| 5350 | CCCUUUUC CUGAUGA GCCGUUAGGC GAA ACCCUGUC | 10961 | GACAGGGUA GAAAAGGG | 3832 |
| 5367 | ACCCCAAA CUGAUGA GCCGUUAGGC GAA AGCGGGCA | 10962 | UGCCCGCUC UUUGGGGU | 3833 |
| 5369 | AGACCCCA CUGAUGA GCCGUUAGGC GAA AGAGCGGG | 10963 | CCCGCUCUU UGGGGUCU | 3834 |
| 5370 | UAGACCCC CUGAUGA GCCGUUAGGC GAA AAGAGCGG | 10964 | CCGCUCUUU GGGGUCUA | 3835 |
| 5376 | CAUCUCUA CUGAUGA GCCGUUAGGC GAA ACCCCAAA | 10965 | UUUGGGGUC UAGAGAUG | 3836 |
| 5378 | CUCAUCUC CUGAUGA GCCGUUAGGC GAA AGACCCCA | 10966 | UGGGGUCUA GAGAUGAG | 3837 |
| 5395 | AUUUUAGA CUGAUGA GCCGUUAGGC GAA ACCCAGGG | 10967 | CCCUGGGUC UCUAAAAU | 3838 |
| 5397 | CCAUUUUA CUGAUGA GCCGUUAGGC GAA AGACCCAG | 10968 | CUGGGUCUC UAAAAUGG | 3839 |
| 5399 | AGCCAUUU CUGAUGA GCCGUUAGGC GAA AGAGACCC | 10969 | GGGUCUCUA AAAUGGCU | 3840 |
| 5408 | UUCUAAGA CUGAUGA GCCGUUAGGC GAA AGCCAUUU | 10970 | AAAUGGCUC UCUUAGAA | 3841 |

189

| | | | | |
|---|---|---|---|---|
| 5410 | ACUUCUAA CUGAUGA GCCGUUAGGC GAA AGAGCCAU | 10971 | AUGGCUCUC UUAGAAGU | 3842 |
| 5412 | CAACUUCU CUGAUGA GCCGUUAGGC GAA AGAGAGCC | 10972 | GGCUCUCUU AGAAGUUG | 3843 |
| 5413 | ACAACUUC CUGAUGA GCCGUUAGGC GAA AAGAGAGC | 10973 | GCUCUCUUA GAAGUUGU | 3844 |
| 5419 | GCACAUAC CUGAUGA GCCGUUAGGC GAA ACUUCUAA | 10974 | UUAGAAGUU GUAUGUGC | 3845 |
| 5422 | UUUGCACA CUGAUGA GCCGUUAGGC GAA ACAACUUC | 10975 | GAAGUUGUA UGUGCAAA | 3846 |
| 5432 | CAGACCAU CUGAUGA GCCGUUAGGC GAA AUUUGCAC | 10976 | GUGCAAAUU AUGGUCUG | 3847 |
| 5433 | ACAGACCA CUGAUGA GCCGUUAGGC GAA AAUUUGCA | 10977 | UGCAAAUUA UGGUCUGU | 3848 |
| 5438 | AGCACACA CUGAUGA GCCGUUAGGC GAA ACCAUAAU | 10978 | AUUAUGGUC UGUGUGCU | 3849 |
| 5447 | CACGACCU CUGAUGA GCCGUUAGGC GAA AGCACACA | 10979 | UGUGUGCUU AGGUCGUG | 3850 |
| 5448 | GCACGACC CUGAUGA GCCGUUAGGC GAA AAGCACAC | 10980 | GUGUGCUUA GGUCGUGC | 3851 |
| 5452 | GUGUGCAC CUGAUGA GCCGUUAGGC GAA ACCUAAGC | 10981 | GCUUAGGUC GUGCACAC | 3852 |
| 5475 | CCAGCUGU CUGAUGA GCCGUUAGGC GAA ACCGGCUC | 10982 | GAGCCGGUC ACAGCUGG | 3853 |
| 5497 | AAAGCAGC CUGAUGA GCCGUUAGGC GAA AUUCAUCG | 10983 | CGAUGAAUA GCUGCUUU | 3854 |
| 5504 | CUCUCCCA CUGAUGA GCCGUUAGGC GAA AGCAGCUA | 10984 | UAGCUGCUU UGGGAGAG | 3855 |
| 5505 | GCUCUCCC CUGAUGA GCCGUUAGGC GAA AAGCAGCU | 10985 | AGCUGCUUU GGGAGAGC | 3856 |
| 5524 | UAAGUGGC CUGAUGA GCCGUUAGGC GAA AGCAUGCU | 10986 | AGCAUGCUA GCCACUUA | 3857 |
| 5531 | AGAGAAUU CUGAUGA GCCGUUAGGC GAA AGUGGCUA | 10987 | UAGCCACUU AAUUCUCU | 3858 |
| 5532 | CAGAGAAU CUGAUGA GCCGUUAGGC GAA AAGUGGCU | 10988 | AGCCACUUA AUUCUCUG | 3859 |
| 5535 | GGUCAGAG CUGAUGA GCCGUUAGGC GAA AUUAAGUG | 10989 | CACUUAAUU CUCUGACC | 3860 |
| 5536 | CGGUCAGA CUGAUGA GCCGUUAGGC GAA AAUUAAGU | 10990 | ACUUAAUUC UCUGACCG | 3861 |
| 5538 | CCCGGUCA CUGAUGA GCCGUUAGGC GAA AGAAUUAA | 10991 | UUAAUUCUC UGACCGGG | 3862 |
| 5554 | GUACCCAU CUGAUGA GCCGUUAGGC GAA AUGCUGGC | 10992 | GCCAGCAUC AUGGGUAC | 3863 |
| 5561 | GGAGCAGG CUGAUGA GCCGUUAGGC GAA ACCCAUGA | 10993 | UCAUGGGUA CCUGCUCC | 3864 |
| 5568 | ACACAGGG CUGAUGA GCCGUUAGGC GAA AGCAGGUA | 10994 | UACCUGCUC CCCUGUGU | 3865 |
| 5577 | GGAUGGGG CUGAUGA GCCGUUAGGC GAA ACACAGGG | 10995 | CCCUGUGUA CCCCAUCC | 3866 |
| 5584 | ACCUUAAG CUGAUGA GCCGUUAGGC GAA AUGGGGUA | 10996 | UACCCCAUC CUUAAGGU | 3867 |
| 5587 | AAAACCUU CUGAUGA GCCGUUAGGC GAA AGGAUGGG | 10997 | CCCAUCCUU AAGGUUUU | 3868 |
| 5588 | GAAAACCU CUGAUGA GCCGUUAGGC GAA AAGGAUGG | 10998 | CCAUCCUUA AGGUUUUC | 3869 |
| 5593 | AGACAGAA CUGAUGA GCCGUUAGGC GAA ACCUUAAG | 10999 | CUUAAGGUU UUCUGUCU | 3870 |
| 5594 | CAGACAGA CUGAUGA GCCGUUAGGC GAA AACCUUAA | 11000 | UUAAGGUUU UCUGUCUG | 3871 |
| 5595 | UCAGACAG CUGAUGA GCCGUUAGGC GAA AAACCUUA | 11001 | UAAGGUUUU CUGUCUGA | 3872 |
| 5596 | AUCAGACA CUGAUGA GCCGUUAGGC GAA AAAACCUU | 11002 | AAGGUUUUC UGUCUGAU | 3873 |
| 5600 | UCUCAUCA CUGAUGA GCCGUUAGGC GAA ACAGAAAA | 11003 | UUUUCUGUC UGAUGAGA | 3874 |
| 5627 | UCAGUGGG CUGAUGA GCCGUUAGGC GAA AUUGCACU | 11004 | AGUGCAAUC CCCACUGA | 3875 |
| 5660 | UGCACCAA CUGAUGA GCCGUUAGGC GAA AGCCACAG | 11005 | CUGUGGCUC UUGGUGCA | 3876 |

| | | | | |
|---|---|---|---|---|
| 5662 | AGUGCACC CUGAUGA GCCGUUAGGC GAA AGAGCCAC | 11006 | GUGGCUCUU GGUGCACU | 3877 |
| 5671 | UGGCUGGU CUGAUGA GCCGUUAGGC GAA AGUGCACC | 11007 | GGUGCACUC ACCAGCCA | 3878 |
| 5685 | UACUUGUC CUGAUGA GCCGUUAGGC GAA AGUCCUGG | 11008 | CCAGGACUA GACAAGUA | 3879 |
| 5693 | CCCUUUCC CUGAUGA GCCGUUAGGC GAA ACUUGUCU | 11009 | AGACAAGUA GGAAAGGG | 3880 |
| 5704 | GUGGCUAG CUGAUGA GCCGUUAGGC GAA AGCCCUUU | 11010 | AAAGGGCUU CUAGCCAC | 3881 |
| 5705 | UGUGGCUA CUGAUGA GCCGUUAGGC GAA AAGCCCUU | 11011 | AAGGGCUUC UAGCCACA | 3882 |
| 5707 | AGUGUGGC CUGAUGA GCCGUUAGGC GAA AGAAGCCC | 11012 | GGGCUUCUA GCCACACU | 3883 |
| 5731 | CCCUACCU CUGAUGA GCCGUUAGGC GAA AUUUUCUU | 11013 | AAGAAAAUC AGGUAGGG | 3884 |
| 5736 | GCCAGCCC CUGAUGA GCCGUUAGGC GAA ACCUGAUU | 11014 | AAUCAGGUA GGGCUGGC | 3885 |
| 5754 | UGGACAAA CUGAUGA GCCGUUAGGC GAA AUGUCUUU | 11015 | AAAGACAUC UUUGUCCA | 3886 |
| 5756 | AAUGGACA CUGAUGA GCCGUUAGGC GAA AGAUGUCU | 11016 | AGACAUCUU UGUCCAUU | 3887 |
| 5757 | GAAUGGAC CUGAUGA GCCGUUAGGC GAA AAGAUGUC | 11017 | GACAUCUUU GUCCAUUC | 3888 |
| 5760 | UGCGAAUG CUGAUGA GCCGUUAGGC GAA ACAAAGAU | 11018 | AUCUUUGUC CAUUCGCA | 3889 |
| 5764 | CUUUUGCG CUGAUGA GCCGUUAGGC GAA AUGGACAA | 11019 | UUGUCCAUU CGCAAAAG | 3890 |
| 5765 | GCUUUUGC CUGAUGA GCCGUUAGGC GAA AAUGGACA | 11020 | UGUCCAUUC GCAAAAGC | 3891 |
| 5775 | GCCGACAA CUGAUGA GCCGUUAGGC GAA AGCUUUUG | 11021 | CAAAAGCUC UUGUCGGC | 3892 |
| 5777 | CAGCCGAC CUGAUGA GCCGUUAGGC GAA AGAGCUUU | 11022 | AAAGCUCUU GUCGGCUG | 3893 |
| 5780 | CUGCAGCC CUGAUGA GCCGUUAGGC GAA ACAAGAGC | 11023 | GCUCUUGUC GGCUGCAG | 3894 |
| 5794 | GCCUGACU CUGAUGA GCCGUUAGGC GAA ACACACUG | 11024 | CAGUGUGUA AGUCAGGC | 3895 |
| 5798 | CAUCGCCU CUGAUGA GCCGUUAGGC GAA ACUUACAC | 11025 | GUGUAAGUC AGGCGAUG | 3896 |
| 5818 | UUCUCUGG CUGAUGA GCCGUUAGGC GAA AGCCUCUG | 11026 | CAGAGGCUA CCAGAGAA | 3897 |
| 5852 | GGAUGAGA CUGAUGA GCCGUUAGGC GAA ACCUCAGG | 11027 | CCUGAGGUU UCUCAUCC | 3898 |
| 5853 | UGGAUGAG CUGAUGA GCCGUUAGGC GAA AACCUCAG | 11028 | CUGAGGUUU CUCAUCCA | 3899 |
| 5854 | CUGGAUGA CUGAUGA GCCGUUAGGC GAA AAACCUCA | 11029 | UGAGGUUUC UCAUCCAG | 3900 |
| 5856 | AUCUGGAU CUGAUGA GCCGUUAGGC GAA AGAAACCU | 11030 | AGGUUUCUC AUCCAGAU | 3901 |
| 5859 | GAUAUCUG CUGAUGA GCCGUUAGGC GAA AUGAGAAA | 11031 | UUUCUCAUC CAGAUAUC | 3902 |
| 5865 | UUGCUGGA CUGAUGA GCCGUUAGGC GAA AUCUGGAU | 11032 | AUCCAGAUA UCCAGCAA | 3903 |
| 5867 | AAUUGCUG CUGAUGA GCCGUUAGGC GAA AUAUCUGG | 11033 | CCAGAUAUC CAGCAAUU | 3904 |
| 5875 | CACCCCCC CUGAUGA GCCGUUAGGC GAA AUUGCUGG | 11034 | CCAGCAAUU GGGGGGUG | 3905 |
| 5896 | GGACCAUC CUGAUGA GCCGUUAGGC GAA AUGGUCUU | 11035 | AAGACCAUA GAUGGUCC | 3906 |
| 5903 | UAAUACAG CUGAUGA GCCGUUAGGC GAA ACCAUCUA | 11036 | UAGAUGGUC CUGUAUUA | 3907 |
| 5908 | CGGAAUAA CUGAUGA GCCGUUAGGC GAA ACAGGACC | 11037 | GGUCCUGUA UUAUUCCG | 3908 |
| 5910 | AUCGGAAU CUGAUGA GCCGUUAGGC GAA AUACAGGA | 11038 | UCCUGUAUU AUUCCGAU | 3909 |
| 5911 | AAUCGGAA CUGAUGA GCCGUUAGGC GAA AAUACAGG | 11039 | CCUGUAUUA UUCCGAUU | 3910 |
| 5913 | AAAAUCGG CUGAUGA GCCGUUAGGC GAA AUAAUACA | 11040 | UGUAUUAUU CCGAUUUU | 3911 |

191

| | | | | |
|---|---|---|---|---|
| 5914 | UAAAAUCG CUGAUGA GCCGUUAGGC GAA AAUAAUAC | 11041 | GUAUUAUUC CGAUUUUA | 3912 |
| 5919 | AUUAUUAA CUGAUGA GCCGUUAGGC GAA AUCGGAAU | 11042 | AUUCCGAUU UUAAUAAU | 3913 |
| 5920 | GAUUAUUA CUGAUGA GCCGUUAGGC GAA AAUCGGAA | 11043 | UUCCGAUUU UAAUAAUC | 3914 |
| 5921 | AGAUUAUU CUGAUGA GCCGUUAGGC GAA AAAUCGGA | 11044 | UCCGAUUUU AAUAAUCU | 3915 |
| 5922 | UAGAUUAU CUGAUGA GCCGUUAGGC GAA AAAAUCGG | 11045 | CCGAUUUUA AUAAUCUA | 3916 |
| 5925 | AAUUAGAU CUGAUGA GCCGUUAGGC GAA AUUAAAAU | 11046 | AUUUUAAUA AUCUAAUU | 3917 |
| 5928 | ACGAAUUA CUGAUGA GCCGUUAGGC GAA AUUAUUAA | 11047 | UUAAUAAUC UAAUUCGU | 3918 |
| 5930 | UCACGAAU CUGAUGA GCCGUUAGGC GAA AGAUUAUU | 11048 | AAUAAUCUA AUUCGUGA | 3919 |
| 5933 | UGAUCACG CUGAUGA GCCGUUAGGC GAA AUUAGAUU | 11049 | AAUCUAAUU CGUGAUCA | 3920 |
| 5934 | AUGAUCAC CUGAUGA GCCGUUAGGC GAA AAUUAGAU | 11050 | AUCUAAUUC GUGAUCAU | 3921 |
| 5940 | CUCUUAAU CUGAUGA GCCGUUAGGC GAA AUCACGAA | 11051 | UUCGUGAUC AUUAAGAG | 3922 |
| 5943 | AGUCUCUU CUGAUGA GCCGUUAGGC GAA AUGAUCAC | 11052 | GUGAUCAUU AAGAGACU | 3923 |
| 5944 | AAGUCUCU CUGAUGA GCCGUUAGGC GAA AAUGAUCA | 11053 | UGAUCAUUA AGAGACUU | 3924 |
| 5952 | AUUUACUA CUGAUGA GCCGUUAGGC GAA AGUCUCUU | 11054 | AAGAGACUU UAGUAAAU | 3925 |
| 5953 | CAUUUACU CUGAUGA GCCGUUAGGC GAA AAGUCUCU | 11055 | AGAGACUUU AGUAAAUG | 3926 |
| 5954 | ACAUUUAC CUGAUGA GCCGUUAGGC GAA AAAGUCUC | 11056 | GAGACUUUA GUAAAUGU | 3927 |
| 5957 | GGGACAUU CUGAUGA GCCGUUAGGC GAA ACUAAAGU | 11057 | ACUUUAGUA AAUGUCCC | 3928 |
| 5963 | GGAAAAGG CUGAUGA GCCGUUAGGC GAA ACAUUUAC | 11058 | GUAAAUGUC CCUUUUCC | 3929 |
| 5967 | UGUGGGAA CUGAUGA GCCGUUAGGC GAA AGGGACAU | 11059 | AUGUCCCUU UUCCCACA | 3930 |
| 5968 | UUGUGGGA CUGAUGA GCCGUUAGGC GAA AAGGGACA | 11060 | UGUCCCUUU UCCCACAA | 3931 |
| 5969 | UUUGUGGG CUGAUGA GCCGUUAGGC GAA AAAGGGAC | 11061 | GUCCCUUUU CCCACAAA | 3932 |
| 5970 | UUUUGUGG CUGAUGA GCCGUUAGGC GAA AAAAGGGA | 11062 | UCCCUUUUC CCACAAAA | 3933 |
| 5981 | CUUUUCUU CUGAUGA GCCGUUAGGC GAA ACUUUUGU | 11063 | ACAAAAGUA AAGAAAAG | 3934 |
| 5992 | AAUCCCGA CUGAUGA GCCGUUAGGC GAA AGCUUUUC | 11064 | GAAAAGCUA UCGGGAUU | 3935 |
| 5994 | AGAAUCCC CUGAUGA GCCGUUAGGC GAA AUAGCUUU | 11065 | AAAGCUAUC GGGAUUCU | 3936 |
| 6000 | AACCAGAG CUGAUGA GCCGUUAGGC GAA AUCCCGAU | 11066 | AUCGGGAUU CUCUGGUU | 3937 |
| 6001 | GAACCAGA CUGAUGA GCCGUUAGGC GAA AAUCCCGA | 11067 | UCGGGAUUC UCUGGUUC | 3938 |
| 6003 | CAGAACCA CUGAUGA GCCGUUAGGC GAA AGAAUCCC | 11068 | GGGAUUCUC UGGUUCUG | 3939 |
| 6008 | UUAAGCAG CUGAUGA GCCGUUAGGC GAA ACCAGAGA | 11069 | UCUCUGGUU CUGCUUAA | 3940 |
| 6009 | UUUAAGCA CUGAUGA GCCGUUAGGC GAA AACCAGAG | 11070 | CUCUGGUUC UGCUUAAA | 3941 |
| 6014 | AAGUCUUU CUGAUGA GCCGUUAGGC GAA AGCAGAAC | 11071 | GUUCUGCUU AAAGACUU | 3942 |
| 6015 | UAAGUCUU CUGAUGA GCCGUUAGGC GAA AAGCAGAA | 11072 | UUCUGCUUA AAGACUUA | 3943 |
| 6022 | CCAAAGCU CUGAUGA GCCGUUAGGC GAA AGUCUUUA | 11073 | UAAAGACUU AGCUUUGG | 3944 |
| 6023 | UCCAAAGC CUGAUGA GCCGUUAGGC GAA AAGUCUUU | 11074 | AAAGACUUA GCUUUGGA | 3945 |
| 6027 | AGGCUCCA CUGAUGA GCCGUUAGGC GAA AGCUAAGU | 11075 | ACUUAGCUU UGGAGCCU | 3946 |

192

| | | | | |
|---|---|---|---|---|
| 6028 | UAGGCUCC CUGAUGA GCCGUUAGGC GAA AAGCUAAG | 11076 | CUUAGCUUU GGAGCCUA | 3947 |
| 6036 | AACUUUCA CUGAUGA GCCGUUAGGC GAA AGGCUCCA | 11077 | UGGAGCCUA UGAAAGUU | 3948 |
| 6044 | GGCUGAUC CUGAUGA GCCGUUAGGC GAA ACUUUCAU | 11078 | AUGAAAGUU GAUCAGCC | 3949 |

Underlined region can be any X sequence or linker, as described herein.

**Table IX: Mouse *flt*1 VEGF Receptor-Hairpin Ribozyme and Substrate Sequence** 237.198

| nt. Position | HP Ribozyme | Rz Seq ID No. | Substrate | Seq ID No. |
|---|---|---|---|---|
| 33 | GUCCCAGC AGAA GACCAU ACCAGAGAAACACACGUUGUGGUACAUUACCUGGUA | 11079 | AUGGUCA GCU GCUGGGAC | 3950 |
| 36 | GGUGUCCC AGAA GCUGAC ACCAGAGAAACACACGUUGUGGUACAUUACCUGGUA | 11080 | GUCAGCU GCU GGGACACC | 3951 |
| 50 | UAAGGCAA AGAA GCGGUG ACCAGAGAAACACACGUUGUGGUACAUUACCUGGUA | 11081 | CACCGCG GUC UUGCCUUA | 3952 |
| 67 | GACACCCG AGAA GCGCGU ACCAGAGAAACACACGUUGUGGUACAUUACCUGGUA | 11082 | ACGCGCU GCU CGGGUGUC | 3953 |
| 79 | CUGUGAGA AGAA GACACC ACCAGAGAAACACACGUUGUGGUACAUUACCUGGUA | 11083 | GGUGUCU GCU UCUCACAG | 3954 |
| 166 | GAAAGAGA AGAA GGCCUG ACCAGAGAAACACACGUUGUGGUACAUUACCUGGUA | 11084 | CAGGCCA GAC UCUCUUUC | 3955 |
| 197 | CAUGAGUG AGAA GCCUCC ACCAGAGAAACACACGUUGUGGUACAUUACCUGGUA | 11085 | GGAGGCA GCC CACUCAUG | 3956 |
| 214 | CGGUCGUG AGAA GAGACC ACCAGAGAAACACACGUUGUGGUACAUUACCUGGUA | 11086 | GGUCUCU GCC CACGACCG | 3957 |
| 266 | CUCCCACA AGAA GAUGGG ACCAGAGAAACACACGUUGUGGUACAUUACCUGGUA | 11087 | CCCAUCG GCC UGUGGGAG | 3958 |
| 487 | GGAUGAUG AGAA GUCUUC ACCAGAGAAACACACGUUGUGGUACAUUACCUGGUA | 11088 | GAAGACA GCU CAUCAUCC | 3959 |
| 501 | CGUCACCC AGAA GGGGAU ACCAGAGAAACACACGUUGUGGUACAUUACCUGGUA | 11089 | AUCCCCU GCC GGGUGACG | 3960 |
| 566 | CUUUGCCC AGAA GGGGUA ACCAGAGAAACACACGUUGUGGUACAUUACCUGGUA | 11090 | UACCCCU GAU GGGCAAAG | 3961 |
| 640 | CGCAGUUC AGAA GUCCUA ACCAGAGAAACACACGUUGUGGUACAUUACCUGGUA | 11091 | UAGGACU GCU GAACUGCG | 3962 |
| 691 | GCCGAUGG AGAA GAUAGU ACCAGAGAAACACACGUUGUGGUACAUUACCUGGUA | 11092 | ACUAUCU GAC CCAUCGGC | 3963 |
| 703 | UUGUAUUG AGAA GCCGAU ACCAGAGAAACACACGUUGUGGUACAUUACCUGGUA | 11093 | AUCGGCA GAC CAAUACAA | 3964 |
| 736 | CUGGGCUC AGAA GGCGUA ACCAGAGAAACACACGUUGUGGUACAUUACCUGGUA | 11094 | UACGCCC GCC GAGCCCAG | 3965 |
| 754 | GCCCGUGG AGAA GUCUCA ACCAGAGAAACACACGUUGUGGUACAUUACCUGGUA | 11095 | UGAGACU GCU CCACGGGC | 3966 |
| 766 | GGACAAGA AGAA GCCCGU ACCAGAGAAACACACGUUGUGGUACAUUACCUGGUA | 11096 | ACGGGCA GAC UCUUGUCC | 3967 |
| 871 | UCCGGUCA AGAA GCUGCC ACCAGAGAAACACACGUUGUGGUACAUUACCUGGUA | 11097 | GGCAGCG GAU UGACCGGA | 3968 |
| 960 | CUUCACGC AGAA GGUGUA ACCAGAGAAACACACGUUGUGGUACAUUACCUGGUA | 11098 | UACACCU GUC GCGUGAAG | 3969 |
| 988 | UGUUGAAA AGAA GGAACG ACCAGAGAAACACACGUUGUGGUACAUUACCUGGUA | 11099 | CGUUCCA GUC UUUCAACA | 3970 |
| 1051 | CCUGCACC AGAA GCUUCC ACCAGAGAAACACACGUUGUGGUACAUUACCUGGUA | 11100 | GGAAGCA GCC GGUGCAGG | 3971 |
| 1081 | GCCGAUAG AGAA GUCUUC ACCAGAGAAACACACGUUGUGGUACAUUACCUGGUA | 11101 | GAAGACG GUC CUAUCGGC | 3972 |
| 1090 | UCAUGGAC AGAA GAUAGG ACCAGAGAAACACACGUUGUGGUACAUUACCUGGUA | 11102 | CCUAUCG GCU GUCCAUGA | 3973 |
| 1093 | CUUUCAUG AGAA GCCGAU ACCAGAGAAACACACGUUGUGGUACAUUACCUGGUA | 11103 | AUCGGCU GUC CAUGAAAG | 3974 |
| 1169 | AAAUAGCG AGAA GACUUC ACCAGAGAAACACACGUUGUGGUACAUUACCUGGUA | 11104 | GAAGUCU GCU CGCUAUUU | 3975 |
| 1315 | UUUCGUAG AGAA GAGGUU ACCAGAGAAACACACGUUGUGGUACAUUACCUGGUA | 11105 | AACCUCA GAU CUACGAAA | 3976 |
| 1363 | UGCUGCCC AGAA GAUAGA ACCAGAGAAACACACGUUGUGGUACAUUACCUGGUA | 11106 | UCUAUCC GCU GGGCAGCA | 3977 |
| 1604 | GUCUGAGA AGAA GCCACC ACCAGAGAAACACACGUUGUGGUACAUUACCUGGUA | 11107 | GGUGGCU GAC UCUCAGAC | 3978 |
| 1612 | UUCCAGGG AGAA GAGAGU ACCAGAGAAACACACGUUGUGGUACAUUACCUGGUA | 11108 | ACUCUCA GAC CCCUGGAA | 3979 |
| 1629 | GGCCCGGC AGAA GUAGAU ACCAGAGAAACACACGUUGUGGUACAUUACCUGGUA | 11109 | AUCUACA GCU GCCGGGCC | 3980 |

194

| | | | | |
|---|---|---|---|---|
| 1632 | GAAGGCCC AGAA GCUGUA ACCAGAGAAACACACGUUGUGGUACAUUACCUGGUA | 11110 | UACAGCU GCC GGGCCUUC | 3981 |
| 1688 | UUCGGCAC AGAA GUGACA ACCAGAGAAACACACGUUGUGGUACAUUACCUGGUA | 11111 | UGUCACA GAU GUGCCGAA | 3982 |
| 1730 | UCUCCUUC AGAA GGCAUC ACCAGAGAAACACACGUUGUGGUACAUUACCUGGUA | 11112 | GAUGCCA GCC GAAGGAGA | 3983 |
| 1753 | CCACACAG AGAA GUUUCA ACCAGAGAAACACACGUUGUGGUACAUUACCUGGUA | 11113 | UGAAACU GUC CUGUGUGG | 3984 |
| 2017 | GGUUUUGA AGAA GGUGUG ACCAGAGAAACACACGUUGUGGUACAUUACCUGGUA | 11114 | CACACCU GCU UCAAAACC | 3985 |
| 2101 | ACCAAGUG AGAA GAGGCG ACCAGAGAAACACACGUUGUGGUACAUUACCUGGUA | 11115 | CGCCUCA GAU CACUUGGU | 3986 |
| 2176 | UUUCAAUA AGAA GCGUGC ACCAGAGAAACACACGUUGUGGUACAUUACCUGGUA | 8583 | GCACGCU GUU UAUUGAAA | 1441 |
| 2258 | GUGAGGUA AGAA GCGCUU ACCAGAGAAACACACGUUGUGGUACAUUACCUGGUA | 11116 | AAGCGCA GCC UACCUCAC | 3987 |
| 2305 | UGAGCGUG AGAA GCUCCA ACCAGAGAAACACACGUUGUGGUACAUUACCUGGUA | 11117 | UGGAGCU GAU CACGCUCA | 3988 |
| 2383 | CGGAAGAA AGAA GCUUCA ACCAGAGAAACACACGUUGUGGUACAUUACCUGGUA | 11118 | UGAAGCG GUC UUCUUCCG | 3989 |
| 2405 | GACAGGUA AGAA GUCUUU ACCAGAGAAACACACGUUGUGGUACAUUACCUGGUA | 11119 | AAAGACA GAC UACCUGUC | 3990 |
| 2432 | GGAACUUC AGAA GGGUCC ACCAGAGAAACACACGUUGUGGUACAUUACCUGGUA | 8587 | GGACCCA GAU GAAGUUCC | 1445 |
| 2464 | CAUAGGGC AGAA GUUCAC ACCAGAGAAACACACGUUGUGGUACAUUACCUGGUA | 11120 | GUGAACG GCU GCCCUAUG | 3991 |
| 2467 | CAUCAUAG AGAA GCCGUU ACCAGAGAAACACACGUUGUGGUACAUUACCUGGUA | 11121 | AACGGCU GCC CUAUGAUG | 3992 |
| 2592 | CACAGUCC AGAA GGUGGG ACCAGAGAAACACACGUUGUGGUACAUUACCUGGUA | 11122 | CCCACCU GCC GGACUGUG | 3993 |
| 2596 | CAGCCACA AGAA GGCAGG ACCAGAGAAACACACGUUGUGGUACAUUACCUGGUA | 11123 | CCUGCCG GAC UGUGGCUG | 3994 |
| 2653 | GUUCGGUC AGAA GAGCUU ACCAGAGAAACACACGUUGUGGUACAUUACCUGGUA | 11124 | AAGCUCU GAU GACCGAAC | 3995 |
| 2743 | CGAUCACC AGAA GAGGCC ACCAGAGAAACACACGUUGUGGUACAUUACCUGGUA | 11125 | GGCCUCU GAU GGUGAUCG | 3996 |
| 2779 | GGUAGUUG AGAA GGUUUC ACCAGAGAAACACACGUUGUGGUACAUUACCUGGUA | 11126 | GAAACCU GUC CAACUACC | 3997 |
| 2814 | CUUGUUGA AGAA GAAUAA ACCAGAGAAACACACGUUGUGGUACAUUACCUGGUA | 11127 | UUAUUCU GUC UCAACAAG | 3998 |
| 2831 | AUAUGCAA AGAA GCGUCC ACCAGAGAAACACACGUUGUGGUACAUUACCUGGUA | 11128 | GGACGCA GCC UUGCAUAU | 3999 |
| 2895 | ACUGUCUA AGAA GGGCUU ACCAGAGAAACACACGUUGUGGUACAUUACCUGGUA | 11129 | AAGCCCC GCC UAGACAGU | 4000 |
| 2913 | GACACUUG AGAA GCUGAC ACCAGAGAAACACACGUUGUGGUACAUUACCUGGUA | 11130 | GUCAGCA GCU CAAGUGUC | 4001 |
| 2928 | GAAGCUGG AGAA GGUGAC ACCAGAGAAACACACGUUGUGGUACAUUACCUGGUA | 11131 | GUCACCA GCU CCAGCUUC | 4002 |
| 2934 | UUCAGGGA AGAA GGAGCU ACCAGAGAAACACACGUUGUGGUACAUUACCUGGUA | 11132 | AGCUCCA GCU UCCCUGAA | 4003 |
| 3001 | UGGUGAGG AGAA GCUUGG ACCAGAGAAACACACGUUGUGGUACAUUACCUGGUA | 11133 | CCAAGCA GCC CCUCACCA | 4004 |
| 3022 | UGUAGGAA AGAA GGUCUU ACCAGAGAAACACACGUUGUGGUACAUUACCUGGUA | 11134 | AAGACCU GAU UUCCUACA | 4005 |
| 3033 | CACUUGGA AGAA GUAGGA ACCAGAGAAACACACGUUGUGGUACAUUACCUGGUA | 11135 | UCCUACA GUU UCCAAGUG | 4006 |
| 3064 | UUCUGGAG AGAA GAAACU ACCAGAGAAACACACGUUGUGGUACAUUACCUGGUA | 11136 | AGUUUCU GUC CUCCAGAA | 4007 |
| 3179 | CUCACAUA AGAA GGGUUC ACCAGAGAAACACACGUUGUGGUACAUUACCUGGUA | 8599 | GAACCCU GAU UAUGUGAG | 4008 |
| 3357 | CUUCAGGC AGAA GCAGAA ACCAGAGAAACACACGUUGUGGUACAUUACCUGGUA | 11137 | UUCUGCA GCC GCCUGAAG | 4009 |
| 3360 | UUCCUUCA AGAA GCUGCA ACCAGAGAAACACACGUUGUGGUACAUUACCUGGUA | 11138 | UGCAGCC GCC UGAAGGAA | 4010 |
| 3379 | GGGUUCUC AGAA GCAUGC ACCAGAGAAACACACGUUGUGGUACAUUACCUGGUA | 11139 | GCAUGCG GAU GAGAACCC | 4011 |
| 3463 | GUUCAGCA AGAA GGGGCC ACCAGAGAAACACACGUUGUGGUACAUUACCUGGUA | 11140 | GGCCCCG GUU UGCUGAAC | 4012 |
| 3496 | UGGCUUGA AGAA GGUCAC ACCAGAGAAACACACGUUGUGGUACAUUACCUGGUA | 11141 | GUGACCU GCU UCAAGCCA | 4013 |

195

| | | | | |
|---|---|---|---|---|
| 3553 | UGUUUCUA AGAA GUAUGG ACCAGAGAAACACACGUUGUGGUACAUUACCUGGUA | 11142 | CCAUACU GAC UAGAAACA | 4014 |
| 3615 | AUCUGCAA AGAA GUCCUU ACCAGAGAAACACACGUUGUGGUACAUUACCUGGUA | 11143 | AAGGACG GCU UUGCAGAU | 4015 |
| 3623 | AAAUGUGG AGAA GCAAAG ACCAGAGAAACACACGUUGUGGUACAUUACCUGGUA | 11144 | CUUUGCA GAU CCACAUUU | 4016 |
| 3650 | CUCACAUC AGAA GAGCUU ACCAGAGAAACACACGUUGUGGUACAUUACCUGGUA | 11145 | AAGCUCU GAU GAUGUGAG | 4017 |
| 3754 | UAGUGUCC AGAA GAUAGU ACCAGAGAAACACACGUUGUGGUACAUUACCUGGUA | 11146 | ACUAUCA GCU GGACACUA | 4018 |
| 3772 | GGGAGCCC AGAA GAGUGC ACCAGAGAAACACACGUUGUGGUACAUUACCUGGUA | 11147 | GCACUCU GCU GGGCUCCC | 4019 |
| 3796 | UCCAGGUG AGAA GCUUCA ACCAGAGAAACACACGUUGUGGUACAUUACCUGGUA | 11148 | UGAAGCG GUU CACCUGGA | 4020 |
| 3881 | CUCGGCAG AGAA GAAAGU ACCAGAGAAACACACGUUGUGGUACAUUACCUGGUA | 11149 | ACUUUCC GAU CUGCCGAG | 4021 |
| 3886 | UGGGCCUC AGAA GAUCGG ACCAGAGAAACACACGUUGUGGUACAUUACCUGGUA | 11150 | CCGAUCU GCC GAGGCCCA | 4022 |
| 3897 | GAAGCAGA AGAA GGGCCU ACCAGAGAAACACACGUUGUGGUACAUUACCUGGUA | 11151 | AGGCCCA GCU UCUGCUUC | 4023 |
| 3903 | GCUGGAGA AGAA GAAGCU ACCAGAGAAACACACGUUGUGGUACAUUACCUGGUA | 11152 | AGCUUCU GCU UCUCCAGC | 4024 |
| 3912 | GUGGCCAC AGAA GGAGAA ACCAGAGAAACACACGUUGUGGUACAUUACCUGGUA | 11153 | UUCUCCA GCU GUGGCCAC | 4025 |
| 3969 | UGGAGAAC AGAA GGACUC ACCAGAGAAACACACGUUGUGGUACAUUACCUGGUA | 11154 | GAGUCCU GCU GUUCUCCA | 4026 |
| 3972 | GGGUGGAG AGAA GCAGGA ACCAGAGAAACACACGUUGUGGUACAUUACCUGGUA | 11155 | UCCUGCU GUU CUCCACCC | 4027 |
| 3986 | GAGUUGUA AGAA GGGGGU ACCAGAGAAACACACGUUGUGGUACAUUACCUGGUA | 11156 | ACCCCCA GAC UACAACUC | 4028 |
| 4018 | UUUAGGCG AGAA GGGAGG ACCAGAGAAACACACGUUGUGGUACAUUACCUGGUA | 11157 | CCUCCCC GCC CGCCUAAA | 4029 |
| 4022 | AAGCUUUA AGAA GGCGGG ACCAGAGAAACACACGUUGUGGUACAUUACCUGGUA | 11158 | CCCGCCC GCC UAAAGCUU | 4030 |
| 4040 | GUUGUCGG AGAA GGUGAG ACCAGAGAAACACACGUUGUGGUACAUUACCUGGUA | 11159 | CUCACCA GCC CCGACAAC | 4031 |
| 4053 | CUGUCAGG AGAA GGUUGU ACCAGAGAAACACACGUUGUGGUACAUUACCUGGUA | 11160 | ACAACCA GCC CCUGACAG | 4032 |
| 4095 | UCCUGUGG AGAA GAAUAG ACCAGAGAAACACACGUUGUGGUACAUUACCUGGUA | 11161 | CUAUUCC GCU CCACAGGA | 4033 |
| 4110 | CGAAAAGC AGAA GGCUCC ACCAGAGAAACACACGUUGUGGUACAUUACCUGGUA | 11162 | GGAGCCA GCU GCUUUUCG | 4034 |
| 4113 | UCACGAAA AGAA GCUGGC ACCAGAGAAACACACGUUGUGGUACAUUACCUGGUA | 11163 | GCCAGCU GCU UUUCGUGA | 4035 |
| 4168 | UUAGUCAA AGAA GCAACA ACCAGAGAAACACACGUUGUGGUACAUUACCUGGUA | 11164 | UGUUGCU GUU UUGACUAA | 4036 |
| 4290 | GGUGGGCG AGAA GUCGCC ACCAGAGAAACACACGUUGUGGUACAUUACCUGGUA | 11165 | GGCGACC GCC CGCCCACC | 4037 |
| 4294 | GGCCGGUG AGAA GGCGGU ACCAGAGAAACACACGUUGUGGUACAUUACCUGGUA | 11166 | ACCGCCC GCC CACCGGCC | 4038 |
| 4329 | AGUCCCAC AGAA GCAGGG ACCAGAGAAACACACGUUGUGGUACAUUACCUGGUA | 11167 | CCCUGCA GCU GUGGGACU | 4039 |
| 4378 | CAGAGCAG AGAA GUGCAU ACCAGAGAAACACACGUUGUGGUACAUUACCUGGUA | 11168 | AUGCACU GAC CUGCUCUG | 4040 |
| 4383 | AGAGACAG AGAA GGUCAG ACCAGAGAAACACACGUUGUGGUACAUUACCUGGUA | 11169 | CUGACCU GCU CUGUCUCU | 4041 |
| 4388 | AUAAGAGA AGAA GAGCAG ACCAGAGAAACACACGUUGUGGUACAUUACCUGGUA | 11170 | CUGCUCU GUC UCUCUUAU | 4042 |
| 4457 | CUCCACAG AGAA GACGCA ACCAGAGAAACACACGUUGUGGUACAUUACCUGGUA | 11171 | UGCGUCC GUC CUGUGGAG | 4043 |
| 4525 | CCCGAAAC AGAA GAGGCC ACCAGAGAAACACACGUUGUGGUACAUUACCUGGUA | 11172 | GGCCUCC GCU GUUUCGGG | 4044 |
| 4528 | GGGCCCGA AGAA GCGGAG ACCAGAGAAACACACGUUGUGGUACAUUACCUGGUA | 11173 | CUCCGCU GUU UCGGGCCC | 4045 |
| 4643 | AAACAGAC AGAA GAAGAC ACCAGAGAAACACACGUUGUGGUACAUUACCUGGUA | 11174 | GUCUUCU GUU GUCUGUUU | 4046 |
| 4650 | GGAUGGUA AGAA GACAAC ACCAGAGAAACACACGUUGUGGUACAUUACCUGGUA | 11175 | GUUGUCU GUU UACCAUCC | 4047 |
| 4724 | ACUAGAGG AGAA GAUGAU ACCAGAGAAACACACGUUGUGGUACAUUACCUGGUA | 11176 | AUCAUCA GUU CCUCUAGU | 4048 |

196

| | | | | |
|---|---|---|---|---|
| 4771 | AUGCGAAG AGAA GGCCUG ACCAGAGAAACACACGUUGUGGUACAUUACCUGGUA | 11177 | CAGGCCU GAC CUUCGCAU | 4049 |
| 4785 | UCCCCGUG AGAA GUAUGC ACCAGAGAAACACACGUUGUGGUACAUUACCUGGUA | 11178 | GCAUACU GCU CACGGGGA | 4050 |
| 4809 | CUAGGCCA AGAA GGACCA ACCAGAGAAACACACGUUGUGGUACAUUACCUGGUA | 11179 | UGGUCCA GUU UGGCCUAG | 4051 |
| 4834 | UUGAGCCC AGAA GUAGGC ACCAGAGAAACACACGUUGUGGUACAUUACCUGGUA | 11180 | GCCUACU GAU GGGCUCAA | 4052 |
| 4912 | AUAUAUAA AGAA GGAUAA ACCAGAGAAACACACGUUGUGGUACAUUACCUGGUA | 11181 | UUAUCCU GUU UUAUAUAU | 4053 |
| 5119 | UCCUCUCA AGAA GCCUUG ACCAGAGAAACACACGUUGUGGUACAUUACCUGGUA | 11182 | CAAGGCA GUC UGAGAGGA | 4054 |
| 5144 | UAAAUAUG AGAA GAUACU ACCAGAGAAACACACGUUGUGGUACAUUACCUGGUA | 11183 | AGUAUCA GCC CAUAUUUA | 4055 |
| 5287 | AGGUAUGA AGAA GAUGAA ACCAGAGAAACACACGUUGUGGUACAUUACCUGGUA | 11184 | UUCAUCU GUU UCAUACCU | 4056 |
| 5363 | CCCCAAAG AGAA GGCACC ACCAGAGAAACACACGUUGUGGUACAUUACCUGGUA | 11185 | GGUGCCC GCU CUUUGGGG | 4057 |
| 5462 | CCGGCUCC AGAA GGUGUG ACCAGAGAAACACACGUUGUGGUACAUUACCUGGUA | 11186 | CACACCU GCC GGAGCCGG | 4058 |
| 5478 | GUCUGCCC AGAA GUGACC ACCAGAGAAACACACGUUGUGGUACAUUACCUGGUA | 11187 | GGUCACA GCU GGGCAGAC | 4059 |
| 5486 | UAUUCAUC AGAA GCCCAG ACCAGAGAAACACACGUUGUGGUACAUUACCUGGUA | 11188 | CUGGGCA GAC GAUGAAUA | 4060 |
| 5500 | UCUCCCAA AGAA GCUAUU ACCAGAGAAACACACGUUGUGGUACAUUACCUGGUA | 11189 | AAUAGCU GCU UUGGGAGA | 4061 |
| 5539 | CUGGCCCG AGAA GAGAAU ACCAGAGAAACACACGUUGUGGUACAUUACCUGGUA | 11190 | AUUCUCU GAC CGGGCCAG | 4062 |
| 5564 | CACAGGGG AGAA GGUACC ACCAGAGAAACACACGUUGUGGUACAUUACCUGGUA | 11191 | GGUACCU GCU CCCCUGUG | 4063 |
| 5597 | UCUCAUCA AGAA GAAAAC ACCAGAGAAACACACGUUGUGGUACAUUACCUGGUA | 11192 | GUUUUCU GUC UGAUGAGA | 4064 |
| 5601 | CCAGUCUC AGAA GACAGA ACCAGAGAAACACACGUUGUGGUACAUUACCUGGUA | 11193 | UCUGUCU GAU GAGACUGG | 4065 |
| 5639 | GGGCUGCA AGAA GUCUCA ACCAGAGAAACACACGUUGUGGUACAUUACCUGGUA | 11194 | UGAGACA GCC UGCAGCCC | 4066 |
| 5646 | CCACAGUG AGAA GCAGGC ACCAGAGAAACACACGUUGUGGUACAUUACCUGGUA | 11195 | GCCUGCA GCC CACUGUGG | 4067 |
| 5781 | CACACUGC AGAA GACAAG ACCAGAGAAACACACGUUGUGGUACAUUACCUGGUA | 11196 | CUUGUCG GCU GCAGUGUG | 4068 |
| 5829 | CUGUUCUC AGAA GUUUCU ACCAGAGAAACACACGUUGUGGUACAUUACCUGGUA | 11197 | AGAAACG GAU GAGAACAG | 4069 |
| 5842 | AAACCUCA AGAA GCUGUU ACCAGAGAAACACACGUUGUGGUACAUUACCUGGUA | 11198 | AACAGCA GCC UGAGGUUU | 4070 |
| 5915 | UUAUUAAA AGAA GAAUAA ACCAGAGAAACACACGUUGUGGUACAUUACCUGGUA | 11199 | UUAUUCC GAU UUUAAUAA | 4071 |
| 6010 | AGUCUUUA AGAA GAACCA ACCAGAGAAACACACGUUGUGGUACAUUACCUGGUA | 11200 | UGGUUCU GCU UAAAGACU | 4072 |

197

Table X: Homologous Hammerhead Ribozyme Target Sites Between Human flt-1 and KDR RNA

| | flt-1 | | | KDR | |
|---|---|---|---|---|---|
| nt. Position | Target Sequence | flt-1 Seq ID No. | nt. Position | Target Sequence | KDR Seq ID No. |
| 3388 | CCGGGAU A UUUAUAA | 4073 | 3151 | CCGGGAU A UUUAUAA | 4073 |
| 2174 | AAUGUAU A CACAGGG | 4074 | 3069 | AgUGUAU c CACAGGG | 4116 |
| 2990 | UGCAAAU A UGGAAAU | 4075 | 2756 | UGCAAAU u UGGAAAc | 4117 |
| 2693 | CUCCCUU A UGAUGCC | 4076 | 2459 | CUgCCUU A UGAUGCC | 4118 |
| 2981 | GUUGAAU A CUGCAAA | 4077 | 2747 | GUgGAAU u CUGCAAA | 4119 |
| 1359 | UAUGGUU A AAAGAUG | 4078 | 2097 | UgUGGUU u AAAGAUa | 4120 |
| 3390 | GGGAUAU U UAUAAGA | 4079 | 3153 | GGGAUAU U UAUAAag | 4121 |
| 3391 | GGAUAUU U AUAAGAA | 4080 | 3154 | GGAUAUU U AUAAagA | 4122 |
| 2925 | ACGUGGU U AACCUGC | 4081 | 2691 | AuGUGGU c AACCUuC | 4123 |
| 7140 | UAUUUCU A GUCAUGA | 4082 | 2340 | UAcUUCU u GUCAUcA | 4124 |
| 1785 | CAAUAAU A GAAGGAA | 4083 | 1515 | CucUAAU u GAAGGAA | 4125 |
| 2731 | GAGACUU A AACUGGG | 4084 | 768 | uuGACUU c AACUGGG | 4126 |
| 3974 | GAUGACU A CCAGGGC | 4085 | 1466 | GAgGACU u CCAGGGa | 4127 |
| 6590 | UUAAUGU A GAAAGAA | 4086 | 2603 | aaAAUGU u GAAAGAA | 4128 |
| 6705 | GCCAUUU A UGACAAA | 4087 | 3227 | aCaAUUU u UGACAgA | 4129 |
| 974 | GUCAAAU U ACUUAGA | 4088 | 147 | uUCAAAU U ACUUgcA | 4130 |
| 1872 | AUAAAGU U GGGACUG | 4089 | 1602 | AcAAAGU c GGGAgaG | 4131 |
| 2333 | ACUUGGU U UAAAAAC | 4090 | 1088 | AaaUGGU a UAAAAAu | 4132 |
| 2775 | AAGUGGU U CAAGCAU | 4091 | 1745 | AcaUGGU a CAAGCuU | 4133 |
| 3533 | UUCUCCU U AGGUGGG | 4092 | 3296 | UUuUCCU U AGGUGcu | 4134 |
| 3534 | UCUCCUU A GGUGGGU | 4093 | 3297 | UuUCCUU A GGUGcuU | 4135 |
| 3625 | GUACUCU A CUCCUGA | 4094 | 4054 | GagCUCU c CUCCUGu | 4136 |
| 1814 | AGCACCU U GGUUGUG | 4095 | 1059 | AGuACCU U GGUUacc | 4137 |
| 2744 | GGCAAAU C ACUUGGA | 4096 | 147 | uuCAAAU u ACUUGcA | 4130 |
| 2783 | CAAGCAU C AGCAUUU | 4097 | 796 | gAAGCAU C AGCAUaa | 4138 |
| 3613 | GAGAGCU C CUGAGUA | 4098 | 2968 | GgaAGCU C CUGAagA | 4139 |
| 4052 | AAGGCCU C GCUCAAG | 4099 | 1923 | ucuGCCU u GCUCAAG | 4140 |
| 5305 | UCUCCAU A UCAAAAC | 4100 | 456 | ggUCCAU u UCAAAuC | 4141 |

| | | | | | |
|---|---|---|---|---|---|
| 7158 | AUGUAUU U UGUAUAC | 4101 | 631 | gUcUAUU a UGUAcAu | 4142 |
| 1836 | CUAGAAU U UCUGGAA | 4102 | 1007 | aUgGAAU c UCUGGug | 4143 |
| 2565 | CUCUCUU C UGGCUCC | 4103 | 2328 | uguUCUU C UGGCUaC | 4144 |
| 4250 | CUGUACU C CACCCCA | 4104 | 3388 | uUaUACU a CACCagA | 4145 |
| 7124 | ACAUGGU U UGGUCCU | 4105 | 3778 | cagUGGU a UGGUuCU | 4146 |
| 436 | AUGGUCU U UGCCUGA | 4106 | 1337 | AcGGUCU a UGCCauu | 4147 |
| 2234 | GCACCAU A CCUCCUG | 4107 | 1344 | augCCAU u CCUCCcc | 4148 |
| 2763 | GGGCUUU U GGAAAAG | 4108 | 990 | uuGCUUU U GGAAguG | 4149 |
| 4229 | CCAGACU A CAACUCG | 4109 | 767 | auuGACU u CAACUgG | 4150 |
| 5301 | GUUUUCU C CAUAUCA | 4110 | 3307 | ugcUUCU C CAUAUCc | 4151 |
| 6015 | AGAAUGU A UGCCUCU | 4111 | 1917 | AcuAUGU c UGCCUug | 4152 |
| 6095 | AUUCCCU A GUGAGCC | 4112 | 1438 | AUaCCCU u GUGAaga | 4153 |
| 6236 | UGUUGUU C CUCUUCU | 4113 | 76 | UagUGUU u CUCUUga | 4154 |
| 5962 | GCUUCCU U UUAUCCA | 4114 | 3099 | auaUCCU c UUAUCgg | 4155 |
| 7629 | UAUAUAU U CUCUGCU | 4115 | 3096 | gAaAUAU c CUCUuaU | 4156 |

Lowercase letters are used to represent sequence variance between flt-1 and KDR RNA

199

Table XI: 2.5 µmol RNA Synthesis Cycle

| Reagent | Equivalents | Amount | Wait Time* |
|---|---|---|---|
| Phosphoramidites | 6.5 | 163 µL | 2.5 |
| *S*-Ethyl Tetrazole | 23.8 | 238 µL | 2.5 |
| Acetic Anhydride | 100 | 233 µL | 5 sec |
| *N*-Methyl Imidazole | 186 | 233 µL | 5 sec |
| TCA | 83.2 | 1.73 mL | 21 sec |
| Iodine | 8.0 | 1.18 mL | 45 sec |
| Acetonitrile | NA | 6.67 mL | NA |

* Wait time does not include contact time during delivery.

200

Table XII. Ribozyme and attenuated control sequences and locations of modified nucleotides. 237.198

| Target Site* | RPI No. | Ribozyme Sequence† (5'–3') | Activity | Seq. ID No. |
|---|---|---|---|---|
| *Flt*-1358-amino | RPI 4118 | 5' $a_s u_s c_s u_s$uuu cUGAUGa*ggc*gaaa*gcc*Gaa AccauacB 3' | Active | 11201 |
| *Flt*-1358-amino (att.) | RPI 4581 | $a_s u_s c_s u_s$uuu cUuAUGa*ggc*gaaa*gcc*Gau AccauacB | Attenuated | 11202 |
| *Flt*-1358-allyl | RPI 4159 | 5' $a_s u_s c_s u_s$uuu cUGAuGa*ggc*gaaa*gcc*Gaa AccauacB 3' | Active | 11203 |
| *Flt*-1358-allyl (att.) | RPI 4583 | $a_s u_s c_s u_s$uuu cUuAuGa*ggc*gaaa*gcc*Gau AccauacB | Attenuated | 11204 |
| *Flt*-4229-amino | RPI 4131 | $g_s a_s g_s u_s$ug cUGAUGa*ggc*gaaa*gcc*Gaa AgucugB | Active | 11205 |
| *Flt*-4229-amino (att.) | RPI 4582 | $g_s a_s g_s u_s$ug cUuAUGa*ggc*gaaa*gcc*Gau AgucugB | Attenuated | 11206 |
| *Flt*-4229-allyl | RPI 4172 | $g_s a_s g_s u_s$ug cUGAuGa*ggc*gaaa*gcc*Gaa AgucugB | Active | 11207 |
| *Flt*-4229-allyl (att.) | RPI 4584 | $g_s a_s g_s u_s$ug cUuAuGa*ggc*gaaa*gcc*Gau AgucugB | Attenuated | 11208 |
| *KDR*-726-amino | RPI 4097 | $u_s a_s c_s a_s$auu cUGAUGa*ggc*gaaa*gcc*Gaa AagacaaB | Active | 11209 |
| *KDR*-726-amino (att.) | RPI 4674 | $u_s a_s c_s a_s$auu cUuAUGa*ggc*gaaa*gcc*Gau AagacaaB | Attenuated | 11210 |
| *KDR*-726-allyl | RPI 4138 | $u_s a_s c_s a_s$auu cUGAuGa*ggc*gaaa*gcc*Gaa AagacaaB | Active | 11211 |
| *KDR*-726allyl (att.) | | $u_s a_s c_s a_s$auu cUuAuGa*ggc*gaaa*gcc*Gau AagacaaB | Attenuated | 11212 |
| *KDR*-3950-amino | RPI 4110 | $c_s u_s g_s g_s$ag cUGAUGa*ggc*gaaa*gcc*Gaa AcacggB | Active | 11213 |
| *KDR*-3950-amino (att.) | RPI 4677 | $c_s u_s g_s g_s$ag cUuAUGa*ggc*gaaa*gcc*Gau AcacggB | Attenuated | 11214 |
| *KDR*-3950-allyl | RPI 4151 | $c_s u_s g_s g_s$ag cUGAuGa*ggc*gaaa*gcc*Gaa AcacggB | Active | 11215 |
| *KDR*-3950-allyl (att.) | | $c_s u_s g_s g_s$ag cUuAuGa*ggc*gaaa*gcc*Gau AcacggB | Attenuated | 11216 |
| | | binding arm/catalytic core & stem II/binding arm | | |

- Ribozyme target sites are named according to the cleavage position in human *Flt-1* (EMBL accession no. X51602) or human *KDR* mRNA (EMBL accession no. L0497).

[†] Modifications are indicated as follows: 2'-*O*-methyl nucleotides, lowercase; ribonucleotides, uppercase G, A; inverted 3'-3' deoxyabasic, B. Two ribozyme motifs were tested [23]. For the $NH_2$-modified ribozymes, U indicates the two core positions where 2'-$NH_2$ uridines are present. *U* indicates 2'-*C*-allyl-uridine modification. The positions of four phosphorothioate linkages at the 5' end are indicated by a subscript "s". Changes in the attenuated controls are underlined. Nucleotides comprising the base paired region of stem II are in *italics*. A 3 bp stem II is shown above. Ribozymes or attenuated controls referred to in the text with a 4 bp stem II have one additional base pair such that the stem II/loop sequence is *ggcc*gaaa*ggcc*.

202

Table XIII. Ribozyme and attenuated control sequences with locations of modified nucleotides. 237.198

| Ribozyme | Sequence† (5'–3') | Activity | Seq. ID Nos. |
|---|---|---|---|
| RPI.4610 (ANGIOZYME™) | $g_sa_sg_su_s$ug cUGAuGa*ggcc*gaaa*ggcc*Gaa AgucugB | Active | 11217 |
| RPI.13141 | $g_sa_sg_su_s$ug cUAGaGa*ggcc*gaaa*ggcc*Gau AgucugB | BAC‡ | 11218 |
| RPI.13030 | $g_sa_sa_sg_s$gu cUAGuGa*ggcc*gaaa*ggcc*Gau AugucB | SAC* | 11219 |
| | binding arm / core & stem II / binding arm | | |

† Modifications are indicated as follows: 2'-*O*-methyl nucleotides, lowercase; ribonucleotides, uppercase G, A; 2'-*C*-allyl uridine, U; inverted 3'-3' deoxyabasic, B. The positions of four phosphorothioate linkages at the 5' end are indicated by a subscript "s". Nucleotides comprising the base paired region of stem II are in *italics*. Nucleotide changes in the core of the attenuated controls are underlined. ANGIOZYME ribozyme is targeted to cleave site 4229 in human flt-1 RNA and is identical to *Flt*-4229-allyl ribozyme (Table XII) except that the ANGIOZYME has a stem II of length 4 bps.

‡ BAC: *B*inding arm, *A*ttenuated core *C*ontrol.

* SAC: *S*crambled arm, *A*ttenuated core *C*ontrol.

Table XIV: NCH Ribozyme and Target Sequences 237/198

Core Sequence = CUGAUGAG GCCGUUAGGC CGAA
Underlined region can be any X sequence or linker, as described herein.

| nt. Position | NCH Ribozyme | Seq ID Nos. | Target | Seq ID Nos. |
|---|---|---|---|---|
| 9 | CCGAGAGG CUGAUGAG GCCGUUAGGC CGAA IUGUCCGC | 11220 | GCGGACAC T CCTCTCGG | 4157 |
| 11 | AGCCGAGA CUGAUGAG GCCGUUAGGC CGAA IAGUGUCC | 11221 | GGACACTC C TCTCGGCT | 4158 |
| 12 | GAGCCGAG CUGAUGAG GCCGUUAGGC CGAA IGAGUGUC | 11222 | GACACTCC T CTCGGCTC | 4159 |
| 14 | AGGAGCCG CUGAUGAG GCCGUUAGGC CGAA IAGGAGUG | 11223 | CACTCCTC T CGGCTCCT | 4160 |
| 19 | CGGGGAGG CUGAUGAG GCCGUUAGGC CGAA ICCGAGAG | 11224 | CTCTCGGC T CCTCCCCG | 4161 |
| 21 | GCCGGGGA CUGAUGAG GCCGUUAGGC CGAA IAGCCGAG | 11225 | CTCGGCTC C TCCCCGGC | 4162 |
| 22 | UGCCGGGG CUGAUGAG GCCGUUAGGC CGAA IGAGCCGA | 11226 | TCGGCTCC T CCCCGGCA | 4163 |
| 24 | GCUGCCGG CUGAUGAG GCCGUUAGGC CGAA IAGGAGCC | 11227 | GGCTCCTC C CCGGCAGC | 4164 |
| 25 | CGCUGCCG CUGAUGAG GCCGUUAGGC CGAA IGAGGAGC | 11228 | GCTCCTCC C CGGCAGCG | 4165 |
| 26 | CCGCUGCC CUGAUGAG GCCGUUAGGC CGAA IGGAGGAG | 11229 | CTCCTCCC C GGCAGCGG | 4166 |
| 30 | GCCGCCGC CUGAUGAG GCCGUUAGGC CGAA ICCGGGGA | 11230 | TCCCCGGC A GCGGCGGC | 4167 |
| 42 | CCGCUCCG CUGAUGAG GCCGUUAGGC CGAA ICCGCCGC | 11231 | GCGGCGGC T CGGAGCGG | 4168 |
| 53 | AGCCCCGG CUGAUGAG GCCGUUAGGC CGAA ICCCGCUC | 11232 | GAGCGGGC T CCGGGGCT | 4169 |
| 55 | CGAGCCCC CUGAUGAG GCCGUUAGGC CGAA IAGCCCGC | 11233 | GCGGGCTC C GGGGCTCG | 4170 |
| 61 | UGCACCCG CUGAUGAG GCCGUUAGGC CGAA ICCCCGGA | 11234 | TCCGGGGC T CGGGTGCA | 4171 |
| 69 | CUGGCCGC CUGAUGAG GCCGUUAGGC CGAA ICACCCGA | 11235 | TCGGGTGC A GCGGCCAG | 4172 |
| 75 | GGCCCGCU CUGAUGAG GCCGUUAGGC CGAA ICCGCUGC | 11236 | GCAGCGGC C AGCGGGCC | 4173 |
| 76 | AGGCCCGC CUGAUGAG GCCGUUAGGC CGAA IGCCGCUG | 11237 | CAGCGGCC A GCGGGCCT | 4174 |
| 83 | CGCCGCCA CUGAUGAG GCCGUUAGGC CGAA ICCCGCUG | 11238 | CAGCGGGC C TGGCGGCG | 4175 |
| 84 | UCGCCGCC CUGAUGAG GCCGUUAGGC CGAA IGCCCGCU | 11239 | AGCGGGCC T GGCGGCGA | 4176 |
| 100 | CUUCCCCG CUGAUGAG GCCGUUAGGC CGAA IUAAUCCU | 11240 | AGGATTAC C CGGGGAAG | 4177 |
| 101 | ACUUCCCC CUGAUGAG GCCGUUAGGC CGAA IGUAAUCC | 11241 | GGATTACC C GGGGAAGT | 4178 |
| 117 | CAGCCAGG CUGAUGAG GCCGUUAGGC CGAA IACAACCA | 11242 | TGGTTGTC T CCTGGCTG | 4179 |
| 119 | UCCAGCCA CUGAUGAG GCCGUUAGGC CGAA IAGACAAC | 11243 | GTTGTCTC C TGGCTGGA | 4180 |
| 120 | CUCCAGCC CUGAUGAG GCCGUUAGGC CGAA IGAGACAA | 11244 | TTGTCTCC T GGCTGGAG | 4181 |
| 124 | GCGGCUCC CUGAUGAG GCCGUUAGGC CGAA ICCAGGAG | 11245 | CTCCTGGC T GGAGCCGC | 4182 |

204

| | | | | |
|---|---|---|---|---|
| 130 | CGUCUCGC CUGAUGAG GCCGUUAGGC CGAA ICUCCAGC | 11246 | GCTGGAGC C GCGAGACG | 4183 |
| 144 | GCGCCCUG CUGAUGAG GCCGUUAGGC CGAA ICGCCCGU | 11247 | ACGGGCGC T CAGGGCGC | 4184 |
| 146 | CCGCGCCC CUGAUGAG GCCGUUAGGC CGAA IAGCGCCC | 11248 | GGGCGCTC A GGGCGCGG | 4185 |
| 158 | CCGCCGCC CUGAUGAG GCCGUUAGGC CGAA ICCCCGCG | 11249 | CGCGGGGC C GGCGGCGG | 4186 |
| 184 | GCCGCCAG CUGAUGAG GCCGUUAGGC CGAA IUCCGUCC | 11250 | GGACGGAC T CTGGCGGC | 4187 |
| 186 | CGGCCGCC CUGAUGAG GCCGUUAGGC CGAA IAGUCCGU | 11251 | ACGGACTC T GGCGGCCG | 4188 |
| 193 | AACGACCC CUGAUGAG GCCGUUAGGC CGAA ICCGCCAG | 11252 | CTGGCGGC C GGGTCGTT | 4189 |
| 205 | GCUCCCCC CUGAUGAG GCCGUUAGGC CGAA ICCAACGA | 11253 | TCGTTGGC C GGGGGAGC | 4190 |
| 220 | UCGCCCGG CUGAUGAG GCCGUUAGGC CGAA ICCCGCGC | 11254 | GCGCGGGC A CCGGGCGA | 4191 |
| 222 | GCUCGCCC CUGAUGAG GCCGUUAGGC CGAA IUGCCCGC | 11255 | GCGGGCAC C GGGCGAGC | 4192 |
| 231 | ACGCGGCC CUGAUGAG GCCGUUAGGC CGAA ICUCGCCC | 11256 | GGGCGAGC A GGCCGCGT | 4193 |
| 235 | CGCGACGC CUGAUGAG GCCGUUAGGC CGAA ICCUGCUC | 11257 | GAGCAGGC C GCGTCGCG | 4194 |
| 245 | CCAUGGUG CUGAUGAG GCCGUUAGGC CGAA ICGCGACG | 11258 | CGTCGCGC T CACCATGG | 4195 |
| 247 | GACCAUGG CUGAUGAG GCCGUUAGGC CGAA IAGCGCGA | 11259 | TCGCGCTC A CCATGGTC | 4196 |
| 249 | CUGACCAU CUGAUGAG GCCGUUAGGC CGAA IUGAGCGC | 11260 | GCGCTCAC C ATGGTCAG | 4197 |
| 250 | GCUGACCA CUGAUGAG GCCGUUAGGC CGAA IGUGAGCG | 11261 | CGCTCACC A TGGTCAGC | 4198 |
| 256 | CCAGUAGC CUGAUGAG GCCGUUAGGC CGAA IACCAUGG | 11262 | CCATGGTC A GCTACTGG | 4199 |
| 259 | GUCCCAGU CUGAUGAG GCCGUUAGGC CGAA ICUGACCA | 11263 | TGGTCAGC T ACTGGGAC | 4200 |
| 262 | GGUGUCCC CUGAUGAG GCCGUUAGGC CGAA IUAGCUGA | 11264 | TCAGCTAC T GGGACACC | 4201 |
| 268 | GACCCCGG CUGAUGAG GCCGUUAGGC CGAA IUCCCAGU | 11265 | ACTGGGAC A CCGGGGTC | 4202 |
| 270 | AGGACCCC CUGAUGAG GCCGUUAGGC CGAA IUGUCCCA | 11266 | TGGGACAC C GGGGTCCT | 4203 |
| 277 | GCACAGCA CUGAUGAG GCCGUUAGGC CGAA IACCCCGG | 11267 | CCGGGGTC C TGCTGTGC | 4204 |
| 278 | CGCACAGC CUGAUGAG GCCGUUAGGC CGAA IGACCCCG | 11268 | CGGGGTCC T GCTGTGCG | 4205 |
| 281 | GCGCGCAC CUGAUGAG GCCGUUAGGC CGAA ICAGGACC | 11269 | GGTCCTGC T GTGCGCGC | 4206 |
| 290 | AGCUGAGC CUGAUGAG GCCGUUAGGC CGAA ICGCGCAC | 11270 | GTGCGCGC T GCTCAGCT | 4207 |
| 293 | GACAGCUG CUGAUGAG GCCGUUAGGC CGAA ICAGCGCG | 11271 | CGCGCTGC T CAGCTGTC | 4208 |
| 295 | CAGACAGC CUGAUGAG GCCGUUAGGC CGAA IAGCAGCG | 11272 | CGCTGCTC A GCTGTCTG | 4209 |
| 298 | AAGCAGAC CUGAUGAG GCCGUUAGGC CGAA ICUGAGCA | 11273 | TGCTCAGC T GTCTGCTT | 4210 |
| 302 | UGAGAAGC CUGAUGAG GCCGUUAGGC CGAA IACAGCUG | 11274 | CAGCTGTC T GCTTCTCA | 4211 |
| 305 | CUGUGAGA CUGAUGAG GCCGUUAGGC CGAA ICAGACAG | 11275 | CTGTCTGC T TCTCACAG | 4212 |
| 308 | AUCCUGUG CUGAUGAG GCCGUUAGGC CGAA IAAGCAGA | 11276 | TCTGCTTC T CACAGGAT | 4213 |
| 310 | AGAUCCUG CUGAUGAG GCCGUUAGGC CGAA IAGAAGCA | 11277 | TGCTTCTC A CAGGATCT | 4214 |
| 312 | CUAGAUCC CUGAUGAG GCCGUUAGGC CGAA IUGAGAAG | 11278 | CTTCTCAC A GGATCTAG | 4215 |

204

| | | | | |
|---|---|---|---|---|
| 318 | CCUGAACU CUGAUGAG GCCGUUAGGC CGAA IAUCCUGU | 11279 | ACAGGATC T AGTTCAGG | 4216 |
| 324 | UUUGAACC CUGAUGAG GCCGUUAGGC CGAA IAACUAGA | 11280 | TCTAGTTC A GGTTCAAA | 4217 |
| 330 | UUUAAUUU CUGAUGAG GCCGUUAGGC CGAA IAACCUGA | 11281 | TCAGGTTC A AAATTAAA | 4218 |
| 344 | UCAGUUCA CUGAUGAG GCCGUUAGGC CGAA IAUCUUUU | 11282 | AAAAGATC C TGAACTGA | 4219 |
| 345 | CUCAGUUC CUGAUGAG GCCGUUAGGC CGAA IGAUCUUU | 11283 | AAAGATCC T GAACTGAG | 4220 |
| 350 | UUAAACUC CUGAUGAG GCCGUUAGGC CGAA IUUCAGGA | 11284 | TCCTGAAC T GAGTTTAA | 4221 |
| 364 | GUGCUGGG CUGAUGAG GCCGUUAGGC CGAA ICCUUUUA | 11285 | TAAAAGGC A CCCAGCAC | 4222 |
| 366 | AUGUGCUG CUGAUGAG GCCGUUAGGC CGAA IUGCCUUU | 11286 | AAAGGCAC C CAGCACAT | 4223 |
| 367 | GAUGUGCU CUGAUGAG GCCGUUAGGC CGAA IGUGCCUU | 11287 | AAGGCACC C AGCACATC | 4224 |
| 368 | UGAUGUGC CUGAUGAG GCCGUUAGGC CGAA IGGUGCCU | 11288 | AGGCACCC A GCACATCA | 4225 |
| 371 | GCAUGAUG CUGAUGAG GCCGUUAGGC CGAA ICUGGGUG | 11289 | CACCCAGC A CATCATGC | 4226 |
| 373 | UUGCAUGA CUGAUGAG GCCGUUAGGC CGAA IUGCUGGG | 11290 | CCCAGCAC A TCATGCAA | 4227 |
| 376 | UGCUUGCA CUGAUGAG GCCGUUAGGC CGAA IAUGUGCU | 11291 | AGCACATC A TGCAAGCA | 4228 |
| 380 | GGCCUGCU CUGAUGAG GCCGUUAGGC CGAA ICAUGAUG | 11292 | CATCATGC A AGCAGGCC | 4229 |
| 384 | GUCUGGCC CUGAUGAG GCCGUUAGGC CGAA ICUUGCAU | 11293 | ATGCAAGC A GGCCAGAC | 4230 |
| 388 | CAGUGUCU CUGAUGAG GCCGUUAGGC CGAA ICCUGCUU | 11294 | AAGCAGGC C AGACACTG | 4231 |
| 389 | GCAGUGUC CUGAUGAG GCCGUUAGGC CGAA IGCCUGCU | 11295 | AGCAGGCC A GACACTGC | 4232 |
| 393 | AGAUGCAG CUGAUGAG GCCGUUAGGC CGAA IUCUGGCC | 11296 | GGCCAGAC A CTGCATCT | 4233 |
| 395 | GGAGAUGC CUGAUGAG GCCGUUAGGC CGAA IUGUCUGG | 11297 | CCAGACAC T GCATCTCC | 4234 |
| 398 | AUUGGAGA CUGAUGAG GCCGUUAGGC CGAA ICAGUGUC | 11298 | GACACTGC A TCTCCAAT | 4235 |
| 401 | UGCAUUGG CUGAUGAG GCCGUUAGGC CGAA IAUGCAGU | 11299 | ACTGCATC T CCAATGCA | 4236 |
| 403 | CCUGCAUU CUGAUGAG GCCGUUAGGC CGAA IAGAUGCA | 11300 | TGCATCTC C AATGCAGG | 4237 |
| 404 | CCCUGCAU CUGAUGAG GCCGUUAGGC CGAA IGAGAUGC | 11301 | GCATCTCC A ATGCAGGG | 4238 |
| 409 | UUCCCCCC CUGAUGAG GCCGUUAGGC CGAA ICAUUGGA | 11302 | TCCAATGC A GGGGGGAA | 4239 |
| 420 | UUAUGGGC CUGAUGAG GCCGUUAGGC CGAA ICUUCCCC | 11303 | GGGGAAGC A GCCCATAA | 4240 |
| 423 | CAUUUAUG CUGAUGAG GCCGUUAGGC CGAA ICUGCUUC | 11304 | GAAGCAGC C CATAAATG | 4241 |
| 424 | CCAUUUAU CUGAUGAG GCCGUUAGGC CGAA IGCUGCUU | 11305 | AAGCAGCC C ATAAATGG | 4242 |
| 425 | ACCAUUUA CUGAUGAG GCCGUUAGGC CGAA IGGCUGCU | 11306 | AGCAGCCC A TAAATGGT | 4243 |
| 435 | UCAGGCAA CUGAUGAG GCCGUUAGGC CGAA IACCAUUU | 11307 | AAATGGTC T TTGCCTGA | 4244 |
| 440 | CCAUUUCA CUGAUGAG GCCGUUAGGC CGAA ICAAAGAC | 11308 | GTCTTTGC C TGAAATGG | 4245 |
| 441 | ACCAUUUC CUGAUGAG GCCGUUAGGC CGAA IGCAAAGA | 11309 | TCTTTGCC T GAAATGGT | 4246 |
| 470 | UUAUGCUC CUGAUGAG GCCGUUAGGC CGAA ICCUUUCG | 11310 | CGAAAGGC T GAGCATAA | 4247 |
| 475 | UUUAGUUA CUGAUGAG GCCGUUAGGC CGAA ICUCAGCC | 11311 | GGCTGAGC A TAACTAAA | 4248 |

| | | | | |
|---|---|---|---|---|
| 480 | GCAGAUUU CUGAUGAG GCCGUUAGGC CGAA IUUAUGCU | 11312 | AGCATAAC T AAATCTGC | 4249 |
| 486 | CCACAGGC CUGAUGAG GCCGUUAGGC CGAA IAUUUAGU | 11313 | ACTAAATC T GCCTGTGG | 4250 |
| 489 | CUUCCACA CUGAUGAG GCCGUUAGGC CGAA ICAGAUUU | 11314 | AAATCTGC C TGTGGAAG | 4251 |
| 490 | UCUUCCAC CUGAUGAG GCCGUUAGGC CGAA IGCAGAUU | 11315 | AATCTGCC T GTGGAAGA | 4252 |
| 505 | GAAUUGUU CUGAUGAG GCCGUUAGGC CGAA ICCAUUUC | 11316 | GAAATGGC A AACAATTC | 4253 |
| 509 | UGCAGAAU CUGAUGAG GCCGUUAGGC CGAA IUUUGCCA | 11317 | TGGCAAAC A ATTCTGCA | 4254 |
| 514 | AGUACUGC CUGAUGAG GCCGUUAGGC CGAA IAAUUGUU | 11318 | AACAATTC T GCAGTACT | 4255 |
| 517 | UAAAGUAC CUGAUGAG GCCGUUAGGC CGAA ICAGAAUU | 11319 | AATTCTGC A GTACTTTA | 4256 |
| 522 | AAGGUUAA CUGAUGAG GCCGUUAGGC CGAA IUACUGCA | 11320 | TGCAGTAC T TTAACCTT | 4257 |
| 528 | GUGUUCAA CUGAUGAG GCCGUUAGGC CGAA IUUAAAGU | 11321 | ACTTTAAC C TTGAACAC | 4258 |
| 529 | UGUGUUCA CUGAUGAG GCCGUUAGGC CGAA IGUUAAAG | 11322 | CTTTAACC T TGAACACA | 4259 |
| 535 | UUGAGCUG CUGAUGAG GCCGUUAGGC CGAA IUUCAAGG | 11323 | CCTTGAAC A CAGCTCAA | 4260 |
| 537 | GCUUGAGC CUGAUGAG GCCGUUAGGC CGAA IUGUUCAA | 11324 | TTGAACAC A GCTCAAGC | 4261 |
| 540 | UUUGCUUG CUGAUGAG GCCGUUAGGC CGAA ICUGUGUU | 11325 | AACACAGC T CAAGCAAA | 4262 |
| 542 | GGUUUGCU CUGAUGAG GCCGUUAGGC CGAA IAGCUGUG | 11326 | CACAGCTC A AGCAAACC | 4263 |
| 546 | GUGUGGUU CUGAUGAG GCCGUUAGGC CGAA ICUUGAGC | 11327 | GCTCAAGC A AACCACAC | 4264 |
| 550 | GCCAGUGU CUGAUGAG GCCGUUAGGC CGAA IUUUGCUU | 11328 | AAGCAAAC C ACACTGGC | 4265 |
| 551 | AGCCAGUG CUGAUGAG GCCGUUAGGC CGAA IGUUUGCU | 11329 | AGCAAACC A CACTGGCT | 4266 |
| 553 | GAAGCCAG CUGAUGAG GCCGUUAGGC CGAA IUGGUUUG | 11330 | CAAACCAC A CTGGCTTC | 4267 |
| 555 | UAGAAGCC CUGAUGAG GCCGUUAGGC CGAA IUGUGGUU | 11331 | AACCACAC T GGCTTCTA | 4268 |
| 559 | GCUGUAGA CUGAUGAG GCCGUUAGGC CGAA ICCAGUGU | 11332 | ACACTGGC T TCTACAGC | 4269 |
| 562 | GCAGCUGU CUGAUGAG GCCGUUAGGC CGAA IAAGCCAG | 11333 | CTGGCTTC T ACAGCTGC | 4270 |
| 565 | UUUGCAGC CUGAUGAG GCCGUUAGGC CGAA IUAGAAGC | 11334 | GCTTCTAC A GCTGCAAA | 4271 |
| 568 | AUAUUUGC CUGAUGAG GCCGUUAGGC CGAA ICUGUAGA | 11335 | TCTACAGC T GCAAATAT | 4272 |
| 571 | UAGAUAUU CUGAUGAG GCCGUUAGGC CGAA ICAGCUGU | 11336 | ACAGCTGC A AATATCTA | 4273 |
| 578 | GUACAGCU CUGAUGAG GCCGUUAGGC CGAA IAUAUUUG | 11337 | CAAATATC T AGCTGTAC | 4274 |
| 582 | GUAGGUAC CUGAUGAG GCCGUUAGGC CGAA ICUAGAUA | 11338 | TATCTAGC T GTACCTAC | 4275 |
| 587 | UUGAAGUA CUGAUGAG GCCGUUAGGC CGAA IUACAGCU | 11339 | AGCTGTAC C TACTTCAA | 4276 |
| 588 | UUUGAAGU CUGAUGAG GCCGUUAGGC CGAA IGUACAGC | 11340 | GCTGTACC T ACTTCAAA | 4277 |
| 591 | UUCUUUGA CUGAUGAG GCCGUUAGGC CGAA IUAGGUAC | 11341 | GTACCTAC T TCAAAGAA | 4278 |
| 594 | UUCUUCUU CUGAUGAG GCCGUUAGGC CGAA IAAGUAGG | 11342 | CCTACTTC A AAGAAGAA | 4279 |
| 609 | GCAGAUUC CUGAUGAG GCCGUUAGGC CGAA IUUUCCUU | 11343 | AAGGAAAC A GAATCTGC | 4280 |
| 615 | UAGAUUGC CUGAUGAG GCCGUUAGGC CGAA IAUUCUGU | 11344 | ACAGAATC T GCAATCTA | 4281 |

| | | | | |
|---|---|---|---|---|
| 618 | AUAUAGAU CUGAUGAG GCCGUUAGGC CGAA ICAGAUUC | 11345 | GAATCTGC A ATCTATAT | 4282 |
| 622 | AAAUAUAU CUGAUGAG GCCGUUAGGC CGAA IAUUGCAG | 11346 | CTGCAATC T ATATATTT | 4283 |
| 642 | GGUCUACC CUGAUGAG GCCGUUAGGC CGAA IUAUCACU | 11347 | AGTGATAC A GGTAGACC | 4284 |
| 650 | CUACGAAA CUGAUGAG GCCGUUAGGC CGAA IUCUACCU | 11348 | AGGTAGAC C TTTCGTAG | 4285 |
| 651 | UCUACGAA CUGAUGAG GCCGUUAGGC CGAA IGUCUACC | 11349 | GGTAGACC T TTCGTAGA | 4286 |
| 667 | GAUUUCAC CUGAUGAG GCCGUUAGGC CGAA IUACAUCU | 11350 | AGATGTAC A GTGAAATC | 4287 |
| 676 | AAUUUCGG CUGAUGAG GCCGUUAGGC CGAA IAUUUCAC | 11351 | GTGAAATC C CCGAAATT | 4288 |
| 677 | UAAUUUCG CUGAUGAG GCCGUUAGGC CGAA IGAUUUCA | 11352 | TGAAATCC C CGAAATTA | 4289 |
| 678 | AUAAUUUC CUGAUGAG GCCGUUAGGC CGAA IGGAUUUC | 11353 | GAAATCCC C GAAATTAT | 4290 |
| 689 | CAGUCAUG CUGAUGAG GCCGUUAGGC CGAA IUAUAAUU | 11354 | AATTATAC A CATGACTG | 4291 |
| 691 | UUCAGUCA CUGAUGAG GCCGUUAGGC CGAA IUGUAUAA | 11355 | TTATACAC A TGACTGAA | 4292 |
| 696 | CUUCCUUC CUGAUGAG GCCGUUAGGC CGAA IUCAUGUG | 11356 | CACATGAC T GAAGGAAG | 4293 |
| 710 | GAAUGACG CUGAUGAG GCCGUUAGGC CGAA ICUCCCUU | 11357 | AAGGGAGC T CGTCATTC | 4294 |
| 715 | GCAGGGAA CUGAUGAG GCCGUUAGGC CGAA IACGAGCU | 11358 | AGCTCGTC A TTCCCTGC | 4295 |
| 719 | CCCGGCAG CUGAUGAG GCCGUUAGGC CGAA IAAUGACG | 11359 | CGTCATTC C CTGCCGGG | 4296 |
| 720 | ACCCGGCA CUGAUGAG GCCGUUAGGC CGAA IGAAUGAC | 11360 | GTCATTCC C TGCCGGGT | 4297 |
| 721 | AACCCGGC CUGAUGAG GCCGUUAGGC CGAA IGGAAUGA | 11361 | TCATTCCC T GCCGGGTT | 4298 |
| 724 | CGUAACCC CUGAUGAG GCCGUUAGGC CGAA ICAGGGAA | 11362 | TTCCCTGC C GGGTTACG | 4299 |
| 735 | AUGUUAGG CUGAUGAG GCCGUUAGGC CGAA IACGUAAC | 11363 | GTTACGTC A CCTAACAT | 4300 |
| 737 | UGAUGUUA CUGAUGAG GCCGUUAGGC CGAA IUGACGUA | 11364 | TACGTCAC C TAACATCA | 4301 |
| 738 | GUGAUGUU CUGAUGAG GCCGUUAGGC CGAA IGUGACGU | 11365 | ACGTCACC T AACATCAC | 4302 |
| 742 | AACAGUGA CUGAUGAG GCCGUUAGGC CGAA IUUAGGUG | 11366 | CACCTAAC A TCACTGTT | 4303 |
| 745 | AGUAACAG CUGAUGAG GCCGUUAGGC CGAA IAUGUUAG | 11367 | CTAACATC A CTGTTACT | 4304 |
| 747 | AAAGUAAC CUGAUGAG GCCGUUAGGC CGAA IUGAUGUU | 11368 | AACATCAC T GTTACTTT | 4305 |
| 753 | UUUUUUAA CUGAUGAG GCCGUUAGGC CGAA IUAACAGU | 11369 | ACTGTTAC T TTAAAAAA | 4306 |
| 767 | UGUCAAGU CUGAUGAG GCCGUUAGGC CGAA IAAACUUU | 11370 | AAAGTTTC C ACTTGACA | 4307 |
| 768 | GUGUCAAG CUGAUGAG GCCGUUAGGC CGAA IGAAACUU | 11371 | AAGTTTCC A CTTGACAC | 4308 |
| 770 | AAGUGUCA CUGAUGAG GCCGUUAGGC CGAA IUGGAAAC | 11372 | GTTTCCAC T TGACACTT | 4309 |
| 775 | GAUCAAAG CUGAUGAG GCCGUUAGGC CGAA IUCAAGUG | 11373 | CACTTGAC A CTTTGATC | 4310 |
| 777 | GGGAUCAA CUGAUGAG GCCGUUAGGC CGAA IUGUCAAG | 11374 | CTTGACAC T TTGATCCC | 4311 |
| 784 | UCCAUCAG CUGAUGAG GCCGUUAGGC CGAA IAUCAAAG | 11375 | CTTTGATC C CTGATGGA | 4312 |
| 785 | UUCCAUCA CUGAUGAG GCCGUUAGGC CGAA IGAUCAAA | 11376 | TTTGATCC C TGATGGAA | 4313 |
| 786 | UUUCCAUC CUGAUGAG GCCGUUAGGC CGAA IGGAUCAA | 11377 | TTGATCCC T GATGGAAA | 4314 |

| | | | | | |
|---|---|---|---|---|---|
| 799 | CCAGAUUA CUGAUGAG GCCGUUAGGC CGAA ICGUUUUC | 11378 | GAAAACGC A TAATCTGG | 4315 |
| 805 | ACUGUCCC CUGAUGAG GCCGUUAGGC CGAA IAUUAUGC | 11379 | GCATAATC T GGGACAGT | 4316 |
| 811 | CUUUCUAC CUGAUGAG GCCGUUAGGC CGAA IUCCCAGA | 11380 | TCTGGGAC A GTAGAAAG | 4317 |
| 823 | UAUGAUGA CUGAUGAG GCCGUUAGGC CGAA ICCCUUUC | 11381 | GAAAGGGC T TCATCATA | 4318 |
| 826 | UGAUAUGA CUGAUGAG GCCGUUAGGC CGAA IAAGCCCU | 11382 | AGGGCTTC A TCATATCA | 4319 |
| 829 | AUUUGAUA CUGAUGAG GCCGUUAGGC CGAA IAUGAAGC | 11383 | GCTTCATC A TATCAAAT | 4320 |
| 834 | GUUGCAUU CUGAUGAG GCCGUUAGGC CGAA IAUAUGAU | 11384 | ATCATATC A AATGCAAC | 4321 |
| 840 | UUGUACGU CUGAUGAG GCCGUUAGGC CGAA ICAUUUGA | 11385 | TCAAATGC A ACGTACAA | 4322 |
| 847 | UAUUUCUU CUGAUGAG GCCGUUAGGC CGAA IUACGUUG | 11386 | CAACGTAC A AAGAAATA | 4323 |
| 860 | AGGUCAGA CUGAUGAG GCCGUUAGGC CGAA ICCCUAUU | 11387 | AATAGGGC T TCTGACCT | 4324 |
| 863 | CACAGGUC CUGAUGAG GCCGUUAGGC CGAA IAAGCCCU | 11388 | AGGGCTTC T GACCTGTG | 4325 |
| 867 | GCUUCACA CUGAUGAG GCCGUUAGGC CGAA IUCAGAAG | 11389 | CTTCTGAC C TGTGAAGC | 4326 |
| 868 | UGCUUCAC CUGAUGAG GCCGUUAGGC CGAA IGUCAGAA | 11390 | TTCTGACC T GTGAAGCA | 4327 |
| 876 | UUGACUGU CUGAUGAG GCCGUUAGGC CGAA ICUUCACA | 11391 | TGTGAAGC A ACAGTCAA | 4328 |
| 879 | CCAUUGAC CUGAUGAG GCCGUUAGGC CGAA IUUGCUUC | 11392 | GAAGCAAC A GTCAATGG | 4329 |
| 883 | AUGCCCAU CUGAUGAG GCCGUUAGGC CGAA IACUGUUG | 11393 | CAACAGTC A ATGGGCAT | 4330 |
| 890 | UAUACAAA CUGAUGAG GCCGUUAGGC CGAA ICCCAUUG | 11394 | CAATGGGC A TTTGTATA | 4331 |
| 903 | AGAUAGUU CUGAUGAG GCCGUUAGGC CGAA IUCUUAUA | 11395 | TATAAGAC A AACTATCT | 4332 |
| 907 | UGUGAGAU CUGAUGAG GCCGUUAGGC CGAA IUUUGUCU | 11396 | AGACAAAC T ATCTCACA | 4333 |
| 911 | GAUGUGUG CUGAUGAG GCCGUUAGGC CGAA IAUAGUUU | 11397 | AAACTATC T CACACATC | 4334 |
| 913 | UCGAUGUG CUGAUGAG GCCGUUAGGC CGAA IAGAUAGU | 11398 | ACTATCTC A CACATCGA | 4335 |
| 915 | UGUCGAUG CUGAUGAG GCCGUUAGGC CGAA IUGAGAUA | 11399 | TATCTCAC A CATCGACA | 4336 |
| 917 | UUUGUCGA CUGAUGAG GCCGUUAGGC CGAA IUGUGAGA | 11400 | TCTCACAC A TCGACAAA | 4337 |
| 923 | UAUUGGUU CUGAUGAG GCCGUUAGGC CGAA IUCGAUGU | 11401 | ACATCGAC A AACCAATA | 4338 |
| 927 | AUUGUAUU CUGAUGAG GCCGUUAGGC CGAA IUUUGUCG | 11402 | CGACAAAC C AATACAAT | 4339 |
| 928 | GAUUGUAU CUGAUGAG GCCGUUAGGC CGAA IGUUUGUC | 11403 | GACAAACC A ATACAATC | 4340 |
| 933 | UCUAUGAU CUGAUGAG GCCGUUAGGC CGAA IUAUUGGU | 11404 | ACCAATAC A ATCATAGA | 4341 |
| 937 | GACAUCUA CUGAUGAG GCCGUUAGGC CGAA IAUUGUAU | 11405 | ATACAATC A TAGATGTC | 4342 |
| 946 | GCUUAUUU CUGAUGAG GCCGUUAGGC CGAA IACAUCUA | 11406 | TAGATGTC C AAATAAGC | 4343 |
| 947 | UGCUUAUU CUGAUGAG GCCGUUAGGC CGAA IGACAUCU | 11407 | AGATGTCC A AATAAGCA | 4344 |
| 955 | GCGUGGUG CUGAUGAG GCCGUUAGGC CGAA ICUUAUUU | 11408 | AAATAAGC A CACCACGC | 4345 |
| 957 | GGGCGUGG CUGAUGAG GCCGUUAGGC CGAA IUGCUUAU | 11409 | ATAAGCAC A CCACGCCC | 4346 |
| 959 | CUGGGCGU CUGAUGAG GCCGUUAGGC CGAA IUGUGCUU | 11410 | AAGCACAC C ACGCCCAG | 4347 |

209

| | | | | |
|---|---|---|---|---|
| 960 | ACUGGGCG CUGAUGAG GCCGUUAGGC CGAA IGUGUGCU | 11411 | AGCACACC A CGCCCAGT | 4348 |
| 964 | UUUGACUG CUGAUGAG GCCGUUAGGC CGAA ICGUGGUG | 11412 | CACCACGC C CAGTCAAA | 4349 |
| 965 | AUUUGACU CUGAUGAG GCCGUUAGGC CGAA IGCGUGGU | 11413 | ACCACGCC C AGTCAAAT | 4350 |
| 966 | AAUUUGAC CUGAUGAG GCCGUUAGGC CGAA IGGCGUGG | 11414 | CCACGCCC A GTCAAATT | 4351 |
| 970 | AAGUAAUU CUGAUGAG GCCGUUAGGC CGAA IACUGGGC | 11415 | GCCCAGTC A AATTACTT | 4352 |
| 977 | GGCCUCUA CUGAUGAG GCCGUUAGGC CGAA IUAAUUUG | 11416 | CAAATTAC T TAGAGGCC | 4353 |
| 985 | AAGAGUAU CUGAUGAG GCCGUUAGGC CGAA ICCUCUAA | 11417 | TTAGAGGC C ATACTCTT | 4354 |
| 986 | CAAGAGUA CUGAUGAG GCCGUUAGGC CGAA IGCCUCUA | 11418 | TAGAGGCC A TACTCTTG | 4355 |
| 990 | AGGACAAG CUGAUGAG GCCGUUAGGC CGAA IUAUGGCC | 11419 | GGCCATAC T CTTGTCCT | 4356 |
| 992 | UGAGGACA CUGAUGAG GCCGUUAGGC CGAA IAGUAUGG | 11420 | CCATACTC T TGTCCTCA | 4357 |
| 997 | ACAAUUGA CUGAUGAG GCCGUUAGGC CGAA IACAAGAG | 11421 | CTCTTGTC C TCAATTGT | 4358 |
| 998 | UACAAUUG CUGAUGAG GCCGUUAGGC CGAA IGACAAGA | 11422 | TCTTGTCC T CAATTGTA | 4359 |
| 1000 | AGUACAAU CUGAUGAG GCCGUUAGGC CGAA IAGGACAA | 11423 | TTGTCCTC A ATTGTACT | 4360 |
| 1008 | GUGGUAGC CUGAUGAG GCCGUUAGGC CGAA IUACAAUU | 11424 | AATTGTAC T GCTACCAC | 4361 |
| 1011 | GGAGUGGU CUGAUGAG GCCGUUAGGC CGAA ICAGUACA | 11425 | TGTACTGC T ACCACTCC | 4362 |
| 1014 | AAGGGAGU CUGAUGAG GCCGUUAGGC CGAA IUAGCAGU | 11426 | ACTGCTAC C ACTCCCTT | 4363 |
| 1015 | CAAGGGAG CUGAUGAG GCCGUUAGGC CGAA IGUAGCAG | 11427 | CTGCTACC A CTCCCTTG | 4364 |
| 1017 | UUCAAGGG CUGAUGAG GCCGUUAGGC CGAA IUGGUAGC | 11428 | GCTACCAC T CCCTTGAA | 4365 |
| 1019 | UGUUCAAG CUGAUGAG GCCGUUAGGC CGAA IAGUGGUA | 11429 | TACCACTC C CTTGAACA | 4366 |
| 1020 | GUGUUCAA CUGAUGAG GCCGUUAGGC CGAA IGAGUGGU | 11430 | ACCACTCC C TTGAACAC | 4367 |
| 1021 | CGUGUUCA CUGAUGAG GCCGUUAGGC CGAA IGGAGUGG | 11431 | CCACTCCC T TGAACACG | 4368 |
| 1027 | AACUCUCG CUGAUGAG GCCGUUAGGC CGAA IUUCAAGG | 11432 | CCTTGAAC A CGAGAGTT | 4369 |
| 1037 | AGGUCAUU CUGAUGAG GCCGUUAGGC CGAA IAACUCUC | 11433 | GAGAGTTC A AATGACCT | 4370 |
| 1044 | UAACUCCA CUGAUGAG GCCGUUAGGC CGAA IUCAUUUG | 11434 | CAAATGAC C TGGAGTTA | 4371 |
| 1045 | GUAACUCC CUGAUGAG GCCGUUAGGC CGAA IGUCAUUU | 11435 | AAATGACC T GGAGTTAC | 4372 |
| 1054 | UUCAUCAG CUGAUGAG GCCGUUAGGC CGAA IUAACUCC | 11436 | GGAGTTAC C CTGATGAA | 4373 |
| 1055 | UUUCAUCA CUGAUGAG GCCGUUAGGC CGAA IGUAACUC | 11437 | GAGTTACC C TGATGAAA | 4374 |
| 1056 | UUUUCAUC CUGAUGAG GCCGUUAGGC CGAA IGGUAACU | 11438 | AGTTACCC T GATGAAAA | 4375 |
| 1077 | CUUACGGA CUGAUGAG GCCGUUAGGC CGAA ICUCUCUU | 11439 | AAGAGAGC T TCCGTAAG | 4376 |
| 1080 | CGCCUUAC CUGAUGAG GCCGUUAGGC CGAA IAAGCUCU | 11440 | AGAGCTTC C GTAAGGCG | 4377 |
| 1099 | AUUGCUUU CUGAUGAG GCCGUUAGGC CGAA IUCAAUUC | 11441 | GAATTGAC C AAAGCAAT | 4378 |
| 1100 | AAUUGCUU CUGAUGAG GCCGUUAGGC CGAA IGUCAAUU | 11442 | AATTGACC A AAGCAATT | 4379 |
| 1105 | AUGGGAAU CUGAUGAG GCCGUUAGGC CGAA ICUUUGGU | 11443 | ACCAAAGC A ATTCCCAT | 4380 |

| | | | | |
|---|---|---|---|---|
| 1110 | UUGGCAUG CUGAUGAG GCCGUUAGGC CGAA IAAUUGCU | 11444 | AGCAATTC C CATGCCAA | 4381 |
| 1111 | GUUGGCAU CUGAUGAG GCCGUUAGGC CGAA IGAAUUGC | 11445 | GCAATTCC C ATGCCAAC | 4382 |
| 1112 | UGUUGGCA CUGAUGAG GCCGUUAGGC CGAA IGGAAUUG | 11446 | CAATTCCC A TGCCAACA | 4383 |
| 1116 | AAUAUGUU CUGAUGAG GCCGUUAGGC CGAA ICAUGGGA | 11447 | TCCCATGC C AACATATT | 4384 |
| 1117 | GAAUAUGU CUGAUGAG GCCGUUAGGC CGAA IGCAUGGG | 11448 | CCCATGCC A ACATATTC | 4385 |
| 1120 | GUAGAAUA CUGAUGAG GCCGUUAGGC CGAA IUUGGCAU | 11449 | ATGCCAAC A TATTCTAC | 4386 |
| 1126 | AACACUGU CUGAUGAG GCCGUUAGGC CGAA IAAUAUGU | 11450 | ACATATTC T ACAGTGTT | 4387 |
| 1129 | AAGAACAC CUGAUGAG GCCGUUAGGC CGAA IUAGAAUA | 11451 | TATTCTAC A GTGTTCTT | 4388 |
| 1136 | CAAUAGUA CUGAUGAG GCCGUUAGGC CGAA IAACACUG | 11452 | CAGTGTTC T TACTATTG | 4389 |
| 1140 | UUGUCAAU CUGAUGAG GCCGUUAGGC CGAA IUAAGAAC | 11453 | GTTCTTAC T ATTGACAA | 4390 |
| 1147 | CUGCAUUU CUGAUGAG GCCGUUAGGC CGAA IUCAAUAG | 11454 | CTATTGAC A AAATGCAG | 4391 |
| 1154 | CUUUGUUC CUGAUGAG GCCGUUAGGC CGAA ICAUUUUG | 11455 | CAAAATGC A GAACAAAG | 4392 |
| 1159 | UUUGUCUU CUGAUGAG GCCGUUAGGC CGAA IUUCUGCA | 11456 | TGCAGAAC A AAGACAAA | 4393 |
| 1165 | AAGUCCUU CUGAUGAG GCCGUUAGGC CGAA IUCUUUGU | 11457 | ACAAAGAC A AAGGACTT | 4394 |
| 1172 | AAGUAUAA CUGAUGAG GCCGUUAGGC CGAA IUCCUUUG | 11458 | CAAAGGAC T TTATACTT | 4395 |
| 1179 | ACACGACA CUGAUGAG GCCGUUAGGC CGAA IUAUAAAG | 11459 | CTTTATAC T TGTCGTGT | 4396 |
| 1199 | UGAAUGAU CUGAUGAG GCCGUUAGGC CGAA IUCCACUC | 11460 | GAGTGGAC C ATCATTCA | 4397 |
| 1200 | UUGAAUGA CUGAUGAG GCCGUUAGGC CGAA IGUCCACU | 11461 | AGTGGACC A TCATTCAA | 4398 |
| 1203 | GAUUUGAA CUGAUGAG GCCGUUAGGC CGAA IAUGGUCC | 11462 | GGACCATC A TTCAAATC | 4399 |
| 1207 | AACAGAUU CUGAUGAG GCCGUUAGGC CGAA IAAUGAUG | 11463 | CATCATTC A AATCTGTT | 4400 |
| 1212 | GUGUUAAC CUGAUGAG GCCGUUAGGC CGAA IAUUUGAA | 11464 | TTCAAATC T GTTAACAC | 4401 |
| 1219 | CACUGAGG CUGAUGAG GCCGUUAGGC CGAA IUUAACAG | 11465 | CTGTTAAC A CCTCAGTG | 4402 |
| 1221 | UGCACUGA CUGAUGAG GCCGUUAGGC CGAA IUGUUAAC | 11466 | GTTAACAC C TCAGTGCA | 4403 |
| 1222 | AUGCACUG CUGAUGAG GCCGUUAGGC CGAA IGUGUUAA | 11467 | TTAACACC T CAGTGCAT | 4404 |
| 1224 | AUAUGCAC CUGAUGAG GCCGUUAGGC CGAA IAGGUGUU | 11468 | AACACCTC A GTGCATAT | 4405 |
| 1229 | CAUAUAUA CUGAUGAG GCCGUUAGGC CGAA ICACUGAG | 11469 | CTCAGTGC A TATATATG | 4406 |
| 1245 | GUGAUGAA CUGAUGAG GCCGUUAGGC CGAA ICUUUAUC | 11470 | GATAAAGC A TTCATCAC | 4407 |
| 1249 | CACAGUGA CUGAUGAG GCCGUUAGGC CGAA IAAUGCUU | 11471 | AAGCATTC A TCACTGTG | 4408 |
| 1252 | UUUCACAG CUGAUGAG GCCGUUAGGC CGAA IAUGAAUG | 11472 | CATTCATC A CTGTGAAA | 4409 |
| 1254 | UGUUUCAC CUGAUGAG GCCGUUAGGC CGAA IUGAUGAA | 11473 | TTCATCAC T GTGAAACA | 4410 |
| 1262 | GUUUUCGA CUGAUGAG GCCGUUAGGC CGAA IUUUCACA | 11474 | TGTGAAAC A TCGAAAAC | 4411 |
| 1271 | GCACCUGC CUGAUGAG GCCGUUAGGC CGAA IUUUUCGA | 11475 | TCGAAAAC A GCAGGTGC | 4412 |
| 1274 | CAAGCACC CUGAUGAG GCCGUUAGGC CGAA ICUGUUUU | 11476 | AAAACAGC A GGTGCTTG | 4413 |

211

| | | | | |
|---|---|---|---|---|
| 1280 | CGGUUUCA CUGAUGAG GCCGUUAGGC CGAA ICACCUGC | 11477 | GCAGGTGC T TGAAACCG | 4414 |
| 1287 | CCAGCUAC CUGAUGAG GCCGUUAGGC CGAA IUUUCAAG | 11478 | CTTGAAAC C GTAGCTGG | 4415 |
| 1293 | CGCUUGCC CUGAUGAG GCCGUUAGGC CGAA ICUACGGU | 11479 | ACCGTAGC T GGCAAGCG | 4416 |
| 1297 | AGACCGCU CUGAUGAG GCCGUUAGGC CGAA ICCAGCUA | 11480 | TAGCTGGC A AGCGGTCT | 4417 |
| 1305 | AGCCGGUA CUGAUGAG GCCGUUAGGC CGAA IACCGCUU | 11481 | AAGCGGTC T TACCGGCT | 4418 |
| 1309 | AGAGAGCC CUGAUGAG GCCGUUAGGC CGAA IUAAGACC | 11482 | GGTCTTAC C GGCTCTCT | 4419 |
| 1313 | UCAUAGAG CUGAUGAG GCCGUUAGGC CGAA ICCGGUAA | 11483 | TTACCGGC T CTCTATGA | 4420 |
| 1315 | UUUCAUAG CUGAUGAG GCCGUUAGGC CGAA IAGCCGGU | 11484 | ACCGGCTC T CTATGAAA | 4421 |
| 1317 | ACUUUCAU CUGAUGAG GCCGUUAGGC CGAA IAGAGCCG | 11485 | CGGCTCTC T ATGAAAGT | 4422 |
| 1332 | GAGGGAAA CUGAUGAG GCCGUUAGGC CGAA ICCUUCAC | 11486 | GTGAAGGC A TTTCCCTC | 4423 |
| 1337 | CCGGCGAG CUGAUGAG GCCGUUAGGC CGAA IAAAUGCC | 11487 | GGCATTTC C CTCGCCGG | 4424 |
| 1338 | UCCGGCGA CUGAUGAG GCCGUUAGGC CGAA IGAAAUGC | 11488 | GCATTTCC C TCGCCGGA | 4425 |
| 1339 | UUCCGGCG CUGAUGAG GCCGUUAGGC CGAA IGGAAAUG | 11489 | CATTTCCC T CGCCGGAA | 4426 |
| 1343 | CAACUUCC CUGAUGAG GCCGUUAGGC CGAA ICGAGGGA | 11490 | TCCCTCGC C GGAAGTTG | 4427 |
| 1373 | CAGUCGCA CUGAUGAG GCCGUUAGGC CGAA IUAACCCA | 11491 | TGGGTTAC C TGCGACTG | 4428 |
| 1374 | UCAGUCGC CUGAUGAG GCCGUUAGGC CGAA IGUAACCC | 11492 | GGGTTACC T GCGACTGA | 4429 |
| 1380 | GAUUUCUC CUGAUGAG GCCGUUAGGC CGAA IUCGCAGG | 11493 | CCTGCGAC T GAGAAATC | 4430 |
| 1389 | UAGCGAGC CUGAUGAG GCCGUUAGGC CGAA IAUUUCUC | 11494 | GAGAAATC T GCTCGCTA | 4431 |
| 1392 | AAAUAGCG CUGAUGAG GCCGUUAGGC CGAA ICAGAUUU | 11495 | AAATCTGC T CGCTATTT | 4432 |
| 1396 | AGUCAAAU CUGAUGAG GCCGUUAGGC CGAA ICGAGCAG | 11496 | CTGCTCGC T ATTTGACT | 4433 |
| 1404 | UAGCCACG CUGAUGAG GCCGUUAGGC CGAA IUCAAAUA | 11497 | TATTTGAC T CGTGGCTA | 4434 |
| 1411 | UAACGAGU CUGAUGAG GCCGUUAGGC CGAA ICCACGAG | 11498 | CTCGTGGC T ACTCGTTA | 4435 |
| 1414 | AAUUAACG CUGAUGAG GCCGUUAGGC CGAA IUAGCCAC | 11499 | GTGGCTAC T CGTTAATT | 4436 |
| 1426 | UACGUCCU CUGAUGAG GCCGUUAGGC CGAA IAUAAUUA | 11500 | TAATTATC A AGGACGTA | 4437 |
| 1437 | UCCUCUUC CUGAUGAG GCCGUUAGGC CGAA IUUACGUC | 11501 | GACGTAAC T GAAGAGGA | 4438 |
| 1449 | UAAUUCCC CUGAUGAG GCCGUUAGGC CGAA ICAUCCUC | 11502 | GAGGATGC A GGGAATTA | 4439 |
| 1461 | AGCAAGAU CUGAUGAG GCCGUUAGGC CGAA IUAUAAUU | 11503 | AATTATAC A ATCTTGCT | 4440 |
| 1465 | GCUCAGCA CUGAUGAG GCCGUUAGGC CGAA IAUUGUAU | 11504 | ATACAATC T TGCTGAGC | 4441 |
| 1469 | UUAUGCUC CUGAUGAG GCCGUUAGGC CGAA ICAAGAUU | 11505 | AATCTTGC T GAGCATAA | 4442 |
| 1474 | CUGUUUUA CUGAUGAG GCCGUUAGGC CGAA ICUCAGCA | 11506 | TGCTGAGC A TAAAACAG | 4443 |
| 1481 | CAUUUGAC CUGAUGAG GCCGUUAGGC CGAA IUUUUAUG | 11507 | CATAAAAC A GTCAAATG | 4444 |
| 1485 | AACACAUU CUGAUGAG GCCGUUAGGC CGAA IACUGUUU | 11508 | AAACAGTC A AATGTGTT | 4445 |
| 1501 | GGCAGUGA CUGAUGAG GCCGUUAGGC CGAA IUUUUUAA | 11509 | TTAAAAAC C TCACTGCC | 4446 |

| | | | | |
|---|---|---|---|---|
| 1502 | UGGCAGUG CUGAUGAG GCCGUUAGGC CGAA IGUUUUUA | 11510 | TAAAAACC T CACTGCCA | 4447 |
| 1504 | AGUGGCAG CUGAUGAG GCCGUUAGGC CGAA IAGGUUUU | 11511 | AAAACCTC A CTGCCACT | 4448 |
| 1506 | AGAGUGGC CUGAUGAG GCCGUUAGGC CGAA IUGAGGUU | 11512 | AACCTCAC T GCCACTCT | 4449 |
| 1509 | AUUAGAGU CUGAUGAG GCCGUUAGGC CGAA ICAGUGAG | 11513 | CTCACTGC C ACTCTAAT | 4450 |
| 1510 | AAUUAGAG CUGAUGAG GCCGUUAGGC CGAA IGCAGUGA | 11514 | TCACTGCC A CTCTAATT | 4451 |
| 1512 | ACAAUUAG CUGAUGAG GCCGUUAGGC CGAA IUGGCAGU | 11515 | ACTGCCAC T CTAATTGT | 4452 |
| 1514 | UGACAAUU CUGAUGAG GCCGUUAGGC CGAA IAGUGGCA | 11516 | TGCCACTC T AATTGTCA | 4453 |
| 1522 | UUUCACAU CUGAUGAG GCCGUUAGGC CGAA IACAAUUA | 11517 | TAATTGTC A ATGTGAAA | 4454 |
| 1532 | AAAUCUGG CUGAUGAG GCCGUUAGGC CGAA IUUUCACA | 11518 | TGTGAAAC C CCAGATTT | 4455 |
| 1533 | UAAAUCUG CUGAUGAG GCCGUUAGGC CGAA IGUUUCAC | 11519 | GTGAAACC C CAGATTTA | 4456 |
| 1534 | GUAAAUCU CUGAUGAG GCCGUUAGGC CGAA IGGUUUCA | 11520 | TGAAACCC C AGATTTAC | 4457 |
| 1535 | CGUAAAUC CUGAUGAG GCCGUUAGGC CGAA IGGGUUUC | 11521 | GAAACCCC A GATTTACG | 4458 |
| 1551 | GAUGACAC CUGAUGAG GCCGUUAGGC CGAA ICCUUUUC | 11522 | GAAAAGGC C GTGTCATC | 4459 |
| 1557 | GGAAACGA CUGAUGAG GCCGUUAGGC CGAA IACACGGC | 11523 | GCCGTGTC A TCGTTTCC | 4460 |
| 1565 | CCGGGUCU CUGAUGAG GCCGUUAGGC CGAA IAAACGAU | 11524 | ATCGTTTC C AGACCCGG | 4461 |
| 1566 | GCCGGGUC CUGAUGAG GCCGUUAGGC CGAA IGAAACGA | 11525 | TCGTTTCC A GACCCGGC | 4462 |
| 1570 | GAGAGCCG CUGAUGAG GCCGUUAGGC CGAA IUCUGGAA | 11526 | TTCCAGAC C CGGCTCTC | 4463 |
| 1571 | AGAGAGCC CUGAUGAG GCCGUUAGGC CGAA IGUCUGGA | 11527 | TCCAGACC C GGCTCTCT | 4464 |
| 1575 | GGGUAGAG CUGAUGAG GCCGUUAGGC CGAA ICCGGGUC | 11528 | GACCCGGC T CTCTACCC | 4465 |
| 1577 | GUGGGUAG CUGAUGAG GCCGUUAGGC CGAA IAGCCGGG | 11529 | CCCGGCTC T CTACCCAC | 4466 |
| 1579 | CAGUGGGU CUGAUGAG GCCGUUAGGC CGAA IAGAGCCG | 11530 | CGGCTCTC T ACCCACTG | 4467 |
| 1582 | GCCCAGUG CUGAUGAG GCCGUUAGGC CGAA IUAGAGAG | 11531 | CTCTCTAC C CACTGGGC | 4468 |
| 1583 | UGCCCAGU CUGAUGAG GCCGUUAGGC CGAA IGUAGAGA | 11532 | TCTCTACC C ACTGGGCA | 4469 |
| 1584 | CUGCCCAG CUGAUGAG GCCGUUAGGC CGAA IGGUAGAG | 11533 | CTCTACCC A CTGGGCAG | 4470 |
| 1586 | UGCUGCCC CUGAUGAG GCCGUUAGGC CGAA IUGGGUAG | 11534 | CTACCCAC T GGGCAGCA | 4471 |
| 1591 | UUGUCUGC CUGAUGAG GCCGUUAGGC CGAA ICCCAGUG | 11535 | CACTGGGC A GCAGACAA | 4472 |
| 1594 | GAUUUGUC CUGAUGAG GCCGUUAGGC CGAA ICUGCCCA | 11536 | TGGGCAGC A GACAAATC | 4473 |
| 1598 | UCAGGAUU CUGAUGAG GCCGUUAGGC CGAA IUCUGCUG | 11537 | CAGCAGAC A AATCCTGA | 4474 |
| 1603 | ACAAGUCA CUGAUGAG GCCGUUAGGC CGAA IAUUUGUC | 11538 | GACAAATC C TGACTTGT | 4475 |
| 1604 | UACAAGUC CUGAUGAG GCCGUUAGGC CGAA IGAUUUGU | 11539 | ACAAATCC T GACTTGTA | 4476 |
| 1608 | GCGGUACA CUGAUGAG GCCGUUAGGC CGAA IUCAGGAU | 11540 | ATCCTGAC T TGTACCGC | 4477 |
| 1614 | CCAUAUGC CUGAUGAG GCCGUUAGGC CGAA IUACAAGU | 11541 | ACTTGTAC C GCATATGG | 4478 |
| 1617 | AUACCAUA CUGAUGAG GCCGUUAGGC CGAA ICGGUACA | 11542 | TGTACCGC A TATGGTAT | 4479 |

| | | | | |
|---|---|---|---|---|
| 1627 | AGGUUGAG CUGAUGAG GCCGUUAGGC CGAA IAUACCAU | 11543 | ATGGTATC C CTCAACCT | 4480 |
| 1628 | UAGGUUGA CUGAUGAG GCCGUUAGGC CGAA IGAUACCA | 11544 | TGGTATCC C TCAACCTA | 4481 |
| 1629 | GUAGGUUG CUGAUGAG GCCGUUAGGC CGAA IGGAUACC | 11545 | GGTATCCC T CAACCTAC | 4482 |
| 1631 | UUGUAGGU CUGAUGAG GCCGUUAGGC CGAA IAGGGAUA | 11546 | TATCCCTC A ACCTACAA | 4483 |
| 1634 | UGAUUGUA CUGAUGAG GCCGUUAGGC CGAA IUUGAGGG | 11547 | CCCTCAAC C TACAATCA | 4484 |
| 1635 | UUGAUUGU CUGAUGAG GCCGUUAGGC CGAA IGUUGAGG | 11548 | CCTCAACC T ACAATCAA | 4485 |
| 1638 | CACUUGAU CUGAUGAG GCCGUUAGGC CGAA IUAGGUUG | 11549 | CAACCTAC A ATCAAGTG | 4486 |
| 1642 | GAACCACU CUGAUGAG GCCGUUAGGC CGAA IAUUGUAG | 11550 | CTACAATC A AGTGGTTC | 4487 |
| 1651 | GGGGUGCC CUGAUGAG GCCGUUAGGC CGAA IAACCACU | 11551 | AGTGGTTC T GGCACCCC | 4488 |
| 1655 | UACAGGGG CUGAUGAG GCCGUUAGGC CGAA ICCAGAAC | 11552 | GTTCTGGC A CCCCTGTA | 4489 |
| 1657 | GUUACAGG CUGAUGAG GCCGUUAGGC CGAA IUGCCAGA | 11553 | TCTGGCAC C CCTGTAAC | 4490 |
| 1658 | GGUUACAG CUGAUGAG GCCGUUAGGC CGAA IGUGCCAG | 11554 | CTGGCACC C CTGTAACC | 4491 |
| 1659 | UGGUUACA CUGAUGAG GCCGUUAGGC CGAA IGGUGCCA | 11555 | TGGCACCC C TGTAACCA | 4492 |
| 1660 | AUGGUUAC CUGAUGAG GCCGUUAGGC CGAA IGGGUGCC | 11556 | GGCACCCC T GTAACCAT | 4493 |
| 1666 | AUGAUUAU CUGAUGAG GCCGUUAGGC CGAA IUUACAGG | 11557 | CCTGTAAC C ATAATCAT | 4494 |
| 1667 | AAUGAUUA CUGAUGAG GCCGUUAGGC CGAA IGUUACAG | 11558 | CTGTAACC A TAATCATT | 4495 |
| 1673 | CUUCGGAA CUGAUGAG GCCGUUAGGC CGAA IAUUAUGG | 11559 | CCATAATC A TTCCGAAG | 4496 |
| 1677 | CUUGCUUC CUGAUGAG GCCGUUAGGC CGAA IAAUGAUU | 11560 | AATCATTC C GAAGCAAG | 4497 |
| 1683 | UCACACCU CUGAUGAG GCCGUUAGGC CGAA ICUUCGGA | 11561 | TCCGAAGC A AGGTGTGA | 4498 |
| 1693 | GGAACAAA CUGAUGAG GCCGUUAGGC CGAA IUCACACC | 11562 | GGTGTGAC T TTTGTTCC | 4499 |
| 1701 | UCAUUAUU CUGAUGAG GCCGUUAGGC CGAA IAACAAAA | 11563 | TTTTGTTC C AATAATGA | 4500 |
| 1702 | UUCAUUAU CUGAUGAG GCCGUUAGGC CGAA IGAACAAA | 11564 | TTTGTTCC A ATAATGAA | 4501 |
| 1716 | AGGAUAAA CUGAUGAG GCCGUUAGGC CGAA IACUCUUC | 11565 | GAAGAGTC C TTTATCCT | 4502 |
| 1717 | CAGGAUAA CUGAUGAG GCCGUUAGGC CGAA IGACUCUU | 11566 | AAGAGTCC T TTATCCTG | 4503 |
| 1723 | AGCAUCCA CUGAUGAG GCCGUUAGGC CGAA IAUAAAGG | 11567 | CCTTTATC C TGGATGCT | 4504 |
| 1724 | CAGCAUCC CUGAUGAG GCCGUUAGGC CGAA IGAUAAAG | 11568 | CTTTATCC T GGATGCTG | 4505 |
| 1731 | UUGCUGUC CUGAUGAG GCCGUUAGGC CGAA ICAUCCAG | 11569 | CTGGATGC T GACAGCAA | 4506 |
| 1735 | CAUGUUGC CUGAUGAG GCCGUUAGGC CGAA IUCAGCAU | 11570 | ATGCTGAC A GCAACATG | 4507 |
| 1738 | UCCCAUGU CUGAUGAG GCCGUUAGGC CGAA ICUGUCAG | 11571 | CTGACAGC A ACATGGGA | 4508 |
| 1741 | GUUUCCCA CUGAUGAG GCCGUUAGGC CGAA IUUGCUGU | 11572 | ACAGCAAC A TGGGAAAC | 4509 |
| 1750 | CUCAAUUC CUGAUGAG GCCGUUAGGC CGAA IUUUCCCA | 11573 | TGGGAAAC A GAATTGAG | 4510 |
| 1762 | CUGAGUGA CUGAUGAG GCCGUUAGGC CGAA ICUCUCAA | 11574 | TTGAGAGC A TCACTCAG | 4511 |
| 1765 | GCGCUGAG CUGAUGAG GCCGUUAGGC CGAA IAUGCUCU | 11575 | AGAGCATC A CTCAGCGC | 4512 |

| | | | | |
|---|---|---|---|---|
| 1767 | AUGCGCUG CUGAUGAG GCCGUUAGGC CGAA IUGAUGCU | 11576 | AGCATCAC T CAGCGCAT | 4513 |
| 1769 | CCAUGCGC CUGAUGAG GCCGUUAGGC CGAA IAGUGAUG | 11577 | CATCACTC A GCGCATGG | 4514 |
| 1774 | UAUUGCCA CUGAUGAG GCCGUUAGGC CGAA ICGCUGAG | 11578 | CTCAGCGC A TGGCAATA | 4515 |
| 1779 | UCUAUUAU CUGAUGAG GCCGUUAGGC CGAA ICCAUGCG | 11579 | CGCATGGC A ATAATAGA | 4516 |
| 1806 | AAGGUGCU CUGAUGAG GCCGUUAGGC CGAA ICCAUCUU | 11580 | AAGATGGC T AGCACCTT | 4517 |
| 1810 | AACCAAGG CUGAUGAG GCCGUUAGGC CGAA ICUAGCCA | 11581 | TGGCTAGC A CCTTGGTT | 4518 |
| 1812 | ACAACCAA CUGAUGAG GCCGUUAGGC CGAA IUGCUAGC | 11582 | GCTAGCAC C TTGGTTGT | 4519 |
| 1813 | CACAACCA CUGAUGAG GCCGUUAGGC CGAA IGUGCUAG | 11583 | CTAGCACC T TGGTTGTG | 4520 |
| 1824 | CUAGAGUC CUGAUGAG GCCGUUAGGC CGAA ICCACAAC | 11584 | GTTGTGGC T GACTCTAG | 4521 |
| 1828 | AAUUCUAG CUGAUGAG GCCGUUAGGC CGAA IUCAGCCA | 11585 | TGGCTGAC T CTAGAATT | 4522 |
| 1830 | GAAAUUCU CUGAUGAG GCCGUUAGGC CGAA IAGUCAGC | 11586 | GCTGACTC T AGAATTTC | 4523 |
| 1839 | UAGAUUCC CUGAUGAG GCCGUUAGGC CGAA IAAAUUCU | 11587 | AGAATTTC T GGAATCTA | 4524 |
| 1846 | GCAAAUGU CUGAUGAG GCCGUUAGGC CGAA IAUUCCAG | 11588 | CTGGAATC T ACATTTGC | 4525 |
| 1849 | UAUGCAAA CUGAUGAG GCCGUUAGGC CGAA IUAGAUUC | 11589 | GAATCTAC A TTTGCATA | 4526 |
| 1855 | GGAAGCUA CUGAUGAG GCCGUUAGGC CGAA ICAAAUGU | 11590 | ACATTTGC A TAGCTTCC | 4527 |
| 1860 | UUAUUGGA CUGAUGAG GCCGUUAGGC CGAA ICUAUGCA | 11591 | TGCATAGC T TCCAATAA | 4528 |
| 1863 | ACUUUAUU CUGAUGAG GCCGUUAGGC CGAA IAAGCUAU | 11592 | ATAGCTTC C AATAAAGT | 4529 |
| 1864 | AACUUUAU CUGAUGAG GCCGUUAGGC CGAA IGAAGCUA | 11593 | TAGCTTCC A ATAAAGTT | 4530 |
| 1878 | CUUCCCAC CUGAUGAG GCCGUUAGGC CGAA IUCCCAAC | 11594 | GTTGGGAC T GTGGGAAG | 4531 |
| 1891 | AAAGCUUA CUGAUGAG GCCGUUAGGC CGAA IUUUCUUC | 11595 | GAAGAAAC A TAAGCTTT | 4532 |
| 1897 | GAUAUAAA CUGAUGAG GCCGUUAGGC CGAA ICUUAUGU | 11596 | ACATAAGC T TTTATATC | 4533 |
| 1906 | CACAUCUG CUGAUGAG GCCGUUAGGC CGAA IAUAUAAA | 11597 | TTTATATC A CAGATGTG | 4534 |
| 1908 | GGCACAUC CUGAUGAG GCCGUUAGGC CGAA IUGAUAUA | 11598 | TATATCAC A GATGTGCC | 4535 |
| 1916 | ACCCAUUU CUGAUGAG GCCGUUAGGC CGAA ICACAUCU | 11599 | AGATGTGC C AAATGGGT | 4536 |
| 1917 | AACCCAUU CUGAUGAG GCCGUUAGGC CGAA IGCACAUC | 11600 | GATGTGCC A AATGGGTT | 4537 |
| 1928 | AGUUAACA CUGAUGAG GCCGUUAGGC CGAA IAAACCCA | 11601 | TGGGTTTC A TGTTAACT | 4538 |
| 1936 | UUUUUCCA CUGAUGAG GCCGUUAGGC CGAA IUUAACAU | 11602 | ATGTTAAC T TGGAAAAA | 4539 |
| 1949 | CUUCCGUC CUGAUGAG GCCGUUAGGC CGAA ICAUUUUU | 11603 | AAAAATGC C GACGGAAG | 4540 |
| 1966 | CAGUUUCA CUGAUGAG GCCGUUAGGC CGAA IUCCUCUC | 11604 | GAGAGGAC C TGAAACTG | 4541 |
| 1967 | ACAGUUUC CUGAUGAG GCCGUUAGGC CGAA IGUCCUCU | 11605 | AGAGGACC T GAAACTGT | 4542 |
| 1973 | UGCAAGAC CUGAUGAG GCCGUUAGGC CGAA IUUUCAGG | 11606 | CCTGAAAC T GTCTTGCA | 4543 |
| 1977 | ACUGUGCA CUGAUGAG GCCGUUAGGC CGAA IACAGUUU | 11607 | AAACTGTC T TGCACAGT | 4544 |
| 1981 | GUUAACUG CUGAUGAG GCCGUUAGGC CGAA ICAAGACA | 11608 | TGTCTTGC A CAGTTAAC | 4545 |

| | | | | |
|---|---|---|---|---|
| 1983 | UUGUUAAC CUGAUGAG GCCGUUAGGC CGAA IUGCAAGA | 11609 | TCTTGCAC A GTTAACAA | 4546 |
| 1990 | UAAGAACU CUGAUGAG GCCGUUAGGC CGAA IUUAACUG | 11610 | CAGTTAAC A AGTTCTTA | 4547 |
| 1996 | UCUGUAUA CUGAUGAG GCCGUUAGGC CGAA IAACUUGU | 11611 | ACAAGTTC T TATACAGA | 4548 |
| 2002 | AACGUCUC CUGAUGAG GCCGUUAGGC CGAA IUAUAAGA | 11612 | TCTTATAC A GAGACGTT | 4549 |
| 2013 | AAAAUCCA CUGAUGAG GCCGUUAGGC CGAA IUAACGUC | 11613 | GACGTTAC T TGGATTTT | 4550 |
| 2024 | CUGUCCGC CUGAUGAG GCCGUUAGGC CGAA IUAAAAUC | 11614 | GATTTTAC T GCGGACAG | 4551 |
| 2031 | UUAUUAAC CUGAUGAG GCCGUUAGGC CGAA IUCCGCAG | 11615 | CTGCGGAC A GTTAATAA | 4552 |
| 2041 | CAUUGUUC CUGAUGAG GCCGUUAGGC CGAA IUUAUUAA | 11616 | TTAATAAC A GAACAATG | 4553 |
| 2046 | UAGUGCAU CUGAUGAG GCCGUUAGGC CGAA IUUCUGUU | 11617 | AACAGAAC A ATGCACTA | 4554 |
| 2051 | UACUGUAG CUGAUGAG GCCGUUAGGC CGAA ICAUUGUU | 11618 | AACAATGC A CTACAGTA | 4555 |
| 2053 | AAUACUGU CUGAUGAG GCCGUUAGGC CGAA IUGCAUUG | 11619 | CAATGCAC T ACAGTATT | 4556 |
| 2056 | GCUAAUAC CUGAUGAG GCCGUUAGGC CGAA IUAGUGCA | 11620 | TGCACTAC A GTATTAGC | 4557 |
| 2065 | UUUUUGCU CUGAUGAG GCCGUUAGGC CGAA ICUAAUAC | 11621 | GTATTAGC A AGCAAAAA | 4558 |
| 2069 | CCAUUUUU CUGAUGAG GCCGUUAGGC CGAA ICUUGCUA | 11622 | TAGCAAGC A AAAAATGG | 4559 |
| 2079 | UUAGUGAU CUGAUGAG GCCGUUAGGC CGAA ICCAUUUU | 11623 | AAAATGGC C ATCACTAA | 4560 |
| 2080 | CUUAGUGA CUGAUGAG GCCGUUAGGC CGAA IGCCAUUU | 11624 | AAATGGCC A TCACTAAG | 4561 |
| 2083 | CUCCUUAG CUGAUGAG GCCGUUAGGC CGAA IAUGGCCA | 11625 | TGGCCATC A CTAAGGAG | 4562 |
| 2085 | UGCUCCUU CUGAUGAG GCCGUUAGGC CGAA IUGAUGGC | 11626 | GCCATCAC T AAGGAGCA | 4563 |
| 2093 | UGAUGGAG CUGAUGAG GCCGUUAGGC CGAA ICUCCUUA | 11627 | TAAGGAGC A CTCCATCA | 4564 |
| 2095 | AGUGAUGG CUGAUGAG GCCGUUAGGC CGAA IUGCUCCU | 11628 | AGGAGCAC T CCATCACT | 4565 |
| 2097 | AGAGUGAU CUGAUGAG GCCGUUAGGC CGAA IAGUGCUC | 11629 | GAGCACTC C ATCACTCT | 4566 |
| 2098 | AAGAGUGA CUGAUGAG GCCGUUAGGC CGAA IGAGUGCU | 11630 | AGCACTCC A TCACTCTT | 4567 |
| 2101 | AUUAAGAG CUGAUGAG GCCGUUAGGC CGAA IAUGGAGU | 11631 | ACTCCATC A CTCTTAAT | 4568 |
| 2103 | AGAUUAAG CUGAUGAG GCCGUUAGGC CGAA IUGAUGGA | 11632 | TCCATCAC T CTTAATCT | 4569 |
| 2105 | UAAGAUUA CUGAUGAG GCCGUUAGGC CGAA IAGUGAUG | 11633 | CATCACTC T TAATCTTA | 4570 |
| 2111 | UGAUGGUA CUGAUGAG GCCGUUAGGC CGAA IAUUAAGA | 11634 | TCTTAATC T TACCATCA | 4571 |
| 2115 | UUCAUGAU CUGAUGAG GCCGUUAGGC CGAA IUAAGAUU | 11635 | AATCTTAC C ATCATGAA | 4572 |
| 2116 | AUUCAUGA CUGAUGAG GCCGUUAGGC CGAA IGUAAGAU | 11636 | ATCTTACC A TCATGAAT | 4573 |
| 2119 | AACAUUCA CUGAUGAG GCCGUUAGGC CGAA IAUGGUAA | 11637 | TTACCATC A TGAATGTT | 4574 |
| 2130 | UCUUGCAG CUGAUGAG GCCGUUAGGC CGAA IAAACAUU | 11638 | AATGTTTC C CTGCAAGA | 4575 |
| 2131 | AUCUUGCA CUGAUGAG GCCGUUAGGC CGAA IGAAACAU | 11639 | ATGTTTCC C TGCAAGAT | 4576 |
| 2132 | AAUCUUGC CUGAUGAG GCCGUUAGGC CGAA IGGAAACA | 11640 | TGTTTCCC T GCAAGATT | 4577 |
| 2135 | CUGAAUCU CUGAUGAG GCCGUUAGGC CGAA ICAGGGAA | 11641 | TTCCCTGC A AGATTCAG | 4578 |

| | | | | |
|---|---|---|---|---|
| 2142 | UAGGUGCC CUGAUGAG GCCGUUAGGC CGAA IAAUCUUG | 11642 | CAAGATTC A GGCACCTA | 4579 |
| 2146 | GGCAUAGG CUGAUGAG GCCGUUAGGC CGAA ICCUGAAU | 11643 | ATTCAGGC A CCTATGCC | 4580 |
| 2148 | CAGGCAUA CUGAUGAG GCCGUUAGGC CGAA IUGCCUGA | 11644 | TCAGGCAC C TATGCCTG | 4581 |
| 2149 | GCAGGCAU CUGAUGAG GCCGUUAGGC CGAA IGUGCCUG | 11645 | CAGGCACC T ATGCCTGC | 4582 |
| 2154 | GCUCUGCA CUGAUGAG GCCGUUAGGC CGAA ICAUAGGU | 11646 | ACCTATGC C TGCAGAGC | 4583 |
| 2155 | GGCUCUGC CUGAUGAG GCCGUUAGGC CGAA IGCAUAGG | 11647 | CCTATGCC T GCAGAGCC | 4584 |
| 2158 | CCUGGCUC CUGAUGAG GCCGUUAGGC CGAA ICAGGCAU | 11648 | ATGCCTGC A GAGCCAGG | 4585 |
| 2163 | ACAUUCCU CUGAUGAG GCCGUUAGGC CGAA ICUCUGCA | 11649 | TGCAGAGC C AGGAATGT | 4586 |
| 2164 | UACAUUCC CUGAUGAG GCCGUUAGGC CGAA IGCUCUGC | 11650 | GCAGAGCC A GGAATGTA | 4587 |
| 2176 | UUCCCCUG CUGAUGAG GCCGUUAGGC CGAA IUAUACAU | 11651 | ATGTATAC A CAGGGGAA | 4588 |
| 2178 | UCUUCCCC CUGAUGAG GCCGUUAGGC CGAA IUGUAUAC | 11652 | GTATACAC A GGGGAAGA | 4589 |
| 2191 | CUUCUGGA CUGAUGAG GCCGUUAGGC CGAA IAUUUCUU | 11653 | AAGAAATC C TCCAGAAG | 4590 |
| 2192 | UCUUCUGG CUGAUGAG GCCGUUAGGC CGAA IGAUUUCU | 11654 | AGAAATCC T CCAGAAGA | 4591 |
| 2194 | UUUCUUCU CUGAUGAG GCCGUUAGGC CGAA IAGGAUUU | 11655 | AAATCCTC C AGAAGAAA | 4592 |
| 2195 | CUUUCUUC CUGAUGAG GCCGUUAGGC CGAA IGAGGAUU | 11656 | AATCCTCC A GAAGAAAG | 4593 |
| 2211 | UCUCUGAU CUGAUGAG GCCGUUAGGC CGAA IUAAUUUC | 11657 | GAAATTAC A ATCAGAGA | 4594 |
| 2215 | CUGAUCUC CUGAUGAG GCCGUUAGGC CGAA IAUUGUAA | 11658 | TTACAATC A GAGATCAG | 4595 |
| 2222 | GUGCUUCC CUGAUGAG GCCGUUAGGC CGAA IAUCUCUG | 11659 | CAGAGATC A GGAAGCAC | 4596 |
| 2229 | AGGUAUGG CUGAUGAG GCCGUUAGGC CGAA ICUUCCUG | 11660 | CAGGAAGC A CCATACCT | 4597 |
| 2231 | GGAGGUAU CUGAUGAG GCCGUUAGGC CGAA IUGCUUCC | 11661 | GGAAGCAC C ATACCTCC | 4598 |
| 2232 | AGGAGGUA CUGAUGAG GCCGUUAGGC CGAA IGUGCUUC | 11662 | GAAGCACC A TACCTCCT | 4599 |
| 2236 | UCGCAGGA CUGAUGAG GCCGUUAGGC CGAA IUAUGGUG | 11663 | CACCATAC C TCCTGCGA | 4600 |
| 2237 | UUCGCAGG CUGAUGAG GCCGUUAGGC CGAA IGUAUGGU | 11664 | ACCATACC T CCTGCGAA | 4601 |
| 2239 | GUUUCGCA CUGAUGAG GCCGUUAGGC CGAA IAGGUAUG | 11665 | CATACCTC C TGCGAAAC | 4602 |
| 2240 | GGUUUCGC CUGAUGAG GCCGUUAGGC CGAA IGAGGUAU | 11666 | ATACCTCC T GCGAAACC | 4603 |
| 2248 | AUCACUGA CUGAUGAG GCCGUUAGGC CGAA IUUUCGCA | 11667 | TGCGAAAC C TCAGTGAT | 4604 |
| 2249 | GAUCACUG CUGAUGAG GCCGUUAGGC CGAA IGUUUCGC | 11668 | GCGAAACC T CAGTGATC | 4605 |
| 2251 | GUGAUCAC CUGAUGAG GCCGUUAGGC CGAA IAGGUUUC | 11669 | GAAACCTC A GTGATCAC | 4606 |
| 2258 | CCACUGUG CUGAUGAG GCCGUUAGGC CGAA IAUCACUG | 11670 | CAGTGATC A CACAGTGG | 4607 |
| 2260 | GGCCACUG CUGAUGAG GCCGUUAGGC CGAA IUGAUCAC | 11671 | GTGATCAC A CAGTGGCC | 4608 |
| 2262 | AUGGCCAC CUGAUGAG GCCGUUAGGC CGAA IUGUGAUC | 11672 | GATCACAC A GTGGCCAT | 4609 |
| 2268 | CUGCUGAU CUGAUGAG GCCGUUAGGC CGAA ICCACUGU | 11673 | ACAGTGGC C ATCAGCAG | 4610 |
| 2269 | ACUGCUGA CUGAUGAG GCCGUUAGGC CGAA IGCCACUG | 11674 | CAGTGGCC A TCAGCAGT | 4611 |

| | | | | |
|---|---|---|---|---|
| 2272 | GGAACUGC CUGAUGAG GCCGUUAGGC CGAA IAUGGCCA | 11675 | TGGCCATC A GCAGTTCC | 4612 |
| 2275 | GGUGGAAC CUGAUGAG GCCGUUAGGC CGAA ICUGAUGG | 11676 | CCATCAGC A GTTCCACC | 4613 |
| 2280 | AAAGUGGU CUGAUGAG GCCGUUAGGC CGAA IAACUGCU | 11677 | AGCAGTTC C ACCACTTT | 4614 |
| 2281 | UAAAGUGG CUGAUGAG GCCGUUAGGC CGAA IGAACUGC | 11678 | GCAGTTCC A CCACTTTA | 4615 |
| 2283 | UCUAAAGU CUGAUGAG GCCGUUAGGC CGAA IUGGAACU | 11679 | AGTTCCAC C ACTTTAGA | 4616 |
| 2284 | GUCUAAAG CUGAUGAG GCCGUUAGGC CGAA IGUGGAAC | 11680 | GTTCCACC A CTTTAGAC | 4617 |
| 2286 | CAGUCUAA CUGAUGAG GCCGUUAGGC CGAA IUGGUGGA | 11681 | TCCACCAC T TTAGACTG | 4618 |
| 2293 | AGCAUGAC CUGAUGAG GCCGUUAGGC CGAA IUCUAAAG | 11682 | CTTTAGAC T GTCATGCT | 4619 |
| 2297 | CAUUAGCA CUGAUGAG GCCGUUAGGC CGAA IACAGUCU | 11683 | AGACTGTC A TGCTAATG | 4620 |
| 2301 | ACACCAUU CUGAUGAG GCCGUUAGGC CGAA ICAUGACA | 11684 | TGTCATGC T AATGGTGT | 4621 |
| 2311 | AGGCUCGG CUGAUGAG GCCGUUAGGC CGAA IACACCAU | 11685 | ATGGTGTC C CCGAGCCT | 4622 |
| 2312 | GAGGCUCG CUGAUGAG GCCGUUAGGC CGAA IGACACCA | 11686 | TGGTGTCC C CGAGCCTC | 4623 |
| 2313 | UGAGGCUC CUGAUGAG GCCGUUAGGC CGAA IGGACACC | 11687 | GGTGTCCC C GAGCCTCA | 4624 |
| 2318 | UGAUCUGA CUGAUGAG GCCGUUAGGC CGAA ICUCGGGG | 11688 | CCCCGAGC C TCAGATCA | 4625 |
| 2319 | GUGAUCUG CUGAUGAG GCCGUUAGGC CGAA IGCUCGGG | 11689 | CCCGAGCC T CAGATCAC | 4626 |
| 2321 | AAGUGAUC CUGAUGAG GCCGUUAGGC CGAA IAGGCUCG | 11690 | CGAGCCTC A GATCACTT | 4627 |
| 2326 | AAACCAAG CUGAUGAG GCCGUUAGGC CGAA IAUCUGAG | 11691 | CTCAGATC A CTTGGTTT | 4628 |
| 2328 | UUAAACCA CUGAUGAG GCCGUUAGGC CGAA IUGAUCUG | 11692 | CAGATCAC T TGGTTTAA | 4629 |
| 2341 | UUUGUGGU CUGAUGAG GCCGUUAGGC CGAA IUUUUUAA | 11693 | TTAAAAAC A ACCACAAA | 4630 |
| 2344 | UAUUUUGU CUGAUGAG GCCGUUAGGC CGAA IUUGUUUU | 11694 | AAAACAAC C ACAAAATA | 4631 |
| 2345 | GUAUUUUG CUGAUGAG GCCGUUAGGC CGAA IGUUGUUU | 11695 | AAACAACC A CAAAATAC | 4632 |
| 2347 | UUGUAUUU CUGAUGAG GCCGUUAGGC CGAA IUGGUUGU | 11696 | ACAACCAC A AAATACAA | 4633 |
| 2354 | GCUCUUGU CUGAUGAG GCCGUUAGGC CGAA IUAUUUUG | 11697 | CAAAATAC A ACAAGAGC | 4634 |
| 2357 | CAGGCUCU CUGAUGAG GCCGUUAGGC CGAA IUUGUAUU | 11698 | AATACAAC A AGAGCCTG | 4635 |
| 2363 | UAAUUCCA CUGAUGAG GCCGUUAGGC CGAA ICUCUUGU | 11699 | ACAAGAGC C TGGAATTA | 4636 |
| 2364 | AUAAUUCC CUGAUGAG GCCGUUAGGC CGAA IGCUCUUG | 11700 | CAAGAGCC T GGAATTAT | 4637 |
| 2381 | UGCUUCCU CUGAUGAG GCCGUUAGGC CGAA IUCCUAAA | 11701 | TTTAGGAC C AGGAAGCA | 4638 |
| 2382 | CUGCUUCC CUGAUGAG GCCGUUAGGC CGAA IGUCCUAA | 11702 | TTAGGACC A GGAAGCAG | 4639 |
| 2389 | CAGCGUGC CUGAUGAG GCCGUUAGGC CGAA ICUUCCUG | 11703 | CAGGAAGC A GCACGCTG | 4640 |
| 2392 | AAACAGCG CUGAUGAG GCCGUUAGGC CGAA ICUGCUUC | 11704 | GAAGCAGC A CGCTGTTT | 4641 |
| 2396 | CAAUAAAC CUGAUGAG GCCGUUAGGC CGAA ICGUGCUG | 11705 | CAGCACGC T GTTTATTG | 4642 |
| 2413 | CUCUUCUG CUGAUGAG GCCGUUAGGC CGAA IACUCUUU | 11706 | AAAGAGTC A CAGAAGAG | 4643 |
| 2415 | UCCUCUUC CUGAUGAG GCCGUUAGGC CGAA IUGACUCU | 11707 | AGAGTCAC A GAAGAGGA | 4644 |

| | | | | |
|---|---|---|---|---|
| 2434 | GCAGUGAU CUGAUGAG GCCGUUAGGC CGAA IACACCUU | 11708 | AAGGTGTC T ATCACTGC | 4645 |
| 2438 | CUUUGCAG CUGAUGAG GCCGUUAGGC CGAA IAUAGACA | 11709 | TGTCTATC A CTGCAAAG | 4646 |
| 2440 | GGCUUUGC CUGAUGAG GCCGUUAGGC CGAA IUGAUAGA | 11710 | TCTATCAC T GCAAAGCC | 4647 |
| 2443 | GGUGGCUU CUGAUGAG GCCGUUAGGC CGAA ICAGUGAU | 11711 | ATCACTGC A AAGCCACC | 4648 |
| 2448 | UGGUUGGU CUGAUGAG GCCGUUAGGC CGAA ICUUUGCA | 11712 | TGCAAAGC C ACCAACCA | 4649 |
| 2449 | CUGGUUGG CUGAUGAG GCCGUUAGGC CGAA IGCUUUGC | 11713 | GCAAAGCC A CCAACCAG | 4650 |
| 2451 | UUCUGGUU CUGAUGAG GCCGUUAGGC CGAA IUGGCUUU | 11714 | AAAGCCAC C AACCAGAA | 4651 |
| 2452 | CUUCUGGU CUGAUGAG GCCGUUAGGC CGAA IGUGGCUU | 11715 | AAGCCACC A ACCAGAAG | 4652 |
| 2455 | GCCCUUCU CUGAUGAG GCCGUUAGGC CGAA IUUGGUGG | 11716 | CCACCAAC C AGAAGGGC | 4653 |
| 2456 | AGCCCUUC CUGAUGAG GCCGUUAGGC CGAA IGUUGGUG | 11717 | CACCAACC A GAAGGGCT | 4654 |
| 2464 | UUCCACAG CUGAUGAG GCCGUUAGGC CGAA ICCCUUCU | 11718 | AGAAGGGC T CTGTGGAA | 4655 |
| 2466 | CUUUCCAC CUGAUGAG GCCGUUAGGC CGAA IAGCCCUU | 11719 | AAGGGCTC T GTGGAAAG | 4656 |
| 2478 | AGGUAUGC CUGAUGAG GCCGUUAGGC CGAA IAACUUUC | 11720 | GAAAGTTC A GCATACCT | 4657 |
| 2481 | GUGAGGUA CUGAUGAG GCCGUUAGGC CGAA ICUGAACU | 11721 | AGTTCAGC A TACCTCAC | 4658 |
| 2485 | AACAGUGA CUGAUGAG GCCGUUAGGC CGAA IUAUGCUG | 11722 | CAGCATAC C TCACTGTT | 4659 |
| 2486 | GAACAGUG CUGAUGAG GCCGUUAGGC CGAA IGUAUGCU | 11723 | AGCATACC T CACTGTTC | 4660 |
| 2488 | UUGAACAG CUGAUGAG GCCGUUAGGC CGAA IAGGUAUG | 11724 | CATACCTC A CTGTTCAA | 4661 |
| 2490 | CCUUGAAC CUGAUGAG GCCGUUAGGC CGAA IUGAGGUA | 11725 | TACCTCAC T GTTCAAGG | 4662 |
| 2495 | AGGUUCCU CUGAUGAG GCCGUUAGGC CGAA IAACAGUG | 11726 | CACTGTTC A AGGAACCT | 4663 |
| 2502 | UUGUCCGA CUGAUGAG GCCGUUAGGC CGAA IUUCCUUG | 11727 | CAAGGAAC C TCGGACAA | 4664 |
| 2503 | CUUGUCCG CUGAUGAG GCCGUUAGGC CGAA IGUUCCUU | 11728 | AAGGAACC T CGGACAAG | 4665 |
| 2509 | AUUAGACU CUGAUGAG GCCGUUAGGC CGAA IUCCGAGG | 11729 | CCTCGGAC A AGTCTAAT | 4666 |
| 2514 | UCCAGAUU CUGAUGAG GCCGUUAGGC CGAA IACUUGUC | 11730 | GACAAGTC T AATCTGGA | 4667 |
| 2519 | UCAGCUCC CUGAUGAG GCCGUUAGGC CGAA IAUUAGAC | 11731 | GTCTAATC T GGAGCTGA | 4668 |
| 2525 | GAGUGAUC CUGAUGAG GCCGUUAGGC CGAA ICUCCAGA | 11732 | TCTGGAGC T GATCACTC | 4669 |
| 2530 | UGUUAGAG CUGAUGAG GCCGUUAGGC CGAA IAUCAGCU | 11733 | AGCTGATC A CTCTAACA | 4670 |
| 2532 | CAUGUUAG CUGAUGAG GCCGUUAGGC CGAA IUGAUCAG | 11734 | CTGATCAC T CTAACATG | 4671 |
| 2534 | UGCAUGUU CUGAUGAG GCCGUUAGGC CGAA IAGUGAUC | 11735 | GATCACTC T AACATGCA | 4672 |
| 2538 | CAGGUGCA CUGAUGAG GCCGUUAGGC CGAA IUUAGAGU | 11736 | ACTCTAAC A TGCACCTG | 4673 |
| 2542 | CACACAGG CUGAUGAG GCCGUUAGGC CGAA ICAUGUUA | 11737 | TAACATGC A CCTGTGTG | 4674 |
| 2544 | GCCACACA CUGAUGAG GCCGUUAGGC CGAA IUGCAUGU | 11738 | ACATGCAC C TGTGTGGC | 4675 |
| 2545 | AGCCACAC CUGAUGAG GCCGUUAGGC CGAA IGUGCAUG | 11739 | CATGCACC T GTGTGGCT | 4676 |
| 2553 | AGAGUCGC CUGAUGAG GCCGUUAGGC CGAA ICCACACA | 11740 | TGTGTGGC T GCGACTCT | 4677 |

| | | | | |
|---|---|---|---|---|
| 2559 | CAGAAGAG CUGAUGAG GCCGUUAGGC CGAA IUCGCAGC | 11741 | GCTGCGAC T CTCTTCTG | 4678 |
| 2561 | GCCAGAAG CUGAUGAG GCCGUUAGGC CGAA IAGUCGCA | 11742 | TGCGACTC T CTTCTGGC | 4679 |
| 2563 | GAGCCAGA CUGAUGAG GCCGUUAGGC CGAA IAGAGUCG | 11743 | CGACTCTC T TCTGGCTC | 4680 |
| 2566 | UAGGAGCC CUGAUGAG GCCGUUAGGC CGAA IAAGAGAG | 11744 | CTCTCTTC T GGCTCCTA | 4681 |
| 2570 | UUAAUAGG CUGAUGAG GCCGUUAGGC CGAA ICCAGAAG | 11745 | CTTCTGGC T CCTATTAA | 4682 |
| 2572 | GGUUAAUA CUGAUGAG GCCGUUAGGC CGAA IAGCCAGA | 11746 | TCTGGCTC C TATTAACC | 4683 |
| 2573 | GGGUUAAU CUGAUGAG GCCGUUAGGC CGAA IGAGCCAG | 11747 | CTGGCTCC T ATTAACCC | 4684 |
| 2580 | AUAAGGAG CUGAUGAG GCCGUUAGGC CGAA IUUAAUAG | 11748 | CTATTAAC C CTCCTTAT | 4685 |
| 2581 | GAUAAGGA CUGAUGAG GCCGUUAGGC CGAA IGUUAAUA | 11749 | TATTAACC C TCCTTATC | 4686 |
| 2582 | GGAUAAGG CUGAUGAG GCCGUUAGGC CGAA IGGUUAAU | 11750 | ATTAACCC T CCTTATCC | 4687 |
| 2584 | UCGGAUAA CUGAUGAG GCCGUUAGGC CGAA IAGGGUUA | 11751 | TAACCCTC C TTATCCGA | 4688 |
| 2585 | UUCGGAUA CUGAUGAG GCCGUUAGGC CGAA IGAGGGUU | 11752 | AACCCTCC T TATCCGAA | 4689 |
| 2590 | CAUUUUUC CUGAUGAG GCCGUUAGGC CGAA IAUAAGGA | 11753 | TCCTTATC C GAAAAATG | 4690 |
| 2607 | UCAGAAGA CUGAUGAG GCCGUUAGGC CGAA IACCUUUU | 11754 | AAAAGGTC T TCTTCTGA | 4691 |
| 2610 | AUUUCAGA CUGAUGAG GCCGUUAGGC CGAA IAAGACCU | 11755 | AGGTCTTC T TCTGAAAT | 4692 |
| 2613 | UUUAUUUC CUGAUGAG GCCGUUAGGC CGAA IAAGAAGA | 11756 | TCTTCTTC T GAAATAAA | 4693 |
| 2625 | AGGUAGUC CUGAUGAG GCCGUUAGGC CGAA IUCUUUAU | 11757 | ATAAAGAC T GACTACCT | 4694 |
| 2629 | UGAUAGGU CUGAUGAG GCCGUUAGGC CGAA IUCAGUCU | 11758 | AGACTGAC T ACCTATCA | 4695 |
| 2632 | AAUUGAUA CUGAUGAG GCCGUUAGGC CGAA IUAGUCAG | 11759 | CTGACTAC C TATCAATT | 4696 |
| 2633 | UAAUUGAU CUGAUGAG GCCGUUAGGC CGAA IGUAGUCA | 11760 | TGACTACC T ATCAATTA | 4697 |
| 2637 | AUUAUAAU CUGAUGAG GCCGUUAGGC CGAA IAUAGGUA | 11761 | TACCTATC A ATTATAAT | 4698 |
| 2650 | UUCAUCUG CUGAUGAG GCCGUUAGGC CGAA IUCCAUUA | 11762 | TAATGGAC C CAGATGAA | 4699 |
| 2651 | CUUCAUCU CUGAUGAG GCCGUUAGGC CGAA IGUCCAUU | 11763 | AATGGACC C AGATGAAG | 4700 |
| 2652 | ACUUCAUC CUGAUGAG GCCGUUAGGC CGAA IGGUCCAU | 11764 | ATGGACCC A GATGAAGT | 4701 |
| 2663 | CAUCCAAA CUGAUGAG GCCGUUAGGC CGAA IAACUUCA | 11765 | TGAAGTTC C TTTGGATG | 4702 |
| 2664 | UCAUCCAA CUGAUGAG GCCGUUAGGC CGAA IGAACUUC | 11766 | GAAGTTCC T TTGGATGA | 4703 |
| 2675 | GCUCACAC CUGAUGAG GCCGUUAGGC CGAA ICUCAUCC | 11767 | GGATGAGC A GTGTGAGC | 4704 |
| 2687 | CAUAAGGG CUGAUGAG GCCGUUAGGC CGAA ICCGCUCA | 11768 | TGAGCGGC T CCCTTATG | 4705 |
| 2689 | AUCAUAAG CUGAUGAG GCCGUUAGGC CGAA IAGCCGCU | 11769 | AGCGGCTC C CTTATGAT | 4706 |
| 2690 | CAUCAUAA CUGAUGAG GCCGUUAGGC CGAA IGAGCCGC | 11770 | GCGGCTCC C TTATGATG | 4707 |
| 2691 | GCAUCAUA CUGAUGAG GCCGUUAGGC CGAA IGGAGCCG | 11771 | CGGCTCCC T TATGATGC | 4708 |
| 2700 | CACUUGCU CUGAUGAG GCCGUUAGGC CGAA ICAUCAUA | 11772 | TATGATGC C AGCAAGTG | 4709 |
| 2701 | CCACUUGC CUGAUGAG GCCGUUAGGC CGAA IGCAUCAU | 11773 | ATGATGCC A GCAAGTGG | 4710 |

220

| | | | | | |
|---|---|---|---|---|---|
| 2704 | CUCCCACU CUGAUGAG GCCGUUAGGC CGAA ICUGGCAU | 11774 | ATGCCAGC A AGTGGGAG | 4711 |
| 2718 | CUCUCCCG CUGAUGAG GCCGUUAGGC CGAA ICAAACUC | 11775 | GAGTTTGC C CGGGAGAG | 4712 |
| 2719 | UCUCUCCC CUGAUGAG GCCGUUAGGC CGAA IGCAAACU | 11776 | AGTTTGCC C GGGAGAGA | 4713 |
| 2729 | CCAGUUUA CUGAUGAG GCCGUUAGGC CGAA IUCUCUCC | 11777 | GGAGAGAC T TAAACTGG | 4714 |
| 2735 | AUUUGCCC CUGAUGAG GCCGUUAGGC CGAA IUUUAAGU | 11778 | ACTTAAAC T GGGCAAAT | 4715 |
| 2740 | AAGUGAUU CUGAUGAG GCCGUUAGGC CGAA ICCCAGUU | 11779 | AACTGGGC A AATCACTT | 4716 |
| 2745 | CUUCCAAG CUGAUGAG GCCGUUAGGC CGAA IAUUUGCC | 11780 | GGCAAATC A CTTGGAAG | 4717 |
| 2747 | CUCUUCCA CUGAUGAG GCCGUUAGGC CGAA IUGAUUUG | 11781 | CAAATCAC T TGGAAGAG | 4718 |
| 2760 | UUUCCAAA CUGAUGAG GCCGUUAGGC CGAA ICCCCUCU | 11782 | AGAGGGGC T TTTGGAAA | 4719 |
| 2777 | CUGAUGCU CUGAUGAG GCCGUUAGGC CGAA IAACCACU | 11783 | AGTGGTTC A AGCATCAG | 4720 |
| 2781 | AAUGCUGA CUGAUGAG GCCGUUAGGC CGAA ICUUGAAC | 11784 | GTTCAAGC A TCAGCATT | 4721 |
| 2784 | CCAAAUGC CUGAUGAG GCCGUUAGGC CGAA IAUGCUUG | 11785 | CAAGCATC A GCATTTGG | 4722 |
| 2787 | AUGCCAAA CUGAUGAG GCCGUUAGGC CGAA ICUGAUGC | 11786 | GCATCAGC A TTTGGCAT | 4723 |
| 2794 | UUUCUUAA CUGAUGAG GCCGUUAGGC CGAA ICCAAAUG | 11787 | CATTTGGC A TTAAGAAA | 4724 |
| 2805 | CACGUAGG CUGAUGAG GCCGUUAGGC CGAA IAUUUCUU | 11788 | AAGAAATC A CCTACGTG | 4725 |
| 2807 | GGCACGUA CUGAUGAG GCCGUUAGGC CGAA IUGAUUUC | 11789 | GAAATCAC C TACGTGCC | 4726 |
| 2808 | CGGCACGU CUGAUGAG GCCGUUAGGC CGAA IGUGAUUU | 11790 | AAATCACC T ACGTGCCG | 4727 |
| 2815 | CACAGUCC CUGAUGAG GCCGUUAGGC CGAA ICACGUAG | 11791 | CTACGTGC C GGACTGTG | 4728 |
| 2820 | ACAGCCAC CUGAUGAG GCCGUUAGGC CGAA IUCCGGCA | 11792 | TGCCGGAC T GTGGCTGT | 4729 |
| 2826 | AUUUUCAC CUGAUGAG GCCGUUAGGC CGAA ICCACAGU | 11793 | ACTGTGGC T GTGAAAAT | 4730 |
| 2837 | CCUCUUUC CUGAUGAG GCCGUUAGGC CGAA ICAUUUUC | 11794 | GAAAATGC T GAAAGAGG | 4731 |
| 2850 | CUGGCCGU CUGAUGAG GCCGUUAGGC CGAA ICCCCCUC | 11795 | GAGGGGGC C ACGGCCAG | 4732 |
| 2851 | GCUGGCCG CUGAUGAG GCCGUUAGGC CGAA IGCCCCCU | 11796 | AGGGGGCC A CGGCCAGC | 4733 |
| 2856 | UACUCGCU CUGAUGAG GCCGUUAGGC CGAA ICCGUGGC | 11797 | GCCACGGC C AGCGAGTA | 4734 |
| 2857 | GUACUCGC CUGAUGAG GCCGUUAGGC CGAA IGCCGUGG | 11798 | CCACGGCC A GCGAGTAC | 4735 |
| 2866 | CAGAGCUU CUGAUGAG GCCGUUAGGC CGAA IUACUCGC | 11799 | GCGAGTAC A AAGCTCTG | 4736 |
| 2871 | GUCAUCAG CUGAUGAG GCCGUUAGGC CGAA ICUUUGUA | 11800 | TACAAAGC T CTGATGAC | 4737 |
| 2873 | CAGUCAUC CUGAUGAG GCCGUUAGGC CGAA IAGCUUUG | 11801 | CAAAGCTC T GATGACTG | 4738 |
| 2880 | UUUAGCUC CUGAUGAG GCCGUUAGGC CGAA IUCAUCAG | 11802 | CTGATGAC T GAGCTAAA | 4739 |
| 2885 | AGAUUUUU CUGAUGAG GCCGUUAGGC CGAA ICUCAGUC | 11803 | GACTGAGC T AAAAATCT | 4740 |
| 2893 | GUGGGUCA CUGAUGAG GCCGUUAGGC CGAA IAUUUUUA | 11804 | TAAAAATC T TGACCCAC | 4741 |
| 2898 | CCAAUGUG CUGAUGAG GCCGUUAGGC CGAA IUCAAGAU | 11805 | ATCTTGAC C CACATTGG | 4742 |
| 2899 | GCCAAUGU CUGAUGAG GCCGUUAGGC CGAA IGUCAAGA | 11806 | TCTTGACC C ACATTGGC | 4743 |

221

| | | | | |
|---|---|---|---|---|
| 2900 | GGCCAAUG CUGAUGAG GCCGUUAGGC CGAA IGGUCAAG | 11807 | CTTGACCC A CATTGGCC | 4744 |
| 2902 | GUGGCCAA CUGAUGAG GCCGUUAGGC CGAA IUGGGUCA | 11808 | TGACCCAC A TTGGCCAC | 4745 |
| 2908 | CAGAUGGU CUGAUGAG GCCGUUAGGC CGAA ICCAAUGU | 11809 | ACATTGGC C ACCATCTG | 4746 |
| 2909 | UCAGAUGG CUGAUGAG GCCGUUAGGC CGAA IGCCAAUG | 11810 | CATTGGCC A CCATCTGA | 4747 |
| 2911 | GUUCAGAU CUGAUGAG GCCGUUAGGC CGAA IUGGCCAA | 11811 | TTGGCCAC C ATCTGAAC | 4748 |
| 2912 | CGUUCAGA CUGAUGAG GCCGUUAGGC CGAA IGUGGCCA | 11812 | TGGCCACC A TCTGAACG | 4749 |
| 2915 | CCACGUUC CUGAUGAG GCCGUUAGGC CGAA IAUGGUGG | 11813 | CCACCATC T GAACGTGG | 4750 |
| 2929 | UCCCAGCA CUGAUGAG GCCGUUAGGC CGAA IUUAACCA | 11814 | TGGTTAAC C TGCTGGGA | 4751 |
| 2930 | CUCCCAGC CUGAUGAG GCCGUUAGGC CGAA IGUUAACC | 11815 | GGTTAACC T GCTGGGAG | 4752 |
| 2933 | AGGCUCCC CUGAUGAG GCCGUUAGGC CGAA ICAGGUUA | 11816 | TAACCTGC T GGGAGCCT | 4753 |
| 2940 | UUGGUGCA CUGAUGAG GCCGUUAGGC CGAA ICUCCCAG | 11817 | CTGGGAGC C TGCACCAA | 4754 |
| 2941 | CUUGGUGC CUGAUGAG GCCGUUAGGC CGAA IGCUCCCA | 11818 | TGGGAGCC T GCACCAAG | 4755 |
| 2944 | UUGCUUGG CUGAUGAG GCCGUUAGGC CGAA ICAGGCUC | 11819 | GAGCCTGC A CCAAGCAA | 4756 |
| 2946 | CCUUGCUU CUGAUGAG GCCGUUAGGC CGAA IUGCAGGC | 11820 | GCCTGCAC C AAGCAAGG | 4757 |
| 2947 | UCCUUGCU CUGAUGAG GCCGUUAGGC CGAA IGUGCAGG | 11821 | CCTGCACC A AGCAAGGA | 4758 |
| 2951 | GCCCUCCU CUGAUGAG GCCGUUAGGC CGAA ICUUGGUG | 11822 | CACCAAGC A AGGAGGGC | 4759 |
| 2960 | CCAUCAGA CUGAUGAG GCCGUUAGGC CGAA ICCCUCCU | 11823 | AGGAGGGC C TCTGATGG | 4760 |
| 2961 | ACCAUCAG CUGAUGAG GCCGUUAGGC CGAA IGCCCUCC | 11824 | GGAGGGCC T CTGATGGT | 4761 |
| 2963 | UCACCAUC CUGAUGAG GCCGUUAGGC CGAA IAGGCCCU | 11825 | AGGGCCTC T GATGGTGA | 4762 |
| 2983 | AUAUUUGC CUGAUGAG GCCGUUAGGC CGAA IUAUUCAA | 11826 | TTGAATAC T GCAAATAT | 4763 |
| 2986 | UCCAUAUU CUGAUGAG GCCGUUAGGC CGAA ICAGUAUU | 11827 | AATACTGC A AATATGGA | 4764 |
| 2999 | AGUUGGAG CUGAUGAG GCCGUUAGGC CGAA IAUUUCCA | 11828 | TGGAAATC T CTCCAACT | 4765 |
| 3001 | GUAGUUGG CUGAUGAG GCCGUUAGGC CGAA IAGAUUUC | 11829 | GAAATCTC T CCAACTAC | 4766 |
| 3003 | AGGUAGUU CUGAUGAG GCCGUUAGGC CGAA IAGAGAUU | 11830 | AATCTCTC C AACTACCT | 4767 |
| 3004 | GAGGUAGU CUGAUGAG GCCGUUAGGC CGAA IGAGAGAU | 11831 | ATCTCTCC A ACTACCTC | 4768 |
| 3007 | CUUGAGGU CUGAUGAG GCCGUUAGGC CGAA IUUGGAGA | 11832 | TCTCCAAC T ACCTCAAG | 4769 |
| 3010 | GCUCUUGA CUGAUGAG GCCGUUAGGC CGAA IUAGUUGG | 11833 | CCAACTAC C TCAAGAGC | 4770 |
| 3011 | UGCUCUUG CUGAUGAG GCCGUUAGGC CGAA IGUAGUUG | 11834 | CAACTACC T CAAGAGCA | 4771 |
| 3013 | UUUGCUCU CUGAUGAG GCCGUUAGGC CGAA IAGGUAGU | 11835 | ACTACCTC A AGAGCAAA | 4772 |
| 3019 | GUCACGUU CUGAUGAG GCCGUUAGGC CGAA ICUCUUGA | 11836 | TCAAGAGC A AACGTGAC | 4773 |
| 3028 | AAAAAAUA CUGAUGAG GCCGUUAGGC CGAA IUCACGUU | 11837 | AACGTGAC T TATTTTTT | 4774 |
| 3038 | CCUUGUUG CUGAUGAG GCCGUUAGGC CGAA IAAAAAAU | 11838 | ATTTTTTC T CAACAAGG | 4775 |
| 3040 | AUCCUUGU CUGAUGAG GCCGUUAGGC CGAA IAGAAAAA | 11839 | TTTTTCTC A ACAAGGAT | 4776 |

222

| | | | | |
|---|---|---|---|---|
| 3043 | UGCAUCCU CUGAUGAG GCCGUUAGGC CGAA IUUGAGAA | 11840 | TTCTCAAC A AGGATGCA | 4777 |
| 3051 | UGUAGUGC CUGAUGAG GCCGUUAGGC CGAA ICAUCCUU | 11841 | AAGGATGC A GCACTACA | 4778 |
| 3054 | AUGUGUAG CUGAUGAG GCCGUUAGGC CGAA ICUGCAUC | 11842 | GATGCAGC A CTACACAT | 4779 |
| 3056 | CCAUGUGU CUGAUGAG GCCGUUAGGC CGAA IUGCUGCA | 11843 | TGCAGCAC T ACACATGG | 4780 |
| 3059 | GCUCCAUG CUGAUGAG GCCGUUAGGC CGAA IUAGUGCU | 11844 | AGCACTAC A CATGGAGC | 4781 |
| 3061 | AGGCUCCA CUGAUGAG GCCGUUAGGC CGAA IUGUAGUG | 11845 | CACTACAC A TGGAGCCT | 4782 |
| 3068 | CUUUCUUA CUGAUGAG GCCGUUAGGC CGAA ICUCCAUG | 11846 | CATGGAGC C TAAGAAAG | 4783 |
| 3069 | UCUUUCUU CUGAUGAG GCCGUUAGGC CGAA IGCUCCAU | 11847 | ATGGAGCC T AAGAAAGA | 4784 |
| 3089 | CCAGGCCU CUGAUGAG GCCGUUAGGC CGAA ICUCCAUU | 11848 | AATGGAGC C AGGCCTGG | 4785 |
| 3090 | UCCAGGCC CUGAUGAG GCCGUUAGGC CGAA IGCUCCAU | 11849 | ATGGAGCC A GGCCTGGA | 4786 |
| 3094 | UUGUUCCA CUGAUGAG GCCGUUAGGC CGAA ICCUGGCU | 11850 | AGCCAGGC C TGGAACAA | 4787 |
| 3095 | CUUGUUCC CUGAUGAG GCCGUUAGGC CGAA IGCCUGGC | 11851 | GCCAGGCC T GGAACAAG | 4788 |
| 3101 | UCUUGCCU CUGAUGAG GCCGUUAGGC CGAA IUUCCAGG | 11852 | CCTGGAAC A AGGCAAGA | 4789 |
| 3106 | UGGUUUCU CUGAUGAG GCCGUUAGGC CGAA ICCUUGUU | 11853 | AACAAGGC A AGAAACCA | 4790 |
| 3113 | CUAGUCUU CUGAUGAG GCCGUUAGGC CGAA IUUUCUUG | 11854 | CAAGAAAC C AAGACTAG | 4791 |
| 3114 | UCUAGUCU CUGAUGAG GCCGUUAGGC CGAA IGUUUCUU | 11855 | AAGAAACC A AGACTAGA | 4792 |
| 3119 | CGCUAUCU CUGAUGAG GCCGUUAGGC CGAA IUCUUGGU | 11856 | ACCAAGAC T AGATAGCG | 4793 |
| 3130 | GCUGCUGG CUGAUGAG GCCGUUAGGC CGAA IACGCUAU | 11857 | ATAGCGTC A CCAGCAGC | 4794 |
| 3132 | UCGCUGCU CUGAUGAG GCCGUUAGGC CGAA IUGACGCU | 11858 | AGCGTCAC C AGCAGCGA | 4795 |
| 3133 | UUCGCUGC CUGAUGAG GCCGUUAGGC CGAA IGUGACGC | 11859 | GCGTCACC A GCAGCGAA | 4796 |
| 3136 | GCUUUCGC CUGAUGAG GCCGUUAGGC CGAA ICUGGUGA | 11860 | TCACCAGC A GCGAAAGC | 4797 |
| 3145 | GCUCGCAA CUGAUGAG GCCGUUAGGC CGAA ICUUUCGC | 11861 | GCGAAAGC T TTGCGAGC | 4798 |
| 3154 | AAAGCCGG CUGAUGAG GCCGUUAGGC CGAA ICUCGCAA | 11862 | TTGCGAGC T CCGGCTTT | 4799 |
| 3156 | UGAAAGCC CUGAUGAG GCCGUUAGGC CGAA IAGCUCGC | 11863 | GCGAGCTC C GGCTTTCA | 4800 |
| 3160 | UUCCUGAA CUGAUGAG GCCGUUAGGC CGAA ICCGGAGC | 11864 | GCTCCGGC T TTCAGGAA | 4801 |
| 3164 | UAUCUUCC CUGAUGAG GCCGUUAGGC CGAA IAAAGCCG | 11865 | CGGCTTTC A GGAAGATA | 4802 |
| 3179 | CAUCACUC CUGAUGAG GCCGUUAGGC CGAA IACUUUUA | 11866 | TAAAAGTC T GAGTGATG | 4803 |
| 3207 | AAACCGUC CUGAUGAG GCCGUUAGGC CGAA IAAUCCUC | 11867 | GAGGATTC T GACGGTTT | 4804 |
| 3217 | CUCCUUGU CUGAUGAG GCCGUUAGGC CGAA IAAACCGU | 11868 | ACGGTTTC T ACAAGGAG | 4805 |
| 3220 | GGGCUCCU CUGAUGAG GCCGUUAGGC CGAA IUAGAAAC | 11869 | GTTTCTAC A AGGAGCCC | 4806 |
| 3227 | UAGUGAUG CUGAUGAG GCCGUUAGGC CGAA ICUCCUUG | 11870 | CAAGGAGC C CATCACTA | 4807 |
| 3228 | AUAGUGAU CUGAUGAG GCCGUUAGGC CGAA IGCUCCUU | 11871 | AAGGAGCC C ATCACTAT | 4808 |
| 3229 | CAUAGUGA CUGAUGAG GCCGUUAGGC CGAA IGGCUCCU | 11872 | AGGAGCCC A TCACTATG | 4809 |

| | | | | |
|---|---|---|---|---|
| 3232 | UUCCAUAG CUGAUGAG GCCGUUAGGC CGAA IAUGGGCU | 11873 | AGCCCATC A CTATGGAA | 4810 |
| 3234 | UCUUCCAU CUGAUGAG GCCGUUAGGC CGAA IUGAUGGG | 11874 | CCCATCAC T ATGGAAGA | 4811 |
| 3245 | AAGAAAUC CUGAUGAG GCCGUUAGGC CGAA IAUCUUCC | 11875 | GGAAGATC T GATTTCTT | 4812 |
| 3252 | AAACUGUA CUGAUGAG GCCGUUAGGC CGAA IAAAUCAG | 11876 | CTGATTTC T TACAGTTT | 4813 |
| 3256 | UUGAAAAC CUGAUGAG GCCGUUAGGC CGAA IUAAGAAA | 11877 | TTTCTTAC A GTTTTCAA | 4814 |
| 3263 | UGGCCACU CUGAUGAG GCCGUUAGGC CGAA IAAAACUG | 11878 | CAGTTTTC A AGTGGCCA | 4815 |
| 3270 | AUGCCUCU CUGAUGAG GCCGUUAGGC CGAA ICCACUUG | 11879 | CAAGTGGC C AGAGGCAT | 4816 |
| 3271 | CAUGCCUC CUGAUGAG GCCGUUAGGC CGAA IGCCACUU | 11880 | AAGTGGCC A GAGGCATG | 4817 |
| 3277 | GAACUCCA CUGAUGAG GCCGUUAGGC CGAA ICCUCUGG | 11881 | CCAGAGGC A TGGAGTTC | 4818 |
| 3286 | GGAAGACA CUGAUGAG GCCGUUAGGC CGAA IAACUCCA | 11882 | TGGAGTTC C TGTCTTCC | 4819 |
| 3287 | UGGAAGAC CUGAUGAG GCCGUUAGGC CGAA IGAACUCC | 11883 | GGAGTTCC T GTCTTCCA | 4820 |
| 3291 | UUUCUGGA CUGAUGAG GCCGUUAGGC CGAA IACAGGAA | 11884 | TTCCTGTC T TCCAGAAA | 4821 |
| 3294 | CACUUUCU CUGAUGAG GCCGUUAGGC CGAA IAAGACAG | 11885 | CTGTCTTC C AGAAAGTG | 4822 |
| 3295 | GCACUUUC CUGAUGAG GCCGUUAGGC CGAA IGAAGACA | 11886 | TGTCTTCC A GAAAGTGC | 4823 |
| 3304 | CCGAUGAA CUGAUGAG GCCGUUAGGC CGAA ICACUUUC | 11887 | GAAAGTGC A TTCATCGG | 4824 |
| 3308 | GGUCCCGA CUGAUGAG GCCGUUAGGC CGAA IAAUGCAC | 11888 | GTGCATTC A TCGGGACC | 4825 |
| 3316 | CGCUGCCA CUGAUGAG GCCGUUAGGC CGAA IUCCCGAU | 11889 | ATCGGGAC C TGGCAGCG | 4826 |
| 3317 | UCGCUGCC CUGAUGAG GCCGUUAGGC CGAA IGUCCCGA | 11890 | TCGGGACC T GGCAGCGA | 4827 |
| 3321 | UUUCUCGC CUGAUGAG GCCGUUAGGC CGAA ICCAGGUC | 11891 | GACCTGGC A GCGAGAAA | 4828 |
| 3331 | UAAAAGAA CUGAUGAG GCCGUUAGGC CGAA IUUUCUCG | 11892 | CGAGAAAC A TTCTTTTA | 4829 |
| 3335 | CAGAUAAA CUGAUGAG GCCGUUAGGC CGAA IAAUGUUU | 11893 | AAACATTC T TTTATCTG | 4830 |
| 3342 | UUGUUCUC CUGAUGAG GCCGUUAGGC CGAA IAUAAAAG | 11894 | CTTTTATC T GAGAACAA | 4831 |
| 3349 | CACCACGU CUGAUGAG GCCGUUAGGC CGAA IUUCUCAG | 11895 | CTGAGAAC A ACGTGGTG | 4832 |
| 3376 | CCGGGCAA CUGAUGAG GCCGUUAGGC CGAA ICCAAAAU | 11896 | ATTTTGGC C TTGCCCGG | 4833 |
| 3377 | CCCGGGCA CUGAUGAG GCCGUUAGGC CGAA IGCCAAAA | 11897 | TTTTGGCC T TGCCCGGG | 4834 |
| 3381 | AUAUCCCG CUGAUGAG GCCGUUAGGC CGAA ICAAGGCC | 11898 | GGCCTTGC C CGGGATAT | 4835 |
| 3382 | AAUAUCCC CUGAUGAG GCCGUUAGGC CGAA IGCAAGGC | 11899 | GCCTTGCC C GGGATATT | 4836 |
| 3400 | AUAAUCGG CUGAUGAG GCCGUUAGGC CGAA IUUCUUAU | 11900 | ATAAGAAC C CCGATTAT | 4837 |
| 3401 | CAUAAUCG CUGAUGAG GCCGUUAGGC CGAA IGUUCUUA | 11901 | TAAGAACC C CGATTATG | 4838 |
| 3402 | ACAUAAUC CUGAUGAG GCCGUUAGGC CGAA IGGUUCUU | 11902 | AAGAACCC C GATTATGT | 4839 |
| 3426 | GGAAGUCG CUGAUGAG GCCGUUAGGC CGAA IUAUCUCC | 11903 | GGAGATAC T CGACTTCC | 4840 |
| 3431 | UCAGAGGA CUGAUGAG GCCGUUAGGC CGAA IUCGAGUA | 11904 | TACTCGAC T TCCTCTGA | 4841 |
| 3434 | AUUUCAGA CUGAUGAG GCCGUUAGGC CGAA IAAGUCGA | 11905 | TCGACTTC C TCTGAAAT | 4842 |

| | | | | |
|---|---|---|---|---|
| 3435 | CAUUUCAG CUGAUGAG GCCGUUAGGC CGAA IGAAGUCG | 11906 | CGACTTCC T CTGAAATG | 4843 |
| 3437 | UCCAUUUC CUGAUGAG GCCGUUAGGC CGAA IAGGAAGU | 11907 | ACTTCCTC T GAAATGGA | 4844 |
| 3450 | GAUUCGGG CUGAUGAG GCCGUUAGGC CGAA ICCAUCCA | 11908 | TGGATGGC T CCCGAATC | 4845 |
| 3452 | UAGAUUCG CUGAUGAG GCCGUUAGGC CGAA IAGCCAUC | 11909 | GATGGCTC C CGAATCTA | 4846 |
| 3453 | AUAGAUUC CUGAUGAG GCCGUUAGGC CGAA IGAGCCAU | 11910 | ATGGCTCC C GAATCTAT | 4847 |
| 3459 | UCAAAGAU CUGAUGAG GCCGUUAGGC CGAA IAUUCGGG | 11911 | CCCGAATC T ATCTTTGA | 4848 |
| 3463 | UUUGUCAA CUGAUGAG GCCGUUAGGC CGAA IAUAGAUU | 11912 | AATCTATC T TTGACAAA | 4849 |
| 3469 | GUAGAUUU CUGAUGAG GCCGUUAGGC CGAA IUCAAAGA | 11913 | TCTTTGAC A AAATCTAC | 4850 |
| 3475 | GGUGCUGU CUGAUGAG GCCGUUAGGC CGAA IAUUUUGU | 11914 | ACAAAATC T ACAGCACC | 4851 |
| 3478 | CUUGGUGC CUGAUGAG GCCGUUAGGC CGAA IUAGAUUU | 11915 | AAATCTAC A GCACCAAG | 4852 |
| 3481 | GCUCUUGG CUGAUGAG GCCGUUAGGC CGAA ICUGUAGA | 11916 | TCTACAGC A CCAAGAGC | 4853 |
| 3483 | UCGCUCUU CUGAUGAG GCCGUUAGGC CGAA IUGCUGUA | 11917 | TACAGCAC C AAGAGCGA | 4854 |
| 3484 | GUCGCUCU CUGAUGAG GCCGUUAGGC CGAA IGUGCUGU | 11918 | ACAGCACC A AGAGCGAC | 4855 |
| 3501 | ACUCCGUA CUGAUGAG GCCGUUAGGC CGAA IACCACAC | 11919 | GTGTGGTC T TACGGAGT | 4856 |
| 3515 | UUUCCCAC CUGAUGAG GCCGUUAGGC CGAA ICAAUACU | 11920 | AGTATTGC T GTGGGAAA | 4857 |
| 3526 | UAAGGAGA CUGAUGAG GCCGUUAGGC CGAA IAUUUCCC | 11921 | GGGAAATC T TCTCCTTA | 4858 |
| 3529 | ACCUAAGG CUGAUGAG GCCGUUAGGC CGAA IAAGAUUU | 11922 | AAATCTTC T CCTTAGGT | 4859 |
| 3531 | CCACCUAA CUGAUGAG GCCGUUAGGC CGAA IAGAAGAU | 11923 | ATCTTCTC C TTAGGTGG | 4860 |
| 3532 | CCCACCUA CUGAUGAG GCCGUUAGGC CGAA IGAGAAGA | 11924 | TCTTCTCC T TAGGTGGG | 4861 |
| 3543 | GGGUAUGG CUGAUGAG GCCGUUAGGC CGAA IACCCACC | 11925 | GGTGGGTC T CCATACCC | 4862 |
| 3545 | CUGGGUAU CUGAUGAG GCCGUUAGGC CGAA IAGACCCA | 11926 | TGGGTCTC C ATACCCAG | 4863 |
| 3546 | CCUGGGUA CUGAUGAG GCCGUUAGGC CGAA IGAGACCC | 11927 | GGGTCTCC A TACCCAGG | 4864 |
| 3550 | UACUCCUG CUGAUGAG GCCGUUAGGC CGAA IUAUGGAG | 11928 | CTCCATAC C CAGGAGTA | 4865 |
| 3551 | GUACUCCU CUGAUGAG GCCGUUAGGC CGAA IGUAUGGA | 11929 | TCCATACC C AGGAGTAC | 4866 |
| 3552 | UGUACUCC CUGAUGAG GCCGUUAGGC CGAA IGGUAUGG | 11930 | CCATACCC A GGAGTACA | 4867 |
| 3560 | CAUCCAUU CUGAUGAG GCCGUUAGGC CGAA IUACUCCU | 11931 | AGGAGTAC A AATGGATG | 4868 |
| 3574 | ACUGCAAA CUGAUGAG GCCGUUAGGC CGAA IUCCUCAU | 11932 | ATGAGGAC T TTTGCAGT | 4869 |
| 3580 | CAGGCGAC CUGAUGAG GCCGUUAGGC CGAA ICAAAAGU | 11933 | ACTTTTGC A GTCGCCTG | 4870 |
| 3586 | UUCCCUCA CUGAUGAG GCCGUUAGGC CGAA ICGACUGC | 11934 | GCAGTCGC C TGAGGGAA | 4871 |
| 3587 | CUUCCCUC CUGAUGAG GCCGUUAGGC CGAA IGCGACUG | 11935 | CAGTCGCC T GAGGGAAG | 4872 |
| 3598 | CAUCCUCA CUGAUGAG GCCGUUAGGC CGAA ICCUUCCC | 11936 | GGGAAGGC A TGAGGATG | 4873 |
| 3612 | UACUCAGG CUGAUGAG GCCGUUAGGC CGAA ICUCUCAU | 11937 | ATGAGAGC T CCTGAGTA | 4874 |
| 3614 | AGUACUCA CUGAUGAG GCCGUUAGGC CGAA IAGCUCUC | 11938 | GAGAGCTC C TGAGTACT | 4875 |

| | | | | |
|---|---|---|---|---|
| 3615 | GAGUACUC CUGAUGAG GCCGUUAGGC CGAA IGAGCUCU | 11939 | AGAGCTCC T GAGTACTC | 4876 |
| 3622 | AGGAGUAG CUGAUGAG GCCGUUAGGC CGAA IUACUCAG | 11940 | CTGAGTAC T CTACTCCT | 4877 |
| 3624 | UCAGGAGU CUGAUGAG GCCGUUAGGC CGAA IAGUACUC | 11941 | GAGTACTC T ACTCCTGA | 4878 |
| 3627 | AUUUCAGG CUGAUGAG GCCGUUAGGC CGAA IUAGAGUA | 11942 | TACTCTAC T CCTGAAAT | 4879 |
| 3629 | AGAUUUCA CUGAUGAG GCCGUUAGGC CGAA IAGUAGAG | 11943 | CTCTACTC C TGAAATCT | 4880 |
| 3630 | UAGAUUUC CUGAUGAG GCCGUUAGGC CGAA IGAGUAGA | 11944 | TCTACTCC T GAAATCTA | 4881 |
| 3637 | GAUCUGAU CUGAUGAG GCCGUUAGGC CGAA IAUUUCAG | 11945 | CTGAAATC T ATCAGATC | 4882 |
| 3641 | GCAUGAUC CUGAUGAG GCCGUUAGGC CGAA IAUAGAUU | 11946 | AATCTATC A GATCATGC | 4883 |
| 3646 | GUCCAGCA CUGAUGAG GCCGUUAGGC CGAA IAUCUGAU | 11947 | ATCAGATC A TGCTGGAC | 4884 |
| 3650 | AGCAGUCC CUGAUGAG GCCGUUAGGC CGAA ICAUGAUC | 11948 | GATCATGC T GGACTGCT | 4885 |
| 3655 | GUGCCAGC CUGAUGAG GCCGUUAGGC CGAA IUCCAGCA | 11949 | TGCTGGAC T GCTGGCAC | 4886 |
| 3658 | UCUGUGCC CUGAUGAG GCCGUUAGGC CGAA ICAGUCCA | 11950 | TGGACTGC T GGCACAGA | 4887 |
| 3662 | GGUCUCUG CUGAUGAG GCCGUUAGGC CGAA ICCAGCAG | 11951 | CTGCTGGC A CAGAGACC | 4888 |
| 3664 | UGGGUCUC CUGAUGAG GCCGUUAGGC CGAA IUGCCAGC | 11952 | GCTGGCAC A GAGACCCA | 4889 |
| 3670 | UUCUUUUG CUGAUGAG GCCGUUAGGC CGAA IUCUCUGU | 11953 | ACAGAGAC C CAAAAGAA | 4890 |
| 3671 | UUUCUUUU CUGAUGAG GCCGUUAGGC CGAA IGUCUCUG | 11954 | CAGAGACC C AAAAGAAA | 4891 |
| 3672 | CUUUCUUU CUGAUGAG GCCGUUAGGC CGAA IGGUCUCU | 11955 | AGAGACCC A AAAGAAAG | 4892 |
| 3683 | CAAAUCUU CUGAUGAG GCCGUUAGGC CGAA ICCUUUCU | 11956 | AGAAAGGC C AAGATTTG | 4893 |
| 3684 | GCAAAUCU CUGAUGAG GCCGUUAGGC CGAA IGCCUUUC | 11957 | GAAAGGCC A AGATTTGC | 4894 |
| 3693 | ACAAGUUC CUGAUGAG GCCGUUAGGC CGAA ICAAAUCU | 11958 | AGATTTGC A GAACTTGT | 4895 |
| 3698 | UUUCCACA CUGAUGAG GCCGUUAGGC CGAA IUUCUGCA | 11959 | TGCAGAAC T TGTGGAAA | 4896 |
| 3710 | AAUCACCU CUGAUGAG GCCGUUAGGC CGAA IUUUUUCC | 11960 | GGAAAAAC T AGGTGATT | 4897 |
| 3722 | UUGCUUGA CUGAUGAG GCCGUUAGGC CGAA ICAAAUCA | 11961 | TGATTTGC T TCAAGCAA | 4898 |
| 3725 | CAUUUGCU CUGAUGAG GCCGUUAGGC CGAA IAAGCAAA | 11962 | TTTGCTTC A AGCAAATG | 4899 |
| 3729 | UGUACAUU CUGAUGAG GCCGUUAGGC CGAA ICUUGAAG | 11963 | CTTCAAGC A AATGTACA | 4900 |
| 3737 | CAUCCUGU CUGAUGAG GCCGUUAGGC CGAA IUACAUUU | 11964 | AAATGTAC A ACAGGATG | 4901 |
| 3740 | UACCAUCC CUGAUGAG GCCGUUAGGC CGAA IUUGUACA | 11965 | TGTACAAC A GGATGGTA | 4902 |
| 3754 | UGGGAUGU CUGAUGAG GCCGUUAGGC CGAA IUCUUUAC | 11966 | GTAAAGAC T ACATCCCA | 4903 |
| 3757 | GAUUGGGA CUGAUGAG GCCGUUAGGC CGAA IUAGUCUU | 11967 | AAGACTAC A TCCCAATC | 4904 |
| 3760 | AUUGAUUG CUGAUGAG GCCGUUAGGC CGAA IAUGUAGU | 11968 | ACTACATC C CAATCAAT | 4905 |
| 3761 | CAUUGAUU CUGAUGAG GCCGUUAGGC CGAA IGAUGUAG | 11969 | CTACATCC C AATCAATG | 4906 |
| 3762 | GCAUUGAU CUGAUGAG GCCGUUAGGC CGAA IGGAUGUA | 11970 | TACATCCC A ATCAATGC | 4907 |
| 3766 | UAUGGCAU CUGAUGAG GCCGUUAGGC CGAA IAUUGGGA | 11971 | TCCCAATC A ATGCCATA | 4908 |

| | | | | |
|---|---|---|---|---|
| 3771 | GUCAGUAU CUGAUGAG GCCGUUAGGC CGAA ICAUUGAU | 11972 | ATCAATGC C ATACTGAC | 4909 |
| 3772 | UGUCAGUA CUGAUGAG GCCGUUAGGC CGAA IGCAUUGA | 11973 | TCAATGCC A TACTGACA | 4910 |
| 3776 | UUCCUGUC CUGAUGAG GCCGUUAGGC CGAA IUAUGGCA | 11974 | TGCCATAC T GACAGGAA | 4911 |
| 3780 | CUAUUUCC CUGAUGAG GCCGUUAGGC CGAA IUCAGUAU | 11975 | ATACTGAC A GGAAATAG | 4912 |
| 3798 | GUUGAGUA CUGAUGAG GCCGUUAGGC CGAA IUAAACCC | 11976 | GGGTTTAC A TACTCAAC | 4913 |
| 3802 | AGGAGUUG CUGAUGAG GCCGUUAGGC CGAA IUAUGUAA | 11977 | TTACATAC T CAACTCCT | 4914 |
| 3804 | GCAGGAGU CUGAUGAG GCCGUUAGGC CGAA IAGUAUGU | 11978 | ACATACTC A ACTCCTGC | 4915 |
| 3807 | AAGGCAGG CUGAUGAG GCCGUUAGGC CGAA IUUGAGUA | 11979 | TACTCAAC T CCTGCCTT | 4916 |
| 3809 | AGAAGGCA CUGAUGAG GCCGUUAGGC CGAA IAGUUGAG | 11980 | CTCAACTC C TGCCTTCT | 4917 |
| 3810 | GAGAAGGC CUGAUGAG GCCGUUAGGC CGAA IGAGUUGA | 11981 | TCAACTCC T GCCTTCTC | 4918 |
| 3813 | UCAGAGAA CUGAUGAG GCCGUUAGGC CGAA ICAGGAGU | 11982 | ACTCCTGC C TTCTCTGA | 4919 |
| 3814 | CUCAGAGA CUGAUGAG GCCGUUAGGC CGAA IGCAGGAG | 11983 | CTCCTGCC T TCTCTGAG | 4920 |
| 3817 | GUCCUCAG CUGAUGAG GCCGUUAGGC CGAA IAAGGCAG | 11984 | CTGCCTTC T CTGAGGAC | 4921 |
| 3819 | AAGUCCUC CUGAUGAG GCCGUUAGGC CGAA IAGAAGGC | 11985 | GCCTTCTC T GAGGACTT | 4922 |
| 3826 | CUUGAAGA CUGAUGAG GCCGUUAGGC CGAA IUCCUCAG | 11986 | CTGAGGAC T TCTTCAAG | 4923 |
| 3829 | UUCCUUGA CUGAUGAG GCCGUUAGGC CGAA IAAGUCCU | 11987 | AGGACTTC T TCAAGGAA | 4924 |
| 3832 | ACUUUCCU CUGAUGAG GCCGUUAGGC CGAA IAAGAAGU | 11988 | ACTTCTTC A AGGAAAGT | 4925 |
| 3846 | UUCGGAGC CUGAUGAG GCCGUUAGGC CGAA IAAAUACU | 11989 | AGTATTTC A GCTCCGAA | 4926 |
| 3849 | AACUUCGG CUGAUGAG GCCGUUAGGC CGAA ICUGAAAU | 11990 | ATTTCAGC T CCGAAGTT | 4927 |
| 3851 | UAAACUUC CUGAUGAG GCCGUUAGGC CGAA IAGCUGAA | 11991 | TTCAGCTC C GAAGTTTA | 4928 |
| 3864 | GAGCUUCC CUGAUGAG GCCGUUAGGC CGAA IAAUUAAA | 11992 | TTTAATTC A GGAAGCTC | 4929 |
| 3871 | AUCAUCAG CUGAUGAG GCCGUUAGGC CGAA ICUUCCUG | 11993 | CAGGAAGC T CTGATGAT | 4930 |
| 3873 | ACAUCAUC CUGAUGAG GCCGUUAGGC CGAA IAGCUUCC | 11994 | GGAAGCTC T GATGATGT | 4931 |
| 3883 | UACAUAUC CUGAUGAG GCCGUUAGGC CGAA IACAUCAU | 11995 | ATGATGTC A GATATGTA | 4932 |
| 3897 | AACUUGAA CUGAUGAG GCCGUUAGGC CGAA ICAUUUAC | 11996 | GTAAATGC T TTCAAGTT | 4933 |
| 3901 | CAUGAACU CUGAUGAG GCCGUUAGGC CGAA IAAAGCAU | 11997 | ATGCTTTC A AGTTCATG | 4934 |
| 3907 | CAGGCUCA CUGAUGAG GCCGUUAGGC CGAA IAACUUGA | 11998 | TCAAGTTC A TGAGCCTG | 4935 |
| 3913 | UCUUUCCA CUGAUGAG GCCGUUAGGC CGAA ICUCAUGA | 11999 | TCATGAGC C TGGAAAGA | 4936 |
| 3914 | UUCUUUCC CUGAUGAG GCCGUUAGGC CGAA IGCUCAUG | 12000 | CATGAGCC T GGAAAGAA | 4937 |
| 3925 | AAAGGUUU CUGAUGAG GCCGUUAGGC CGAA IAUUCUUU | 12001 | AAAGAATC A AAACCTTT | 4938 |
| 3930 | UCUUCAAA CUGAUGAG GCCGUUAGGC CGAA IUUUUGAU | 12002 | ATCAAAAC C TTTGAAGA | 4939 |
| 3931 | UUCUUCAA CUGAUGAG GCCGUUAGGC CGAA IGUUUUGA | 12003 | TCAAAACC T TTGAAGAA | 4940 |
| 3941 | UCGGUAAA CUGAUGAG GCCGUUAGGC CGAA IUUCUUCA | 12004 | TGAAGAAC T TTTACCGA | 4941 |

| | | | | |
|---|---|---|---|---|
| 3947 | UGGCAUUC CUGAUGAG GCCGUUAGGC CGAA IUAAAAGU | 12005 | ACTTTTAC C GAATGCCA | 4942 |
| 3954 | AUGGAGGU CUGAUGAG GCCGUUAGGC CGAA ICAUUCGG | 12006 | CCGAATGC C ACCTCCAT | 4943 |
| 3955 | CAUGGAGG CUGAUGAG GCCGUUAGGC CGAA IGCAUUCG | 12007 | CGAATGCC A CCTCCATG | 4944 |
| 3957 | AACAUGGA CUGAUGAG GCCGUUAGGC CGAA IUGGCAUU | 12008 | AATGCCAC C TCCATGTT | 4945 |
| 3958 | AAACAUGG CUGAUGAG GCCGUUAGGC CGAA IGUGGCAU | 12009 | ATGCCACC T CCATGTTT | 4946 |
| 3960 | UCAAACAU CUGAUGAG GCCGUUAGGC CGAA IAGGUGGC | 12010 | GCCACCTC C ATGTTTGA | 4947 |
| 3961 | AUCAAACA CUGAUGAG GCCGUUAGGC CGAA IGAGGUGG | 12011 | CCACCTCC A TGTTTGAT | 4948 |
| 3973 | GCCCUGGU CUGAUGAG GCCGUUAGGC CGAA IUCAUCAA | 12012 | TTGATGAC T ACCAGGGC | 4949 |
| 3976 | GUCGCCCU CUGAUGAG GCCGUUAGGC CGAA IUAGUCAU | 12013 | ATGACTAC C AGGGCGAC | 4950 |
| 3977 | UGUCGCCC CUGAUGAG GCCGUUAGGC CGAA IGUAGUCA | 12014 | TGACTACC A GGGCGACA | 4951 |
| 3985 | AGUGCUGC CUGAUGAG GCCGUUAGGC CGAA IUCGCCCU | 12015 | AGGGCGAC A GCAGCACT | 4952 |
| 3988 | CAGAGUGC CUGAUGAG GCCGUUAGGC CGAA ICUGUCGC | 12016 | GCGACAGC A GCACTCTG | 4953 |
| 3991 | CAACAGAG CUGAUGAG GCCGUUAGGC CGAA ICUGCUGU | 12017 | ACAGCAGC A CTCTGTTG | 4954 |
| 3993 | GCCAACAG CUGAUGAG GCCGUUAGGC CGAA IUGCUGCU | 12018 | AGCAGCAC T CTGTTGGC | 4955 |
| 3995 | AGGCCAAC CUGAUGAG GCCGUUAGGC CGAA IAGUGCUG | 12019 | CAGCACTC T GTTGGCCT | 4956 |
| 4002 | AUGGGAGA CUGAUGAG GCCGUUAGGC CGAA ICCAACAG | 12020 | CTGTTGGC C TCTCCCAT | 4957 |
| 4003 | CAUGGGAG CUGAUGAG GCCGUUAGGC CGAA IGCCAACA | 12021 | TGTTGGCC T CTCCCATG | 4958 |
| 4005 | AGCAUGGG CUGAUGAG GCCGUUAGGC CGAA IAGGCCAA | 12022 | TTGGCCTC T CCCATGCT | 4959 |
| 4007 | UCAGCAUG CUGAUGAG GCCGUUAGGC CGAA IAGAGGCC | 12023 | GGCCTCTC C CATGCTGA | 4960 |
| 4008 | UUCAGCAU CUGAUGAG GCCGUUAGGC CGAA IGAGAGGC | 12024 | GCCTCTCC C ATGCTGAA | 4961 |
| 4009 | CUUCAGCA CUGAUGAG GCCGUUAGGC CGAA IGGAGAGG | 12025 | CCTCTCCC A TGCTGAAG | 4962 |
| 4013 | AGCGCUUC CUGAUGAG GCCGUUAGGC CGAA ICAUGGGA | 12026 | TCCCATGC T GAAGCGCT | 4963 |
| 4021 | CCAGGUGA CUGAUGAG GCCGUUAGGC CGAA ICGCUUCA | 12027 | TGAAGCGC T TCACCTGG | 4964 |
| 4024 | AGUCCAGG CUGAUGAG GCCGUUAGGC CGAA IAAGCGCU | 12028 | AGCGCTTC A CCTGGACT | 4965 |
| 4026 | UCAGUCCA CUGAUGAG GCCGUUAGGC CGAA IUGAAGCG | 12029 | CGCTTCAC C TGGACTGA | 4966 |
| 4027 | GUCAGUCC CUGAUGAG GCCGUUAGGC CGAA IGUGAAGC | 12030 | GCTTCACC T GGACTGAC | 4967 |
| 4032 | UUGCUGUC CUGAUGAG GCCGUUAGGC CGAA IUCCAGGU | 12031 | ACCTGGAC T GACAGCAA | 4968 |
| 4036 | GGGUUUGC CUGAUGAG GCCGUUAGGC CGAA IUCAGUCC | 12032 | GGACTGAC A GCAAACCC | 4969 |
| 4039 | CUUGGGUU CUGAUGAG GCCGUUAGGC CGAA ICUGUCAG | 12033 | CTGACAGC A AACCCAAG | 4970 |
| 4043 | AGGCCUUG CUGAUGAG GCCGUUAGGC CGAA IUUUGCUG | 12034 | CAGCAAAC C CAAGGCCT | 4971 |
| 4044 | GAGGCCUU CUGAUGAG GCCGUUAGGC CGAA IGUUUGCU | 12035 | AGCAAACC C AAGGCCTC | 4972 |
| 4045 | CGAGGCCU CUGAUGAG GCCGUUAGGC CGAA IGGUUUGC | 12036 | GCAAACCC A AGGCCTCG | 4973 |
| 4050 | UUGAGCGA CUGAUGAG GCCGUUAGGC CGAA ICCUUGGG | 12037 | CCCAAGGC C TCGCTCAA | 4974 |

| | | | | |
|---|---|---|---|---|
| 4051 | CUUGAGCG CUGAUGAG GCCGUUAGGC CGAA IGCCUUGG | 12038 | CCAAGGCC T CGCTCAAG | 4975 |
| 4055 | CAAUCUUG CUGAUGAG GCCGUUAGGC CGAA ICGAGGCC | 12039 | GGCCTCGC T CAAGATTG | 4976 |
| 4057 | GUCAAUCU CUGAUGAG GCCGUUAGGC CGAA IAGCGAGG | 12040 | CCTCGCTC A AGATTGAC | 4977 |
| 4066 | UACUCUCA CUGAUGAG GCCGUUAGGC CGAA IUCAAUCU | 12041 | AGATTGAC T TGAGAGTA | 4978 |
| 4077 | CUUUUACU CUGAUGAG GCCGUUAGGC CGAA IUUACUCU | 12042 | AGAGTAAC C AGTAAAAG | 4979 |
| 4078 | ACUUUUAC CUGAUGAG GCCGUUAGGC CGAA IGUUACUC | 12043 | GAGTAACC A GTAAAAGT | 4980 |
| 4100 | CAUCAGAC CUGAUGAG GCCGUUAGGC CGAA ICCCCGAC | 12044 | GTCGGGGC T GTCTGATG | 4981 |
| 4104 | CUGACAUC CUGAUGAG GCCGUUAGGC CGAA IACAGCCC | 12045 | GGGCTGTC T GATGTCAG | 4982 |
| 4111 | GGGCCUGC CUGAUGAG GCCGUUAGGC CGAA IACAUCAG | 12046 | CTGATGTC A GCAGGCCC | 4983 |
| 4114 | ACUGGGCC CUGAUGAG GCCGUUAGGC CGAA ICUGACAU | 12047 | ATGTCAGC A GGCCCAGT | 4984 |
| 4118 | AGAAACUG CUGAUGAG GCCGUUAGGC CGAA ICCUGCUG | 12048 | CAGCAGGC C CAGTTTCT | 4985 |
| 4119 | CAGAAACU CUGAUGAG GCCGUUAGGC CGAA IGCCUGCU | 12049 | AGCAGGCC C AGTTTCTG | 4986 |
| 4120 | GCAGAAAC CUGAUGAG GCCGUUAGGC CGAA IGGCCUGC | 12050 | GCAGGCCC A GTTTCTGC | 4987 |
| 4126 | GGAAUGGC CUGAUGAG GCCGUUAGGC CGAA IAAACUGG | 12051 | CCAGTTTC T GCCATTCC | 4988 |
| 4129 | GCUGGAAU CUGAUGAG GCCGUUAGGC CGAA ICAGAAAC | 12052 | GTTTCTGC C ATTCCAGC | 4989 |
| 4130 | AGCUGGAA CUGAUGAG GCCGUUAGGC CGAA IGCAGAAA | 12053 | TTTCTGCC A TTCCAGCT | 4990 |
| 4134 | CCACAGCU CUGAUGAG GCCGUUAGGC CGAA IAAUGGCA | 12054 | TGCCATTC C AGCTGTGG | 4991 |
| 4135 | CCCACAGC CUGAUGAG GCCGUUAGGC CGAA IGAAUGGC | 12055 | GCCATTCC A GCTGTGGG | 4992 |
| 4138 | GUGCCCAC CUGAUGAG GCCGUUAGGC CGAA ICUGGAAU | 12056 | ATTCCAGC T GTGGGCAC | 4993 |
| 4145 | CGCUGACG CUGAUGAG GCCGUUAGGC CGAA ICCCACAG | 12057 | CTGTGGGC A CGTCAGCG | 4994 |
| 4150 | GCCUUCGC CUGAUGAG GCCGUUAGGC CGAA IACGUGCC | 12058 | GGCACGTC A GCGAAGGC | 4995 |
| 4159 | CCUGCGCU CUGAUGAG GCCGUUAGGC CGAA ICCUUCGC | 12059 | GCGAAGGC A AGCGCAGG | 4996 |
| 4165 | GGUGAACC CUGAUGAG GCCGUUAGGC CGAA ICGCUUGC | 12060 | GCAAGCGC A GGTTCACC | 4997 |
| 4171 | GUCGUAGG CUGAUGAG GCCGUUAGGC CGAA IAACCUGC | 12061 | GCAGGTTC A CCTACGAC | 4998 |
| 4173 | UGGUCGUA CUGAUGAG GCCGUUAGGC CGAA IUGAACCU | 12062 | AGGTTCAC C TACGACCA | 4999 |
| 4174 | GUGGUCGU CUGAUGAG GCCGUUAGGC CGAA IGUGAACC | 12063 | GGTTCACC T ACGACCAC | 5000 |
| 4180 | CUCAGCGU CUGAUGAG GCCGUUAGGC CGAA IUCGUAGG | 12064 | CCTACGAC C ACGCTGAG | 5001 |
| 4181 | GCUCAGCG CUGAUGAG GCCGUUAGGC CGAA IGUCGUAG | 12065 | CTACGACC A CGCTGAGC | 5002 |
| 4185 | UCCAGCUC CUGAUGAG GCCGUUAGGC CGAA ICGUGGUC | 12066 | GACCACGC T GAGCTGGA | 5003 |
| 4190 | UCCUUUCC CUGAUGAG GCCGUUAGGC CGAA ICUCAGCG | 12067 | CGCTGAGC T GGAAAGGA | 5004 |
| 4210 | CGGGGAGC CUGAUGAG GCCGUUAGGC CGAA ICACGCGA | 12068 | TCGCGTGC T GCTCCCCG | 5005 |
| 4213 | GGGCGGGG CUGAUGAG GCCGUUAGGC CGAA ICAGCACG | 12069 | CGTGCTGC T CCCCGCCC | 5006 |
| 4215 | GGGGGCGG CUGAUGAG GCCGUUAGGC CGAA IAGCAGCA | 12070 | TGCTGCTC C CCGCCCCC | 5007 |

| | | | | |
|---|---|---|---|---|
| 4216 | UGGGGGCG CUGAUGAG GCCGUUAGGC CGAA IGAGCAGC | 12071 | GCTGCTCC C CGCCCCCA | 5008 |
| 4217 | CUGGGGGC CUGAUGAG GCCGUUAGGC CGAA IGGAGCAG | 12072 | CTGCTCCC C GCCCCCAG | 5009 |
| 4220 | AGUCUGGG CUGAUGAG GCCGUUAGGC CGAA ICGGGGAG | 12073 | CTCCCCGC C CCCAGACT | 5010 |
| 4221 | UAGUCUGG CUGAUGAG GCCGUUAGGC CGAA IGCGGGGA | 12074 | TCCCCGCC C CCAGACTA | 5011 |
| 4222 | GUAGUCUG CUGAUGAG GCCGUUAGGC CGAA IGGCGGGG | 12075 | CCCCGCCC C CAGACTAC | 5012 |
| 4223 | UGUAGUCU CUGAUGAG GCCGUUAGGC CGAA IGGGCGGG | 12076 | CCCGCCCC C AGACTACA | 5013 |
| 4224 | UUGUAGUC CUGAUGAG GCCGUUAGGC CGAA IGGGGCGG | 12077 | CCGCCCCC A GACTACAA | 5014 |
| 4228 | CGAGUUGU CUGAUGAG GCCGUUAGGC CGAA IUCUGGGG | 12078 | CCCCAGAC T ACAACTCG | 5015 |
| 4231 | CACCGAGU CUGAUGAG GCCGUUAGGC CGAA IUAGUCUG | 12079 | CAGACTAC A ACTCGGTG | 5016 |
| 4234 | GACCACCG CUGAUGAG GCCGUUAGGC CGAA IUUGUAGU | 12080 | ACTACAAC T CGGTGGTC | 5017 |
| 4243 | GGAGUACA CUGAUGAG GCCGUUAGGC CGAA IACCACCG | 12081 | CGGTGGTC C TGTACTCC | 5018 |
| 4244 | UGGAGUAC CUGAUGAG GCCGUUAGGC CGAA IGACCACC | 12082 | GGTGGTCC T GTACTCCA | 5019 |
| 4249 | UGGGGUGG CUGAUGAG GCCGUUAGGC CGAA IUACAGGA | 12083 | TCCTGTAC T CCACCCCA | 5020 |
| 4251 | GGUGGGGU CUGAUGAG GCCGUUAGGC CGAA IAGUACAG | 12084 | CTGTACTC C ACCCCACC | 5021 |
| 4252 | GGGUGGGG CUGAUGAG GCCGUUAGGC CGAA IGAGUACA | 12085 | TGTACTCC A CCCCACCC | 5022 |
| 4254 | AUGGGUGG CUGAUGAG GCCGUUAGGC CGAA IUGGAGUA | 12086 | TACTCCAC C CCACCCAT | 5023 |
| 4255 | GAUGGGUG CUGAUGAG GCCGUUAGGC CGAA IGUGGAGU | 12087 | ACTCCACC C CACCCATC | 5024 |
| 4256 | AGAUGGGU CUGAUGAG GCCGUUAGGC CGAA IGGUGGAG | 12088 | CTCCACCC C ACCCATCT | 5025 |
| 4257 | UAGAUGGG CUGAUGAG GCCGUUAGGC CGAA IGGGUGGA | 12089 | TCCACCCC A CCCATCTA | 5026 |
| 4259 | UCUAGAUG CUGAUGAG GCCGUUAGGC CGAA IUGGGGUG | 12090 | CACCCCAC C CATCTAGA | 5027 |
| 4260 | CUCUAGAU CUGAUGAG GCCGUUAGGC CGAA IGUGGGGU | 12091 | ACCCCACC C ATCTAGAG | 5028 |
| 4261 | ACUCUAGA CUGAUGAG GCCGUUAGGC CGAA IGGUGGGG | 12092 | CCCCACCC A TCTAGAGT | 5029 |
| 4264 | CAAACUCU CUGAUGAG GCCGUUAGGC CGAA IAUGGGUG | 12093 | CACCCATC T AGAGTTTG | 5030 |
| 4275 | AGGCUUCG CUGAUGAG GCCGUUAGGC CGAA IUCAAACU | 12094 | AGTTTGAC A CGAAGCCT | 5031 |
| 4282 | AGAAAUAA CUGAUGAG GCCGUUAGGC CGAA ICUUCGUG | 12095 | CACGAAGC C TTATTTCT | 5032 |
| 4283 | UAGAAAUA CUGAUGAG GCCGUUAGGC CGAA IGCUUCGU | 12096 | ACGAAGCC T TATTTCTA | 5033 |
| 4290 | GUGCUUCU CUGAUGAG GCCGUUAGGC CGAA IAAAUAAG | 12097 | CTTATTTC T AGAAGCAC | 5034 |
| 4297 | UACACAUG CUGAUGAG GCCGUUAGGC CGAA ICUUCUAG | 12098 | CTAGAAGC A CATGTGTA | 5035 |
| 4299 | AAUACACA CUGAUGAG GCCGUUAGGC CGAA IUGCUUCU | 12099 | AGAAGCAC A TGTGTATT | 5036 |
| 4313 | UUCCUGGG CUGAUGAG GCCGUUAGGC CGAA IUAUAAAU | 12100 | ATTTATAC C CCCAGGAA | 5037 |
| 4314 | UUUCCUGG CUGAUGAG GCCGUUAGGC CGAA IGUAUAAA | 12101 | TTTATACC C CCAGGAAA | 5038 |
| 4315 | GUUUCCUG CUGAUGAG GCCGUUAGGC CGAA IGGUAUAA | 12102 | TTATACCC C CAGGAAAC | 5039 |
| 4316 | AGUUUCCU CUGAUGAG GCCGUUAGGC CGAA IGGGUAUA | 12103 | TATACCCC C AGGAAACT | 5040 |

| | | | | | |
|---|---|---|---|---|---|
| 4317 | UAGUUUCC CUGAUGAG GCCGUUAGGC CGAA IGGGGUAU | 12104 | ATACCCCC A GGAAACTA | 5041 |
| 4324 | CAAAAGCU CUGAUGAG GCCGUUAGGC CGAA IUUUCCUG | 12105 | CAGGAAAC T AGCTTTTG | 5042 |
| 4328 | CUGGCAAA CUGAUGAG GCCGUUAGGC CGAA ICUAGUUU | 12106 | AAACTAGC T TTTGCCAG | 5043 |
| 4334 | AUAAUACU CUGAUGAG GCCGUUAGGC CGAA ICAAAAGC | 12107 | GCTTTTGC C AGTATTAT | 5044 |
| 4335 | CAUAAUAC CUGAUGAG GCCGUUAGGC CGAA IGCAAAAG | 12108 | CTTTTGCC A GTATTATG | 5045 |
| 4345 | CUUAUAUA CUGAUGAG GCCGUUAGGC CGAA ICAUAAUA | 12109 | TATTATGC A TATATAAG | 5046 |
| 4359 | GAUAAAGG CUGAUGAG GCCGUUAGGC CGAA IUAAACUU | 12110 | AAGTTTAC A CCTTTATC | 5047 |
| 4361 | AAGAUAAA CUGAUGAG GCCGUUAGGC CGAA IUGUAAAC | 12111 | GTTTACAC C TTTATCTT | 5048 |
| 4362 | AAAGAUAA CUGAUGAG GCCGUUAGGC CGAA IGUGUAAA | 12112 | TTTACACC T TTATCTTT | 5049 |
| 4368 | CCAUGGAA CUGAUGAG GCCGUUAGGC CGAA IAUAAAGG | 12113 | CCTTTATC T TTCCATGG | 5050 |
| 4372 | GCUCCCAU CUGAUGAG GCCGUUAGGC CGAA IAAAGAUA | 12114 | TATCTTTC C ATGGGAGC | 5051 |
| 4373 | GGCUCCCA CUGAUGAG GCCGUUAGGC CGAA IGAAAGAU | 12115 | ATCTTTCC A TGGGAGCC | 5052 |
| 4381 | AAGCAGCU CUGAUGAG GCCGUUAGGC CGAA ICUCCCAU | 12116 | ATGGGAGC C AGCTGCTT | 5053 |
| 4382 | AAAGCAGC CUGAUGAG GCCGUUAGGC CGAA IGCUCCCA | 12117 | TGGGAGCC A GCTGCTTT | 5054 |
| 4385 | CAAAAAGC CUGAUGAG GCCGUUAGGC CGAA ICUGGCUC | 12118 | GAGCCAGC T GCTTTTTG | 5055 |
| 4388 | UCACAAAA CUGAUGAG GCCGUUAGGC CGAA ICAGCUGG | 12119 | CCAGCTGC T TTTTGTGA | 5056 |
| 4412 | AAAAAAAA CUGAUGAG GCCGUUAGGC CGAA ICACUAUU | 12120 | AATAGTGC T TTTTTTTT | 5057 |
| 4426 | UUCUUGUU CUGAUGAG GCCGUUAGGC CGAA IUCAAAAA | 12121 | TTTTTGAC T AACAAGAA | 5058 |
| 4430 | UACAUUCU CUGAUGAG GCCGUUAGGC CGAA IUUAGUCA | 12122 | TGACTAAC A AGAATGTA | 5059 |
| 4441 | CUAUCUGG CUGAUGAG GCCGUUAGGC CGAA IUUACAUU | 12123 | AATGTAAC T CCAGATAG | 5060 |
| 4443 | CUCUAUCU CUGAUGAG GCCGUUAGGC CGAA IAGUUACA | 12124 | TGTAACTC C AGATAGAG | 5061 |
| 4444 | UCUCUAUC CUGAUGAG GCCGUUAGGC CGAA IGAGUUAC | 12125 | GTAACTCC A GATAGAGA | 5062 |
| 4462 | UCUUCACU CUGAUGAG GCCGUUAGGC CGAA IUCACUAU | 12126 | ATAGTGAC A AGTGAAGA | 5063 |
| 4473 | AGCAGUAG CUGAUGAG GCCGUUAGGC CGAA IUUCUUCA | 12127 | TGAAGAAC A CTACTGCT | 5064 |
| 4475 | UUAGCAGU CUGAUGAG GCCGUUAGGC CGAA IUGUUCUU | 12128 | AAGAACAC T ACTGCTAA | 5065 |
| 4478 | GAUUUAGC CUGAUGAG GCCGUUAGGC CGAA IUAGUGUU | 12129 | AACACTAC T GCTAAATC | 5066 |
| 4481 | GAGGAUUU CUGAUGAG GCCGUUAGGC CGAA ICAGUAGU | 12130 | ACTACTGC T AAATCCTC | 5067 |
| 4487 | UAACAUGA CUGAUGAG GCCGUUAGGC CGAA IAUUUAGC | 12131 | GCTAAATC C TCATGTTA | 5068 |
| 4488 | GUAACAUG CUGAUGAG GCCGUUAGGC CGAA IGAUUUAG | 12132 | CTAAATCC T CATGTTAC | 5069 |
| 4490 | GAGUAACA CUGAUGAG GCCGUUAGGC CGAA IAGGAUUU | 12133 | AAATCCTC A TGTTACTC | 5070 |
| 4497 | UAACACUG CUGAUGAG GCCGUUAGGC CGAA IUAACAUG | 12134 | CATGTTAC T CAGTGTTA | 5071 |
| 4499 | UCUAACAC CUGAUGAG GCCGUUAGGC CGAA IAGUAACA | 12135 | TGTTACTC A GTGTTAGA | 5072 |
| 4514 | UUUAGGAA CUGAUGAG GCCGUUAGGC CGAA IAUUUCUC | 12136 | GAGAAATC C TTCCTAAA | 5073 |

231

| | | | | |
|---|---|---|---|---|
| 4515 | GUUUAGGA CUGAUGAG GCCGUUAGGC CGAA IGAUUUCU | 12137 | AGAAATCC T TCCTAAAC | 5074 |
| 4518 | UGGGUUUA CUGAUGAG GCCGUUAGGC CGAA IAAGGAUU | 12138 | AATCCTTC C TAAACCCA | 5075 |
| 4519 | UUGGGUUU CUGAUGAG GCCGUUAGGC CGAA IGAAGGAU | 12139 | ATCCTTCC T AAACCCAA | 5076 |
| 4524 | AGUCAUUG CUGAUGAG GCCGUUAGGC CGAA IUUUAGGA | 12140 | TCCTAAAC C CAATGACT | 5077 |
| 4525 | AAGUCAUU CUGAUGAG GCCGUUAGGC CGAA IGUUUAGG | 12141 | CCTAAACC C AATGACTT | 5078 |
| 4526 | GAAGUCAU CUGAUGAG GCCGUUAGGC CGAA IGGUUUAG | 12142 | CTAAACCC A ATGACTTC | 5079 |
| 4532 | AGCAGGGA CUGAUGAG GCCGUUAGGC CGAA IUCAUUGG | 12143 | CCAATGAC T TCCCTGCT | 5080 |
| 4535 | UGGAGCAG CUGAUGAG GCCGUUAGGC CGAA IAAGUCAU | 12144 | ATGACTTC C CTGCTCCA | 5081 |
| 4536 | UUGGAGCA CUGAUGAG GCCGUUAGGC CGAA IGAAGUCA | 12145 | TGACTTCC C TGCTCCAA | 5082 |
| 4537 | GUUGGAGC CUGAUGAG GCCGUUAGGC CGAA IGGAAGUC | 12146 | GACTTCCC T GCTCCAAC | 5083 |
| 4540 | GGGGUUGG CUGAUGAG GCCGUUAGGC CGAA ICAGGGAA | 12147 | TTCCCTGC T CCAACCCC | 5084 |
| 4542 | CGGGGGUU CUGAUGAG GCCGUUAGGC CGAA IAGCAGGG | 12148 | CCCTGCTC C AACCCCCG | 5085 |
| 4543 | GCGGGGGU CUGAUGAG GCCGUUAGGC CGAA IGAGCAGG | 12149 | CCTGCTCC A ACCCCCGC | 5086 |
| 4546 | GUGGCGGG CUGAUGAG GCCGUUAGGC CGAA IUUGGAGC | 12150 | GCTCCAAC C CCCGCCAC | 5087 |
| 4547 | GGUGGCGG CUGAUGAG GCCGUUAGGC CGAA IGUUGGAG | 12151 | CTCCAACC C CCGCCACC | 5088 |
| 4548 | AGGUGGCG CUGAUGAG GCCGUUAGGC CGAA IGGUUGGA | 12152 | TCCAACCC C CGCCACCT | 5089 |
| 4549 | GAGGUGGC CUGAUGAG GCCGUUAGGC CGAA IGGGUUGG | 12153 | CCAACCCC C GCCACCTC | 5090 |
| 4552 | CCUGAGGU CUGAUGAG GCCGUUAGGC CGAA ICGGGGGU | 12154 | ACCCCCGC C ACCTCAGG | 5091 |
| 4553 | CCCUGAGG CUGAUGAG GCCGUUAGGC CGAA IGCGGGGG | 12155 | CCCCCGCC A CCTCAGGG | 5092 |
| 4555 | UGCCCUGA CUGAUGAG GCCGUUAGGC CGAA IUGGCGGG | 12156 | CCCGCCAC C TCAGGGCA | 5093 |
| 4556 | GUGCCCUG CUGAUGAG GCCGUUAGGC CGAA IGUGGCGG | 12157 | CCGCCACC T CAGGGCAC | 5094 |
| 4558 | GCGUGCCC CUGAUGAG GCCGUUAGGC CGAA IAGGUGGC | 12158 | GCCACCTC A GGGCACGC | 5095 |
| 4563 | GUCCUGCG CUGAUGAG GCCGUUAGGC CGAA ICCCUGAG | 12159 | CTCAGGGC A CGCAGGAC | 5096 |
| 4567 | ACUGGUCC CUGAUGAG GCCGUUAGGC CGAA ICGUGCCC | 12160 | GGGCACGC A GGACCAGT | 5097 |
| 4572 | AUCAAACU CUGAUGAG GCCGUUAGGC CGAA IUCCUGCG | 12161 | CGCAGGAC C AGTTTGAT | 5098 |
| 4573 | AAUCAAAC CUGAUGAG GCCGUUAGGC CGAA IGUCCUGC | 12162 | GCAGGACC A GTTTGATT | 5099 |
| 4589 | AUCAGUGC CUGAUGAG GCCGUUAGGC CGAA ICUCCUCA | 12163 | TGAGGAGC T GCACTGAT | 5100 |
| 4592 | GUGAUCAG CUGAUGAG GCCGUUAGGC CGAA ICAGCUCC | 12164 | GGAGCTGC A CTGATCAC | 5101 |
| 4594 | GGGUGAUC CUGAUGAG GCCGUUAGGC CGAA IUGCAGCU | 12165 | AGCTGCAC T GATCACCC | 5102 |
| 4599 | GCAUUGGG CUGAUGAG GCCGUUAGGC CGAA IAUCAGUG | 12166 | CACTGATC A CCCAATGC | 5103 |
| 4601 | AUGCAUUG CUGAUGAG GCCGUUAGGC CGAA IUGAUCAG | 12167 | CTGATCAC C CAATGCAT | 5104 |
| 4602 | GAUGCAUU CUGAUGAG GCCGUUAGGC CGAA IGUGAUCA | 12168 | TGATCACC C AATGCATC | 5105 |
| 4603 | UGAUGCAU CUGAUGAG GCCGUUAGGC CGAA IGGUGAUC | 12169 | GATCACCC A ATGCATCA | 5106 |

232

| | | | | |
|---|---|---|---|---|
| 4608 | GUACGUGA CUGAUGAG GCCGUUAGGC CGAA ICAUUGGG | 12170 | CCCAATGC A TCACGTAC | 5107 |
| 4611 | GGGGUACG CUGAUGAG GCCGUUAGGC CGAA IAUGCAUU | 12171 | AATGCATC A CGTACCCC | 5108 |
| 4617 | CCCAGUGG CUGAUGAG GCCGUUAGGC CGAA IUACGUGA | 12172 | TCACGTAC C CCACTGGG | 5109 |
| 4618 | GCCCAGUG CUGAUGAG GCCGUUAGGC CGAA IGUACGUG | 12173 | CACGTACC C CACTGGGC | 5110 |
| 4619 | GGCCCAGU CUGAUGAG GCCGUUAGGC CGAA IGGUACGU | 12174 | ACGTACCC C ACTGGGCC | 5111 |
| 4620 | UGGCCCAG CUGAUGAG GCCGUUAGGC CGAA IGGGUACG | 12175 | CGTACCCC A CTGGGCCA | 5112 |
| 4622 | GCUGGCCC CUGAUGAG GCCGUUAGGC CGAA IUGGGGUA | 12176 | TACCCCAC T GGGCCAGC | 5113 |
| 4627 | GCAGGGCU CUGAUGAG GCCGUUAGGC CGAA ICCCAGUG | 12177 | CACTGGGC C AGCCCTGC | 5114 |
| 4628 | UGCAGGGC CUGAUGAG GCCGUUAGGC CGAA IGCCCAGU | 12178 | ACTGGGCC A GCCCTGCA | 5115 |
| 4631 | GGCUGCAG CUGAUGAG GCCGUUAGGC CGAA ICUGGCCC | 12179 | GGGCCAGC C CTGCAGCC | 5116 |
| 4632 | GGGCUGCA CUGAUGAG GCCGUUAGGC CGAA IGCUGGCC | 12180 | GGCCAGCC C TGCAGCCC | 5117 |
| 4633 | UGGGCUGC CUGAUGAG GCCGUUAGGC CGAA IGGCUGGC | 12181 | GCCAGCCC T GCAGCCCA | 5118 |
| 4636 | UUUUGGGC CUGAUGAG GCCGUUAGGC CGAA ICAGGGCU | 12182 | AGCCCTGC A GCCCAAAA | 5119 |
| 4639 | GGGUUUUG CUGAUGAG GCCGUUAGGC CGAA ICUGCAGG | 12183 | CCTGCAGC C CAAAACCC | 5120 |
| 4640 | UGGGUUUU CUGAUGAG GCCGUUAGGC CGAA IGCUGCAG | 12184 | CTGCAGCC C AAAACCCA | 5121 |
| 4641 | CUGGGUUU CUGAUGAG GCCGUUAGGC CGAA IGGCUGCA | 12185 | TGCAGCCC A AAACCCAG | 5122 |
| 4646 | UUGCCCUG CUGAUGAG GCCGUUAGGC CGAA IUUUUGGG | 12186 | CCCAAAAC C CAGGGCAA | 5123 |
| 4647 | GUUGCCCU CUGAUGAG GCCGUUAGGC CGAA IGUUUUGG | 12187 | CCAAAACC C AGGGCAAC | 5124 |
| 4648 | UGUUGCCC CUGAUGAG GCCGUUAGGC CGAA IGGUUUUG | 12188 | CAAAACCC A GGGCAACA | 5125 |
| 4653 | GGGCUUGU CUGAUGAG GCCGUUAGGC CGAA ICCCUGGG | 12189 | CCCAGGGC A ACAAGCCC | 5126 |
| 4656 | AACGGGCU CUGAUGAG GCCGUUAGGC CGAA IUUGCCCU | 12190 | AGGGCAAC A AGCCCGTT | 5127 |
| 4660 | GGCUAACG CUGAUGAG GCCGUUAGGC CGAA ICUUGUUG | 12191 | CAACAAGC C CGTTAGCC | 5128 |
| 4661 | GGGCUAAC CUGAUGAG GCCGUUAGGC CGAA IGCUUGUU | 12192 | AACAAGCC C GTTAGCCC | 5129 |
| 4668 | UCCCCUGG CUGAUGAG GCCGUUAGGC CGAA ICUAACGG | 12193 | CCGTTAGC C CCAGGGGA | 5130 |
| 4669 | AUCCCCUG CUGAUGAG GCCGUUAGGC CGAA IGCUAACG | 12194 | CGTTAGCC C CAGGGGAT | 5131 |
| 4670 | GAUCCCCU CUGAUGAG GCCGUUAGGC CGAA IGGCUAAC | 12195 | GTTAGCCC C AGGGGATC | 5132 |
| 4671 | UGAUCCCC CUGAUGAG GCCGUUAGGC CGAA IGGGCUAA | 12196 | TTAGCCCC A GGGGATCA | 5133 |
| 4679 | CCAGCCAG CUGAUGAG GCCGUUAGGC CGAA IAUCCCCU | 12197 | AGGGGATC A CTGGCTGG | 5134 |
| 4681 | GGCCAGCC CUGAUGAG GCCGUUAGGC CGAA IUGAUCCC | 12198 | GGGATCAC T GGCTGGCC | 5135 |
| 4685 | CUCAGGCC CUGAUGAG GCCGUUAGGC CGAA ICCAGUGA | 12199 | TCACTGGC T GGCCTGAG | 5136 |
| 4689 | GUUGCUCA CUGAUGAG GCCGUUAGGC CGAA ICCAGCCA | 12200 | TGGCTGGC C TGAGCAAC | 5137 |
| 4690 | UGUUGCUC CUGAUGAG GCCGUUAGGC CGAA IGCCAGCC | 12201 | GGCTGGCC T GAGCAACA | 5138 |
| 4695 | CGAGAUGU CUGAUGAG GCCGUUAGGC CGAA ICUCAGGC | 12202 | GCCTGAGC A ACATCTCG | 5139 |

232

| | | | | |
|---|---|---|---|---|
| 4698 | UCCCGAGA CUGAUGAG GCCGUUAGGC CGAA IUUGCUCA | 12203 | TGAGCAAC A TCTCGGGA | 5140 |
| 4701 | GACUCCCG CUGAUGAG GCCGUUAGGC CGAA IAUGUUGC | 12204 | GCAACATC T CGGGAGTC | 5141 |
| 4710 | CUGCUAGA CUGAUGAG GCCGUUAGGC CGAA IACUCCCG | 12205 | CGGGAGTC C TCTAGCAG | 5142 |
| 4711 | CCUGCUAG CUGAUGAG GCCGUUAGGC CGAA IGACUCCC | 12206 | GGGAGTCC T CTAGCAGG | 5143 |
| 4713 | GGCCUGCU CUGAUGAG GCCGUUAGGC CGAA IAGGACUC | 12207 | GAGTCCTC T AGCAGGCC | 5144 |
| 4717 | CUUAGGCC CUGAUGAG GCCGUUAGGC CGAA ICUAGAGG | 12208 | CCTCTAGC A GGCCTAAG | 5145 |
| 4721 | AUGUCUUA CUGAUGAG GCCGUUAGGC CGAA ICCUGCUA | 12209 | TAGCAGGC C TAAGACAT | 5146 |
| 4722 | CAUGUCUU CUGAUGAG GCCGUUAGGC CGAA IGCCUGCU | 12210 | AGCAGGCC T AAGACATG | 5147 |
| 4728 | UCCUCACA CUGAUGAG GCCGUUAGGC CGAA IUCUUAGG | 12211 | CCTAAGAC A TGTGAGGA | 5148 |
| 4754 | UUGCUUUU CUGAUGAG GCCGUUAGGC CGAA ICUUUUUU | 12212 | AAAAAAGC A AAAAGCAA | 5149 |
| 4761 | UUCUCCCU CUGAUGAG GCCGUUAGGC CGAA ICUUUUUG | 12213 | CAAAAAGC A AGGGAGAA | 5150 |
| 4779 | CUUCUCCC CUGAUGAG GCCGUUAGGC CGAA IUUUCUCU | 12214 | AGAGAAAC C GGGAGAAG | 5151 |
| 4790 | CUUUCUCA CUGAUGAG GCCGUUAGGC CGAA ICCUUCUC | 12215 | GAGAAGGC A TGAGAAAG | 5152 |
| 4811 | CCACAUGG CUGAUGAG GCCGUUAGGC CGAA ICGUCUCA | 12216 | TGAGACGC A CCATGTGG | 5153 |
| 4813 | GCCCACAU CUGAUGAG GCCGUUAGGC CGAA IUGCGUCU | 12217 | AGACGCAC C ATGTGGGC | 5154 |
| 4814 | UGCCCACA CUGAUGAG GCCGUUAGGC CGAA IGUGCGUC | 12218 | GACGCACC A TGTGGGCA | 5155 |
| 4822 | CCCCUCCG CUGAUGAG GCCGUUAGGC CGAA ICCCACAU | 12219 | ATGTGGGC A CGGAGGGG | 5156 |
| 4839 | CAUUGCUG CUGAUGAG GCCGUUAGGC CGAA ICCCCGUC | 12220 | GACGGGGC T CAGCAATG | 5157 |
| 4841 | GGCAUUGC CUGAUGAG GCCGUUAGGC CGAA IAGCCCCG | 12221 | CGGGGCTC A GCAATGCC | 5158 |
| 4844 | AAUGGCAU CUGAUGAG GCCGUUAGGC CGAA ICUGAGCC | 12222 | GGCTCAGC A ATGCCATT | 5159 |
| 4849 | ACUGAAAU CUGAUGAG GCCGUUAGGC CGAA ICAUUGCU | 12223 | AGCAATGC C ATTTCAGT | 5160 |
| 4850 | CACUGAAA CUGAUGAG GCCGUUAGGC CGAA IGCAUUGC | 12224 | GCAATGCC A TTTCAGTG | 5161 |
| 4855 | GAAGCCAC CUGAUGAG GCCGUUAGGC CGAA IAAAUGGC | 12225 | GCCATTTC A GTGGCTTC | 5162 |
| 4861 | AGCUGGGA CUGAUGAG GCCGUUAGGC CGAA ICCACUGA | 12226 | TCAGTGGC T TCCCAGCT | 5163 |
| 4864 | CAGAGCUG CUGAUGAG GCCGUUAGGC CGAA IAAGCCAC | 12227 | GTGGCTTC C CAGCTCTG | 5164 |
| 4865 | UCAGAGCU CUGAUGAG GCCGUUAGGC CGAA IGAAGCCA | 12228 | TGGCTTCC C AGCTCTGA | 5165 |
| 4866 | GUCAGAGC CUGAUGAG GCCGUUAGGC CGAA IGGAAGCC | 12229 | GGCTTCCC A GCTCTGAC | 5166 |
| 4869 | AGGGUCAG CUGAUGAG GCCGUUAGGC CGAA ICUGGGAA | 12230 | TTCCCAGC T CTGACCCT | 5167 |
| 4871 | GAAGGGUC CUGAUGAG GCCGUUAGGC CGAA IAGCUGGG | 12231 | CCCAGCTC T GACCCTTC | 5168 |
| 4875 | UGUAGAAG CUGAUGAG GCCGUUAGGC CGAA IUCAGAGC | 12232 | GCTCTGAC C CTTCTACA | 5169 |
| 4876 | AUGUAGAA CUGAUGAG GCCGUUAGGC CGAA IGUCAGAG | 12233 | CTCTGACC C TTCTACAT | 5170 |
| 4877 | AAUGUAGA CUGAUGAG GCCGUUAGGC CGAA IGGUCAGA | 12234 | TCTGACCC T TCTACATT | 5171 |
| 4880 | UCAAAUGU CUGAUGAG GCCGUUAGGC CGAA IAAGGGUC | 12235 | GACCCTTC T ACATTTGA | 5172 |

| | | | | |
|---|---|---|---|---|
| 4883 | CCCUCAAA CUGAUGAG GCCGUUAGGC CGAA IUAGAAGG | 12236 | CCTTCTAC A TTTGAGGG | 5173 |
| 4893 | CCUGGCUG CUGAUGAG GCCGUUAGGC CGAA ICCCUCAA | 12237 | TTGAGGGC C CAGCCAGG | 5174 |
| 4894 | UCCUGGCU CUGAUGAG GCCGUUAGGC CGAA IGCCCUCA | 12238 | TGAGGGCC C AGCCAGGA | 5175 |
| 4895 | CUCCUGGC CUGAUGAG GCCGUUAGGC CGAA IGGCCCUC | 12239 | GAGGGCCC A GCCAGGAG | 5176 |
| 4898 | CUGCUCCU CUGAUGAG GCCGUUAGGC CGAA ICUGGGCC | 12240 | GGCCCAGC C AGGAGCAG | 5177 |
| 4899 | UCUGCUCC CUGAUGAG GCCGUUAGGC CGAA IGCUGGGC | 12241 | GCCCAGCC A GGAGCAGA | 5178 |
| 4905 | UGUCCAUC CUGAUGAG GCCGUUAGGC CGAA ICUCCUGG | 12242 | CCAGGAGC A GATGGACA | 5179 |
| 4913 | CUCAUCGC CUGAUGAG GCCGUUAGGC CGAA IUCCAUCU | 12243 | AGATGGAC A GCGATGAG | 5180 |
| 4927 | CCAGAAAA CUGAUGAG GCCGUUAGGC CGAA IUCCCCUC | 12244 | GAGGGGAC A TTTTCTGG | 5181 |
| 4933 | CAGAAUCC CUGAUGAG GCCGUUAGGC CGAA IAAAAUGU | 12245 | ACATTTTC T GGATTCTG | 5182 |
| 4940 | UGCCUCCC CUGAUGAG GCCGUUAGGC CGAA IAAUCCAG | 12246 | CTGGATTC T GGGAGGCA | 5183 |
| 4948 | CCUUUUCU CUGAUGAG GCCGUUAGGC CGAA ICCUCCCA | 12247 | TGGGAGGC A AGAAAAGG | 5184 |
| 4959 | AAGAUAUU CUGAUGAG GCCGUUAGGC CGAA IUCCUUUU | 12248 | AAAAGGAC A AATATCTT | 5185 |
| 4966 | UCCAAAAA CUGAUGAG GCCGUUAGGC CGAA IAUAUUUG | 12249 | CAAATATC T TTTTTGGA | 5186 |
| 4977 | UUUGCUUU CUGAUGAG GCCGUUAGGC CGAA IUUCCAAA | 12250 | TTTGGAAC T AAAGCAAA | 5187 |
| 4983 | CUAAAAUU CUGAUGAG GCCGUUAGGC CGAA ICUUUAGU | 12251 | ACTAAAGC A AATTTTAG | 5188 |
| 4994 | UAGGUAAA CUGAUGAG GCCGUUAGGC CGAA IUCUAAAA | 12252 | TTTTAGAC C TTTACCTA | 5189 |
| 4995 | AUAGGUAA CUGAUGAG GCCGUUAGGC CGAA IGUCUAAA | 12253 | TTTAGACC T TTACCTAT | 5190 |
| 5000 | CUUCCAUA CUGAUGAG GCCGUUAGGC CGAA IUAAAGGU | 12254 | ACCTTTAC C TATGGAAG | 5191 |
| 5001 | ACUUCCAU CUGAUGAG GCCGUUAGGC CGAA IGUAAAGG | 12255 | CCTTTACC T ATGGAAGT | 5192 |
| 5015 | AUGGACAU CUGAUGAG GCCGUUAGGC CGAA IAACCACU | 12256 | AGTGGTTC T ATGTCCAT | 5193 |
| 5021 | AUGAGAAU CUGAUGAG GCCGUUAGGC CGAA IACAUAGA | 12257 | TCTATGTC C ATTCTCAT | 5194 |
| 5022 | AAUGAGAA CUGAUGAG GCCGUUAGGC CGAA IGACAUAG | 12258 | CTATGTCC A TTCTCATT | 5195 |
| 5026 | CACGAAUG CUGAUGAG GCCGUUAGGC CGAA IAAUGGAC | 12259 | GTCCATTC T CATTCGTG | 5196 |
| 5028 | GCCACGAA CUGAUGAG GCCGUUAGGC CGAA IAGAAUGG | 12260 | CCATTCTC A TTCGTGGC | 5197 |
| 5037 | UCAAAACA CUGAUGAG GCCGUUAGGC CGAA ICCACGAA | 12261 | TTCGTGGC A TGTTTTGA | 5198 |
| 5054 | ACCCUCAG CUGAUGAG GCCGUUAGGC CGAA ICUACAAA | 12262 | TTTGTAGC A CTGAGGGT | 5199 |
| 5056 | CCACCCUC CUGAUGAG GCCGUUAGGC CGAA IUGCUACA | 12263 | TGTAGCAC T GAGGGTGG | 5200 |
| 5066 | GAGUUGAG CUGAUGAG GCCGUUAGGC CGAA ICCACCCU | 12264 | AGGGTGGC A CTCAACTC | 5201 |
| 5068 | CAGAGUUG CUGAUGAG GCCGUUAGGC CGAA IUGCCACC | 12265 | GGTGGCAC T CAACTCTG | 5202 |
| 5070 | CUCAGAGU CUGAUGAG GCCGUUAGGC CGAA IAGUGCCA | 12266 | TGGCACTC A ACTCTGAG | 5203 |
| 5073 | GGGCUCAG CUGAUGAG GCCGUUAGGC CGAA IUUGAGUG | 12267 | CACTCAAC T CTGAGCCC | 5204 |
| 5075 | AUGGGCUC CUGAUGAG GCCGUUAGGC CGAA IAGUUGAG | 12268 | CTCAACTC T GAGCCCAT | 5205 |

| | | | | |
|---|---|---|---|---|
| 5080 | AAAGUAUG CUGAUGAG GCCGUUAGGC CGAA ICUCAGAG | 12269 | CTCTGAGC C CATACTTT | 5206 |
| 5081 | AAAAGUAU CUGAUGAG GCCGUUAGGC CGAA IGCUCAGA | 12270 | TCTGAGCC C ATACTTTT | 5207 |
| 5082 | CAAAAGUA CUGAUGAG GCCGUUAGGC CGAA IGGCUCAG | 12271 | CTGAGCCC A TACTTTTG | 5208 |
| 5086 | GAGCCAAA CUGAUGAG GCCGUUAGGC CGAA IUAUGGGC | 12272 | GCCCATAC T TTTGGCTC | 5209 |
| 5093 | ACUAGAGG CUGAUGAG GCCGUUAGGC CGAA ICCAAAAG | 12273 | CTTTTGGC T CCTCTAGT | 5210 |
| 5095 | UUACUAGA CUGAUGAG GCCGUUAGGC CGAA IAGCCAAA | 12274 | TTTGGCTC C TCTAGTAA | 5211 |
| 5096 | CUUACUAG CUGAUGAG GCCGUUAGGC CGAA IGAGCCAA | 12275 | TTGGCTCC T CTAGTAAG | 5212 |
| 5098 | AUCUUACU CUGAUGAG GCCGUUAGGC CGAA IAGGAGCC | 12276 | GGCTCCTC T AGTAAGAT | 5213 |
| 5109 | GUUUUCAG CUGAUGAG GCCGUUAGGC CGAA ICAUCUUA | 12277 | TAAGATGC A CTGAAAAC | 5214 |
| 5111 | AAGUUUUC CUGAUGAG GCCGUUAGGC CGAA IUGCAUCU | 12278 | AGATGCAC T GAAAACTT | 5215 |
| 5118 | UCUGGCUA CUGAUGAG GCCGUUAGGC CGAA IUUUUCAG | 12279 | CTGAAAAC T TAGCCAGA | 5216 |
| 5123 | CUAACUCU CUGAUGAG GCCGUUAGGC CGAA ICUAAGUU | 12280 | AACTTAGC C AGAGTTAG | 5217 |
| 5124 | CCUAACUC CUGAUGAG GCCGUUAGGC CGAA IGCUAAGU | 12281 | ACTTAGCC A GAGTTAGG | 5218 |
| 5138 | UGGCCUGG CUGAUGAG GCCGUUAGGC CGAA IACAACCU | 12282 | AGGTTGTC T CCAGGCCA | 5219 |
| 5140 | CAUGGCCU CUGAUGAG GCCGUUAGGC CGAA IAGACAAC | 12283 | GTTGTCTC C AGGCCATG | 5220 |
| 5141 | UCAUGGCC CUGAUGAG GCCGUUAGGC CGAA IGAGACAA | 12284 | TTGTCTCC A GGCCATGA | 5221 |
| 5145 | GCCAUCAU CUGAUGAG GCCGUUAGGC CGAA ICCUGGAG | 12285 | CTCCAGGC C ATGATGGC | 5222 |
| 5146 | GGCCAUCA CUGAUGAG GCCGUUAGGC CGAA IGCCUGGA | 12286 | TCCAGGCC A TGATGGCC | 5223 |
| 5154 | CAGUGUAA CUGAUGAG GCCGUUAGGC CGAA ICCAUCAU | 12287 | ATGATGGC C TTACACTG | 5224 |
| 5155 | UCAGUGUA CUGAUGAG GCCGUUAGGC CGAA IGCCAUCA | 12288 | TGATGGCC T TACACTGA | 5225 |
| 5159 | AUUUUCAG CUGAUGAG GCCGUUAGGC CGAA IUAAGGCC | 12289 | GGCCTTAC A CTGAAAAT | 5226 |
| 5161 | ACAUUUUC CUGAUGAG GCCGUUAGGC CGAA IUGUAAGG | 12290 | CCTTACAC T GAAAATGT | 5227 |
| 5171 | AUAGAAUG CUGAUGAG GCCGUUAGGC CGAA IACAUUUU | 12291 | AAAATGTC A CATTCTAT | 5228 |
| 5173 | AAAUAGAA CUGAUGAG GCCGUUAGGC CGAA IUGACAUU | 12292 | AATGTCAC A TTCTATTT | 5229 |
| 5177 | CCCAAAAU CUGAUGAG GCCGUUAGGC CGAA IAAUGUGA | 12293 | TCACATTC T ATTTTGGG | 5230 |
| 5201 | AAGUGUCU CUGAUGAG GCCGUUAGGC CGAA IACUAUAU | 12294 | ATATAGTC C AGACACTT | 5231 |
| 5202 | UAAGUGUC CUGAUGAG GCCGUUAGGC CGAA IGACUAUA | 12295 | TATAGTCC A GACACTTA | 5232 |
| 5206 | GAGUUAAG CUGAUGAG GCCGUUAGGC CGAA IUCUGGAC | 12296 | GTCCAGAC A CTTAACTC | 5233 |
| 5208 | UUGAGUUA CUGAUGAG GCCGUUAGGC CGAA IUGUCUGG | 12297 | CCAGACAC T TAACTCAA | 5234 |
| 5213 | AGAAAUUG CUGAUGAG GCCGUUAGGC CGAA IUUAAGUG | 12298 | CACTTAAC T CAATTTCT | 5235 |
| 5215 | CAAGAAAU CUGAUGAG GCCGUUAGGC CGAA IAGUUAAG | 12299 | CTTAACTC A ATTTCTTG | 5236 |
| 5221 | UAAUACCA CUGAUGAG GCCGUUAGGC CGAA IAAAUUGA | 12300 | TCAATTTC T TGGTATTA | 5237 |
| 5233 | UGCAAAAC CUGAUGAG GCCGUUAGGC CGAA IAAUAAUA | 12301 | TATTATTC T GTTTTGCA | 5238 |

| | | | | |
|---|---|---|---|---|
| 5241 | ACUAACUG CUGAUGAG GCCGUUAGGC CGAA ICAAAACA | 12302 | TGTTTTGC A CAGTTAGT | 5239 |
| 5243 | CAACUAAC CUGAUGAG GCCGUUAGGC CGAA IUGCAAAA | 12303 | TTTTGCAC A GTTAGTTG | 5240 |
| 5263 | UUCUUCUC CUGAUGAG GCCGUUAGGC CGAA ICUUUCUU | 12304 | AAGAAAGC T GAGAAGAA | 5241 |
| 5281 | CUCAGGAC CUGAUGAG GCCGUUAGGC CGAA ICAUUUUC | 12305 | GAAAATGC A GTCCTGAG | 5242 |
| 5285 | UCUCCUCA CUGAUGAG GCCGUUAGGC CGAA IACUGCAU | 12306 | ATGCAGTC C TGAGGAGA | 5243 |
| 5286 | CUCUCCUC CUGAUGAG GCCGUUAGGC CGAA IGACUGCA | 12307 | TGCAGTCC T GAGGAGAG | 5244 |
| 5300 | UGAUAUGG CUGAUGAG GCCGUUAGGC CGAA IAAAACUC | 12308 | GAGTTTTC T CCATATCA | 5245 |
| 5302 | UUUGAUAU CUGAUGAG GCCGUUAGGC CGAA IAGAAAAC | 12309 | GTTTTCTC C ATATCAAA | 5246 |
| 5303 | UUUUGAUA CUGAUGAG GCCGUUAGGC CGAA IGAGAAAA | 12310 | TTTTCTCC A TATCAAAA | 5247 |
| 5308 | CCUCGUUU CUGAUGAG GCCGUUAGGC CGAA IAUAUGGA | 12311 | TCCATATC A AAACGAGG | 5248 |
| 5319 | CCUCCAUC CUGAUGAG GCCGUUAGGC CGAA ICCCUCGU | 12312 | ACGAGGGC T GATGGAGG | 5249 |
| 5337 | GACCUUAU CUGAUGAG GCCGUUAGGC CGAA IACCUUUU | 12313 | AAAAGGTC A ATAAGGTC | 5250 |
| 5346 | UCUUCCCU CUGAUGAG GCCGUUAGGC CGAA IACCUUAU | 12314 | ATAAGGTC A AGGGAAGA | 5251 |
| 5356 | AGAGACGG CUGAUGAG GCCGUUAGGC CGAA IUCUUCCC | 12315 | GGGAAGAC C CCGTCTCT | 5252 |
| 5357 | UAGAGACG CUGAUGAG GCCGUUAGGC CGAA IGUCUUCC | 12316 | GGAAGACC C CGTCTCTA | 5253 |
| 5358 | AUAGAGAC CUGAUGAG GCCGUUAGGC CGAA IGGUCUUC | 12317 | GAAGACCC C GTCTCTAT | 5254 |
| 5362 | UGGUAUAG CUGAUGAG GCCGUUAGGC CGAA IACGGGGU | 12318 | ACCCCGTC T CTATACCA | 5255 |
| 5364 | GUUGGUAU CUGAUGAG GCCGUUAGGC CGAA IAGACGGG | 12319 | CCCGTCTC T ATACCAAC | 5256 |
| 5369 | GUUUGGUU CUGAUGAG GCCGUUAGGC CGAA IUAUAGAG | 12320 | CTCTATAC C AACCAAAC | 5257 |
| 5370 | GGUUUGGU CUGAUGAG GCCGUUAGGC CGAA IGUAUAGA | 12321 | TCTATACC A ACCAAACC | 5258 |
| 5373 | AUUGGUUU CUGAUGAG GCCGUUAGGC CGAA IUUGGUAU | 12322 | ATACCAAC C AAACCAAT | 5259 |
| 5374 | AAUUGGUU CUGAUGAG GCCGUUAGGC CGAA IGUUGGUA | 12323 | TACCAACC A AACCAATT | 5260 |
| 5378 | GGUGAAUU CUGAUGAG GCCGUUAGGC CGAA IUUUGGUU | 12324 | AACCAAAC C AATTCACC | 5261 |
| 5379 | UGGUGAAU CUGAUGAG GCCGUUAGGC CGAA IGUUUGGU | 12325 | ACCAAACC A ATTCACCA | 5262 |
| 5384 | UGUGUUGG CUGAUGAG GCCGUUAGGC CGAA IAAUUGGU | 12326 | ACCAATTC A CCAACACA | 5263 |
| 5386 | ACUGUGUU CUGAUGAG GCCGUUAGGC CGAA IUGAAUUG | 12327 | CAATTCAC C AACACAGT | 5264 |
| 5387 | AACUGUGU CUGAUGAG GCCGUUAGGC CGAA IGUGAAUU | 12328 | AATTCACC A ACACAGTT | 5265 |
| 5390 | CCCAACUG CUGAUGAG GCCGUUAGGC CGAA IUUGGUGA | 12329 | TCACCAAC A CAGTTGGG | 5266 |
| 5392 | GUCCCAAC CUGAUGAG GCCGUUAGGC CGAA IUGUUGGU | 12330 | ACCAACAC A GTTGGGAC | 5267 |
| 5401 | GUGUUUUG CUGAUGAG GCCGUUAGGC CGAA IUCCCAAC | 12331 | GTTGGGAC C CAAAACAC | 5268 |
| 5402 | UGUGUUUU CUGAUGAG GCCGUUAGGC CGAA IGUCCCAA | 12332 | TTGGGACC C AAAACACA | 5269 |
| 5403 | CUGUGUUU CUGAUGAG GCCGUUAGGC CGAA IGGUCCCA | 12333 | TGGGACCC A AAACACAG | 5270 |
| 5408 | ACUUCCUG CUGAUGAG GCCGUUAGGC CGAA IUUUUGGG | 12334 | CCCAAAAC A CAGGAAGT | 5271 |

237

| | | | | |
|---|---|---|---|---|
| 5410 | UGACUUCC CUGAUGAG GCCGUUAGGC CGAA IUGUUUUG | 12335 | CAAAACAC A GGAAGTCA | 5272 |
| 5418 | AACGUGAC CUGAUGAG GCCGUUAGGC CGAA IACUUCCU | 12336 | AGGAAGTC A GTCACGTT | 5273 |
| 5422 | AGGAAACG CUGAUGAG GCCGUUAGGC CGAA IACUGACU | 12337 | AGTCAGTC A CGTTTCCT | 5274 |
| 5429 | AAUGAAAA CUGAUGAG GCCGUUAGGC CGAA IAAACGUG | 12338 | CACGTTTC C TTTTCATT | 5275 |
| 5430 | AAAUGAAA CUGAUGAG GCCGUUAGGC CGAA IGAAACGU | 12339 | ACGTTTCC T TTTCATTT | 5276 |
| 5435 | CCAUUAAA CUGAUGAG GCCGUUAGGC CGAA IAAAAGGA | 12340 | TCCTTTTC A TTTAATGG | 5277 |
| 5450 | GAGAUAGU CUGAUGAG GCCGUUAGGC CGAA IAAUCCCC | 12341 | GGGGATTC C ACTATCTC | 5278 |
| 5451 | UGAGAUAG CUGAUGAG GCCGUUAGGC CGAA IGAAUCCC | 12342 | GGGATTCC A CTATCTCA | 5279 |
| 5453 | UGUGAGAU CUGAUGAG GCCGUUAGGC CGAA IUGGAAUC | 12343 | GATTCCAC T ATCTCACA | 5280 |
| 5457 | UUAGUGUG CUGAUGAG GCCGUUAGGC CGAA IAUAGUGG | 12344 | CCACTATC T CACACTAA | 5281 |
| 5459 | GAUUAGUG CUGAUGAG GCCGUUAGGC CGAA IAGAUAGU | 12345 | ACTATCTC A CACTAATC | 5282 |
| 5461 | CAGAUUAG CUGAUGAG GCCGUUAGGC CGAA IUGAGAUA | 12346 | TATCTCAC A CTAATCTG | 5283 |
| 5463 | UUCAGAUU CUGAUGAG GCCGUUAGGC CGAA IUGUGAGA | 12347 | TCTCACAC T AATCTGAA | 5284 |
| 5468 | AUCCUUUC CUGAUGAG GCCGUUAGGC CGAA IAUUAGUG | 12348 | CACTAATC T GAAAGGAT | 5285 |
| 5487 | CCAGCUAA CUGAUGAG GCCGUUAGGC CGAA ICUCUUCC | 12349 | GGAAGAGC A TTAGCTGG | 5286 |
| 5493 | UAUGCGCC CUGAUGAG GCCGUUAGGC CGAA ICUAAUGC | 12350 | GCATTAGC T GGCGCATA | 5287 |
| 5499 | GCUUAAUA CUGAUGAG GCCGUUAGGC CGAA ICGCCAGC | 12351 | GCTGGCGC A TATTAAGC | 5288 |
| 5508 | GCUUAAAG CUGAUGAG GCCGUUAGGC CGAA ICUUAAUA | 12352 | TATTAAGC A CTTTAAGC | 5289 |
| 5510 | GAGCUUAA CUGAUGAG GCCGUUAGGC CGAA IUGCUUAA | 12353 | TTAAGCAC T TTAAGCTC | 5290 |
| 5517 | ACUCAAGG CUGAUGAG GCCGUUAGGC CGAA ICUUAAAG | 12354 | CTTTAAGC T CCTTGAGT | 5291 |
| 5519 | UUACUCAA CUGAUGAG GCCGUUAGGC CGAA IAGCUUAA | 12355 | TTAAGCTC C TTGAGTAA | 5292 |
| 5520 | UUUACUCA CUGAUGAG GCCGUUAGGC CGAA IGAGCUUA | 12356 | TAAGCTCC T TGAGTAAA | 5293 |
| 5550 | AAAUACCU CUGAUGAG GCCGUUAGGC CGAA ICAUAAAU | 12357 | ATTTATGC A AGGTATTT | 5294 |
| 5560 | CCAACUGG CUGAUGAG GCCGUUAGGC CGAA IAAAUACC | 12358 | GGTATTTC T CCAGTTGG | 5295 |
| 5562 | UCCCAACU CUGAUGAG GCCGUUAGGC CGAA IAGAAAUA | 12359 | TATTTCTC C AGTTGGGA | 5296 |
| 5563 | GUCCCAAC CUGAUGAG GCCGUUAGGC CGAA IGAGAAAU | 12360 | ATTTCTCC A GTTGGGAC | 5297 |
| 5572 | AUAUCCUG CUGAUGAG GCCGUUAGGC CGAA IUCCCAAC | 12361 | GTTGGGAC T CAGGATAT | 5298 |
| 5574 | UAAUAUCC CUGAUGAG GCCGUUAGGC CGAA IAGUCCCA | 12362 | TGGGACTC A GGATATTA | 5299 |
| 5593 | CUAGUGAU CUGAUGAG GCCGUUAGGC CGAA ICUCAUUA | 12363 | TAATGAGC C ATCACTAG | 5300 |
| 5594 | UCUAGUGA CUGAUGAG GCCGUUAGGC CGAA IGCUCAUU | 12364 | AATGAGCC A TCACTAGA | 5301 |
| 5597 | UCUUCUAG CUGAUGAG GCCGUUAGGC CGAA IAUGGCUC | 12365 | GAGCCATC A CTAGAAGA | 5302 |
| 5599 | UUUCUUCU CUGAUGAG GCCGUUAGGC CGAA IUGAUGGC | 12366 | GCCATCAC T AGAAGAAA | 5303 |
| 5611 | UGAAAAUG CUGAUGAG GCCGUUAGGC CGAA ICUUUUCU | 12367 | AGAAAAGC C CATTTTCA | 5304 |

| | | | | |
|---|---|---|---|---|
| 5612 | UUGAAAAU CUGAUGAG GCCGUUAGGC CGAA IGCUUUUC | 12368 | GAAAAGCC C ATTTTCAA | 5305 |
| 5613 | GUUGAAAA CUGAUGAG GCCGUUAGGC CGAA IGGCUUUU | 12369 | AAAAGCCC A TTTTCAAC | 5306 |
| 5619 | AAAGCAGU CUGAUGAG GCCGUUAGGC CGAA IAAAAUGG | 12370 | CCATTTTC A ACTGCTTT | 5307 |
| 5622 | UUCAAAGC CUGAUGAG GCCGUUAGGC CGAA IUUGAAAA | 12371 | TTTTCAAC T GCTTTGAA | 5308 |
| 5625 | AGUUUCAA CUGAUGAG GCCGUUAGGC CGAA ICAGUUGA | 12372 | TCAACTGC T TTGAAACT | 5309 |
| 5633 | CCCAGGCA CUGAUGAG GCCGUUAGGC CGAA IUUUCAAA | 12373 | TTTGAAAC T TGCCTGGG | 5310 |
| 5637 | AGACCCCA CUGAUGAG GCCGUUAGGC CGAA ICAAGUUU | 12374 | AAACTTGC C TGGGGTCT | 5311 |
| 5638 | CAGACCCC CUGAUGAG GCCGUUAGGC CGAA IGCAAGUU | 12375 | AACTTGCC T GGGGTCTG | 5312 |
| 5645 | UCAUGCUC CUGAUGAG GCCGUUAGGC CGAA IACCCCAG | 12376 | CTGGGGTC T GAGCATGA | 5313 |
| 5650 | UCCCAUCA CUGAUGAG GCCGUUAGGC CGAA ICUCAGAC | 12377 | GTCTGAGC A TGATGGGA | 5314 |
| 5669 | UCCUACCC CUGAUGAG GCCGUUAGGC CGAA IUCUCCCU | 12378 | AGGGAGAC A GGGTAGGA | 5315 |
| 5686 | GAAGAGUA CUGAUGAG GCCGUUAGGC CGAA ICGCCCUU | 12379 | AAGGGCGC C TACTCTTC | 5316 |
| 5687 | UGAAGAGU CUGAUGAG GCCGUUAGGC CGAA IGCGCCCU | 12380 | AGGGCGCC T ACTCTTCA | 5317 |
| 5690 | CCCUGAAG CUGAUGAG GCCGUUAGGC CGAA IUAGGCGC | 12381 | GCGCCTAC T CTTCAGGG | 5318 |
| 5692 | GACCCUGA CUGAUGAG GCCGUUAGGC CGAA IAGUAGGC | 12382 | GCCTACTC T TCAGGGTC | 5319 |
| 5695 | UUAGACCC CUGAUGAG GCCGUUAGGC CGAA IAAGAGUA | 12383 | TACTCTTC A GGGTCTAA | 5320 |
| 5701 | UGAUCUUU CUGAUGAG GCCGUUAGGC CGAA IACCCUGA | 12384 | TCAGGGTC T AAAGATCA | 5321 |
| 5709 | GGCCCACU CUGAUGAG GCCGUUAGGC CGAA IAUCUUUA | 12385 | TAAAGATC A AGTGGGCC | 5322 |
| 5717 | CGAUCCAA CUGAUGAG GCCGUUAGGC CGAA ICCCACUU | 12386 | AAGTGGGC C TTGGATCG | 5323 |
| 5718 | GCGAUCCA CUGAUGAG GCCGUUAGGC CGAA IGCCCACU | 12387 | AGTGGGCC T TGGATCGC | 5324 |
| 5727 | GCCAGCUU CUGAUGAG GCCGUUAGGC CGAA ICGAUCCA | 12388 | TGGATCGC T AAGCTGGC | 5325 |
| 5732 | ACAGAGCC CUGAUGAG GCCGUUAGGC CGAA ICUUAGCG | 12389 | CGCTAAGC T GGCTCTGT | 5326 |
| 5736 | UCAAACAG CUGAUGAG GCCGUUAGGC CGAA ICCAGCUU | 12390 | AAGCTGGC T CTGTTTGA | 5327 |
| 5738 | CAUCAAAC CUGAUGAG GCCGUUAGGC CGAA IAGCCAGC | 12391 | GCTGGCTC T GTTTGATG | 5328 |
| 5748 | GCAUAAAU CUGAUGAG GCCGUUAGGC CGAA ICAUCAAA | 12392 | TTTGATGC T ATTTATGC | 5329 |
| 5757 | CCCUAACU CUGAUGAG GCCGUUAGGC CGAA ICAUAAAU | 12393 | ATTTATGC A AGTTAGGG | 5330 |
| 5768 | AAAUACAU CUGAUGAG GCCGUUAGGC CGAA IACCCUAA | 12394 | TTAGGGTC T ATGTATTT | 5331 |
| 5786 | GAAGAGUA CUGAUGAG GCCGUUAGGC CGAA ICGCAUCC | 12395 | GGATGCGC C TACTCTTC | 5332 |
| 5787 | UGAAGAGU CUGAUGAG GCCGUUAGGC CGAA IGCGCAUC | 12396 | GATGCGCC T ACTCTTCA | 5333 |
| 5790 | CCCUGAAG CUGAUGAG GCCGUUAGGC CGAA IUAGGCGC | 12381 | GCGCCTAC T CTTCAGGG | 5318 |
| 5792 | GACCCUGA CUGAUGAG GCCGUUAGGC CGAA IAGUAGGC | 12382 | GCCTACTC T TCAGGGTC | 5319 |
| 5795 | UUAGACCC CUGAUGAG GCCGUUAGGC CGAA IAAGAGUA | 12383 | TACTCTTC A GGGTCTAA | 5320 |
| 5801 | UGAUCUUU CUGAUGAG GCCGUUAGGC CGAA IACCCUGA | 12384 | TCAGGGTC T AAAGATCA | 5321 |

| | | | | |
|---|---|---|---|---|
| 5809 | GGCCCACU CUGAUGAG GCCGUUAGGC CGAA IAUCUUUA | 12385 | TAAAGATC A AGTGGGCC | 5322 |
| 5817 | CGAUCCAA CUGAUGAG GCCGUUAGGC CGAA ICCCACUU | 12386 | AAGTGGGC C TTGGATCG | 5323 |
| 5818 | GCGAUCCA CUGAUGAG GCCGUUAGGC CGAA IGCCCACU | 12387 | AGTGGGCC T TGGATCGC | 5324 |
| 5827 | GCCAGCUU CUGAUGAG GCCGUUAGGC CGAA ICGAUCCA | 12388 | TGGATCGC T AAGCTGGC | 5325 |
| 5832 | ACAGAGCC CUGAUGAG GCCGUUAGGC CGAA ICUUAGCG | 12389 | CGCTAAGC T GGCTCTGT | 5326 |
| 5836 | UCAAACAG CUGAUGAG GCCGUUAGGC CGAA ICCAGCUU | 12390 | AAGCTGGC T CTGTTTGA | 5327 |
| 5838 | CAUCAAAC CUGAUGAG GCCGUUAGGC CGAA IAGCCAGC | 12391 | GCTGGCTC T GTTTGATG | 5328 |
| 5848 | GCAUAAAU CUGAUGAG GCCGUUAGGC CGAA ICAUCAAA | 12392 | TTTGATGC T ATTTATGC | 5329 |
| 5857 | CCCUAACU CUGAUGAG GCCGUUAGGC CGAA ICAUAAAU | 12393 | ATTTATGC A AGTTAGGG | 5330 |
| 5868 | AAAUACAU CUGAUGAG GCCGUUAGGC CGAA IACCCUAA | 12394 | TTAGGGTC T ATGTATTT | 5331 |
| 5885 | GAAGGUGC CUGAUGAG GCCGUUAGGC CGAA IACAUCCU | 12397 | AGGATGTC T GCACCTTC | 5334 |
| 5888 | GCAGAAGG CUGAUGAG GCCGUUAGGC CGAA ICAGACAU | 12398 | ATGTCTGC A CCTTCTGC | 5335 |
| 5890 | CUGCAGAA CUGAUGAG GCCGUUAGGC CGAA IUGCAGAC | 12399 | GTCTGCAC C TTCTGCAG | 5336 |
| 5891 | GCUGCAGA CUGAUGAG GCCGUUAGGC CGAA IGUGCAGA | 12400 | TCTGCACC T TCTGCAGC | 5337 |
| 5894 | CUGGCUGC CUGAUGAG GCCGUUAGGC CGAA IAAGGUGC | 12401 | GCACCTTC T GCAGCCAG | 5338 |
| 5897 | UGACUGGC CUGAUGAG GCCGUUAGGC CGAA ICAGAAGG | 12402 | CCTTCTGC A GCCAGTCA | 5339 |
| 5900 | UUCUGACU CUGAUGAG GCCGUUAGGC CGAA ICUGCAGA | 12403 | TCTGCAGC C AGTCAGAA | 5340 |
| 5901 | CUUCUGAC CUGAUGAG GCCGUUAGGC CGAA IGCUGCAG | 12404 | CTGCAGCC A GTCAGAAG | 5341 |
| 5905 | CCAGCUUC CUGAUGAG GCCGUUAGGC CGAA IACUGGCU | 12405 | AGCCAGTC A GAAGCTGG | 5342 |
| 5911 | GCCUCUCC CUGAUGAG GCCGUUAGGC CGAA ICUUCUGA | 12406 | TCAGAAGC T GGAGAGGC | 5343 |
| 5920 | UCCACUGU CUGAUGAG GCCGUUAGGC CGAA ICCUCUCC | 12407 | GGAGAGGC A ACAGTGGA | 5344 |
| 5923 | CAAUCCAC CUGAUGAG GCCGUUAGGC CGAA IUUGCCUC | 12408 | GAGGCAAC A GTGGATTG | 5345 |
| 5933 | CAAGAAGC CUGAUGAG GCCGUUAGGC CGAA ICAAUCCA | 12409 | TGGATTGC T GCTTCTTG | 5346 |
| 5936 | CCCCAAGA CUGAUGAG GCCGUUAGGC CGAA ICAGCAAU | 12410 | ATTGCTGC T TCTTGGGG | 5347 |
| 5939 | UCUCCCCA CUGAUGAG GCCGUUAGGC CGAA IAAGCAGC | 12411 | GCTGCTTC T TGGGGAGA | 5348 |
| 5957 | UAAAAGGA CUGAUGAG GCCGUUAGGC CGAA ICAUACUC | 12412 | GAGTATGC T TCCTTTTA | 5349 |
| 5960 | GGAUAAAA CUGAUGAG GCCGUUAGGC CGAA IAAGCAUA | 12413 | TATGCTTC C TTTTATCC | 5350 |
| 5961 | UGGAUAAA CUGAUGAG GCCGUUAGGC CGAA IGAAGCAU | 12414 | ATGCTTCC T TTTATCCA | 5351 |
| 5968 | AAUUACAU CUGAUGAG GCCGUUAGGC CGAA IAUAAAAG | 12415 | CTTTTATC C ATGTAATT | 5352 |
| 5969 | AAAUUACA CUGAUGAG GCCGUUAGGC CGAA IGAUAAAA | 12416 | TTTTATCC A TGTAATTT | 5353 |
| 5981 | GGUUCUAC CUGAUGAG GCCGUUAGGC CGAA IUUAAAUU | 12417 | AATTTAAC T GTAGAACC | 5354 |
| 5989 | AGAGCUCA CUGAUGAG GCCGUUAGGC CGAA IUUCUACA | 12418 | TGTAGAAC C TGAGCTCT | 5355 |
| 5990 | UAGAGCUC CUGAUGAG GCCGUUAGGC CGAA IGUUCUAC | 12419 | GTAGAACC T GAGCTCTA | 5356 |

240

| | | | | |
|---|---|---|---|---|
| 5995 | UUACUUAG CUGAUGAG GCCGUUAGGC CGAA ICUCAGGU | 12420 | ACCTGAGC T CTAAGTAA | 5357 |
| 5997 | GGUUACUU CUGAUGAG GCCGUUAGGC CGAA IAGCUCAG | 12421 | CTGAGCTC T AAGTAACC | 5358 |
| 6005 | CAUUCUUC CUGAUGAG GCCGUUAGGC CGAA IUUACUUA | 12422 | TAAGTAAC C GAAGAATG | 5359 |
| 6019 | AGAACAGA CUGAUGAG GCCGUUAGGC CGAA ICAUACAU | 12423 | ATGTATGC C TCTGTTCT | 5360 |
| 6020 | AAGAACAG CUGAUGAG GCCGUUAGGC CGAA IGCAUACA | 12424 | TGTATGCC T CTGTTCTT | 5361 |
| 6022 | AUAAGAAC CUGAUGAG GCCGUUAGGC CGAA IAGGCAUA | 12425 | TATGCCTC T GTTCTTAT | 5362 |
| 6027 | GGCACAUA CUGAUGAG GCCGUUAGGC CGAA IAACAGAG | 12426 | CTCTGTTC T TATGTGCC | 5363 |
| 6035 | AAGGAUGU CUGAUGAG GCCGUUAGGC CGAA ICACAUAA | 12427 | TTATGTGC C ACATCCTT | 5364 |
| 6036 | CAAGGAUG CUGAUGAG GCCGUUAGGC CGAA IGCACAUA | 12428 | TATGTGCC A CATCCTTG | 5365 |
| 6038 | AACAAGGA CUGAUGAG GCCGUUAGGC CGAA IUGGCACA | 12429 | TGTGCCAC A TCCTTGTT | 5366 |
| 6041 | UUAAACAA CUGAUGAG GCCGUUAGGC CGAA IAUGUGGC | 12430 | GCCACATC C TTGTTTAA | 5367 |
| 6042 | UUUAAACA CUGAUGAG GCCGUUAGGC CGAA IGAUGUGG | 12431 | CCACATCC T TGTTTAAA | 5368 |
| 6054 | AUACAGAG CUGAUGAG GCCGUUAGGC CGAA ICCUUUAA | 12432 | TTAAAGGC T CTCTGTAT | 5369 |
| 6056 | UCAUACAG CUGAUGAG GCCGUUAGGC CGAA IAGCCUUU | 12433 | AAAGGCTC T CTGTATGA | 5370 |
| 6058 | CUUCAUAC CUGAUGAG GCCGUUAGGC CGAA IAGAGCCU | 12434 | AGGCTCTC T GTATGAAG | 5371 |
| 6076 | CUGAUGAC CUGAUGAG GCCGUUAGGC CGAA IUCCCAUC | 12435 | GATGGGAC C GTCATCAG | 5372 |
| 6080 | UGUGCUGA CUGAUGAG GCCGUUAGGC CGAA IACGGUCC | 12436 | GGACCGTC A TCAGCACA | 5373 |
| 6083 | GAAUGUGC CUGAUGAG GCCGUUAGGC CGAA IAUGACGG | 12437 | CCGTCATC A GCACATTC | 5374 |
| 6086 | AGGGAAUG CUGAUGAG GCCGUUAGGC CGAA ICUGAUGA | 12438 | TCATCAGC A CATTCCCT | 5375 |
| 6088 | CUAGGGAA CUGAUGAG GCCGUUAGGC CGAA IUGCUGAU | 12439 | ATCAGCAC A TTCCCTAG | 5376 |
| 6092 | CUCACUAG CUGAUGAG GCCGUUAGGC CGAA IAAUGUGC | 12440 | GCACATTC C CTAGTGAG | 5377 |
| 6093 | GCUCACUA CUGAUGAG GCCGUUAGGC CGAA IGAAUGUG | 12441 | CACATTCC C TAGTGAGC | 5378 |
| 6094 | GGCUCACU CUGAUGAG GCCGUUAGGC CGAA IGGAAUGU | 12442 | ACATTCCC T AGTGAGCC | 5379 |
| 6102 | AGCCAGUA CUGAUGAG GCCGUUAGGC CGAA ICUCACUA | 12443 | TAGTGAGC C TACTGGCT | 5380 |
| 6103 | GAGCCAGU CUGAUGAG GCCGUUAGGC CGAA IGCUCACU | 12444 | AGTGAGCC T ACTGGCTC | 5381 |
| 6106 | CAGGAGCC CUGAUGAG GCCGUUAGGC CGAA IUAGGCUC | 12445 | GAGCCTAC T GGCTCCTG | 5382 |
| 6110 | CUGCCAGG CUGAUGAG GCCGUUAGGC CGAA ICCAGUAG | 12446 | CTACTGGC T CCTGGCAG | 5383 |
| 6112 | CGCUGCCA CUGAUGAG GCCGUUAGGC CGAA IAGCCAGU | 12447 | ACTGGCTC C TGGCAGCG | 5384 |
| 6113 | CCGCUGCC CUGAUGAG GCCGUUAGGC CGAA IGAGCCAG | 12448 | CTGGCTCC T GGCAGCGG | 5385 |
| 6117 | AAAGCCGC CUGAUGAG GCCGUUAGGC CGAA ICCAGGAG | 12449 | CTCCTGGC A GCGGCTTT | 5386 |
| 6123 | UCCACAAA CUGAUGAG GCCGUUAGGC CGAA ICCGCUGC | 12450 | GCAGCGGC T TTTGTGGA | 5387 |
| 6136 | GGCUAGUG CUGAUGAG GCCGUUAGGC CGAA IUCUUCCA | 12451 | TGGAAGAC T CACTAGCC | 5388 |
| 6138 | CUGGCUAG CUGAUGAG GCCGUUAGGC CGAA IAGUCUUC | 12452 | GAAGACTC A CTAGCCAG | 5389 |

240

| | | | | |
|---|---|---|---|---|
| 6140 | UUCUGGCU CUGAUGAG GCCGUUAGGC CGAA IUGAGUCU | 12453 | AGACTCAC T AGCCAGAA | 5390 |
| 6144 | UCUCUUCU CUGAUGAG GCCGUUAGGC CGAA ICUAGUGA | 12454 | TCACTAGC C AGAAGAGA | 5391 |
| 6145 | CUCUCUUC CUGAUGAG GCCGUUAGGC CGAA IGCUAGUG | 12455 | CACTAGCC A GAAGAGAG | 5392 |
| 6163 | GAGAGGAC CUGAUGAG GCCGUUAGGC CGAA IUCCCACU | 12456 | AGTGGGAC A GTCCTCTC | 5393 |
| 6167 | GGUGGAGA CUGAUGAG GCCGUUAGGC CGAA IACUGUCC | 12457 | GGACAGTC C TCTCCACC | 5394 |
| 6168 | UGGUGGAG CUGAUGAG GCCGUUAGGC CGAA IGACUGUC | 12458 | GACAGTCC T CTCCACCA | 5395 |
| 6170 | CUUGGUGG CUGAUGAG GCCGUUAGGC CGAA IAGGACUG | 12459 | CAGTCCTC T CCACCAAG | 5396 |
| 6172 | AUCUUGGU CUGAUGAG GCCGUUAGGC CGAA IAGAGGAC | 12460 | GTCCTCTC C ACCAAGAT | 5397 |
| 6173 | GAUCUUGG CUGAUGAG GCCGUUAGGC CGAA IGAGAGGA | 12461 | TCCTCTCC A CCAAGATC | 5398 |
| 6175 | UAGAUCUU CUGAUGAG GCCGUUAGGC CGAA IUGGAGAG | 12462 | CTCTCCAC C AAGATCTA | 5399 |
| 6176 | UUAGAUCU CUGAUGAG GCCGUUAGGC CGAA IGUGGAGA | 12463 | TCTCCACC A AGATCTAA | 5400 |
| 6182 | UUGGAUUU CUGAUGAG GCCGUUAGGC CGAA IAUCUUGG | 12464 | CCAAGATC T AAATCCAA | 5401 |
| 6188 | UUUUGUUU CUGAUGAG GCCGUUAGGC CGAA IAUUUAGA | 12465 | TCTAAATC C AAACAAAA | 5402 |
| 6189 | CUUUUGUU CUGAUGAG GCCGUUAGGC CGAA IGAUUUAG | 12466 | CTAAATCC A AACAAAAG | 5403 |
| 6193 | CCUGCUUU CUGAUGAG GCCGUUAGGC CGAA IUUUGGAU | 12467 | ATCCAAAC A AAAGCAGG | 5404 |
| 6199 | CUCUAGCC CUGAUGAG GCCGUUAGGC CGAA ICUUUUGU | 12468 | ACAAAAGC A GGCTAGAG | 5405 |
| 6203 | CUGGCUCU CUGAUGAG GCCGUUAGGC CGAA ICCUGCUU | 12469 | AAGCAGGC T AGAGCCAG | 5406 |
| 6209 | UCUCUUCU CUGAUGAG GCCGUUAGGC CGAA ICUCUAGC | 12470 | GCTAGAGC C AGAAGAGA | 5407 |
| 6210 | CUCUCUUC CUGAUGAG GCCGUUAGGC CGAA IGCUCUAG | 12471 | CTAGAGCC A GAAGAGAG | 5408 |
| 6222 | CAAAGAUU CUGAUGAG GCCGUUAGGC CGAA IUCCUCUC | 12472 | GAGAGGAC A AATCTTTG | 5409 |
| 6227 | AACAACAA CUGAUGAG GCCGUUAGGC CGAA IAUUUGUC | 12473 | GACAAATC T TTGTTGTT | 5410 |
| 6237 | AAAGAAGA CUGAUGAG GCCGUUAGGC CGAA IAACAACA | 12474 | TGTTGTTC C TCTTCTTT | 5411 |
| 6238 | UAAAGAAG CUGAUGAG GCCGUUAGGC CGAA IGAACAAC | 12475 | GTTGTTCC T CTTCTTTA | 5412 |
| 6240 | UGUAAAGA CUGAUGAG GCCGUUAGGC CGAA IAGGAACA | 12476 | TGTTCCTC T TCTTTACA | 5413 |
| 6243 | AUGUGUAA CUGAUGAG GCCGUUAGGC CGAA IAAGAGGA | 12477 | TCCTCTTC T TTACACAT | 5414 |
| 6248 | UGCGUAUG CUGAUGAG GCCGUUAGGC CGAA IUAAAGAA | 12478 | TTCTTTAC A CATACGCA | 5415 |
| 6250 | UUUGCGUA CUGAUGAG GCCGUUAGGC CGAA IUGUAAAG | 12479 | CTTTACAC A TACGCAAA | 5416 |
| 6256 | AGGUGGUU CUGAUGAG GCCGUUAGGC CGAA ICGUAUGU | 12480 | ACATACGC A AACCACCT | 5417 |
| 6260 | UCACAGGU CUGAUGAG GCCGUUAGGC CGAA IUUUGCGU | 12481 | ACGCAAAC C ACCTGTGA | 5418 |
| 6261 | GUCACAGG CUGAUGAG GCCGUUAGGC CGAA IGUUUGCG | 12482 | CGCAAACC A CCTGTGAC | 5419 |
| 6263 | CUGUCACA CUGAUGAG GCCGUUAGGC CGAA IUGGUUUG | 12483 | CAAACCAC C TGTGACAG | 5420 |
| 6264 | GCUGUCAC CUGAUGAG GCCGUUAGGC CGAA IGUGGUUU | 12484 | AAACCACC T GTGACAGC | 5421 |
| 6270 | UUGCCAGC CUGAUGAG GCCGUUAGGC CGAA IUCACAGG | 12485 | CCTGTGAC A GCTGGCAA | 5422 |

| | | | | |
|---|---|---|---|---|
| 6273 | AAAUUGCC CUGAUGAG GCCGUUAGGC CGAA ICUGUCAC | 12486 | GTGACAGC T GGCAATTT | 5423 |
| 6277 | UAUAAAAU CUGAUGAG GCCGUUAGGC CGAA ICCAGCUG | 12487 | CAGCTGGC A ATTTTATA | 5424 |
| 6290 | CAGUUACC CUGAUGAG GCCGUUAGGC CGAA IAUUUAUA | 12488 | TATAAATC A GGTAACTG | 5425 |
| 6297 | CUCCUUCC CUGAUGAG GCCGUUAGGC CGAA IUUACCUG | 12489 | CAGGTAAC T GGAAGGAG | 5426 |
| 6313 | UUUUUCUG CUGAUGAG GCCGUUAGGC CGAA IUUUAACC | 12490 | GGTTAAAC T CAGAAAAA | 5427 |
| 6315 | CUUUUUUC CUGAUGAG GCCGUUAGGC CGAA IAGUUUAA | 12491 | TTAAACTC A GAAAAAAG | 5428 |
| 6329 | UUGACUGA CUGAUGAG GCCGUUAGGC CGAA IUCUUCUU | 12492 | AAGAAGAC C TCAGTCAA | 5429 |
| 6330 | AUUGACUG CUGAUGAG GCCGUUAGGC CGAA IGUCUUCU | 12493 | AGAAGACC T CAGTCAAT | 5430 |
| 6332 | GAAUUGAC CUGAUGAG GCCGUUAGGC CGAA IAGGUCUU | 12494 | AAGACCTC A GTCAATTC | 5431 |
| 6336 | UAGAGAAU CUGAUGAG GCCGUUAGGC CGAA IACUGAGG | 12495 | CCTCAGTC A ATTCTCTA | 5432 |
| 6341 | AAAAGUAG CUGAUGAG GCCGUUAGGC CGAA IAAUUGAC | 12496 | GTCAATTC T CTACTTTT | 5433 |
| 6343 | AAAAAAGU CUGAUGAG GCCGUUAGGC CGAA IAGAAUUG | 12497 | CAATTCTC T ACTTTTTT | 5434 |
| 6346 | AAAAAAAA CUGAUGAG GCCGUUAGGC CGAA IUAGAGAA | 12498 | TTCTCTAC T TTTTTTTT | 5435 |
| 6363 | UCUGAUUU CUGAUGAG GCCGUUAGGC CGAA IAAAAAAA | 12499 | TTTTTTTC C AAATCAGA | 5436 |
| 6364 | AUCUGAUU CUGAUGAG GCCGUUAGGC CGAA IGAAAAAA | 12500 | TTTTTTCC A AATCAGAT | 5437 |
| 6369 | CUAUUAUC CUGAUGAG GCCGUUAGGC CGAA IAUUUGGA | 12501 | TCCAAATC A GATAATAG | 5438 |
| 6379 | AUUUGCUG CUGAUGAG GCCGUUAGGC CGAA ICUAUUAU | 12502 | ATAATAGC C CAGCAAAT | 5439 |
| 6380 | UAUUUGCU CUGAUGAG GCCGUUAGGC CGAA IGCUAUUA | 12503 | TAATAGCC C AGCAAATA | 5440 |
| 6381 | CUAUUUGC CUGAUGAG GCCGUUAGGC CGAA IGGCUAUU | 12504 | AATAGCCC A GCAAATAG | 5441 |
| 6384 | UCACUAUU CUGAUGAG GCCGUUAGGC CGAA ICUGGGCU | 12505 | AGCCCAGC A AATAGTGA | 5442 |
| 6397 | GUUUUAUU CUGAUGAG GCCGUUAGGC CGAA IUUAUCAC | 12506 | GTGATAAC A AATAAAAC | 5443 |
| 6406 | ACAGCUAA CUGAUGAG GCCGUUAGGC CGAA IUUUUAUU | 12507 | AATAAAAC C TTAGCTGT | 5444 |
| 6407 | AACAGCUA CUGAUGAG GCCGUUAGGC CGAA IGUUUUAU | 12508 | ATAAAACC T TAGCTGTT | 5445 |
| 6412 | ACAUGAAC CUGAUGAG GCCGUUAGGC CGAA ICUAAGGU | 12509 | ACCTTAGC T GTTCATGT | 5446 |
| 6417 | UCAAGACA CUGAUGAG GCCGUUAGGC CGAA IAACAGCU | 12510 | AGCTGTTC A TGTCTTGA | 5447 |
| 6422 | UGAAAUCA CUGAUGAG GCCGUUAGGC CGAA IACAUGAA | 12511 | TTCATGTC T TGATTTCA | 5448 |
| 6430 | UUAAUUAU CUGAUGAG GCCGUUAGGC CGAA IAAAUCAA | 12512 | TTGATTTC A ATAATTAA | 5449 |
| 6442 | AAUGAUUA CUGAUGAG GCCGUUAGGC CGAA IAAUUAAU | 12513 | ATTAATTC T TAATCATT | 5450 |
| 6448 | UCUCUUAA CUGAUGAG GCCGUUAGGC CGAA IAUUAAGA | 12514 | TCTTAATC A TTAAGAGA | 5451 |
| 6458 | UUUAUUAU CUGAUGAG GCCGUUAGGC CGAA IUCUCUUA | 12515 | TAAGAGAC C ATAATAAA | 5452 |
| 6459 | AUUUAUUA CUGAUGAG GCCGUUAGGC CGAA IGUCUCUU | 12516 | AAGAGACC A TAATAAAT | 5453 |
| 6470 | UGAAAAGG CUGAUGAG GCCGUUAGGC CGAA IUAUUUAU | 12517 | ATAAATAC T CCTTTTCA | 5454 |
| 6472 | CUUGAAAA CUGAUGAG GCCGUUAGGC CGAA IAGUAUUU | 12518 | AAATACTC C TTTTCAAG | 5455 |

| | | | | |
|---|---|---|---|---|
| 6473 | UCUUGAAA CUGAUGAG GCCGUUAGGC CGAA IGAGUAUU | 12519 | AATACTCC T TTTCAAGA | 5456 |
| 6478 | UUUUCUCU CUGAUGAG GCCGUUAGGC CGAA IAAAAGGA | 12520 | TCCTTTTC A AGAGAAAA | 5457 |
| 6489 | AAUGGUUU CUGAUGAG GCCGUUAGGC CGAA ICUUUUCU | 12521 | AGAAAAGC A AAACCATT | 5458 |
| 6494 | AUUCUAAU CUGAUGAG GCCGUUAGGC CGAA IUUUUGCU | 12522 | AGCAAAAC C ATTAGAAT | 5459 |
| 6495 | AAUUCUAA CUGAUGAG GCCGUUAGGC CGAA IGUUUUGC | 12523 | GCAAAACC A TTAGAATT | 5460 |
| 6509 | AGGAGCUG CUGAUGAG GCCGUUAGGC CGAA IUAACAAU | 12524 | ATTGTTAC T CAGCTCCT | 5461 |
| 6511 | GAAGGAGC CUGAUGAG GCCGUUAGGC CGAA IAGUAACA | 12525 | TGTTACTC A GCTCCTTC | 5462 |
| 6514 | UUUGAAGG CUGAUGAG GCCGUUAGGC CGAA ICUGAGUA | 12526 | TACTCAGC T CCTTCAAA | 5463 |
| 6516 | AGUUUGAA CUGAUGAG GCCGUUAGGC CGAA IAGCUGAG | 12527 | CTCAGCTC C TTCAAACT | 5464 |
| 6517 | GAGUUUGA CUGAUGAG GCCGUUAGGC CGAA IGAGCUGA | 12528 | TCAGCTCC T TCAAACTC | 5465 |
| 6520 | CCUGAGUU CUGAUGAG GCCGUUAGGC CGAA IAAGGAGC | 12529 | GCTCCTTC A AACTCAGG | 5466 |
| 6524 | CAAACCUG CUGAUGAG GCCGUUAGGC CGAA IUUUGAAG | 12530 | CTTCAAAC T CAGGTTTG | 5467 |
| 6526 | UACAAACC CUGAUGAG GCCGUUAGGC CGAA IAGUUUGA | 12531 | TCAAACTC A GGTTTGTA | 5468 |
| 6537 | CUCAUGUA CUGAUGAG GCCGUUAGGC CGAA ICUACAAA | 12532 | TTTGTAGC A TACATGAG | 5469 |
| 6541 | UGGACUCA CUGAUGAG GCCGUUAGGC CGAA IUAUGCUA | 12533 | TAGCATAC A TGAGTCCA | 5470 |
| 6548 | UGAUGGAU CUGAUGAG GCCGUUAGGC CGAA IACUCAUG | 12534 | CATGAGTC C ATCCATCA | 5471 |
| 6549 | CUGAUGGA CUGAUGAG GCCGUUAGGC CGAA IGACUCAU | 12535 | ATGAGTCC A TCCATCAG | 5472 |
| 6552 | UGACUGAU CUGAUGAG GCCGUUAGGC CGAA IAUGGACU | 12536 | AGTCCATC C ATCAGTCA | 5473 |
| 6553 | UUGACUGA CUGAUGAG GCCGUUAGGC CGAA IGAUGGAC | 12537 | GTCCATCC A TCAGTCAA | 5474 |
| 6556 | UCUUUGAC CUGAUGAG GCCGUUAGGC CGAA IAUGGAUG | 12538 | CATCCATC A GTCAAAGA | 5475 |
| 6560 | CCAUUCUU CUGAUGAG GCCGUUAGGC CGAA IACUGAUG | 12539 | CATCAGTC A AAGAATGG | 5476 |
| 6572 | CUCCAGAU CUGAUGAG GCCGUUAGGC CGAA IAACCAUU | 12540 | AATGGTTC C ATCTGGAG | 5477 |
| 6573 | ACUCCAGA CUGAUGAG GCCGUUAGGC CGAA IGAACCAU | 12541 | ATGGTTCC A TCTGGAGT | 5478 |
| 6576 | AAGACUCC CUGAUGAG GCCGUUAGGC CGAA IAUGGAAC | 12542 | GTTCCATC T GGAGTCTT | 5479 |
| 6583 | CUACAUUA CUGAUGAG GCCGUUAGGC CGAA IACUCCAG | 12543 | CTGGAGTC T TAATGTAG | 5480 |
| 6608 | UUAUUACA CUGAUGAG GCCGUUAGGC CGAA IUCUCCAU | 12544 | ATGGAGAC T TGTAATAA | 5481 |
| 6622 | UUGUAACU CUGAUGAG GCCGUUAGGC CGAA ICUCAUUA | 12545 | TAATGAGC T AGTTACAA | 5482 |
| 6629 | AAGCACUU CUGAUGAG GCCGUUAGGC CGAA IUAACUAG | 12546 | CTAGTTAC A AAGTGCTT | 5483 |
| 6636 | AAUGAACA CUGAUGAG GCCGUUAGGC CGAA ICACUUUG | 12547 | CAAAGTGC T TGTTCATT | 5484 |
| 6642 | UAUUUUAA CUGAUGAG GCCGUUAGGC CGAA IAACAAGC | 12548 | GCTTGTTC A TTAAAATA | 5485 |
| 6653 | AUUUUCAG CUGAUGAG GCCGUUAGGC CGAA ICUAUUUU | 12549 | AAAATAGC A CTGAAAAT | 5486 |
| 6655 | CAAUUUUC CUGAUGAG GCCGUUAGGC CGAA IUGCUAUU | 12550 | AATAGCAC T GAAAATTG | 5487 |
| 6668 | UUAAUUCA CUGAUGAG GCCGUUAGGC CGAA IUUUCAAU | 12551 | ATTGAAAC A TGAATTAA | 5488 |

| | | | | |
|---|---|---|---|---|
| 6678 | AUAUUAUC CUGAUGAG GCCGUUAGGC CGAA IUUAAUUC | 12552 | GAATTAAC T GATAATAT | 5489 |
| 6689 | AAAUGAUU CUGAUGAG GCCGUUAGGC CGAA IAAUAUUA | 12553 | TAATATTC C AATCATTT | 5490 |
| 6690 | CAAAUGAU CUGAUGAG GCCGUUAGGC CGAA IGAAUAUU | 12554 | AATATTCC A ATCATTTG | 5491 |
| 6694 | AUGGCAAA CUGAUGAG GCCGUUAGGC CGAA IAUUGGAA | 12555 | TTCCAATC A TTTGCCAT | 5492 |
| 6700 | UCAUAAAU CUGAUGAG GCCGUUAGGC CGAA ICAAAUGA | 12556 | TCATTTGC C ATTTATGA | 5493 |
| 6701 | GUCAUAAA CUGAUGAG GCCGUUAGGC CGAA IGCAAAUG | 12557 | CATTTGCC A TTTATGAC | 5494 |
| 6710 | ACCAUUUU CUGAUGAG GCCGUUAGGC CGAA IUCAUAAA | 12558 | TTTATGAC A AAAATGGT | 5495 |
| 6723 | UUUGUUAG CUGAUGAG GCCGUUAGGC CGAA ICCAACCA | 12559 | TGGTTGGC A CTAACAAA | 5496 |
| 6725 | UCUUUGUU CUGAUGAG GCCGUUAGGC CGAA IUGCCAAC | 12560 | GTTGGCAC T AACAAAGA | 5497 |
| 6729 | UCGUUCUU CUGAUGAG GCCGUUAGGC CGAA IUUAGUGC | 12561 | GCACTAAC A AAGAACGA | 5498 |
| 6740 | AAAGGAAG CUGAUGAG GCCGUUAGGC CGAA ICUCGUUC | 12562 | GAACGAGC A CTTCCTTT | 5499 |
| 6742 | UGAAAGGA CUGAUGAG GCCGUUAGGC CGAA IUGCUCGU | 12563 | ACGAGCAC T TCCTTTCA | 5500 |
| 6745 | CUCUGAAA CUGAUGAG GCCGUUAGGC CGAA IAAGUGCU | 12564 | AGCACTTC C TTTCAGAG | 5501 |
| 6746 | ACUCUGAA CUGAUGAG GCCGUUAGGC CGAA IGAAGUGC | 12565 | GCACTTCC T TTCAGAGT | 5502 |
| 6750 | AGAAACUC CUGAUGAG GCCGUUAGGC CGAA IAAAGGAA | 12566 | TTCCTTTC A GAGTTTCT | 5503 |
| 6758 | AUUAUCUC CUGAUGAG GCCGUUAGGC CGAA IAAACUCU | 12567 | AGAGTTTC T GAGATAAT | 5504 |
| 6778 | ACCCAGAC CUGAUGAG GCCGUUAGGC CGAA IUUCCACG | 12568 | CGTGGAAC A GTCTGGGT | 5505 |
| 6782 | UUCCACCC CUGAUGAG GCCGUUAGGC CGAA IACUGUUC | 12569 | GAACAGTC T GGGTGGAA | 5506 |
| 6797 | AUGGUUUC CUGAUGAG GCCGUUAGGC CGAA ICCCCAUU | 12570 | AATGGGGC T GAAACCAT | 5507 |
| 6803 | UUGCACAU CUGAUGAG GCCGUUAGGC CGAA IUUUCAGC | 12571 | GCTGAAAC C ATGTGCAA | 5508 |
| 6804 | CUUGCACA CUGAUGAG GCCGUUAGGC CGAA IGUUUCAG | 12572 | CTGAAACC A TGTGCAAG | 5509 |
| 6810 | CACAGACU CUGAUGAG GCCGUUAGGC CGAA ICACAUGG | 12573 | CCATGTGC A AGTCTGTG | 5510 |
| 6815 | CAAGACAC CUGAUGAG GCCGUUAGGC CGAA IACUUGCA | 12574 | TGCAAGTC T GTGTCTTG | 5511 |
| 6821 | GACUGACA CUGAUGAG GCCGUUAGGC CGAA IACACAGA | 12575 | TCTGTGTC T TGTCAGTC | 5512 |
| 6826 | UCUUGGAC CUGAUGAG GCCGUUAGGC CGAA IACAAGAC | 12576 | GTCTTGTC A GTCCAAGA | 5513 |
| 6830 | CACUUCUU CUGAUGAG GCCGUUAGGC CGAA IACUGACA | 12577 | TGTCAGTC C AAGAAGTG | 5514 |
| 6831 | UCACUUCU CUGAUGAG GCCGUUAGGC CGAA IGACUGAC | 12578 | GTCAGTCC A AGAAGTGA | 5515 |
| 6841 | CAUCUCGG CUGAUGAG GCCGUUAGGC CGAA IUCACUUC | 12579 | GAAGTGAC A CCGAGATG | 5516 |
| 6843 | AACAUCUC CUGAUGAG GCCGUUAGGC CGAA IUGUCACU | 12580 | AGTGACAC C GAGATGTT | 5517 |
| 6864 | AAGGCACG CUGAUGAG GCCGUUAGGC CGAA IUCCCUAA | 12581 | TTAGGGAC C CGTGCCTT | 5518 |
| 6865 | CAAGGCAC CUGAUGAG GCCGUUAGGC CGAA IGUCCCUA | 12582 | TAGGGACC C GTGCCTTG | 5519 |
| 6870 | GGAAACAA CUGAUGAG GCCGUUAGGC CGAA ICACGGGU | 12583 | ACCCGTGC C TTGTTTCC | 5520 |
| 6871 | AGGAAACA CUGAUGAG GCCGUUAGGC CGAA IGCACGGG | 12584 | CCCGTGCC T TGTTTCCT | 5521 |

245

| | | | | |
|---|---|---|---|---|
| 6878 | GUGGGCUA CUGAUGAG GCCGUUAGGC CGAA IAAACAAG | 12585 | CTTGTTTC C TAGCCCAC | 5522 |
| 6879 | UGUGGGCU CUGAUGAG GCCGUUAGGC CGAA IGAAACAA | 12586 | TTGTTTCC T AGCCCACA | 5523 |
| 6883 | UUCUUGUG CUGAUGAG GCCGUUAGGC CGAA ICUAGGAA | 12587 | TTCCTAGC C CACAAGAA | 5524 |
| 6884 | AUUCUUGU CUGAUGAG GCCGUUAGGC CGAA IGCUAGGA | 12588 | TCCTAGCC C ACAAGAAT | 5525 |
| 6885 | CAUUCUUG CUGAUGAG GCCGUUAGGC CGAA IGGCUAGG | 12589 | CCTAGCCC A CAAGAATG | 5526 |
| 6887 | UGCAUUCU CUGAUGAG GCCGUUAGGC CGAA IUGGGCUA | 12590 | TAGCCCAC A AGAATGCA | 5527 |
| 6895 | UUGAUGUU CUGAUGAG GCCGUUAGGC CGAA ICAUUCUU | 12591 | AAGAATGC A AACATCAA | 5528 |
| 6899 | CUGUUUGA CUGAUGAG GCCGUUAGGC CGAA IUUUGCAU | 12592 | ATGCAAAC A TCAAACAG | 5529 |
| 6902 | UAUCUGUU CUGAUGAG GCCGUUAGGC CGAA IAUGUUUG | 12593 | CAAACATC A AACAGATA | 5530 |
| 6906 | CGAGUAUC CUGAUGAG GCCGUUAGGC CGAA IUUUGAUG | 12594 | CATCAAAC A GATACTCG | 5531 |
| 6912 | GGCUAGCG CUGAUGAG GCCGUUAGGC CGAA IUAUCUGU | 12595 | ACAGATAC T CGCTAGCC | 5532 |
| 6916 | AUGAGGCU CUGAUGAG GCCGUUAGGC CGAA ICGAGUAU | 12596 | ATACTCGC T AGCCTCAT | 5533 |
| 6920 | UUAAAUGA CUGAUGAG GCCGUUAGGC CGAA ICUAGCGA | 12597 | TCGCTAGC C TCATTTAA | 5534 |
| 6921 | UUUAAAUG CUGAUGAG GCCGUUAGGC CGAA IGCUAGCG | 12598 | CGCTAGCC T CATTTAAA | 5535 |
| 6923 | AAUUUAAA CUGAUGAG GCCGUUAGGC CGAA IAGGCUAG | 12599 | CTAGCCTC A TTTAAATT | 5536 |
| 6949 | GCCAAAGA CUGAUGAG GCCGUUAGGC CGAA ICACUCCU | 12600 | AGGAGTGC A TCTTTGGC | 5537 |
| 6952 | UCGGCCAA CUGAUGAG GCCGUUAGGC CGAA IAUGCACU | 12601 | AGTGCATC T TTGGCCGA | 5538 |
| 6958 | CCACUGUC CUGAUGAG GCCGUUAGGC CGAA ICCAAAGA | 12602 | TCTTTGGC C GACAGTGG | 5539 |
| 6962 | UACACCAC CUGAUGAG GCCGUUAGGC CGAA IUCGGCCA | 12603 | TGGCCGAC A GTGGTGTA | 5540 |
| 6973 | ACACACAC CUGAUGAG GCCGUUAGGC CGAA IUUACACC | 12604 | GGTGTAAC T GTGTGTGT | 5541 |
| 7041 | AAUAGUUA CUGAUGAG GCCGUUAGGC CGAA ICACAAAA | 12605 | TTTTGTGC A TAACTATT | 5542 |
| 7046 | CCUUAAAU CUGAUGAG GCCGUUAGGC CGAA IUUAUGCA | 12606 | TGCATAAC T ATTTAAGG | 5543 |
| 7059 | AAAAUUCC CUGAUGAG GCCGUUAGGC CGAA IUUUCCUU | 12607 | AAGGAAAC T GGAATTTT | 5544 |
| 7076 | UGUAUAAA CUGAUGAG GCCGUUAGGC CGAA IUAACUUU | 12608 | AAAGTTAC T TTTATACA | 5545 |
| 7084 | UCUUGGUU CUGAUGAG GCCGUUAGGC CGAA IUAUAAAA | 12609 | TTTTATAC A AACCAAGA | 5546 |
| 7088 | AUAUUCUU CUGAUGAG GCCGUUAGGC CGAA IUUUGUAU | 12610 | ATACAAAC C AAGAATAT | 5547 |
| 7089 | UAUAUUCU CUGAUGAG GCCGUUAGGC CGAA IGUUUGUA | 12611 | TACAAACC A AGAATATA | 5548 |
| 7101 | AUAUCUGU CUGAUGAG GCCGUUAGGC CGAA ICAUAUAU | 12612 | ATATATGC T ACAGATAT | 5549 |
| 7104 | CUUAUAUC CUGAUGAG GCCGUUAGGC CGAA IUAGCAUA | 12613 | TATGCTAC A GATATAAG | 5550 |
| 7115 | ACCAUGUC CUGAUGAG GCCGUUAGGC CGAA IUCUUAUA | 12614 | TATAAGAC A GACATGGT | 5551 |
| 7119 | CCAAACCA CUGAUGAG GCCGUUAGGC CGAA IUCUGUCU | 12615 | AGACAGAC A TGGTTTGG | 5552 |
| 7130 | GAAAUAUA CUGAUGAG GCCGUUAGGC CGAA IACCAAAC | 12616 | GTTTGGTC C TATATTTC | 5553 |
| 7131 | AGAAAUAU CUGAUGAG GCCGUUAGGC CGAA IGACCAAA | 12617 | TTTGGTCC T ATATTTCT | 5554 |

| | | | | |
|---|---|---|---|---|
| 7139 | UCAUGACU CUGAUGAG GCCGUUAGGC CGAA IAAAUAUA | 12618 | TATATTTC T AGTCATGA | 5555 |
| 7144 | AUUCAUCA CUGAUGAG GCCGUUAGGC CGAA IACUAGAA | 12619 | TTCTAGTC A TGATGAAT | 5556 |
| 7166 | AUGAAGAU CUGAUGAG GCCGUUAGGC CGAA IUAUACAA | 12620 | TTGTATAC C ATCTTCAT | 5557 |
| 7167 | UAUGAAGA CUGAUGAG GCCGUUAGGC CGAA IGUAUACA | 12621 | TGTATACC A TCTTCATA | 5558 |
| 7170 | UUAUAUGA CUGAUGAG GCCGUUAGGC CGAA IAUGGUAU | 12622 | ATACCATC T TCATATAA | 5559 |
| 7173 | AUAUUAUA CUGAUGAG GCCGUUAGGC CGAA IAAGAUGG | 12623 | CCATCTTC A TATAATAT | 5560 |
| 7184 | UAUUUUUA CUGAUGAG GCCGUUAGGC CGAA IUAUAUUA | 12624 | TAATATAC T TAAAAATA | 5561 |
| 7197 | CCCAAUUA CUGAUGAG GCCGUUAGGC CGAA IAAAUAUU | 12625 | AATATTTC T TAATTGGG | 5562 |
| 7220 | AUUAAGUU CUGAUGAG GCCGUUAGGC CGAA IUACGAUU | 12626 | AATCGTAC C AACTTAAT | 5563 |
| 7221 | AAUUAAGU CUGAUGAG GCCGUUAGGC CGAA IGUACGAU | 12627 | ATCGTACC A ACTTAATT | 5564 |
| 7224 | AUCAAUUA CUGAUGAG GCCGUUAGGC CGAA IUUGGUAC | 12628 | GTACCAAC T TAATTGAT | 5565 |
| 7237 | AGUUGCCA CUGAUGAG GCCGUUAGGC CGAA IUUUAUCA | 12629 | TGATAAAC T TGGCAACT | 5566 |
| 7242 | AAAGCAGU CUGAUGAG GCCGUUAGGC CGAA ICCAAGUU | 12630 | AACTTGGC A ACTGCTTT | 5567 |
| 7245 | AUAAAAGC CUGAUGAG GCCGUUAGGC CGAA IUUGCCAA | 12631 | TTGGCAAC T GCTTTTAT | 5568 |
| 7248 | AACAUAAA CUGAUGAG GCCGUUAGGC CGAA ICAGUUGC | 12632 | GCAACTGC T TTTATGTT | 5569 |
| 7258 | AAGGAGAC CUGAUGAG GCCGUUAGGC CGAA IAACAUAA | 12633 | TTATGTTC T GTCTCCTT | 5570 |
| 7262 | AUGGAAGG CUGAUGAG GCCGUUAGGC CGAA IACAGAAC | 12634 | GTTCTGTC T CCTTCCAT | 5571 |
| 7264 | UUAUGGAA CUGAUGAG GCCGUUAGGC CGAA IAGACAGA | 12635 | TCTGTCTC C TTCCATAA | 5572 |
| 7265 | UUUAUGGA CUGAUGAG GCCGUUAGGC CGAA IGAGACAG | 12636 | CTGTCTCC T TCCATAAA | 5573 |
| 7268 | AAAUUUAU CUGAUGAG GCCGUUAGGC CGAA IAAGGAGA | 12637 | TCTCCTTC C ATAAATTT | 5574 |
| 7269 | AAAAUUUA CUGAUGAG GCCGUUAGGC CGAA IGAAGGAG | 12638 | CTCCTTCC A TAAATTTT | 5575 |
| 7280 | UAGUAUUU CUGAUGAG GCCGUUAGGC CGAA IAAAAAUU | 12639 | AATTTTTC A AAATACTA | 5576 |
| 7287 | GUUGAAUU CUGAUGAG GCCGUUAGGC CGAA IUAUUUUG | 12640 | CAAAATAC T AATTCAAC | 5577 |
| 7293 | UUCUUUGU CUGAUGAG GCCGUUAGGC CGAA IAAUUAGU | 12641 | ACTAATTC A ACAAAGAA | 5578 |
| 7296 | UUUUUCUU CUGAUGAG GCCGUUAGGC CGAA IUUGAAUU | 12642 | AATTCAAC A AAGAAAAA | 5579 |
| 7307 | AAAAAAAG CUGAUGAG GCCGUUAGGC CGAA ICUUUUUC | 12643 | GAAAAAGC T CTTTTTTT | 5580 |
| 7309 | GAAAAAAA CUGAUGAG GCCGUUAGGC CGAA IAGCUUUU | 12644 | AAAAGCTC T TTTTTTTC | 5581 |
| 7318 | UUAUUUUA CUGAUGAG GCCGUUAGGC CGAA IAAAAAAA | 12645 | TTTTTTTC C TAAAATAA | 5582 |
| 7319 | UUUAUUUU CUGAUGAG GCCGUUAGGC CGAA IGAAAAAA | 12646 | TTTTTTCC T AAAATAAA | 5583 |
| 7329 | UAAAUUUG CUGAUGAG GCCGUUAGGC CGAA IUUUAUUU | 12647 | AAATAAAC T CAAATTTA | 5584 |
| 7331 | GAUAAAUU CUGAUGAG GCCGUUAGGC CGAA IAGUUUAU | 12648 | ATAAACTC A AATTTATC | 5585 |
| 7340 | CUAAACAA CUGAUGAG GCCGUUAGGC CGAA IAUAAAUU | 12649 | AATTTATC C TTGTTTAG | 5586 |
| 7341 | UCUAAACA CUGAUGAG GCCGUUAGGC CGAA IGAUAAAU | 12650 | ATTTATCC T TGTTTAGA | 5587 |

247

| | | | | |
|---|---|---|---|---|
| 7352 | UUUUUCUC CUGAUGAG GCCGUUAGGC CGAA ICUCUAAA | 12651 | TTTAGAGC A GAGAAAAA | 5588 |
| 7372 | CAUUUCAA CUGAUGAG GCCGUUAGGC CGAA IUUUUUCU | 12652 | AGAAAAAC T TTGAAATG | 5589 |
| 7384 | AUUUUUUG CUGAUGAG GCCGUUAGGC CGAA IACCAUUU | 12653 | AAATGGTC T CAAAAAAT | 5590 |
| 7386 | CAAUUUUU CUGAUGAG GCCGUUAGGC CGAA IAGACCAU | 12654 | ATGGTCTC A AAAAATTG | 5591 |
| 7396 | AAAUAUUU CUGAUGAG GCCGUUAGGC CGAA ICAAUUUU | 12655 | AAAATTGC T AAATATTT | 5592 |
| 7407 | UUUUCCAU CUGAUGAG GCCGUUAGGC CGAA IAAAAUAU | 12656 | ATATTTTC A ATGGAAAA | 5593 |
| 7417 | UAACAUUU CUGAUGAG GCCGUUAGGC CGAA IUUUUCCA | 12657 | TGGAAAAC T AAATGTTA | 5594 |
| 7433 | AUACAAUC CUGAUGAG GCCGUUAGGC CGAA ICUAAACU | 12658 | AGTTTAGC T GATTGTAT | 5595 |
| 7455 | AAGUGAAA CUGAUGAG GCCGUUAGGC CGAA IUUCGAAA | 12659 | TTTCGAAC C TTTCACTT | 5596 |
| 7456 | AAAGUGAA CUGAUGAG GCCGUUAGGC CGAA IGUUCGAA | 12660 | TTCGAACC T TTCACTTT | 5597 |
| 7460 | ACAAAAAG CUGAUGAG GCCGUUAGGC CGAA IAAAGGUU | 12661 | AACCTTTC A CTTTTTGT | 5598 |
| 7462 | AAACAAAA CUGAUGAG GCCGUUAGGC CGAA IUGAAAGG | 12662 | CCTTTCAC T TTTTGTTT | 5599 |
| 7478 | GUGAAAUA CUGAUGAG GCCGUUAGGC CGAA IUAAAACA | 12663 | TGTTTTAC C TATTTCAC | 5600 |
| 7479 | UGUGAAAU CUGAUGAG GCCGUUAGGC CGAA IGUAAAAC | 12664 | GTTTTACC T ATTTCACA | 5601 |
| 7485 | CACAGUUG CUGAUGAG GCCGUUAGGC CGAA IAAAUAGG | 12665 | CCTATTTC A CAACTGTG | 5602 |
| 7487 | UACACAGU CUGAUGAG GCCGUUAGGC CGAA IUGAAAUA | 12666 | TATTTCAC A ACTGTGTA | 5603 |
| 7490 | AUUUACAC CUGAUGAG GCCGUUAGGC CGAA IUUGUGAA | 12667 | TTCACAAC T GTGTAAAT | 5604 |
| 7502 | GAAUUAUU CUGAUGAG GCCGUUAGGC CGAA ICAAUUUA | 12668 | TAAATTGC C AATAATTC | 5605 |
| 7503 | GGAAUUAU CUGAUGAG GCCGUUAGGC CGAA IGCAAUUU | 12669 | AAATTGCC A ATAATTCC | 5606 |
| 7511 | CAUGGACA CUGAUGAG GCCGUUAGGC CGAA IAAUUAUU | 12670 | AATAATTC C TGTCCATG | 5607 |
| 7512 | UCAUGGAC CUGAUGAG GCCGUUAGGC CGAA IGAAUUAU | 12671 | ATAATTCC T GTCCATGA | 5608 |
| 7516 | AUUUUCAU CUGAUGAG GCCGUUAGGC CGAA IACAGGAA | 12672 | TTCCTGTC C ATGAAAAT | 5609 |
| 7517 | CAUUUUCA CUGAUGAG GCCGUUAGGC CGAA IGACAGGA | 12673 | TCCTGTCC A TGAAAATG | 5610 |
| 7527 | GGAUAAUU CUGAUGAG GCCGUUAGGC CGAA ICAUUUUC | 12674 | GAAAATGC A AATTATCC | 5611 |
| 7535 | UCUACACU CUGAUGAG GCCGUUAGGC CGAA IAUAAUUU | 12675 | AAATTATC C AGTGTAGA | 5612 |
| 7536 | AUCUACAC CUGAUGAG GCCGUUAGGC CGAA IGAUAAUU | 12676 | AATTATCC A GTGTAGAT | 5613 |
| 7554 | AGGGUGAU CUGAUGAG GCCGUUAGGC CGAA IUCAAAUA | 12677 | TATTTGAC C ATCACCCT | 5614 |
| 7555 | UAGGGUGA CUGAUGAG GCCGUUAGGC CGAA IGUCAAAU | 12678 | ATTTGACC A TCACCCTA | 5615 |
| 7558 | CCAUAGGG CUGAUGAG GCCGUUAGGC CGAA IAUGGUCA | 12679 | TGACCATC A CCCTATGG | 5616 |
| 7560 | AUCCAUAG CUGAUGAG GCCGUUAGGC CGAA IUGAUGGU | 12680 | ACCATCAC C CTATGGAT | 5617 |
| 7561 | UAUCCAUA CUGAUGAG GCCGUUAGGC CGAA IGUGAUGG | 12681 | CCATCACC C TATGGATA | 5618 |
| 7562 | AUAUCCAU CUGAUGAG GCCGUUAGGC CGAA IGGUGAUG | 12682 | CATCACCC T ATGGATAT | 5619 |
| 7575 | GCAAAACU CUGAUGAG GCCGUUAGGC CGAA ICCAAUAU | 12683 | ATATTGGC T AGTTTTGC | 5620 |

| | | | | |
|---|---|---|---|---|
| 7584 | UUAAUAAA CUGAUGAG GCCGUUAGGC CGAA ICAAAACU | 12684 | AGTTTTGC C TTTATTAA | 5621 |
| 7585 | CUUAAUAA CUGAUGAG GCCGUUAGGC CGAA IGCAAAAC | 12685 | GTTTTGCC T TTATTAAG | 5622 |
| 7595 | AAUGAAUU CUGAUGAG GCCGUUAGGC CGAA ICUUAAUA | 12686 | TATTAAGC A AATTCATT | 5623 |
| 7601 | GGCUGAAA CUGAUGAG GCCGUUAGGC CGAA IAAUUUGC | 12687 | GCAAATTC A TTTCAGCC | 5624 |
| 7606 | AUUCAGGC CUGAUGAG GCCGUUAGGC CGAA IAAAUGAA | 12688 | TTCATTTC A GCCTGAAT | 5625 |
| 7609 | GACAUUCA CUGAUGAG GCCGUUAGGC CGAA ICUGAAAU | 12689 | ATTTCAGC C TGAATGTC | 5626 |
| 7610 | AGACAUUC CUGAUGAG GCCGUUAGGC CGAA IGCUGAAA | 12690 | TTTCAGCC T GAATGTCT | 5627 |
| 7618 | AUAUAGGC CUGAUGAG GCCGUUAGGC CGAA IACAUUCA | 12691 | TGAATGTC T GCCTATAT | 5628 |
| 7621 | AAUAUAUA CUGAUGAG GCCGUUAGGC CGAA ICAGACAU | 12692 | ATGTCTGC C TATATATT | 5629 |
| 7622 | GAAUAUAU CUGAUGAG GCCGUUAGGC CGAA IGCAGACA | 12693 | TGTCTGCC T ATATATTC | 5630 |
| 7631 | AAGAGCAG CUGAUGAG GCCGUUAGGC CGAA IAAUAUAU | 12694 | ATATATTC T CTGCTCTT | 5631 |
| 7633 | CAAAGAGC CUGAUGAG GCCGUUAGGC CGAA IAGAAUAU | 12695 | ATATTCTC T GCTCTTTG | 5632 |
| 7636 | AUACAAAG CUGAUGAG GCCGUUAGGC CGAA ICAGAGAA | 12696 | TTCTCTGC T CTTTGTAT | 5633 |
| 7638 | GAAUACAA CUGAUGAG GCCGUUAGGC CGAA IAGCAGAG | 12697 | CTCTGCTC T TTGTATTC | 5634 |
| 7647 | UUCAAAGG CUGAUGAG GCCGUUAGGC CGAA IAAUACAA | 12698 | TTGTATTC T CCTTTGAA | 5635 |
| 7649 | GGUUCAAA CUGAUGAG GCCGUUAGGC CGAA IAGAAUAC | 12699 | GTATTCTC C TTTGAACC | 5636 |
| 7650 | GGGUUCAA CUGAUGAG GCCGUUAGGC CGAA IGAGAAUA | 12700 | TATTCTCC T TTGAACCC | 5637 |
| 7657 | UUUUAACG CUGAUGAG GCCGUUAGGC CGAA IUUCAAAG | 12701 | CTTTGAAC C CGTTAAAA | 5638 |
| 7658 | GUUUUAAC CUGAUGAG GCCGUUAGGC CGAA IGUUCAAA | 12702 | TTTGAACC C GTTAAAAC | 5639 |
| 7667 | CCACAGGA CUGAUGAG GCCGUUAGGC CGAA IUUUUAAC | 12703 | GTTAAAAC A TCCTGTGG | 5640 |
| 7670 | GUGCCACA CUGAUGAG GCCGUUAGGC CGAA IAUGUUUU | 12704 | AAAACATC C TGTGGCAC | 5641 |
| 7671 | AGUGCCAC CUGAUGAG GCCGUUAGGC CGAA IGAUGUUU | 12705 | AAACATCC T GTGGCACT | 5642 |

Table XV: G-Cleaver Ribozyme and Target Sequences 237.198

| nt. Position | Ribozyme Sequence | Seq. ID Nos | Target | Seq. ID Nos |
|---|---|---|---|---|
| 67 | CGCUG UGAUG GCAUGCACUAUGC GCG ACCCGAGCCC | 12706 | GGGCTCGGGT G CAGCG | 5643 |
| 91 | AUCCU UGAUG GCAUGCACUAUGC GCG GCCGCCAGGC | 12707 | GCCTGGCGGC G AGGAT | 5644 |
| 114 | GGAGA UGAUG GCAUGCACUAUGC GCG AACCACUUCC | 12708 | GGAAGTGGTT G TCTCC | 5645 |
| 131 | UCUCG UGAUG GCAUGCACUAUGC GCG GGCUCCAGCC | 12709 | GGCTGGAGCC G CGAGA | 5646 |
| 133 | CGUCU UGAUG GCAUGCACUAUGC GCG GCGGCUCCAG | 12710 | CTGGAGCCGC G AGACG | 5647 |
| 142 | CUGAG UGAUG GCAUGCACUAUGC GCG GCCCGUCUCG | 12711 | CGAGACGGGC G CTCAG | 5648 |
| 151 | CCCCG UGAUG GCAUGCACUAUGC GCG GCCCUGAGCG | 12712 | CGCTCAGGGC G CGGGG | 5649 |
| 168 | UCGUU UGAUG GCAUGCACUAUGC GCG GCCGCCGCCG | 12713 | CGGCGGCGGC G AACGA | 5650 |
| 172 | CCUCU UGAUG GCAUGCACUAUGC GCG GUUCGCCGCC | 12714 | GGCGGCGAAC G AGAGG | 5651 |
| 214 | GCCCG UGAUG GCAUGCACUAUGC GCG GCUCCCCCGG | 12715 | CCGGGGGAGC G CGGGC | 5652 |
| 227 | CUGCU UGAUG GCAUGCACUAUGC GCG GCCCGGUGCC | 12716 | GGCACCGGGC G AGCAG | 5653 |
| 236 | CGACG UGAUG GCAUGCACUAUGC GCG GGCCUGCUCG | 12717 | CGAGCAGGCC G CGTCG | 5654 |
| 241 | GAGCG UGAUG GCAUGCACUAUGC GCG GACGCGGCCU | 12718 | AGGCCGCGTC G CGCTC | 5655 |
| 243 | GUGAG UGAUG GCAUGCACUAUGC GCG GCGACGCGGC | 12719 | GCCGCGTCGC G CTCAC | 5656 |
| 279 | CACAG UGAUG GCAUGCACUAUGC GCG AGGACCCCGG | 12720 | CCGGGGTCCT G CTGTG | 5657 |
| 282 | GCGCA UGAUG GCAUGCACUAUGC GCG AGCAGGACCC | 12721 | GGGTCCTGCT G TGCGC | 5658 |
| 284 | GCGCG UGAUG GCAUGCACUAUGC GCG ACAGCAGGAC | 12722 | GTCCTGCTGT G CGCGC | 5659 |
| 286 | CAGCG UGAUG GCAUGCACUAUGC GCG GCACAGCAGG | 12723 | CCTGCTGTGC G CGCTG | 5660 |
| 288 | AGCAG UGAUG GCAUGCACUAUGC GCG GCGCACAGCA | 12724 | TGCTGTGCGC G CTGCT | 5661 |
| 291 | CUGAG UGAUG GCAUGCACUAUGC GCG AGCGCGCACA | 12725 | TGTGCGCGCT G CTCAG | 5662 |
| 299 | GCAGA UGAUG GCAUGCACUAUGC GCG AGCUGAGCAG | 12726 | CTGCTCAGCT G TCTGC | 5663 |
| 303 | AGAAG UGAUG GCAUGCACUAUGC GCG AGACAGCUGA | 12727 | TCAGCTGTCT G CTTCT | 5664 |
| 346 | CAGUU UGAUG GCAUGCACUAUGC GCG AGGAUCUUUU | 12728 | AAAAGATCCT G AACTG | 5665 |
| 351 | AAACU UGAUG GCAUGCACUAUGC GCG AGUUCAGGAU | 12729 | ATCCTGAACT G AGTTT | 5666 |
| 378 | GCUUG UGAUG GCAUGCACUAUGC GCG AUGAUGUGCU | 12730 | AGCACATCAT G CAAGC | 5667 |
| 396 | AGAUG UGAUG GCAUGCACUAUGC GCG AGUGUCUGGC | 12731 | GCCAGACACT G CATCT | 5668 |
| 407 | CCCUG UGAUG GCAUGCACUAUGC GCG AUUGGAGAUG | 12732 | CATCTCCAAT G CAGGG | 5669 |
| 438 | UCAGG UGAUG GCAUGCACUAUGC GCG AAAGACCAUU | 12733 | AATGGTCTTT G CCTGA | 5670 |
| 442 | CAUUU UGAUG GCAUGCACUAUGC GCG AGGCAAAGAC | 12734 | GTCTTTGCCT G AAATG | 5671 |

| | | | | |
|---|---|---|---|---|
| 450 | UUACU UGAUG GCAUGCACUAUGC GCG ACCAUUUCAG | 12735 | CTGAAATGGT G AGTAA | 5672 |
| 463 | CCUUU UGAUG GCAUGCACUAUGC GCG GCUUUCCUUA | 12736 | TAAGGAAAGC G AAAGG | 5673 |
| 471 | AUGCU UGAUG GCAUGCACUAUGC GCG AGCCUUUCGC | 12737 | GCGAAAGGCT G AGCAT | 5674 |
| 487 | ACAGG UGAUG GCAUGCACUAUGC GCG AGAUUUAGUU | 12738 | AACTAAATCT G CCTGT | 5675 |
| 491 | UUCCA UGAUG GCAUGCACUAUGC GCG AGGCAGAUUU | 12739 | AAATCTGCCT G TGGAA | 5676 |
| 515 | UACUG UGAUG GCAUGCACUAUGC GCG AGAAUUGUUU | 12740 | AAACAATTCT G CAGTA | 5677 |
| 531 | GUGUU UGAUG GCAUGCACUAUGC GCG AAGGUUAAAG | 12741 | CTTTAACCTT G AACAC | 5678 |
| 569 | AUUUG UGAUG GCAUGCACUAUGC GCG AGCUGUAGAA | 12742 | TTCTACAGCT G CAAAT | 5679 |
| 583 | AGGUA UGAUG GCAUGCACUAUGC GCG AGCUAGAUAU | 12743 | ATATCTAGCT G TACCT | 5680 |
| 616 | GAUUG UGAUG GCAUGCACUAUGC GCG AGAUUCUGUU | 12744 | AACAGAATCT G CAATC | 5681 |
| 637 | UGUAU UGAUG GCAUGCACUAUGC GCG ACUAAUAAAU | 12745 | ATTTATTAGT G ATACA | 5682 |
| 663 | CUGUA UGAUG GCAUGCACUAUGC GCG AUCUCUACGA | 12746 | TCGTAGAGAT G TACAG | 5683 |
| 670 | GAUUU UGAUG GCAUGCACUAUGC GCG ACUGUACAUC | 12747 | GATGTACAGT G AAATC | 5684 |
| 679 | AAUUU UGAUG GCAUGCACUAUGC GCG GGGGAUUUCA | 12748 | TGAAATCCCC G AAATT | 5685 |
| 693 | UCAGU UGAUG GCAUGCACUAUGC GCG AUGUGUAUAA | 12749 | TTATACACAT G ACTGA | 5686 |
| 697 | UCCUU UGAUG GCAUGCACUAUGC GCG AGUCAUGUGU | 12750 | ACACATGACT G AAGGA | 5687 |
| 722 | CCCGG UGAUG GCAUGCACUAUGC GCG AGGGAAUGAC | 12751 | GTCATTCCCT G CCGGG | 5688 |
| 748 | AGUAA UGAUG GCAUGCACUAUGC GCG AGUGAUGUUA | 12752 | TAACATCACT G TTACT | 5689 |
| 772 | AGUGU UGAUG GCAUGCACUAUGC GCG AAGUGGAAAC | 12753 | GTTTCCACTT G ACACT | 5690 |
| 780 | GGGAU UGAUG GCAUGCACUAUGC GCG AAAGUGUCAA | 12754 | TTGACACTTT G ATCCC | 5691 |
| 787 | UCCAU UGAUG GCAUGCACUAUGC GCG AGGGAUCAAA | 12755 | TTTGATCCCT G ATGGA | 5692 |
| 797 | UUAUG UGAUG GCAUGCACUAUGC GCG GUUUUCCAUC | 12756 | GATGGAAAAC G CATAA | 5693 |
| 838 | CGUUG UGAUG GCAUGCACUAUGC GCG AUUUGAUAUG | 12757 | CATATCAAAT G CAACG | 5694 |
| 864 | CAGGU UGAUG GCAUGCACUAUGC GCG AGAAGCCCUA | 12758 | TAGGGCTTCT G ACCTG | 5695 |
| 869 | CUUCA UGAUG GCAUGCACUAUGC GCG AGGUCAGAAG | 12759 | CTTCTGACCT G TGAAG | 5696 |
| 871 | UGCUU UGAUG GCAUGCACUAUGC GCG ACAGGUCAGA | 12760 | TCTGACCTGT G AAGCA | 5697 |
| 894 | UUAUA UGAUG GCAUGCACUAUGC GCG AAAUGCCCAU | 12761 | ATGGGCATTT G TATAA | 5698 |
| 920 | UUUGU UGAUG GCAUGCACUAUGC GCG GAUGUGUGAG | 12762 | CTCACACATC G ACAAA | 5699 |
| 943 | UUGGA UGAUG GCAUGCACUAUGC GCG AUCUAUGAUU | 12763 | AATCATAGAT G TCCAA | 5700 |
| 962 | CUGGG UGAUG GCAUGCACUAUGC GCG GUGGUGUGCU | 12764 | AGCACACCAC G CCCAG | 5701 |
| 994 | GAGGA UGAUG GCAUGCACUAUGC GCG AAGAGUAUGG | 12765 | CCATACTCTT G TCCTC | 5702 |
| 1004 | CAGUA UGAUG GCAUGCACUAUGC GCG AAUUGAGGAC | 12766 | GTCCTCAATT G TACTG | 5703 |
| 1009 | GGUAG UGAUG GCAUGCACUAUGC GCG AGUACAAUUG | 12767 | CAATTGTACT G CTACC | 5704 |

| | | | | |
|---|---|---|---|---|
| 1023 | GUGUU UGAUG GCAUGCACUAUGC GCG AAGGGAGUGG | 12768 | CCACTCCCTT G AACAC | 5705 |
| 1029 | ACUCU UGAUG GCAUGCACUAUGC GCG GUGUUCAAGG | 12769 | CCTTGAACAC G AGAGT | 5706 |
| 1041 | CAGGU UGAUG GCAUGCACUAUGC GCG AUUUGAACUC | 12770 | GAGTTCAAAT G ACCTG | 5707 |
| 1057 | UUCAU UGAUG GCAUGCACUAUGC GCG AGGGUAACUC | 12771 | GAGTTACCCT G ATGAA | 5708 |
| 1060 | UUUUU UGAUG GCAUGCACUAUGC GCG AUCAGGGUAA | 12772 | TTACCCTGAT G AAAAA | 5709 |
| 1088 | UUCGU UGAUG GCAUGCACUAUGC GCG GCCUUACGGA | 12773 | TCCGTAAGGC G ACGAA | 5710 |
| 1091 | CAAUU UGAUG GCAUGCACUAUGC GCG GUCGCCUUAC | 12774 | GTAAGGCGAC G AATTG | 5711 |
| 1096 | UUGGU UGAUG GCAUGCACUAUGC GCG AAUUCGUCGC | 12775 | GCGACGAATT G ACCAA | 5712 |
| 1114 | GUUGG UGAUG GCAUGCACUAUGC GCG AUGGGAAUUG | 12776 | CAATTCCCAT G CCAAC | 5713 |
| 1132 | AAGAA UGAUG GCAUGCACUAUGC GCG ACUGUAGAAU | 12777 | ATTCTACAGT G TTCTT | 5714 |
| 1144 | UUUGU UGAUG GCAUGCACUAUGC GCG AAUAGUAAGA | 12778 | TCTTACTATT G ACAAA | 5715 |
| 1152 | UUCUG UGAUG GCAUGCACUAUGC GCG AUUUUGUCAA | 12779 | TTGACAAAAT G CAGAA | 5716 |
| 1181 | CACGA UGAUG GCAUGCACUAUGC GCG AAGUAUAAAG | 12780 | CTTTATACTT G TCGTG | 5717 |
| 1186 | CCUUA UGAUG GCAUGCACUAUGC GCG ACGACAAGUA | 12781 | TACTTGTCGT G TAAGG | 5718 |
| 1213 | GUUAA UGAUG GCAUGCACUAUGC GCG AGAUUUGAAU | 12782 | ATTCAAATCT G TTAAC | 5719 |
| 1227 | AUAUG UGAUG GCAUGCACUAUGC GCG ACUGAGGUGU | 12783 | ACACCTCAGT G CATAT | 5720 |
| 1237 | UUUAU UGAUG GCAUGCACUAUGC GCG AUAUAUAUGC | 12784 | GCATATATAT G ATAAA | 5721 |
| 1255 | UUUCA UGAUG GCAUGCACUAUGC GCG AGUGAUGAAU | 12785 | ATTCATCACT G TGAAA | 5722 |
| 1257 | UGUUU UGAUG GCAUGCACUAUGC GCG ACAGUGAUGA | 12786 | TCATCACTGT G AAACA | 5723 |
| 1265 | GUUUU UGAUG GCAUGCACUAUGC GCG GAUGUUUCAC | 12787 | GTGAAACATC G AAAAC | 5724 |
| 1278 | UCAAG UGAUG GCAUGCACUAUGC GCG ACCUGCUGUU | 12788 | AACAGCAGGT G CTTGA | 5725 |
| 1282 | GGUUU UGAUG GCAUGCACUAUGC GCG AAGCACCUGC | 12789 | GCAGGTGCTT G AAACC | 5726 |
| 1320 | ACUUU UGAUG GCAUGCACUAUGC GCG AUAGAGAGCC | 12790 | GGCTCTCTAT G AAAGT | 5727 |
| 1326 | GCCUU UGAUG GCAUGCACUAUGC GCG ACUUUCAUAG | 12791 | CTATGAAAGT G AAGGC | 5728 |
| 1341 | UCCGG UGAUG GCAUGCACUAUGC GCG GAGGGAAAUG | 12792 | CATTTCCCTC G CCGGA | 5729 |
| 1351 | CCAUA UGAUG GCAUGCACUAUGC GCG AACUUCCGGC | 12793 | GCCGGAAGTT G TATGG | 5730 |
| 1375 | AGUCG UGAUG GCAUGCACUAUGC GCG AGGUAACCCA | 12794 | TGGGTTACCT G CGACT | 5731 |
| 1377 | UCAGU UGAUG GCAUGCACUAUGC GCG GCAGGUAACC | 12795 | GGTTACCTGC G ACTGA | 5732 |
| 1381 | UUUCU UGAUG GCAUGCACUAUGC GCG AGUCGCAGGU | 12796 | ACCTGCGACT G AGAAA | 5733 |
| 1390 | GCGAG UGAUG GCAUGCACUAUGC GCG AGAUUUCUCA | 12797 | TGAGAAATCT G CTCGC | 5734 |
| 1394 | AAUAG UGAUG GCAUGCACUAUGC GCG GAGCAGAUUU | 12798 | AAATCTGCTC G CTATT | 5735 |
| 1401 | CGAGU UGAUG GCAUGCACUAUGC GCG AAAUAGCGAG | 12799 | CTCGCTATTT G ACTCG | 5736 |
| 1438 | CUCUU UGAUG GCAUGCACUAUGC GCG AGUUACGUCC | 12800 | GGACGTAACT G AAGAG | 5737 |

| | | | | |
|---|---|---|---|---|
| 1447 | CCCUG UGAUG GCAUGCACUAUGC GCG AUCCUCUUCA | 12801 | TGAAGAGGAT G CAGGG | 5738 |
| 1467 | CUCAG UGAUG GCAUGCACUAUGC GCG AAGAUUGUAU | 12802 | ATACAATCTT G CTGAG | 5739 |
| 1470 | AUGCU UGAUG GCAUGCACUAUGC GCG AGCAAGAUUG | 12803 | CAATCTTGCT G AGCAT | 5740 |
| 1489 | AAACA UGAUG GCAUGCACUAUGC GCG AUUUGACUGU | 12804 | ACAGTCAAAT G TGTTT | 5741 |
| 1491 | UUAAA UGAUG GCAUGCACUAUGC GCG ACAUUUGACU | 12805 | AGTCAAATGT G TTTAA | 5742 |
| 1507 | AGUGG UGAUG GCAUGCACUAUGC GCG AGUGAGGUUU | 12806 | AAACCTCACT G CCACT | 5743 |
| 1519 | AUUGA UGAUG GCAUGCACUAUGC GCG AAUUAGAGUG | 12807 | CACTCTAATT G TCAAT | 5744 |
| 1525 | UUUCA UGAUG GCAUGCACUAUGC GCG AUUGACAAUU | 12808 | AATTGTCAAT G TGAAA | 5745 |
| 1527 | GGUUU UGAUG GCAUGCACUAUGC GCG ACAUUGACAA | 12809 | TTGTCAATGT G AAACC | 5746 |
| 1543 | CUUUU UGAUG GCAUGCACUAUGC GCG GUAAAUCUGG | 12810 | CCAGATTTAC G AAAAG | 5747 |
| 1554 | GAUGA UGAUG GCAUGCACUAUGC GCG ACGGCCUUUU | 12811 | AAAAGGCCGT G TCATC | 5748 |
| 1605 | CAAGU UGAUG GCAUGCACUAUGC GCG AGGAUUUGUC | 12812 | GACAAATCCT G ACTTG | 5749 |
| 1610 | CGGUA UGAUG GCAUGCACUAUGC GCG AAGUCAGGAU | 12813 | ATCCTGACTT G TACCG | 5750 |
| 1615 | AUAUG UGAUG GCAUGCACUAUGC GCG GGUACAAGUC | 12814 | GACTTGTACC G CATAT | 5751 |
| 1661 | GGUUA UGAUG GCAUGCACUAUGC GCG AGGGGUGCCA | 12815 | TGGCACCCCT G TAACC | 5752 |
| 1678 | UGCUU UGAUG GCAUGCACUAUGC GCG GGAAUGAUUA | 12816 | TAATCATTCC G AAGCA | 5753 |
| 1688 | AGUCA UGAUG GCAUGCACUAUGC GCG ACCUUGCUUC | 12817 | GAAGCAAGGT G TGACT | 5754 |
| 1690 | AAAGU UGAUG GCAUGCACUAUGC GCG ACACCUUGCU | 12818 | AGCAAGGTGT G ACTTT | 5755 |
| 1697 | UGGAA UGAUG GCAUGCACUAUGC GCG AAAAGUCACA | 12819 | TGTGACTTTT G TTCCA | 5756 |
| 1708 | CUCUU UGAUG GCAUGCACUAUGC GCG AUUAUUGGAA | 12820 | TTCCAATAAT G AAGAG | 5757 |
| 1729 | GUCAG UGAUG GCAUGCACUAUGC GCG AUCCAGGAUA | 12821 | TATCCTGGAT G CTGAC | 5758 |
| 1732 | GCUGU UGAUG GCAUGCACUAUGC GCG AGCAUCCAGG | 12822 | CCTGGATGCT G ACAGC | 5759 |
| 1756 | GCUCU UGAUG GCAUGCACUAUGC GCG AAUUCUGUUU | 12823 | AAACAGAATT G AGAGC | 5760 |
| 1772 | CCAUG UGAUG GCAUGCACUAUGC GCG GCUGAGUGAU | 12824 | ATCACTCAGC G CATGG | 5761 |
| 1819 | AGCCA UGAUG GCAUGCACUAUGC GCG AACCAAGGUG | 12825 | CACCTTGGTT G TGGCT | 5762 |
| 1825 | AGAGU UGAUG GCAUGCACUAUGC GCG AGCCACAACC | 12826 | GGTTGTGGCT G ACTCT | 5763 |
| 1853 | CUAUG UGAUG GCAUGCACUAUGC GCG AAAUGUAGAU | 12827 | ATCTACATTT G CATAG | 5764 |
| 1879 | UCCCA UGAUG GCAUGCACUAUGC GCG AGUCCCAACU | 12828 | AGTTGGGACT G TGGGA | 5765 |
| 1912 | UGGCA UGAUG GCAUGCACUAUGC GCG AUCUGUGAUA | 12829 | TATCACAGAT G TGCCA | 5766 |
| 1914 | UUUGG UGAUG GCAUGCACUAUGC GCG ACAUCUGUGA | 12830 | TCACAGATGT G CCAAA | 5767 |
| 1930 | GUUAA UGAUG GCAUGCACUAUGC GCG AUGAAACCCA | 12831 | TGGGTTTCAT G TTAAC | 5768 |
| 1947 | GUCGG UGAUG GCAUGCACUAUGC GCG AUUUUUUCCA | 12832 | TGGAAAAAAT G CCGAC | 5769 |
| 1950 | UCCGU UGAUG GCAUGCACUAUGC GCG GGCAUUUUUU | 12833 | AAAAAATGCC G ACGGA | 5770 |

253

| | | | | |
|---|---|---|---|---|
| 1968 | AGUUU UGAUG GCAUGCACUAUGC GCG AGGUCCUCUC | 12834 | GAGAGGACCT G AAACT | 5771 |
| 1974 | CAAGA UGAUG GCAUGCACUAUGC GCG AGUUUCAGGU | 12835 | ACCTGAAACT G TCTTG | 5772 |
| 1979 | CUGUG UGAUG GCAUGCACUAUGC GCG AAGACAGUUU | 12836 | AAACTGTCTT G CACAG | 5773 |
| 2025 | GUCCG UGAUG GCAUGCACUAUGC GCG AGUAAAAUCC | 12837 | GGATTTTACT G CGGAC | 5774 |
| 2049 | UAGUG UGAUG GCAUGCACUAUGC GCG AUUGUUCUGU | 12838 | ACAGAACAAT G CACTA | 5775 |
| 2121 | ACAUU UGAUG GCAUGCACUAUGC GCG AUGAUGGUAA | 12839 | TTACCATCAT G AATGT | 5776 |
| 2125 | GGAAA UGAUG GCAUGCACUAUGC GCG AUUCAUGAUG | 12840 | CATCATGAAT G TTTCC | 5777 |
| 2133 | UCUUG UGAUG GCAUGCACUAUGC GCG AGGGAAACAU | 12841 | ATGTTTCCCT G CAAGA | 5778 |
| 2152 | GCAGG UGAUG GCAUGCACUAUGC GCG AUAGGUGCCU | 12842 | AGGCACCTAT G CCTGC | 5779 |
| 2156 | CUCUG UGAUG GCAUGCACUAUGC GCG AGGCAUAGGU | 12843 | ACCTATGCCT G CAGAG | 5780 |
| 2170 | GUAUA UGAUG GCAUGCACUAUGC GCG AUUCCUGGCU | 12844 | AGCCAGGAAT G TATAC | 5781 |
| 2241 | UUUCG UGAUG GCAUGCACUAUGC GCG AGGAGGUAUG | 12845 | CATACCTCCT G CGAAA | 5782 |
| 2243 | GGUUU UGAUG GCAUGCACUAUGC GCG GCAGGAGGUA | 12846 | TACCTCCTGC G AAACC | 5783 |
| 2254 | GUGAU UGAUG GCAUGCACUAUGC GCG ACUGAGGUUU | 12847 | AAACCTCAGT G ATCAC | 5784 |
| 2294 | CAUGA UGAUG GCAUGCACUAUGC GCG AGUCUAAAGU | 12848 | ACTTTAGACT G TCATG | 5785 |
| 2299 | AUUAG UGAUG GCAUGCACUAUGC GCG AUGACAGUCU | 12849 | AGACTGTCAT G CTAAT | 5786 |
| 2308 | GGGGA UGAUG GCAUGCACUAUGC GCG ACCAUUAGCA | 12850 | TGCTAATGGT G TCCCC | 5787 |
| 2314 | AGGCU UGAUG GCAUGCACUAUGC GCG GGGGACACCA | 12851 | TGGTGTCCCC G AGCCT | 5788 |
| 2394 | AACAG UGAUG GCAUGCACUAUGC GCG GUGCUGCUUC | 12852 | GAAGCAGCAC G CTGTT | 5789 |
| 2397 | AUAAA UGAUG GCAUGCACUAUGC GCG AGCGUGCUGC | 12853 | GCAGCACGCT G TTTAT | 5790 |
| 2404 | UCUUU UGAUG GCAUGCACUAUGC GCG AAUAAACAGC | 12854 | GCTGTTTATT G AAAGA | 5791 |
| 2425 | ACCUU UGAUG GCAUGCACUAUGC GCG AUCCUCUUCU | 12855 | AGAAGAGGAT G AAGGT | 5792 |
| 2431 | AUAGA UGAUG GCAUGCACUAUGC GCG ACCUUCAUCC | 12856 | GGATGAAGGT G TCTAT | 5793 |
| 2441 | CUUUG UGAUG GCAUGCACUAUGC GCG AGUGAUAGAC | 12857 | GTCTATCACT G CAAAG | 5794 |
| 2467 | UUCCA UGAUG GCAUGCACUAUGC GCG AGAGCCCUUC | 12858 | GAAGGGCTCT G TGGAA | 5795 |
| 2491 | UUGAA UGAUG GCAUGCACUAUGC GCG AGUGAGGUAU | 12859 | ATACCTCACT G TTCAA | 5796 |
| 2526 | GUGAU UGAUG GCAUGCACUAUGC GCG AGCUCCAGAU | 12860 | ATCTGGAGCT G ATCAC | 5797 |
| 2540 | AGGUG UGAUG GCAUGCACUAUGC GCG AUGUUAGAGU | 12861 | ACTCTAACAT G CACCT | 5798 |
| 2546 | CCACA UGAUG GCAUGCACUAUGC GCG AGGUGCAUGU | 12862 | ACATGCACCT G TGTGG | 5799 |
| 2548 | AGCCA UGAUG GCAUGCACUAUGC GCG ACAGGUGCAU | 12863 | ATGCACCTGT G TGGCT | 5800 |
| 2554 | AGUCG UGAUG GCAUGCACUAUGC GCG AGCCACACAG | 12864 | CTGTGTGGCT G CGACT | 5801 |
| 2556 | AGAGU UGAUG GCAUGCACUAUGC GCG GCAGCCACAC | 12865 | GTGTGGCTGC G ACTCT | 5802 |
| 2591 | UUUUU UGAUG GCAUGCACUAUGC GCG GGAUAAGGAG | 12866 | CTCCTTATCC G AAAAA | 5803 |

254

| | | | | |
|---|---|---|---|---|
| 2598 | CUUUU UGAUG GCAUGCACUAUGC GCG AUUUUUCGGA | 12867 | TCCGAAAAAT G AAAAG | 5804 |
| 2614 | UAUUU UGAUG GCAUGCACUAUGC GCG AGAAGAAGAC | 12868 | GTCTTCTTCT G AAATA | 5805 |
| 2626 | GUAGU UGAUG GCAUGCACUAUGC GCG AGUCUUUAUU | 12869 | AATAAAGACT G ACTAC | 5806 |
| 2656 | AACUU UGAUG GCAUGCACUAUGC GCG AUCUGGGUCC | 12870 | GGACCCAGAT G AAGTT | 5807 |
| 2671 | CUGCU UGAUG GCAUGCACUAUGC GCG AUCCAAAGGA | 12871 | TCCTTTGGAT G AGCAG | 5808 |
| 2678 | GCUCA UGAUG GCAUGCACUAUGC GCG ACUGCUCAUC | 12872 | GATGAGCAGT G TGAGC | 5809 |
| 2680 | CCGCU UGAUG GCAUGCACUAUGC GCG ACACUGCUCA | 12873 | TGAGCAGTGT G AGCGG | 5810 |
| 2695 | GGCAU UGAUG GCAUGCACUAUGC GCG AUAAGGGAGC | 12874 | GCTCCCTTAT G ATGCC | 5811 |
| 2698 | GCUGG UGAUG GCAUGCACUAUGC GCG AUCAUAAGGG | 12875 | CCCTTATGAT G CCAGC | 5812 |
| 2716 | CCGGG UGAUG GCAUGCACUAUGC GCG AAACUCCCAC | 12876 | GTGGGAGTTT G CCCGG | 5813 |
| 2813 | UCCGG UGAUG GCAUGCACUAUGC GCG ACGUAGGUGA | 12877 | TCACCTACGT G CCGGA | 5814 |
| 2821 | AGCCA UGAUG GCAUGCACUAUGC GCG AGUCCGGCAC | 12878 | GTGCCGGACT G TGGCT | 5815 |
| 2827 | UUUCA UGAUG GCAUGCACUAUGC GCG AGCCACAGUC | 12879 | GACTGTGGCT G TGAAA | 5816 |
| 2829 | AUUUU UGAUG GCAUGCACUAUGC GCG ACAGCCACAG | 12880 | CTGTGGCTGT G AAAAT | 5817 |
| 2835 | UUCAG UGAUG GCAUGCACUAUGC GCG AUUUUCACAG | 12881 | CTGTGAAAAT G CTGAA | 5818 |
| 2838 | UCUUU UGAUG GCAUGCACUAUGC GCG AGCAUUUUCA | 12882 | TGAAAATGCT G AAAGA | 5819 |
| 2860 | GUACU UGAUG GCAUGCACUAUGC GCG GCUGGCCGUG | 12883 | CACGGCCAGC G AGTAC | 5820 |
| 2874 | GUCAU UGAUG GCAUGCACUAUGC GCG AGAGCUUUGU | 12884 | ACAAAGCTCT G ATGAC | 5821 |
| 2877 | UCAGU UGAUG GCAUGCACUAUGC GCG AUCAGAGCUU | 12885 | AAGCTCTGAT G ACTGA | 5822 |
| 2881 | UAGCU UGAUG GCAUGCACUAUGC GCG AGUCAUCAGA | 12886 | TCTGATGACT G AGCTA | 5823 |
| 2895 | UGGGU UGAUG GCAUGCACUAUGC GCG AAGAUUUUUA | 12887 | TAAAAATCTT G ACCCA | 5824 |
| 2916 | ACGUU UGAUG GCAUGCACUAUGC GCG AGAUGGUGGC | 12888 | GCCACCATCT G AACGT | 5825 |
| 2931 | CCCAG UGAUG GCAUGCACUAUGC GCG AGGUUAACCA | 12889 | TGGTTAACCT G CTGGG | 5826 |
| 2942 | UGGUG UGAUG GCAUGCACUAUGC GCG AGGCUCCCAG | 12890 | CTGGGAGCCT G CACCA | 5827 |
| 2964 | ACCAU UGAUG GCAUGCACUAUGC GCG AGAGGCCCUC | 12891 | GAGGGCCTCT G ATGGT | 5828 |
| 2970 | ACAAU UGAUG GCAUGCACUAUGC GCG ACCAUCAGAG | 12892 | CTCTGATGGT G ATTGT | 5829 |
| 2974 | UUCAA UGAUG GCAUGCACUAUGC GCG AAUCACCAUC | 12893 | GATGGTGATT G TTGAA | 5830 |
| 2977 | GUAUU UGAUG GCAUGCACUAUGC GCG AACAAUCACC | 12894 | GGTGATTGTT G AATAC | 5831 |
| 2984 | AUUUG UGAUG GCAUGCACUAUGC GCG AGUAUUCAAC | 12895 | GTTGAATACT G CAAAT | 5832 |
| 3025 | UAAGU UGAUG GCAUGCACUAUGC GCG ACGUUUGCUC | 12896 | GAGCAAACGT G ACTTA | 5833 |
| 3049 | UGCUG UGAUG GCAUGCACUAUGC GCG AUCCUUGUUG | 12897 | CAACAAGGAT G CAGCA | 5834 |
| 3139 | GCUUU UGAUG GCAUGCACUAUGC GCG GCUGCUGGUG | 12898 | CACCAGCAGC G AAAGC | 5835 |
| 3148 | GCUCG UGAUG GCAUGCACUAUGC GCG AAAGCUUUCG | 12899 | CGAAAGCTTT G CGAGC | 5836 |

| | | | | |
|---|---|---|---|---|
| 3150 | GAGCU UGAUG GCAUGCACUAUGC GCG GCAAAGCUUU | 12900 | AAAGCTTTGC G AGCTC | 5837 |
| 3180 | UCACU UGAUG GCAUGCACUAUGC GCG AGACUUUUAU | 12901 | ATAAAAGTCT G AGTGA | 5838 |
| 3184 | AACAU UGAUG GCAUGCACUAUGC GCG ACUCAGACUU | 12902 | AAGTCTGAGT G ATGTT | 5839 |
| 3187 | CUCAA UGAUG GCAUGCACUAUGC GCG AUCACUCAGA | 12903 | TCTGAGTGAT G TTGAG | 5840 |
| 3190 | UUCCU UGAUG GCAUGCACUAUGC GCG AACAUCACUC | 12904 | GAGTGATGTT G AGGAA | 5841 |
| 3208 | ACCGU UGAUG GCAUGCACUAUGC GCG AGAAUCCUCC | 12905 | GGAGGATTCT G ACGGT | 5842 |
| 3246 | GAAAU UGAUG GCAUGCACUAUGC GCG AGAUCUUCCA | 12906 | TGGAAGATCT G ATTTC | 5843 |
| 3288 | GAAGA UGAUG GCAUGCACUAUGC GCG AGGAACUCCA | 12907 | TGGAGTTCCT G TCTTC | 5844 |
| 3302 | GAAUG UGAUG GCAUGCACUAUGC GCG ACUUUCUGGA | 12908 | TCCAGAAAGT G CATTC | 5845 |
| 3324 | UUUCU UGAUG GCAUGCACUAUGC GCG GCUGCCAGGU | 12909 | ACCTGGCAGC G AGAAA | 5846 |
| 3343 | GUUCU UGAUG GCAUGCACUAUGC GCG AGAUAAAAGA | 12910 | TCTTTTATCT G AGAAC | 5847 |
| 3357 | AUCUU UGAUG GCAUGCACUAUGC GCG ACCACGUUGU | 12911 | ACAACGTGGT G AAGAT | 5848 |
| 3365 | AAUCA UGAUG GCAUGCACUAUGC GCG AAAUCUUCAC | 12912 | GTGAAGATTT G TGATT | 5849 |
| 3367 | AAAAU UGAUG GCAUGCACUAUGC GCG ACAAAUCUUC | 12913 | GAAGATTTGT G ATTTT | 5850 |
| 3379 | CCGGG UGAUG GCAUGCACUAUGC GCG AAGGCCAAAA | 12914 | TTTTGGCCTT G CCCGG | 5851 |
| 3403 | AUAAU UGAUG GCAUGCACUAUGC GCG GGGGUUCUUA | 12915 | TAAGAACCCC G ATTAT | 5852 |
| 3409 | UCUCA UGAUG GCAUGCACUAUGC GCG AUAAUCGGGG | 12916 | CCCCGATTAT G TGAGA | 5853 |
| 3411 | UUUCU UGAUG GCAUGCACUAUGC GCG ACAUAAUCGG | 12917 | CCGATTATGT G AGAAA | 5854 |
| 3428 | GAAGU UGAUG GCAUGCACUAUGC GCG GAGUAUCUCC | 12918 | GGAGATACTC G ACTTC | 5855 |
| 3438 | CAUUU UGAUG GCAUGCACUAUGC GCG AGAGGAAGUC | 12919 | GACTTCCTCT G AAATG | 5856 |
| 3454 | AGAUU UGAUG GCAUGCACUAUGC GCG GGGAGCCAUC | 12920 | GATGGCTCCC G AATCT | 5857 |
| 3466 | UUUGU UGAUG GCAUGCACUAUGC GCG AAAGAUAGAU | 12921 | ATCTATCTTT G ACAAA | 5858 |
| 3490 | CACGU UGAUG GCAUGCACUAUGC GCG GCUCUUGGUG | 12922 | CACCAAGAGC G ACGTG | 5859 |
| 3495 | GACCA UGAUG GCAUGCACUAUGC GCG ACGUCGCUCU | 12923 | AGAGCGACGT G TGGTC | 5860 |
| 3513 | CACAG UGAUG GCAUGCACUAUGC GCG AAUACUCCGU | 12924 | ACGGAGTATT G CTGTG | 5861 |
| 3516 | UCCCA UGAUG GCAUGCACUAUGC GCG AGCAAUACUC | 12925 | GAGTATTGCT G TGGGA | 5862 |
| 3568 | GUCCU UGAUG GCAUGCACUAUGC GCG AUCCAUUUGU | 12926 | ACAAATGGAT G AGGAC | 5863 |
| 3578 | GACUG UGAUG GCAUGCACUAUGC GCG AAAAGUCCUC | 12927 | GAGGACTTTT G CAGTC | 5864 |
| 3584 | UCAGG UGAUG GCAUGCACUAUGC GCG GACUGCAAAA | 12928 | TTTTGCAGTC G CCTGA | 5865 |
| 3588 | UCCCU UGAUG GCAUGCACUAUGC GCG AGGCGACUGC | 12929 | GCAGTCGCCT G AGGGA | 5866 |
| 3600 | AUCCU UGAUG GCAUGCACUAUGC GCG AUGCCUUCCC | 12930 | GGGAAGGCAT G AGGAT | 5867 |
| 3606 | GCUCU UGAUG GCAUGCACUAUGC GCG AUCCUCAUGC | 12931 | GCATGAGGAT G AGAGC | 5868 |
| 3616 | GUACU UGAUG GCAUGCACUAUGC GCG AGGAGCUCUC | 12932 | GAGAGCTCCT G AGTAC | 5869 |

256

| | | | | |
|---|---|---|---|---|
| 3631 | GAUUU UGAUG GCAUGCACUAUGC GCG AGGAGUAGAG | 12933 | CTCTACTCCT G AAATC | 5870 |
| 3648 | UCCAG UGAUG GCAUGCACUAUGC GCG AUGAUCUGAU | 12934 | ATCAGATCAT G CTGGA | 5871 |
| 3656 | GCCAG UGAUG GCAUGCACUAUGC GCG AGUCCAGCAU | 12935 | ATGCTGGACT G CTGGC | 5872 |
| 3691 | UUCUG UGAUG GCAUGCACUAUGC GCG AAAUCUUGGC | 12936 | GCCAAGATTT G CAGAA | 5873 |
| 3700 | UUCCA UGAUG GCAUGCACUAUGC GCG AAGUUCUGCA | 12937 | TGCAGAACTT G TGGAA | 5874 |
| 3715 | CAAAU UGAUG GCAUGCACUAUGC GCG ACCUAGUUUU | 12938 | AAAACTAGGT G ATTTG | 5875 |
| 3720 | UGAAG UGAUG GCAUGCACUAUGC GCG AAAUCACCUA | 12939 | TAGGTGATTT G CTTCA | 5876 |
| 3733 | UUGUA UGAUG GCAUGCACUAUGC GCG AUUUGCUUGA | 12940 | TCAAGCAAAT G TACAA | 5877 |
| 3769 | UAUGG UGAUG GCAUGCACUAUGC GCG AUUGAUUGGG | 12941 | CCCAATCAAT G CCATA | 5878 |
| 3777 | CCUGU UGAUG GCAUGCACUAUGC GCG AGUAUGGCAU | 12942 | ATGCCATACT G ACAGG | 5879 |
| 3811 | GAAGG UGAUG GCAUGCACUAUGC GCG AGGAGUUGAG | 12943 | CTCAACTCCT G CCTTC | 5880 |
| 3820 | GUCCU UGAUG GCAUGCACUAUGC GCG AGAGAAGGCA | 12944 | TGCCTTCTCT G AGGAC | 5881 |
| 3852 | AACUU UGAUG GCAUGCACUAUGC GCG GGAGCUGAAA | 12945 | TTTCAGCTCC G AAGTT | 5882 |
| 3874 | AUCAU UGAUG GCAUGCACUAUGC GCG AGAGCUUCCU | 12946 | AGGAAGCTCT G ATGAT | 5883 |
| 3877 | GACAU UGAUG GCAUGCACUAUGC GCG AUCAGAGCUU | 12947 | AAGCTCTGAT G ATGTC | 5884 |
| 3880 | UCUGA UGAUG GCAUGCACUAUGC GCG AUCAUCAGAG | 12948 | CTCTGATGAT G TCAGA | 5885 |
| 3889 | AUUUA UGAUG GCAUGCACUAUGC GCG AUAUCUGACA | 12949 | TGTCAGATAT G TAAAT | 5886 |
| 3895 | GAAAG UGAUG GCAUGCACUAUGC GCG AUUUACAUAU | 12950 | ATATGTAAAT G CTTTC | 5887 |
| 3909 | AGGCU UGAUG GCAUGCACUAUGC GCG AUGAACUUGA | 12951 | TCAAGTTCAT G AGCCT | 5888 |
| 3934 | UUCUU UGAUG GCAUGCACUAUGC GCG AAAGGUUUUG | 12952 | CAAAACCTTT G AAGAA | 5889 |
| 3948 | GCAUU UGAUG GCAUGCACUAUGC GCG GGUAAAAGUU | 12953 | AACTTTTACC G AATGC | 5890 |
| 3952 | GGUGG UGAUG GCAUGCACUAUGC GCG AUUCGGUAAA | 12954 | TTTACCGAAT G CCACC | 5891 |
| 3963 | UCAAA UGAUG GCAUGCACUAUGC GCG AUGGAGGUGG | 12955 | CCACCTCCAT G TTTGA | 5892 |
| 3967 | GUCAU UGAUG GCAUGCACUAUGC GCG AAACAUGGAG | 12956 | CTCCATGTTT G ATGAC | 5893 |
| 3970 | GUAGU UGAUG GCAUGCACUAUGC GCG AUCAAACAUG | 12957 | CATGTTTGAT G ACTAC | 5894 |
| 3982 | GCUGU UGAUG GCAUGCACUAUGC GCG GCCCUGGUAG | 12958 | CTACCAGGGC G ACAGC | 5895 |
| 3996 | GCCAA UGAUG GCAUGCACUAUGC GCG AGAGUGCUGC | 12959 | GCAGCACTCT G TTGGC | 5896 |
| 4011 | UUCAG UGAUG GCAUGCACUAUGC GCG AUGGGAGAGG | 12960 | CCTCTCCCAT G CTGAA | 5897 |
| 4014 | CGCUU UGAUG GCAUGCACUAUGC GCG AGCAUGGGAG | 12961 | CTCCCATGCT G AAGCG | 5898 |
| 4019 | UGAAG UGAUG GCAUGCACUAUGC GCG GCUUCAGCAU | 12962 | ATGCTGAAGC G CTTCA | 5899 |
| 4033 | GCUGU UGAUG GCAUGCACUAUGC GCG AGUCCAGGUG | 12963 | CACCTGGACT G ACAGC | 5900 |
| 4053 | UUGAG UGAUG GCAUGCACUAUGC GCG GAGGCCUUGG | 12964 | CCAAGGCCTC G CTCAA | 5901 |
| 4063 | CAAGU UGAUG GCAUGCACUAUGC GCG AAUCUUGAGC | 12965 | GCTCAAGATT G ACTTG | 5902 |

257

| | | | | |
|---|---|---|---|---|
| 4068 | ACUCU UGAUG GCAUGCACUAUGC GCG AAGUCAAUCU | 12966 | AGATTGACTT G AGAGT | 5903 |
| 4101 | UCAGA UGAUG GCAUGCACUAUGC GCG AGCCCCGACU | 12967 | AGTCGGGGCT G TCTGA | 5904 |
| 4105 | GACAU UGAUG GCAUGCACUAUGC GCG AGACAGCCCC | 12968 | GGGGCTGTCT G ATGTC | 5905 |
| 4108 | GCUGA UGAUG GCAUGCACUAUGC GCG AUCAGACAGC | 12969 | GCTGTCTGAT G TCAGC | 5906 |
| 4127 | AAUGG UGAUG GCAUGCACUAUGC GCG AGAAACUGGG | 12970 | CCCAGTTTCT G CCATT | 5907 |
| 4139 | GCCCA UGAUG GCAUGCACUAUGC GCG AGCUGGAAUG | 12971 | CATTCCAGCT G TGGGC | 5908 |
| 4153 | GCCUU UGAUG GCAUGCACUAUGC GCG GCUGACGUGC | 12972 | GCACGTCAGC G AAGGC | 5909 |
| 4163 | ACCUG UGAUG GCAUGCACUAUGC GCG GCUUGCCUUC | 12973 | GAAGGCAAGC G CAGGT | 5910 |
| 4177 | GUGGU UGAUG GCAUGCACUAUGC GCG GUAGGUGAAC | 12974 | GTTCACCTAC G ACCAC | 5911 |
| 4183 | CUCAG UGAUG GCAUGCACUAUGC GCG GUGGUCGUAG | 12975 | CTACGACCAC G CTGAG | 5912 |
| 4186 | CAGCU UGAUG GCAUGCACUAUGC GCG AGCGUGGUCG | 12976 | CGACCACGCT G AGCTG | 5913 |
| 4204 | GCACG UGAUG GCAUGCACUAUGC GCG GAUUUUCCUU | 12977 | AAGGAAAATC G CGTGC | 5914 |
| 4208 | AGCAG UGAUG GCAUGCACUAUGC GCG ACGCGAUUUU | 12978 | AAAATCGCGT G CTGCT | 5915 |
| 4211 | GGGAG UGAUG GCAUGCACUAUGC GCG AGCACGCGAU | 12979 | ATCGCGTGCT G CTCCC | 5916 |
| 4218 | GGGGG UGAUG GCAUGCACUAUGC GCG GGGGAGCAGC | 12980 | GCTGCTCCCC G CCCCC | 5917 |
| 4245 | GAGUA UGAUG GCAUGCACUAUGC GCG AGGACCACCG | 12981 | CGGTGGTCCT G TACTC | 5918 |
| 4272 | CGUGU UGAUG GCAUGCACUAUGC GCG AAACUCUAGA | 12982 | TCTAGAGTTT G ACACG | 5919 |
| 4277 | GGCUU UGAUG GCAUGCACUAUGC GCG GUGUCAAACU | 12983 | AGTTTGACAC G AAGCC | 5920 |
| 4301 | AUACA UGAUG GCAUGCACUAUGC GCG AUGUGCUUCU | 12984 | AGAAGCACAT G TGTAT | 5921 |
| 4303 | AAAUA UGAUG GCAUGCACUAUGC GCG ACAUGUGCUU | 12985 | AAGCACATGT G TATTT | 5922 |
| 4332 | ACUGG UGAUG GCAUGCACUAUGC GCG AAAAGCUAGU | 12986 | ACTAGCTTTT G CCAGT | 5923 |
| 4343 | AUAUG UGAUG GCAUGCACUAUGC GCG AUAAUACUGG | 12987 | CCAGTATTAT G CATAT | 5924 |
| 4386 | AAAAG UGAUG GCAUGCACUAUGC GCG AGCUGGCUCC | 12988 | GGAGCCAGCT G CTTTT | 5925 |
| 4393 | AAUCA UGAUG GCAUGCACUAUGC GCG AAAAAGCAGC | 12989 | GCTGCTTTTT G TGATT | 5926 |
| 4395 | AAAAU UGAUG GCAUGCACUAUGC GCG ACAAAAAGCA | 12990 | TGCTTTTTGT G ATTTT | 5927 |
| 4410 | AAAAG UGAUG GCAUGCACUAUGC GCG ACUAUUAAAA | 12991 | TTTTAATAGT G CTTTT | 5928 |
| 4423 | UUAGU UGAUG GCAUGCACUAUGC GCG AAAAAAAAAA | 12992 | TTTTTTTTTT G ACTAA | 5929 |
| 4436 | AGUUA UGAUG GCAUGCACUAUGC GCG AUUCUUGUUA | 12993 | TAACAAGAAT G TAACT | 5930 |
| 4459 | CUUGU UGAUG GCAUGCACUAUGC GCG ACUAUUUCUC | 12994 | GAGAAATAGT G ACAAG | 5931 |
| 4466 | UUCUU UGAUG GCAUGCACUAUGC GCG ACUUGUCACU | 12995 | AGTGACAAGT G AAGAA | 5932 |
| 4479 | UUUAG UGAUG GCAUGCACUAUGC GCG AGUAGUGUUC | 12996 | GAACACTACT G CTAAA | 5933 |
| 4492 | AGUAA UGAUG GCAUGCACUAUGC GCG AUGAGGAUUU | 12997 | AAATCCTCAT G TTACT | 5934 |
| 4502 | UCUAA UGAUG GCAUGCACUAUGC GCG ACUGAGUAAC | 12998 | GTTACTCAGT G TTAGA | 5935 |

| | | | | |
|---|---|---|---|---|
| 4529 | GAAGU UGAUG GCAUGCACUAUGC GCG AUUGGGUUUA | 12999 | TAAACCCAAT G ACTTC | 5936 |
| 4538 | UGGAG UGAUG GCAUGCACUAUGC GCG AGGGAAGUCA | 13000 | TGACTTCCCT G CTCCA | 5937 |
| 4550 | GGUGG UGAUG GCAUGCACUAUGC GCG GGGGGUUGGA | 13001 | TCCAACCCCC G CCACC | 5938 |
| 4565 | UCCUG UGAUG GCAUGCACUAUGC GCG GUGCCCUGAG | 13002 | CTCAGGGCAC G CAGGA | 5939 |
| 4578 | UCAAU UGAUG GCAUGCACUAUGC GCG AAACUGGUCC | 13003 | GGACCAGTTT G ATTGA | 5940 |
| 4582 | CUCCU UGAUG GCAUGCACUAUGC GCG AAUCAAACUG | 13004 | CAGTTTGATT G AGGAG | 5941 |
| 4590 | CAGUG UGAUG GCAUGCACUAUGC GCG AGCUCCUCAA | 13005 | TTGAGGAGCT G CACTG | 5942 |
| 4595 | GUGAU UGAUG GCAUGCACUAUGC GCG AGUGCAGCUC | 13006 | GAGCTGCACT G ATCAC | 5943 |
| 4606 | UGAUG UGAUG GCAUGCACUAUGC GCG AUUGGGUGAU | 13007 | ATCACCCAAT G CATCA | 5944 |
| 4634 | GGCUG UGAUG GCAUGCACUAUGC GCG AGGGCUGGCC | 13008 | GGCCAGCCCT G CAGCC | 5945 |
| 4691 | UUGCU UGAUG GCAUGCACUAUGC GCG AGGCCAGCCA | 13009 | TGGCTGGCCT G AGCAA | 5946 |
| 4730 | CCUCA UGAUG GCAUGCACUAUGC GCG AUGUCUUAGG | 13010 | CCTAAGACAT G TGAGG | 5947 |
| 4732 | CUCCU UGAUG GCAUGCACUAUGC GCG ACAUGUCUUA | 13011 | TAAGACATGT G AGGAG | 5948 |
| 4792 | UUUCU UGAUG GCAUGCACUAUGC GCG AUGCCUUCUC | 13012 | GAGAAGGCAT G AGAAA | 5949 |
| 4804 | CGUCU UGAUG GCAUGCACUAUGC GCG AAAUUCUUUC | 13013 | GAAAGAATTT G AGACG | 5950 |
| 4809 | UGGUG UGAUG GCAUGCACUAUGC GCG GUCUCAAAUU | 13014 | AATTTGAGAC G CACCA | 5951 |
| 4816 | GCCCA UGAUG GCAUGCACUAUGC GCG AUGGUGCGUC | 13015 | GACGCACCAT G TGGGC | 5952 |
| 4847 | AAUGG UGAUG GCAUGCACUAUGC GCG AUUGCUGAGC | 13016 | GCTCAGCAAT G CCATT | 5953 |
| 4872 | AGGGU UGAUG GCAUGCACUAUGC GCG AGAGCUGGGA | 13017 | TCCCAGCTCT G ACCCT | 5954 |
| 4887 | GCCCU UGAUG GCAUGCACUAUGC GCG AAAUGUAGAA | 13018 | TTCTACATTT G AGGGC | 5955 |
| 4916 | CUCAU UGAUG GCAUGCACUAUGC GCG GCUGUCCAUC | 13019 | GATGGACAGC G ATGAG | 5956 |
| 4919 | CCCCU UGAUG GCAUGCACUAUGC GCG AUCGCUGUCC | 13020 | GGACAGCGAT G AGGGG | 5957 |
| 5018 | AUGGA UGAUG GCAUGCACUAUGC GCG AUAGAACCAC | 13021 | GTGGTTCTAT G TCCAT | 5958 |
| 5039 | CAAAA UGAUG GCAUGCACUAUGC GCG AUGCCACGAA | 13022 | TTCGTGGCAT G TTTTG | 5959 |
| 5044 | CAAAU UGAUG GCAUGCACUAUGC GCG AAAACAUGCC | 13023 | GGCATGTTTT G ATTTG | 5960 |
| 5049 | UGCUA UGAUG GCAUGCACUAUGC GCG AAAUCAAAAC | 13024 | GTTTTGATTT G TAGCA | 5961 |
| 5057 | ACCCU UGAUG GCAUGCACUAUGC GCG AGUGCUACAA | 13025 | TTGTAGCACT G AGGGT | 5962 |
| 5076 | GGGCU UGAUG GCAUGCACUAUGC GCG AGAGUUGAGU | 13026 | ACTCAACTCT G AGCCC | 5963 |
| 5107 | CAGUG UGAUG GCAUGCACUAUGC GCG AUCUUACUAG | 13027 | CTAGTAAGAT G CACTG | 5964 |
| 5112 | GUUUU UGAUG GCAUGCACUAUGC GCG AGUGCAUCUU | 13028 | AAGATGCACT G AAAAC | 5965 |
| 5135 | GGAGA UGAUG GCAUGCACUAUGC GCG AACCUAACUC | 13029 | GAGTTAGGTT G TCTCC | 5966 |
| 5148 | GCCAU UGAUG GCAUGCACUAUGC GCG AUGGCCUGGA | 13030 | TCCAGGCCAT G ATGGC | 5967 |
| 5162 | AUUUU UGAUG GCAUGCACUAUGC GCG AGUGUAAGGC | 13031 | GCCTTACACT G AAAAT | 5968 |

| | | | | |
|---|---|---|---|---|
| 5168 | UGUGA UGAUG GCAUGCACUAUGC GCG AUUUUCAGUG | 13032 | CACTGAAAAT G TCACA | 5969 |
| 5234 | CAAAA UGAUG GCAUGCACUAUGC GCG AGAAUAAUAC | 13033 | GTATTATTCT G TTTTG | 5970 |
| 5239 | CUGUG UGAUG GCAUGCACUAUGC GCG AAAACAGAAU | 13034 | ATTCTGTTTT G CACAG | 5971 |
| 5251 | UUUCA UGAUG GCAUGCACUAUGC GCG AACUAACUGU | 13035 | ACAGTTAGTT G TGAAA | 5972 |
| 5253 | UCUUU UGAUG GCAUGCACUAUGC GCG ACAACUAACU | 13036 | AGTTAGTTGT G AAAGA | 5973 |
| 5264 | CUUCU UGAUG GCAUGCACUAUGC GCG AGCUUUCUUU | 13037 | AAAGAAAGCT G AGAAG | 5974 |
| 5273 | AUUUU UGAUG GCAUGCACUAUGC GCG AUUCUUCUCA | 13038 | TGAGAAGAAT G AAAAT | 5975 |
| 5279 | GACUG UGAUG GCAUGCACUAUGC GCG AUUUUCAUUC | 13039 | GAATGAAAAT G CAGTC | 5976 |
| 5287 | CUCCU UGAUG GCAUGCACUAUGC GCG AGGACUGCAU | 13040 | ATGCAGTCCT G AGGAG | 5977 |
| 5313 | GCCCU UGAUG GCAUGCACUAUGC GCG GUUUUGAUAU | 13041 | ATATCAAAAC G AGGGC | 5978 |
| 5320 | UCCAU UGAUG GCAUGCACUAUGC GCG AGCCCUCGUU | 13042 | AACGAGGGCT G ATGGA | 5979 |
| 5469 | CCUUU UGAUG GCAUGCACUAUGC GCG AGAUUAGUGU | 13043 | ACACTAATCT G AAAGG | 5980 |
| 5477 | UUCCA UGAUG GCAUGCACUAUGC GCG AUCCUUUCAG | 13044 | CTGAAAGGAT G TGGAA | 5981 |
| 5497 | AUAUG UGAUG GCAUGCACUAUGC GCG GCCAGCUAAU | 13045 | ATTAGCTGGC G CATAT | 5982 |
| 5522 | UUACU UGAUG GCAUGCACUAUGC GCG AAGGAGCUUA | 13046 | TAAGCTCCTT G AGTAA | 5983 |
| 5539 | AAUUA UGAUG GCAUGCACUAUGC GCG AUACCACCUU | 13047 | AAGGTGGTAT G TAATT | 5984 |
| 5548 | CCUUG UGAUG GCAUGCACUAUGC GCG AUAAAUUACA | 13048 | TGTAATTTAT G CAAGG | 5985 |
| 5589 | UGGCU UGAUG GCAUGCACUAUGC GCG AUUAACUAAU | 13049 | ATTAGTTAAT G AGCCA | 5986 |
| 5623 | CAAAG UGAUG GCAUGCACUAUGC GCG AGUUGAAAAU | 13050 | ATTTTCAACT G CTTTG | 5987 |
| 5628 | AGUUU UGAUG GCAUGCACUAUGC GCG AAAGCAGUUG | 13051 | CAACTGCTTT G AAACT | 5988 |
| 5635 | CCAGG UGAUG GCAUGCACUAUGC GCG AAGUUUCAAA | 13052 | TTTGAAACTT G CCTGG | 5989 |
| 5646 | AUGCU UGAUG GCAUGCACUAUGC GCG AGACCCCAGG | 13053 | CCTGGGGTCT G AGCAT | 5990 |
| 5652 | CCCAU UGAUG GCAUGCACUAUGC GCG AUGCUCAGAC | 13054 | GTCTGAGCAT G ATGGG | 5991 |
| 5684 | GUAGG UGAUG GCAUGCACUAUGC GCG GCCCUUUCCU | 13055 | AGGAAAGGGC G CCTAC | 5992 |
| 5725 | CUUAG UGAUG GCAUGCACUAUGC GCG GAUCCAAGGC | 13056 | GCCTTGGATC G CTAAG | 5993 |
| 5739 | UCAAA UGAUG GCAUGCACUAUGC GCG AGAGCCAGCU | 13057 | AGCTGGCTCT G TTTGA | 5994 |
| 5743 | AGCAU UGAUG GCAUGCACUAUGC GCG AAACAGAGCC | 13058 | GGCTCTGTTT G ATGCT | 5995 |
| 5746 | AAUAG UGAUG GCAUGCACUAUGC GCG AUCAAACAGA | 13059 | TCTGTTTGAT G CTATT | 5996 |
| 5755 | ACUUG UGAUG GCAUGCACUAUGC GCG AUAAAUAGCA | 13060 | TGCTATTTAT G CAAGT | 5997 |
| 5771 | AAAUA UGAUG GCAUGCACUAUGC GCG AUAGACCCUA | 13061 | TAGGGTCTAT G TATTT | 5998 |
| 5782 | AGGCG UGAUG GCAUGCACUAUGC GCG AUCCUAAAUA | 13062 | TATTTAGGAT G CGCCT | 5999 |
| 5784 | GUAGG UGAUG GCAUGCACUAUGC GCG GCAUCCUAAA | 13063 | TTTAGGATGC G CCTAC | 6000 |
| 5825 | CUUAG UGAUG GCAUGCACUAUGC GCG GAUCCAAGGC | 13056 | GCCTTGGATC G CTAAG | 5993 |

260

| | | | | |
|---|---|---|---|---|
| 5839 | UCAAA UGAUG GCAUGCACUAUGC GCG AGAGCCAGCU | 13057 | AGCTGGCTCT G TTTGA | 5994 |
| 5843 | AGCAU UGAUG GCAUGCACUAUGC GCG AAACAGAGCC | 13058 | GGCTCTGTTT G ATGCT | 5995 |
| 5846 | AAUAG UGAUG GCAUGCACUAUGC GCG AUCAAACAGA | 13059 | TCTGTTTGAT G CTATT | 5996 |
| 5855 | ACUUG UGAUG GCAUGCACUAUGC GCG AUAAAUAGCA | 13060 | TGCTATTTAT G CAAGT | 5997 |
| 5871 | AAAUA UGAUG GCAUGCACUAUGC GCG AUAGACCCUA | 13061 | TAGGGTCTAT G TATTT | 5998 |
| 5882 | GCAGA UGAUG GCAUGCACUAUGC GCG AUCCUAAAUA | 13064 | TATTTAGGAT G TCTGC | 6001 |
| 5886 | AGGUG UGAUG GCAUGCACUAUGC GCG AGACAUCCUA | 13065 | TAGGATGTCT G CACCT | 6002 |
| 5895 | GGCUG UGAUG GCAUGCACUAUGC GCG AGAAGGUGCA | 13066 | TGCACCTTCT G CAGCC | 6003 |
| 5931 | AGCAG UGAUG GCAUGCACUAUGC GCG AAUCCACUGU | 13067 | ACAGTGGATT G CTGCT | 6004 |
| 5934 | AGAAG UGAUG GCAUGCACUAUGC GCG AGCAAUCCAC | 13068 | GTGGATTGCT G CTTCT | 6005 |
| 5955 | GGAAG UGAUG GCAUGCACUAUGC GCG AUACUCUUCU | 13069 | AGAAGAGTAT G CTTCC | 6006 |
| 5971 | AAUUA UGAUG GCAUGCACUAUGC GCG AUGGAUAAAA | 13070 | TTTTATCCAT G TAATT | 6007 |
| 5982 | UUCUA UGAUG GCAUGCACUAUGC GCG AGUUAAAUUA | 13071 | TAATTTAACT G TAGAA | 6008 |
| 5991 | GAGCU UGAUG GCAUGCACUAUGC GCG AGGUUCUACA | 13072 | TGTAGAACCT G AGCTC | 6009 |
| 6006 | UUCUU UGAUG GCAUGCACUAUGC GCG GGUUACUUAG | 13073 | CTAAGTAACC G AAGAA | 6010 |
| 6013 | GCAUA UGAUG GCAUGCACUAUGC GCG AUUCUUCGGU | 13074 | ACCGAAGAAT G TATGC | 6011 |
| 6017 | AGAGG UGAUG GCAUGCACUAUGC GCG AUACAUUCUU | 13075 | AAGAATGTAT G CCTCT | 6012 |
| 6023 | AAGAA UGAUG GCAUGCACUAUGC GCG AGAGGCAUAC | 13076 | GTATGCCTCT G TTCTT | 6013 |
| 6031 | UGGCA UGAUG GCAUGCACUAUGC GCG AUAAGAACAG | 13077 | CTGTTCTTAT G TGCCA | 6014 |
| 6033 | UGUGG UGAUG GCAUGCACUAUGC GCG ACAUAAGAAC | 13078 | GTTCTTATGT G CCACA | 6015 |
| 6044 | UUAAA UGAUG GCAUGCACUAUGC GCG AAGGAUGUGG | 13079 | CCACATCCTT G TTTAA | 6016 |
| 6059 | UCAUA UGAUG GCAUGCACUAUGC GCG AGAGAGCCUU | 13080 | AAGGCTCTCT G TATGA | 6017 |
| 6063 | CUCUU UGAUG GCAUGCACUAUGC GCG AUACAGAGAG | 13081 | CTCTCTGTAT G AAGAG | 6018 |
| 6098 | AGGCU UGAUG GCAUGCACUAUGC GCG ACUAGGGAAU | 13082 | ATTCCCTAGT G AGCCT | 6019 |
| 6127 | UUCCA UGAUG GCAUGCACUAUGC GCG AAAAGCCGCU | 13083 | AGCGGCTTTT G TGGAA | 6020 |
| 6230 | AACAA UGAUG GCAUGCACUAUGC GCG AAAGAUUUGU | 13084 | ACAAATCTTT G TTGTT | 6021 |
| 6233 | AGGAA UGAUG GCAUGCACUAUGC GCG AACAAAGAUU | 13085 | AATCTTTGTT G TTCCT | 6022 |
| 6254 | GUUUG UGAUG GCAUGCACUAUGC GCG GUAUGUGUAA | 13086 | TTACACATAC G CAAAC | 6023 |
| 6265 | UGUCA UGAUG GCAUGCACUAUGC GCG AGGUGGUUUG | 13087 | CAAACCACCT G TGACA | 6024 |
| 6267 | GCUGU UGAUG GCAUGCACUAUGC GCG ACAGGUGGUU | 13088 | AACCACCTGT G ACAGC | 6025 |
| 6391 | GUUAU UGAUG GCAUGCACUAUGC GCG ACUAUUUGCU | 13089 | AGCAAATAGT G ATAAC | 6026 |
| 6413 | AUGAA UGAUG GCAUGCACUAUGC GCG AGCUAAGGUU | 13090 | AACCTTAGCT G TTCAT | 6027 |
| 6419 | CAAGA UGAUG GCAUGCACUAUGC GCG AUGAACAGCU | 13091 | AGCTGTTCAT G TCTTG | 6028 |

| | | | | |
|---|---|---|---|---|
| 6424 | GAAAU UGAUG GCAUGCACUAUGC GCG AAGACAUGAA | 13092 | TTCATGTCTT G ATTTC | 6029 |
| 6504 | AGUAA UGAUG GCAUGCACUAUGC GCG AAUUCUAAUG | 13093 | CATTAGAATT G TTACT | 6030 |
| 6532 | UGCUA UGAUG GCAUGCACUAUGC GCG AAACCUGAGU | 13094 | ACTCAGGTTT G TAGCA | 6031 |
| 6543 | GGACU UGAUG GCAUGCACUAUGC GCG AUGUAUGCUA | 13095 | TAGCATACAT G AGTCC | 6032 |
| 6588 | UUCUA UGAUG GCAUGCACUAUGC GCG AUUAAGACUC | 13096 | GAGTCTTAAT G TAGAA | 6033 |
| 6610 | UAUUA UGAUG GCAUGCACUAUGC GCG AAGUCUCCAU | 13097 | ATGGAGACTT G TAATA | 6034 |
| 6618 | UAGCU UGAUG GCAUGCACUAUGC GCG AUUAUUACAA | 13098 | TTGTAATAAT G AGCTA | 6035 |
| 6634 | ACAAG UGAUG GCAUGCACUAUGC GCG ACUUUGUAAC | 13099 | GTTACAAAGT G CTTGT | 6036 |
| 6638 | AUGAA UGAUG GCAUGCACUAUGC GCG AAGCACUUUG | 13100 | CAAAGTGCTT G TTCAT | 6037 |
| 6656 | AUUUU UGAUG GCAUGCACUAUGC GCG AGUGCUAUUU | 13101 | AAATAGCACT G AAAAT | 6038 |
| 6663 | UGUUU UGAUG GCAUGCACUAUGC GCG AAUUUUCAGU | 13102 | ACTGAAAATT G AAACA | 6039 |
| 6670 | UAAUU UGAUG GCAUGCACUAUGC GCG AUGUUUCAAU | 13103 | ATTGAAACAT G AATTA | 6040 |
| 6679 | AUUAU UGAUG GCAUGCACUAUGC GCG AGUUAAUUCA | 13104 | TGAATTAACT G ATAAT | 6041 |
| 6698 | AAUGG UGAUG GCAUGCACUAUGC GCG AAAUGAUUGG | 13105 | CCAATCATTT G CCATT | 6042 |
| 6707 | UUUGU UGAUG GCAUGCACUAUGC GCG AUAAAUGGCA | 13106 | TGCCATTTAT G ACAAA | 6043 |
| 6736 | GUGCU UGAUG GCAUGCACUAUGC GCG GUUCUUUGUU | 13107 | AACAAAGAAC G AGCAC | 6044 |
| 6759 | UAUCU UGAUG GCAUGCACUAUGC GCG AGAAACUCUG | 13108 | CAGAGTTTCT G AGATA | 6045 |
| 6767 | ACGUA UGAUG GCAUGCACUAUGC GCG AUUAUCUCAG | 13109 | CTGAGATAAT G TACGT | 6046 |
| 6798 | GGUUU UGAUG GCAUGCACUAUGC GCG AGCCCCAUUC | 13110 | GAATGGGGCT G AAACC | 6047 |
| 6806 | UUGCA UGAUG GCAUGCACUAUGC GCG AUGGUUUCAG | 13111 | CTGAAACCAT G TGCAA | 6048 |
| 6808 | ACUUG UGAUG GCAUGCACUAUGC GCG ACAUGGUUUC | 13112 | GAAACCATGT G CAAGT | 6049 |
| 6816 | AGACA UGAUG GCAUGCACUAUGC GCG AGACUUGCAC | 13113 | GTGCAAGTCT G TGTCT | 6050 |
| 6818 | CAAGA UGAUG GCAUGCACUAUGC GCG ACAGACUUGC | 13114 | GCAAGTCTGT G TCTTG | 6051 |
| 6823 | ACUGA UGAUG GCAUGCACUAUGC GCG AAGACACAGA | 13115 | TCTGTGTCTT G TCAGT | 6052 |
| 6838 | GGUGU UGAUG GCAUGCACUAUGC GCG ACUUCUUGGA | 13116 | TCCAAGAAGT G ACACC | 6053 |
| 6844 | CAUCU UGAUG GCAUGCACUAUGC GCG GGUGUCACUU | 13117 | AAGTGACACC G AGATG | 6054 |
| 6849 | AUUAA UGAUG GCAUGCACUAUGC GCG AUCUCGGUGU | 13118 | ACACCGAGAT G TTAAT | 6055 |
| 6868 | CAAGG UGAUG GCAUGCACUAUGC GCG ACGGGUCCCU | 13119 | AGGGACCCGT G CCTTG | 6056 |
| 6873 | GGAAA UGAUG GCAUGCACUAUGC GCG AAGGCACGGG | 13120 | CCCGTGCCTT G TTTCC | 6057 |
| 6893 | GUUUG UGAUG GCAUGCACUAUGC GCG AUUCUUGUGG | 13121 | CCACAAGAAT G CAAAC | 6058 |
| 6914 | GCUAG UGAUG GCAUGCACUAUGC GCG GAGUAUCUGU | 13122 | ACAGATACTC G CTAGC | 6059 |
| 6932 | UUAAU UGAUG GCAUGCACUAUGC GCG AAUUUAAAUG | 13123 | CATTTAAATT G ATTAA | 6060 |
| 6947 | AGAUG UGAUG GCAUGCACUAUGC GCG ACUCCUCCUU | 13124 | AAGGAGGAGT G CATCT | 6061 |

262

| | | | | |
|---|---|---|---|---|
| 6959 | ACUGU UGAUG GCAUGCACUAUGC GCG GGCCAAAGAU | 13125 | ATCTTTGGCC G ACAGT | 6062 |
| 6968 | AGUUA UGAUG GCAUGCACUAUGC GCG ACCACUGUCG | 13126 | CGACAGTGGT G TAACT | 6063 |
| 6974 | ACACA UGAUG GCAUGCACUAUGC GCG AGUUACACCA | 13127 | TGGTGTAACT G TGTGT | 6064 |
| 6976 | ACACA UGAUG GCAUGCACUAUGC GCG ACAGUUACAC | 13128 | GTGTAACTGT G TGTGT | 6065 |
| 6978 | ACACA UGAUG GCAUGCACUAUGC GCG ACACAGUUAC | 13129 | GTAACTGTGT G TGTGT | 6066 |
| 6980 | ACACA UGAUG GCAUGCACUAUGC GCG ACACACAGUU | 13130 | AACTGTGTGT G TGTGT | 6067 |
| 6982 | ACACA UGAUG GCAUGCACUAUGC GCG ACACACACAG | 13131 | CTGTGTGTGT G TGTGT | 6068 |
| 6984 | ACACA UGAUG GCAUGCACUAUGC GCG ACACACACAC | 13132 | GTGTGTGTGT G TGTGT | 6069 |
| 6986 | ACACA UGAUG GCAUGCACUAUGC GCG ACACACACAC | 13132 | GTGTGTGTGT G TGTGT | 6069 |
| 6988 | ACACA UGAUG GCAUGCACUAUGC GCG ACACACACAC | 13132 | GTGTGTGTGT G TGTGT | 6069 |
| 6990 | ACACA UGAUG GCAUGCACUAUGC GCG ACACACACAC | 13132 | GTGTGTGTGT G TGTGT | 6069 |
| 6992 | ACACA UGAUG GCAUGCACUAUGC GCG ACACACACAC | 13132 | GTGTGTGTGT G TGTGT | 6069 |
| 6994 | ACACA UGAUG GCAUGCACUAUGC GCG ACACACACAC | 13132 | GTGTGTGTGT G TGTGT | 6069 |
| 6996 | ACACA UGAUG GCAUGCACUAUGC GCG ACACACACAC | 13132 | GTGTGTGTGT G TGTGT | 6069 |
| 6998 | ACACA UGAUG GCAUGCACUAUGC GCG ACACACACAC | 13132 | GTGTGTGTGT G TGTGT | 6069 |
| 7000 | ACACA UGAUG GCAUGCACUAUGC GCG ACACACACAC | 13132 | GTGTGTGTGT G TGTGT | 6069 |
| 7002 | ACACA UGAUG GCAUGCACUAUGC GCG ACACACACAC | 13132 | GTGTGTGTGT G TGTGT | 6069 |
| 7004 | ACACA UGAUG GCAUGCACUAUGC GCG ACACACACAC | 13132 | GTGTGTGTGT G TGTGT | 6069 |
| 7006 | ACACA UGAUG GCAUGCACUAUGC GCG ACACACACAC | 13132 | GTGTGTGTGT G TGTGT | 6069 |
| 7008 | ACACA UGAUG GCAUGCACUAUGC GCG ACACACACAC | 13132 | GTGTGTGTGT G TGTGT | 6069 |
| 7010 | CCACA UGAUG GCAUGCACUAUGC GCG ACACACACAC | 13133 | GTGTGTGTGT G TGTGG | 6070 |
| 7012 | ACCCA UGAUG GCAUGCACUAUGC GCG ACACACACAC | 13134 | GTGTGTGTGT G TGGGT | 6071 |
| 7018 | ACCCA UGAUG GCAUGCACUAUGC GCG ACCCACACAC | 13135 | GTGTGTGGGT G TGGGT | 6072 |
| 7024 | ACAUA UGAUG GCAUGCACUAUGC GCG ACCCACACCC | 13136 | GGGTGTGGGT G TATGT | 6073 |
| 7028 | ACACA UGAUG GCAUGCACUAUGC GCG AUACACCCAC | 13137 | GTGGGTGTAT G TGTGT | 6074 |
| 7030 | AAACA UGAUG GCAUGCACUAUGC GCG ACAUACACCC | 13138 | GGGTGTATGT G TGTTT | 6075 |
| 7032 | CAAAA UGAUG GCAUGCACUAUGC GCG ACACAUACAC | 13139 | GTGTATGTGT G TTTTG | 6076 |
| 7037 | AUGCA UGAUG GCAUGCACUAUGC GCG AAAACACACA | 13140 | TGTGTGTTTT G TGCAT | 6077 |
| 7039 | UUAUG UGAUG GCAUGCACUAUGC GCG ACAAAACACA | 13141 | TGTGTTTTGT G CATAA | 6078 |
| 7099 | UGUAG UGAUG GCAUGCACUAUGC GCG AUAUAUUCUU | 13142 | AAGAATATAT G CTACA | 6079 |
| 7146 | UUCAU UGAUG GCAUGCACUAUGC GCG AUGACUAGAA | 13143 | TTCTAGTCAT G ATGAA | 6080 |
| 7149 | ACAUU UGAUG GCAUGCACUAUGC GCG AUCAUGACUA | 13144 | TAGTCATGAT G AATGT | 6081 |
| 7153 | AAAUA UGAUG GCAUGCACUAUGC GCG AUUCAUCAUG | 13145 | CATGATGAAT G TATTT | 6082 |

263

| | | | | |
|---|---|---|---|---|
| 7160 | GUAUA UGAUG GCAUGCACUAUGC GCG AAAAUACAUU | 13146 | AATGTATTTT G TATAC | 6083 |
| 7210 | GAUUA UGAUG GCAUGCACUAUGC GCG AAAUCCCAAU | 13147 | ATTGGGATTT G TAATC | 6084 |
| 7230 | UUUAU UGAUG GCAUGCACUAUGC GCG AAUUAAGUUG | 13148 | CAACTTAATT G ATAAA | 6085 |
| 7246 | AAAAG UGAUG GCAUGCACUAUGC GCG AGUUGCCAAG | 13149 | CTTGGCAACT G CTTTT | 6086 |
| 7254 | CAGAA UGAUG GCAUGCACUAUGC GCG AUAAAAGCAG | 13150 | CTGCTTTTAT G TTCTG | 6087 |
| 7259 | GGAGA UGAUG GCAUGCACUAUGC GCG AGAACAUAAA | 13151 | TTTATGTTCT G TCTCC | 6088 |
| 7343 | CUAAA UGAUG GCAUGCACUAUGC GCG AAGGAUAAAU | 13152 | ATTTATCCTT G TTTAG | 6089 |
| 7375 | CAUUU UGAUG GCAUGCACUAUGC GCG AAAGUUUUUC | 13153 | GAAAAACTTT G AAATG | 6090 |
| 7394 | UUUAG UGAUG GCAUGCACUAUGC GCG AAUUUUUUGA | 13154 | TCAAAAAATT G CTAAA | 6091 |
| 7422 | ACUAA UGAUG GCAUGCACUAUGC GCG AUUUAGUUUU | 13155 | AAAACTAAAT G TTAGT | 6092 |
| 7434 | ACAAU UGAUG GCAUGCACUAUGC GCG AGCUAAACUA | 13156 | TAGTTTAGCT G ATTGT | 6093 |
| 7438 | CCAUA UGAUG GCAUGCACUAUGC GCG AAUCAGCUAA | 13157 | TTAGCTGATT G TATGG | 6094 |
| 7451 | AGGUU UGAUG GCAUGCACUAUGC GCG GAAAACCCCA | 13158 | TGGGGTTTTC G AACCT | 6095 |
| 7467 | ACAAA UGAUG GCAUGCACUAUGC GCG AAAAAGUGAA | 13159 | TTCACTTTTT G TTTGT | 6096 |
| 7471 | UAAAA UGAUG GCAUGCACUAUGC GCG AAACAAAAAG | 13160 | CTTTTTGTTT G TTTTA | 6097 |
| 7491 | UUACA UGAUG GCAUGCACUAUGC GCG AGUUGUGAAA | 13161 | TTTCACAACT G TGTAA | 6098 |
| 7493 | AUUUA UGAUG GCAUGCACUAUGC GCG ACAGUUGUGA | 13162 | TCACAACTGT G TAAAT | 6099 |
| 7500 | AUUGG UGAUG GCAUGCACUAUGC GCG AAUUUACACA | 13163 | TGTGTAAATT G CCAAT | 6100 |
| 7513 | AUGGA UGAUG GCAUGCACUAUGC GCG AGGAAUUAUU | 13164 | AATAATTCCT G TCCAT | 6101 |
| 7519 | AUUUU UGAUG GCAUGCACUAUGC GCG AUGGACAGGA | 13165 | TCCTGTCCAT G AAAAT | 6102 |
| 7525 | AUUUG UGAUG GCAUGCACUAUGC GCG AUUUUCAUGG | 13166 | CCATGAAAAT G CAAAT | 6103 |
| 7539 | AUCUA UGAUG GCAUGCACUAUGC GCG ACUGGAUAAU | 13167 | ATTATCCAGT G TAGAT | 6104 |
| 7551 | AUGGU UGAUG GCAUGCACUAUGC GCG AAAUAUAUCU | 13168 | AGATATATTT G ACCAT | 6105 |
| 7582 | AAAGG UGAUG GCAUGCACUAUGC GCG AAAACUAGCC | 13169 | GGCTAGTTTT G CCTTT | 6106 |
| 7611 | ACAUU UGAUG GCAUGCACUAUGC GCG AGGCUGAAAU | 13170 | ATTTCAGCCT G AATGT | 6107 |
| 7615 | GCAGA UGAUG GCAUGCACUAUGC GCG AUUCAGGCUG | 13171 | CAGCCTGAAT G TCTGC | 6108 |
| 7619 | AUAGG UGAUG GCAUGCACUAUGC GCG AGACAUUCAG | 13172 | CTGAATGTCT G CCTAT | 6109 |
| 7634 | AAGAG UGAUG GCAUGCACUAUGC GCG AGAGAAUAUA | 13173 | TATATTCTCT G CTCTT | 6110 |
| 7641 | GAAUA UGAUG GCAUGCACUAUGC GCG AAAGAGCAGA | 13174 | TCTGCTCTTT G TATTC | 6111 |
| 7653 | GGGUU UGAUG GCAUGCACUAUGC GCG AAAGGAGAAU | 13175 | ATTCTCCTTT G AACCC | 6112 |
| 7672 | UGCCA UGAUG GCAUGCACUAUGC GCG AGGAUGUUUU | 13176 | AAAACATCCT G TGGCA | 6113 |

Table XVI: Human KDR NCH Ribozyme and Target Sequences 237.198

Core Sequence = CUGAUGAG GCCGUUAGGC CGAA
Underlined region can be any X sequence or linker, as described herein.

| nt. Position | Ribozyme Sequence | Seq. ID Nos | Target | Seq. ID Nos. |
|---|---|---|---|---|
| 11 | CGGCCAGC CUGAUGAG GCCGUUAGGC CGAA ICACCUUG | 13177 | CAAGGTGC T GCTGGCCG | 6114 |
| 14 | CGACGGCC CUGAUGAG GCCGUUAGGC CGAA ICAGCACC | 13178 | GGTGCTGC T GGCCGTCG | 6115 |
| 18 | AGGGCGAC CUGAUGAG GCCGUUAGGC CGAA ICCAGCAG | 13179 | CTGCTGGC C GTCGCCCT | 6116 |
| 24 | AGCCACAG CUGAUGAG GCCGUUAGGC CGAA ICGACGGC | 13180 | GCCGTCGC C CTGTGGCT | 6117 |
| 25 | GAGCCACA CUGAUGAG GCCGUUAGGC CGAA IGCGACGG | 13181 | CCGTCGCC C TGTGGCTC | 6118 |
| 26 | AGAGCCAC CUGAUGAG GCCGUUAGGC CGAA IGGCGACG | 13182 | CGTCGCCC T GTGGCTCT | 6119 |
| 32 | CCACGCAG CUGAUGAG GCCGUUAGGC CGAA ICCACAGG | 13183 | CCTGTGGC T CTGCGTGG | 6120 |
| 34 | CUCCACGC CUGAUGAG GCCGUUAGGC CGAA IAGCCACA | 13184 | TGTGGCTC T GCGTGGAG | 6121 |
| 45 | GCGGCCCG CUGAUGAG GCCGUUAGGC CGAA IUCUCCAC | 13185 | GTGGAGAC C CGGGCCGC | 6122 |
| 46 | GGCGGCCC CUGAUGAG GCCGUUAGGC CGAA IGUCUCCA | 13186 | TGGAGACC C GGGCCGCC | 6123 |
| 51 | ACAGAGGC CUGAUGAG GCCGUUAGGC CGAA ICCCGGGU | 13187 | ACCCGGGC C GCCTCTGT | 6124 |
| 54 | CCCACAGA CUGAUGAG GCCGUUAGGC CGAA ICGGCCCG | 13188 | CGGGCCGC C TCTGTGGG | 6125 |
| 55 | ACCCACAG CUGAUGAG GCCGUUAGGC CGAA IGCGGCCC | 13189 | GGGCCGCC T CTGTGGGT | 6126 |
| 57 | AAACCCAC CUGAUGAG GCCGUUAGGC CGAA IAGGCGGC | 13190 | GCCGCCTC T GTGGGTTT | 6127 |
| 68 | AAACACUA CUGAUGAG GCCGUUAGGC CGAA ICAAACCC | 13191 | GGGTTTGC C TAGTGTTT | 6128 |
| 69 | GAAACACU CUGAUGAG GCCGUUAGGC CGAA IGCAAACC | 13192 | GGTTTGCC T AGTGTTTC | 6129 |
| 78 | AGAUCAAG CUGAUGAG GCCGUUAGGC CGAA IAAACACU | 13193 | AGTGTTTC T CTTGATCT | 6130 |
| 80 | GCAGAUCA CUGAUGAG GCCGUUAGGC CGAA IAGAAACA | 13194 | TGTTTCTC T TGATCTGC | 6131 |
| 86 | GCCUGGGC CUGAUGAG GCCGUUAGGC CGAA IAUCAAGA | 13195 | TCTTGATC T GCCCAGGC | 6132 |
| 89 | UGAGCCUG CUGAUGAG GCCGUUAGGC CGAA ICAGAUCA | 13196 | TGATCTGC C CAGGCTCA | 6133 |
| 90 | CUGAGCCU CUGAUGAG GCCGUUAGGC CGAA IGCAGAUC | 13197 | GATCTGCC C AGGCTCAG | 6134 |
| 91 | GCUGAGCC CUGAUGAG GCCGUUAGGC CGAA IGGCAGAU | 13198 | ATCTGCCC A GGCTCAGC | 6135 |
| 95 | GUAUGCUG CUGAUGAG GCCGUUAGGC CGAA ICCUGGGC | 13199 | GCCCAGGC T CAGCATAC | 6136 |
| 97 | UUGUAUGC CUGAUGAG GCCGUUAGGC CGAA IAGCCUGG | 13200 | CCAGGCTC A GCATACAA | 6137 |
| 100 | UUUUUGUA CUGAUGAG GCCGUUAGGC CGAA ICUGAGCC | 13201 | GGCTCAGC A TACAAAAA | 6138 |
| 104 | UGUCUUUU CUGAUGAG GCCGUUAGGC CGAA IUAUGCUG | 13202 | CAGCATAC A AAAAGACA | 6139 |
| 112 | UGUAAGUA CUGAUGAG GCCGUUAGGC CGAA IUCUUUUU | 13203 | AAAAAGAC A TACTTACA | 6140 |

265

| | | | | |
|---|---|---|---|---|
| 116 | UAAUUGUA CUGAUGAG GCCGUUAGGC CGAA IUAUGUCU | 13204 | AGACATAC T TACAATTA | 6141 |
| 120 | GCCUUAAU CUGAUGAG GCCGUUAGGC CGAA IUAAGUAU | 13205 | ATACTTAC A ATTAAGGC | 6142 |
| 129 | GUUGUAUU CUGAUGAG GCCGUUAGGC CGAA ICCUUAAU | 13206 | ATTAAGGC T AATACAAC | 6143 |
| 135 | UGAAGAGU CUGAUGAG GCCGUUAGGC CGAA IUAUUAGC | 13207 | GCTAATAC A ACTCTTCA | 6144 |
| 138 | AUUUGAAG CUGAUGAG GCCGUUAGGC CGAA IUUGUAUU | 13208 | AATACAAC T CTTCAAAT | 6145 |
| 140 | UAAUUUGA CUGAUGAG GCCGUUAGGC CGAA IAGUUGUA | 13209 | TACAACTC T TCAAATTA | 6146 |
| 143 | AAGUAAUU CUGAUGAG GCCGUUAGGC CGAA IAAGAGUU | 13210 | AACTCTTC A AATTACTT | 6147 |
| 150 | CCCCUGCA CUGAUGAG GCCGUUAGGC CGAA IUAAUUUG | 13211 | CAAATTAC T TGCAGGGG | 6148 |
| 154 | CUGUCCCC CUGAUGAG GCCGUUAGGC CGAA ICAAGUAA | 13212 | TTACTTGC A GGGGACAG | 6149 |
| 161 | AGUCCCUC CUGAUGAG GCCGUUAGGC CGAA IUCCCCUG | 13213 | CAGGGGAC A GAGGGACT | 6150 |
| 169 | CCAGUCCA CUGAUGAG GCCGUUAGGC CGAA IUCCCUCU | 13214 | AGAGGGAC T TGGACTGG | 6151 |
| 175 | CCAAAGCC CUGAUGAG GCCGUUAGGC CGAA IUCCAAGU | 13215 | ACTTGGAC T GGCTTTGG | 6152 |
| 179 | UGGGCCAA CUGAUGAG GCCGUUAGGC CGAA ICCAGUCC | 13216 | GGACTGGC T TTGGCCCA | 6153 |
| 185 | GAUUAUUG CUGAUGAG GCCGUUAGGC CGAA ICCAAAGC | 13217 | GCTTTGGC C CAATAATC | 6154 |
| 186 | UGAUUAUU CUGAUGAG GCCGUUAGGC CGAA IGCCAAAG | 13218 | CTTTGGCC C AATAATCA | 6155 |
| 187 | CUGAUUAU CUGAUGAG GCCGUUAGGC CGAA IGGCCAAA | 13219 | TTTGGCCC A ATAATCAG | 6156 |
| 194 | UGCCACUC CUGAUGAG GCCGUUAGGC CGAA IAUUAUUG | 13220 | CAATAATC A GAGTGGCA | 6157 |
| 202 | UUGCUCAC CUGAUGAG GCCGUUAGGC CGAA ICCACUCU | 13221 | AGAGTGGC A GTGAGCAA | 6158 |
| 209 | CCACCCUU CUGAUGAG GCCGUUAGGC CGAA ICUCACUG | 13222 | CAGTGAGC A AAGGGTGG | 6159 |
| 225 | CUGCACUC CUGAUGAG GCCGUUAGGC CGAA IUCACCUC | 13223 | GAGGTGAC T GAGTGCAG | 6160 |
| 232 | GCCAUCGC CUGAUGAG GCCGUUAGGC CGAA ICACUCAG | 13224 | CTGAGTGC A GCGATGGC | 6161 |
| 241 | ACAGAAGA CUGAUGAG GCCGUUAGGC CGAA ICCAUCGC | 13225 | GCGATGGC C TCTTCTGT | 6162 |
| 242 | UACAGAAG CUGAUGAG GCCGUUAGGC CGAA IGCCAUCG | 13226 | CGATGGCC T CTTCTGTA | 6163 |
| 244 | CUUACAGA CUGAUGAG GCCGUUAGGC CGAA IAGGCCAU | 13227 | ATGGCCTC T TCTGTAAG | 6164 |
| 247 | UGUCUUAC CUGAUGAG GCCGUUAGGC CGAA IAAGAGGC | 13228 | GCCTCTTC T GTAAGACA | 6165 |
| 255 | AUUGUGAG CUGAUGAG GCCGUUAGGC CGAA IUCUUACA | 13229 | TGTAAGAC A CTCACAAT | 6166 |
| 257 | GAAUUGUG CUGAUGAG GCCGUUAGGC CGAA IUGUCUUA | 13230 | TAAGACAC T CACAATTC | 6167 |
| 259 | UGGAAUUG CUGAUGAG GCCGUUAGGC CGAA IAGUGUCU | 13231 | AGACACTC A CAATTCCA | 6168 |
| 261 | UUUGGAAU CUGAUGAG GCCGUUAGGC CGAA IUGAGUGU | 13232 | ACACTCAC A ATTCCAAA | 6169 |
| 266 | UCACUUUU CUGAUGAG GCCGUUAGGC CGAA IAAUUGUG | 13233 | CACAATTC C AAAAGTGA | 6170 |
| 267 | AUCACUUU CUGAUGAG GCCGUUAGGC CGAA IGAAUUGU | 13234 | ACAATTCC A AAAGTGAT | 6171 |
| 286 | GGCUCCAG CUGAUGAG GCCGUUAGGC CGAA IUCAUUUC | 13235 | GAAATGAC A CTGGAGCC | 6172 |
| 288 | UAGGCUCC CUGAUGAG GCCGUUAGGC CGAA IUGUCAUU | 13236 | AATGACAC T GGAGCCTA | 6173 |

266

| | | | | |
|---|---|---|---|---|
| 294 | CACUUGUA CUGAUGAG GCCGUUAGGC CGAA ICUCCAGU | 13237 | ACTGGAGC C TACAAGTG | 6174 |
| 295 | GCACUUGU CUGAUGAG GCCGUUAGGC CGAA IGCUCCAG | 13238 | CTGGAGCC T ACAAGTGC | 6175 |
| 298 | GAAGCACU CUGAUGAG GCCGUUAGGC CGAA IUAGGCUC | 13239 | GAGCCTAC A AGTGCTTC | 6176 |
| 304 | CCGGUAGA CUGAUGAG GCCGUUAGGC CGAA ICACUUGU | 13240 | ACAAGTGC T TCTACCGG | 6177 |
| 307 | UUCCCGGU CUGAUGAG GCCGUUAGGC CGAA IAAGCACU | 13241 | AGTGCTTC T ACCGGGAA | 6178 |
| 310 | AGUUUCCC CUGAUGAG GCCGUUAGGC CGAA IUAGAAGC | 13242 | GCTTCTAC C GGGAAACT | 6179 |
| 318 | GCCAAGUC CUGAUGAG GCCGUUAGGC CGAA IUUUCCCG | 13243 | CGGGAAAC T GACTTGGC | 6180 |
| 322 | CGAGGCCA CUGAUGAG GCCGUUAGGC CGAA IUCAGUUU | 13244 | AAACTGAC T TGGCCTCG | 6181 |
| 327 | AUGACCGA CUGAUGAG GCCGUUAGGC CGAA ICCAAGUC | 13245 | GACTTGGC C TCGGTCAT | 6182 |
| 328 | AAUGACCG CUGAUGAG GCCGUUAGGC CGAA IGCCAAGU | 13246 | ACTTGGCC T CGGTCATT | 6183 |
| 334 | GACAUAAA CUGAUGAG GCCGUUAGGC CGAA IACCGAGG | 13247 | CCTCGGTC A TTTATGTC | 6184 |
| 343 | UUGAACAU CUGAUGAG GCCGUUAGGC CGAA IACAUAAA | 13248 | TTTATGTC T ATGTTCAA | 6185 |
| 350 | UGUAAUCU CUGAUGAG GCCGUUAGGC CGAA IAACAUAG | 13249 | CTATGTTC A AGATTACA | 6186 |
| 358 | UGGAGAUC CUGAUGAG GCCGUUAGGC CGAA IUAAUCUU | 13250 | AAGATTAC A GATCTCCA | 6187 |
| 363 | AUAAAUGG CUGAUGAG GCCGUUAGGC CGAA IAUCUGUA | 13251 | TACAGATC T CCATTTAT | 6188 |
| 365 | CAAUAAAU CUGAUGAG GCCGUUAGGC CGAA IAGAUCUG | 13252 | CAGATCTC C ATTTATTG | 6189 |
| 366 | GCAAUAAA CUGAUGAG GCCGUUAGGC CGAA IGAGAUCU | 13253 | AGATCTCC A TTTATTGC | 6190 |
| 375 | CUAACAGA CUGAUGAG GCCGUUAGGC CGAA ICAAUAAA | 13254 | TTTATTGC T TCTGTTAG | 6191 |
| 378 | UCACUAAC CUGAUGAG GCCGUUAGGC CGAA IAAGCAAU | 13255 | ATTGCTTC T GTTAGTGA | 6192 |
| 388 | UCCAUGUU CUGAUGAG GCCGUUAGGC CGAA IUCACUAA | 13256 | TTAGTGAC C AACATGGA | 6193 |
| 389 | CUCCAUGU CUGAUGAG GCCGUUAGGC CGAA IGUCACUA | 13257 | TAGTGACC A ACATGGAG | 6194 |
| 392 | CGACUCCA CUGAUGAG GCCGUUAGGC CGAA IUUGGUCA | 13258 | TGACCAAC A TGGAGTCG | 6195 |
| 406 | CUCAGUAA CUGAUGAG GCCGUUAGGC CGAA IUACACGA | 13259 | TCGTGTAC A TTACTGAG | 6196 |
| 411 | UUGUUCUC CUGAUGAG GCCGUUAGGC CGAA IUAAUGUA | 13260 | TACATTAC T GAGAACAA | 6197 |
| 418 | UUUGUUUU CUGAUGAG GCCGUUAGGC CGAA IUUCUCAG | 13261 | CTGAGAAC A AAAACAAA | 6198 |
| 424 | CACAGUUU CUGAUGAG GCCGUUAGGC CGAA IUUUUUGU | 13262 | ACAAAAAC A AAACTGTG | 6199 |
| 429 | AUCACCAC CUGAUGAG GCCGUUAGGC CGAA IUUUUGUU | 13263 | AACAAAAC T GTGGTGAT | 6200 |
| 440 | CGAGACAU CUGAUGAG GCCGUUAGGC CGAA IAAUCACC | 13264 | GGTGATTC C ATGTCTCG | 6201 |
| 441 | CCGAGACA CUGAUGAG GCCGUUAGGC CGAA IGAAUCAC | 13265 | GTGATTCC A TGTCTCGG | 6202 |
| 446 | UGGACCCG CUGAUGAG GCCGUUAGGC CGAA IACAUGGA | 13266 | TCCATGTC T CGGGTCCA | 6203 |
| 453 | UUUGAAAU CUGAUGAG GCCGUUAGGC CGAA IACCCGAG | 13267 | CTCGGGTC C ATTTCAAA | 6204 |
| 454 | AUUUGAAA CUGAUGAG GCCGUUAGGC CGAA IGACCCGA | 13268 | TCGGGTCC A TTTCAAAT | 6205 |
| 459 | UUGAGAUU CUGAUGAG GCCGUUAGGC CGAA IAAAUGGA | 13269 | TCCATTTC A AATCTCAA | 6206 |

| | | | | |
|---|---|---|---|---|
| 464 | ACACGUUG CUGAUGAG GCCGUUAGGC CGAA IAUUUGAA | 13270 | TTCAAATC T CAACGTGT | 6207 |
| 466 | UGACACGU CUGAUGAG GCCGUUAGGC CGAA IAGAUUUG | 13271 | CAAATCTC A ACGTGTCA | 6208 |
| 474 | GCACAAAG CUGAUGAG GCCGUUAGGC CGAA IACACGUU | 13272 | AACGTGTC A CTTTGTGC | 6209 |
| 476 | UUGCACAA CUGAUGAG GCCGUUAGGC CGAA IUGACACG | 13273 | CGTGTCAC T TTGTGCAA | 6210 |
| 483 | GGGUAUCU CUGAUGAG GCCGUUAGGC CGAA ICACAAAG | 13274 | CTTTGTGC A AGATACCC | 6211 |
| 490 | CUUUUCUG CUGAUGAG GCCGUUAGGC CGAA IUAUCUUG | 13275 | CAAGATAC C CAGAAAAG | 6212 |
| 491 | UCUUUUCU CUGAUGAG GCCGUUAGGC CGAA IGUAUCUU | 13276 | AAGATACC C AGAAAAGA | 6213 |
| 492 | CUCUUUUC CUGAUGAG GCCGUUAGGC CGAA IGGUAUCU | 13277 | AGATACCC A GAAAAGAG | 6214 |
| 509 | UACCAUCA CUGAUGAG GCCGUUAGGC CGAA IAACAAAU | 13278 | ATTTGTTC C TGATGGTA | 6215 |
| 510 | UUACCAUC CUGAUGAG GCCGUUAGGC CGAA IGAACAAA | 13279 | TTTGTTCC T GATGGTAA | 6216 |
| 520 | GGAAAUUC CUGAUGAG GCCGUUAGGC CGAA IUUACCAU | 13280 | ATGGTAAC A GAATTTCC | 6217 |
| 528 | CUGUCCCA CUGAUGAG GCCGUUAGGC CGAA IAAAUUCU | 13281 | AGAATTTC C TGGGACAG | 6218 |
| 529 | GCUGUCCC CUGAUGAG GCCGUUAGGC CGAA IGAAAUUC | 13282 | GAATTTCC T GGGACAGC | 6219 |
| 535 | CUUCUUGC CUGAUGAG GCCGUUAGGC CGAA IUCCCAGG | 13283 | CCTGGGAC A GCAAGAAG | 6220 |
| 538 | GCCCUUCU CUGAUGAG GCCGUUAGGC CGAA ICUGUCCC | 13284 | GGGACAGC A AGAAGGGC | 6221 |
| 547 | AAUAGUAA CUGAUGAG GCCGUUAGGC CGAA ICCCUUCU | 13285 | AGAAGGGC T TTACTATT | 6222 |
| 552 | CUGGGAAU CUGAUGAG GCCGUUAGGC CGAA IUAAAGCC | 13286 | GGCTTTAC T ATTCCCAG | 6223 |
| 557 | UGUAGCUG CUGAUGAG GCCGUUAGGC CGAA IAAUAGUA | 13287 | TACTATTC C CAGCTACA | 6224 |
| 558 | AUGUAGCU CUGAUGAG GCCGUUAGGC CGAA IGAAUAGU | 13288 | ACTATTCC C AGCTACAT | 6225 |
| 559 | CAUGUAGC CUGAUGAG GCCGUUAGGC CGAA IGGAAUAG | 13289 | CTATTCCC A GCTACATG | 6226 |
| 562 | GAUCAUGU CUGAUGAG GCCGUUAGGC CGAA ICUGGGAA | 13290 | TTCCCAGC T ACATGATC | 6227 |
| 565 | GCUGAUCA CUGAUGAG GCCGUUAGGC CGAA IUAGCUGG | 13291 | CCAGCTAC A TGATCAGC | 6228 |
| 571 | AGCAUAGC CUGAUGAG GCCGUUAGGC CGAA IAUCAUGU | 13292 | ACATGATC A GCTATGCT | 6229 |
| 574 | GCCAGCAU CUGAUGAG GCCGUUAGGC CGAA ICUGAUCA | 13293 | TGATCAGC T ATGCTGGC | 6230 |
| 579 | ACCAUGCC CUGAUGAG GCCGUUAGGC CGAA ICAUAGCU | 13294 | AGCTATGC T GGCATGGT | 6231 |
| 583 | GAAGACCA CUGAUGAG GCCGUUAGGC CGAA ICCAGCAU | 13295 | ATGCTGGC A TGGTCTTC | 6232 |
| 589 | UUCACAGA CUGAUGAG GCCGUUAGGC CGAA IACCAUGC | 13296 | GCATGGTC T TCTGTGAA | 6233 |
| 592 | UGCUUCAC CUGAUGAG GCCGUUAGGC CGAA IAAGACCA | 13297 | TGGTCTTC T GTGAAGCA | 6234 |
| 600 | UUAAUUUU CUGAUGAG GCCGUUAGGC CGAA ICUUCACA | 13298 | TGTGAAGC A AAAATTAA | 6235 |
| 622 | AAUAGACU CUGAUGAG GCCGUUAGGC CGAA IUAACUUU | 13299 | AAAGTTAC C AGTCTATT | 6236 |
| 623 | UAAUAGAC CUGAUGAG GCCGUUAGGC CGAA IGUAACUU | 13300 | AAGTTACC A GTCTATTA | 6237 |
| 627 | UACAUAAU CUGAUGAG GCCGUUAGGC CGAA IACUGGUA | 13301 | TACCAGTC T ATTATGTA | 6238 |
| 637 | GACAACUA CUGAUGAG GCCGUUAGGC CGAA IUACAUAA | 13302 | TTATGTAC A TAGTTGTC | 6239 |

| | | | | |
|---|---|---|---|---|
| 677 | ACGGACUC CUGAUGAG GCCGUUAGGC CGAA IAACCACA | 13303 | TGTGGTTC T GAGTCCGT | 6240 |
| 683 | CAUGAGAC CUGAUGAG GCCGUUAGGC CGAA IACUCAGA | 13304 | TCTGAGTC C GTCTCATG | 6241 |
| 687 | AUUCCAUG CUGAUGAG GCCGUUAGGC CGAA IACGGACU | 13305 | AGTCCGTC T CATGGAAT | 6242 |
| 689 | CAAUUCCA CUGAUGAG GCCGUUAGGC CGAA IAGACGGA | 13306 | TCCGTCTC A TGGAATTG | 6243 |
| 701 | CAACAGAU CUGAUGAG GCCGUUAGGC CGAA IUUCAAUU | 13307 | AATTGAAC T ATCTGTTG | 6244 |
| 705 | UCUCCAAC CUGAUGAG GCCGUUAGGC CGAA IAUAGUUC | 13308 | GAACTATC T GTTGGAGA | 6245 |
| 719 | UUAAGACA CUGAUGAG GCCGUUAGGC CGAA ICUUUUCU | 13309 | AGAAAAGC T TGTCTTAA | 6246 |
| 724 | ACAAUUUA CUGAUGAG GCCGUUAGGC CGAA IACAAGCU | 13310 | AGCTTGTC T TAAATTGT | 6247 |
| 735 | GUUCUUGC CUGAUGAG GCCGUUAGGC CGAA IUACAAUU | 13311 | AATTGTAC A GCAAGAAC | 6248 |
| 738 | UCAGUUCU CUGAUGAG GCCGUUAGGC CGAA ICUGUACA | 13312 | TGTACAGC A AGAACTGA | 6249 |
| 744 | UUUAGUUC CUGAUGAG GCCGUUAGGC CGAA IUUCUUGC | 13313 | GCAAGAAC T GAACTAAA | 6250 |
| 749 | CCACAUUU CUGAUGAG GCCGUUAGGC CGAA IUUCAGUU | 13314 | AACTGAAC T AAATGTGG | 6251 |
| 766 | CCAGUUGA CUGAUGAG GCCGUUAGGC CGAA IUCAAUCC | 13315 | GGATTGAC T TCAACTGG | 6252 |
| 769 | UUCCCAGU CUGAUGAG GCCGUUAGGC CGAA IAAGUCAA | 13316 | TTGACTTC A ACTGGGAA | 6253 |
| 772 | GUAUUCCC CUGAUGAG GCCGUUAGGC CGAA IUUGAAGU | 13317 | ACTTCAAC T GGGAATAC | 6254 |
| 781 | CGAAGAAG CUGAUGAG GCCGUUAGGC CGAA IUAUUCCC | 13318 | GGGAATAC C CTTCTTCG | 6255 |
| 782 | UCGAAGAA CUGAUGAG GCCGUUAGGC CGAA IGUAUUCC | 13319 | GGAATACC C TTCTTCGA | 6256 |
| 783 | UUCGAAGA CUGAUGAG GCCGUUAGGC CGAA IGGUAUUC | 13320 | GAATACCC T TCTTCGAA | 6257 |
| 786 | UGCUUCGA CUGAUGAG GCCGUUAGGC CGAA IAAGGGUA | 13321 | TACCCTTC T TCGAAGCA | 6258 |
| 794 | UAUGCUGA CUGAUGAG GCCGUUAGGC CGAA ICUUCGAA | 13322 | TTCGAAGC A TCAGCATA | 6259 |
| 797 | UCUUAUGC CUGAUGAG GCCGUUAGGC CGAA IAUGCUUC | 13323 | GAAGCATC A GCATAAGA | 6260 |
| 800 | GUUUCUUA CUGAUGAG GCCGUUAGGC CGAA ICUGAUGC | 13324 | GCATCAGC A TAAGAAAC | 6261 |
| 809 | GGUUUACA CUGAUGAG GCCGUUAGGC CGAA IUUUCUUA | 13325 | TAAGAAAC T TGTAAACC | 6262 |
| 817 | UAGGUCUC CUGAUGAG GCCGUUAGGC CGAA IUUUACAA | 13326 | TTGTAAAC C GAGACCTA | 6263 |
| 823 | GGUUUUUA CUGAUGAG GCCGUUAGGC CGAA IUCUCGGU | 13327 | ACCGAGAC C TAAAAACC | 6264 |
| 824 | GGGUUUUU CUGAUGAG GCCGUUAGGC CGAA IGUCUCGG | 13328 | CCGAGACC T AAAAACCC | 6265 |
| 831 | CCAGACUG CUGAUGAG GCCGUUAGGC CGAA IUUUUUAG | 13329 | CTAAAAAC C CAGTCTGG | 6266 |
| 832 | CCCAGACU CUGAUGAG GCCGUUAGGC CGAA IGUUUUUA | 13330 | TAAAAACC C AGTCTGGG | 6267 |
| 833 | UCCCAGAC CUGAUGAG GCCGUUAGGC CGAA IGGUUUUU | 13331 | AAAAACCC A GTCTGGGA | 6268 |
| 837 | UCACUCCC CUGAUGAG GCCGUUAGGC CGAA IACUGGGU | 13332 | ACCCAGTC T GGGAGTGA | 6269 |
| 865 | AGUUAAGG CUGAUGAG GCCGUUAGGC CGAA ICUCAAAA | 13333 | TTTTGAGC A CCTTAACT | 6270 |
| 867 | AUAGUUAA CUGAUGAG GCCGUUAGGC CGAA IUGCUCAA | 13334 | TTGAGCAC C TTAACTAT | 6271 |
| 868 | UAUAGUUA CUGAUGAG GCCGUUAGGC CGAA IGUGCUCA | 13335 | TGAGCACC T TAACTATA | 6272 |

| | | | | |
|---|---|---|---|---|
| 873 | CCAUCUAU CUGAUGAG GCCGUUAGGC CGAA IUUAAGGU | 13336 | ACCTTAAC T ATAGATGG | 6273 |
| 888 | UCACUCCG CUGAUGAG GCCGUUAGGC CGAA IUUACACC | 13337 | GGTGTAAC C CGGAGTGA | 6274 |
| 889 | GUCACUCC CUGAUGAG GCCGUUAGGC CGAA IGUUACAC | 13338 | GTGTAACC C GGAGTGAC | 6275 |
| 898 | CAAUCCUU CUGAUGAG GCCGUUAGGC CGAA IUCACUCC | 13339 | GGAGTGAC C AAGGATTG | 6276 |
| 899 | ACAAUCCU CUGAUGAG GCCGUUAGGC CGAA IGUCACUC | 13340 | GAGTGACC A AGGATTGT | 6277 |
| 910 | UGCACAGG CUGAUGAG GCCGUUAGGC CGAA IUACAAUC | 13341 | GATTGTAC A CCTGTGCA | 6278 |
| 912 | GCUGCACA CUGAUGAG GCCGUUAGGC CGAA IUGUACAA | 13342 | TTGTACAC C TGTGCAGC | 6279 |
| 913 | UGCUGCAC CUGAUGAG GCCGUUAGGC CGAA IGUGUACA | 13343 | TGTACACC T GTGCAGCA | 6280 |
| 918 | CUGGAUGC CUGAUGAG GCCGUUAGGC CGAA ICACAGGU | 13344 | ACCTGTGC A GCATCCAG | 6281 |
| 921 | CCACUGGA CUGAUGAG GCCGUUAGGC CGAA ICUGCACA | 13345 | TGTGCAGC A TCCAGTGG | 6282 |
| 924 | AGCCCACU CUGAUGAG GCCGUUAGGC CGAA IAUGCUGC | 13346 | GCAGCATC C AGTGGGCT | 6283 |
| 925 | CAGCCCAC CUGAUGAG GCCGUUAGGC CGAA IGAUGCUG | 13347 | CAGCATCC A GTGGGCTG | 6284 |
| 932 | UGGUCAUC CUGAUGAG GCCGUUAGGC CGAA ICCCACUG | 13348 | CAGTGGGC T GATGACCA | 6285 |
| 939 | UUCUUCUU CUGAUGAG GCCGUUAGGC CGAA IUCAUCAG | 13349 | CTGATGAC C AAGAAGAA | 6286 |
| 940 | GUUCUUCU CUGAUGAG GCCGUUAGGC CGAA IGUCAUCA | 13350 | TGATGACC A AGAAGAAC | 6287 |
| 949 | AAAUGUGC CUGAUGAG GCCGUUAGGC CGAA IUUCUUCU | 13351 | AGAAGAAC A GCACATTT | 6288 |
| 952 | GACAAAUG CUGAUGAG GCCGUUAGGC CGAA ICUGUUCU | 13352 | AGAACAGC A CATTTGTC | 6289 |
| 954 | CUGACAAA CUGAUGAG GCCGUUAGGC CGAA IUGCUGUU | 13353 | AACAGCAC A TTTGTCAG | 6290 |
| 961 | AUGGACCC CUGAUGAG GCCGUUAGGC CGAA IACAAAUG | 13354 | CATTTGTC A GGGTCCAT | 6291 |
| 967 | UUUUUCAU CUGAUGAG GCCGUUAGGC CGAA IACCCUGA | 13355 | TCAGGGTC C ATGAAAAA | 6292 |
| 968 | GUUUUUCA CUGAUGAG GCCGUUAGGC CGAA IGACCCUG | 13356 | CAGGGTCC A TGAAAAAC | 6293 |
| 977 | CAACAAAA CUGAUGAG GCCGUUAGGC CGAA IUUUUUCA | 13357 | TGAAAAAC C TTTTGTTG | 6294 |
| 978 | GCAACAAA CUGAUGAG GCCGUUAGGC CGAA IGUUUUUC | 13358 | GAAAAACC T TTTGTTGC | 6295 |
| 987 | CUUCCAAA CUGAUGAG GCCGUUAGGC CGAA ICAACAAA | 13359 | TTTGTTGC T TTTGGAAG | 6296 |
| 1000 | AGAUUCCA CUGAUGAG GCCGUUAGGC CGAA ICCACUUC | 13360 | GAAGTGGC A TGGAATCT | 6297 |
| 1008 | UCCACCAG CUGAUGAG GCCGUUAGGC CGAA IAUUCCAU | 13361 | ATGGAATC T CTGGTGGA | 6298 |
| 1010 | CUUCCACC CUGAUGAG GCCGUUAGGC CGAA IAGAUUCC | 13362 | GGAATCTC T GGTGGAAG | 6299 |
| 1020 | CCCACCGU CUGAUGAG GCCGUUAGGC CGAA ICUUCCAC | 13363 | GTGGAAGC C ACGGTGGG | 6300 |
| 1021 | CCCCACCG CUGAUGAG GCCGUUAGGC CGAA IGCUUCCA | 13364 | TGGAAGCC A CGGTGGGG | 6301 |
| 1039 | AGGGAUUC CUGAUGAG GCCGUUAGGC CGAA IACACGCU | 13365 | AGCGTGTC A GAATCCCT | 6302 |
| 1045 | CUUCGCAG CUGAUGAG GCCGUUAGGC CGAA IAUUCUGA | 13366 | TCAGAATC C CTGCGAAG | 6303 |
| 1046 | ACUUCGCA CUGAUGAG GCCGUUAGGC CGAA IGAUUCUG | 13367 | CAGAATCC C TGCGAAGT | 6304 |
| 1047 | UACUUCGC CUGAUGAG GCCGUUAGGC CGAA IGGAUUCU | 13368 | AGAATCCC T GCGAAGTA | 6305 |

270

| | | | | |
|---|---|---|---|---|
| 1057 | GUAACCAA CUGAUGAG GCCGUUAGGC CGAA IUACUUCG | 13369 | CGAAGTAC C TTGGTTAC | 6306 |
| 1058 | GGUAACCA CUGAUGAG GCCGUUAGGC CGAA IGUACUUC | 13370 | GAAGTACC T TGGTTACC | 6307 |
| 1066 | UGGGGGUG CUGAUGAG GCCGUUAGGC CGAA IUAACCAA | 13371 | TTGGTTAC C CACCCCCA | 6308 |
| 1067 | CUGGGGGU CUGAUGAG GCCGUUAGGC CGAA IGUAACCA | 13372 | TGGTTACC C ACCCCCAG | 6309 |
| 1068 | UCUGGGGG CUGAUGAG GCCGUUAGGC CGAA IGGUAACC | 13373 | GGTTACCC A CCCCCAGA | 6310 |
| 1070 | UUUCUGGG CUGAUGAG GCCGUUAGGC CGAA IUGGGUAA | 13374 | TTACCCAC C CCCAGAAA | 6311 |
| 1071 | AUUUCUGG CUGAUGAG GCCGUUAGGC CGAA IGUGGGUA | 13375 | TACCCACC C CCAGAAAT | 6312 |
| 1072 | UAUUUCUG CUGAUGAG GCCGUUAGGC CGAA IGGUGGGU | 13376 | ACCCACCC C CAGAAATA | 6313 |
| 1073 | UUAUUUCU CUGAUGAG GCCGUUAGGC CGAA IGGGUGGG | 13377 | CCCACCCC C AGAAATAA | 6314 |
| 1074 | UUUAUUUC CUGAUGAG GCCGUUAGGC CGAA IGGGGUGG | 13378 | CCACCCCC A GAAATAAA | 6315 |
| 1103 | ACUCAAGG CUGAUGAG GCCGUUAGGC CGAA IUAUUCCA | 13379 | TGGAATAC C CCTTGAGT | 6316 |
| 1104 | GACUCAAG CUGAUGAG GCCGUUAGGC CGAA IGUAUUCC | 13380 | GGAATACC C CTTGAGTC | 6317 |
| 1105 | GGACUCAA CUGAUGAG GCCGUUAGGC CGAA IGGUAUUC | 13381 | GAATACCC C TTGAGTCC | 6318 |
| 1106 | UGGACUCA CUGAUGAG GCCGUUAGGC CGAA IGGGUAUU | 13382 | AATACCCC T TGAGTCCA | 6319 |
| 1113 | GUGUGAUU CUGAUGAG GCCGUUAGGC CGAA IACUCAAG | 13383 | CTTGAGTC C AATCACAC | 6320 |
| 1114 | UGUGUGAU CUGAUGAG GCCGUUAGGC CGAA IGACUCAA | 13384 | TTGAGTCC A ATCACACA | 6321 |
| 1118 | UAAUUGUG CUGAUGAG GCCGUUAGGC CGAA IAUUGGAC | 13385 | GTCCAATC A CACAATTA | 6322 |
| 1120 | UUUAAUUG CUGAUGAG GCCGUUAGGC CGAA IUGAUUGG | 13386 | CCAATCAC A CAATTAAA | 6323 |
| 1122 | GCUUUAAU CUGAUGAG GCCGUUAGGC CGAA IUGUGAUU | 13387 | AATCACAC A ATTAAAGC | 6324 |
| 1136 | UCAGUACA CUGAUGAG GCCGUUAGGC CGAA ICCCCGCU | 13388 | AGCGGGGC A TGTACTGA | 6325 |
| 1142 | UAAUCGUC CUGAUGAG GCCGUUAGGC CGAA IUACAUGC | 13389 | GCATGTAC T GACGATTA | 6326 |
| 1171 | AUUUCCUG CUGAUGAG GCCGUUAGGC CGAA IUCUCUUU | 13390 | AAAGAGAC A CAGGAAAT | 6327 |
| 1173 | UAAUUUCC CUGAUGAG GCCGUUAGGC CGAA IUGUCUCU | 13391 | AGAGACAC A GGAAATTA | 6328 |
| 1183 | GAUGACAG CUGAUGAG GCCGUUAGGC CGAA IUAAUUUC | 13392 | GAAATTAC A CTGTCATC | 6329 |
| 1185 | AGGAUGAC CUGAUGAG GCCGUUAGGC CGAA IUGUAAUU | 13393 | AATTACAC T GTCATCCT | 6330 |
| 1189 | GGUAAGGA CUGAUGAG GCCGUUAGGC CGAA IACAGUGU | 13394 | ACACTGTC A TCCTTACC | 6331 |
| 1192 | AUUGGUAA CUGAUGAG GCCGUUAGGC CGAA IAUGACAG | 13395 | CTGTCATC C TTACCAAT | 6332 |
| 1193 | GAUUGGUA CUGAUGAG GCCGUUAGGC CGAA IGAUGACA | 13396 | TGTCATCC T TACCAATC | 6333 |
| 1197 | AUGGGAUU CUGAUGAG GCCGUUAGGC CGAA IUAAGGAU | 13397 | ATCCTTAC C AATCCCAT | 6334 |
| 1198 | AAUGGGAU CUGAUGAG GCCGUUAGGC CGAA IGUAAGGA | 13398 | TCCTTACC A ATCCCATT | 6335 |
| 1202 | UUGAAAUG CUGAUGAG GCCGUUAGGC CGAA IAUUGGUA | 13399 | TACCAATC C CATTTCAA | 6336 |
| 1203 | UUUGAAAU CUGAUGAG GCCGUUAGGC CGAA IGAUUGGU | 13400 | ACCAATCC C ATTTCAAA | 6337 |
| 1204 | CUUUGAAA CUGAUGAG GCCGUUAGGC CGAA IGGAUUGG | 13401 | CCAATCCC A TTTCAAAG | 6338 |

| | | | | |
|---|---|---|---|---|
| 1209 | UUCUCCUU CUGAUGAG GCCGUUAGGC CGAA IAAAUGGG | 13402 | CCCATTTC A AAGGAGAA | 6339 |
| 1220 | CAUGGCUC CUGAUGAG GCCGUUAGGC CGAA ICUUCUCC | 13403 | GGAGAAGC A GAGCCATG | 6340 |
| 1225 | GACCACAU CUGAUGAG GCCGUUAGGC CGAA ICUCUGCU | 13404 | AGCAGAGC C ATGTGGTC | 6341 |
| 1226 | AGACCACA CUGAUGAG GCCGUUAGGC CGAA IGCUCUGC | 13405 | GCAGAGCC A TGTGGTCT | 6342 |
| 1234 | AACCAGAG CUGAUGAG GCCGUUAGGC CGAA IACCACAU | 13406 | ATGTGGTC T CTCTGGTT | 6343 |
| 1236 | ACAACCAG CUGAUGAG GCCGUUAGGC CGAA IAGACCAC | 13407 | GTGGTCTC T CTGGTTGT | 6344 |
| 1238 | ACACAACC CUGAUGAG GCCGUUAGGC CGAA IAGAGACC | 13408 | GGTCTCTC T GGTTGTGT | 6345 |
| 1252 | CUGGGGUG CUGAUGAG GCCGUUAGGC CGAA IACAUACA | 13409 | TGTATGTC C CACCCCAG | 6346 |
| 1253 | UCUGGGGU CUGAUGAG GCCGUUAGGC CGAA IGACAUAC | 13410 | GTATGTCC C ACCCCAGA | 6347 |
| 1254 | AUCUGGGG CUGAUGAG GCCGUUAGGC CGAA IGGACAUA | 13411 | TATGTCCC A CCCCAGAT | 6348 |
| 1256 | CAAUCUGG CUGAUGAG GCCGUUAGGC CGAA IUGGGACA | 13412 | TGTCCCAC C CCAGATTG | 6349 |
| 1257 | CCAAUCUG CUGAUGAG GCCGUUAGGC CGAA IGUGGGAC | 13413 | GTCCCACC C CAGATTGG | 6350 |
| 1258 | ACCAAUCU CUGAUGAG GCCGUUAGGC CGAA IGGUGGGA | 13414 | TCCCACCC C AGATTGGT | 6351 |
| 1259 | CACCAAUC CUGAUGAG GCCGUUAGGC CGAA IGGGUGGG | 13415 | CCCACCCC A GATTGGTG | 6352 |
| 1275 | GAGAUUAG CUGAUGAG GCCGUUAGGC CGAA IAUUUCUC | 13416 | GAGAAATC T CTAATCTC | 6353 |
| 1277 | GAGAGAUU CUGAUGAG GCCGUUAGGC CGAA IAGAUUUC | 13417 | GAAATCTC T AATCTCTC | 6354 |
| 1282 | CACAGGAG CUGAUGAG GCCGUUAGGC CGAA IAUUAGAG | 13418 | CTCTAATC T CTCCTGTG | 6355 |
| 1284 | UCCACAGG CUGAUGAG GCCGUUAGGC CGAA IAGAUUAG | 13419 | CTAATCTC T CCTGTGGA | 6356 |
| 1286 | AAUCCACA CUGAUGAG GCCGUUAGGC CGAA IAGAGAUU | 13420 | AATCTCTC C TGTGGATT | 6357 |
| 1287 | GAAUCCAC CUGAUGAG GCCGUUAGGC CGAA IGAGAGAU | 13421 | ATCTCTCC T GTGGATTC | 6358 |
| 1296 | UACUGGUA CUGAUGAG GCCGUUAGGC CGAA IAAUCCAC | 13422 | GTGGATTC C TACCAGTA | 6359 |
| 1297 | GUACUGGU CUGAUGAG GCCGUUAGGC CGAA IGAAUCCA | 13423 | TGGATTCC T ACCAGTAC | 6360 |
| 1300 | GCCGUACU CUGAUGAG GCCGUUAGGC CGAA IUAGGAAU | 13424 | ATTCCTAC C AGTACGGC | 6361 |
| 1301 | UGCCGUAC CUGAUGAG GCCGUUAGGC CGAA IGUAGGAA | 13425 | TTCCTACC A GTACGGCA | 6362 |
| 1309 | UUGAGUGG CUGAUGAG GCCGUUAGGC CGAA ICCGUACU | 13426 | AGTACGGC A CCACTCAA | 6363 |
| 1311 | GUUUGAGU CUGAUGAG GCCGUUAGGC CGAA IUGCCGUA | 13427 | TACGGCAC C ACTCAAAC | 6364 |
| 1312 | CGUUUGAG CUGAUGAG GCCGUUAGGC CGAA IGUGCCGU | 13428 | ACGGCACC A CTCAAACG | 6365 |
| 1314 | AGCGUUUG CUGAUGAG GCCGUUAGGC CGAA IUGGUGCC | 13429 | GGCACCAC T CAAACGCT | 6366 |
| 1316 | UCAGCGUU CUGAUGAG GCCGUUAGGC CGAA IAGUGGUG | 13430 | CACCACTC A AACGCTGA | 6367 |
| 1322 | UACAUGUC CUGAUGAG GCCGUUAGGC CGAA ICGUUUGA | 13431 | TCAAACGC T GACATGTA | 6368 |
| 1326 | ACCGUACA CUGAUGAG GCCGUUAGGC CGAA IUCAGCGU | 13432 | ACGCTGAC A TGTACGGT | 6369 |
| 1336 | AAUGGCAU CUGAUGAG GCCGUUAGGC CGAA IACCGUAC | 13433 | GTACGGTC T ATGCCATT | 6370 |
| 1341 | GGAGGAAU CUGAUGAG GCCGUUAGGC CGAA ICAUAGAC | 13434 | GTCTATGC C ATTCCTCC | 6371 |

| | | | | |
|---|---|---|---|---|
| 1342 | GGGAGGAA CUGAUGAG GCCGUUAGGC CGAA IGCAUAGA | 13435 | TCTATGCC A TTCCTCCC | 6372 |
| 1346 | GCGGGGGA CUGAUGAG GCCGUUAGGC CGAA IAAUGGCA | 13436 | TGCCATTC C TCCCCCGC | 6373 |
| 1347 | UGCGGGGG CUGAUGAG GCCGUUAGGC CGAA IGAAUGGC | 13437 | GCCATTCC T CCCCCGCA | 6374 |
| 1349 | GAUGCGGG CUGAUGAG GCCGUUAGGC CGAA IAGGAAUG | 13438 | CATTCCTC C CCCGCATC | 6375 |
| 1350 | UGAUGCGG CUGAUGAG GCCGUUAGGC CGAA IGAGGAAU | 13439 | ATTCCTCC C CCGCATCA | 6376 |
| 1351 | GUGAUGCG CUGAUGAG GCCGUUAGGC CGAA IGGAGGAA | 13440 | TTCCTCCC C CGCATCAC | 6377 |
| 1352 | UGUGAUGC CUGAUGAG GCCGUUAGGC CGAA IGGGAGGA | 13441 | TCCTCCCC C GCATCACA | 6378 |
| 1355 | GGAUGUGA CUGAUGAG GCCGUUAGGC CGAA ICGGGGGA | 13442 | TCCCCCGC A TCACATCC | 6379 |
| 1358 | AGUGGAUG CUGAUGAG GCCGUUAGGC CGAA IAUGCGGG | 13443 | CCCGCATC A CATCCACT | 6380 |
| 1360 | CCAGUGGA CUGAUGAG GCCGUUAGGC CGAA IUGAUGCG | 13444 | CGCATCAC A TCCACTGG | 6381 |
| 1363 | AUACCAGU CUGAUGAG GCCGUUAGGC CGAA IAUGUGAU | 13445 | ATCACATC C ACTGGTAT | 6382 |
| 1364 | AAUACCAG CUGAUGAG GCCGUUAGGC CGAA IGAUGUGA | 13446 | TCACATCC A CTGGTATT | 6383 |
| 1366 | CCAAUACC CUGAUGAG GCCGUUAGGC CGAA IUGGAUGU | 13447 | ACATCCAC T GGTATTGG | 6384 |
| 1376 | CCUCCAAC CUGAUGAG GCCGUUAGGC CGAA ICCAAUAC | 13448 | GTATTGGC A GTTGGAGG | 6385 |
| 1395 | GGCUCGUU CUGAUGAG GCCGUUAGGC CGAA ICGCACUC | 13449 | GAGTGCGC C AACGAGCC | 6386 |
| 1396 | GGGCUCGU CUGAUGAG GCCGUUAGGC CGAA IGCGCACU | 13450 | AGTGCGCC A ACGAGCCC | 6387 |
| 1403 | CUUGGCUG CUGAUGAG GCCGUUAGGC CGAA ICUCGUUG | 13451 | CAACGAGC C CAGCCAAG | 6388 |
| 1404 | GCUUGGCU CUGAUGAG GCCGUUAGGC CGAA IGCUCGUU | 13452 | AACGAGCC C AGCCAAGC | 6389 |
| 1405 | AGCUUGGC CUGAUGAG GCCGUUAGGC CGAA IGGCUCGU | 13453 | ACGAGCCC A GCCAAGCT | 6390 |
| 1408 | GACAGCUU CUGAUGAG GCCGUUAGGC CGAA ICUGGGCU | 13454 | AGCCCAGC C AAGCTGTC | 6391 |
| 1409 | AGACAGCU CUGAUGAG GCCGUUAGGC CGAA IGCUGGGC | 13455 | GCCCAGCC A AGCTGTCT | 6392 |
| 1413 | ACUGAGAC CUGAUGAG GCCGUUAGGC CGAA ICUUGGCU | 13456 | AGCCAAGC T GTCTCAGT | 6393 |
| 1417 | UGUCACUG CUGAUGAG GCCGUUAGGC CGAA IACAGCUU | 13457 | AAGCTGTC T CAGTGACA | 6394 |
| 1419 | UUUGUCAC CUGAUGAG GCCGUUAGGC CGAA IAGACAGC | 13458 | GCTGTCTC A GTGACAAA | 6395 |
| 1425 | UAUGGGUU CUGAUGAG GCCGUUAGGC CGAA IUCACUGA | 13459 | TCAGTGAC A AACCCATA | 6396 |
| 1429 | AGGGUAUG CUGAUGAG GCCGUUAGGC CGAA IUUUGUCA | 13460 | TGACAAAC C CATACCCT | 6397 |
| 1430 | AAGGGUAU CUGAUGAG GCCGUUAGGC CGAA IGUUUGUC | 13461 | GACAAACC C ATACCCTT | 6398 |
| 1431 | CAAGGGUA CUGAUGAG GCCGUUAGGC CGAA IGGUUUGU | 13462 | ACAAACCC A TACCCTTG | 6399 |
| 1435 | UUCACAAG CUGAUGAG GCCGUUAGGC CGAA IUAUGGGU | 13463 | ACCCATAC C CTTGTGAA | 6400 |
| 1436 | CUUCACAA CUGAUGAG GCCGUUAGGC CGAA IGUAUGGG | 13464 | CCCATACC C TTGTGAAG | 6401 |
| 1437 | UCUUCACA CUGAUGAG GCCGUUAGGC CGAA IGGUAUGG | 13465 | CCATACCC T TGTGAAGA | 6402 |
| 1465 | UCCCUGGA CUGAUGAG GCCGUUAGGC CGAA IUCCUCCA | 13466 | TGGAGGAC T TCCAGGGA | 6403 |
| 1468 | UCCUCCCU CUGAUGAG GCCGUUAGGC CGAA IAAGUCCU | 13467 | AGGACTTC C AGGGAGGA | 6404 |

| | | | | |
|---|---|---|---|---|
| 1469 | UUCCUCCC CUGAUGAG GCCGUUAGGC CGAA IGAAGUCC | 13468 | GGACTTCC A GGGAGGAA | 6405 |
| 1502 | GAGCAAAU CUGAUGAG GCCGUUAGGC CGAA IAUUUUUA | 13469 | TAAAAATC A ATTTGCTC | 6406 |
| 1509 | UCAAUUAG CUGAUGAG GCCGUUAGGC CGAA ICAAAUUG | 13470 | CAATTTGC T CTAATTGA | 6407 |
| 1511 | CUUCAAUU CUGAUGAG GCCGUUAGGC CGAA IAGCAAAU | 13471 | ATTTGCTC T AATTGAAG | 6408 |
| 1528 | UACAGUUU CUGAUGAG GCCGUUAGGC CGAA IUUUUUUC | 13472 | GAAAAAAC A AAACTGTA | 6409 |
| 1533 | GUACUUAC CUGAUGAG GCCGUUAGGC CGAA IUUUUGUU | 13473 | AACAAAAC T GTAAGTAC | 6410 |
| 1542 | AUAACAAG CUGAUGAG GCCGUUAGGC CGAA IUACUUAC | 13474 | GTAAGTAC C CTTGTTAT | 6411 |
| 1543 | GAUAACAA CUGAUGAG GCCGUUAGGC CGAA IGUACUUA | 13475 | TAAGTACC C TTGTTATC | 6412 |
| 1544 | GGAUAACA CUGAUGAG GCCGUUAGGC CGAA IGGUACUU | 13476 | AAGTACCC T TGTTATCC | 6413 |
| 1552 | UGCCGCUU CUGAUGAG GCCGUUAGGC CGAA IAUAACAA | 13477 | TTGTTATC C AAGCGGCA | 6414 |
| 1553 | UUGCCGCU CUGAUGAG GCCGUUAGGC CGAA IGAUAACA | 13478 | TGTTATCC A AGCGGCAA | 6415 |
| 1560 | GACACAUU CUGAUGAG GCCGUUAGGC CGAA ICCGCUUG | 13479 | CAAGCGGC A AATGTGTC | 6416 |
| 1569 | UACAAAGC CUGAUGAG GCCGUUAGGC CGAA IACACAUU | 13480 | AATGTGTC A GCTTTGTA | 6417 |
| 1572 | UUGUACAA CUGAUGAG GCCGUUAGGC CGAA ICUGACAC | 13481 | GTGTCAGC T TTGTACAA | 6418 |
| 1579 | UUCACAUU CUGAUGAG GCCGUUAGGC CGAA IUACAAAG | 13482 | CTTTGTAC A AATGTGAA | 6419 |
| 1594 | GACUUUGU CUGAUGAG GCCGUUAGGC CGAA IACCGCUU | 13483 | AAGCGGTC A ACAAAGTC | 6420 |
| 1597 | CCCGACUU CUGAUGAG GCCGUUAGGC CGAA IUUGACCG | 13484 | CGGTCAAC A AAGTCGGG | 6421 |
| 1624 | GUGGAAGG CUGAUGAG GCCGUUAGGC CGAA IAUCACCC | 13485 | GGGTGATC T CCTTCCAC | 6422 |
| 1626 | ACGUGGAA CUGAUGAG GCCGUUAGGC CGAA IAGAUCAC | 13486 | GTGATCTC C TTCCACGT | 6423 |
| 1627 | CACGUGGA CUGAUGAG GCCGUUAGGC CGAA IGAGAUCA | 13487 | TGATCTCC T TCCACGTG | 6424 |
| 1630 | GGUCACGU CUGAUGAG GCCGUUAGGC CGAA IAAGGAGA | 13488 | TCTCCTTC C ACGTGACC | 6425 |
| 1631 | UGGUCACG CUGAUGAG GCCGUUAGGC CGAA IGAAGGAG | 13489 | CTCCTTCC A CGTGACCA | 6426 |
| 1638 | GGACCCCU CUGAUGAG GCCGUUAGGC CGAA IUCACGUG | 13490 | CACGTGAC C AGGGGTCC | 6427 |
| 1639 | AGGACCCC CUGAUGAG GCCGUUAGGC CGAA IGUCACGU | 13491 | ACGTGACC A GGGGTCCT | 6428 |
| 1646 | UAAUUUCA CUGAUGAG GCCGUUAGGC CGAA IACCCCUG | 13492 | CAGGGGTC C TGAAATTA | 6429 |
| 1647 | GUAAUUUC CUGAUGAG GCCGUUAGGC CGAA IGACCCCU | 13493 | AGGGGTCC T GAAATTAC | 6430 |
| 1656 | GGUUGCAA CUGAUGAG GCCGUUAGGC CGAA IUAAUUUC | 13494 | GAAATTAC T TTGCAACC | 6431 |
| 1661 | UGUCAGGU CUGAUGAG GCCGUUAGGC CGAA ICAAAGUA | 13495 | TACTTTGC A ACCTGACA | 6432 |
| 1664 | GCAUGUCA CUGAUGAG GCCGUUAGGC CGAA IUUGCAAA | 13496 | TTTGCAAC C TGACATGC | 6433 |
| 1665 | UGCAUGUC CUGAUGAG GCCGUUAGGC CGAA IGUUGCAA | 13497 | TTGCAACC T GACATGCA | 6434 |
| 1669 | GGGCUGCA CUGAUGAG GCCGUUAGGC CGAA IUCAGGUU | 13498 | AACCTGAC A TGCAGCCC | 6435 |
| 1673 | CAGUGGGC CUGAUGAG GCCGUUAGGC CGAA ICAUGUCA | 13499 | TGACATGC A GCCCACTG | 6436 |
| 1676 | GCUCAGUG CUGAUGAG GCCGUUAGGC CGAA ICUGCAUG | 13500 | CATGCAGC C CACTGAGC | 6437 |

| | | | | |
|---|---|---|---|---|
| 1677 | UGCUCAGU CUGAUGAG GCCGUUAGGC CGAA IGCUGCAU | 13501 | ATGCAGCC C ACTGAGCA | 6438 |
| 1678 | CUGCUCAG CUGAUGAG GCCGUUAGGC CGAA IGGCUGCA | 13502 | TGCAGCCC A CTGAGCAG | 6439 |
| 1680 | UCCUGCUC CUGAUGAG GCCGUUAGGC CGAA IUGGGCUG | 13503 | CAGCCCAC T GAGCAGGA | 6440 |
| 1685 | CGCUCUCC CUGAUGAG GCCGUUAGGC CGAA ICUCAGUG | 13504 | CACTGAGC A GGAGAGCG | 6441 |
| 1698 | CACCACAA CUGAUGAG GCCGUUAGGC CGAA IACACGCU | 13505 | AGCGTGTC T TTGTGGTG | 6442 |
| 1708 | GUCUGCAG CUGAUGAG GCCGUUAGGC CGAA ICACCACA | 13506 | TGTGGTGC A CTGCAGAC | 6443 |
| 1710 | CUGUCUGC CUGAUGAG GCCGUUAGGC CGAA IUGCACCA | 13507 | TGGTGCAC T GCAGACAG | 6444 |
| 1713 | GAUCUGUC CUGAUGAG GCCGUUAGGC CGAA ICAGUGCA | 13508 | TGCACTGC A GACAGATC | 6445 |
| 1717 | CGUAGAUC CUGAUGAG GCCGUUAGGC CGAA IUCUGCAG | 13509 | CTGCAGAC A GATCTACG | 6446 |
| 1722 | UCAAACGU CUGAUGAG GCCGUUAGGC CGAA IAUCUGUC | 13510 | GACAGATC T ACGTTTGA | 6447 |
| 1735 | CCAUGUGA CUGAUGAG GCCGUUAGGC CGAA IUUCUCAA | 13511 | TTGAGAAC C TCACATGG | 6448 |
| 1736 | ACCAUGUG CUGAUGAG GCCGUUAGGC CGAA IGUUCUCA | 13512 | TGAGAACC T CACATGGT | 6449 |
| 1738 | GUACCAUG CUGAUGAG GCCGUUAGGC CGAA IAGGUUCU | 13513 | AGAACCTC A CATGGTAC | 6450 |
| 1740 | UUGUACCA CUGAUGAG GCCGUUAGGC CGAA IUGAGGUU | 13514 | AACCTCAC A TGGTACAA | 6451 |
| 1747 | GCCAAGCU CUGAUGAG GCCGUUAGGC CGAA IUACCAUG | 13515 | CATGGTAC A AGCTTGGC | 6452 |
| 1751 | GUGGGCCA CUGAUGAG GCCGUUAGGC CGAA ICUUGUAC | 13516 | GTACAAGC T TGGCCCAC | 6453 |
| 1756 | AGGCUGUG CUGAUGAG GCCGUUAGGC CGAA ICCAAGCU | 13517 | AGCTTGGC C CACAGCCT | 6454 |
| 1757 | GAGGCUGU CUGAUGAG GCCGUUAGGC CGAA IGCCAAGC | 13518 | GCTTGGCC C ACAGCCTC | 6455 |
| 1758 | AGAGGCUG CUGAUGAG GCCGUUAGGC CGAA IGGCCAAG | 13519 | CTTGGCCC A CAGCCTCT | 6456 |
| 1760 | GCAGAGGC CUGAUGAG GCCGUUAGGC CGAA IUGGGCCA | 13520 | TGGCCCAC A GCCTCTGC | 6457 |
| 1763 | UUGGCAGA CUGAUGAG GCCGUUAGGC CGAA ICUGUGGG | 13521 | CCCACAGC C TCTGCCAA | 6458 |
| 1764 | AUUGGCAG CUGAUGAG GCCGUUAGGC CGAA IGCUGUGG | 13522 | CCACAGCC T CTGCCAAT | 6459 |
| 1766 | GGAUUGGC CUGAUGAG GCCGUUAGGC CGAA IAGGCUGU | 13523 | ACAGCCTC T GCCAATCC | 6460 |
| 1769 | CAUGGAUU CUGAUGAG GCCGUUAGGC CGAA ICAGAGGC | 13524 | GCCTCTGC C AATCCATG | 6461 |
| 1770 | ACAUGGAU CUGAUGAG GCCGUUAGGC CGAA IGCAGAGG | 13525 | CCTCTGCC A ATCCATGT | 6462 |
| 1774 | UCCCACAU CUGAUGAG GCCGUUAGGC CGAA IAUUGGCA | 13526 | TGCCAATC C ATGTGGGA | 6463 |
| 1775 | CUCCCACA CUGAUGAG GCCGUUAGGC CGAA IGAUUGGC | 13527 | GCCAATCC A TGTGGGAG | 6464 |
| 1790 | CAGGUGUG CUGAUGAG GCCGUUAGGC CGAA ICAACUCU | 13528 | AGAGTTGC C CACACCTG | 6465 |
| 1791 | ACAGGUGU CUGAUGAG GCCGUUAGGC CGAA IGCAACUC | 13529 | GAGTTGCC C ACACCTGT | 6466 |
| 1792 | AACAGGUG CUGAUGAG GCCGUUAGGC CGAA IGGCAACU | 13530 | AGTTGCCC A CACCTGTT | 6467 |
| 1794 | CAAACAGG CUGAUGAG GCCGUUAGGC CGAA IUGGGCAA | 13531 | TTGCCCAC A CCTGTTTG | 6468 |
| 1796 | UGCAAACA CUGAUGAG GCCGUUAGGC CGAA IUGUGGGC | 13532 | GCCCACAC C TGTTTGCA | 6469 |
| 1797 | UUGCAAAC CUGAUGAG GCCGUUAGGC CGAA IGUGUGGG | 13533 | CCCACACC T GTTTGCAA | 6470 |

| | | | | |
|---|---|---|---|---|
| 1804 | CAAGUUCU CUGAUGAG GCCGUUAGGC CGAA ICAAACAG | 13534 | CTGTTTGC A AGAACTTG | 6471 |
| 1810 | AGUAUCCA CUGAUGAG GCCGUUAGGC CGAA IUUCUUGC | 13535 | GCAAGAAC T TGGATACT | 6472 |
| 1818 | UUCCAAAG CUGAUGAG GCCGUUAGGC CGAA IUAUCCAA | 13536 | TTGGATAC T CTTTGGAA | 6473 |
| 1820 | AUUUCCAA CUGAUGAG GCCGUUAGGC CGAA IAGUAUCC | 13537 | GGATACTC T TTGGAAAT | 6474 |
| 1836 | AACAUGGU CUGAUGAG GCCGUUAGGC CGAA ICAUUCAA | 13538 | TTGAATGC C ACCATGTT | 6475 |
| 1837 | GAACAUGG CUGAUGAG GCCGUUAGGC CGAA IGCAUUCA | 13539 | TGAATGCC A CCATGTTC | 6476 |
| 1839 | GAGAACAU CUGAUGAG GCCGUUAGGC CGAA IUGGCAUU | 13540 | AATGCCAC C ATGTTCTC | 6477 |
| 1840 | AGAGAACA CUGAUGAG GCCGUUAGGC CGAA IGUGGCAU | 13541 | ATGCCACC A TGTTCTCT | 6478 |
| 1846 | GCUAUUAG CUGAUGAG GCCGUUAGGC CGAA IAACAUGG | 13542 | CCATGTTC T CTAATAGC | 6479 |
| 1848 | GUGCUAUU CUGAUGAG GCCGUUAGGC CGAA IAGAACAU | 13543 | ATGTTCTC T AATAGCAC | 6480 |
| 1855 | GUCAUUUG CUGAUGAG GCCGUUAGGC CGAA ICUAUUAG | 13544 | CTAATAGC A CAAATGAC | 6481 |
| 1857 | AUGUCAUU CUGAUGAG GCCGUUAGGC CGAA IUGCUAUU | 13545 | AATAGCAC A AATGACAT | 6482 |
| 1864 | GAUCAAAA CUGAUGAG GCCGUUAGGC CGAA IUCAUUUG | 13546 | CAAATGAC A TTTTGATC | 6483 |
| 1873 | AAGCUCCA CUGAUGAG GCCGUUAGGC CGAA IAUCAAAA | 13547 | TTTTGATC A TGGAGCTT | 6484 |
| 1880 | CAUUCUUA CUGAUGAG GCCGUUAGGC CGAA ICUCCAUG | 13548 | CATGGAGC T TAAGAATG | 6485 |
| 1890 | UGCAAGGA CUGAUGAG GCCGUUAGGC CGAA ICAUUCUU | 13549 | AAGAATGC A TCCTTGCA | 6486 |
| 1893 | UCCUGCAA CUGAUGAG GCCGUUAGGC CGAA IAUGCAUU | 13550 | AATGCATC C TTGCAGGA | 6487 |
| 1894 | GUCCUGCA CUGAUGAG GCCGUUAGGC CGAA IGAUGCAU | 13551 | ATGCATCC T TGCAGGAC | 6488 |
| 1898 | CUUGGUCC CUGAUGAG GCCGUUAGGC CGAA ICAAGGAU | 13552 | ATCCTTGC A GGACCAAG | 6489 |
| 1903 | GUCUCCUU CUGAUGAG GCCGUUAGGC CGAA IUCCUGCA | 13553 | TGCAGGAC C AAGGAGAC | 6490 |
| 1904 | AGUCUCCU CUGAUGAG GCCGUUAGGC CGAA IGUCCUGC | 13554 | GCAGGACC A AGGAGACT | 6491 |
| 1912 | GCAGACAU CUGAUGAG GCCGUUAGGC CGAA IUCUCCUU | 13555 | AAGGAGAC T ATGTCTGC | 6492 |
| 1918 | AGCAAGGC CUGAUGAG GCCGUUAGGC CGAA IACAUAGU | 13556 | ACTATGTC T GCCTTGCT | 6493 |
| 1921 | UUGAGCAA CUGAUGAG GCCGUUAGGC CGAA ICAGACAU | 13557 | ATGTCTGC C TTGCTCAA | 6494 |
| 1922 | CUUGAGCA CUGAUGAG GCCGUUAGGC CGAA IGCAGACA | 13558 | TGTCTGCC T TGCTCAAG | 6495 |
| 1926 | CUGUCUUG CUGAUGAG GCCGUUAGGC CGAA ICAAGGCA | 13559 | TGCCTTGC T CAAGACAG | 6496 |
| 1928 | UCCUGUCU CUGAUGAG GCCGUUAGGC CGAA IAGCAAGG | 13560 | CCTTGCTC A AGACAGGA | 6497 |
| 1933 | GGUCUUCC CUGAUGAG GCCGUUAGGC CGAA IUCUUGAG | 13561 | CTCAAGAC A GGAAGACC | 6498 |
| 1941 | CUUUUCUU CUGAUGAG GCCGUUAGGC CGAA IUCUUCCU | 13562 | AGGAAGAC C AAGAAAAG | 6499 |
| 1942 | UCUUUUCU CUGAUGAG GCCGUUAGGC CGAA IGUCUUCC | 13563 | GGAAGACC A AGAAAAGA | 6500 |
| 1952 | CCACGCAA CUGAUGAG GCCGUUAGGC CGAA IUCUUUUC | 13564 | GAAAAGAC A TTGCGTGG | 6501 |
| 1963 | GAGCUGCC CUGAUGAG GCCGUUAGGC CGAA IACCACGC | 13565 | GCGTGGTC A GGCAGCTC | 6502 |
| 1967 | CUGUGAGC CUGAUGAG GCCGUUAGGC CGAA ICCUGACC | 13566 | GGTCAGGC A GCTCACAG | 6503 |

276

| | | | | |
|---|---|---|---|---|
| 1970 | GGACUGUG CUGAUGAG GCCGUUAGGC CGAA ICUGCCUG | 13567 | CAGGCAGC T CACAGTCC | 6504 |
| 1972 | UAGGACUG CUGAUGAG GCCGUUAGGC CGAA IAGCUGCC | 13568 | GGCAGCTC A CAGTCCTA | 6505 |
| 1974 | UCUAGGAC CUGAUGAG GCCGUUAGGC CGAA IUGAGCUG | 13569 | CAGCTCAC A GTCCTAGA | 6506 |
| 1978 | ACGCUCUA CUGAUGAG GCCGUUAGGC CGAA IACUGUGA | 13570 | TCACAGTC C TAGAGCGT | 6507 |
| 1979 | CACGCUCU CUGAUGAG GCCGUUAGGC CGAA IGACUGUG | 13571 | CACAGTCC T AGAGCGTG | 6508 |
| 1992 | AUCGUGGG CUGAUGAG GCCGUUAGGC CGAA ICCACACG | 13572 | CGTGTGGC A CCCACGAT | 6509 |
| 1994 | UGAUCGUG CUGAUGAG GCCGUUAGGC CGAA IUGCCACA | 13573 | TGTGGCAC C CACGATCA | 6510 |
| 1995 | GUGAUCGU CUGAUGAG GCCGUUAGGC CGAA IGUGCCAC | 13574 | GTGGCACC C ACGATCAC | 6511 |
| 1996 | UGUGAUCG CUGAUGAG GCCGUUAGGC CGAA IGGUGCCA | 13575 | TGGCACCC A CGATCACA | 6512 |
| 2002 | GUUUCCUG CUGAUGAG GCCGUUAGGC CGAA IAUCGUGG | 13576 | CCACGATC A CAGGAAAC | 6513 |
| 2004 | AGGUUUCC CUGAUGAG GCCGUUAGGC CGAA IUGAUCGU | 13577 | ACGATCAC A GGAAACCT | 6514 |
| 2011 | AUUCUCCA CUGAUGAG GCCGUUAGGC CGAA IUUUCCUG | 13578 | CAGGAAAC C TGGAGAAT | 6515 |
| 2012 | GAUUCUCC CUGAUGAG GCCGUUAGGC CGAA IGUUUCCU | 13579 | AGGAAACC T GGAGAATC | 6516 |
| 2021 | UUGUCGUC CUGAUGAG GCCGUUAGGC CGAA IAUUCUCC | 13580 | GGAGAATC A GACGACAA | 6517 |
| 2028 | CCAAUACU CUGAUGAG GCCGUUAGGC CGAA IUCGUCUG | 13581 | CAGACGAC A AGTATTGG | 6518 |
| 2044 | GACUUCGA CUGAUGAG GCCGUUAGGC CGAA ICUUUCCC | 13582 | GGGAAAGC A TCGAAGTC | 6519 |
| 2053 | CGUGCAUG CUGAUGAG GCCGUUAGGC CGAA IACUUCGA | 13583 | TCGAAGTC T CATGCACG | 6520 |
| 2055 | GCCGUGCA CUGAUGAG GCCGUUAGGC CGAA IAGACUUC | 13584 | GAAGTCTC A TGCACGGC | 6521 |
| 2059 | AGAUGCCG CUGAUGAG GCCGUUAGGC CGAA ICAUGAGA | 13585 | TCTCATGC A CGGCATCT | 6522 |
| 2064 | UUCCCAGA CUGAUGAG GCCGUUAGGC CGAA ICCGUGCA | 13586 | TGCACGGC A TCTGGGAA | 6523 |
| 2067 | GGAUUCCC CUGAUGAG GCCGUUAGGC CGAA IAUGCCGU | 13587 | ACGGCATC T GGGAATCC | 6524 |
| 2075 | GUGGAGGG CUGAUGAG GCCGUUAGGC CGAA IAUUCCCA | 13588 | TGGGAATC C CCCTCCAC | 6525 |
| 2076 | UGUGGAGG CUGAUGAG GCCGUUAGGC CGAA IGAUUCCC | 13589 | GGGAATCC C CCTCCACA | 6526 |
| 2077 | CUGUGGAG CUGAUGAG GCCGUUAGGC CGAA IGGAUUCC | 13590 | GGAATCCC C CTCCACAG | 6527 |
| 2078 | UCUGUGGA CUGAUGAG GCCGUUAGGC CGAA IGGGAUUC | 13591 | GAATCCCC C TCCACAGA | 6528 |
| 2079 | AUCUGUGG CUGAUGAG GCCGUUAGGC CGAA IGGGGAUU | 13592 | AATCCCCC T CCACAGAT | 6529 |
| 2081 | UGAUCUGU CUGAUGAG GCCGUUAGGC CGAA IAGGGGGA | 13593 | TCCCCCTC C ACAGATCA | 6530 |
| 2082 | AUGAUCUG CUGAUGAG GCCGUUAGGC CGAA IGAGGGGG | 13594 | CCCCCTCC A CAGATCAT | 6531 |
| 2084 | ACAUGAUC CUGAUGAG GCCGUUAGGC CGAA IUGGAGGG | 13595 | CCCTCCAC A GATCATGT | 6532 |
| 2089 | AAACCACA CUGAUGAG GCCGUUAGGC CGAA IAUCUGUG | 13596 | CACAGATC A TGTGGTTT | 6533 |
| 2112 | UCUACAAG CUGAUGAG GCCGUUAGGC CGAA IUCUCAUU | 13597 | AATGAGAC C CTTGTAGA | 6534 |
| 2113 | UUCUACAA CUGAUGAG GCCGUUAGGC CGAA IGUCUCAU | 13598 | ATGAGACC C TTGTAGAA | 6535 |
| 2114 | CUUCUACA CUGAUGAG GCCGUUAGGC CGAA IGGUCUCA | 13599 | TGAGACCC T TGTAGAAG | 6536 |

| | | | | |
|---|---|---|---|---|
| 2125 | AAUGCCUG CUGAUGAG GCCGUUAGGC CGAA IUCUUCUA | 13600 | TAGAAGAC T CAGGCATT | 6537 |
| 2127 | ACAAUGCC CUGAUGAG GCCGUUAGGC CGAA IAGUCUUC | 13601 | GAAGACTC A GGCATTGT | 6538 |
| 2131 | CAAUACAA CUGAUGAG GCCGUUAGGC CGAA ICCUGAGU | 13602 | ACTCAGGC A TTGTATTG | 6539 |
| 2152 | GAGGUUCC CUGAUGAG GCCGUUAGGC CGAA IUUCCCAU | 13603 | ATGGGAAC C GGAACCTC | 6540 |
| 2158 | GAUAGUGA CUGAUGAG GCCGUUAGGC CGAA IUUCCGGU | 13604 | ACCGGAAC C TCACTATC | 6541 |
| 2159 | GGAUAGUG CUGAUGAG GCCGUUAGGC CGAA IGUUCCGG | 13605 | CCGGAACC T CACTATCC | 6542 |
| 2161 | GCGGAUAG CUGAUGAG GCCGUUAGGC CGAA IAGGUUCC | 13606 | GGAACCTC A CTATCCGC | 6543 |
| 2163 | CUGCGGAU CUGAUGAG GCCGUUAGGC CGAA IUGAGGUU | 13607 | AACCTCAC T ATCCGCAG | 6544 |
| 2167 | CACUCUGC CUGAUGAG GCCGUUAGGC CGAA IAUAGUGA | 13608 | TCACTATC C GCAGAGTG | 6545 |
| 2170 | CCUCACUC CUGAUGAG GCCGUUAGGC CGAA ICGGAUAG | 13609 | CTATCCGC A GAGTGAGG | 6546 |
| 2194 | GGUGUAGA CUGAUGAG GCCGUUAGGC CGAA ICCUUCGU | 13610 | ACGAAGGC C TCTACACC | 6547 |
| 2195 | AGGUGUAG CUGAUGAG GCCGUUAGGC CGAA IGCCUUCG | 13611 | CGAAGGCC T CTACACCT | 6548 |
| 2197 | GCAGGUGU CUGAUGAG GCCGUUAGGC CGAA IAGGCCUU | 13612 | AAGGCCTC T ACACCTGC | 6549 |
| 2200 | CUGGCAGG CUGAUGAG GCCGUUAGGC CGAA IUAGAGGC | 13613 | GCCTCTAC A CCTGCCAG | 6550 |
| 2202 | GCCUGGCA CUGAUGAG GCCGUUAGGC CGAA IUGUAGAG | 13614 | CTCTACAC C TGCCAGGC | 6551 |
| 2203 | UGCCUGGC CUGAUGAG GCCGUUAGGC CGAA IGUGUAGA | 13615 | TCTACACC T GCCAGGCA | 6552 |
| 2206 | GCAUGCCU CUGAUGAG GCCGUUAGGC CGAA ICAGGUGU | 13616 | ACACCTGC C AGGCATGC | 6553 |
| 2207 | UGCAUGCC CUGAUGAG GCCGUUAGGC CGAA IGCAGGUG | 13617 | CACCTGCC A GGCATGCA | 6554 |
| 2211 | ACACUGCA CUGAUGAG GCCGUUAGGC CGAA ICCUGGCA | 13618 | TGCCAGGC A TGCAGTGT | 6555 |
| 2215 | AAGAACAC CUGAUGAG GCCGUUAGGC CGAA ICAUGCCU | 13619 | AGGCATGC A GTGTTCTT | 6556 |
| 2222 | CACAGCCA CUGAUGAG GCCGUUAGGC CGAA IAACACUG | 13620 | CAGTGTTC T TGGCTGTG | 6557 |
| 2227 | UUUUGCAC CUGAUGAG GCCGUUAGGC CGAA ICCAAGAA | 13621 | TTCTTGGC T GTGCAAAA | 6558 |
| 2232 | UCCACUUU CUGAUGAG GCCGUUAGGC CGAA ICACAGCC | 13622 | GGCTGTGC A AAAGTGGA | 6559 |
| 2244 | AUGAAAAA CUGAUGAG GCCGUUAGGC CGAA ICCUCCAC | 13623 | GTGGAGGC A TTTTTCAT | 6560 |
| 2251 | UUCUAUUA CUGAUGAG GCCGUUAGGC CGAA IAAAAAUG | 13624 | CATTTTTC A TAATAGAA | 6561 |
| 2265 | UUUUCCUG CUGAUGAG GCCGUUAGGC CGAA ICACCUUC | 13625 | GAAGGTGC C CAGGAAAA | 6562 |
| 2266 | CUUUUCCU CUGAUGAG GCCGUUAGGC CGAA IGCACCUU | 13626 | AAGGTGCC C AGGAAAAG | 6563 |
| 2267 | UCUUUUCC CUGAUGAG GCCGUUAGGC CGAA IGGCACCU | 13627 | AGGTGCCC A GGAAAAGA | 6564 |
| 2281 | GAUUUCCA CUGAUGAG GCCGUUAGGC CGAA IUUCGUCU | 13628 | AGACGAAC T TGGAAATC | 6565 |
| 2290 | UAGAAUAA CUGAUGAG GCCGUUAGGC CGAA IAUUUCCA | 13629 | TGGAAATC A TTATTCTA | 6566 |
| 2297 | UGCCUACU CUGAUGAG GCCGUUAGGC CGAA IAAUAAUG | 13630 | CATTATTC T AGTAGGCA | 6567 |
| 2305 | CACCGUCG CUGAUGAG GCCGUUAGGC CGAA ICCUACUA | 13631 | TAGTAGGC A CGACGGTG | 6568 |
| 2319 | AAGAACAU CUGAUGAG GCCGUUAGGC CGAA ICAAUCAC | 13632 | GTGATTGC C ATGTTCTT | 6569 |

| | | | | |
|---|---|---|---|---|
| 2320 | GAAGAACA CUGAUGAG GCCGUUAGGC CGAA IGCAAUCA | 13633 | TGATTGCC A TGTTCTTC | 6570 |
| 2326 | UAGCCAGA CUGAUGAG GCCGUUAGGC CGAA IAACAUGG | 13634 | CCATGTTC T TCTGGCTA | 6571 |
| 2329 | AAGUAGCC CUGAUGAG GCCGUUAGGC CGAA IAAGAACA | 13635 | TGTTCTTC T GGCTACTT | 6572 |
| 2333 | CAAGAAGU CUGAUGAG GCCGUUAGGC CGAA ICCAGAAG | 13636 | CTTCTGGC T ACTTCTTG | 6573 |
| 2336 | UGACAAGA CUGAUGAG GCCGUUAGGC CGAA IUAGCCAG | 13637 | CTGGCTAC T TCTTGTCA | 6574 |
| 2339 | UGAUGACA CUGAUGAG GCCGUUAGGC CGAA IAAGUAGC | 13638 | GCTACTTC T TGTCATCA | 6575 |
| 2344 | UAGGAUGA CUGAUGAG GCCGUUAGGC CGAA IACAAGAA | 13639 | TTCTTGTC A TCATCCTA | 6576 |
| 2347 | CCCUAGGA CUGAUGAG GCCGUUAGGC CGAA IAUGACAA | 13640 | TTGTCATC A TCCTAGGG | 6577 |
| 2350 | GGUCCCUA CUGAUGAG GCCGUUAGGC CGAA IAUGAUGA | 13641 | TCATCATC C TAGGGACC | 6578 |
| 2351 | CGGUCCCU CUGAUGAG GCCGUUAGGC CGAA IGAUGAUG | 13642 | CATCATCC T AGGGACCG | 6579 |
| 2358 | CGCUUAAC CUGAUGAG GCCGUUAGGC CGAA IUCCCUAG | 13643 | CTAGGGAC C GTTAAGCG | 6580 |
| 2370 | CCUCCAUU CUGAUGAG GCCGUUAGGC CGAA ICCCGCUU | 13644 | AAGCGGGC C AATGGAGG | 6581 |
| 2371 | CCCUCCAU CUGAUGAG GCCGUUAGGC CGAA IGCCCGCU | 13645 | AGCGGGCC A ATGGAGGG | 6582 |
| 2384 | CUGUCUUC CUGAUGAG GCCGUUAGGC CGAA IUUCCCCU | 13646 | AGGGGAAC T GAAGACAG | 6583 |
| 2391 | AAGUAGCC CUGAUGAG GCCGUUAGGC CGAA IUCUUCAG | 13647 | CTGAAGAC A GGCTACTT | 6584 |
| 2395 | GGACAAGU CUGAUGAG GCCGUUAGGC CGAA ICCUGUCU | 13648 | AGACAGGC T ACTTGTCC | 6585 |
| 2398 | GAUGGACA CUGAUGAG GCCGUUAGGC CGAA IUAGCCUG | 13649 | CAGGCTAC T TGTCCATC | 6586 |
| 2403 | AUGACGAU CUGAUGAG GCCGUUAGGC CGAA IACAAGUA | 13650 | TACTTGTC C ATCGTCAT | 6587 |
| 2404 | CAUGACGA CUGAUGAG GCCGUUAGGC CGAA IGACAAGU | 13651 | ACTTGTCC A TCGTCATG | 6588 |
| 2410 | UGGAUCCA CUGAUGAG GCCGUUAGGC CGAA IACGAUGG | 13652 | CCATCGTC A TGGATCCA | 6589 |
| 2417 | GUUCAUCU CUGAUGAG GCCGUUAGGC CGAA IAUCCAUG | 13653 | CATGGATC C AGATGAAC | 6590 |
| 2418 | AGUUCAUC CUGAUGAG GCCGUUAGGC CGAA IGAUCCAU | 13654 | ATGGATCC A GATGAACT | 6591 |
| 2426 | CCAAUGGG CUGAUGAG GCCGUUAGGC CGAA IUUCAUCU | 13655 | AGATGAAC T CCCATTGG | 6592 |
| 2428 | AUCCAAUG CUGAUGAG GCCGUUAGGC CGAA IAGUUCAU | 13656 | ATGAACTC C CATTGGAT | 6593 |
| 2429 | CAUCCAAU CUGAUGAG GCCGUUAGGC CGAA IGAGUUCA | 13657 | TGAACTCC C ATTGGATG | 6594 |
| 2430 | UCAUCCAA CUGAUGAG GCCGUUAGGC CGAA IGGAGUUC | 13658 | GAACTCCC A TTGGATGA | 6595 |
| 2441 | GUUCACAA CUGAUGAG GCCGUUAGGC CGAA IUUCAUCC | 13659 | GGATGAAC A TTGTGAAC | 6596 |
| 2453 | CAUAAGGC CUGAUGAG GCCGUUAGGC CGAA IUCGUUCA | 13660 | TGAACGAC T GCCTTATG | 6597 |
| 2456 | CAUCAUAA CUGAUGAG GCCGUUAGGC CGAA ICAGUCGU | 13661 | ACGACTGC C TTATGATG | 6598 |
| 2457 | GCAUCAUA CUGAUGAG GCCGUUAGGC CGAA IGCAGUCG | 13662 | CGACTGCC T TATGATGC | 6599 |
| 2466 | CAUUUGCU CUGAUGAG GCCGUUAGGC CGAA ICAUCAUA | 13663 | TATGATGC C AGCAAATG | 6600 |
| 2467 | CCAUUUGC CUGAUGAG GCCGUUAGGC CGAA IGCAUCAU | 13664 | ATGATGCC A GCAAATGG | 6601 |
| 2470 | UUCCCAUU CUGAUGAG GCCGUUAGGC CGAA ICUGGCAU | 13665 | ATGCCAGC A AATGGGAA | 6602 |

279

| | | | | |
|---|---|---|---|---|
| 2482 | GUCUCUGG CUGAUGAG GCCGUUAGGC CGAA IAAUUCCC | 13666 | GGGAATTC C CCAGAGAC | 6603 |
| 2483 | GGUCUCUG CUGAUGAG GCCGUUAGGC CGAA IGAAUUCC | 13667 | GGAATTCC C CAGAGACC | 6604 |
| 2484 | CGGUCUCU CUGAUGAG GCCGUUAGGC CGAA IGGAAUUC | 13668 | GAATTCCC C AGAGACCG | 6605 |
| 2485 | CCGGUCUC CUGAUGAG GCCGUUAGGC CGAA IGGGAAUU | 13669 | AATTCCCC A GAGACCGG | 6606 |
| 2491 | GUUCAGCC CUGAUGAG GCCGUUAGGC CGAA IUCUCUGG | 13670 | CCAGAGAC C GGCTGAAC | 6607 |
| 2495 | CUAGGUUC CUGAUGAG GCCGUUAGGC CGAA ICCGGUCU | 13671 | AGACCGGC T GAACCTAG | 6608 |
| 2500 | CUUACCUA CUGAUGAG GCCGUUAGGC CGAA IUUCAGCC | 13672 | GGCTGAAC C TAGGTAAG | 6609 |
| 2501 | GCUUACCU CUGAUGAG GCCGUUAGGC CGAA IGUUCAGC | 13673 | GCTGAACC T AGGTAAGC | 6610 |
| 2510 | GGCCAAGA CUGAUGAG GCCGUUAGGC CGAA ICUUACCU | 13674 | AGGTAAGC C TCTTGGCC | 6611 |
| 2511 | CGGCCAAG CUGAUGAG GCCGUUAGGC CGAA IGCUUACC | 13675 | GGTAAGCC T CTTGGCCG | 6612 |
| 2513 | CACGGCCA CUGAUGAG GCCGUUAGGC CGAA IAGGCUUA | 13676 | TAAGCCTC T TGGCCGTG | 6613 |
| 2518 | GGCACCAC CUGAUGAG GCCGUUAGGC CGAA ICCAAGAG | 13677 | CTCTTGGC C GTGGTGCC | 6614 |
| 2526 | UGGCCAAA CUGAUGAG GCCGUUAGGC CGAA ICACCACG | 13678 | CGTGGTGC C TTTGGCCA | 6615 |
| 2527 | UUGGCCAA CUGAUGAG GCCGUUAGGC CGAA IGCACCAC | 13679 | GTGGTGCC T TTGGCCAA | 6616 |
| 2533 | AAUCUCUU CUGAUGAG GCCGUUAGGC CGAA ICCAAAGG | 13680 | CCTTTGGC C AAGAGATT | 6617 |
| 2534 | CAAUCUCU CUGAUGAG GCCGUUAGGC CGAA IGCCAAAG | 13681 | CTTTGGCC A AGAGATTG | 6618 |
| 2547 | AAGGCAUC CUGAUGAG GCCGUUAGGC CGAA ICUUCAAU | 13682 | ATTGAAGC A GATGCCTT | 6619 |
| 2553 | AUUCCAAA CUGAUGAG GCCGUUAGGC CGAA ICAUCUGC | 13683 | GCAGATGC C TTTGGAAT | 6620 |
| 2554 | AAUUCCAA CUGAUGAG GCCGUUAGGC CGAA IGCAUCUG | 13684 | CAGATGCC T TTGGAATT | 6621 |
| 2566 | UGCUGUCU CUGAUGAG GCCGUUAGGC CGAA IUCAAUUC | 13685 | GAATTGAC A AGACAGCA | 6622 |
| 2571 | CAAGUUGC CUGAUGAG GCCGUUAGGC CGAA IUCUUGUC | 13686 | GACAAGAC A GCAACTTG | 6623 |
| 2574 | CUGCAAGU CUGAUGAG GCCGUUAGGC CGAA ICUGUCUU | 13687 | AAGACAGC A ACTTGCAG | 6624 |
| 2577 | GUCCUGCA CUGAUGAG GCCGUUAGGC CGAA IUUGCUGU | 13688 | ACAGCAAC T TGCAGGAC | 6625 |
| 2581 | UACUGUCC CUGAUGAG GCCGUUAGGC CGAA ICAAGUUG | 13689 | CAACTTGC A GGACAGTA | 6626 |
| 2586 | ACUGCUAC CUGAUGAG GCCGUUAGGC CGAA IUCCUGCA | 13690 | TGCAGGAC A GTAGCAGT | 6627 |
| 2592 | AUUUUGAC CUGAUGAG GCCGUUAGGC CGAA ICUACUGU | 13691 | ACAGTAGC A GTCAAAAT | 6628 |
| 2596 | CAACAUUU CUGAUGAG GCCGUUAGGC CGAA IACUGCUA | 13692 | TAGCAGTC A AAATGTTG | 6629 |
| 2616 | CUGUGUGU CUGAUGAG GCCGUUAGGC CGAA ICUCCUUC | 13693 | GAAGGAGC A ACACACAG | 6630 |
| 2619 | UCACUGUG CUGAUGAG GCCGUUAGGC CGAA IUUGCUCC | 13694 | GGAGCAAC A CACAGTGA | 6631 |
| 2621 | GCUCACUG CUGAUGAG GCCGUUAGGC CGAA IUGUUGCU | 13695 | AGCAACAC A CAGTGAGC | 6632 |
| 2623 | AUGCUCAC CUGAUGAG GCCGUUAGGC CGAA IUGUGUUG | 13696 | CAACACAC A GTGAGCAT | 6633 |
| 2630 | GAGCUCGA CUGAUGAG GCCGUUAGGC CGAA ICUCACUG | 13697 | CAGTGAGC A TCGAGCTC | 6634 |
| 2637 | GACAUGAG CUGAUGAG GCCGUUAGGC CGAA ICUCGAUG | 13698 | CATCGAGC T CTCATGTC | 6635 |

280

| | | | | |
|---|---|---|---|---|
| 2639 | CAGACAUG CUGAUGAG GCCGUUAGGC CGAA IAGCUCGA | 13699 | TCGAGCTC T CATGTCTG | 6636 |
| 2641 | UUCAGACA CUGAUGAG GCCGUUAGGC CGAA IAGAGCUC | 13700 | GAGCTCTC A TGTCTGAA | 6637 |
| 2646 | UUGAGUUC CUGAUGAG GCCGUUAGGC CGAA IACAUGAG | 13701 | CTCATGTC T GAACTCAA | 6638 |
| 2651 | GGAUCUUG CUGAUGAG GCCGUUAGGC CGAA IUUCAGAC | 13702 | GTCTGAAC T CAAGATCC | 6639 |
| 2653 | GAGGAUCU CUGAUGAG GCCGUUAGGC CGAA IAGUUCAG | 13703 | CTGAACTC A AGATCCTC | 6640 |
| 2659 | AUGAAUGA CUGAUGAG GCCGUUAGGC CGAA IAUCUUGA | 13704 | TCAAGATC C TCATTCAT | 6641 |
| 2660 | UAUGAAUG CUGAUGAG GCCGUUAGGC CGAA IGAUCUUG | 13705 | CAAGATCC T CATTCATA | 6642 |
| 2662 | AAUAUGAA CUGAUGAG GCCGUUAGGC CGAA IAGGAUCU | 13706 | AGATCCTC A TTCATATT | 6643 |
| 2666 | GACCAAUA CUGAUGAG GCCGUUAGGC CGAA IAAUGAGG | 13707 | CCTCATTC A TATTGGTC | 6644 |
| 2675 | UGAGAUGG CUGAUGAG GCCGUUAGGC CGAA IACCAAUA | 13708 | TATTGGTC A CCATCTCA | 6645 |
| 2677 | AUUGAGAU CUGAUGAG GCCGUUAGGC CGAA IUGACCAA | 13709 | TTGGTCAC C ATCTCAAT | 6646 |
| 2678 | CAUUGAGA CUGAUGAG GCCGUUAGGC CGAA IGUGACCA | 13710 | TGGTCACC A TCTCAATG | 6647 |
| 2681 | CCACAUUG CUGAUGAG GCCGUUAGGC CGAA IAUGGUGA | 13711 | TCACCATC T CAATGTGG | 6648 |
| 2683 | GACCACAU CUGAUGAG GCCGUUAGGC CGAA IAGAUGGU | 13712 | ACCATCTC A ATGTGGTC | 6649 |
| 2692 | UAGAAGGU CUGAUGAG GCCGUUAGGC CGAA IACCACAU | 13713 | ATGTGGTC A ACCTTCTA | 6650 |
| 2695 | ACCUAGAA CUGAUGAG GCCGUUAGGC CGAA IUUGACCA | 13714 | TGGTCAAC C TTCTAGGT | 6651 |
| 2696 | CACCUAGA CUGAUGAG GCCGUUAGGC CGAA IGUUGACC | 13715 | GGTCAACC T TCTAGGTG | 6652 |
| 2699 | AGGCACCU CUGAUGAG GCCGUUAGGC CGAA IAAGGUUG | 13716 | CAACCTTC T AGGTGCCT | 6653 |
| 2706 | UUGGUACA CUGAUGAG GCCGUUAGGC CGAA ICACCUAG | 13717 | CTAGGTGC C TGTACCAA | 6654 |
| 2707 | CUUGGUAC CUGAUGAG GCCGUUAGGC CGAA IGCACCUA | 13718 | TAGGTGCC T GTACCAAG | 6655 |
| 2712 | CCUGGCUU CUGAUGAG GCCGUUAGGC CGAA IUACAGGC | 13719 | GCCTGTAC C AAGCCAGG | 6656 |
| 2713 | UCCUGGCU CUGAUGAG GCCGUUAGGC CGAA IGUACAGG | 13720 | CCTGTACC A AGCCAGGA | 6657 |
| 2717 | GCCCUCCU CUGAUGAG GCCGUUAGGC CGAA ICUUGGUA | 13721 | TACCAAGC C AGGAGGGC | 6658 |
| 2718 | GGCCCUCC CUGAUGAG GCCGUUAGGC CGAA IGCUUGGU | 13722 | ACCAAGCC A GGAGGGCC | 6659 |
| 2726 | CCAUGAGU CUGAUGAG GCCGUUAGGC CGAA ICCCUCCU | 13723 | AGGAGGGC C ACTCATGG | 6660 |
| 2727 | ACCAUGAG CUGAUGAG GCCGUUAGGC CGAA IGCCCUCC | 13724 | GGAGGGCC A CTCATGGT | 6661 |
| 2729 | UCACCAUG CUGAUGAG GCCGUUAGGC CGAA IUGGCCCU | 13725 | AGGGCCAC T CATGGTGA | 6662 |
| 2731 | AAUCACCA CUGAUGAG GCCGUUAGGC CGAA IAGUGGCC | 13726 | GGCCACTC A TGGTGATT | 6663 |
| 2749 | AAAUUUGC CUGAUGAG GCCGUUAGGC CGAA IAAUUCCA | 13727 | TGGAATTC T GCAAATTT | 6664 |
| 2752 | UCCAAAUU CUGAUGAG GCCGUUAGGC CGAA ICAGAAUU | 13728 | AATTCTGC A AATTTGGA | 6665 |
| 2764 | AGUGGACA CUGAUGAG GCCGUUAGGC CGAA IUUUCCAA | 13729 | TTGGAAAC C TGTCCACT | 6666 |
| 2765 | AAGUGGAC CUGAUGAG GCCGUUAGGC CGAA IGUUUCCA | 13730 | TGGAAACC T GTCCACTT | 6667 |
| 2769 | AGGUAAGU CUGAUGAG GCCGUUAGGC CGAA IACAGGUU | 13731 | AACCTGTC C ACTTACCT | 6668 |

| | | | | | |
|---|---|---|---|---|---|
| 2770 | CAGGUAAG CUGAUGAG GCCGUUAGGC CGAA IGACAGGU | 13732 | ACCTGTCC A CTTACCTG | 6669 |
| 2772 | CUCAGGUA CUGAUGAG GCCGUUAGGC CGAA IUGGACAG | 13733 | CTGTCCAC T TACCTGAG | 6670 |
| 2776 | GCUCCUCA CUGAUGAG GCCGUUAGGC CGAA IUAAGUGG | 13734 | CCACTTAC C TGAGGAGC | 6671 |
| 2777 | UGCUCCUC CUGAUGAG GCCGUUAGGC CGAA IGUAAGUG | 13735 | CACTTACC T GAGGAGCA | 6672 |
| 2785 | AUUUCUCU CUGAUGAG GCCGUUAGGC CGAA ICUCCUCA | 13736 | TGAGGAGC A AGAGAAAT | 6673 |
| 2803 | CUUGUAGG CUGAUGAG GCCGUUAGGC CGAA IACAAAUU | 13737 | AATTTGTC C CCTACAAG | 6674 |
| 2804 | UCUUGUAG CUGAUGAG GCCGUUAGGC CGAA IGACAAAU | 13738 | ATTTGTCC C CTACAAGA | 6675 |
| 2805 | GUCUUGUA CUGAUGAG GCCGUUAGGC CGAA IGGACAAA | 13739 | TTTGTCCC C TACAAGAC | 6676 |
| 2806 | GGUCUUGU CUGAUGAG GCCGUUAGGC CGAA IGGGACAA | 13740 | TTGTCCCC T ACAAGACC | 6677 |
| 2809 | UUUGGUCU CUGAUGAG GCCGUUAGGC CGAA IUAGGGGA | 13741 | TCCCCTAC A AGACCAAA | 6678 |
| 2814 | GCCCCUUU CUGAUGAG GCCGUUAGGC CGAA IUCUUGUA | 13742 | TACAAGAC C AAAGGGGC | 6679 |
| 2815 | UGCCCCUU CUGAUGAG GCCGUUAGGC CGAA IGUCUUGU | 13743 | ACAAGACC A AAGGGGCA | 6680 |
| 2823 | CGGAAUCG CUGAUGAG GCCGUUAGGC CGAA ICCCCUUU | 13744 | AAAGGGGC A CGATTCCG | 6681 |
| 2830 | CCCUUGAC CUGAUGAG GCCGUUAGGC CGAA IAAUCGUG | 13745 | CACGATTC C GTCAAGGG | 6682 |
| 2834 | CUUUCCCU CUGAUGAG GCCGUUAGGC CGAA IACGGAAU | 13746 | ATTCCGTC A AGGGAAAG | 6683 |
| 2845 | UCCAACGU CUGAUGAG GCCGUUAGGC CGAA IUCUUUCC | 13747 | GGAAAGAC T ACGTTGGA | 6684 |
| 2856 | ACAGGGAU CUGAUGAG GCCGUUAGGC CGAA ICUCCAAC | 13748 | GTTGGAGC A ATCCCTGT | 6685 |
| 2860 | AUCCACAG CUGAUGAG GCCGUUAGGC CGAA IAUUGCUC | 13749 | GAGCAATC C CTGTGGAT | 6686 |
| 2861 | GAUCCACA CUGAUGAG GCCGUUAGGC CGAA IGAUUGCU | 13750 | AGCAATCC C TGTGGATC | 6687 |
| 2862 | AGAUCCAC CUGAUGAG GCCGUUAGGC CGAA IGGAUUGC | 13751 | GCAATCCC T GTGGATCT | 6688 |
| 2870 | GCCGUUUC CUGAUGAG GCCGUUAGGC CGAA IAUCCACA | 13752 | TGTGGATC T GAAACGGC | 6689 |
| 2881 | GCUGUCCA CUGAUGAG GCCGUUAGGC CGAA ICGCCGUU | 13753 | AACGGCGC T TGGACAGC | 6690 |
| 2887 | GGUGAUGC CUGAUGAG GCCGUUAGGC CGAA IUCCAAGC | 13754 | GCTTGGAC A GCATCACC | 6691 |
| 2890 | ACUGGUGA CUGAUGAG GCCGUUAGGC CGAA ICUGUCCA | 13755 | TGGACAGC A TCACCAGT | 6692 |
| 2893 | GCUACUGG CUGAUGAG GCCGUUAGGC CGAA IAUGCUGU | 13756 | ACAGCATC A CCAGTAGC | 6693 |
| 2895 | UGGCUACU CUGAUGAG GCCGUUAGGC CGAA IUGAUGCU | 13757 | AGCATCAC C AGTAGCCA | 6694 |
| 2896 | CUGGCUAC CUGAUGAG GCCGUUAGGC CGAA IGUGAUGC | 13758 | GCATCACC A GTAGCCAG | 6695 |
| 2902 | UGAGCUCU CUGAUGAG GCCGUUAGGC CGAA ICUACUGG | 13759 | CCAGTAGC C AGAGCTCA | 6696 |
| 2903 | CUGAGCUC CUGAUGAG GCCGUUAGGC CGAA IGCUACUG | 13760 | CAGTAGCC A GAGCTCAG | 6697 |
| 2908 | GCUGGCUG CUGAUGAG GCCGUUAGGC CGAA ICUCUGGC | 13761 | GCCAGAGC T CAGCCAGC | 6698 |
| 2910 | GAGCUGGC CUGAUGAG GCCGUUAGGC CGAA IAGCUCUG | 13762 | CAGAGCTC A GCCAGCTC | 6699 |
| 2913 | CCAGAGCU CUGAUGAG GCCGUUAGGC CGAA ICUGAGCU | 13763 | AGCTCAGC C AGCTCTGG | 6700 |
| 2914 | UCCAGAGC CUGAUGAG GCCGUUAGGC CGAA IGCUGAGC | 13764 | GCTCAGCC A GCTCTGGA | 6701 |

282

| | | | | |
|---|---|---|---|---|
| 2917 | AAAUCCAG CUGAUGAG GCCGUUAGGC CGAA ICUGGCUG | 13765 | CAGCCAGC T CTGGATTT | 6702 |
| 2919 | ACAAAUCC CUGAUGAG GCCGUUAGGC CGAA IAGCUGGC | 13766 | GCCAGCTC T GGATTTGT | 6703 |
| 2940 | UCACUGAG CUGAUGAG GCCGUUAGGC CGAA IACUUCUC | 13767 | GAGAAGTC C CTCAGTGA | 6704 |
| 2941 | AUCACUGA CUGAUGAG GCCGUUAGGC CGAA IGACUUCU | 13768 | AGAAGTCC C TCAGTGAT | 6705 |
| 2942 | CAUCACUG CUGAUGAG GCCGUUAGGC CGAA IGGACUUC | 13769 | GAAGTCCC T CAGTGATG | 6706 |
| 2944 | UACAUCAC CUGAUGAG GCCGUUAGGC CGAA IAGGGACU | 13770 | AGTCCCTC A GTGATGTA | 6707 |
| 2967 | UCUUCAGG CUGAUGAG GCCGUUAGGC CGAA ICUUCCUC | 13771 | GAGGAAGC T CCTGAAGA | 6708 |
| 2969 | GAUCUUCA CUGAUGAG GCCGUUAGGC CGAA IAGCUUCC | 13772 | GGAAGCTC C TGAAGATC | 6709 |
| 2970 | AGAUCUUC CUGAUGAG GCCGUUAGGC CGAA IGAGCUUC | 13773 | GAAGCTCC T GAAGATCT | 6710 |
| 2978 | CCUUAUAC CUGAUGAG GCCGUUAGGC CGAA IAUCUUCA | 13774 | TGAAGATC T GTATAAGG | 6711 |
| 2989 | GGUCAGGA CUGAUGAG GCCGUUAGGC CGAA IUCCUUAU | 13775 | ATAAGGAC T TCCTGACC | 6712 |
| 2992 | CAAGGUCA CUGAUGAG GCCGUUAGGC CGAA IAAGUCCU | 13776 | AGGACTTC C TGACCTTG | 6713 |
| 2993 | CCAAGGUC CUGAUGAG GCCGUUAGGC CGAA IGAAGUCC | 13777 | GGACTTCC T GACCTTGG | 6714 |
| 2997 | UGCUCCAA CUGAUGAG GCCGUUAGGC CGAA IUCAGGAA | 13778 | TTCCTGAC C TTGGAGCA | 6715 |
| 2998 | AUGCUCCA CUGAUGAG GCCGUUAGGC CGAA IGUCAGGA | 13779 | TCCTGACC T TGGAGCAT | 6716 |
| 3005 | AGAUGAGA CUGAUGAG GCCGUUAGGC CGAA ICUCCAAG | 13780 | CTTGGAGC A TCTCATCT | 6717 |
| 3008 | AACAGAUG CUGAUGAG GCCGUUAGGC CGAA IAUGCUCC | 13781 | GGAGCATC T CATCTGTT | 6718 |
| 3010 | GUAACAGA CUGAUGAG GCCGUUAGGC CGAA IAGAUGCU | 13782 | AGCATCTC A TCTGTTAC | 6719 |
| 3013 | GCUGUAAC CUGAUGAG GCCGUUAGGC CGAA IAUGAGAU | 13783 | ATCTCATC T GTTACAGC | 6720 |
| 3019 | UUGGAAGC CUGAUGAG GCCGUUAGGC CGAA IUAACAGA | 13784 | TCTGTTAC A GCTTCCAA | 6721 |
| 3022 | CACUUGGA CUGAUGAG GCCGUUAGGC CGAA ICUGUAAC | 13785 | GTTACAGC T TCCAAGTG | 6722 |
| 3025 | AGCCACUU CUGAUGAG GCCGUUAGGC CGAA IAAGCUGU | 13786 | ACAGCTTC C AAGTGGCT | 6723 |
| 3026 | UAGCCACU CUGAUGAG GCCGUUAGGC CGAA IGAAGCUG | 13787 | CAGCTTCC A AGTGGCTA | 6724 |
| 3033 | AUGCCCUU CUGAUGAG GCCGUUAGGC CGAA ICCACUUG | 13788 | CAAGTGGC T AAGGGCAT | 6725 |
| 3040 | GAACUCCA CUGAUGAG GCCGUUAGGC CGAA ICCCUUAG | 13789 | CTAAGGGC A TGGAGTTC | 6726 |
| 3049 | CGAUGCCA CUGAUGAG GCCGUUAGGC CGAA IAACUCCA | 13790 | TGGAGTTC T TGGCATCG | 6727 |
| 3054 | UUUCGCGA CUGAUGAG GCCGUUAGGC CGAA ICCAAGAA | 13791 | TTCTTGGC A TCGCGAAA | 6728 |
| 3070 | GUCCCUGU CUGAUGAG GCCGUUAGGC CGAA IAUACACU | 13792 | AGTGTATC C ACAGGGAC | 6729 |
| 3071 | GGUCCCUG CUGAUGAG GCCGUUAGGC CGAA IGAUACAC | 13793 | GTGTATCC A CAGGGACC | 6730 |
| 3073 | CAGGUCCC CUGAUGAG GCCGUUAGGC CGAA IUGGAUAC | 13794 | GTATCCAC A GGGACCTG | 6731 |
| 3079 | UGCCGCCA CUGAUGAG GCCGUUAGGC CGAA IUCCCUGU | 13795 | ACAGGGAC C TGGCGGCA | 6732 |
| 3080 | GUGCCGCC CUGAUGAG GCCGUUAGGC CGAA IGUCCCUG | 13796 | CAGGGACC T GGCGGCAC | 6733 |
| 3087 | AUAUUUCG CUGAUGAG GCCGUUAGGC CGAA ICCGCCAG | 13797 | CTGGCGGC A CGAAATAT | 6734 |

283

| | | | | |
|---|---|---|---|---|
| 3097 | CGAUAAGA CUGAUGAG GCCGUUAGGC CGAA IAUAUUUC | 13798 | GAAATATC C TCTTATCG | 6735 |
| 3098 | CCGAUAAG CUGAUGAG GCCGUUAGGC CGAA IGAUAUUU | 13799 | AAATATCC T CTTATCGG | 6736 |
| 3100 | CUCCGAUA CUGAUGAG GCCGUUAGGC CGAA IAGGAUAU | 13800 | ATATCCTC T TATCGGAG | 6737 |
| 3127 | AAAGUCAC CUGAUGAG GCCGUUAGGC CGAA IAUUUUAA | 13801 | TTAAAATC T GTGACTTT | 6738 |
| 3133 | CAAGCCAA CUGAUGAG GCCGUUAGGC CGAA IUCACAGA | 13802 | TCTGTGAC T TTGGCTTG | 6739 |
| 3139 | CCGGGCCA CUGAUGAG GCCGUUAGGC CGAA ICCAAAGU | 13803 | ACTTTGGC T TGGCCCGG | 6740 |
| 3144 | AUAUCCCG CUGAUGAG GCCGUUAGGC CGAA ICCAAGCC | 13804 | GGCTTGGC C CGGGATAT | 6741 |
| 3145 | AAUAUCCC CUGAUGAG GCCGUUAGGC CGAA IGCCAAGC | 13805 | GCTTGGCC C GGGATATT | 6742 |
| 3164 | CAUAAUCU CUGAUGAG GCCGUUAGGC CGAA IAUCUUUA | 13806 | TAAAGATC C AGATTATG | 6743 |
| 3165 | ACAUAAUC CUGAUGAG GCCGUUAGGC CGAA IGAUCUUU | 13807 | AAAGATCC A GATTATGT | 6744 |
| 3175 | UCCUUUUC CUGAUGAG GCCGUUAGGC CGAA IACAUAAU | 13808 | ATTATGTC A GAAAAGGA | 6745 |
| 3189 | GGGAGGCG CUGAUGAG GCCGUUAGGC CGAA ICAUCUCC | 13809 | GGAGATGC T CGCCTCCC | 6746 |
| 3193 | CAAAGGGA CUGAUGAG GCCGUUAGGC CGAA ICGAGCAU | 13810 | ATGCTCGC C TCCCTTTG | 6747 |
| 3194 | UCAAAGGG CUGAUGAG GCCGUUAGGC CGAA IGCGAGCA | 13811 | TGCTCGCC T CCCTTTGA | 6748 |
| 3196 | UUUCAAAG CUGAUGAG GCCGUUAGGC CGAA IAGGCGAG | 13812 | CTCGCCTC C CTTTGAAA | 6749 |
| 3197 | AUUUCAAA CUGAUGAG GCCGUUAGGC CGAA IGAGGCGA | 13813 | TCGCCTCC C TTTGAAAT | 6750 |
| 3198 | CAUUUCAA CUGAUGAG GCCGUUAGGC CGAA IGGAGGCG | 13814 | CGCCTCCC T TTGAAATG | 6751 |
| 3213 | GUUUCUGG CUGAUGAG GCCGUUAGGC CGAA ICCAUCCA | 13815 | TGGATGGC C CCAGAAAC | 6752 |
| 3214 | UGUUUCUG CUGAUGAG GCCGUUAGGC CGAA IGCCAUCC | 13816 | GGATGGCC C CAGAAACA | 6753 |
| 3215 | UUGUUUCU CUGAUGAG GCCGUUAGGC CGAA IGGCCAUC | 13817 | GATGGCCC C AGAAACAA | 6754 |
| 3216 | AUUGUUUC CUGAUGAG GCCGUUAGGC CGAA IGGGCCAU | 13818 | ATGGCCCC A GAAACAAT | 6755 |
| 3222 | UCAAAAAU CUGAUGAG GCCGUUAGGC CGAA IUUUCUGG | 13819 | CCAGAAAC A ATTTTTGA | 6756 |
| 3232 | GUACACUC CUGAUGAG GCCGUUAGGC CGAA IUCAAAAA | 13820 | TTTTTGAC A GAGTGTAC | 6757 |
| 3241 | CUGGAUUG CUGAUGAG GCCGUUAGGC CGAA IUACACUC | 13821 | GAGTGTAC A CAATCCAG | 6758 |
| 3243 | CUCUGGAU CUGAUGAG GCCGUUAGGC CGAA IUGUACAC | 13822 | GTGTACAC A ATCCAGAG | 6759 |
| 3247 | GUCACUCU CUGAUGAG GCCGUUAGGC CGAA IAUUGUGU | 13823 | ACACAATC C AGAGTGAC | 6760 |
| 3248 | CGUCACUC CUGAUGAG GCCGUUAGGC CGAA IGAUUGUG | 13824 | CACAATCC A GAGTGACG | 6761 |
| 3259 | AAAAGACC CUGAUGAG GCCGUUAGGC CGAA IACGUCAC | 13825 | GTGACGTC T GGTCTTTT | 6762 |
| 3264 | ACACCAAA CUGAUGAG GCCGUUAGGC CGAA IACCAGAC | 13826 | GTCTGGTC T TTTGGTGT | 6763 |
| 3278 | UUUCCCAC CUGAUGAG GCCGUUAGGC CGAA ICAAAACA | 13827 | TGTTTTGC T GTGGGAAA | 6764 |
| 3294 | GCACCUAA CUGAUGAG GCCGUUAGGC CGAA IAAAAUAU | 13828 | ATATTTTC C TTAGGTGC | 6765 |
| 3295 | AGCACCUA CUGAUGAG GCCGUUAGGC CGAA IGAAAAUA | 13829 | TATTTTCC T TAGGTGCT | 6766 |
| 3303 | UAUGGAGA CUGAUGAG GCCGUUAGGC CGAA ICACCUAA | 13830 | TTAGGTGC T TCTCCATA | 6767 |

| | | | | |
|---|---|---|---|---|
| 3306 | GGAUAUGG CUGAUGAG GCCGUUAGGC CGAA IAAGCACC | 13831 | GGTGCTTC T CCATATCC | 6768 |
| 3308 | CAGGAUAU CUGAUGAG GCCGUUAGGC CGAA IAGAAGCA | 13832 | TGCTTCTC C ATATCCTG | 6769 |
| 3309 | CCAGGAUA CUGAUGAG GCCGUUAGGC CGAA IGAGAAGC | 13833 | GCTTCTCC A TATCCTGG | 6770 |
| 3314 | UUACCCCA CUGAUGAG GCCGUUAGGC CGAA IAUAUGGA | 13834 | TCCATATC C TGGGGTAA | 6771 |
| 3315 | UUUACCCC CUGAUGAG GCCGUUAGGC CGAA IGAUAUGG | 13835 | CCATATCC T GGGGTAAA | 6772 |
| 3363 | CUCAUUCU CUGAUGAG GCCGUUAGGC CGAA IUUCCUUC | 13836 | GAAGGAAC T AGAATGAG | 6773 |
| 3375 | UAAUCAGG CUGAUGAG GCCGUUAGGC CGAA ICCCUCAU | 13837 | ATGAGGGC C CCTGATTA | 6774 |
| 3376 | AUAAUCAG CUGAUGAG GCCGUUAGGC CGAA IGCCCUCA | 13838 | TGAGGGCC C CTGATTAT | 6775 |
| 3377 | UAUAAUCA CUGAUGAG GCCGUUAGGC CGAA IGGCCCUC | 13839 | GAGGGCCC C TGATTATA | 6776 |
| 3378 | GUAUAAUC CUGAUGAG GCCGUUAGGC CGAA IGGGCCCU | 13840 | AGGGCCCC T GATTATAC | 6777 |
| 3387 | UCUGGUGU CUGAUGAG GCCGUUAGGC CGAA IUAUAAUC | 13841 | GATTATAC T ACACCAGA | 6778 |
| 3390 | AUUUCUGG CUGAUGAG GCCGUUAGGC CGAA IUAGUAUA | 13842 | TATACTAC A CCAGAAAT | 6779 |
| 3392 | ACAUUUCU CUGAUGAG GCCGUUAGGC CGAA IUGUAGUA | 13843 | TACTACAC C AGAAATGT | 6780 |
| 3393 | UACAUUUC CUGAUGAG GCCGUUAGGC CGAA IGUGUAGU | 13844 | ACTACACC A GAAATGTA | 6781 |
| 3403 | CAUGGUCU CUGAUGAG GCCGUUAGGC CGAA IUACAUUU | 13845 | AAATGTAC C AGACCATG | 6782 |
| 3404 | GCAUGGUC CUGAUGAG GCCGUUAGGC CGAA IGUACAUU | 13846 | AATGTACC A GACCATGC | 6783 |
| 3408 | UCCAGCAU CUGAUGAG GCCGUUAGGC CGAA IUCUGGUA | 13847 | TACCAGAC C ATGCTGGA | 6784 |
| 3409 | GUCCAGCA CUGAUGAG GCCGUUAGGC CGAA IGUCUGGU | 13848 | ACCAGACC A TGCTGGAC | 6785 |
| 3413 | AGCAGUCC CUGAUGAG GCCGUUAGGC CGAA ICAUGGUC | 13849 | GACCATGC T GGACTGCT | 6786 |
| 3418 | GUGCCAGC CUGAUGAG GCCGUUAGGC CGAA IUCCAGCA | 11949 | TGCTGGAC T GCTGGCAC | 4886 |
| 3421 | CCCGUGCC CUGAUGAG GCCGUUAGGC CGAA ICAGUCCA | 13850 | TGGACTGC T GGCACGGG | 6787 |
| 3425 | GCUCCCCG CUGAUGAG GCCGUUAGGC CGAA ICCAGCAG | 13851 | CTGCTGGC A CGGGGAGC | 6788 |
| 3434 | UCUGACUG CUGAUGAG GCCGUUAGGC CGAA ICUCCCCG | 13852 | CGGGGAGC C CAGTCAGA | 6789 |
| 3435 | CUCUGACU CUGAUGAG GCCGUUAGGC CGAA IGCUCCCC | 13853 | GGGGAGCC C AGTCAGAG | 6790 |
| 3436 | UCUCUGAC CUGAUGAG GCCGUUAGGC CGAA IGGCUCCC | 13854 | GGGAGCCC A GTCAGAGA | 6791 |
| 3440 | UGGGUCUC CUGAUGAG GCCGUUAGGC CGAA IACUGGGC | 13855 | GCCCAGTC A GAGACCCA | 6792 |
| 3446 | AAAACGUG CUGAUGAG GCCGUUAGGC CGAA IUCUCUGA | 13856 | TCAGAGAC C CACGTTTT | 6793 |
| 3447 | GAAAACGU CUGAUGAG GCCGUUAGGC CGAA IGUCUCUG | 13857 | CAGAGACC C ACGTTTTC | 6794 |
| 3448 | UGAAAACG CUGAUGAG GCCGUUAGGC CGAA IGGUCUCU | 13858 | AGAGACCC A CGTTTTCA | 6795 |
| 3456 | ACCAACUC CUGAUGAG GCCGUUAGGC CGAA IAAAACGU | 13859 | ACGTTTTC A GAGTTGGT | 6796 |
| 3470 | UUCCCAAA CUGAUGAG GCCGUUAGGC CGAA IUUCCACC | 13860 | GGTGGAAC A TTTGGGAA | 6797 |
| 3482 | CUUGCAAG CUGAUGAG GCCGUUAGGC CGAA IAUUUCCC | 13861 | GGGAAATC T CTTGCAAG | 6798 |
| 3484 | AGCUUGCA CUGAUGAG GCCGUUAGGC CGAA IAGAUUUC | 13862 | GAAATCTC T TGCAAGCT | 6799 |

285

| | | | | |
|---|---|---|---|---|
| 3488 | CAUUAGCU CUGAUGAG GCCGUUAGGC CGAA ICAAGAGA | 13863 | TCTCTTGC A AGCTAATG | 6800 |
| 3492 | UGAGCAUU CUGAUGAG GCCGUUAGGC CGAA ICUUGCAA | 13864 | TTGCAAGC T AATGCTCA | 6801 |
| 3498 | UCCUGCUG CUGAUGAG GCCGUUAGGC CGAA ICAUUAGC | 13865 | GCTAATGC T CAGCAGGA | 6802 |
| 3500 | CAUCCUGC CUGAUGAG GCCGUUAGGC CGAA IAGCAUUA | 13866 | TAATGCTC A GCAGGATG | 6803 |
| 3503 | UGCCAUCC CUGAUGAG GCCGUUAGGC CGAA ICUGAGCA | 13867 | TGCTCAGC A GGATGGCA | 6804 |
| 3511 | GUAGUCUU CUGAUGAG GCCGUUAGGC CGAA ICCAUCCU | 13868 | AGGATGGC A AAGACTAC | 6805 |
| 3517 | AACAAUGU CUGAUGAG GCCGUUAGGC CGAA IUCUUUGC | 13869 | GCAAAGAC T ACATTGTT | 6806 |
| 3520 | AAGAACAA CUGAUGAG GCCGUUAGGC CGAA IUAGUCUU | 13870 | AAGACTAC A TTGTTCTT | 6807 |
| 3527 | AUAUCGGA CUGAUGAG GCCGUUAGGC CGAA IAACAAUG | 13871 | CATTGTTC T TCCGATAT | 6808 |
| 3530 | CUGAUAUC CUGAUGAG GCCGUUAGGC CGAA IAAGAACA | 13872 | TGTTCTTC C GATATCAG | 6809 |
| 3537 | AAAGUCUC CUGAUGAG GCCGUUAGGC CGAA IAUAUCGG | 13873 | CCGATATC A GAGACTTT | 6810 |
| 3543 | AUGCUCAA CUGAUGAG GCCGUUAGGC CGAA IUCUCUGA | 13874 | TCAGAGAC T TTGAGCAT | 6811 |
| 3550 | CUCUUCCA CUGAUGAG GCCGUUAGGC CGAA ICUCAAAG | 13875 | CTTTGAGC A TGGAAGAG | 6812 |
| 3564 | GAGAGUCC CUGAUGAG GCCGUUAGGC CGAA IAAUCCUC | 13876 | GAGGATTC T GGACTCTC | 6813 |
| 3569 | GCAGAGAG CUGAUGAG GCCGUUAGGC CGAA IUCCAGAA | 13877 | TTCTGGAC T CTCTCTGC | 6814 |
| 3571 | AGGCAGAG CUGAUGAG GCCGUUAGGC CGAA IAGUCCAG | 13878 | CTGGACTC T CTCTGCCT | 6815 |
| 3573 | GUAGGCAG CUGAUGAG GCCGUUAGGC CGAA IAGAGUCC | 13879 | GGACTCTC T CTGCCTAC | 6816 |
| 3575 | AGGUAGGC CUGAUGAG GCCGUUAGGC CGAA IAGAGAGU | 13880 | ACTCTCTC T GCCTACCT | 6817 |
| 3578 | GUGAGGUA CUGAUGAG GCCGUUAGGC CGAA ICAGAGAG | 13881 | CTCTCTGC C TACCTCAC | 6818 |
| 3579 | GGUGAGGU CUGAUGAG GCCGUUAGGC CGAA IGCAGAGA | 13882 | TCTCTGCC T ACCTCACC | 6819 |
| 3582 | ACAGGUGA CUGAUGAG GCCGUUAGGC CGAA IUAGGCAG | 13883 | CTGCCTAC C TCACCTGT | 6820 |
| 3583 | AACAGGUG CUGAUGAG GCCGUUAGGC CGAA IGUAGGCA | 13884 | TGCCTACC T CACCTGTT | 6821 |
| 3585 | GAAACAGG CUGAUGAG GCCGUUAGGC CGAA IAGGUAGG | 13885 | CCTACCTC A CCTGTTTC | 6822 |
| 3587 | AGGAAACA CUGAUGAG GCCGUUAGGC CGAA IUGAGGUA | 13886 | TACCTCAC C TGTTTCCT | 6823 |
| 3588 | CAGGAAAC CUGAUGAG GCCGUUAGGC CGAA IGUGAGGU | 13887 | ACCTCACC T GTTTCCTG | 6824 |
| 3594 | UCCAUACA CUGAUGAG GCCGUUAGGC CGAA IAAACAGG | 13888 | CCTGTTTC C TGTATGGA | 6825 |
| 3595 | CUCCAUAC CUGAUGAG GCCGUUAGGC CGAA IGAAACAG | 13889 | CTGTTTCC T GTATGGAG | 6826 |
| 3622 | GAAUUUGG CUGAUGAG GCCGUUAGGC CGAA IUCACAUA | 13890 | TATGTGAC C CCAAATTC | 6827 |
| 3623 | GGAAUUUG CUGAUGAG GCCGUUAGGC CGAA IGUCACAU | 13891 | ATGTGACC C CAAATTCC | 6828 |
| 3624 | UGGAAUUU CUGAUGAG GCCGUUAGGC CGAA IGGUCACA | 13892 | TGTGACCC C AAATTCCA | 6829 |
| 3625 | AUGGAAUU CUGAUGAG GCCGUUAGGC CGAA IGGGUCAC | 13893 | GTGACCCC A AATTCCAT | 6830 |
| 3631 | GUCAUAAU CUGAUGAG GCCGUUAGGC CGAA IAAUUUGG | 13894 | CCAAATTC C ATTATGAC | 6831 |
| 3632 | UGUCAUAA CUGAUGAG GCCGUUAGGC CGAA IGAAUUUG | 13895 | CAAATTCC A TTATGACA | 6832 |

| | | | | |
|---|---|---|---|---|
| 3640 | UGCUGUGU CUGAUGAG GCCGUUAGGC CGAA IUCAUAAU | 13896 | ATTATGAC A ACACAGCA | 6833 |
| 3643 | UCCUGCUG CUGAUGAG GCCGUUAGGC CGAA IUUGUCAU | 13897 | ATGACAAC A CAGCAGGA | 6834 |
| 3645 | AUUCCUGC CUGAUGAG GCCGUUAGGC CGAA IUGUUGUC | 13898 | GACAACAC A GCAGGAAT | 6835 |
| 3648 | CUGAUUCC CUGAUGAG GCCGUUAGGC CGAA ICUGUGUU | 13899 | AACACAGC A GGAATCAG | 6836 |
| 3655 | AUACUGAC CUGAUGAG GCCGUUAGGC CGAA IAUUCCUG | 13900 | CAGGAATC A GTCAGTAT | 6837 |
| 3659 | GCAGAUAC CUGAUGAG GCCGUUAGGC CGAA IACUGAUU | 13901 | AATCAGTC A GTATCTGC | 6838 |
| 3665 | UGUUCUGC CUGAUGAG GCCGUUAGGC CGAA IAUACUGA | 13902 | TCAGTATC T GCAGAACA | 6839 |
| 3668 | UACUGUUC CUGAUGAG GCCGUUAGGC CGAA ICAGAUAC | 13903 | GTATCTGC A GAACAGTA | 6840 |
| 3673 | UCGCUUAC CUGAUGAG GCCGUUAGGC CGAA IUUCUGCA | 13904 | TGCAGAAC A GTAAGCGA | 6841 |
| 3688 | CACAGGCC CUGAUGAG GCCGUUAGGC CGAA ICUCUUUC | 13905 | GAAAGAGC C GGCCTGTG | 6842 |
| 3692 | CACUCACA CUGAUGAG GCCGUUAGGC CGAA ICCGGCUC | 13906 | GAGCCGGC C TGTGAGTG | 6843 |
| 3693 | ACACUCAC CUGAUGAG GCCGUUAGGC CGAA IGCCGGCU | 13907 | AGCCGGCC T GTGAGTGT | 6844 |
| 3708 | UCUUCAAA CUGAUGAG GCCGUUAGGC CGAA IUUUUUAC | 13908 | GTAAAAAC A TTTGAAGA | 6845 |
| 3721 | UUCUAACG CUGAUGAG GCCGUUAGGC CGAA IAUAUCUU | 13909 | AAGATATC C CGTTAGAA | 6846 |
| 3722 | CUUCUAAC CUGAUGAG GCCGUUAGGC CGAA IGAUAUCU | 13910 | AGATATCC C GTTAGAAG | 6847 |
| 3734 | UUACUUCU CUGAUGAG GCCGUUAGGC CGAA IUUCUUCU | 13911 | AGAAGAAC C AGAAGTAA | 6848 |
| 3735 | UUUACUUC CUGAUGAG GCCGUUAGGC CGAA IGUUCUUC | 13912 | GAAGAACC A GAAGTAAA | 6849 |
| 3751 | GUCAUCUG CUGAUGAG GCCGUUAGGC CGAA IAUUACUU | 13913 | AAGTAATC C CAGATGAC | 6850 |
| 3752 | UGUCAUCU CUGAUGAG GCCGUUAGGC CGAA IGAUUACU | 13914 | AGTAATCC C AGATGACA | 6851 |
| 3753 | UUGUCAUC CUGAUGAG GCCGUUAGGC CGAA IGGAUUAC | 13915 | GTAATCCC A GATGACAA | 6852 |
| 3760 | CGUCUGGU CUGAUGAG GCCGUUAGGC CGAA IUCAUCUG | 13916 | CAGATGAC A ACCAGACG | 6853 |
| 3763 | GUCCGUCU CUGAUGAG GCCGUUAGGC CGAA IUUGUCAU | 13917 | ATGACAAC C AGACGGAC | 6854 |
| 3764 | UGUCCGUC CUGAUGAG GCCGUUAGGC CGAA IGUUGUCA | 13918 | TGACAACC A GACGGACA | 6855 |
| 3772 | CAUACCAC CUGAUGAG GCCGUUAGGC CGAA IUCCGUCU | 13919 | AGACGGAC A GTGGTATG | 6856 |
| 3785 | CUGAGGCA CUGAUGAG GCCGUUAGGC CGAA IAACCAUA | 13920 | TATGGTTC T TGCCTCAG | 6857 |
| 3789 | UCUUCUGA CUGAUGAG GCCGUUAGGC CGAA ICAAGAAC | 13921 | GTTCTTGC C TCAGAAGA | 6858 |
| 3790 | CUCUUCUG CUGAUGAG GCCGUUAGGC CGAA IGCAAGAA | 13922 | TTCTTGCC T CAGAAGAG | 6859 |
| 3792 | AGCUCUUC CUGAUGAG GCCGUUAGGC CGAA IAGGCAAG | 13923 | CTTGCCTC A GAAGAGCT | 6860 |
| 3800 | AAGUUUUC CUGAUGAG GCCGUUAGGC CGAA ICUCUUCU | 13924 | AGAAGAGC T GAAAACTT | 6861 |
| 3807 | UCUUCCAA CUGAUGAG GCCGUUAGGC CGAA IUUUUCAG | 13925 | CTGAAAAC T TTGGAAGA | 6862 |
| 3817 | UUUGGUUC CUGAUGAG GCCGUUAGGC CGAA IUCUUCCA | 13926 | TGGAAGAC A GAACCAAA | 6863 |
| 3822 | GAUAAUUU CUGAUGAG GCCGUUAGGC CGAA IUUCUGUC | 13927 | GACAGAAC C AAATTATC | 6864 |
| 3823 | AGAUAAUU CUGAUGAG GCCGUUAGGC CGAA IGUUCUGU | 13928 | ACAGAACC A AATTATCT | 6865 |

287

| | | | | |
|---|---|---|---|---|
| 3831 | AAAGAUGG CUGAUGAG GCCGUUAGGC CGAA IAUAAUUU | 13929 | AAATTATC T CCATCTTT | 6866 |
| 3833 | CAAAAGAU CUGAUGAG GCCGUUAGGC CGAA IAGAUAAU | 13930 | ATTATCTC C ATCTTTTG | 6867 |
| 3834 | CCAAAAGA CUGAUGAG GCCGUUAGGC CGAA IGAGAUAA | 13931 | TTATCTCC A TCTTTTGG | 6868 |
| 3837 | CCACCAAA CUGAUGAG GCCGUUAGGC CGAA IAUGGAGA | 13932 | TCTCCATC T TTTGGTGG | 6869 |
| 3854 | UUUUGCUG CUGAUGAG GCCGUUAGGC CGAA ICACCAUU | 13933 | AATGGTGC C CAGCAAAA | 6870 |
| 3855 | CUUUUGCU CUGAUGAG GCCGUUAGGC CGAA IGCACCAU | 13934 | ATGGTGCC C AGCAAAAG | 6871 |
| 3856 | GCUUUUGC CUGAUGAG GCCGUUAGGC CGAA IGGCACCA | 13935 | TGGTGCCC A GCAAAAGC | 6872 |
| 3859 | CCUGCUUU CUGAUGAG GCCGUUAGGC CGAA ICUGGGCA | 13936 | TGCCCAGC A AAAGCAGG | 6873 |
| 3865 | AGACUCCC CUGAUGAG GCCGUUAGGC CGAA ICUUUUGC | 13937 | GCAAAAGC A GGGAGTCT | 6874 |
| 3873 | GAUGCCAC CUGAUGAG GCCGUUAGGC CGAA IACUCCCU | 13938 | AGGGAGTC T GTGGCATC | 6875 |
| 3879 | CCUUCAGA CUGAUGAG GCCGUUAGGC CGAA ICCACAGA | 13939 | TCTGTGGC A TCTGAAGG | 6876 |
| 3882 | GAGCCUUC CUGAUGAG GCCGUUAGGC CGAA IAUGCCAC | 13940 | GTGGCATC T GAAGGCTC | 6877 |
| 3889 | CUGGUUUG CUGAUGAG GCCGUUAGGC CGAA ICCUUCAG | 13941 | CTGAAGGC T CAAACCAG | 6878 |
| 3891 | GUCUGGUU CUGAUGAG GCCGUUAGGC CGAA IAGCCUUC | 13942 | GAAGGCTC A AACCAGAC | 6879 |
| 3895 | GCUUGUCU CUGAUGAG GCCGUUAGGC CGAA IUUUGAGC | 13943 | GCTCAAAC C AGACAAGC | 6880 |
| 3896 | CGCUUGUC CUGAUGAG GCCGUUAGGC CGAA IGUUUGAG | 13944 | CTCAAACC A GACAAGCG | 6881 |
| 3900 | UAGCCGCU CUGAUGAG GCCGUUAGGC CGAA IUCUGGUU | 13945 | AACCAGAC A AGCGGCTA | 6882 |
| 3907 | GGACUGGU CUGAUGAG GCCGUUAGGC CGAA ICCGCUUG | 13946 | CAAGCGGC T ACCAGTCC | 6883 |
| 3910 | UCCGGACU CUGAUGAG GCCGUUAGGC CGAA IUAGCCGC | 13947 | GCGGCTAC C AGTCCGGA | 6884 |
| 3911 | AUCCGGAC CUGAUGAG GCCGUUAGGC CGAA IGUAGCCG | 13948 | CGGCTACC A GTCCGGAT | 6885 |
| 3915 | UGAUAUCC CUGAUGAG GCCGUUAGGC CGAA IACUGGUA | 13949 | TACCAGTC C GGATATCA | 6886 |
| 3923 | CAUCGGAG CUGAUGAG GCCGUUAGGC CGAA IAUAUCCG | 13950 | CGGATATC A CTCCGATG | 6887 |
| 3925 | GUCAUCGG CUGAUGAG GCCGUUAGGC CGAA IUGAUAUC | 13951 | GATATCAC T CCGATGAC | 6888 |
| 3927 | GUGUCAUC CUGAUGAG GCCGUUAGGC CGAA IAGUGAUA | 13952 | TATCACTC C GATGACAC | 6889 |
| 3934 | GGUGUCUG CUGAUGAG GCCGUUAGGC CGAA IUCAUCGG | 13953 | CCGATGAC A CAGACACC | 6890 |
| 3936 | GUGGUGUC CUGAUGAG GCCGUUAGGC CGAA IUGUCAUC | 13954 | GATGACAC A GACACCAC | 6891 |
| 3940 | CACGGUGG CUGAUGAG GCCGUUAGGC CGAA IUCUGUGU | 13955 | ACACAGAC A CCACCGTG | 6892 |
| 3942 | UACACGGU CUGAUGAG GCCGUUAGGC CGAA IUGUCUGU | 13956 | ACAGACAC C ACCGTGTA | 6893 |
| 3943 | GUACACGG CUGAUGAG GCCGUUAGGC CGAA IGUGUCUG | 13957 | CAGACACC A CCGTGTAC | 6894 |
| 3945 | GAGUACAC CUGAUGAG GCCGUUAGGC CGAA IUGGUGUC | 13958 | GACACCAC C GTGTACTC | 6895 |
| 3952 | CUCACUGG CUGAUGAG GCCGUUAGGC CGAA IUACACGG | 13959 | CCGTGTAC T CCAGTGAG | 6896 |
| 3954 | UCCUCACU CUGAUGAG GCCGUUAGGC CGAA IAGUACAC | 13960 | GTGTACTC C AGTGAGGA | 6897 |
| 3955 | UUCCUCAC CUGAUGAG GCCGUUAGGC CGAA IGAGUACA | 13961 | TGTACTCC A GTGAGGAA | 6898 |

| | | | | | |
|---|---|---|---|---|---|
| 3966 | AAAAGUUC CUGAUGAG GCCGUUAGGC CGAA ICUUCCUC | 13962 | GAGGAAGC A GAACTTTT | 6899 |
| 3971 | GCUUUAAA CUGAUGAG GCCGUUAGGC CGAA IUUCUGCU | 13963 | AGCAGAAC T TTTAAAGC | 6900 |
| 3980 | UCUCUAUC CUGAUGAG GCCGUUAGGC CGAA ICUUUAAA | 13964 | TTTAAAGC T GATAGAGA | 6901 |
| 3998 | UACCGGUU CUGAUGAG GCCGUUAGGC CGAA ICACUCCA | 13965 | TGGAGTGC A AACCGGTA | 6902 |
| 4002 | GUGCUACC CUGAUGAG GCCGUUAGGC CGAA IUUUGCAC | 13966 | GTGCAAAC C GGTAGCAC | 6903 |
| 4009 | CUGGGCUG CUGAUGAG GCCGUUAGGC CGAA ICUACCGG | 13967 | CCGGTAGC A CAGCCCAG | 6904 |
| 4011 | AUCUGGGC CUGAUGAG GCCGUUAGGC CGAA IUGCUACC | 13968 | GGTAGCAC A GCCCAGAT | 6905 |
| 4014 | AGAAUCUG CUGAUGAG GCCGUUAGGC CGAA ICUGUGCU | 13969 | AGCACAGC C CAGATTCT | 6906 |
| 4015 | GAGAAUCU CUGAUGAG GCCGUUAGGC CGAA IGCUGUGC | 13970 | GCACAGCC C AGATTCTC | 6907 |
| 4016 | GGAGAAUC CUGAUGAG GCCGUUAGGC CGAA IGGCUGUG | 13971 | CACAGCCC A GATTCTCC | 6908 |
| 4022 | CAGGCUGG CUGAUGAG GCCGUUAGGC CGAA IAAUCUGG | 13972 | CCAGATTC T CCAGCCTG | 6909 |
| 4024 | GUCAGGCU CUGAUGAG GCCGUUAGGC CGAA IAGAAUCU | 13973 | AGATTCTC C AGCCTGAC | 6910 |
| 4025 | UGUCAGGC CUGAUGAG GCCGUUAGGC CGAA IGAGAAUC | 13974 | GATTCTCC A GCCTGACA | 6911 |
| 4028 | CCGUGUCA CUGAUGAG GCCGUUAGGC CGAA ICUGGAGA | 13975 | TCTCCAGC C TGACACGG | 6912 |
| 4029 | CCCGUGUC CUGAUGAG GCCGUUAGGC CGAA IGCUGGAG | 13976 | CTCCAGCC T GACACGGG | 6913 |
| 4033 | GGUCCCCG CUGAUGAG GCCGUUAGGC CGAA IUCAGGCU | 13977 | AGCCTGAC A CGGGGACC | 6914 |
| 4041 | CUCAGUGU CUGAUGAG GCCGUUAGGC CGAA IUCCCCGU | 13978 | ACGGGGAC C ACACTGAG | 6915 |
| 4042 | GCUCAGUG CUGAUGAG GCCGUUAGGC CGAA IGUCCCCG | 13979 | CGGGGACC A CACTGAGC | 6916 |
| 4044 | GAGCUCAG CUGAUGAG GCCGUUAGGC CGAA IUGGUCCC | 13980 | GGGACCAC A CTGAGCTC | 6917 |
| 4046 | GAGAGCUC CUGAUGAG GCCGUUAGGC CGAA IUGUGGUC | 13981 | GACCACAC T GAGCTCTC | 6918 |
| 4051 | AGGAGGAG CUGAUGAG GCCGUUAGGC CGAA ICUCAGUG | 13982 | CACTGAGC T CTCCTCCT | 6919 |
| 4053 | ACAGGAGG CUGAUGAG GCCGUUAGGC CGAA IAGCUCAG | 13983 | CTGAGCTC T CCTCCTGT | 6920 |
| 4055 | AAACAGGA CUGAUGAG GCCGUUAGGC CGAA IAGAGCUC | 13984 | GAGCTCTC C TCCTGTTT | 6921 |
| 4056 | UAAACAGG CUGAUGAG GCCGUUAGGC CGAA IGAGAGCU | 13985 | AGCTCTCC T CCTGTTTA | 6922 |
| 4058 | UUUAAACA CUGAUGAG GCCGUUAGGC CGAA IAGGAGAG | 13986 | CTCTCCTC C TGTTTAAA | 6923 |
| 4059 | UUUUAAAC CUGAUGAG GCCGUUAGGC CGAA IGAGGAGA | 13987 | TCTCCTCC T GTTTAAAA | 6924 |
| 4074 | GGUGUGGA CUGAUGAG GCCGUUAGGC CGAA ICUUCCUU | 13988 | AAGGAAGC A TCCACACC | 6925 |
| 4077 | UGGGGUGU CUGAUGAG GCCGUUAGGC CGAA IAUGCUUC | 13989 | GAAGCATC C ACACCCCA | 6926 |
| 4078 | UUGGGGUG CUGAUGAG GCCGUUAGGC CGAA IGAUGCUU | 13990 | AAGCATCC A CACCCCAA | 6927 |
| 4080 | AGUUGGGG CUGAUGAG GCCGUUAGGC CGAA IUGGAUGC | 13991 | GCATCCAC A CCCCAACT | 6928 |
| 4082 | GGAGUUGG CUGAUGAG GCCGUUAGGC CGAA IUGUGGAU | 13992 | ATCCACAC C CCAACTCC | 6929 |
| 4083 | GGGAGUUG CUGAUGAG GCCGUUAGGC CGAA IGUGUGGA | 13993 | TCCACACC C CAACTCCC | 6930 |
| 4084 | CGGGAGUU CUGAUGAG GCCGUUAGGC CGAA IGGUGUGG | 13994 | CCACACCC C AACTCCCG | 6931 |

289

| | | | | |
|---|---|---|---|---|
| 4085 | CCGGGAGU CUGAUGAG GCCGUUAGGC CGAA IGGGUGUG | 13995 | CACACCCC A ACTCCCGG | 6932 |
| 4088 | UGUCCGGG CUGAUGAG GCCGUUAGGC CGAA IUUGGGGU | 13996 | ACCCCAAC T CCCGGACA | 6933 |
| 4090 | GAUGUCCG CUGAUGAG GCCGUUAGGC CGAA IAGUUGGG | 13997 | CCCAACTC C CGGACATC | 6934 |
| 4091 | UGAUGUCC CUGAUGAG GCCGUUAGGC CGAA IGAGUUGG | 13998 | CCAACTCC C GGACATCA | 6935 |
| 4096 | UCAUGUGA CUGAUGAG GCCGUUAGGC CGAA IUCCGGGA | 13999 | TCCCGGAC A TCACATGA | 6936 |
| 4099 | CUCUCAUG CUGAUGAG GCCGUUAGGC CGAA IAUGUCCG | 14000 | CGGACATC A CATGAGAG | 6937 |
| 4101 | ACCUCUCA CUGAUGAG GCCGUUAGGC CGAA IUGAUGUC | 14001 | GACATCAC A TGAGAGGT | 6938 |
| 4111 | AUCUGAGC CUGAUGAG GCCGUUAGGC CGAA IACCUCUC | 14002 | GAGAGGTC T GCTCAGAT | 6939 |
| 4114 | AAAAUCUG CUGAUGAG GCCGUUAGGC CGAA ICAGACCU | 14003 | AGGTCTGC T CAGATTTT | 6940 |
| 4116 | UCAAAAUC CUGAUGAG GCCGUUAGGC CGAA IAGCAGAC | 14004 | GTCTGCTC A GATTTTGA | 6941 |
| 4135 | UGGUGGAA CUGAUGAG GCCGUUAGGC CGAA IAACAACA | 14005 | TGTTGTTC T TTCCACCA | 6942 |
| 4139 | CUGCUGGU CUGAUGAG GCCGUUAGGC CGAA IAAAGAAC | 14006 | GTTCTTTC C ACCAGCAG | 6943 |
| 4140 | CCUGCUGG CUGAUGAG GCCGUUAGGC CGAA IGAAAGAA | 14007 | TTCTTTCC A CCAGCAGG | 6944 |
| 4142 | UUCCUGCU CUGAUGAG GCCGUUAGGC CGAA IUGGAAAG | 14008 | CTTTCCAC C AGCAGGAA | 6945 |
| 4143 | CUUCCUGC CUGAUGAG GCCGUUAGGC CGAA IGUGGAAA | 14009 | TTTCCACC A GCAGGAAG | 6946 |
| 4146 | CUACUUCC CUGAUGAG GCCGUUAGGC CGAA ICUGGUGG | 14010 | CCACCAGC A GGAAGTAG | 6947 |
| 4156 | UCAAAUGC CUGAUGAG GCCGUUAGGC CGAA ICUACUUC | 14011 | GAAGTAGC C GCATTTGA | 6948 |
| 4159 | AAAUCAAA CUGAUGAG GCCGUUAGGC CGAA ICGGCUAC | 14012 | GTAGCCGC A TTTGATTT | 6949 |
| 4170 | UGUCGAAA CUGAUGAG GCCGUUAGGC CGAA IAAAAUCA | 14013 | TGATTTTC A TTTCGACA | 6950 |
| 4178 | UUUUCUGU CUGAUGAG GCCGUUAGGC CGAA IUCGAAAU | 14014 | ATTTCGAC A ACAGAAAA | 6951 |
| 4181 | CCUUUUUC CUGAUGAG GCCGUUAGGC CGAA IUUGUCGA | 14015 | TCGACAAC A GAAAAAGG | 6952 |
| 4192 | CAGUCCGA CUGAUGAG GCCGUUAGGC CGAA IUCCUUUU | 14016 | AAAAGGAC C TCGGACTG | 6953 |
| 4193 | GCAGUCCG CUGAUGAG GCCGUUAGGC CGAA IGUCCUUU | 14017 | AAAGGACC T CGGACTGC | 6954 |
| 4199 | CUCCCUGC CUGAUGAG GCCGUUAGGC CGAA IUCCGAGG | 14018 | CCTCGGAC T GCAGGGAG | 6955 |
| 4202 | UGGCUCCC CUGAUGAG GCCGUUAGGC CGAA ICAGUCCG | 14019 | CGGACTGC A GGGAGCCA | 6956 |
| 4209 | GAAGAGCU CUGAUGAG GCCGUUAGGC CGAA ICUCCCUG | 14020 | CAGGGAGC C AGCTCTTC | 6957 |
| 4210 | AGAAGAGC CUGAUGAG GCCGUUAGGC CGAA IGCUCCCU | 14021 | AGGGAGCC A GCTCTTCT | 6958 |
| 4213 | CCUAGAAG CUGAUGAG GCCGUUAGGC CGAA ICUGGCUC | 14022 | GAGCCAGC T CTTCTAGG | 6959 |
| 4215 | AGCCUAGA CUGAUGAG GCCGUUAGGC CGAA IAGCUGGC | 14023 | GCCAGCTC T TCTAGGCT | 6960 |
| 4218 | ACAAGCCU CUGAUGAG GCCGUUAGGC CGAA IAAGAGCU | 14024 | AGCTCTTC T AGGCTTGT | 6961 |

290

Table XVII: KDR G-Cleaver Ribozyme and Target Sequences 237.198

| nt. Position | Ribozyme Sequence | Seq. ID. Nos | Target | Seq. ID Nos |
|---|---|---|---|---|
| 12 | GCCAG UGAUG GCAUGCACUAUGC GCG AGCACCUUGC | 14025 | GCAAGGTGCT G CTGGC | 6962 |
| 22 | CAGGG UGAUG GCAUGCACUAUGC GCG GACGGCCAGC | 14026 | GCTGGCCGTC G CCCTG | 6963 |
| 35 | CCACG UGAUG GCAUGCACUAUGC GCG AGAGCCACAG | 14027 | CTGTGGCTCT G CGTGG | 6964 |
| 52 | AGAGG UGAUG GCAUGCACUAUGC GCG GGCCCGGGUC | 14028 | GACCCGGGCC G CCTCT | 6965 |
| 66 | CUAGG UGAUG GCAUGCACUAUGC GCG AAACCCACAG | 14029 | CTGTGGGTTT G CCTAG | 6966 |
| 82 | CAGAU UGAUG GCAUGCACUAUGC GCG AAGAGAAACA | 14030 | TGTTTCTCTT G ATCTG | 6967 |
| 87 | CUGGG UGAUG GCAUGCACUAUGC GCG AGAUCAAGAG | 14031 | CTCTTGATCT G CCCAG | 6968 |
| 152 | CCCUG UGAUG GCAUGCACUAUGC GCG AAGUAAUUUG | 14032 | CAAATTACTT G CAGGG | 6969 |
| 205 | UUGCU UGAUG GCAUGCACUAUGC GCG ACUGCCACUC | 14033 | GAGTGGCAGT G AGCAA | 6970 |
| 222 | UCAGU UGAUG GCAUGCACUAUGC GCG ACCUCCACCC | 14034 | GGGTGGAGGT G ACTGA | 6971 |
| 226 | GCACU UGAUG GCAUGCACUAUGC GCG AGUCACCUCC | 14035 | GGAGGTGACT G AGTGC | 6972 |
| 230 | CGCUG UGAUG GCAUGCACUAUGC GCG ACUCAGUCAC | 14036 | GTGACTGAGT G CAGCG | 6973 |
| 235 | GCCAU UGAUG GCAUGCACUAUGC GCG GCUGCACUCA | 14037 | TGAGTGCAGC G ATGGC | 6974 |
| 273 | CCGAU UGAUG GCAUGCACUAUGC GCG ACUUUUGGAA | 14038 | TTCCAAAAGT G ATCGG | 6975 |
| 283 | AGUGU UGAUG GCAUGCACUAUGC GCG AUUUCCGAUC | 14039 | GATCGGAAAT G ACACT | 6976 |
| 302 | AGAAG UGAUG GCAUGCACUAUGC GCG ACUUGUAGGC | 14040 | GCCTACAAGT G CTTCT | 6977 |
| 319 | CAAGU UGAUG GCAUGCACUAUGC GCG AGUUUCCCGG | 14041 | CCGGGAAACT G ACTTG | 6978 |
| 373 | AGAAG UGAUG GCAUGCACUAUGC GCG AAUAAAUGGA | 14042 | TCCATTTATT G CTTCT | 6979 |
| 385 | UUGGU UGAUG GCAUGCACUAUGC GCG ACUAACAGAA | 14043 | TTCTGTTAGT G ACCAA | 6980 |
| 412 | GUUCU UGAUG GCAUGCACUAUGC GCG AGUAAUGUAC | 14044 | GTACATTACT G AGAAC | 6981 |
| 435 | GGAAU UGAUG GCAUGCACUAUGC GCG ACCACAGUUU | 14045 | AAACTGTGGT G ATTCC | 6982 |
| 481 | UCUUG UGAUG GCAUGCACUAUGC GCG ACAAAGUGAC | 14046 | GTCACTTTGT G CAAGA | 6983 |
| 511 | ACCAU UGAUG GCAUGCACUAUGC GCG AGGAACAAAU | 14047 | ATTTGTTCCT G ATGGT | 6984 |
| 567 | CUGAU UGAUG GCAUGCACUAUGC GCG AUGUAGCUGG | 14048 | CCAGCTACAT G ATCAG | 6985 |
| 577 | GCCAG UGAUG GCAUGCACUAUGC GCG AUAGCUGAUC | 14049 | GATCAGCTAT G CTGGC | 6986 |
| 595 | UGCUU UGAUG GCAUGCACUAUGC GCG ACAGAAGACC | 14050 | GGTCTTCTGT G AAGCA | 6987 |
| 610 | UUCAU UGAUG GCAUGCACUAUGC GCG AUUAAUUUUU | 14051 | AAAAATTAAT G ATGAA | 6988 |
| 613 | ACUUU UGAUG GCAUGCACUAUGC GCG AUCAUUAAUU | 14052 | AATTAATGAT G AAAGT | 6989 |
| 667 | CACAU UGAUG GCAUGCACUAUGC GCG AUAAAUCCUA | 14053 | TAGGATTTAT G ATGTG | 6990 |

291

| | | | | |
|---|---|---|---|---|
| 678 | GGACU UGAUG GCAUGCACUAUGC GCG AGAACCACAU | 14054 | ATGTGGTTCT G AGTCC | 6991 |
| 697 | UAGUU UGAUG GCAUGCACUAUGC GCG AAUUCCAUGA | 14055 | TCATGGAATT G AACTA | 6992 |
| 745 | UAGUU UGAUG GCAUGCACUAUGC GCG AGUUCUUGCU | 14056 | AGCAAGAACT G AACTA | 6993 |
| 763 | GAAGU UGAUG GCAUGCACUAUGC GCG AAUCCCCACA | 14057 | TGTGGGGATT G ACTTC | 6994 |
| 789 | UGCUU UGAUG GCAUGCACUAUGC GCG GAAGAAGGGU | 14058 | ACCCTTCTTC G AAGCA | 6995 |
| 818 | GGUCU UGAUG GCAUGCACUAUGC GCG GGUUUACAAG | 14059 | CTTGTAAACC G AGACC | 6996 |
| 844 | CAUCU UGAUG GCAUGCACUAUGC GCG ACUCCCAGAC | 14060 | GTCTGGGAGT G AGATG | 6997 |
| 849 | UUCUU UGAUG GCAUGCACUAUGC GCG AUCUCACUCC | 14061 | GGAGTGAGAT G AAGAA | 6998 |
| 861 | GUGCU UGAUG GCAUGCACUAUGC GCG AAAAAUUUCU | 14062 | AGAAATTTTT G AGCAC | 6999 |
| 895 | UUGGU UGAUG GCAUGCACUAUGC GCG ACUCCGGGUU | 14063 | AACCCGGAGT G ACCAA | 7000 |
| 916 | UGCUG UGAUG GCAUGCACUAUGC GCG ACAGGUGUAC | 14064 | GTACACCTGT G CAGCA | 7001 |
| 933 | GUCAU UGAUG GCAUGCACUAUGC GCG AGCCCACUGG | 14065 | CCAGTGGGCT G ATGAC | 7002 |
| 936 | UUGGU UGAUG GCAUGCACUAUGC GCG AUCAGCCCAC | 14066 | GTGGGCTGAT G ACCAA | 7003 |
| 970 | UUUUU UGAUG GCAUGCACUAUGC GCG AUGGACCCUG | 14067 | CAGGGTCCAT G AAAAA | 7004 |
| 985 | AAAAG UGAUG GCAUGCACUAUGC GCG AACAAAAGGU | 14068 | ACCTTTTGTT G CTTTT | 7005 |
| 1048 | CUUCG UGAUG GCAUGCACUAUGC GCG AGGGAUUCUG | 14069 | CAGAATCCCT G CGAAG | 7006 |
| 1050 | UACUU UGAUG GCAUGCACUAUGC GCG GCAGGGAUUC | 14070 | GAATCCCTGC G AAGTA | 7007 |
| 1108 | GGACU UGAUG GCAUGCACUAUGC GCG AAGGGGUAUU | 14071 | AATACCCCTT G AGTCC | 7008 |
| 1143 | AUCGU UGAUG GCAUGCACUAUGC GCG AGUACAUGCC | 14072 | GGCATGTACT G ACGAT | 7009 |
| 1146 | AUAAU UGAUG GCAUGCACUAUGC GCG GUCAGUACAU | 14073 | ATGTACTGAC G ATTAT | 7010 |
| 1158 | UCACU UGAUG GCAUGCACUAUGC GCG ACUUCCAUAA | 14074 | TTATGGAAGT G AGTGA | 7011 |
| 1162 | UCUUU UGAUG GCAUGCACUAUGC GCG ACUCACUUCC | 14075 | GGAAGTGAGT G AAAGA | 7012 |
| 1267 | UUUCU UGAUG GCAUGCACUAUGC GCG ACCAAUCUGG | 14076 | CCAGATTGGT G AGAAA | 7013 |
| 1320 | GUCAG UGAUG GCAUGCACUAUGC GCG GUUUGAGUGG | 14077 | CCACTCAAAC G CTGAC | 7014 |
| 1323 | CAUGU UGAUG GCAUGCACUAUGC GCG AGCGUUUGAG | 14078 | CTCAAACGCT G ACATG | 7015 |
| 1339 | AAUGG UGAUG GCAUGCACUAUGC GCG AUAGACCGUA | 14079 | TACGGTCTAT G CCATT | 7016 |
| 1353 | UGAUG UGAUG GCAUGCACUAUGC GCG GGGGGAGGAA | 14080 | TTCCTCCCCC G CATCA | 7017 |
| 1391 | UGGCG UGAUG GCAUGCACUAUGC GCG ACUCUUCCUC | 14081 | GAGGAAGAGT G CGCCA | 7018 |
| 1393 | GUUGG UGAUG GCAUGCACUAUGC GCG GCACUCUUCC | 14082 | GGAAGAGTGC G CCAAC | 7019 |
| 1399 | GGGCU UGAUG GCAUGCACUAUGC GCG GUUGGCGCAC | 14083 | GTGCGCCAAC G AGCCC | 7020 |
| 1422 | UUUGU UGAUG GCAUGCACUAUGC GCG ACUGAGACAG | 14084 | CTGTCTCAGT G ACAAA | 7021 |
| 1441 | UUCUU UGAUG GCAUGCACUAUGC GCG ACAAGGGUAU | 14085 | ATACCCTTGT G AAGAA | 7022 |
| 1486 | AACUU UGAUG GCAUGCACUAUGC GCG AAUUUUAUUU | 14086 | AAATAAAATT G AAGTT | 7023 |

292

| | | | | |
|---|---|---|---|---|
| 1507 | UAGAG UGAUG GCAUGCACUAUGC GCG AAAUUGAUUU | 14087 | AAATCAATTT G CTCTA | 7024 |
| 1516 | UCCUU UGAUG GCAUGCACUAUGC GCG AAUUAGAGCA | 14088 | TGCTCTAATT G AAGGA | 7025 |
| 1585 | CGCUU UGAUG GCAUGCACUAUGC GCG ACAUUUGUAC | 14089 | GTACAAATGT G AAGCG | 7026 |
| 1620 | GAGAU UGAUG GCAUGCACUAUGC GCG ACCCUCUCUC | 14090 | GAGAGAGGGT G ATCTC | 7027 |
| 1635 | CUGGU UGAUG GCAUGCACUAUGC GCG ACGUGGAAGG | 14091 | CCTTCCACGT G ACCAG | 7028 |
| 1648 | AAUUU UGAUG GCAUGCACUAUGC GCG AGGACCCCUG | 14092 | CAGGGGTCCT G AAATT | 7029 |
| 1659 | GGUUG UGAUG GCAUGCACUAUGC GCG AAAGUAAUUU | 14093 | AAATTACTTT G CAACC | 7030 |
| 1666 | CAUGU UGAUG GCAUGCACUAUGC GCG AGGUUGCAAA | 14094 | TTTGCAACCT G ACATG | 7031 |
| 1671 | GGCUG UGAUG GCAUGCACUAUGC GCG AUGUCAGGUU | 14095 | AACCTGACAT G CAGCC | 7032 |
| 1681 | CUGCU UGAUG GCAUGCACUAUGC GCG AGUGGGCUGC | 14096 | GCAGCCCACT G AGCAG | 7033 |
| 1706 | CAGUG UGAUG GCAUGCACUAUGC GCG ACCACAAAGA | 14097 | TCTTTGTGGT G CACTG | 7034 |
| 1711 | GUCUG UGAUG GCAUGCACUAUGC GCG AGUGCACCAC | 14098 | GTGGTGCACT G CAGAC | 7035 |
| 1729 | GUUCU UGAUG GCAUGCACUAUGC GCG AAACGUAGAU | 14099 | ATCTACGTTT G AGAAC | 7036 |
| 1767 | AUUGG UGAUG GCAUGCACUAUGC GCG AGAGGCUGUG | 14100 | CACAGCCTCT G CCAAT | 7037 |
| 1788 | GUGGG UGAUG GCAUGCACUAUGC GCG AACUCUCCCA | 14101 | TGGGAGAGTT G CCCAC | 7038 |
| 1802 | UCUUG UGAUG GCAUGCACUAUGC GCG AAACAGGUGU | 14102 | ACACCTGTTT G CAAGA | 7039 |
| 1830 | GCAUU UGAUG GCAUGCACUAUGC GCG AAUUUCCAAA | 14103 | TTTGGAAATT G AATGC | 7040 |
| 1834 | GGUGG UGAUG GCAUGCACUAUGC GCG AUUCAAUUUC | 14104 | GAAATTGAAT G CCACC | 7041 |
| 1861 | AAUGU UGAUG GCAUGCACUAUGC GCG AUUUGUGCUA | 14105 | TAGCACAAAT G ACATT | 7042 |
| 1869 | AUGAU UGAUG GCAUGCACUAUGC GCG AAAAUGUCAU | 14106 | ATGACATTTT G ATCAT | 7043 |
| 1888 | GGAUG UGAUG GCAUGCACUAUGC GCG AUUCUUAAGC | 14107 | GCTTAAGAAT G CATCC | 7044 |
| 1896 | UCCUG UGAUG GCAUGCACUAUGC GCG AAGGAUGCAU | 14108 | ATGCATCCTT G CAGGA | 7045 |
| 1919 | CAAGG UGAUG GCAUGCACUAUGC GCG AGACAUAGUC | 14109 | GACTATGTCT G CCTTG | 7046 |
| 1924 | UUGAG UGAUG GCAUGCACUAUGC GCG AAGGCAGACA | 14110 | TGTCTGCCTT G CTCAA | 7047 |
| 1955 | CCACG UGAUG GCAUGCACUAUGC GCG AAUGUCUUUU | 14111 | AAAAGACATT G CGTGG | 7048 |
| 1998 | GUGAU UGAUG GCAUGCACUAUGC GCG GUGGGUGCCA | 14112 | TGGCACCCAC G ATCAC | 7049 |
| 2025 | CUUGU UGAUG GCAUGCACUAUGC GCG GUCUGAUUCU | 14113 | AGAATCAGAC G ACAAG | 7050 |
| 2047 | GACUU UGAUG GCAUGCACUAUGC GCG GAUGCUUUCC | 14114 | GGAAAGCATC G AAGTC | 7051 |
| 2057 | CCGUG UGAUG GCAUGCACUAUGC GCG AUGAGACUUC | 14115 | GAAGTCTCAT G CACGG | 7052 |
| 2107 | GGUCU UGAUG GCAUGCACUAUGC GCG AUUAUCUUUA | 14116 | TAAAGATAAT G AGACC | 7053 |
| 2139 | UCCUU UGAUG GCAUGCACUAUGC GCG AAUACAAUGC | 14117 | GCATTGTATT G AAGGA | 7054 |
| 2168 | CUCUG UGAUG GCAUGCACUAUGC GCG GGAUAGUGAG | 14118 | CTCACTATCC G CAGAG | 7055 |
| 2175 | UUCCU UGAUG GCAUGCACUAUGC GCG ACUCUGCGGA | 14119 | TCCGCAGAGT G AGGAA | 7056 |

| | | | | |
|---|---|---|---|---|
| 2188 | GCCUU UGAUG GCAUGCACUAUGC GCG GUCCUCCUUC | 14120 | GAAGGAGGAC G AAGGC | 7057 |
| 2204 | CCUGG UGAUG GCAUGCACUAUGC GCG AGGUGUAGAG | 14121 | CTCTACACCT G CCAGG | 7058 |
| 2213 | CACUG UGAUG GCAUGCACUAUGC GCG AUGCCUGGCA | 14122 | TGCCAGGCAT G CAGTG | 7059 |
| 2230 | UUUUG UGAUG GCAUGCACUAUGC GCG ACAGCCAAGA | 14123 | TCTTGGCTGT G CAAAA | 7060 |
| 2263 | CUGGG UGAUG GCAUGCACUAUGC GCG ACCUUCUAUU | 14124 | AATAGAAGGT G CCCAG | 7061 |
| 2277 | AAGUU UGAUG GCAUGCACUAUGC GCG GUCUUUUCCU | 14125 | AGGAAAAGAC G AACTT | 7062 |
| 2307 | ACCGU UGAUG GCAUGCACUAUGC GCG GUGCCUACUA | 14126 | TAGTAGGCAC G ACGGT | 7063 |
| 2313 | GCAAU UGAUG GCAUGCACUAUGC GCG ACCGUCGUGC | 14127 | GCACGACGGT G ATTGC | 7064 |
| 2317 | CAUGG UGAUG GCAUGCACUAUGC GCG AAUCACCGUC | 14128 | GACGGTGATT G CCATG | 7065 |
| 2385 | GUCUU UGAUG GCAUGCACUAUGC GCG AGUUCCCCUC | 14129 | GAGGGGAACT G AAGAC | 7066 |
| 2422 | GAGUU UGAUG GCAUGCACUAUGC GCG AUCUGGAUCC | 14130 | GGATCCAGAT G AACTC | 7067 |
| 2437 | AUGUU UGAUG GCAUGCACUAUGC GCG AUCCAAUGGG | 14131 | CCCATTGGAT G AACAT | 7068 |
| 2446 | UCGUU UGAUG GCAUGCACUAUGC GCG ACAAUGUUCA | 14132 | TGAACATTGT G AACGA | 7069 |
| 2450 | GCAGU UGAUG GCAUGCACUAUGC GCG GUUCACAAUG | 14133 | CATTGTGAAC G ACTGC | 7070 |
| 2454 | UAAGG UGAUG GCAUGCACUAUGC GCG AGUCGUUCAC | 14134 | GTGAACGACT G CCTTA | 7071 |
| 2461 | GGCAU UGAUG GCAUGCACUAUGC GCG AUAAGGCAGU | 14135 | ACTGCCTTAT G ATGCC | 7072 |
| 2464 | GCUGG UGAUG GCAUGCACUAUGC GCG AUCAUAAGGC | 14136 | GCCTTATGAT G CCAGC | 7073 |
| 2496 | AGGUU UGAUG GCAUGCACUAUGC GCG AGCCGGUCUC | 14137 | GAGACCGGCT G AACCT | 7074 |
| 2524 | AAAGG UGAUG GCAUGCACUAUGC GCG ACCACGGCCA | 14138 | TGGCCGTGGT G CCTTT | 7075 |
| 2542 | UGCUU UGAUG GCAUGCACUAUGC GCG AAUCUCUUGG | 14139 | CCAAGAGATT G AAGCA | 7076 |
| 2551 | AAAGG UGAUG GCAUGCACUAUGC GCG AUCUGCUUCA | 14140 | TGAAGCAGAT G CCTTT | 7077 |
| 2563 | CUUGU UGAUG GCAUGCACUAUGC GCG AAUUCCAAAG | 14141 | CTTTGGAATT G ACAAG | 7078 |
| 2579 | UCCUG UGAUG GCAUGCACUAUGC GCG AAGUUGCUGU | 14142 | ACAGCAACTT G CAGGA | 7079 |
| 2604 | UCUUU UGAUG GCAUGCACUAUGC GCG AACAUUUUGA | 14143 | TCAAAATGTT G AAAGA | 7080 |
| 2626 | AUGCU UGAUG GCAUGCACUAUGC GCG ACUGUGUGUU | 14144 | AACACACAGT G AGCAT | 7081 |
| 2633 | GAGCU UGAUG GCAUGCACUAUGC GCG GAUGCUCACU | 14145 | AGTGAGCATC G AGCTC | 7082 |
| 2647 | GAGUU UGAUG GCAUGCACUAUGC GCG AGACAUGAGA | 14146 | TCTCATGTCT G AACTC | 7083 |
| 2704 | ACAGG UGAUG GCAUGCACUAUGC GCG ACCUAGAAGG | 14147 | CCTTCTAGGT G CCTGT | 7084 |
| 2736 | ACAAU UGAUG GCAUGCACUAUGC GCG ACCAUGAGUG | 14148 | CACTCATGGT G ATTGT | 7085 |
| 2750 | AUUUG UGAUG GCAUGCACUAUGC GCG AGAAUUCCAC | 14149 | GTGGAATTCT G CAAAT | 7086 |
| 2778 | CUCCU UGAUG GCAUGCACUAUGC GCG AGGUAAGUGG | 14150 | CCACTTACCT G AGGAG | 7087 |
| 2794 | AAAUU UGAUG GCAUGCACUAUGC GCG AUUUCUCUUG | 14151 | CAAGAGAAAT G AATTT | 7088 |
| 2825 | GGAAU UGAUG GCAUGCACUAUGC GCG GUGCCCCUUU | 14152 | AAAGGGGCAC G ATTCC | 7089 |

294

| | | | | |
|---|---|---|---|---|
| 2871 | CGUUU UGAUG GCAUGCACUAUGC GCG AGAUCCACAG | 14153 | CTGTGGATCT G AAACG | 7090 |
| 2879 | CCAAG UGAUG GCAUGCACUAUGC GCG GCCGUUUCAG | 14154 | CTGAAACGGC G CTTGG | 7091 |
| 2947 | UACAU UGAUG GCAUGCACUAUGC GCG ACUGAGGGAC | 14155 | GTCCCTCAGT G ATGTA | 7092 |
| 2971 | AUCUU UGAUG GCAUGCACUAUGC GCG AGGAGCUUCC | 14156 | GGAAGCTCCT G AAGAT | 7093 |
| 2994 | AAGGU UGAUG GCAUGCACUAUGC GCG AGGAAGUCCU | 14157 | AGGACTTCCT G ACCTT | 7094 |
| 3057 | UUUCG UGAUG GCAUGCACUAUGC GCG GAUGCCAAGA | 14158 | TCTTGGCATC G CGAAA | 7095 |
| 3059 | ACUUU UGAUG GCAUGCACUAUGC GCG GCGAUGCCAA | 14159 | TTGGCATCGC G AAAGT | 7096 |
| 3089 | UAUUU UGAUG GCAUGCACUAUGC GCG GUGCCGCCAG | 14160 | CTGGCGGCAC G AAATA | 7097 |
| 3130 | AAAGU UGAUG GCAUGCACUAUGC GCG ACAGAUUUUA | 14161 | TAAAATCTGT G ACTTT | 7098 |
| 3187 | GCGAG UGAUG GCAUGCACUAUGC GCG AUCUCCUUUU | 14162 | AAAAGGAGAT G CTCGC | 7099 |
| 3191 | GGAGG UGAUG GCAUGCACUAUGC GCG GAGCAUCUCC | 14163 | GGAGATGCTC G CCTCC | 7100 |
| 3201 | CAUUU UGAUG GCAUGCACUAUGC GCG AAAGGGAGGC | 14164 | GCCTCCCTTT G AAATG | 7101 |
| 3229 | UCUGU UGAUG GCAUGCACUAUGC GCG AAAAAUUGUU | 14165 | AACAATTTTT G ACAGA | 7102 |
| 3253 | GACGU UGAUG GCAUGCACUAUGC GCG ACUCUGGAUU | 14166 | AATCCAGAGT G ACGTC | 7103 |
| 3276 | CACAG UGAUG GCAUGCACUAUGC GCG AAAACACCAA | 14167 | TTGGTGTTTT G CTGTG | 7104 |
| 3301 | AGAAG UGAUG GCAUGCACUAUGC GCG ACCUAAGGAA | 14168 | TTCCTTAGGT G CTTCT | 7105 |
| 3328 | UUCAU UGAUG GCAUGCACUAUGC GCG AAUCUUUACC | 14169 | GGTAAAGATT G ATGAA | 7106 |
| 3331 | UUCUU UGAUG GCAUGCACUAUGC GCG AUCAAUCUUU | 14170 | AAAGATTGAT G AAGAA | 7107 |
| 3347 | UCAAU UGAUG GCAUGCACUAUGC GCG GCCUACAAAA | 14171 | TTTTGTAGGC G ATTGA | 7108 |
| 3351 | UCUUU UGAUG GCAUGCACUAUGC GCG AAUCGCCUAC | 14172 | GTAGGCGATT G AAAGA | 7109 |
| 3369 | GCCCU UGAUG GCAUGCACUAUGC GCG AUUCUAGUUC | 14173 | GAACTAGAAT G AGGGC | 7110 |
| 3379 | AUAAU UGAUG GCAUGCACUAUGC GCG AGGGGCCCUC | 14174 | GAGGGCCCCT G ATTAT | 7111 |
| 3411 | UCCAG UGAUG GCAUGCACUAUGC GCG AUGGUCUGGU | 14175 | ACCAGACCAT G CTGGA | 7112 |
| 3419 | GCCAG UGAUG GCAUGCACUAUGC GCG AGUCCAGCAU | 12935 | ATGCTGGACT G CTGGC | 5872 |
| 3486 | GCUUG UGAUG GCAUGCACUAUGC GCG AAGAGAUUUC | 14176 | GAAATCTCTT G CAAGC | 7113 |
| 3496 | CUGAG UGAUG GCAUGCACUAUGC GCG AUUAGCUUGC | 14177 | GCAAGCTAAT G CTCAG | 7114 |
| 3531 | GAUAU UGAUG GCAUGCACUAUGC GCG GGAAGAACAA | 14178 | TTGTTCTTCC G ATATC | 7115 |
| 3546 | AUGCU UGAUG GCAUGCACUAUGC GCG AAAGUCUCUG | 14179 | CAGAGACTTT G AGCAT | 7116 |
| 3576 | GUAGG UGAUG GCAUGCACUAUGC GCG AGAGAGAGUC | 14180 | GACTCTCTCT G CCTAC | 7117 |
| 3619 | GGGGU UGAUG GCAUGCACUAUGC GCG ACAUACUUCC | 14181 | GGAAGTATGT G ACCCC | 7118 |
| 3637 | GUUGU UGAUG GCAUGCACUAUGC GCG AUAAUGGAAU | 14182 | ATTCCATTAT G ACAAC | 7119 |
| 3666 | UUCUG UGAUG GCAUGCACUAUGC GCG AGAUACUGAC | 14183 | GTCAGTATCT G CAGAA | 7120 |
| 3680 | UCUUU UGAUG GCAUGCACUAUGC GCG GCUUACUGUU | 14184 | AACAGTAAGC G AAAGA | 7121 |

295

| | | | | |
|---|---|---|---|---|
| 3696 | ACACU UGAUG GCAUGCACUAUGC GCG ACAGGCCGGC | 14185 | GCCGGCCTGT G AGTGT | 7122 |
| 3712 | AUCUU UGAUG GCAUGCACUAUGC GCG AAAUGUUUUU | 14186 | AAAAACATTT G AAGAT | 7123 |
| 3757 | GUUGU UGAUG GCAUGCACUAUGC GCG AUCUGGGAUU | 14187 | AATCCCAGAT G ACAAC | 7124 |
| 3787 | UGAGG UGAUG GCAUGCACUAUGC GCG AAGAACCAUA | 14188 | TATGGTTCTT G CCTCA | 7125 |
| 3801 | GUUUU UGAUG GCAUGCACUAUGC GCG AGCUCUUCUG | 14189 | CAGAAGAGCT G AAAAC | 7126 |
| 3852 | CUGGG UGAUG GCAUGCACUAUGC GCG ACCAUUCCAC | 14190 | GTGGAATGGT G CCCAG | 7127 |
| 3883 | GCCUU UGAUG GCAUGCACUAUGC GCG AGAUGCCACA | 14191 | TGTGGCATCT G AAGGC | 7128 |
| 3928 | GUCAU UGAUG GCAUGCACUAUGC GCG GGAGUGAUAU | 14192 | ATATCACTCC G ATGAC | 7129 |
| 3931 | UGUGU UGAUG GCAUGCACUAUGC GCG AUCGGAGUGA | 14193 | TCACTCCGAT G ACACA | 7130 |
| 3958 | UUCCU UGAUG GCAUGCACUAUGC GCG ACUGGAGUAC | 14194 | GTACTCCAGT G AGGAA | 7131 |
| 3981 | UCUAU UGAUG GCAUGCACUAUGC GCG AGCUUUAAAA | 14195 | TTTTAAAGCT G ATAGA | 7132 |
| 3996 | GUUUG UGAUG GCAUGCACUAUGC GCG ACUCCAAUCU | 14196 | AGATTGGAGT G CAAAC | 7133 |
| 4030 | CGUGU UGAUG GCAUGCACUAUGC GCG AGGCUGGAGA | 14197 | TCTCCAGCCT G ACACG | 7134 |
| 4047 | GAGCU UGAUG GCAUGCACUAUGC GCG AGUGUGGUCC | 14198 | GGACCACACT G AGCTC | 7135 |
| 4103 | CCUCU UGAUG GCAUGCACUAUGC GCG AUGUGAUGUC | 14199 | GACATCACAT G AGAGG | 7136 |
| 4112 | CUGAG UGAUG GCAUGCACUAUGC GCG AGACCUCUCA | 14200 | TGAGAGGTCT G CTCAG | 7137 |
| 4123 | CACUU UGAUG GCAUGCACUAUGC GCG AAAAUCUGAG | 14201 | CTCAGATTTT G AAGTG | 7138 |
| 4157 | AAAUG UGAUG GCAUGCACUAUGC GCG GGCUACUUCC | 14202 | GGAAGTAGCC G CATTT | 7139 |
| 4163 | AAAAU UGAUG GCAUGCACUAUGC GCG AAAUGCGGCU | 14203 | AGCCGCATTT G ATTTT | 7140 |
| 4175 | GUUGU UGAUG GCAUGCACUAUGC GCG GAAAUGAAAA | 14204 | TTTTCATTTC G ACAAC | 7141 |
| 4200 | CCCUG UGAUG GCAUGCACUAUGC GCG AGUCCGAGGU | 14205 | ACCTCGGACT G CAGGG | 7142 |

Other embodiments are within the following claims.

SEQUENCE LISTING

The patent contains a lengthy "Sequence Listing" section. A copy of the "Sequence Listing" is available in electronic form from the USPTO web site (http://seqdata.uspto.gov/sequence.html?DocID=6566127B1). An electronic copy of the "Sequence Listing" will also be available from the USPTO upon request and payment of the fee set forth in 37 CFR 1.19(b)(3).

What is claimed is:

1. An enzymatic nucleic acid molecule which specifically cleaves flt-1 RNA, wherein the enzymatic nucleic acid molecule comprises SEQ ID NO: 14222.

2. A mammalian cell comprising the enzymatic nucleic acid molecule of claim 1, wherein said mammalian cell is not a living human.

3. The mammalian cell of claim 2, wherein said mammalian cell is a human cell.

4. The enzymatic nucleic acid molecule of claim 1, wherein the enzymatic nucleic acid molecule is chemically synthesized.

5. A composition comprising the enzymatic nucleic acid of claim 1 and a pharmaceutically acceptable carrier.

* * * * *